US008846657B2

(12) United States Patent
Christopher et al.

(10) Patent No.: US 8,846,657 B2
(45) Date of Patent: Sep. 30, 2014

(54) SUBSTITUTED IMIDAZOPYRIDINES AS HDM2 INHIBITORS

(71) Applicant: Merck Sharp & Dohme Corp.

(72) Inventors: Matthew P. Christopher, Brookline, MA (US); Francesc Xavier Fradera Llinas, Brookline, MA (US); Michelle Machacek, Brookline, MA (US); Michelle Martinez, Watertown, MA (US); Michael Hale Reutershan, Brighton, MA (US); Manami Shizuka, Lexington, MA (US); Binyuan Sun, Needham Heights, MA (US); Christopher Francis Thompson, Arlington, MA (US); B. Wesley Trotter, Medfield, MA (US); Matthew E. Voss, Singapore (SG); Michael D. Altman, Needham, MA (US); Stephane L. Bogen, Somerset, NJ (US); Ronald J. Doll, Convent Station, NJ (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 14/132,946

(22) Filed: Dec. 18, 2013

(65) Prior Publication Data

US 2014/0179680 A1    Jun. 26, 2014

Related U.S. Application Data

(60) Provisional application No. 61/740,232, filed on Dec. 20, 2012, provisional application No. 61/777,472, filed on Mar. 12, 2013.

(51) Int. Cl.
   *A61K 31/553* (2006.01)
   *C07D 471/04* (2006.01)
   *C07D 471/08* (2006.01)
   *C07D 498/04* (2006.01)

(52) U.S. Cl.
   CPC .......... *C07D 471/04* (2013.01); *C07D 471/08* (2013.01); *C07D 498/04* (2013.01)
   USPC .................................. 514/211.15

(58) Field of Classification Search
   CPC .............. A61K 31/4355; A61K 31/437; C07D 471/00; C07D 471/04
   USPC .................................. 514/211.15
   See application file for complete search history.

(56) References Cited

U.S. PATENT DOCUMENTS

| | | | |
|---|---|---|---|
| 3,919,193 A | 11/1975 | Mian et al. | |
| 4,315,000 A | 2/1982 | Cook | |
| 4,654,350 A | 3/1987 | Irmscher et al. | |
| 6,403,584 B1 | 6/2002 | de Laszlo et al. | |
| 6,645,987 B2 | 11/2003 | Chackalamannil et al. | |
| 7,060,713 B2 | 6/2006 | Kim et al. | |
| 7,115,598 B2 | 10/2006 | Lu et al. | |
| 7,495,007 B2 | 2/2009 | Chen et al. | |
| 7,576,082 B2 | 8/2009 | Luk et al. | |
| 7,807,672 B2 | 10/2010 | Deng et al. | |
| 7,851,626 B2 | 12/2010 | Ding et al. | |
| 7,884,107 B2 | 2/2011 | Ma et al. | |
| 8,017,607 B2 | 9/2011 | Bartkovitz et al. | |
| 8,088,815 B2 | 1/2012 | Bartkovitz et al. | |
| 8,629,133 B2 | 1/2014 | Sugimoto et al. | |
| 2004/0116328 A1 | 6/2004 | Yoshikawa | |
| 2004/0197893 A1 | 10/2004 | Schubert et al. | |
| 2004/0259867 A1 | 12/2004 | Fotouhi | |
| 2004/0259884 A1 | 12/2004 | Haley et al. | |
| 2005/0037383 A1 | 2/2005 | Taremi et al. | |
| 2005/0282803 A1 | 12/2005 | Haley et al. | |
| 2007/0167437 A1 | 7/2007 | Fotouhi et al. | |
| 2007/0213341 A1 | 9/2007 | Chen et al. | |
| 2008/0004286 A1 | 1/2008 | Wang et al. | |
| 2008/0004287 A1 | 1/2008 | Ma et al. | |
| 2008/0009486 A1 | 1/2008 | Chen et al. | |
| 2008/0039409 A1 | 2/2008 | Nakajima et al. | |
| 2008/0255119 A1 | 10/2008 | Dominique et al. | |
| 2008/0262200 A1 | 10/2008 | Nash | |
| 2009/0068144 A1 | 3/2009 | Weber et al. | |
| 2009/0312310 A1 | 12/2009 | Kawato et al. | |
| 2010/0216770 A1 | 8/2010 | Storck et al. | |
| 2010/0317661 A1 | 12/2010 | Wang et al. | |

(Continued)

FOREIGN PATENT DOCUMENTS

DE          2529533          1/1977
DE       102005012681       3/2005

(Continued)

OTHER PUBLICATIONS

3H-Imidazo[4,5-c]pyridine-4,6 (H, 7H)—dione, 7-amino-3-[2-(dimethylamino)ethyl]-4H-Imidazolo[4,5-c]pyridine-4,6 (5H)-dione,7-amino-3-[2-(dimethylamino)ethl]-3,7-dihydro-(9CI), CAS AN 497141-21-6, Mar. 7, 2003, AN 497141-21-6, XP002720119, Chemical Abstract Service.
Bande et al., A Convenient Route for the Synthesis of 3-Deazaspongosine, European Journal of Organic Chemistry, Nov. 22, 2013, 231-236, 2014-1.
Barak, mdm2 expression is induced by wild type p53 activity, The EMBO Journal, 1993, 461-468, 12-2.
Blaydes, Tolerance of high leels of wild-type p53 in transformed epithelial cells dependent on auto-regulation by mdm-2, Oncogene, 1997, 1859-1868, 14.
Bottger, Identification of novel mdm2 binding peptides by phage display, Oncogene, 1996, 2141-2147, 13.

(Continued)

*Primary Examiner* — Wu-Cheng Winston Shen
*Assistant Examiner* — Christopher R Stone
(74) *Attorney, Agent, or Firm* — Li Su; Laura M. Ginkel

(57) ABSTRACT

The present invention provides substituted imidazopyridines as described herein or a pharmaceutically acceptable salt or solvate thereof. The representative compounds are useful as inhibitors of the HDM2 protein. Also disclosed are pharmaceutical compositions comprising the above compounds and potential methods of treating cancer using the same.

30 Claims, No Drawings

(56) References Cited

U.S. PATENT DOCUMENTS

| | | |
|---|---|---|
| 2011/0112052 A1 | 5/2011 | Wang et al. |
| 2011/0130398 A1 | 6/2011 | Bartkovitz et al. |
| 2011/0201635 A1 | 8/2011 | Liu et al. |
| 2011/0269809 A1 | 11/2011 | Chu et al. |
| 2011/0313167 A1 | 12/2011 | Doemling |
| 2011/0319378 A1 | 12/2011 | Bartberger et al. |
| 2012/0010235 A1 | 1/2012 | Chu et al. |
| 2012/0149660 A1 | 6/2012 | Liu et al. |
| 2012/0264738 A1 | 10/2012 | Sugimoto et al. |

FOREIGN PATENT DOCUMENTS

| | | |
|---|---|---|
| EP | 155911 | 3/1985 |
| EP | 0947494 | 10/1999 |
| EP | 1463501 | 9/2002 |
| EP | 1690863 | 8/2006 |
| EP | 2203447 | 9/2008 |
| JP | 9249566 | 9/1997 |
| JP | 2004115416 | 4/2004 |
| WO | WO0015657 | 3/2000 |
| WO | WO03041715 | 5/2003 |
| WO | W003051359 | 6/2003 |
| WO | WO03051360 | 6/2003 |
| WO | WO03066586 | 8/2003 |
| WO | WO2004005278 | 1/2004 |
| WO | WO2004080460 | 9/2004 |
| WO | WO2005110996 | 11/2005 |
| WO | WO2005115399 | 12/2005 |
| WO | WO2006024837 | 3/2006 |
| WO | WO2006032631 | 3/2006 |
| WO | WO2006069287 | 6/2006 |
| WO | WO2006091646 | 8/2006 |
| WO | WO2006097261 | 9/2006 |
| WO | WO2006097323 | 9/2006 |
| WO | WO2006136606 | 12/2006 |
| WO | WO2007047793 | 4/2007 |
| WO | WO2007063013 | 6/2007 |
| WO | WO2007070398 A1 | 6/2007 |
| WO | WO2007104714 | 9/2007 |
| WO | WO2007107543 | 9/2007 |
| WO | WO2007107545 | 9/2007 |
| WO | WO2008005268 | 1/2008 |
| WO | WO2008034039 | 3/2008 |
| WO | WO2008034736 | 3/2008 |
| WO | WO2008036168 | 3/2008 |
| WO | WO2008055812 | 5/2008 |
| WO | WO2008065068 | 6/2008 |
| WO | WO2008119741 | 10/2008 |
| WO | WO2008130614 | 10/2008 |
| WO | WO2008141917 | 11/2008 |
| WO | WO2008141975 | 11/2008 |
| WO | WO2009019274 | 2/2009 |
| WO | WO2009037308 | 3/2009 |
| WO | WO2009037343 | 3/2009 |
| WO | WO2009047161 | 4/2009 |
| WO | WO2009121914 | 10/2009 |
| WO | WO2009151069 | 12/2009 |
| WO | WO2010028862 | 3/2010 |
| WO | WO2011023677 | 3/2011 |
| WO | WO2011045257 | 4/2011 |
| WO | WO2011046771 A1 | 4/2011 |
| WO | WO2011076786 | 6/2011 |
| WO | WO2011098398 | 8/2011 |
| WO | WO2011134925 | 11/2011 |
| WO | WO2011153509 | 12/2011 |
| WO | WO2012007409 | 1/2012 |
| WO | WO2012022707 | 2/2012 |
| WO | WO2012034954 | 3/2012 |
| WO | WO2012038307 | 3/2012 |
| WO | WO2012045018 | 4/2012 |
| WO | WO2012065022 | 5/2012 |
| WO | WO2012076513 | 6/2012 |
| WO | WO2012080389 | 6/2012 |
| WO | WO2012083181 | 6/2012 |
| WO | WO2012121361 | 9/2012 |
| WO | WO2012175520 | 12/2012 |
| WO | WO2012176123 | 12/2012 |
| WO | WO2013049250 | 4/2013 |
| WO | WO2013080141 | 6/2013 |
| WO | WO2013111105 | 8/2013 |
| WO | WO2013135648 | 9/2013 |
| WO | WO2014038606 | 3/2014 |

OTHER PUBLICATIONS

Cannon, J.G., Analog Design, Burger's Medicinal Chemistry and Drug Discovery, Chapter Nineteen Fifth Ed., 1995, 783-802, 1, Wiley-Interscience.

Chene, Inhibiting the p53-MDM2 interaction: An important target for cancer therapy, Nature Reviews, 2003, 102-109, 3.

Chene, Inhibition of the p53-MDM2 interaction: Targeting a protein-protein Interface, Molecular Cancer Research, 2004, 20-28, 2.

Cook et al., Synthesis of 7- and 9-.beta.-D-ribofuranosides of 3-deaza-6-thioguanine and 3-deaza-2,6-diaminopurine by a novel rignt closure of 4(5)-cyano-5(4)-cyanomethylimidazole.beta.-D-ribofuranosides, The Journal of Organic Chemistry, Jan. 1, 1978, 289-293, 43-2.

Ding, Structure-Based Design of Potent Non-Peptide MDM2 Inhibitors, J. Am. Chem. Soc., 2005, 10130-10131, 127-29.

Ding, Structure-Based Design of Spiro-oxindoles as Potent, Specific Small-Molecule Inhibitors of the MDM2-p53 Interaction, Journal of Medicinal Chemistry, 2006, 3432-3435, 49-12.

Donehower, Mice deficient for p53 are developmentally normal but susceptible to spontaneous tumours, Nature, Mar. 19, 1992, 215-221, 356.

Duncan, Isolation and Structure Elucidation of chlorofusin, a Novel p53-MDM2 Antagonist from a Fusarium sp., J. Am. Chem. Soc., 2001, 554-560, 123-4.

English Translation of JP09249566, Takeda Chem Ind. Ltd.-Sep. 22, 1997.

Fotouhi, Small Molecule Inhibitors of p53/MDM2 Interaction, Current Topics in Medicinal Chemistry, 2005, 159-165, 5-2.

Freedman, Nuclear Export Is Required for Degradation of Endogenous p53 by MDM2 and Human Papillomavirus E6, Molecular and Cellular Biology, 1988, 7288-7293, 18-12.

Galatin, A Nonpeptidic Sulfonamide Inhibits the p53—mdm2 Interaction and Activates p53-Dependent Transcription in mdm2-Overexpressing Cells, J. Med. Chem., 2004, 4163-4165, 47-17.

Grasberger, Discovery and Cocrystal Structure of Benzodiazepinedione HDM2 Antagonists that Activate p53 in Cells, J. Med. Chem., 2005, 909-912, 48-4.

Gupta et al., A new synthesis of certain 7-(beta.-D-ribofuranosyl) and 7-(2-deoxy-.beta.-D-ribofuranosyl) derivatives of 3-deazaguanine via the sodium salt glycosylation procedure, Nucleic Acids Research, Jul. 25, 1985, 5341-5352, 13-14, Oxford University Press, GB.

Hainaut, Database of p53 gene somatic mutations in human tumors and cell lines: updated compilation and future prospects, Nucleic Acids Research, 1997, 151-157, 25-1.

Hall, Genetic Alterations of Cyclins, Cyclin-Dependent Kinases, and Cdk Inhibitors in Human Cancer, Advances in Cancer Research, 1996, 67-108, 68.

Honda, Activity of MDM2, a ubiquitin ligase, toward p53 or itself is dependent on the Ring finger domain of the ligase, Oncogene, 2000, 1473-1476, 19.

Honda, Oncoprotein MDM2 is a ubiquitin ligase E3 for tumor suppressor p53, FEBS Letters, 1997, 25-27, 420.

Jordan, VC, Tamoxifen: A Most Unlikely Pioneering Medicine, Nature Reviews: Drug Discovery, 2003, 205-213, 2.

Ko, p53: puzzle and paradigm, Genes & Development, 1996, 1054-1072, 10.

Kojima, MDM antagonists induce p53-dependent apoptosis in AML: implications for leukemia therapy, Blood, Nov. 1, 2005, 3150-3159, 106-9.

Kussie, Paul H., Structure of the MDM2 Oncoprotein Bound to the p53 Tumor Suppressor Transactivation Domain, Science, 1996, 948-953, 274, WO.

Levine, p53, the Cellular Gatekeeper for Growth and Division, Cell, Feb. 7, 1997, 323-331, 88.

(56) References Cited

OTHER PUBLICATIONS

Lu, Discovery of a Nanomolar Inhibitor of the Human Murine Double Minute 2 (MDM2)—p53 Interaction through an Integrated, Virtual Database Screening Strategy, Journal of Medicinal Chemistry, 2006, 3759-3762, 49-13.

Lutz Weber, Patented inhibitors of p53-Mdm2 interaction (2006-2008), Expert Opin. Ther. Patents, 2010, 179-191, 20-2.

May, Twenty years of p53 research: structural and functional aspects of the p53 protein, Oncogene, 1999, 7621-7636, 18.

McGee et al., Synthesis and antiviral activity of the 3-deaza analog of 9-[(1,3-dihydroxy-2-propoxy)methyl]guanine, Nucleosides & Nucleotides, Jan. 1, 1990, 815-826, 9-6, Marcel Dekker Inc.

Mian et al., Syntheses and Antitumor Activity of 2-Deoxyribofuranosides of 3-Deazaguanine, Journal of Medicinal Chemistry, Feb. 1, 1983, 286-291, 26-2.

Momand, MDM2—master regulator of the p53 tumor suppressor protein, Gene, 2000, 15-29, 242.

Momand, The mdm-2 Oncogene Product Forms a Complex with the p53 Protein and Inhibits p53—Mediated Transactivation, Cell, Jun. 26, 1992, 1237-1245, 69.

NPL-EnglAbstract-DE102005012681, Gleich Anmelder, Mar. 18, 2005.

NPL-EnglAbstract-DE2529533, Inc Pharmaceuticals, Jan. 27, 1997.

NPL-EnglAbstract-EP155911, Ciba Beigy AG, Mar. 13, 1985.

NPL-EnglAbstract-JP2004115416, Japan Engergy Corp., Apr. 15, 2004.

NPL-EnglAbstract-WO2009-151069, Daiichi Sankyo Company, Limited, Dec. 17, 2009.

NPL-EnglAbstract-WO2014038606, Daiichi Sankyo Company Limited, Mar. 13, 2014.

Oliner, Oncoprotein MDM2 conceals the activation domain of tumour suppressor p53, Letters to Nature, Apr. 29, 193, 857-860, 362.

Oren, Decision making by p53: life, death and cancer, Cell Death and Differentiation, 2003, 431-442, 10.

Poonian et al, Synthesis of Arabinofuranosyl Derivatives of 3-Deazaguanine, Journal of Medicinal Chemistry, 1979, 958-962, 22-8.

Roth, Nucleo-cytoplasmic shuttling of the hdm2 oncoprotein regulates the levels of the p53 protein via a pathway used by the human immunodeficiency virus rev protein, The EMBO Journal, 1998, 554-564, 17-2.

Seela et al., 3-Deazaguanine N7-and N9-(2'-Deoxy-B-D-ribofuranosides):Building Blocks for Solid-Phase Synthesis and Incorporation into Oligodeoxyribonucleotides, Helvetica Chimica Acta, Dec. 11, 1991, 1790-1800, 74-8.

Sherr, The Pezcoller Lecture: Cancer Cell Cycles Revisited, Cancer Research, Jul. 15, 2000, 3689-3695, 60.

Stack et al., Synthesis of a New Fluorescent Probe Specific for Catechols, Organic Letters, Dec. 1, 2002, 4487-4490, 4-25.

Stoll, Chalcone Derivatives Antagonize Interactions between the Human Oncoprotein MDM2 and p53, Biochemistry, 2001, 336-344, 40-2.

Tao, Nucleocytoplasmic shuttling of oncoprotein Hdm2 is required for Hdm2-mediated degradation of p53, Proc. Natl. Acad. Sci., USA, Mar. 1999, 3077-3080, 96.

Vassilev, In Vivo Activation of the p53 Pathway by Small-Molecule antagonists of MDM2, Science, Feb. 6, 2004, 844-848, 303.

Vassilev, p53 Activation by Small Molecules: Application in Oncology, Journal of Medicinal Chemistry, Jul. 14, 2005, 4491-4499, 48-14.

Vorbrueggen et al., Synthesis of Nucleosides, CAPLUS, 2008, AN 2008-1383646, XP002720120, John C. Wiley & Sons, Inc.

Wu, The p53-mdm-2 autoregulatory feedback loop, Genes & Development, 1993, 1126-1132, 7.

Xu et al., 7-Alkyl-N-substituted-3-deazaguanines. Synthesis, DNA polymerase III inhibition and antibacterial activity, Bioorganic & Medicinal Chemistry Letters, May 23, 2011, 4197-4202, 21-14, Pergamon, Amsterdam, NL.

Yang, Small molecule inhibitors of HDM2 ubiquitin ligase activity stabilize and activate p53 in cells, Cancer Cell, Jun. 2005, 547-559, 7.

Zheleva, The p53-Mdm2 Pathway: Targets for the Development of New Anticancer Therapeutics, Mini Reviews in Medicinal Chem, 2003, 257-270, 3-3.

SEQUENCE LISTING

<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: labeled peptide
<220> FEATURE:
<221> NAME/KEY: MOD_RES
<222> LOCATION: (3)..(3)
<223> OTHER INFORMATION: Dpr
<220> FEATURE:
<221> NAME/KEY: MOD_RES
<222> LOCATION: (4)..(4)
<223> OTHER INFORMATION: 1-AMINO-CYCLOHEXANE CARBOXYLIC ACID
<220> FEATURE:
<221> NAME/KEY: MOD_RES
<222> LOCATION: (5)..(5)
<223> OTHER INFORMATION: 6-BR

<400> SEQUENCE: 1

Phe Arg Xaa Xaa Trp Glu Glu Leu
1               5

SUBSTITUTED IMIDAZOPYRIDINES AS HDM2 INHIBITORS

FIELD OF THE INVENTION

The present invention relates to novel compounds useful as Human Double Minute 2 ("HDM2") protein inhibitors, regulators or modulators, pharmaceutical compositions containing the compounds and potential methods of treatment using the compounds and compositions to potentially treat diseases such as, for example, cancer, diseases involving abnormal cell proliferation, and diseases caused by inadequate p53 levels.

BACKGROUND OF THE INVENTION

The tumor suppressor protein p53 plays a central role in maintaining the integrity of the genome in a cell by regulating the expression of a diverse array of genes responsible for DNA repair, cell cycle and growth arrest, and apoptosis [May et al., Oncogene 18 (53) (1999) p. 7621-7636; Oren, Cell Death Differ. 10 (4) (2003) p. 431-442, Hall and Peters, Adv. Cancer Res., 68: (1996) p. 67-108; Hainaut et al., Nucleic Acid Res., 25: (1997) p. 151-157; Sherr, Cancer Res., 60: (2000) p. 3689-95]. In response to oncogenic stress signals, the cell triggers the p53 transcription factor to activate genes implicated in the regulation cell cycle, which thereby initiates either apoptosis or cell cycle arrest. Apoptosis facilitates the elimination of damaged cells from the organism, while cell cycle arrest enables damaged cells to repair genetic damage [reviewed in Ko et al., Genes & Devel. 10: (1996) p. 1054-1072; Levine, Cell 88: (1997) p. 323-331]. The loss of the safeguard functions of p53 predisposes damaged cells to progress to a cancerous state. Inactivating p53 in mice consistently leads to an unusually high rate of tumors [Donehower et al., Nature, 356: (1992) p. 215-221].

The p53 transcription factor promotes the expression of a number of cell cycle regulatory genes, including its own negative regulator, the gene encoding the Mouse Double Minute 2 (MDM2) protein [Chene, Nature Reviews Cancer 3: (2003) p. 102-109; Momand, Gene 242 (1-2): (2000) p. 15-29; Zheleva et al. Mini. Rev. Med. Chem. 3 (3): (2003) p. 257-270]. The MDM2 protein (designated HDM2 in humans) acts to down-regulate p53 activity in an auto-regulatory manner [Wu et al, Genes Dev., 7: (1993) p. 1126-1132; Bairak et al., EMBO J, 12: (1993) p. 461-468]. In the absence of oncogenic stress signals, i.e., under normal cellular conditions, the MDM2 protein serves to maintain p53 activity at low levels [Wu et al, Genes Dev., 7: (1993) p. 1126-1132; Barak et al., EMBO J, 12: (1993) p. 461-468]. However, in response to cellular DNA damage or under cellular stress, p53 activity increases helping to prevent the propagation of permanently damaged clones of cells by induction of cell cycle and growth arrest or apoptosis.

The regulation of p53 function relies on an appropriate balance between the two components of this p53-MDM2 auto-regulatory system. Indeed, this balance appears to be essential for cell survival. There are at least three ways that MDM2 acts to down-regulate p53 activity. First, MDM2 can bind to the N-terminal transcriptional activation domain of p53 to block expression of p53-responsive genes [Kussie et al., Science, 274: (1996) p. 948-953; Oliner et al., Nature, 362: (1993) p. 857-860; Momand et al, Cell, 69: (1992) p. 1237-1245]. Second, MDM2 shuttles p53 from the nucleus to the cytoplasm to facilitate the proteolytic degradation of p53 [Roth et al, EMBO J, 17: (1998) p. 554-564; Freedman et al., Mol Cell Biol, 18: (1998) p. 7288-7293; Tao and Levine, Proc. Natl. Acad. Sci. 96: (1999) p. 3077-3080]. Finally, MDM2 possesses an intrinsic E3 ligase activity for conjugating ubiquitin to p53 for degradation within the ubiquitin-dependent 26S proteosome pathway [Honda et al., FEBS Lett, 420: (1997) p. 25-27; Yasuda, Oncogene 19: (2000) p. 1473-1476]. Thus, MDM2 impedes the ability of the p53 transcription factor to promote the expression of its target genes by binding p53 in the nucleus. Attenuating the p53-MDM2 auto-regulatory system can have a critical effect on cell homeostasis. Consistently, a correlation between the overexpression of MDM2 and tumor formation has been reported [Chene, Nature 3: (2003) p. 102-109]. Functional inactivation of wild type p53 is found in many types of human tumors. Restoring the function of p53 in tumor cells by anti-MDM2 therapy would result in slowing the tumor proliferation and instead stimulate apoptosis. Not surprisingly then, there is currently a substantial effort being made to identify new anticancer agents that hinder the ability of HDM2 to interact with p53 [Chene, Nature 3: (2003) p. 102-109]. Antibodies, peptides, and antisense oligonucleotides have been demonstrated to destroy the p53-MDM2 interaction, which would release p53 from the negative control of MDM2, leading to activation of the p53 pathway allowing the normal signals of growth arrest and/or apoptosis to function, which offers a potential therapeutic approach to treating cancer and other diseases characterized by abnormal cell proliferation. [See, e.g., Blaydes et al., Oncogene 14: (1997) p. 1859-1868; Bottger et al., Oncogene 13 (10): (1996) p. 2141-2147].

Small molecules, said to antagonize the p53-MDM2 interaction, have been described. WO 00/15657 (Zeneca Limited) describes piperizine-4-phenyl derivatives as inhibitors of the interaction between MDM2 and p53. Grasberger et al. (J. Med. Chem., 48 (2005) p. 909-912) (Johnson & Johnson Pharmaceutical Research & Development L.L. C.) describes discovery and co-crystal structure of benzodiazepinedione as HDM2 antagonists that activate p53 in cells. Galatin et al. (J. Med. Chem. 47 (2004) p. 4163-4165) describes a nonpeptidic sulfonamide inhibitor of the p53-MDM2 interaction and activator of p53 dependent transcription in MDM2-overexpressing cells.

U.S. Pub. No. 2004/0259867 A1 and 2004/0259884 A1 describes Cis-imidazoles (Hoffmann La Roche Inc.) and WO2005/110996A1 and WO 03/051359 describes Cis-Imidazolines (Hoffmann La Roche Inc.) as compounds that inhibit the interaction of MDM2 with p53-like peptides resulting in antiproliferation. WO 2004/080460 A1 describes substituted piperidine compounds as MDM2-p53 inhibitors for treating cancer (Hoffmann La Roche Inc.). EP 0947494 A1 describes phenoxy acetic acid derivatives and phenoxy methyltetrazole that act as antagonists of MDM2 and interfere with the protein-protein interaction between MDM2 and p53, which results in anti-tumor properties (Hoffmann La Roche Inc.). Duncan et al., J. Am. Chem. Soc. 123 (4): (2001) p. 554-560 describes a p-53-MDM2 antagonist, chlorofusin, from a *Fusarium* Sp. Stoll et al., Biochemistry 40 (2) (2001) p. 336-344 describes chalcone derivatives that antagonize interactions between the human oncoprotein MDM2 and p53.

There is a need for effective inhibitors of the HDM2 or MDM2 protein in order to treat or prevent cancer, other disease states associated with cell proliferation, diseases associated with HDM2, or diseases caused by inadequate p53 activity. The present application discloses compounds that have potency in inhibiting or antagonizing the HDM2-p53 and MDM2-p53 interaction and/or activating p53 proteins in cells.

In its many embodiments, the present invention provides novel compounds having HDM2 or MDM2 antagonist activity, methods of preparing such compounds, pharmaceutical compositions comprising one or more of such compounds, methods of preparing pharmaceutical formulations comprising one or more of such compounds, potential methods of treatment or prevention of one or more diseases associated with HDM2, MDM2, p53, or p53 peptides by administering such compounds or pharmaceutical compositions.

SUMMARY OF THE INVENTION

In its many embodiments, the present invention provides a novel class of substituted imidazopyridine compounds, pharmaceutical compositions comprising one or more said compounds, and potential methods for using said compounds for treating or preventing a disease associated with the HDM2 protein.

Accordingly, in one aspect the present invention provides a compound of Formula I:

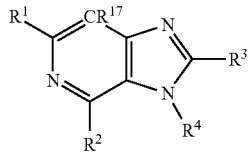

I

DETAILED DESCRIPTION OF THE INVENTION

In one embodiment, the present invention provides compounds illustrated as Formula I, as described above, or pharmaceutically acceptable salts or solvates thereof. Accordingly, in one aspect the present invention provides a compound of Formula I:

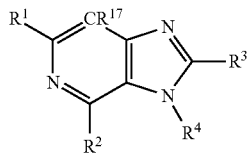

I

Wherein
$R^1$ is selected from the group consisting of H, $C_1$-$C_6$alkyl, —$(CR^a_2)_z COOR^{11}$, -T-NHR$^5$, —$(CR^a_2)_z NR^5 SO_2 R^6$, —$(CR^a_2)_z SO_2 NR^5 R^6$, —$(CR^a_2)_z C(O)NR^c SO_2 N(R^c)_2$, —$(CR^a_2)_z C(O)NR^c SO_2 R^c$, —$(CR^a_2)_z C(O)R^5$, —$(CR^a_2)_z CONR^5 R^6$, —$(CR^a_2)_z CONR^5 OR^6$, —$(CR^a_2)_z NR^5 C(O)R^6$, —$(CR^a_2)_n OR^5$, —$(CR^a_2)_z S(O)R^c$, —$(CR^a_2)_z S(O)_2 R^c$, and nitrogen containing 5 or 6-membered heterocyclic, heteroaryl or heterocyclenyl ring, wherein the alkyl and 5 or 6-membered ring can be optionally substituted with OR$^c$, SR$^c$, NH$_2$, nitro, CN, amide, COOR$^{11}$, $C_1$-$C_6$alkyl, $C_1$-$C_6$haloalkyl, $C_1$-$C_6$haloalkoxy, $C_1$-$C_6$hydroxyalkyl, $C_2$-$C_6$alkenyl, $C_1$-$C_6$alkyl-C(=O)O—, $C_1$-$C_6$alkyl-C(=O)—, $C_2$-$C_6$alkynyl, halo group, hydroxyalkoxy, —SO$_2$NR$^c$R$^c$, —NR$^c$SO$_2$R$^c$, $C_1$-$C_6$alkylsulfonyl, $C_1$-$C_6$alkylamino or di($C_1$-$C_6$)alkylamino;
$R^2$ is selected from the group consisting of aryl, heteroaryl, $C_3$-$C_8$cycloalkyl, —W—$(CR^a R^g)_t R^7$, and heterocyclic, wherein W is NR$^c$ or O, wherein the aryl, heteroaryl, or heterocyclic is optionally substituted with $R^{12}$ selected from the group consisting of halo, CN, halo$C_1$-$C_6$alkyl, $C_1$-$C_6$alkyl, —$(CR^a_2)_z OR^c$, —$(CR^a_2)_z NHR^8$, —$(CR^a_2)_z C(O)NR^c R^c$, —$(CR^a_2)_z COOR^{10}$, —$(CR^a_2)_z aryl$, —$(CR^a_2)_z heteroaryl$, —$(CR^a_2)_z heterocyclic$, —$(CR^a_2)_z C_3$-$C_8$cycloalkyl, —$(CR^a_2)_z cyclenyl$, and —$(CR^a_2)_z heterocyclenyl$, wherein the alkyl, aryl, heteroaryl, heterocyclic, cycloalkyl, cyclenyl and heterocyclenyl of $R^{12}$ can be optionally substituted with OH, NH$_2$, nitro, CN, CON(R$^c$)$_2$, —$(CR^a_2)_z COOR^{10}$, $C_1$-$C_6$alkoxy, $C_1$-$C_6$alkyl, $C_1$-$C_6$haloalkyl, $C_1$-$C_6$haloalkoxy, $C_1$-$C_6$hydroxyalkyl, $C_2$-$C_6$alkenyl, $C_1$-$C_6$alkyl-C(=O)O—, $C_1$-$C_6$alkyl-C(=O)—, $C_2$-$C_6$alkynyl, halo group, hydroxyalkoxy, —SO$_2$NR$^c$R$^c$, —NR$^c$SO$_2$R$^c$, $C_1$-$C_6$alkylsulfonyl, $C_1$-$C_6$alkylamino or di($C_1$-$C_6$)alkylamino;
$R^3$ is selected from the group consisting of H, —$(CR^a_2)_q NR^c R^8$, —$(CR^a_2)_q OR^8$, —$(CR^a_2)_q SR^8$, —$(CR^a_2)_q C(O)R^8$, —$(CR^a_2)_q S(O)R^8$, —$(CR^a_2)_q S(O)_2 R^8$, —$(CR^a_2)_q CONR^c R^8$, —$(CR^a_2)_q NR^c C(O)R^8$, -T-alkyl, $C_2$-$C_6$alkenyl, -T-aryl, -T-heteroaryl, -T-heterocyclic, -T-$C_3$-$C_7$cycloalkyl, -T-cyclenyl, and -T-heterocyclenyl,
wherein the alkyl, alkenyl, aryl, heteroaryl, heterocyclic, cycloalkyl, cyclenyl and heterocyclenyl can be optionally substituted with halo, SR$^c$, OR$^c$, halo$C_1$-$C_6$alkyl, halo$C_1$-$C_6$alkoxy, —$(CR^a_2)_z CN$, $C_1$-$C_6$alkyl, $C_2$-$C_6$alkenyl, $C_2$-$C_6$alkynyl, —$(CR^a_2)_z C(O)OR^{11}$, —$(CR^a_2)_z C(O)R^8$, —$(CR^a_2)_z OR^8$, —$(CR^a_2)_z NR^c R^8$, —$(CR^a_2)_z S(O)_2 R^8$, —$(CR^a_2)_z C(O)NR^c R^8$, —$(CR^a_2)_z aryl$, —$(CR^a_2)_z heteroaryl$, —$(CR^a_2)_z$, $C_3$-$C_8$cycloalkyl, —$(CR^a_2)_z heterocyclic$, —$(CR^a_2)_z heterocyclenyl$, —$(CR^a_2)_z cyclenyl$, —$(CR^a_2)_z SO_2 NR^c R^8$, or —$(CR^a_2)_z O(CR^a_2)_z Y(CR^a_2)_v U$,
said alkyl, alkenyl, alkynyl, aryl, heteroaryl, cycloalkyl, heterocyclic, heterocyclenyl and cyclenyl can further be substituted with OH, SH, NH$_2$, nitro, CN, CON(R$^c$)$_2$, COOR$^{10}$, $C_1$-$C_6$alkoxy, $C_1$-$C_6$alkyl, $C_2$-$C_6$alkenyl, $C_1$-$C_6$haloalkyl, $C_1$-$C_6$haloalkoxy, $C_1$-$C_6$hydroxyalkyl, $C_1$-$C_6$alkyl-C(=O)O—, $C_1$-$C_6$alkyl-C(=O)—, $C_2$-$C_6$alkynyl, halo group, hydroxyalkoxy, —SO$_2$NR$^c$R$^c$, —SO$_2$R$^c$, —NR$^c$SO$_2$R$^c$, $C_1$-$C_6$alkylsulfonyl, $C_1$-$C_6$alkylamino or di($C_1$-$C_6$)alkylamino;
$R^4$ is selected from the group consisting of $C_1$-$C_6$alkyl, —$(CR^a_2)_m aryl$, —$(CR^a_2)_m heteroaryl$, —$(CR^a_2)_m heterocyclic$, —$(CR^a_2)_m C_3$-$C_8$cycloalkyl, —$(CR^a_2)_m cyclenyl$, and —$(CR^a_2)_m heterocyclenyl$, wherein the alkyl, aryl, heteroaryl, heterocyclic, cycloalkyl, cyclenyl, and heterocyclenyl can be optionally substituted with OH, SH, NH$_2$, nitro, CN, CON(R$^c$)$_2$, COOR$^{11}$, $C_1$-$C_6$alkoxy, $C_1$-$C_6$alkyl, $C_3$-$C_6$cycloalkyl, halo$C_2$-$C_6$alkenyl, $C_2$-$C_6$alkenyl, $C_2$-$C_6$alkenoxy, $C_1$-$C_6$haloalkyl, $C_1$-$C_6$haloalkoxy, $C_1$-$C_6$hydroxyalkyl, $C_1$-$C_6$alkyl-C(=O)O—, $C_1$-$C_6$alkyl-C(=O)—, $C_2$-$C_6$alkynyl, halo group, hydroxyalkoxy, —SO$_2$NR$^c$R$^c$, —NR$^c$SO$_2$R$^c$, $C_1$-$C_6$alkylsulfonyl, $C_1$-$C_6$alkylamino or di($C_1$-$C_6$)alkylamino;
$R^5$ is independently selected from the group consisting of H, $C_1$-$C_6$alkyl, —$C_0$-$C_6$alkyl-$C_3$-$C_8$cycloalkyl, —$C_0$-$C_6$alkyl-heteroaryl, —$C_0$-$C_6$alkyl-aryl, and —$C_0$-$C_6$alkylheterocyclic, wherein the alkyl, cycloalkyl, heteroaryl, aryl, and heterocyclic can be optionally substituted with $C_2$-$C_3$alkenyl, $C_3$-$C_6$cycloalkyl, $C_1$-$C_3$alkoxy, OH, halo, NH$_2$, $C_1$-$C_3$alkylamino, $C_1$-$C_3$dialkylamino or COOR$^{11}$;
$R^6$ is independently selected from the group consisting of H, $C_1$-$C_6$alkyl, —$C_0$-$C_6$alkyl-$C_3$-$C_8$cycloalkyl, —$C_0$-$C_6$alkyl-heteroaryl, —$C_0$-$C_6$alkyl-aryl, and —$C_0$-$C_6$alkylheterocyclic, wherein the alkyl, cycloalkyl, heteroaryl, aryl, and heterocyclic can be optionally substituted with $C_2$-$C_3$alkenyl, $C_3$-$C_6$cycloalkyl, $C_1$-$C_3$alkoxy, OH, halo, NH$_2$, $C_1$-$C_3$alkylamino, $C_1$-$C_3$dialkylamino or COOR$^{11}$;
$R^7$ is selected from the group consisting of H, $C_1$-$C_6$alkyl, $C_2$-$C_6$alkenyl, $C_3$-$C_8$cycloalkyl, aryl, heteroaryl, heterocyclic, wherein the alkyl, alkenyl, cycloalkyl, aryl, heteroaryl or heterocyclic can be optionally substituted with halo, nitro, CN, $C_1$-$C_6$haloalkyl, $C_1$-$C_6$haloalkoxy, $C_2$-$C_6$alkenyl, $C_2$-$C_6$alkynyl, $C_1$-$C_6$alkyl, —$C_0$-$C_6$alkyl-$C_3$-$C_8$cycloalkyl, —$C_0$-$C_6$alkyl-heteroaryl, —$C_0$-$C_6$alkyl-aryl, —$C_0$-$C_6$alkylheterocyclic, —$C_0$-$C_6$alkylheterocyclenyl, —$C_0$-$C_6$alkylcyclenyl, —$(CR^a_2)_z NR^6R^6$, —$(CR^a_2)_z NR^6SO_2R^6$, —$(CR^a_2)_z SO_2NR^6R^6$, —$(CR^a_2)_z C(O)R^6$, —$(CR^a_2)_z C(O)OR^{10}$, —$(CR^a_2)_z CONR^6R^6$, —$(CR^a_2)_z CONR^6OR^6$, —$(CR^a_2)_z NR^6C(O)R^6$, —$(CR^a_2)_z OR^6$, —$(CR^a_2)_z S(O)R^c$, and —$(CR^a_2)_z S(O)_2R^c$;

$R^8$ is independently selected from the group consisting of H, —$(CR^a_2)_s$-heteroaryl, —$(CR^a_2)_s$-aryl, —$(CR^a_2)_s$-heterocyclic, —$(CR^a_2)_s$-heterocyclenyl, —$(CR^a_2)_s$-cyclenyl, —$(CR^a_2)_s C_3$-$C_7$cycloalkyl, and $C_1$-$C_6$alkyl, wherein the heteroaryl, aryl, heterocyclic, heterocyclenyl, cyclenyl, cycloalkyl, and alkyl can be optionally substituted with OH, $NH_2$, nitro, CN, $CON(R^c)_2$, $COOR^{11}$, $C_1$-$C_6$alkoxy, $C_1$-$C_6$alkyl, $C_2$-$C_6$alkenyl, heterocyclic, $C_1$-$C_6$haloalkyl, $C_1$-$C_6$haloalkoxy, $C_1$-$C_6$hydroxyalkyl, $C_1$-$C_6$alkyl—C(=O)O—, $C_1$-$C_6$alkyl-C(=O)—, $C_2$-$C_6$alkynyl, halo group, hydroxyalkoxy, —$SO_2NR^cR^c$, —$NR^cSO_2R^c$, $C_1$-$C_6$alkylsulfonyl, $C_1$-$C_6$alkylamino or di($C_1$-$C_6$)alkylamino;

$R^g$ is independently selected from the group consisting of H, $C_1$-$C_6$alkyl, $C_1$-$C_6$haloalkyl, $C_3$-$C_8$cycloalkyl, aryl, heteroaryl, and heterocyclic, wherein the alkyl, cycloalkyl, aryl, heteroaryl, and heterocyclic can be optionally substituted with —$C_0$-$C_6$alkylOR$^c$, —$C_0$-$C_6$alkylN(R$^c$)$_2$, $COOR^{10}$, nitro, CN, $C_1$-$C_6$alkyl, $C_1$-$C_6$haloalkyl, $C_1$-$C_6$haloalkoxy, $C_1$-$C_6$hydroxyalkyl, $C_2$-$C_6$alkenyl, $C_1$-$C_6$alkyl-C(=O)O—, $C_1$-$C_6$alkyl-C(=O)—, $C_2$-$C_6$alkynyl, halo group, hydroxyalkoxy, —$SO_2NR^cR^c$, —$NR^cSO_2R^c$, $C_1$-$C_6$alkylsulfonyl, heterocyclic, or C(O)NHR$^c$;

$R^{10}$ is independently selected from the group consisting of $C_1$-$C_6$alkyl, —$(CR^c_2)_z C_3$-$C_8$cycloalkyl, —$(CR^c_2)_z$-heteroaryl, —$(CR^c_2)_z$-aryl, and —$(CR^c_2)_z$-heterocyclic, wherein the heteroaryl, aryl, heterocyclic, cycloalkyl and alkyl can be optionally substituted with $C_1$-$C_6$alkyl, OH, halo, or halo$C_1$-$C_6$alkyl;

$R^{11}$ is independently selected from the group consisting of H, $C_1$-$C_6$alkyl, —$(CR^c_2)_z C_3$-$C_8$cycloalkyl, —$(CR^c_2)_z$-heteroaryl, —$(CR^c_2)_z$-aryl, and —$(CR^c_2)_z$-heterocyclic wherein the heteroaryl, aryl, heterocyclic, cycloalkyl and alkyl can be optionally substituted with $C_1$-$C_6$alkyl, $C_1$-$C_6$alkoxy, OH, halo, or halo$C_1$-$C_6$alkyl;

$R^{17}$ is independently selected from the group consisting of H, halo, COOH, oxadiazolone, $C_1$-$C_6$alkyl, $C_1$-$C_6$alkoxy, NR$^c$R$^c$, —$(CR^c_2)_z C_3$-$C_8$cycloalkyl, —$(CR^c_2)_z$heteroaryl, —$(CR^c_2)_z$aryl, and —$(CR^c_2)_z$heterocyclic wherein the heteroaryl, aryl, heterocyclic, cycloalkyl and alkyl can be optionally substituted with $C_1$-$C_6$alkyl, OH, halo, or halo$C_1$-$C_6$alkyl;

$R^a$ is independently H, $C(O)NR^c_2$, OR$^c$, $NH_2$, halo, $C_1$-$C_6$alkyl, or $C_2$-$C_6$alkenyl, said alkyl or alkenyl is optionally substituted with OH, $C_1$-$C_4$alkoxy, $NH_2$, halo, halo$C_1$-$C_4$alkyl, $C_3$-$C_6$cycloalkyl, or $C_2$-$C_4$alkenyl;

$R^c$ is independently H or $C_1$-$C_4$alkyl optionally substituted with $C_2$-$C_3$alkenyl, $C_3$-$C_6$cycloalkyl, $C_1$-$C_3$alkoxy, OH, halo, $NH_2$, $C_1$-$C_3$alkylamino, or $C_1$-$C_3$dialkylamino;

T is independently $C_2$-$C_3$alkenyl, —C(O)—, —$(CR^a_2)_q$—, —C(=$CH_2$)—, —$(CR^a_2)_q$—C(=$CH_2$)—, —C(=$CH_2$)—$(CR^a_2)_q$—, —C(=NH)—, —$(CR^a_2)_q$—C(=NH)—, or —C(=NH)—$(CR^a_2)_q$—;

Y is a bond, —C(O)NR$^c$—, —NR$^c$C(O)—, or —NR$^c$—;

U is H, $COOR^{11}$, OH, heteroaryl or heterocyclic;

n is independently 0, 1, 2 or 3;

m is independently 0, 1 or 2;

q is independently 0, 1, 2, or 3;

s is independently 0, 1 or 2;

t is independently 0, 1, or 2;

v is independently 1, 2, 3 or 4;

z is independently 0, 1, 2, 3 or 4;

or a pharmaceutically acceptable salt thereof.

The present invention also provides the following compounds under Formula I:

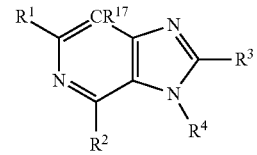

Wherein $R^1$ is selected from the group consisting of H, $C_1$-$C_6$alkyl, —$(CR^a_2)_z COOR^{11}$, -T-NHR$^5$, —$(CR^a_2)_z NR^5SO_2R^6$, —$(CR^a_2)_z SO_2NR^5R^6$, —$(CR^a_2)_z C(O)NR^cSO_2N(R^c)_2$, —$(CR^a_2)_z C(O)NR^cSO_2R^c$, —$(CR^a_2)_z C(O)R^5$, —$(CR^a_2)_z CONR^5R^6$, —$(CR^a_2)_z CONR^5OR^6$, —$(CR^a_2)_z NR^5C(O)R^6$, —$(CR^a_2)_n OR^5$, —$(CR^a_2)_z S(O)R^c$, —$(CR^a_2)_z S(O)_2R^c$, and nitrogen containing 5 or 6-membered heterocyclic, heteroaryl or heterocyclenyl ring, wherein the alkyl and 5 or 6-membered ring can be optionally substituted with OR$^c$, SR$^c$, $NH_2$, nitro, CN, amide, $COOR^{11}$, $C_1$-$C_6$alkyl, $C_1$-$C_6$haloalkyl, $C_1$-$C_6$haloalkoxy, $C_1$-$C_6$hydroxyalkyl, $C_2$-$C_6$alkenyl, $C_1$-$C_6$alkyl-C(=O)O—, $C_1$-$C_6$alkyl-C(=O)—, $C_2$-$C_6$alkynyl, halo group, hydroxyalkoxy, —$SO_2NR^cR^c$, —$NR^cSO_2R^c$, $C_1$-$C_6$alkylsulfonyl, $C_1$-$C_6$alkylamino or di($C_1$-$C_6$)alkylamino;

$R^2$ is selected from the group consisting of aryl, heteroaryl, —W—$(CR^aR^g)_t R^7$, and heterocyclic, wherein W is NR$^C$ or O, wherein the aryl, heteroaryl, or heterocyclic is optionally substituted with $R^{12}$ selected from the group consisting of halo, CN, halo$C_1$-$C_6$alkyl, $C_1$-$C_6$alkyl, —$(CR^a_2)_z OR^c$, —$(CR^a_2)_z NHR^8$, —$(CR^a_2)_z C(O)NR^cR^c$, —$(CR^a_2)_z$aryl, —$(CR^a_2)_z$heteroaryl, —$(CR^a_2)_z$heterocyclic, —$(CR^a_2)_z C_3$-$C_8$cycloalkyl, —$(CR^a_2)_z$cyclenyl, and —$(CR^a_2)_z$heterocyclenyl, wherein the alkyl, aryl, heteroaryl, heterocyclic, cycloalkyl, cyclenyl and heterocyclenyl of $R^{12}$ can be optionally substituted with OH, $NH_2$, nitro, CN, $CON(R^c)_2$, —$(CR^a_2)_z COOR^{10}$, $C_1$-$C_6$alkoxy, $C_r$ $C_6$alkyl, $C_1$-$C_6$haloalkyl, $C_1$-$C_6$haloalkoxy, $C_1$-$C_6$hydroxyalkyl, $C_2$-$C_6$alkenyl, $C_1$-$C_6$alkyl-C(=O)O—, $C_1$-$C_6$alkyl-C(=O)—, $C_2$-$C_6$alkynyl, halo group, hydroxyalkoxy, —$SO_2NR^cR^c$, —$NR^cSO_2R^c$, $C_1$-$C_6$alkylsulfonyl, $C_1$-$C_6$alkylamino or di($C_1$-$C_6$)alkylamino;

$R^3$ is selected from the group consisting of H, —$(CR^a_2)_q NR^cR^8$, —$(CR^a_2)_q OR^8$, —$(CR^a_2)_q SR^8$, —$(CR^a_2)_q C(O)R^8$, —$(CR^a_2)_q S(O)R^8$, —$(CR^a_2)_q S(O)_2R^8$, —$(CR^a_2)_q CONR^cR^8$, —$(CR^a_2)_q NR^cC(O)R^8$, -T-alkyl, $C_2$-$C_6$alkenyl, -T-aryl, -T-heteroaryl, -T-heterocyclic, -T-$C_3$-$C_7$cycloalkyl, -T-cyclenyl, and -T-heterocyclenyl, wherein the alkyl, alkenyl, aryl, heteroaryl, heterocyclic, cycloalkyl, cyclenyl and heterocyclenyl can be optionally substituted with halo, OR$^c$, halo$C_1$-$C_6$alkyl, halo$C_1$-$C_6$alkoxy, —$(CR^a_2)_z CN$, $C_1$-$C_6$alkyl, $C_2$-$C_6$alkenyl, $C_2$-$C_6$alkynyl, —$(CR^a_2)_z C(O)OR^{11}$, —$(CR^a_2)_z C(O)R^8$, —$(CR^a_2)_z OR^8$, —$(CR^a_2)_z NR^8$, —$(CR^a_2)_z S(O)_2R^8$, —$(CR^a_2)_z C(O)NR^8R^8$, —$(CR^a_2)_z$aryl, —$(CR^a_2)_z$heteroaryl, —$(CR^a_2)_z C_3$-$C_8$cycloalkyl, —$(CR^a_2)_z$heterocyclic, —$(CR^a_2)_z$heterocyclenyl, —$(CR^a_2)_z$cyclenyl, —$(CR^a_2)_z SO_2NR^cR^8$, or —$(CR^a_2)_z O(CR^a_2)_z Y(CR^a_2)_v U$, said alkyl, alkenyl, alkynyl, aryl, heteroaryl, cycloalkyl, heterocyclic, heterocyclenyl and cyclenyl can further be substituted with OH, $NH_2$, nitro, CN, $CON(R^c)_2$, $COOR^{10}$, $C_1$-$C_6$alkoxy, $C_1$-$C_6$alkyl, $C_2$-$C_6$alkenyl, $C_1$-$C_6$haloalkyl, $C_1$-$C_6$haloalkoxy, $C_1$-$C_6$hydroxyalkyl, $C_1$-$C_6$alkyl-C($=$O)O—, $C_1$-$C_6$alkyl-C($=$O)—, $C_2$-$C_6$alkynyl, halo group, hydroxyalkoxy, —$SO_2NR^cR^c$, —$NR^cSO_2R^c$, $C_1$-$C_6$alkylsulfonyl, $C_1$-$C_6$alkylamino or di($C_1$-$C_6$)alkylamino;

$R^4$ is selected from the group consisting of $C_1$-$C_6$alkyl, —$(CR^a_2)_m$aryl, —$(CR^a_2)_m$heteroaryl, —$(CR^a_2)_m$heterocyclic, —$(CR^a_2)_m C_3$-$C_8$cycloalkyl, —$(CR^a_2)_m$cyclenyl, and —$(CR^a_2)_m$heterocyclenyl, wherein the alkyl, aryl, heteroaryl, heterocyclic, cycloalkyl, cyclenyl, and heterocyclenyl can be optionally substituted with OH, SH, $NH_2$, nitro, CN, CON$(R^c)_2$, $COOR^{11}$, $C_1$-$C_6$alkoxy, $C_1$-$C_6$alkyl, $C_3$-$C_6$cycloalkyl, halo$C_2$-$C_6$alkenyl, $C_2$-$C_6$alkenyl, $C_2$-$C_6$alkenoxy, $C_1$-$C_6$haloalkyl, $C_1$-$C_6$haloalkoxy, $C_1$-$C_6$hydroxyalkyl, $C_1$-$C_6$alkyl-C($=$O)O—, $C_1$-$C_6$alkyl-C($=$O)—, $C_2$-$C_6$alkynyl, halo group, hydroxyalkoxy, —$SO_2NR^cR^c$, —$NR^cSO_2R^c$, $C_1$-$C_6$alkylsulfonyl, $C_1$-$C_6$alkylamino or di($C_1$-$C_6$)alkylamino;

$R^5$ is independently selected from the group consisting of H, $C_1$-$C_6$alkyl, —$C_0$-$C_6$alkyl-$C_3$-$C_8$cycloalkyl, —$C_0$-$C_6$alkyl-heteroaryl, —$C_0$-$C_6$alkyl-aryl, and —$C_0$-$C_6$alkylheterocyclic, wherein the alkyl, cycloalkyl, heteroaryl, aryl, and heterocyclic can be optionally substituted with $C_2$-$C_3$alkenyl, $C_3$-$C_6$cycloalkyl, $C_1$-$C_3$alkoxy, OH, halo, $NH_2$, $C_1$-$C_3$alkylamino, $C_1$-$C_3$dialkylamino or $COOR^{11}$;

$R^6$ is independently selected from the group consisting of H, $C_1$-$C_6$alkyl, —$C_0$-$C_6$alkyl-$C_3$-$C_8$cycloalkyl, —$C_0$-$C_6$alkyl-heteroaryl, —$C_0$-$C_6$alkyl-aryl, and —$C_0$-$C_6$alkylheterocyclic, wherein the alkyl, cycloalkyl, heteroaryl, aryl, and heterocyclic can be optionally substituted with $C_2$-$C_3$alkenyl, $C_3$-$C_6$cycloalkyl, $C_1$-$C_3$alkoxy, OH, halo, $NH_2$, $C_1$-$C_3$alkylamino, $C_1$-$C_3$dialkylamino or $COOR^{11}$;

$R^7$ is selected from the group consisting of H, $C_1$-$C_6$alkyl, $C_2$-$C_6$alkenyl, $C_3$-$C_8$cycloalkyl, aryl, heteroaryl, heterocyclic, wherein the alkyl, alkenyl, cycloalkyl, aryl, heteroaryl or heterocyclic can be optionally substituted with halo, nitro, CN, $C_1$-$C_6$haloalkyl, $C_1$-$C_6$haloalkoxy, $C_2$-$C_6$alkenyl, $C_2$-$C_6$alkynyl, $C_1$-$C_6$alkyl, —$C_0$-$C_6$alkyl-$C_3$-$C_8$cycloalkyl, —$C_0$-$C_6$alkyl-heteroaryl, —$C_0$-$C_6$alkyl-aryl, —$C_0$-$C_6$alkylheterocyclenyl, —$C_0$-$C_6$alkylcyclenyl, —$(CR^a_2)_z NR^5 R^6$, —$(CR^a_2)_z NR^5 SO_2 R^6$, —$(CR^a_2)_z SO_2 NR^5 R^6$, —$(CR^a_2)_z C(O)R^5$, —$(CR^a_2)_z C(O)OR^{10}$, —$(CR^a_2)_z CONR^5 R^6$, —$(CR^a_2)_z CONR^5 OR^6$, —$(CR^a_2)_z NR^5 C(O)R^6$, —$(CR^a_2)_z OR^5$, —$(CR^a_2)_z S(O)R^c$, and —$(CR^a_2)_z S(O)_2 R^c$;

$R^8$ is independently selected from the group consisting of H, —$(CR^a_2)_s$-heteroaryl, —$(CR^a_2)_s$-aryl, —$(CR^a_2)_s$-heterocyclic, —$(CR^a_2)_s$-heterocyclenyl, —$(CR^a_2)_s$-cyclenyl, —$(CR^a_2)_s C_3$-$C_7$cycloalkyl, and $C_1$-$C_6$alkyl, wherein the heteroaryl, aryl, heterocyclic, heterocyclenyl, cyclenyl, cycloalkyl, and alkyl can be optionally substituted with OH, $NH_2$, nitro, CN, $CON(R^c)_2$, $COOR^{11}$, $C_1$-$C_6$alkoxy, $C_1$-$C_6$alkyl, $C_2$-$C_6$alkenyl, $C_1$-$C_6$haloalkyl, $C_1$-$C_6$haloalkoxy, $C_1$-$C_6$hydroxyalkyl, $C_1$-$C_6$alkyl-C($=$O)O—, $C_1$-$C_6$alkyl-C($=$O)—, $C_2$-$C_6$alkynyl, halo group, hydroxyalkoxy, —$SO_2NR^cR^c$, —$NR^cSO_2R^c$, $C_1$-$C_6$alkylsulfonyl, $C_1$-$C_6$alkylamino or di($C_1$-$C_6$)alkylamino;

$R^g$ is independently selected from the group consisting of H, $C_1$-$C_6$alkyl, $C_1$-$C_6$haloalkyl, $C_3$-$C_8$cycloalkyl, aryl, heteroaryl, and heterocyclic, wherein the alkyl, cycloalkyl, aryl, heteroaryl, and heterocyclic can be optionally substituted with —$C_0$-$C_6$alkyl$OR^c$, —$C_0$-$C_6$alkyl$N(R^c)_2$, $COOR^{10}$, nitro, CN, $C_1$-$C_6$alkyl, $C_1$-$C_6$haloalkyl, $C_1$-$C_6$haloalkoxy, $C_1$-$C_6$hydroxyalkyl, $C_2$-$C_6$alkenyl, $C_1$-$C_6$alkyl-C($=$O)O—, $C_1$-$C_6$alkyl-C($=$O)—, $C_2$-$C_6$alkynyl, halo group, hydroxyalkoxy, —$SO_2NR^cR^c$, —$NR^cSO_2R^c$, $C_1$-$C_6$alkylsulfonyl, heterocyclic, or C(O)$NHR^c$;

$R^{10}$ is independently selected from the group consisting of $C_1$-$C_6$alkyl, —$(CR^c_2)_z C_3$-$C_8$cycloalkyl, —$(CR^c_2)_z$-heteroaryl, —$(CR^c_2)_z$-aryl, and —$(CR^c_2)_z$-heterocyclic, wherein the heteroaryl, aryl, heterocyclic, cycloalkyl and alkyl can be optionally substituted with $C_1$-$C_6$alkyl, OH, halo, or halo$C_1$-$C_6$alkyl;

$R^{11}$ is independently selected from the group consisting of H, $C_1$-$C_6$alkyl, —$(CR^c_2)_z C_3$-$C_8$cycloalkyl, —$(CR^c_2)_z$-heteroaryl, —$(CR^c_2)_z$aryl, and —$(CR^c_2)_z$heterocyclic wherein the heteroaryl, aryl, heterocyclic, cycloalkyl and alkyl can be optionally substituted with $C_1$-$C_6$alkyl, OH, halo, or halo$C_1$-$C_6$alkyl;

$R^{17}$ is independently selected from the group consisting of H, halo, COOH, oxadiazolone, $C_1$-$C_6$alkyl, —$(CR^c_2)_z C_3$-$C_8$cycloalkyl, —$(CR^c_2)_z$heteroaryl, —$(CR^c_2)_z$aryl, and —$(CR^c_2)_z$heterocyclic wherein the heteroaryl, aryl, heterocyclic, cycloalkyl and alkyl can be optionally substituted with $C_1$-$C_6$alkyl, OH, halo, or halo$C_1$-$C_6$alkyl;

$R^a$ is independently H, C(O)$NR^c_2$, $OR^c$, $NH_2$, halo, $C_1$-$C_6$alkyl, or $C_2$-$C_6$alkenyl, said alkyl or alkenyl is optionally substituted with OH, $C_1$-$C_4$alkoxy, $NH_2$, halo, halo$C_1$-$C_4$alkyl, $C_3$-$C_6$cycloalkyl, or $C_2$-$C_4$alkenyl;

$R^c$ is independently H or $C_1$-$C_4$alkyl optionally substituted with $C_2$-$C_3$alkenyl, $C_3$-$C_6$cycloalkyl, $C_1$-$C_3$alkoxy, OH, halo, $NH_2$, $C_1$-$C_3$alkylamino, or $C_1$-$C_3$dialkylamino;

T is independently $C_2$-$C_3$alkenyl, —C(O)—, —$(CR^a_2)_q$—, —C($=$CH$_2$)—, —$(CR^a_2)_q$—C($=$CH$_2$)—, —C($=$CH$_2$)—$(CR^a_2)_q$—, —C($=$NH)—, —$(CR^a_2)_q$—C($=$NH)—, or —C($=$NH)—$(CR^a_2)_q$—;

Y is a bond, —C(O)$NR^c$—, —$NR^c$C(O)—, or —$NR^c$—;

U is H, $COOR^{11}$, OH, heteroaryl or heterocyclic;

n is independently 0, 1, 2 or 3;

m is independently 0, 1 or 2;

q is independently 0, 1, 2, or 3;

s is independently 0, 1 or 2;

t is independently 0, 1, or 2;

v is independently 1, 2, 3 or 4;

z is independently 0, 1, 2, 3 or 4;

or a pharmaceutically acceptable salt thereof.

In a first embodiment, $R^1$ is selected from the group consisting of $C_1$-$C_6$alkyl, —$(CR^a_2)_z COOR^{11}$, -T-$NHR^5$, —$(CR^a_2)_z NR^6 SO_2 R^6$, —$(CR^a_2)_z SO_2 NR^6 R^6$, —$(CR^a_2)_z C(O)NR^c SO_2 N(R^c)_2$, —$(CR^a_2)_z C(O)R^6$, —$(CR^a_2)_z CONR^6 R^6$, —$(CR^a_2)_z CONR^6 OR^6$, —$(CR^a_2)_z NR^6 C(O)R^6$, —$(CR^a_2)_n OR^6$, —$(CR^a_2)_z S(O)R^c$, —$(CR^a_2)_z S(O)_2 R^c$, and nitrogen containing 5-membered heterocyclic, heteroaryl or heterocyclenyl ring, wherein the alkyl and 5-membered ring can be optionally substituted with $OR^c$, $SR^c$, $NH_2$, nitro, CN, amide, $COOR^{11}$, $C_1$-$C_6$alkyl, $C_1$-$C_6$haloalkyl, $C_1$-$C_6$haloalkoxy, $C_1$-$C_6$hydroxyalkyl, $C_2$-$C_6$alkenyl, $C_1$-$C_6$alkyl-C($=$O)O—, $C_1$-$C_6$alkyl-C($=$O)—, $C_2$-$C_6$alkynyl, halo group, hydroxyalkoxy, —$SO_2NR^cR^c$, —$NR^cSO_2R^c$, $C_1$-$C_6$alkylsulfonyl, $C_1$-$C_6$alkylamino or di($C_1$-$C_6$)alkylamino;

$R^2$ is selected from the group consisting of aryl, heteroaryl, —W—$(CR^aR^g)_v R^7$, and heterocyclic, wherein W is $NR^c$ or O, wherein the aryl, heteroaryl, or heterocyclic is optionally substituted with $R^{12}$ selected from the group consisting of halo, CN, halo$C_1$-$C_6$alkyl, $C_1$-$C_6$alkyl, —$(CR^a_2)_z OR^c$, —$(CR^a_2)_z NHR^8$, —$(CR^a_2)_z C(O)NR^cR^c$, —$(CR^a_2)_z COOR^{10}$, —$(CR^a_2)_z$aryl, —$(CR^a_2)_z$heteroaryl, —(CR$^a_2$)$_z$heterocyclic, —(CR$^a_2$)$_z$C$_3$-C$_8$cycloalkyl, —(CR$^a_2$)$_z$cyclenyl, and —(CR$^a_2$)$_z$heterocyclenyl, wherein the alkyl, aryl, heteroaryl, heterocyclic, cycloalkyl, cyclenyl and heterocyclenyl of R$^{12}$ can be optionally substituted with OH, NH$_2$, nitro, CN, CON(R$^c$)$_2$, —(CR$^a_2$)$_z$COOR$^{10}$, C$_1$-C$_6$alkoxy, C$_1$-C$_6$alkyl, C$_1$-C$_6$haloalkyl, C$_1$-C$_6$haloalkoxy, C$_1$-C$_6$hydroxyalkyl, C$_2$-C$_6$alkenyl, C$_1$-C$_6$alkyl-C(=O)O—, C$_1$-C$_6$alkyl-C(=O)—, C$_2$-C$_6$alkynyl, halo group, hydroxyalkoxy, —SO$_2$NR$^c$R$^c$, —NR$^c$SO$_2$R$^c$, C$_1$-C$_6$alkylsulfonyl, C$_1$-C$_6$alkylamino or di(C$_1$-C$_6$)alkylamino;

R$^3$ is selected from the group consisting of H, —(CR$^a_2$)$_q$NR$^c$R$^8$, —(CR$^a_2$)$_q$OR$^8$, —(CR$^a_2$)$_q$SR$^8$, —(CR$^a_2$)$_q$C(O)R$^8$, —(CR$^a_2$)$_q$S(O)R$^8$, —(CR$^a_2$)$_q$S(O)$_2$R$^8$, —(CR$^a_2$)$_q$CONR$^c$R$^8$, —(CR$^a_2$)$_q$NR$^c$C(O)R$^8$, -T-C$_1$-C$_6$alkyl, C$_2$-C$_6$alkenyl, -T-aryl, -T-heteroaryl, -T-heterocyclic, -T-C$_3$-C$_7$cycloalkyl, -T-cyclenyl, and -T-heterocyclenyl, wherein the alkyl, alkenyl, aryl, heteroaryl, heterocyclic, cycloalkyl, cyclenyl and heterocyclenyl can be optionally substituted with halo, SH, OR$^c$, haloC$_1$-C$_6$alkyl, haloC$_1$-C$_6$alkoxy, —(CR$^a_2$)$_z$CN, C$_1$-C$_6$alkyl, C$_2$-C$_6$alkenyl, C$_2$-C$_6$alkynyl, —(CR$^a_2$)$_z$C(O)OR$^{11}$, —(CR$^a_2$)$_z$C(O)R$^8$, —(CR$^a_2$)$_z$OR$^8$, —(CR$^a_2$)$_z$NR$^c$R$^8$, —(CR$^a_2$)$_z$S(O)$_2$R$^8$, —(CR$^a_2$)$_z$C(O)NR$^c$R$^8$, —(CR$^a_2$)$_z$aryl, —(CR$^a_2$)$_z$heteroaryl, —(CR$^a_2$)$_z$C$_3$-C$_8$cycloalkyl, —(CR$^a_2$)$_z$heterocyclic, —(CR$^a_2$)$_z$heterocyclenyl, —(CR$^a_2$)$_z$cyclenyl, —(CR$^a_2$)$_z$SO$_2$NR$^c$R$^8$, or —(CR$^a_2$)$_z$O(CR$^a_2$)$_z$Y(CR$^a_2$)$_v$U, said alkyl, alkenyl, alkynyl, aryl, heteroaryl, cycloalkyl, heterocyclic, heterocyclenyl and cyclenyl can further be substituted with SH, OH, NH$_2$, nitro, CN, CON(R$^c$)$_2$, COOR$^{10}$, C$_1$-C$_6$alkoxy, C$_1$-C$_6$alkyl, C$_1$-C$_6$alkoxyC$_1$-C$_6$alkyl, C$_2$-C$_6$alkenyl, C$_1$-C$_6$haloalkyl, C$_1$-C$_6$haloalkoxy, C$_1$-C$_6$hydroxyalkyl, C$_1$-C$_6$alkyl-C(=O)O—, C$_1$-C$_6$alkyl-C(=O)—, C$_2$-C$_6$alkynyl, halo group, hydroxyalkoxy, —SO$_2$NR$^c$R$^c$, —NR$^c$SO$_2$R$^c$, C$_r$, C$_6$alkylsulfonyl, C$_1$-C$_6$alkylamino or di(C$_1$-C$_6$)alkylamino;

R$^4$ is selected from the group consisting of C$_1$-C$_6$alkyl, —(CR$^a_2$)$_m$aryl, —(CR$^a_2$)$_m$heteroaryl, —(CR$^a_2$)$_m$heterocyclic, —(CR$^a_2$)$_m$C$_3$-C$_8$cycloalkyl, —(CR$^a_2$)$_m$cyclenyl, and —(CR$^a_2$)$_m$heterocyclenyl, wherein the alkyl, aryl, heteroaryl, heterocyclic, cycloalkyl, cyclenyl, and heterocyclenyl can be optionally substituted with OH, SH, NH$_2$, nitro, CN, CON(R$^c$)$_2$, COOR$^{11}$, C$_1$-C$_6$alkoxy, C$_1$-C$_6$alkyl, C$_3$-C$_6$cycloalkyl, haloC$_2$-C$_6$alkenyl, C$_2$-C$_6$alkenyl, C$_2$-C$_6$alkenoxy, C$_1$-C$_6$haloalkyl, C$_1$-C$_6$haloalkoxy, C$_1$-C$_6$hydroxyalkyl, C$_1$-C$_6$alkyl-C(=O)O—, C$_1$-C$_6$alkyl-C(=O)—, C$_2$-C$_6$alkynyl, halo group, hydroxyalkoxy, —SO$_2$NR$^c$R$^c$, —NR$^c$SO$_2$R$^c$, C$_1$-C$_6$alkylsulfonyl, C$_1$-C$_6$alkylamino or di(C$_1$-C$_6$)alkylamino;

R$^5$ is independently selected from the group consisting of H, C$_1$-C$_6$alkyl, —C$_0$-C$_6$alkyl-C$_3$-C$_8$cycloalkyl, —C$_0$-C$_6$alkyl-heteroaryl, —C$_0$-C$_6$alkyl-aryl, and —C$_0$-C$_6$alkylheterocyclic, wherein the alkyl, cycloalkyl, heteroaryl, aryl, and heterocyclic can be optionally substituted with C$_2$-C$_3$alkenyl, C$_3$-C$_6$cycloalkyl, C$_1$-C$_3$alkoxy, OH, halo, NH$_2$, C$_1$-C$_3$alkylamino, C$_1$-C$_3$dialkylamino or COOR$^{11}$;

R$^6$ is independently selected from the group consisting of H, C$_1$-C$_6$alkyl, —C$_0$-C$_6$alkyl-C$_3$-C$_8$cycloalkyl, —C$_0$-C$_6$alkyl-heteroaryl, —C$_0$-C$_6$alkyl-aryl, and —C$_0$-C$_6$alkylheterocyclic, wherein the alkyl, cycloalkyl, heteroaryl, aryl, and heterocyclic can be optionally substituted with C$_2$-C$_3$alkenyl, C$_3$-C$_6$cycloalkyl, C$_1$-C$_3$alkoxy, OH, halo, NH$_2$, C$_1$-C$_3$alkylamino, C$_1$-C$_3$dialkylamino or COOR$^{11}$;

R$^7$ is selected from the group consisting of H, C$_1$-C$_6$alkyl, C$_2$-C$_6$alkenyl, C$_3$-C$_8$cycloalkyl, aryl, heteroaryl, heterocyclic, wherein the alkyl, alkenyl, cycloalkyl, aryl, heteroaryl or heterocyclic can be optionally substituted with halo, nitro, CN, C$_1$-C$_6$haloalkyl, C$_1$-C$_6$haloalkoxy, C$_2$-C$_6$alkenyl, C$_2$-C$_6$alkynyl, C$_1$-C$_6$alkyl, —C$_0$-C$_6$alkyl-C$_3$-C$_8$cycloalkyl, —C$_0$-C$_6$alkyl-heteroaryl, —C$_0$-C$_6$alkyl-aryl, —C$_0$-C$_6$alkylheterocyclic, —C$_0$-C$_6$alkylheterocyclenyl, —C$_0$-C$_6$alkylcyclenyl, —(CR$^a_2$)$_z$NHR$^5$, —(CR$^a_2$)$_z$NR$^5$SO$_2$R$^6$, —(CR$^a_2$)$_z$SO$_2$NR$^5$R$^6$, —(CR$^a_2$)$_z$C(O)R$^5$, —(CR$^a_2$)$_z$C(O)OR$^{10}$, —(CR$^a_2$)$_z$CONR$^5$R$^6$, —(CR$^a_2$)$_z$CONR$^5$OR$^6$, —(CR$^a_2$)$_z$NR$^5$C(O)R$^6$, —(CR$^a_2$)$_z$OR$^5$, —(CR$^a_2$)$_z$S(O)R$^c$, and —(CR$^a_2$)$_z$S(O)$_2$R$^c$;

R$^8$ is independently selected from the group consisting of H, —(CR$^a_2$)$_s$-heteroaryl, —(CR$^a_2$)$_s$-aryl, —(CR$^a_2$)$_s$-heterocyclic, —(CR$^a_2$)$_s$-heterocyclenyl, —(CR$^a_2$)$_s$-cyclenyl, —(CR$^a_2$)$_s$C$_3$-C$_7$cycloalkyl, and C$_1$-C$_6$alkyl, wherein the heteroaryl, aryl, heterocyclic, heterocyclenyl, cyclenyl, cycloalkyl, and alkyl can be optionally substituted with OH, NH$_2$, nitro, CN, CON(R$^c$)$_2$, COOR$^{11}$, C$_1$-C$_6$alkoxy, C$_1$-C$_6$alkyl, C$_2$-C$_6$alkenyl, C$_1$-C$_6$haloalkyl, C$_1$-C$_6$haloalkoxy, C$_1$-C$_6$hydroxyalkyl, C$_1$-C$_6$alkyl-C(=O)O—, C$_1$-C$_6$alkyl-C(=O)—, C$_2$-C$_6$alkynyl, halo group, hydroxyalkoxy, —SO$_2$NR$^c$R$^c$, —NR$^c$SO$_2$R$^c$, C$_1$-C$_6$alkylsulfonyl, C$_1$-C$_6$alkylamino or di(C$_1$-C$_6$)alkylamino;

R$^g$ is independently selected from the group consisting of H, C$_1$-C$_6$alkyl, C$_1$-C$_6$haloalkyl, C$_3$-C$_8$cycloalkyl, aryl, heteroaryl, and heterocyclic, wherein the alkyl, cycloalkyl, aryl, heteroaryl, and heterocyclic can be optionally substituted with —C$_0$-C$_6$alkylOR$^c$, C$_0$-C$_6$alkylN(R$^c$)$_2$, COOR$^{10}$, nitro, CN, C$_1$-C$_6$alkyl, C$_1$-C$_6$haloalkyl, C$_1$-C$_6$haloalkoxy, C$_1$-C$_6$hydroxyalkyl, C$_2$-C$_6$alkenyl, C$_1$-C$_6$alkyl-C(=O)O—, C$_1$-C$_6$alkyl-C(=O)—, C$_2$-C$_6$alkynyl, halo group, hydroxyalkoxy, —SO$_2$NR$^c$R$^c$, —NR$^c$SO$_2$R$^c$, C$_1$-C$_6$alkylsulfonyl, heterocyclic, or C(O)NHR$^c$;

R$^{10}$ is independently selected from the group consisting of C$_1$-C$_6$alkyl, —(CR$^c_2$)$_z$C$_3$-C$_8$cycloalkyl, —(CR$^c_2$)$_z$-heteroaryl, —(CR$^c_2$)$_z$aryl, and —(CR$^c_2$)$_z$-heterocyclic, wherein the heteroaryl, aryl, heterocyclic, cycloalkyl and alkyl can be optionally substituted with C$_1$-C$_6$alkyl, OH, halo, or haloC$_1$-C$_6$alkyl;

R$^{11}$ is independently selected from the group consisting of H, C$_1$-C$_6$alkyl, —(CR$^c_2$)$_z$C$_3$-C$_8$cycloalkyl, —(CR$^c_2$)$_z$-heteroaryl, —(CR$^c_2$)$_z$aryl, and —(CR$^c_2$)$_z$heterocyclic wherein the heteroaryl, aryl, heterocyclic, cycloalkyl and alkyl can be optionally substituted with C$_1$-C$_6$alkyl, OH, halo, or haloC$_1$-C$_6$alkyl;

R$^{17}$ is independently selected from the group consisting of H, halo, C$_1$-C$_6$alkyl, —(CR$^c_2$)$_z$C$_3$-C$_8$cycloalkyl, —(CR$^c_2$)$_z$-heteroaryl, —(CR$^c_2$)$_z$aryl, and —(CR$^c_2$)$_z$heterocyclic wherein the heteroaryl, aryl, heterocyclic, cycloalkyl and alkyl can be optionally substituted with C$_1$-C$_6$alkyl, OH, halo, or haloC$_1$-C$_6$alkyl;

R$^a$ is independently H, OR$^c$, NH$_2$, halo, C$_1$-C$_6$alkyl, or C$_2$-C$_6$alkenyl, said alkyl or alkenyl is optionally substituted with OH, C$_1$-C$_4$alkoxy, NH$_2$, halo, haloC$_1$-C$_4$alkyl, C$_3$-C$_6$cycloalkyl, or C$_2$-C$_4$alkenyl;

R$^c$ is independently H or C$_1$-C$_3$alkyl optionally substituted with C$_2$-C$_3$alkenyl, C$_3$-C$_6$cycloalkyl, C$_1$-C$_3$alkoxy, OH, halo, NH$_2$, C$_1$-C$_3$alkylamino, or C$_1$-C$_3$dialkylamino;

T is independently C$_2$-C$_3$alkenyl, —(CR$^a_2$)$_q$—, —C(=CH$_2$)—, —(CR$^a_2$)$_q$—C(=CH$_2$)—, —C(=CH$_2$)—(CR$^a_2$)$_q$—, —C(=NH)—, —(CR$^a_2$)$_q$—C(=NH)—, or —C(=NH)—(CR$^a_2$)$_q$—;

Y is a bond, —C(O)NR$^c$—, —NR$^c$C(O)—, or —NR$^c$—;

U is H, COOR$^{11}$, OH, heteroaryl or heterocyclic;

n is independently 0, 1, 2 or 3;

m is independently 0, 1 or 2;

q is independently 0, 1, 2, or 3;

s is independently 0, 1 or 2;

t is independently 0, 1, or 2;

v is independently 1, 2, 3 or 4;
z is independently 0, 1, 2 or 3;
In one embodiment, $R^{10}$ is independently $C_1$-$C_6$alkyl optionally substituted with OH, halo, or halo$C_1$-$C_6$alkyl.

In a second embodiment, $R^1$ is selected from the group consisting of COOR$^{11}$, —NHR$^c$, —NR$^c$SO$_2$R$^c$, —SO$_2$NR$^c$R$^c$, —C(O)R$^D$, —CONR$^c$R$^c$, —CONR$^c$OR$^c$, —OR$^S$, and nitrogen containing 5-membered heterocyclenyl or heteroaryl ring, wherein the 5-membered ring can be optionally substituted with OR$^c$, SR$^c$, NH$_2$, nitro, CN, amide, COOR$^{11}$, $C_1$-$C_6$alkyl, $C_1$-$C_6$haloalkyl, $C_1$-$C_6$haloalkoxy, $C_1$-$C_6$hydroxyalkyl, $C_2$-$C_6$alkenyl, $C_1$-$C_6$alkyl-C(=O)O—, $C_1$-$C_6$alkyl-C(=O)—, $C_2$-$C_6$alkynyl, halo group, hydroxyalkoxy, —SO$_2$NR$^c$R$^c$, —NR$^c$SO$_2$R$^c$, $C_1$-$C_6$alkylsulfonyl, $C_1$-$C_6$alkylamino or di($C_1$-$C_6$)alkylamino;

$R^2$ is selected from the group consisting of aryl, heteroaryl, W—(CR$^a$R$^g$)R$^7$, and heterocyclic, wherein W is NR$^C$ or O, wherein the aryl, heteroaryl, and heterocyclic is optionally substituted with $R^{12}$ selected from the group consisting of halo, CN, halo$C_1$-$C_6$alkyl, $C_1$-$C_6$alkyl, —(CR$^a_2$)OR$^c$, and —(CR$^a_2$)C(O)NR$^c$R$^c$, wherein the alkyl of $R^{12}$ can be optionally substituted with OH, CN, halo, halo$C_1$-$C_6$alkyl, or CON(R$^c$)$_2$;

$R^3$ is selected from the group consisting of —NR$^c$R$^8$, —OR$^8$, —SR$^8$, —C(O)R$^8$, —S(O)R$^8$, —S(O)$_2$R$^8$, —CONR$^c$R$^8$, —NR$^c$O(O)R$^8$, -T-$C_1$-$C_6$alkyl, $C_2$-$C_6$alkenyl, -T-aryl, -T-heteroaryl, -T-heterocyclic, -T-$C_3$-$C_7$cycloalkyl, -T-cyclenyl, and -T-heterocyclenyl, wherein the alkyl, alkenyl, aryl, heteroaryl, heterocyclic, cycloalkyl, cyclenyl and heterocyclenyl can be optionally substituted with halo, OR$^c$, halo$C_1$-$C_6$alkyl, halo$C_1$-$C_6$alkoxy, —(CR$^a_2$)$_z$CN, $C_1$-$C_6$alkyl, $C_2$-$C_6$alkenyl, $C_2$-$C_6$alkynyl, —(CR$^a_2$)$_z$C(O)OR$^{11}$, —(CR$^a_2$)$_z$C(O)R$^8$, —(CR$^a_2$)$_z$OR$^8$, —(CR$^a_2$)$_z$NR$^c$R$^8$, —(CR$^a_2$)$_z$S(O)$_2$R$^8$, —(CR$^a_2$)$_z$C(O)NR$^c$R$^8$, —(CR$^a_2$)$_z$aryl, —(CR$^a_2$)$_z$heteroaryl, —(CR$^a_2$)$_z$C$_3$-$C_8$cycloalkyl, —(CR$^a_2$)$_z$heterocyclic, —(CR$^a_2$)$_z$SO$_2$NR$^c$R$^8$, or —(CR$^a_2$)$_z$O(CR$^a_2$)$_z$Y(CR$^a_2$)$_z$U, said alkyl, alkenyl, alkynyl, aryl, heteroaryl, cycloalkyl, and heterocyclic can further be substituted with OH, halo, or $C_2$-$C_6$alkenyl;

$R^4$ is selected from the group consisting of —(CR$^a_2$)aryl, —(CR$^a_2$)heteroaryl, —(CR$^a_2$)heterocyclic, —(CR$^a_2$)C$_3$-C$_8$cycloalkyl, —(CR$^a_2$)cyclenyl, and —(CR$^a_2$)heterocyclenyl, wherein the aryl, heteroaryl, heterocyclic, cycloalkyl, cyclenyl, and heterocyclenyl can be optionally substituted with OH, SH, NH$_2$, nitro, CN, CON(R$^c$)$_2$, COOR$^{11}$, $C_1$-$C_6$alkoxy, $C_1$-$C_6$alkyl, $C_3$-$C_6$cycloalkyl, halo$C_2$-$C_6$alkenyl, $C_2$-$C_6$alkenyl, $C_2$-$C_6$alkenoxy, $C_1$-$C_6$haloalkyl, $C_1$-$C_6$haloalkoxy, $C_1$-$C_6$hydroxyalkyl, $C_1$-$C_6$alkyl-C(=O)O—, $C_1$-$C_6$alkyl-C(=O)—, $C_2$-$C_6$alkynyl, halo group, hydroxyalkoxy, —SO$_2$NR$^c$R$^c$, —NR$^c$SO$_2$R$^c$, $C_1$-$C_6$alkylsulfonyl, $C_1$-$C_6$alkylamino or di($C_1$-$C_6$)alkylamino;

$R^7$ is selected from the group consisting of $C_1$-$C_6$alkyl, $C_3$-$C_8$cycloalkyl, heteroaryl, aryl, and heterocyclic, wherein the alkyl, cycloalkyl, heteroaryl, aryl or heterocyclic can be optionally substituted with halo, nitro, CN, $C_1$-$C_6$haloalkyl, $C_1$-$C_6$haloalkoxy, $C_1$-$C_6$alkyl, or —(CR$^a_2$)$_z$OR$^c$;

$R^8$ is independently selected from the group consisting of —(CR$^a_2$)-heteroaryl, —(CR$^a_2$)-aryl, —(CR$^a_2$)-heterocyclic, —(CR$^a_2$)-heterocyclenyl, —(CR$^a_2$)cyclenyl, —(CR$^a_2$)cycloalkyl, and $C_1$-$C_6$alkyl, wherein the heteroaryl, aryl, heterocyclic, heterocyclenyl, cyclenyl, cycloalkyl, and alkyl can be optionally substituted with OH, $C_1$-$C_6$alkoxy, $C_1$-$C_6$alkyl, $C_1$-$C_6$haloalkyl, $C_1$-$C_6$haloalkoxy, $C_1$-$C_6$hydroxyalkyl, or halo group;

$R^g$ is H, $C_1$-$C_3$alkyl, $C_1$-$C_3$haloalkyl, $C_3$-$C_4$cycloalkyl, wherein the alkyl or cycloalkyl can be optionally substituted with OR$^c$, N(R$^c$)$_2$, heterocyclic, C(O)NHCH$_2$CH$_2$OH, C(O)NH$_2$, or C(O)NHC$_1$-$C_3$alkyl;

$R^{11}$ is independently selected from the group consisting of H and $C_1$-$C_6$alkyl, wherein alkyl can be optionally substituted with OH or halo;

$R^{17}$ is independently selected from the group consisting of H or halo;

$R^a$ is independently H, OR$^c$, NH$_2$, halo, $C_1$-$C_6$alkyl, or $C_2$-$C_6$alkenyl, said alkyl or alkenyl is optionally substituted with OH, $C_1$-$C_4$alkoxy, NH$_2$, F, CF$_3$, $C_3$-$C_6$cycloalkyl, or $C_2$-$C_4$alkenyl;

$R^c$ is independently H or $C_1$-$C_3$alkyl optionally substituted with $C_2$-$C_3$alkenyl, $C_3$-$C_6$cycloalkyl, $C_1$-$C_3$alkoxy, OH, halo, NH$_2$, $C_1$-$C_3$alkylamino, or $C_1$-$C_3$dialkylamino;

T is independently —(CR$^a_2$)$_q$—, or —C(=CH$_2$)—;

Y is a bond, —C(O)NR$^c$—, —NR$^c$C(O)—, or —NR$^c$—;

U is H, COOR$^{11}$, OH, heteroaryl or heterocyclic;

q is independently 0 or 1;

v is independently 1 or 2; and z is independently 0, 1 or 2.

In a third embodiment, $R^1$ is selected from the group consisting of COOR$^{11}$, —NHR$^c$, —NR$^c$SO$_2$R$^c$, —SO$_2$NR$^c$R$^c$, —C(O)R$^D$, —CONR$^c$R$^c$, —CONR$^c$OR$^c$, —OR$^c$, and nitrogen containing 5-membered heterocyclenyl ring, wherein the 5-membered ring can be optionally substituted with OR$^c$, SR$^c$, NH$_2$, nitro, CN, amide, COOR$^{11}$, $C_1$-$C_6$alkyl, $C_1$-$C_6$haloalkyl, $C_1$-$C_6$haloalkoxy, $C_1$-$C_6$hydroxyalkyl, $C_2$-$C_6$alkenyl, $C_1$-$C_6$alkyl-C(=O)O—, $C_1$-$C_6$alkyl-C(=O)—, $C_2$-$C_6$alkynyl, halo group, hydroxyalkoxy, —SO$_2$NR$^c$R$^c$, —NR$^c$SO$_2$R$^c$, $C_1$-$C_6$alkylsulfonyl, $C_1$-$C_6$alkylamino or di($C_1$-$C_6$)alkylamino;

$R^2$ is selected from the group consisting of aryl, heteroaryl, and —NR$^S$—(CR$^a$R$^g$)R$^7$, wherein the aryl, or heteroaryl is optionally substituted with $R^{12}$ selected from the group consisting of halo, CN, halo$C_1$-$C_6$alkyl, $C_1$-$C_6$alkyl, —(CR$^a_2$)OR$^c$, wherein the alkyl of $R^{12}$ can be optionally substituted with OH, CN, halo, halo$C_1$-$C_6$alkyl, or CON(R$^c$)$_2$;

$R^3$ is selected from the group consisting of -T-aryl, -T-heteroaryl, and -T-heterocyclic, wherein the heteroaryl, and heterocyclic can be optionally substituted with halo, OR$^c$, halo$C_1$-$C_6$alkyl, halo$C_1$-$C_6$alkoxy, —(CR$^a_2$)$_z$CN, $C_1$-$C_6$alkyl, $C_2$-$C_6$alkenyl, $C_2$-$C_6$alkynyl, —(CR$^a_2$)$_z$C(O)OR$^{11}$, —(CR$^a_2$)$_z$C(O)R$^8$, —(CR$^a_2$)$_z$OR$^8$, —(CR$^a_2$)$_z$NR$^c$R$^8$, —(CR$^a_2$)$_z$S(O)$_2$R$^8$, —(CR$^a_2$)$_z$C(O)NR$^c$R$^8$, —(CR$^a_2$)$_z$aryl, —(CR$^a_2$)$_z$heteroaryl, —(CR$^a_2$)$_z$C$_3$-$C_8$cycloalkyl, —(CR$^a_2$)$_z$heterocyclic, —(CR$^a_2$)$_z$SO$_2$NR$^c$R$^8$, or —(CR$^a_2$)$_z$O(CR$^a_2$)$_z$Y(CR$^a_2$)$_z$U;

said alkyl, alkenyl, alkynyl, aryl, heteroaryl, cycloalkyl, and heterocyclic can further be substituted with OH, halo, or $C_2$-$C_6$alkenyl;

$R^4$ is selected from the group consisting of —(CR$^a_2$)aryl, —(CR$^a_2$)C$_3$-$C_6$cycloalkyl, and —(CR$^a_2$)C$_3$-$C_6$ cyclenyl, wherein the aryl, cycloalkyl, and cyclenyl can be optionally substituted with OH, SH, NH$_2$, nitro, CN, CON(R$^c$)$_2$, COOR$^{11}$, $C_1$-$C_6$alkoxy, $C_1$-$C_6$alkyl, $C_3$-$C_6$cycloalkyl, halo$C_2$-$C_6$alkenyl, $C_2$-$C_6$alkenyl, $C_2$-$C_6$alkenoxy, $C_1$-$C_6$haloalkyl, $C_1$-$C_6$haloalkoxy, $C_1$-$C_6$hydroxyalkyl, $C_1$-$C_6$alkyl-C(=O)O—, $C_1$-$C_6$alkyl-C(=O)—, $C_2$-$C_6$alkynyl, halo group, hydroxyalkoxy, —SO$_2$NR$^c$R$^c$, —NR$^c$SO$_2$R$^c$, $C_1$-$C_6$alkylsulfonyl, $C_1$-$C_6$alkylamino or di($C_1$-$C_6$)alkylamino;

$R^7$ is $C_3$-$C_6$cycloalkyl optionally substituted with halo, nitro, CN, $C_1$-$C_6$haloalkyl, $C_1$-$C_6$haloalkoxy, $C_1$-$C_6$alkyl, or —(CR$^a_2$)$_z$OR$^c$;

$R^g$ is $C_1$-$C_3$alkyl;

$R^{17}$ is H;

and all other substituents are defined in the first embodiment under Formula I.

In a fourth embodiment, $R^1$ is COOH or a nitrogen containing 5-membered heteroaryl, heterocyclyl or heterocyclenyl ring selected from the group consisting of tetrazolyl, oxadiazolyl, oxadiazolone, dihydro-oxadiazolyl, triazolyl, dihydro-triazolyl, dihydro-triazolone, pyrrolidinyl, and imidazolyl, wherein the nitrogen containing 5-membered ring can be optionally substituted with halo, $C_1$-$C_6$alkyl, halo$C_1$-$C_6$alkyl, $NH_2$, $OR^c$, $SR^c$, COOH, or —$NR^cSO_2R^c$.

and all other substituents are as defined in the first embodiment.

In a fifth embodiment of the foregoing embodiments, $R^1$ is COOH or a nitrogen containing 5-membered heteroaryl, heterocyclyl or heterocyclenyl ring selected from the group consisting of tetrazolyl, oxadiazolyl, oxadiazolone, dihydro-oxadiazolyl, triazolyl, dihydro-triazolyl, dihydro-triazolone, pyrrolidinyl, and imidazolyl, wherein the nitrogen containing 5-membered ring can be optionally substituted with halo, $C_1$-$C_6$alkyl, halo$C_1$-$C_6$alkyl, $NH_2$, $OR^c$, $SR^c$, COOH, or —$NR^cSO_2R^c$.

In a sixth embodiment of the foregoing embodiments, $R^1$ is COOH, 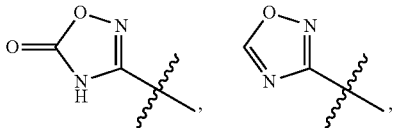

wherein $R^d$ is $CH_3$ or H.

In one embodiment, $R^1$ is wherein $R^d$ is $CH_3$ or H.

In another embodiment, $R^1$ is COOH or

In another embodiment, $R^1$ is COOH,

or

In a further embodiment, $R^1$ is

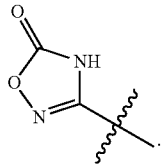 [SMILES: *c1noc(=O)[nH]1]

In yet a further embodiment, $R^1$ is

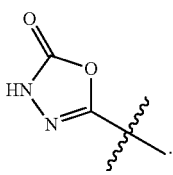 [SMILES: *c1n[nH]c(=O)o1]

In another aspect of the invention for the foregoing embodiments, $R^7$ is cyclopropyl, cyclobutyl, cyclopentyl, or cyclohexyl. In another embodiment, $R^7$ is cyclobutyl.

In another aspect of the invention for the foregoing embodiments, $R^2$ is

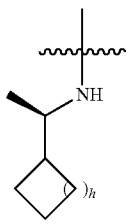 or 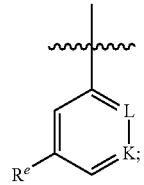

$R^e$ is H, $-(CR^a{}_2)_zC(O)OR^{10}$, halo, haloC$_1$-C$_3$alkyl or C$_1$-C$_3$alkyl;

K and L are independently CR$^{14}$ or N;

$R^{14}$ is independently H, halo, CN, haloC$_1$-C$_6$alkyl, C$_1$-C$_6$alkyl, $-(CR^a{}_2)_zC(O)NR^cR^c$, $-(CR^a{}_2)_zOR^c$, $-(CR^a{}_2)_z$aryl, $-(CR^a{}_2)_z$heteroaryl, $-(CR^a{}_2)_z$heterocyclic, $-(CR^a{}_2)_zC_3$-C$_8$cycloalkyl, $-(CR^a{}_2)_z$cyclenyl, $-(CR^a{}_2)_z$heterocyclenyl, wherein the alkyl, aryl, heteroaryl, heterocyclic, cycloalkyl, cyclenyl or heterocyclenyl can be optionally substituted with OH, CN, halo, haloC$_1$-C$_3$alkyl, or CON(R$^c$)$_2$; and h is 0 or 1.

In one embodiment, $R^2$ is

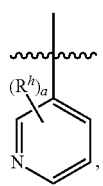 , 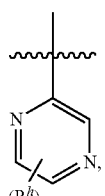 , 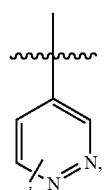 , 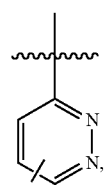

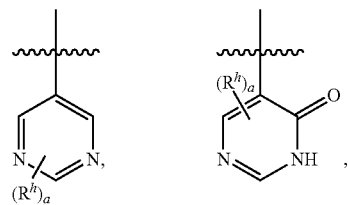

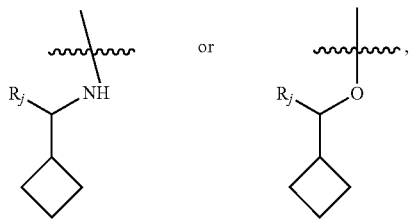

and $R_j$ is H or methyl, $R^h$ is halo, NR$^c$R$^c$, hydroxyC$_1$-C$_4$alkyl, hydroxyC$_1$-C$_4$alkoxy, $-$CO$_1$$-$C$_3$alkylOC$_1$-C$_3$alkyl, C$_1$-C$_4$alkyl or C$_1$-C$_4$alkoxy;

a is 0, 1 or 2.

In one embodiment, $R^2$ is

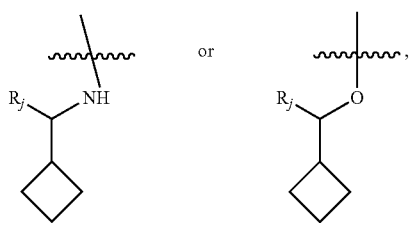

and $R_j$ is H or methyl.

In another embodiment, $R^2$ is

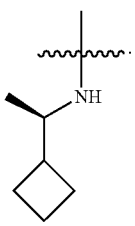 [SMILES: *N[C@H](C)C1CCC1]

In a further embodiment, $R^2$ is

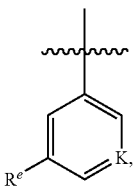

In yet a further embodiment, $R^2$ is

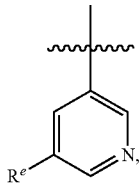

and $R^e$ is halo.

In another aspect of the invention for the foregoing embodiments, $R^3$ is -T-heterocyclic optionally substituted with halo, $OR^c$, haloC$_1$-C$_6$alkyl, haloC$_1$-C$_6$alkoxy, CN, C$_1$-C$_6$alkyl, C$_2$-C$_6$alkenyl, C$_2$-C$_6$alkynyl, —(CR$^a{}_2$)$_z$C(O)OR$^{11}$, —(CR$^a{}_2$)$_z$C(O)R$^8$, —(CR$^a{}_2$)$_z$OR$^8$, —(CR$^a{}_2$)$_z$NR$^c$R$^8$, —(CR$^a{}_2$)$_z$S(O)$_2$R$^8$, —(CR$^a{}_2$)$_z$C(O)NR$^c$R$^8$, —(CR$^a{}_2$)$_z$aryl, —(CR$^a{}_2$)$_z$heteroaryl, —(CR$^a{}_2$)$_z$C$_3$-C$_8$cycloalkyl, —(CR$^a{}_2$)$_z$heterocyclic, —(CR$^a{}_2$)$_z$SO$_2$NR$^c$R$^8$, or —(CR$^a{}_2$)$_z$O(CR$^a{}_2$)$_z$Y(CR$^a{}_2$)$_z$U;
said alkyl, alkenyl, alkynyl, aryl, heteroaryl, cycloalkyl, and heterocyclic can further be substituted with OH, halo, or C$_2$-C$_6$alkenyl.

In one embodiment, the heteroaryl or heterocyclic group of $R^3$ is pyridyl, morpholinyl, thiomorpholinyl, phenyl, piperidinyl, benzothiophenyl, thiazolyl, pyrimidinyl, oxazolyl, imidazolyl, pyrazolyl, piperizinyl, tetrahydrofuranyl, benzofuranyl, quinoxalinyl, pyrazolyl, naphthalenyl, dihydro-indenyl, quinolinyl, isoindolyl, isoquinolinyl, isoxazolyl, furanyl, oxadiazolyl, octahydroquinolinyl, octahydroisoquinolinyl, azetidinyl, oxazepanyl, or oxazolidinyl.

In yet another aspect of the invention for the foregoing embodiments, $R^3$ is

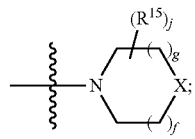

X is NR$^{19}$, CR$^{16}{}_2$, S, or O;
$R^{15}$ is independently selected from the group consisting of phenyl, 5 or 6-membered heterocyclic or heteroaryl, haloC$_1$-C$_6$alkyl, haloC$_2$-C$_6$alkenyl, halo, haloC$_1$-C$_6$alkoxy, C$_1$-C$_6$alkoxy, C$_1$-C$_6$alkoxyC$_1$-C$_6$alkyl, C$_1$-C$_6$alkyl, C$_2$-C$_6$alkenyl, C$_3$-C$_6$cycloalkyl, amino, CN, OH, and SH;
two adjacent $R^{15}$ form a fused C$_3$-C$_7$cycloalkyl or heterocyclic ring; two non-adjacent $R^{15}$ form a C$_1$-C$_3$alkylene; or two $R^{15}$ attached to the same carbon form a C$_3$-C$_7$cycloalkyl or heterocyclic ring, wherein the phenyl, heteroaryl, cycloalkyl or heterocyclic can be optionally substituted with $R^{13}$ selected from the group consisting of haloC$_1$-C$_6$alkyl, haloC$_2$-C$_6$alkenyl, halo, haloC$_1$-C$_6$alkoxy, C$_1$-C$_6$alkoxy, C$_1$-C$_6$alkoxyC$_1$-C$_6$alkyl, C$_1$-C$_6$alkyl, C$_2$-C$_6$alkenyl, amino, CN, OH, or SH;
$R^{16}$ is independently selected from the group consisting of H, haloC$_1$-C$_6$alkyl, haloC$_2$-C$_6$alkenyl, halo, haloC$_1$-C$_6$alkoxy, C$_1$-C$_6$alkoxy, C$_1$-C$_6$alkoxyC$_1$-C$_6$alkyl, C$_1$-C$_6$alkyl, C$_2$-C$_6$alkenyl, amino, CN, OH, and SH;
$R^{19}$ is independently selected from the group consisting of H, haloC$_1$-C$_6$alkyl, haloC$_2$-C$_6$alkenyl, C$_1$-C$_6$alkoxyC$_1$-C$_6$alkyl, C$_1$-C$_6$alkyl, C$_2$-C$_6$alkenyl;
f is 0, 1 or 2;
g is 0, 1 or 2;
j is independently 0, 1, 2, 3, 4, 5, 6, 7, or 8.

In one embodiment, $R^{15}$ is independently selected from the group consisting of phenyl, 5 or 6-membered heterocyclic or heteroaryl, haloC$_1$-C$_6$alkyl, haloC$_2$-C$_6$alkenyl, halo, haloC$_1$-C$_6$alkoxy, C$_1$-C$_6$alkoxy, C$_1$-C$_6$alkoxyC$_1$-C$_6$alkyl, C$_2$-C$_6$alkenyl, C$_3$-C$_6$cycloalkyl, amino, CN, OH, and SH;
two adjacent $R^{15}$ form a fused C$_3$-C$_7$cycloalkyl or heterocyclic ring; or two $R^{15}$ attached to the same carbon form a C$_3$-C$_7$cycloalkyl or heterocyclic ring, wherein the phenyl, heteroaryl, cycloalkyl or heterocyclic can be optionally substituted with $R^{13}$ selected from the group consisting of haloC$_1$-C$_6$alkyl, haloC$_2$-C$_6$alkenyl, halo, haloC$_1$-C$_6$alkoxy, C$_1$-C$_6$alkoxy, C$_1$-C$_6$alkoxyC$_1$-C$_6$alkyl, C$_1$-C$_6$alkyl, C$_2$-C$_6$alkenyl, amino, CN, OH, or SH;
$R^{16}$ is independently selected from the group consisting of H, haloC$_1$-C$_6$alkyl, haloC$_2$-C$_6$alkenyl, halo, haloC$_1$-C$_6$alkoxy, C$_1$-C$_6$alkoxy, C$_1$-C$_6$alkoxyC$_1$-C$_6$alkyl, C$_2$-C$_6$alkenyl, amino, CN, OH, and SH.

In another embodiment, $R^{15}$ is independently halo, C$_1$-C$_3$alkyl, C$_1$-C$_3$haloalkyl, C$_3$alkoxy, C$_1$-C$_3$alkoxyC$_1$-C$_3$alkyl, or NH$_2$.

In one embodiment, j is independently 0, 1 or 2.

In one embodiment, f is 0 or 1.

In one embodiment,

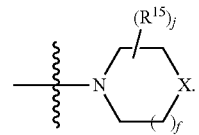

In a yet another aspect of the invention for the foregoing embodiments, $R^3$ is

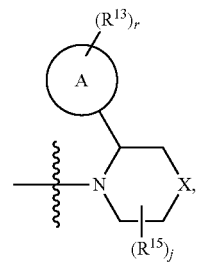

X is CR$^{16}{}_2$, S, or O;
$R^{13}$, $R^{15}$ and $R^{16}$ are independently H, haloC$_1$-C$_6$alkyl, haloC$_2$-C$_6$alkenyl, halo, haloC$_1$-C$_6$alkoxy, C$_1$-C$_6$alkoxy, C$_1$-C$_6$alkoxyC$_1$-C$_6$alkyl, C$_3$-C$_6$cycloalkyl, C$_2$-C$_6$alkenyl, amino, CN, OH, or SH;
A is phenyl, or 5-6 membered heteroaryl;
r is independently 0, 1, 2, 3, 4, or 5; and
j is independently 0, 1, 2, or 3.

In one embodiment, $R^{13}$, $R^{15}$ and $R^{16}$ are independently H, halo, C$_1$-C$_6$alkyl, C$_1$-C$_6$haloalkyl, C$_1$-C$_6$alkoxy or NH$_2$.

In one embodiment, r is independently 0 or 1; j is independently 0 or 1.

In another embodiment, X is O.

In a further embodiment, A is phenyl, pyridyl or oxadiazolyl.

In another embodiment,

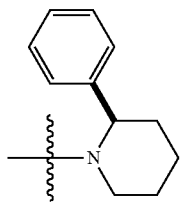 or 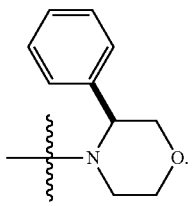

In a further embodiment,

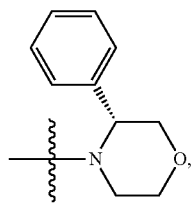 or 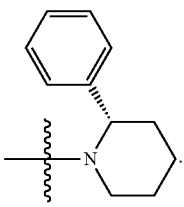

In another aspect of the invention for the foregoing embodiments, $R^3$ is

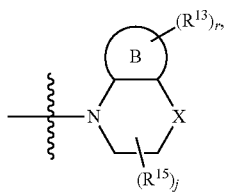

Ring B is a fused $C_3$-$C_7$cycloalkyl;
X is $CR^{16}_2$, S, or O;
$R^{13}$, $R^{15}$ and $R^{16}$ are independently H, haloC$_1$-C$_6$alkyl, haloC$_2$-C$_6$alkenyl, halo, haloC$_1$-C$_6$alkoxy, C$_1$-C$_6$alkoxy, C$_1$-C$_6$alkoxyC$_1$-C$_6$alkyl, C$_1$-C$_6$alkyl, C$_3$-C$_6$cycloalkyl, C$_2$-C$_6$alkenyl, amino, CN, OH, or SH;
r is independently 0, 1, 2, 3, 4, 5, 6, 7 or 8; and
j is independently 0, 1, 2, 3, or 4.
In one embodiment, $R^{13}$, $R^{15}$ and $R^{16}$ are independently H, halo, C$_1$-C$_6$alkyl, C$_1$-C$_6$haloalkyl, C$_1$-C$_6$alkoxy or NH$_2$.
In one embodiment, r is independently 0 or 1; j is independently 0 or 1.
In another embodiment, X is O.
In a further aspect of the invention for the foregoing embodiments, $R^3$ is

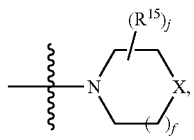

$R^{15}$ is independently haloC$_1$-C$_6$alkyl, haloC$_2$-C$_6$alkenyl, halo, haloC$_1$-C$_6$alkoxy, C$_1$-C$_6$alkoxy, C$_1$-C$_6$alkoxyC$_1$-C$_6$alkyl, C$_2$-C$_6$alkenyl, C$_3$-C$_6$cycloalkyl, amino, CN, OH, or SH; f is 0, 1 or 2; j is independently 0, 1, 2, 3, 4, 5, or 6.
In one embodiment, $R^{15}$ is independently halo, C$_1$-C$_3$alkyl, C$_1$-C$_3$haloalkyl, C$_1$-C$_3$alkoxy, C$_1$-C$_3$alkoxyC$_1$-C$_3$alkyl, or NH$_2$.
In one embodiment, j is independently 0, 1 or 2.
In one embodiment, f is 0 or 1.

In a further aspect of the invention for the foregoing embodiments, $R^3$ is

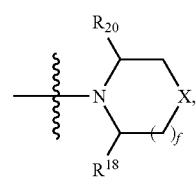

X is CH$_2$ or O;
$R^{18}$ and $R^{20}$ are independently H, haloC$_1$-C$_6$alkyl, haloC$_2$-C$_6$alkenyl, halo, haloC$_1$-C$_6$alkoxy, C$_1$-C$_6$alkoxy, C$_1$-C$_6$alkoxyC$_1$-C$_6$alkyl, C$_1$-C$_6$alkyl, C$_3$-C$_6$cycloalkyl, C$_2$-C$_6$alkenyl, amino, CN, OH, or SH; and
f is 0, 1 or 2.

In yet a further aspect of the invention for the foregoing embodiments, $R^3$ is

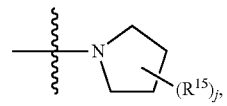

$R^{15}$ is independently haloC$_1$-C$_6$alkyl, haloC$_2$-C$_6$alkenyl, halo, haloC$_1$-C$_6$alkoxy, C$_1$-C$_6$alkoxy, C$_1$-C$_6$alkoxyC$_1$-C$_6$alkyl, C$_3$-C$_6$cycloalkyl, C$_2$-C$_6$alkenyl, amino, CN, OH, or SH;
j is independently 0, 1, 2, 3, or 4.
In one embodiment, $R^{15}$ is independently halo, C$_1$-C$_3$alkyl, C$_1$-C$_3$haloalkyl, C$_1$-C$_3$alkoxy, C$_1$-C$_3$alkoxyC$_1$-C$_3$alkyl, or NH$_2$.
In one embodiment, j is independently 0 or 1.

In another aspect of the invention,
$R^1$ is COOH, C(O)OR$^c$, C(O)NR$^c$R$^c$, C(O)NR$^c$SO$_2$R$^c$, C(O)NR$^c$SO$_2$NR$^c$R$^c$, NR$^c$SO$_2$R$^c$, wherein $R^d$ is methyl or H.

$R^2$ is 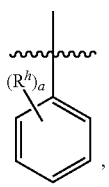, 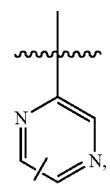, 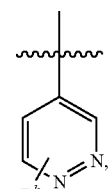,

-continued

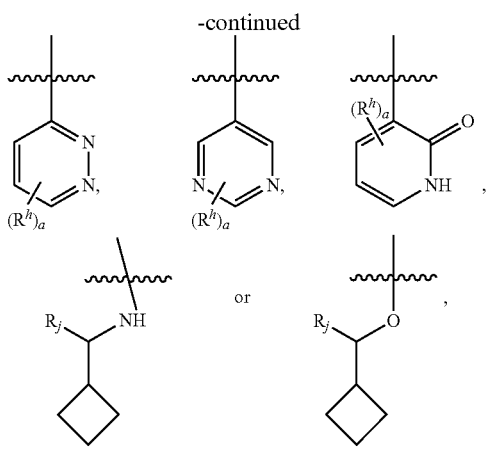

$R_j$ is H or methyl.
$R^h$ is independently halo, $NR^cR^c$, hydroxy$C_1$-$C_4$alkyl, hydroxy$C_1$-$C_4$alkoxy, —O$C_1$-$C_3$alkylO$C_1$-$C_3$alkyl, $C_1$-$C_4$alkyl or $C_1$-$C_4$alkoxy;
a is 0, 1 or 2;
$R^3$ is

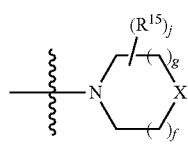

X is O, S, $NR^{16}$, $CR^{16}{}_2$, or $SO_2$;
$R^{15}$ is independently selected from the group consisting of phenyl, 5 or 6-membered heteroaryl, heterocyclic, halo$C_1$-$C_3$alkyl, halo, halo$C_1$-$C_3$alkoxy$C_0$-$C_3$alkyl, $C_1$-$C_3$alkoxy, $C_1$-$C_3$alkoxy$C_1$-$C_3$alkyl, $C_1$-$C_3$alkoxy$C_1$-$C_3$alkoxy, $C_1$-$C_3$alkoxy$C_3$-$C_5$cycloalkyl, $C_1$-$C_6$alkyl, $C_3$-$C_6$cycloalkyl, $C(O)R^f$, $C(O)NR^c{}_2$, and hydroxy$C_1$-$C_3$alkyl;
two non-adjacent $R^{15}$ form a $C_2$-$C_3$ alkylene bridge;
two adjacent $R^{15}$ form a fused $C_3$-$C_6$cycloalkyl or 4, 5 or 6-membered heterocyclic ring;
or two $R^{15}$ attached to the same carbon form =O, a $C_3$-$C_6$cycloalkyl or 5 or 6-membered heterocyclic ring, wherein the phenyl, heteroaryl, cycloalkyl or heterocyclic can be optionally substituted with halo, or $C_1$-$C_3$alkyl;
$R^{16}$ is independently selected from the group consisting of H, halo$C_1$-$C_3$alkyl, halo, halo$C_1$-$C_3$alkoxy$C_0$-$C_3$alkyl, $C_1$-$C_3$alkoxy, $C_1$-$C_3$alkoxy$C_1$-$C_3$alkyl, $C_1$-$C_6$alkyl, $C_3$-$C_6$cycloalkyl, $C(O)R^f$, $C(O)NR^c{}_2$, $S(O)_2R^c$, $C(O)OR^c$ and hydroxy$C_1$-$C_3$alkyl;
$R^c$ is independently H or $C_1$-$C_3$alkyl optionally substituted with halo or $C_1$-$C_3$alkoxy;
$R^{10}$ is independently $C_1$-$C_3$alkyl optionally substituted with halo;
$R^f$ is independently H, $C_1$-$C_3$alkyl or $C_3$-$C_4$cycloalkyl, wherein the alkyl or cycloalkyl is optionally substituted with halo, $C_1$-$C_3$alkoxy, or 4-6 membered heterocyclic;
f is 0, 1 or 2;
g is 0, or 1;
j is independently 0, 1, or 2;
or $R^3$ is $NR^8R^c$, T-$C_1$-$C_6$alkyl, -T-aryl, -T-heteroaryl, T-heterocyclic, T-$C_3$-$C_7$cycloalkyl, wherein the alkyl, aryl, heteroaryl, heterocyclic, and cycloalkyl can be optionally substituted with halo, $OR^c$, $SR^c$, $SO_2R^c$, halo$C_1$-$C_3$alkyl, halo$C_1$-$C_3$alkoxy, or $C_1$-$C_3$alkyl;

$R^8$ is H, $C_1$-$C_6$alkyl, aryl$C_1$-$C_6$alkyl, or heterocyclic, wherein the alkyl, aryl or heterocyclic is optionally substituted with $C_1$-$C_3$alkoxy, or halo$C_1$-$C_3$alkyl;
T is independently —(C$R^a{}_2$)—, —C(=CH$_2$)—, or —C(O)—;
$R^a$ is independently H, $OR^c$, halo, or $C_1$-$C_3$alkyl, said alkyl is optionally substituted with OH, $C_1$-$C_3$alkoxy, halo, or halo$C_1$-$C_3$alkyl;
$R^4$ is

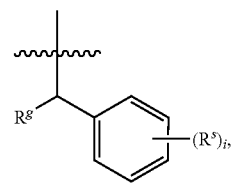

or

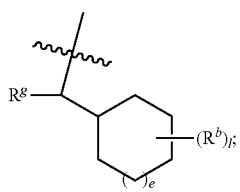

$R^b$ and $R^s$ are independently H, halo, halo$C_1$-$C_3$alkyl or $C_1$-$C_3$alkyl;
$R^g$ is H, C(O)NH$R^c$, or methyl;
i and I are independently 0, 1, 2, 3, 4 or 5; and
e is 0, 1 or 2.
In a further aspect of the invention,
$R^1$ is COOH, C(O)N$R^c$SO$_2R^c$, C(O)N$R^c$SO$_2$N$R^cR^c$,

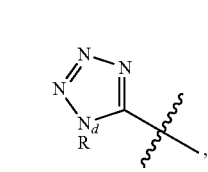 , 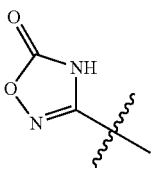 or

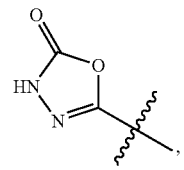 , wherein $R^d$ is methyl or H.
$R^2$ is

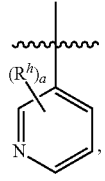 , 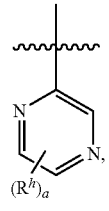 , 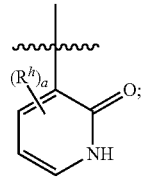 ;

$R^h$ is independently halo, hydroxy$C_1$-$C_4$alkyl, hydroxy$C_1$-$C_4$alkoxy, —O$C_1$-$C_3$alkylO$C_1$-$C_3$alkyl, $C_1$-$C_4$alkyl or $C_1$-$C_4$alkoxy;

a is 0, 1 or 2;

$R^3$ is

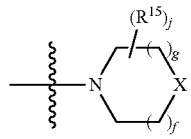

X is $NR^{16}$, $CR^{16}_2$, or $SO_2$;

$R^{15}$ is independently selected from the group consisting of phenyl, 5 or 6-membered heteroaryl, heterocyclic, halo$C_1$-$C_3$alkyl, halo, halo$C_1$-$C_3$alkoxy$C_0$-$C_3$alkyl, $C_1$-$C_3$alkoxy, $C_1$-$C_3$alkoxy$C_1$-$C_3$alkyl, $C_1$-$C_6$alkyl, $C_3$-$C_6$cycloalkyl, C(O)$R^f$, C(O)$NR^c_2$, and hydroxy$C_1$-$C_3$alkyl;

two non-adjacent $R^{15}$ form a $C_2$-$C_3$ alkylene bridge;

two adjacent $R^{15}$ form a fused $C_3$-$C_6$cycloalkyl or 5 or 6-membered heterocyclic ring;

or two $R^{15}$ attached to the same carbon form =O, a $C_3$-$C_6$cycloalkyl or 5 or 6-membered heterocyclic ring, wherein the phenyl, heteroaryl, cycloalkyl or heterocyclic can be optionally substituted with halo, or $C_1$-$C_3$alkyl;

$R^{16}$ is independently selected from the group consisting of H, halo$C_1$-$C_3$alkyl, halo, halo$C_1$-$C_3$alkoxy$C_0$-$C_3$alkyl, $C_1$-$C_3$alkoxy, $C_1$-$C_3$alkoxy$C_1$-$C_3$alkyl, $C_1$-$C_6$alkyl, $C_3$-$C_6$cycloalkyl, C(O)$R^f$, C(O)$NR^c_2$, and hydroxy$C_1$-$C_3$alkyl;

$R^c$ is independently H or $C_1$-$C_3$alkyl optionally substituted with halo;

$R^f$ is independently H, $C_1$-$C_3$alkyl or $C_3$-$C_4$cycloalkyl;

f is 0, 1 or 2;

g is 0, or 1;

j is independently 0, 1, or 2;

or $R^3$ is $NR^8R^c$, T-$C_1$-$C_6$alkyl, -T-aryl, -T-heteroaryl, T-heterocyclic, T-$C_3$-$C_7$cycloalkyl, wherein the alkyl, aryl, heteroaryl, heterocyclic, and cycloalkyl can be optionally substituted with halo, $OR^c$, $SO_2R^c$, halo$C_1$-$C_3$alkyl, halo$C_1$-$C_3$alkoxy, or $C_1$-$C_3$alkyl;

$R^8$ is H, $C_1$-$C_6$alkyl, aryl$C_1$-$C_6$alkyl, or heterocyclic, wherein the alkyl, aryl or heterocyclic is optionally substituted with $C_1$-$C_3$alkoxy, or halo$C_1$-$C_3$alkyl;

T is independently —(C$R^a_2$)—, —C(=CH$_2$)—, or —C(O)—;

$R^a$ is independently H, $OR^c$, halo, or $C_1$-$C_3$alkyl, said alkyl is optionally substituted with OH, $C_1$-$C_3$alkoxy, halo, or halo$C_1$-$C_3$alkyl;

$R^4$ is

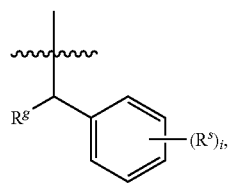

or

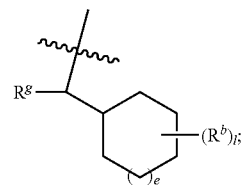

$R^b$ and $R^s$ are independently H, halo, halo$C_1$-$C_3$alkyl or $C_1$-$C_3$alkyl;

$R^g$ is H, C(O)$NHR^c$, or methyl;

i and l are independently 0, 1, 2, 3, 4 or 5; and e is 0, 1 or 2.

In one embodiment, $R^3$ is

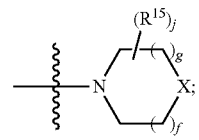

X is $NR^{16}$, $CR^{16}_2$, or $SO_2$;

$R^{15}$ is independently selected from the group consisting of phenyl, heteroaryl group selected from oxadiazol, oxazol, triazol, thiazol, and isooxazol, halo$C_1$-$C_3$alkyl, halo, halo$C_1$-$C_3$alkoxy$C_0$-$C_3$alkyl, $C_1$-$C_3$alkoxy, $C_1$-$C_3$alkoxy$C_1$-$C_3$alkyl, $C_1$-$C_6$alkyl, $C_3$-$C_6$cycloalkyl, C(O)$R^f$, C(O)$NR^c_2$, and hydroxy$C_1$-$C_3$alkyl;

two non-adjacent $R^{15}$ form a $C_2$-$C_3$alkylene bridge;

two adjacent $R^{15}$ form a fused $C_3$-$C_6$cycloalkyl, furo or pyrano ring;

or two $R^{15}$ attached to the same carbon form =O, a $C_3$-$C_6$cycloalkyl or 5 or 6-membered heterocyclic ring, wherein the phenyl, heteroaryl, cycloalkyl or heterocyclic can be optionally substituted with halo, or $C_1$-$C_3$alkyl;

In another embodiment, $R^2$ is

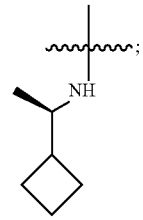 [SMILES: *N[C@H](C)C1CCC1]

$R^3$ is phenyl or pyridyl, wherein the phenyl or pyridyl can be optionally substituted with halo, $OR^c$, halo$C_1$-$C_3$alkyl, halo$C_1$-$C_3$alkoxy, or $C_1$-$C_3$alkyl;

In another embodiment, $R^3$ is

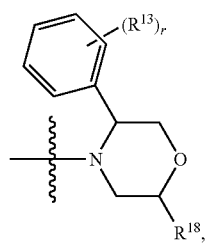 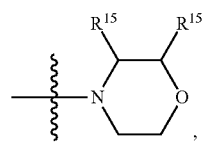

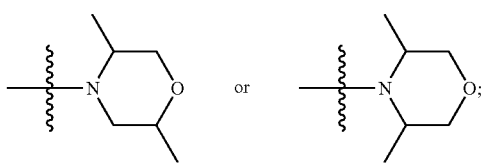 or 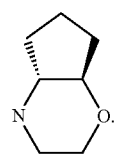

$R^{13}$ is independently H or halo;
$R^{15}$ is independently H or $C_1$-$C_6$alkyl;
$R^{18}$ is H or $C_1$-$C_6$alkyl; and
r is independently 0, 1, or 2;

In yet another embodiment, $R^3$ is

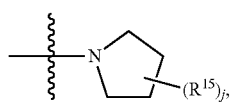

$R^{15}$ is independently a 5-membered heteroaryl, halo$C_1$-$C_6$alkyl, halo, halo$C_1$-$C_6$alkoxy, $C_1$-$C_6$alkoxy, $C_1$-$C_6$alkoxy$C_1$-$C_6$alkyl, $C_1$-$C_6$alkyl, $C_3$-$C_6$cycloalkyl, C(O)N($R^c$)$_2$, or OH;
j is independently 0, 1, 2, or 3.

In a further embodiment, $R^3$ is

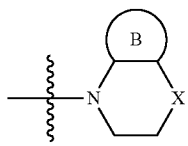

or

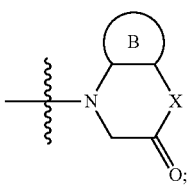

Ring B is a fused $C_3$-$C_6$cycloalkyl or fused 5 or 6-membered heterocyclic, wherein
O is the heteroatom;
X is $CH_2$, NH or O.

In yet a further embodiment, $R^3$ is

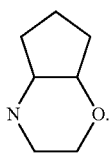

In yet one embodiment, $R^3$ is

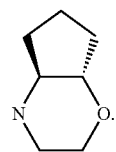

In yet a another embodiment, $R^3$ is

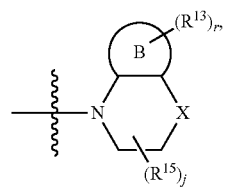

In a further embodiment, $R^3$ is

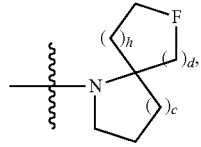

Ring B is a fused $C_3$-$C_6$cycloalkyl or fused 5 or 6-membered heterocyclic, wherein
O is the heteroatom in the heterocyclic;
X is $CH_2$, or NH;
$R^{13}$ is independently H, halo$C_1$-$C_3$alkyl, halo or $C_1$-$C_3$alkyl;
$R^{15}$ is independently H, halo$C_1$-$C_3$alkyl, halo, OH, C(O)$R^f$, $C_1$-$C_3$alkoxy, $C_1$-$C_3$alkyl,
or two $R^{15}$ from the same carbon form =O;
$R^f$ is independently H, $C_1$-$C_3$alkyl or $C_3$-$C_4$cycloalkyl;
r is independently 0, or 1; and
j is independently 0, or 1.

In yet a further embodiment, $R^3$ is

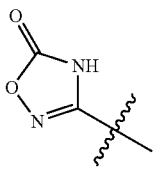

F is O or $CH_2$;
h is 0, 1 or 2;
c is 0, 1 or 2; and
d is 0, 1 or 2.

In another aspect of the foregoing embodiments, $R^1$ is COOH

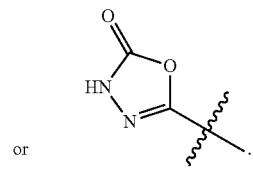

$R^2$ is $R^e$

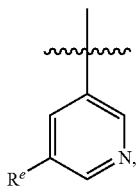

and $R^e$ is halo.

In yet a further aspect of the invention for the foregoing embodiments, $R^4$ is —CH$_2$—Y or —CH$_2$(CH$_3$)—Y, wherein Y is phenyl or cyclohexyl optionally substituted with haloC$_1$-C$_3$alkyl, haloC$_2$-C$_3$alkenyl, halo, C$_3$-C$_4$cycloalkyl, haloC$_1$-C$_3$alkoxy, C$_1$-C$_3$alkoxy, C$_2$-C$_3$alkenoxy, C$_1$-C$_3$alkyl, C$_2$-C$_3$alkenyl, amino, CN, OH, or SH.

In one embodiment, $R^4$ is —CH$_2$—Y or —CH$_2$(CH$_3$)—Y, wherein Y is phenyl or cyclohexyl, optionally substituted with CF$_3$, CHF$_2$, halo, cyclopropyl, OCF$_3$, OCH$_3$, methyl, amino, CN, OH, or SH.

In one embodiment,
$R^4$ is

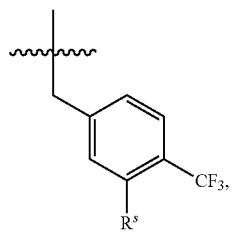

or

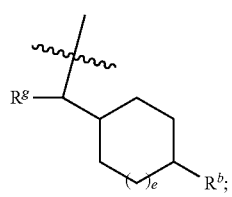

$R^b$ is H, haloC$_1$-C$_3$alkyl or C$_1$-C$_3$alkyl;
$R^g$ is H, or methyl;
$R^s$ is H or halo;
e is 0 or 1.

In one embodiment,
$R^4$ is

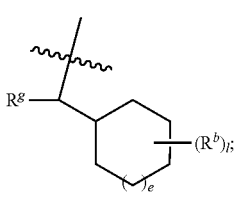

$R^b$ is independently H, halo, haloC$_1$-C$_3$alkyl or C$_1$-C$_3$alkyl;
$R^g$ is H, C(O)NHR$^c$, or methyl;

$R^c$ is independently H or C$_1$-C$_3$alkyl optionally substituted with halo;
I is 0, 1, 2, 3, 4 or 5; and
e is 0, 1 or 2.

In another embodiment, $R^4$ is CH$_2$-cyclohexyl,

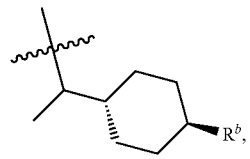

benzyl,

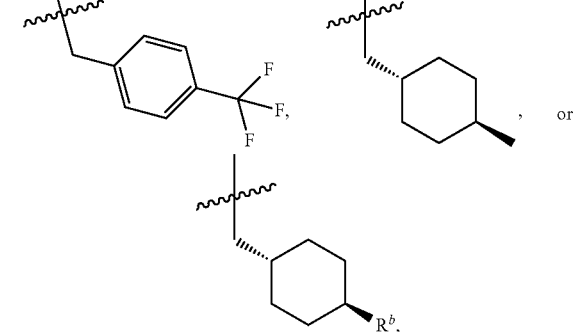

and $R^b$ is H, haloC$_1$-C$_3$alkyl, haloC$_2$-C$_3$alkenyl, halo, haloC$_1$-C$_3$alkoxy, C$_1$-C$_3$alkoxy, C$_1$-C$_3$alkyl, C$_2$-C$_3$alkenyl, amino, CN, OH, or SH.

In another embodiment, $R^4$ is $R^g$ and $R^b$ are independently H or methyl.
In a further embodiment, $R^4$ is In one embodiment, $R^4$ is

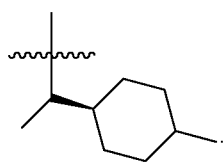

In a another embodiment, $R^4$ is

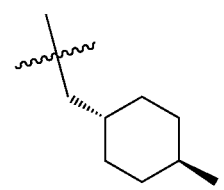 [SMILES: *C[C@H]1CC[C@H](C)CC1]

In yet a further embodiment, $R^4$ is

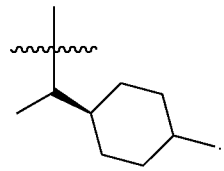

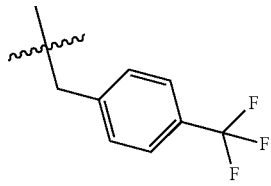 [SMILES: *Cc1ccc(C(F)(F)F)cc1]

or

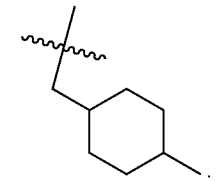 [SMILES: *CC1CCC(C)CC1]

In another embodiment, $R^4$ is

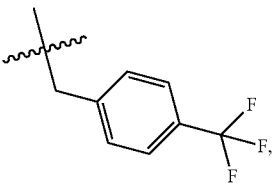 [SMILES: *Cc1ccc(C(F)(F)F)cc1]

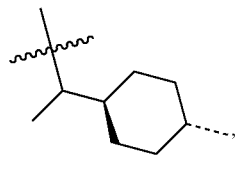 [SMILES: *C(C)[C@H]1CC[C@H](C)CC1]

or

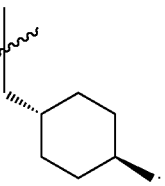

Specific examples of the compounds of the invention include, but not limited to:

(R)-4-((1-cyclobutylethyl)amino)-2-(4-isopropylpyridin-2-yl)-7-methyl-3-(4-(trifluoromethyl)benzyl)-3H-imidazo[4,5-c]pyridine-6-carboxylic acid;

4-{[(1R)-1-cyclobutylethyl]amino}-2-[4-(1-methylethyl)pyridin-2-yl]-3-[4-(trifluoromethyl)benzyl]-3H-imidazo[4,5-c]pyridine-6-carboxylic acid;

4-{[(1R)-1-cyclobutylethyl]amino}-2-(3-methylphenyl)-3-[4-(trifluoromethyl)benzyl]-3H-imidazo[4,5-c]pyridine-6-carboxylic acid;

4-{[(1R)-1-cyclobutylethyl]amino}-3-[(trans-4-methylcyclohexyl)methyl]-2-[4-(1-methylethyl)pyridin-2-yl]-3H-imidazo[4,5-c]pyridine-6-carboxylic acid;

3-{4-(5-chloropyridin-3-yl)-3-[(trans-4-methylcyclohexyl)methyl]-2-[(3R)-3-phenylmorpholin-4-yl]-3H-imidazo[4,5-c]pyridin-6-yl}-1,2,4-oxadiazol-5(4H)-one;

5-{4-(5-chloropyridin-3-yl)-3-[(trans-4-methylcyclohexyl)methyl]-2-[(3R)-3-phenylmorpholin-4-yl]-3H-imidazo[4,5-c]pyridin-6-yl}-1,3,4-oxadiazol-2(3H)-one;

3-{3-[(trans-4-methylcyclohexyl)methyl]-4-(3-methylphenyl)-2-[(3R)-3-phenylmorpholin-4-yl]-3H-imidazo[4,5-c]pyridin-6-yl}-1,2,4-oxadiazol-5(4H)-one;

3-{4-(3-chlorophenyl)-3-[(trans-4-methylcyclohexyl)methyl]-2-[(3R)-3-phenylmorpholin-4-yl]-3H-imidazo[4,5-c]pyridin-6-yl}-1,2,4-oxadiazol-5(4H)-one;

5-{4-(3-chlorophenyl)-3-[(trans-4-methylcyclohexyl)methyl]-2-[(3R)-3-phenylmorpholin-4-yl]-3H-imidazo[4,5-c]pyridin-6-yl}-1,3,4-oxadiazol-2(3H)-one;

3-{4-(5-chloropyridin-3-yl)-2-[(2S)-2-(fluoromethyl)pyrrolidin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-((4aR,7aR)-hexahydrocyclopenta[b][1,4]oxazin-4(4aH)-yl)-3-[(trans-4-methylcyclohexyl)methyl]-3H-imidazo[4,5-c]pyridin-6-yl}-1,2,4-oxadiazol-5(4H)-one;

3-(4-(5-chloropyridin-3-yl)-3-((trans-4-methylcyclohexyl)methyl)-2-(S)-2-(trifluoromethyl)pyrrolidin-1-yl)-3H-imidazo[4,5-c]pyridin-6-yl)-1,2,4-oxadiazol-5(4H)-one;

3-{4-(5-chloropyridin-3-yl)-2-(hexahydrocyclopenta[b][1,4]oxazin-4(4aH)-yl)-3-[(trans-4-methylcyclohexyl)methyl]-3H-imidazo[4,5-c]pyridin-6-yl}-1,2,4-oxadiazol-5(4H)-one;

3-[4-(5-chloropyridin-3-yl)-3-[(trans-4-methylcyclohexyl)methyl]-2-(octahydro-4H-1,4-benzoxazin-4-yl)-3H-imidazo[4,5-c]pyridin-6-yl]-1,2,4-oxadiazol-5(4H)-one;

5-{4-(5-chloropyridin-3-yl)-2-(hexahydrocyclopenta[b][1,4]oxazin-4(4aH)-yl)-3-[(trans-4-methylcyclohexyl)methyl]-3H-imidazo[4,5-c]pyridin-6-yl}-1,3,4-oxadiazol-2(3H)-one;

3-{4-(5-chloropyridin-3-yl)-2-[(2S)-2-(1-methoxy-1-methylethyl)pyrrolidin-1-yl]-3-[(trans-4-methylcyclohexyl)methyl]-3H-imidazo[4,5-c]pyridin-6-yl}-1,2,4-oxadiazol-5(4H)-one;

5-{4-(5-chloropyridin-3-yl)-2-[(2S)-2-(fluoromethyl)pyrrolidin-1-yl]-3-[(trans-4-methylcyclohexyl)methyl]-3H-imidazo[4,5-c]pyridin-6-yl}-1,3,4-oxadiazol-2(3H)-one;

3-{4-(5-chloropyridin-3-yl)-2-((4aS,7aS)-hexahydrocyclopenta[b][1,4]oxazin-4(4aH)-yl)-3-[(trans-4-methylcyclohexyl)methyl]-3H-imidazo[4,5-c]pyridin-6-yl}-1,2,4-oxadiazol-5(4H)-one;

3-[4-(5-chloropyridin-3-yl)-3-[(trans-4-methylcyclohexyl)methyl]-2-(octahydro-4H-1,4-benzoxazin-4-yl)-3H-imidazo[4,5-c]pyridin-6-yl]-1,2,4-oxadiazol-5(4H)-one;

5-[4-(5-chloropyridin-3-yl)-3-[(trans-4-methylcyclohexyl)methyl]-2-(octahydro-4H-1,4-benzoxazin-4-yl)-3H-imidazo[4,5-c]pyridin-6-yl]-1,3,4-oxadiazol-2(3H)-one;

5-{4-(5-chloropyridin-3-yl)-2-[(2S)-2-(1-methoxy-1-methylethyl)pyrrolidin-1-yl]-3-[(trans-4-methylcyclohexyl)methyl]-3H-imidazo[4,5-c]pyridin-6-yl}-1,3,4-oxadiazol-2(3H)-one;

5-{4-(5-chloropyridin-3-yl)-2-((4aS,7aS)-hexahydrocyclopenta[b][1,4]oxazin-4(4aH)-yl)-3-[(trans-4-methylcyclohexyl)methyl]-3H-imidazo[4,5-c]pyridin-6-yl}-1,3,4-oxadiazol-2(3H)-one;

5-{4-(5-chloropyridin-3-yl)-2-((4aR,7aR)-hexahydrocyclopenta[b][1,4]oxazin-4(4aH)-yl)-3-[(trans-4-methylcyclohexyl)methyl]-3H-imidazo[4,5-c]pyridin-6-yl}-1,3,4-oxadiazol-2(3H)-one;

3-{4-(5-chloropyridin-3-yl)-2-[(3R,5R)-3,5-dimethylmorpholin-4-yl]-3-[(trans-4-methylcyclohexyl)methyl]-3H-imidazo[4,5-c]pyridin-6-yl}-1,2,4-oxadiazol-5(4H)-one;

5-[4-(5-chloropyridin-3-yl)-3-[(trans-4-methylcyclohexyl)methyl]-2-(octahydro-4H-1,4-benzoxazin-4-yl)-3H-imidazo[4,5-c]pyridin-6-yl]-1,3,4-oxadiazol-2(3H)-one;

5-{4-(5-chloropyridin-3-yl)-2-[(3R,5R)-3,5-dimethylmorpholin-4-yl]-3-[(trans-4-methylcyclohexyl)methyl]-3H-imidazo[4,5-c]pyridin-6-yl}-1,3,4-oxadiazol-2(3H)-one;

5-{4-(5-chloropyridin-3-yl)-3-[(trans-4-methylcyclohexyl)methyl]-2-[(2S)-2-(trifluoromethyl)pyrrolidin-1-yl]-3H-imidazo[4,5-c]pyridin-6-yl}-1,3,4-oxadiazol-2(3H)-one;

4-(5-chloropyridin-3-yl)-3-[(trans-4-methylcyclohexyl)methyl]-2-[(3R)-3-phenylmorpholin-4-yl]-3H-imidazo[4,5-c]pyridine-6-carboxylic acid;

3-{4-(5-chloropyridin-3-yl)-3-[(trans-4-methylcyclohexyl)methyl]-2-[(3R)-3-methylmorpholin-4-yl]-3H-imidazo[4,5-c]pyridin-6-yl}-1,2,4-oxadiazol-5(4H)-one;

3-{4-(5-chloropyridin-3-yl)-2-[(3S,5S)-3,5-dimethylmorpholin-4-yl]-3-[(trans-4-methylcyclohexyl)methyl]-3H-imidazo[4,5-c]pyridin-6-yl}-1,2,4-oxadiazol-5(4H)-one;

3-{7-bromo-4-(5-chloropyridin-3-yl)-3-[(trans-4-methylcyclohexyl)methyl]-2-[(3R)-3-phenylmorpholin-4-yl]-3H-imidazo[4,5-c]pyridin-6-yl}-1,2,4-oxadiazol-5(4H)-one;

3-[4-(5-chloropyridin-3-yl)-3-[(trans-4-methylcyclohexyl)methyl]-2-(octahydro-1H-cyclopenta[b]pyridin-1-yl)-3H-imidazo[4,5-c]pyridin-6-yl]-1,2,4-oxadiazol-5(4H)-one;

3-{4-(5-chloropyridin-3-yl)-3-[(trans-4-methylcyclohexyl)methyl]-2-[6-(trifluoromethyl)-2-azabicyclo[3.1.0]hex-2-yl]-3H-imidazo[4,5-c]pyridin-6-yl}-1,2,4-oxadiazol-5(4H)-one;

3-{4-(5-chloropyridin-3-yl)-2-(3-ethylmorpholin-4-yl)-3-[(trans-4-methylcyclohexyl)methyl]-3H-imidazo[4,5-c]pyridin-6-yl}-1,2,4-oxadiazol-5(4H)-one;

3-[4-(5-chloropyridin-3-yl)-3-[(trans-4-methylcyclohexyl)methyl]-2-(2-oxa-5-azabicyclo[4.1.0]hept-5-yl)-3H-imidazo[4,5-c]pyridin-6-yl]-1,2,4-oxadiazol-5(4H)-one;

3-{4-(5-chloropyridin-3-yl)-2-(2,5-dimethylmorpholin-4-yl)-3-[(trans-4-methylcyclohexyl)methyl]-3H-imidazo[4,5-c]pyridin-6-yl}-1,2,4-oxadiazol-5(4H)-one;

3-[4-(5-chloropyridin-3-yl)-3-[(trans-4-methylcyclohexyl)methyl]-2-(3-methyl-1,4-oxazepan-4-yl)-3H-imidazo[4,5-c]pyridin-6-yl]-1,2,4-oxadiazol-5(4H)-one;

3-{4-(5-chloropyridin-3-yl)-3-[(trans-4-methylcyclohexyl)methyl]-2-[2-(1-methylethyl)pyrrolidin-1-yl]-3H-imidazo[4,5-c]pyridin-6-yl}-1,2,4-oxadiazol-5(4H)-one;

3-{4-(5-chloropyridin-3-yl)-2-[(2R,5R)-2,5-dimethylpyrrolidin-1-yl]-3-[(trans-4-methylcyclohexyl)methyl]-3H-imidazo[4,5-c]pyridin-6-yl}-1,2,4-oxadiazol-5(4H)-one;

4-(5-chloropyridin-3-yl)-3-[(trans-4-methylcyclohexyl)methyl]-2-[(2S)-2-(trifluoromethyl)pyrrolidin-1-yl]-3H-imidazo[4,5-c]pyridine-6-carboxylic acid;

3-{4-(5-chloropyridin-3-yl)-2-[3-(2-fluorophenyl)morpholin-4-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[2-(1-methoxyethyl)pyrrolidin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[3-(2-fluorophenyl)morpholin-4-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-(2,3-dimethylpyrrolidin-1-yl)-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-(2-cyclopropylpyrrolidin-1-yl)-3-[(trans-4-methylcyclohexyl)methyl]-3H-imidazo[4,5-c]pyridin-6-yl}-1,2,4-oxadiazol-5(4H)-one;

3-{2-(2-tert-butylpyrrolidin-1-yl)-4-(5-chloropyridin-3-yl)-3-[(trans-4-methylcyclohexyl)methyl]-3H-imidazo[4,5-c]pyridin-6-yl}-1,2,4-oxadiazol-5(4H)-one;

3-{2-(5-azaspiro[3.4]oct-5-yl)-4-(5-chloropyridin-3-yl)-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[2-(1,1-dimethylpropyl)pyrrolidin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-3-[(trans-4-methylcyclohexyl)methyl]-2-[2-(4-methyl-1,2,5-oxadiazol-3-yl)pyrrolidin-1-yl]-3H-imidazo[4,5-c]pyridin-6-yl}-1,2,4-oxadiazol-5(4H)-one;

3-{4-(5-chloropyridin-3-yl)-3-[(trans-4-methylcyclohexyl)methyl]-2-[(2R)-2-methylpiperidin-1-yl]-3H-imidazo[4,5-c]pyridin-6-yl}-1,2,4-oxadiazol-5(4H)-one; and 3-{4-(5-chloropyridin-3-yl)-2-[(2R,4R)-4-hydroxy-2-methylpyrrolidin-1-yl]-3-[(trans-4-methylcyclohexyl)methyl]-3H-imidazo[4,5-c]pyridin-6-yl}-1,2,4-oxadiazol-5(4H)-one;

or a stereoisomer thereof;
or a pharmaceutically acceptable salt thereof;
or a pharmaceutically acceptable salt of the stereoisomer thereof.

Other specific examples of the compounds of the invention include, but not limited to:

3-{4-(5-chloropyridin-3-yl)-3-[(trans-4-methylcyclohexyl)methyl]-2-[2-(4-methyl-1,2,5-oxadiazol-3-yl)pyrrolidin-1-yl]-3H-imidazo[4,5-c]pyridin-6-yl}-1,2,4-oxadiazol-5(4H)-one;

4-(5-chloropyridin-3-yl)-2-((4aR,7aR)-hexahydrocyclopenta[b][1,4]oxazin-4(4aH)-yl)-3-((trans-4-methylcyclohexyl)methyl)-3H-imidazo[4,5-c]pyridine-6-carboxylic acid;

4-(5-chloropyridin-3-yl)-2-[(2S)-2-(fluoromethyl)pyrrolidin-1-yl]-3-[(trans-4-methylcyclohexyl)methyl]-3H-imidazo[4,5-c]pyridine-6-carboxylic acid;

3-[4-(5-chloropyridin-3-yl)-3-[(trans-4-methylcyclohexyl)methyl]-2-(trans-2-methyl-5-phenylmorpholin-4-yl)-3H-imidazo[4,5-c]pyridin-6-yl]-1,2,4-oxadiazol-5(4H)-one;

3-{4-(5-chloropyridin-3-yl)-2-[(2R,4R)-4-methoxy-2-methylpyrrolidin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-(hexahydro-4H-furo[3,4-b][1,4]oxazin-4-yl)-3-[(trans-4-methylcyclohexyl)methyl]-3H-imidazo[4,5-c]pyridin-6-yl}-1,2,4-oxadiazol-5(4H)-one;

1-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-N,N-dimethyl-D-prolinamide;

1-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-N-ethyl-N-methyl-D-prolinamide;

3-{4-(5-chloropyridin-3-yl)-2-[2-(3-ethyl-5-methyl isoxazol-4-yl)pyrrolidin-1-yl]-3-[(trans-4-methylcyclohexyl)methyl]-3H-imidazo[4,5-c]pyridin-6-yl}-1,2,4-oxadiazol-5(4H)-one;

3-[4-(5-chloropyridin-3-yl)-3-[(trans-4-methylcyclohexyl)methyl]-2-{2-[(1-methylethoxy)methyl]pyrrolidin-1-yl}-3H-imidazo[4,5-c]pyridin-6-yl]-1,2,4-oxadiazol-5(4H)-one;

3-[4-(5-chloropyridin-3-yl)-3-[(trans-4-methylcyclohexyl)methyl]-2-{2-[(trifluoromethoxy)methyl]pyrrolidin-1-yl}-3H-imidazo[4,5-c]pyridin-6-yl]-1,2,4-oxadiazol-5(4H)-one;

3-{4-(5-chloropyridin-3-yl)-3-[(trans-4-methylcyclohexyl)methyl]-2-[(2R)-2-methylpyrrolidin-1-yl]-3H-imidazo[4,5-c]pyridin-6-yl}-1,2,4-oxadiazol-5(4H)-one;

3-{4-(5-chloropyridin-3-yl)-2-[(2S)-2-(methoxymethyl)pyrrolidin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(2S)-2-(difluoromethyl)pyrrolidin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-(trans-2,3-dimethylmorpholin-4-yl)-3-[(trans-4-methylcyclohexyl)methyl]-3H-imidazo[4,5-c]pyridin-6-yl}-1,2,4-oxadiazol-5(4H)-one;

3-[4-(5-chloropyridin-3-yl)-3-[(trans-4-methylcyclohexyl)methyl]-2-(7-oxa-1-azaspiro[4.4]non-1-yl)-3H-imidazo[4,5-c]pyridin-6-yl]-1,2,4-oxadiazol-5(4H)-one;

3-[4-(5-chloropyridin-3-yl)-3-[(trans-4-methylcyclohexyl)methyl]-2-(8-oxa-1-azaspiro[4.5]dec-1-yl)-3H-imidazo[4,5-c]pyridin-6-yl]-1,2,4-oxadiazol-5(4H)-one;

3-{4-(5-chloropyridin-3-yl)-2-(hexahydro-2H-pyrano[4,3-b]pyridin-1(5H)-yl)-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-3-[(trans-4-methylcyclohexyl)methyl]-2-[2-(1H-1,2,3-triazol-5-yl)pyrrolidin-1-yl]-3H-imidazo[4,5-c]pyridin-6-yl}-1,2,4-oxadiazol-5(4H)-one;

3-{4-(5-chloropyridin-3-yl)-3-[(trans-4-methylcyclohexyl)methyl]-2-[2-(1-methyl-1H-1,2,4-triazol-3-yl)pyrrolidin-1-yl]-3H-imidazo[4,5-c]pyridin-6-yl}-1,2,4-oxadiazol-5(4H)-one;

3-{4-(5-chloropyridin-3-yl)-3-[(trans-4-methylcyclohexyl)methyl]-2-[2-(1-methyl-1H-1,2,4-triazol-5-yl)pyrrolidin-1-yl]-3H-imidazo[4,5-c]pyridin-6-yl}-1,2,4-oxadiazol-5(4H)-one;

3-{4-(5-chloropyridin-3-yl)-3-[(trans-4-methylcyclohexyl)methyl]-2-[(2S)-2-(1,3-thiazol-2-yl)pyrrolidin-1-yl]-3H-imidazo[4,5-c]pyridin-6-yl}-1,2,4-oxadiazol-5(4H)-one;

3-{4-(5-chloropyridin-3-yl)-3-[(trans-4-methylcyclohexyl)methyl]-2-[2-(3-methylisoxazol-5-yl)pyrrolidin-1-yl]-3H-imidazo[4,5-c]pyridin-6-yl}-1,2,4-oxadiazol-5(4H)-one;

3-{4-(5-chloropyridin-3-yl)-2-[2-(3,5-dimethyl isoxazol-4-yl)pyrrolidin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-3-[(trans-4-methylcyclohexyl)methyl]-2-[2-(3-methyl-1,2,4-oxadiazol-5-yl)pyrrolidin-1-yl]-3H-imidazo[4,5-c]pyridin-6-yl}-1,2,4-oxadiazol-5(4H)-one;

1-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-N-ethyl-D-prolinamide;

(5R)-4-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-1,5-dimethylpiperazin-2-one;

3-{4-(5-chloropyridin-3-yl)-2-[(2R)-5-methoxy-2-methylpiperidin-1-yl]-3-[(trans-4-methylcyclohexyl)methyl]-3H-imidazo[4,5-c]pyridin-6-yl}-1,2,4-oxadiazol-5(4H)-one;

3-[4-(5-chloropyridin-3-yl)-3-[(trans-4-methylcyclohexyl)methyl]-2-(3-methyl-1,1-dioxidothiomorpholin-4-yl)-3H-imidazo[4,5-c]pyridin-6-yl]-1,2,4-oxadiazol-5(4H)-one;

3-{4-(5-chloropyridin-3-yl)-2-(2-methoxy-7-azabicyclo[2.2.1]hept-7-yl)-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(2S,4R)-4-methoxy-2-(1-methylethyl)pyrrolidin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(2S,4R)-4-hydroxy-2-(1-methylethyl)pyrrolidin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(2S,4R)-2-(fluoromethyl)-4-methoxypyrrolidin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(2R,4R)-2-(fluoromethyl)-4-methoxypyrrolidin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(4aR,7aR)-hexahydrocyclopenta[b][1,4]oxazin-4(4aH)-yl]-3-[1-(trans-4-methylcyclohexyl)ethyl]-3H-imidazo[4,5-c]pyridin-6-yl}-1,2,4-oxadiazol-5(4H)-one;

3-(4-(5-chloropyridin-3-yl)-3-(1-(trans-4-methylcyclohexyl)ethyl)-2-((R)-3-methylmorpholino)-3H-imidazo[4,5-c]pyridin-6-yl)-1,2,4-oxadiazol-5(4H)-one;

(5R)-4-[4-(5-chloropyridin-3-yl)-3-[(1R)-1-(4-methylcyclohexyl)ethyl]-6-(5-oxo-4,5-dihydro-1,2,4-oxadiazol-3-yl)-3H-imidazo[4,5-c]pyridin-2-yl]-1,5-dimethylpiperazin-2-one;

3-{4-(5-chloropyridin-3-yl)-2-[(2S,4R)-2-(fluoromethyl)-4-methoxypyrrolidin-1-yl]-3-[(1R)-1-(4-methylcyclohexyl)ethyl]-3H-imidazo[4,5-c]pyridin-6-yl}-1,2,4-oxadiazol-5(4H)-one;

3-(4-(5-chloropyridin-3-yl)-2-((2S,4R)-4-hydroxy-2-isopropylpyrrolidin-1-yl)-3-((R)-1-(trans-4-methylcyclohexyl)ethyl)-3H-imidazo[4,5-c]pyridin-6-yl)-1,2,4-oxadiazol-5(4H)-one;

3-(4-(5-chloropyridin-3-yl)-2-((2R,4R)-4-methoxy-2-methylpyrrolidin-1-yl)-3-((R)-1-(trans-4-methylcyclohexyl)ethyl)-3H-imidazo[4,5-c]pyridin-6-yl)-1,2,4-oxadiazol-5(4H)-one;

3-(4-(5-chloropyridin-3-yl)-2-((2R,4R)-4-hydroxy-2-methylpyrrolidin-1-yl)-3-((R)-1-(trans-4-methylcyclohexyl)ethyl)-3H-imidazo[4,5-c]pyridin-6-yl)-1,2,4-oxadiazol-5(4H)-one;

3-{2-[(2R)-4-acetyl-2-methylpiperazin-1-yl]-4-(5-chloropyridin-3-yl)-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(2R)-4-(cyclopropylcarbonyl)-2-methylpiperazin-1-yl]-3-[(trans-4-methylcyclohexyl)methyl]-3H-imidazo[4,5-c]pyridin-6-yl}-1,2,4-oxadiazol-5(4H)-one;

3-{2-[(2R,6R)-4-acetyl-2,6-dimethylpiperazin-1-yl]-4-(5-chloropyridin-3-yl)-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(2R,6R)-4-(cyclopropylcarbonyl)-2,6-dimethylpiperazin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[cyclopentyl(ethoxy)methyl]-3-[(trans-4-methylcyclohexyl)methyl]-3H-imidazo[4,5-c]pyridin-6-yl}-1,2,4-oxadiazol-5(4H)-one;

5-{4-(5-chloropyridin-3-yl)-2-[cyclopentyl(ethoxy)methyl]-3-[(trans-4-methylcyclohexyl)methyl]-3H-imidazo[4,5-c]pyridin-6-yl}-1,3,4-oxadiazol-2(3H)-one;

3-(4-(5-chloropyridin-3-yl)-2-(1-ethoxyethyl)-3-((trans-4-methylcyclohexyl)methyl)-3H-imidazo[4,5-c]pyridin-6-yl)-1,2,4-oxadiazol-5(4H)-one;

3-(4-(5-chloropyridin-3-yl)-2-(1-ethoxypropyl)-3-((trans-4-methylcyclohexyl)methyl)-3H-imidazo[4,5-c]pyridin-6-yl)-1,2,4-oxadiazol-5(4H)-one;

3-(4-(5-chloropyridin-3-yl)-3-((trans-4-methylcyclohexyl)methyl)-2-(1-(2,2,2-trifluoroethoxy)propyl)-3H-imidazo[4,5-c]pyridin-6-yl)-1,2,4-oxadiazol-5(4H)-one;

3-(4-(5-chloropyridin-3-yl)-3-((trans-4-methylcyclohexyl)methyl)-2-(1-propoxypropyl)-3H-imidazo[4,5-c]pyridin-6-yl)-1,2,4-oxadiazol-5(4H)-one;

3-{4-(5-chloropyridin-3-yl)-2-[ethoxy(phenyl)methyl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(2,4-difluorophenyl)(hydroxy)methyl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(2-fluorophenyl)(hydroxy)methyl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-(1-hydroxy-2-methoxy-1-phenylethyl)-3-[(trans-4-methylcyclohexyl)methyl]-3H-imidazo[4,5-c]pyridin-6-yl}-1,2,4-oxadiazol-5(4H)-one;

3-(4-(5-chloropyridin-3-yl)-2-(ethoxy(pyridin-2-yl)methyl)-3-((trans-4-methylcyclohexyl)methyl)-3H-imidazo[4,5-c]pyridin-6-yl)-1,2,4-oxadiazol-5(4H)-one;

3-(4-(5-chloropyridin-3-yl)-2-(ethoxy(pyridin-3-yl)methyl)-3-((trans-4-methylcyclohexyl)methyl)-3H-imidazo[4,5-c]pyridin-6-yl)-1,2,4-oxadiazol-5(4H)-one;

3-{4-(5-chloropyridin-3-yl)-2-[(2-fluorophenyl)carbonyl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[1-fluoro-1-(2-fluorophenyl)ethyl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[1-(2,4-difluorophenyl)-1-fluoroethyl]-3-[(trans-4-methylcyclohexyl)methyl]-3H-imidazo[4,5-c]pyridin-6-yl}-1,2,4-oxadiazol-5(4H)-one;

3-[4-(5-chloropyridin-3-yl)-3-[(trans-4-methylcyclohexyl)methyl]-2-(1-phenylethenyl)-3H-imidazo[4,5-c]pyridin-6-yl]-1,2,4-oxadiazol-5(4H)-one;

3-{4-(5-chloropyridin-3-yl)-2-(2-methoxy-1-phenylethyl)-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[1-(2-fluorophenyl)ethenyl]-3-[(trans-4-methylcyclohexyl)methyl]-3H-imidazo[4,5-c]pyridin-6-yl}-1,2,4-oxadiazol-5(4H)-one; and 3-[4-(5-chloropyridin-3-yl)-3-[(trans-4-methylcyclohexyl)methyl]-2-(1-methylidenebutyl)-3H-imidazo[4,5-c]pyridin-6-yl]-1,2,4-oxadiazol-5(4H)-one; or a stereoisomer thereof;
or a pharmaceutically acceptable salt thereof;
or a pharmaceutically acceptable salt of the stereoisomer thereof.

Additional specific examples of the compounds of the invention include, but not limited to:

3-{4-(5-chloropyridin-3-yl)-3-[(trans-4-methylcyclohexyl)methyl]-2-[methyl(2,2,2-trifluoroethyl)amino]-3H-imidazo[4,5-c]pyridin-6-yl}-1,2,4-oxadiazol-5(4H)-one;

3-(4-(5-chloropyridin-3-yl)-2-((trans-4-methoxytetrahydrofuran-3-yl)(methyl)amino)-3-((trans-4-methylcyclohexyl)methyl)-3H-imidazo[4,5-c]pyridin-6-yl)-1,2,4-oxadiazol-5(4H)-one;

3-{4-(5-chloropyridin-3-yl)-3-[(trans-4-methylcyclohexyl)methyl]-2-[2-(1-methyl-1H-1,2,3-triazol-4-yl)pyrrolidin-1-yl]-3H-imidazo[4,5-c]pyridin-6-yl}-1,2,4-oxadiazol-5(4H)-one;

1-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-N-ethyl-N-methyl-L-prolinamide;

3-{4-(5-chloropyridin-3-yl)-2-[(2-fluorophenyl)amino]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[2-(1-ethyl-1H-pyrazol-5-yl)pyrrolidin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-3-[(trans-4-methylcyclohexyl)methyl]-2-[2-(1-methyl-1H-pyrazol-4-yl)pyrrolidin-1-yl]-3H-imidazo[4,5-c]pyridin-6-yl}-1,2,4-oxadiazol-5(4H)-one;

3-{4-(5-chloropyridin-3-yl)-3-[(trans-4-methylcyclohexyl)methyl]-2-[2-(5-methyl-1,2,4-oxadiazol-3-yl)pyrrolidin-1-yl]-3H-imidazo[4,5-c]pyridin-6-yl}-1,2,4-oxadiazol-5(4H)-one;

3-{4-(5-chloropyridin-3-yl)-3-[(trans-4-methylcyclohexyl)methyl]-2-[2-(3-methyl-1,2,4-oxadiazol-5-yl)pyrrolidin-1-yl]-3H-imidazo[4,5-c]pyridin-6-yl}-1,2,4-oxadiazol-5(4H)-one;

3-[4-(5-chloropyridin-3-yl)-3-[(trans-4-methylcyclohexyl)methyl]-2-(6-oxa-1-azaspiro[3.3]hept-1-yl)-3H-imidazo[4,5-c]pyridin-6-yl]-1,2,4-oxadiazol-5(4H)-one;

3-{4-(5-chloropyridin-3-yl)-2-[(2-methoxy-2-methylpropyl)(methyl)amino]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-3-[(trans-4-methylcyclohexyl)methyl]-2-[2-(2-methyl-1,3-thiazol-4-yl)pyrrolidin-1-yl]-3H-imidazo[4,5-c]pyridin-6-yl}-1,2,4-oxadiazol-5(4H)-one;

3-{4-(5-chloropyridin-3-yl)-2-[(2-methoxyethyl)(methyl)amino]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[ethyl(2-methoxyethyl)amino]-3-[(trans-4-methylcyclohexyl)methyl]-3H-imidazo[4,5-c]pyridin-6-yl}-1,2,4-oxadiazol-5(4H)-one;

1-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-N,N-dimethyl-L-prolinamide;

3-{4-(5-chloropyridin-3-yl)-2-[(2-methoxyethyl)(propyl)amino]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-3-[(trans-4-methylcyclohexyl)methyl]-2-[(1-pyridin-2-ylethyl)amino]-3H-imidazo[4,5-c]pyridin-6-yl}-1,2,4-oxadiazol-5(4H)-one;

1-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-N-ethyl-L-prolinamide;

3-{2-[(2S,5S)-2,5-bis(methoxymethyl)pyrrolidin-1-yl]-4-(5-chloropyridin-3-yl)-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[cis-4-methoxy-2-methylpiperidin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[trans-4-methoxy-2-methylpiperidin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[cis-4-methoxy-2-methylpiperidin-1-yl]-3-[(trans-4-methylcyclohexyl)methyl]-3H-imidazo[4,5-c]pyridin-6-yl}-1,2,4-oxadiazol-5(4H)-one;

(4aS,7aS)-4-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-1-methyloctahydro-2H-cyclopenta[b]pyrazin-2-one;

4-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-5-ethyl-1-methylpiperazin-2-one;

3-{4-(5-chloropyridin-3-yl)-2-(hexahydro-2H-pyrano[4,3-b]pyridin-1(5H)-yl)-3-[(trans-4-methylcyclohexyl)methyl]-3H-imidazo[4,5-c]pyridin-6-yl}-1,2,4-oxadiazol-5(4H)-one;

benzyl (4aR,8aR)-1-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]octahydro-6H-pyrido[3,4-b][1,4]oxazine-6-carboxylate;

3-{4-(5-chloropyridin-3-yl)-3-[(trans-4-methylcyclohexyl)methyl]-2-[(4aR,8aR)-octahydro-1H-pyrido[3,4-b][1,4]oxazin-1-yl]-3H-imidazo[4,5-c]pyridin-6-yl}-1,2,4-oxadiazol-5(4H)-one;

3-{2-[(4aR,8aR)-6-benzyloctahydro-1H-pyrido[3,4-b][1,4]oxazin-1-yl]-4-(5-chloropyridin-3-yl)-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-(2-hydroxy-7-azabicyclo[2.2.1]hept-7-yl)-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-(2-methoxy-7-azabicyclo[2.2.1]hept-7-yl)-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(2S,4S)-4-hydroxy-4-methyl-2-(1-methylethyl)pyrrolidin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(2S,4R)-4-methoxy-2-(methoxymethyl)pyrrolidin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-(3-hydroxyoctahydroquinolin-1(2H)-yl)-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(2S,4R)-4-methoxy-2-(1-methoxycyclopropyl)pyrrolidin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(2R,4R)-4-methoxy-2-(1-methoxycyclopropyl)pyrrolidin-1-yl]-3-[(trans-4-methylcyclohexyl)methyl]-3H-imidazo[4,5-c]pyridin-6-yl}-1,2,4-oxadiazol-5(4H)-one;

3-[4-(5-chloropyridin-3-yl)-3-[(trans-4-methylcyclohexyl)methyl]-2-(3-methylthiomorpholin-4-yl)-3H-imidazo[4,5-c]pyridin-6-yl]-1,2,4-oxadiazol-5(4H)-one;

3-{4-(5-chloropyridin-3-yl)-2-[(2S,4R)-2-(difluoromethyl)-4-methoxypyrrolidin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(2S,4R)-4-ethoxy-2-(fluoromethyl)pyrrolidin-1-yl]-3-[(trans-4-methylcyclohexyl)methyl]-3H-imidazo[4,5-c]pyridin-6-yl}-1,2,4-oxadiazol-5(4H)-one;

(4aR,7aR)-4-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-1-ethyloctahydro-2H-cyclopenta[b]pyrazin-2-one;

3-{4-(5-chloropyridin-3-yl)-2-[(2S,4R)-4-(2-methoxyethoxy)-2-(1-methylethyl)pyrrolidin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(trans)-5,5-difluorohexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-3-[(trans-4-methylcyclohexyl)methyl]-2-[(trans)-3-methylhexahydrocyclopenta[b][1,4]oxazin-4(4aH)-yl]-3H-imidazo[4,5-c]pyridin-6-yl}-1,2,4-oxadiazol-5(4H)-one;

3-{4-(5-chloropyridin-3-yl)-2-[(2R,3R)-3-ethyl-2-methylmorpholin-4-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(trans)-6,6-difluorohexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-3-[(trans-4-methylcyclohexyl)methyl]-2-[(3R)-3-pyridin-2-ylmorpholin-4-yl]-3H-imidazo[4,5-c]pyridin-6-yl}-1,2,4-oxadiazol-5(4H)-one;

3-{4-(5-chloropyridin-3-yl)-2-(hexahydro-4H,5H-pyrano[4,3-b][1,4]oxazin-4-yl)-3-[(trans-4-methylcyclohexyl)methyl]-3H-imidazo[4,5-c]pyridin-6-yl}-1,2,4-oxadiazol-5(4H)-one;

3-[4-(5-chloropyridin-3-yl)-3-[(trans-4-methylcyclohexyl)methyl]-2-(2-methylhexahydro-4H,5H-pyrano[4,3-b][1,4]oxazin-4-yl)-3H-imidazo[4,5-c]pyridin-6-yl]-1,2,4-oxadiazol-5(4H)-one;

3-{4-(5-chloropyridin-3-yl)-2-[(trans)-hexahydro-4H-furo[3,4-b][1,4]oxazin-4-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(trans)-6-fluorohexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-(hexahydro-2H-cyclopenta[b][1,4]oxazepin-5(5aH)-yl)-3-[(trans-4-methylcyclohexyl)methyl]-3H-imidazo[4,5-c]pyridin-6-yl}-1,2,4-oxadiazol-5(4H)-one;

3-[4-(5-chloropyridin-3-yl)-3-[(trans-4-methylcyclohexyl)methyl]-2-(2,2,3-trimethylmorpholin-4-yl)-3H-imidazo[4,5-c]pyridin-6-yl]-1,2,4-oxadiazol-5(4H)-one;

3-[4-(5-chloropyridin-3-yl)-3-[(trans-4-methylcyclohexyl)methyl]-2-(2-methyloctahydro-4H-1,4-benzoxazin-4-yl)-3H-imidazo[4,5-c]pyridin-6-yl]-1,2,4-oxadiazol-5(4H)-one;

3-{2-(benzylamino)-4-(5-chloropyridin-3-yl)-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(2-methoxy-1-methylethyl)amino]-3-[(trans-4-methylcyclohexyl)methyl]-3H-imidazo[4,5-c]pyridin-6-yl}-1,2,4-oxadiazol-5(4H)-one;

3-{2-[benzyl(methyl)amino]-4-(5-chloropyridin-3-yl)-3-[(trans-4-methylcyclohexyl)methyl]-3H-imidazo[4,5-c]pyridin-6-yl}-1,2,4-oxadiazol-5(4H)-one;

3-[4-(5-chloropyridin-3-yl)-3-[(trans-4-methylcyclohexyl)methyl]-2-(2-methylhexahydrocyclopenta[b][1,4]oxazin-4(4aH)-yl)-3H-imidazo[4,5-c]pyridin-6-yl]-1,2,4-oxadiazol-5(4H)-one;

3-{4-(5-chloropyridin-3-yl)-3-[(trans-4-methylcyclohexyl)methyl]-2-[(2R,3R)-2,3,6-trimethylmorpholin-4-yl]-3H-imidazo[4,5-c]pyridin-6-yl}-1,2,4-oxadiazol-5(4H)-one;

3-{4-(5-chloropyridin-3-yl)-2-[(2-methoxy-1-methylethyl)(methyl)amino]-3-[(trans-4-methylcyclohexyl)methyl]-3H-imidazo[4,5-c]pyridin-6-yl}-1,2,4-oxadiazol-5(4H)-one;

3-[4-(5-chloropyridin-3-yl)-3-[(trans-4-methylcyclohexyl)methyl]-2-(pyridin-2-ylamino)-3H-imidazo[4,5-c]pyridin-6-yl]-1,2,4-oxadiazol-5(4H)-one;

4-(5-chloropyridin-3-yl)-3-[(trans-4-methylcyclohexyl)methyl]-2-(pyridin-2-ylamino)-3H-imidazo[4,5-c]pyridine-6-carboxylic acid;

3-{4-(5-chloropyridin-3-yl)-3-[(trans-4-methylcyclohexyl)methyl]-2-[methyl(phenyl)amino]-3H-imidazo[4,5-c]pyridin-6-yl}-1,2,4-oxadiazol-5(4H)-one;

4-(5-chloropyridin-3-yl)-3-[(trans-4-methylcyclohexyl)methyl]-2-[methyl(phenyl)amino]-3H-imidazo[4,5-c]pyridine-6-carboxylic acid;

3-{4-(5-chloropyridin-3-yl)-3-[(trans-4-methylcyclohexyl)methyl]-2-(phenylamino)-3H-imidazo[4,5-c]pyridin-6-yl}-1,2,4-oxadiazol-5(4H)-one;

3-{4-(5-chloropyridin-3-yl)-2-[(4aR,7aR)-hexahydrocyclopenta[b][1,4]oxazin-4(4aH)-yl]-3-[(1R or S)-1-(trans-4-methylcyclohexyl)ethyl]-3H-imidazo[4,5-c]pyridin-6-yl}-1,2,4-oxadiazol-5(4H)-one;

3-(4-(5-chloropyridin-3-yl)-3-(1-(trans-4-methylcyclohexyl)ethyl)-2-((R)-3-methylmorpholino)-3H-imidazo[4,5-c]pyridin-6-yl)-1,2,4-oxadiazol-5(4H)-one;

(5R)-4-[4-(5-chloropyridin-3-yl)-3-[1-(trans-4-methylcyclohexyl)ethyl]-6-(5-oxo-4,5-dihydro-1,2,4-oxadiazol-3-yl)-3H-imidazo[4,5-c]pyridin-2-yl]-1,5-dimethylpiperazin-2-one;

3-{4-(5-chloropyridin-3-yl)-2-[(2S,4R)-2-(fluoromethyl)-4-methoxypyrrolidin-1-yl]-3-[1-(trans-4-methylcyclohexyl)ethyl]-3H-imidazo[4,5-c]pyridin-6-yl}-1,2,4-oxadiazol-5(4H)-one;

3-{4-(5-chloropyridin-3-yl)-2-[(2S,4R)-4-hydroxy-2-(propan-2-yl)pyrrolidin-1-yl]-3-[1-(trans-4-methylcyclohexyl)ethyl]-3H-imidazo[4,5-c]pyridin-6-yl}-1,2,4-oxadiazol-5(4H)-one;

3-{4-(5-chloropyridin-3-yl)-2-[(2R,4R)-4-methoxy-2-methylpyrrolidin-1-yl]-3-[1-(trans-4-methylcyclohexyl)ethyl]-3H-imidazo[4,5-c]pyridin-6-yl}-1,2,4-oxadiazol-5(4H)-one;

3-{4-(5-chloropyridin-3-yl)-2-[(2R,4R)-4-hydroxy-2-methylpyrrolidin-1-yl]-3-[1-(trans-4-methylcyclohexyl)ethyl]-3H-imidazo[4,5-c]pyridin-6-yl}-1,2,4-oxadiazol-5(4H)-one;

3-{4-(5-chloropyridin-3-yl)-2-[(2R,6R)-2,6-dimethyl-4-(methylsulfonyl)piperazin-1-yl]-3-[(trans-4-methylcyclohexyl)methyl]-3H-imidazo[4,5-c]pyridin-6-yl}-1,2,4-oxadiazol-5(4H)-one;

ethyl (3R,5R)-4-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-3,5-dimethylpiperazine-1-carboxylate;

(3R,5R)-4-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-N-ethyl-3,5-dimethylpiperazine-1-carboxamide;

3-{4-(5-chloropyridin-3-yl)-2-[(2R,6R)-2,6-dimethyl-4-propanoylpiperazin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(2R,6R)-4-(cyclobutylcarbonyl)-2,6-dimethylpiperazin-1-yl]-3-[(trans-4-methylcyclohexyl)methyl]-3H-imidazo[4,5-c]pyridin-6-yl}-1,2,4-oxadiazol-5(4H)-one;

3-{2-[(2R,6R)-4-butanoyl-2,6-dimethylpiperazin-1-yl]-4-(5-chloropyridin-3-yl)-3-[(trans-4-methylcyclohexyl)methyl]-3H-imidazo[4,5-c]pyridin-6-yl}-1,2,4-oxadiazol-5(4H)-one;

methyl (3R,5R)-4-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-3,5-dimethylpiperazine-1-carboxylate;

1-methylethyl (3R,5R)-4-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-3,5-dimethylpiperazine-1-carboxylate;

(3R,5R)-4-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-3,5-dimethyl-N-propylpiperazine-1-carboxamide;

(3R,5R)-4-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-3,5-dimethyl-N-(1-methylethyl)piperazine-1-carboxamide;

3-{2-(4-acetyl-2,3-dimethylpiperazin-1-yl)-4-(5-chloropyridin-3-yl)-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[4-(cyclopropylcarbonyl)-2,3-dimethylpiperazin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(2R,6R)-2,6-dimethyl-4-(2-methylpropanoyl)piperazin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(4aR,7a R)-4-(cyclopropylcarbonyl)octahydro-1H-cyclopenta[b]pyrazin-1-yl]-3-[(trans-4-methylcyclohexyl)methyl]-3H-imidazo[4,5-c]pyridin-6-yl}-1,2,4-oxadiazol-5(4H)-one;

3-{2-[(4aR,7aR)-4-acetyloctahydro-1H-cyclopenta[b]pyrazin-1-yl]-4-(5-chloropyridin-3-yl)-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(4a R,7a R)-4-(difluoroacetyl)octahydro-1H-cyclopenta[b]pyrazin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(4a R,7a R)-4-(cyclobutylcarbonyl)octahydro-1H-cyclopenta[b]pyrazin-1-yl]-3-[(trans-4-methylcyclohexyl)methyl]-3H-imidazo[4,5-c]pyridin-6-yl}-1,2,4-oxadiazol-5(4H)-one;

(3R,5R)-4-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-N,N,3,5-tetramethylpiperazine-1-carboxamide;

(3R,5R)-4-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-N-ethyl-N,3,5-trimethylpiperazine-1-carboxamide;

3-{4-(5-chloropyridin-3-yl)-2-{(2R,6R)-4-[(1-fluorocyclopropyl)carbonyl]-2,6-dimethylpiperazin-1-yl}-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-{(2R,6R)-4-[(2,2-difluorocyclopropyl)carbonyl]-2,6-dimethylpiperazin-1-yl}-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(2R,6R)-4-(difluoroacetyl)-2,6-dimethylpiperazin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-{(2R,6R)-2,6-dimethyl-4-[(3-methyloxetan-3-yl)carbonyl]piperazin-1-yl}-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-{(2R,6R)-2,6-dimethyl-4-[(1-methylcyclopropyl)carbonyl]piperazin-1-yl}-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(2R,6R)-2,6-dimethyl-4-(oxetan-3-ylcarbonyl)piperazin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(2R,6R)-4-(methoxyacetyl)-2,6-dimethylpiperazin-1-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-(1-ethoxy-2-hydroxyethyl)-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-(1-ethoxy-2-methoxyethyl)-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[cyclopropyl(ethoxy)methyl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[ethoxy(tetrahydro-2H-pyran-4-yl)methyl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[cyclopropyl(2-methoxyethoxy)methyl]-3-[(trans-4-methylcyclohexyl)methyl]-3H-imidazo[4,5-c]pyridin-6-yl}-1,2,4-oxadiazol-5(4H)-one;

3-(4-(5-chloropyridin-3-yl)-2-(ethoxy(pyridin-2-yl)methyl)-3-((trans-4-methylcyclohexyl)methyl)-3H-imidazo[4,5-c]pyridin-6-yl)-1,2,4-oxadiazol-5(4H)-one;

3-{4-(5-chloropyridin-3-yl)-2-[ethoxy(1,3-thiazol-4-yl)methyl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[ethoxy(1-methyl-1H-pyrazol-3-yl)methyl]-3-[(trans-4-25 methylcyclohexyl)methyl]-3H-imidazo[4,5-c]pyridin-6-yl}-1,2,4-oxadiazol-5(4H)-one;

3-{4-(5-chloropyridin-3-yl)-2-[ethoxy(1,3-thiazol-4-yl)methyl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-3-[(trans-4-methylcyclohexyl)methyl]-2-[pyridin-2-yl(2,2,2-trifluoroethoxy)methyl]-3H-imidazo[4,5-c]pyridin-6-yl}-1,2,4-oxadiazol-5(4H)-one;

3-{4-(5-chloropyridin-3-yl)-2-[(1R or S)-1-fluoro-1-(3-fluoropyridin-2-yl)ethyl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(1R or S)-1-fluoro-1-(3-fluoropyridin-4-yl)ethyl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(1R or S)-1-fluoro-1-(3-methylpyridin-2-yl)ethyl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(1R or S)-1-fluoro-1-(pyridin-2-yl)ethyl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-(1-fluoro-2-methoxy-1-methylethyl)-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[1-(3-fluoropyridin-2-yl)ethyl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[1-(methoxymethyl)butyl]-3-[(trans-4-methylcyclohexyl)methyl]-3H-imidazo[4,5-c]pyridin-6-yl}-1,2,4-oxadiazol-5(4H)-one;

3-[4-(5-chloropyridin-3-yl)-3-[(trans-4-methylcyclohexyl)methyl]-2-(1-methylethenyl)-3H-imidazo[4,5-c]pyridin-6-yl]-1,2,4-oxadiazol-5(4H)-one;

3-{4-(5-chloropyridin-3-yl)-2-(2-methoxy-1-methylethyl)-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-(2-ethoxy-1-methylethyl)-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-3-[(trans-4-methylcyclohexyl)methyl]-2-[1-methyl-2-(1-methylethoxy)ethyl]-3H-imidazo[4,5-c]pyridin-6-yl}-1,2,4-oxadiazol-5(4H)-one;

3-{4-(5-chloropyridin-3-yl)-2-[1-(methoxymethyl)propyl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[2-methoxy-1-(methoxymethyl)ethyl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[1-(methoxymethyl)-2-methylpropyl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-3-[(trans-4-methylcyclohexyl)methyl]-2-[4-(1-methylethyl)pyridin-2-yl]-3H-imidazo[4,5-c]pyridin-6-yl}-1,2,4-oxadiazol-5(4H)-one;

3-{7-bromo-4-(5-chloropyridin-3-yl)-3-[(trans-4-methylcyclohexyl)methyl]-2-[(3R)-3-phenylmorpholin-4-yl]-3H-imidazo[4,5-c]pyridin-6-yl}-1,2,4-oxadiazol-5(4H)-one;

3-{7-chloro-4-(5-chloropyridin-3-yl)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-7-fluoro-2-[(4aR,7aR)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(4aR,7aR)-hexahydrocyclopenta[b][1,4]oxazin-4(4aH)-yl]-7-methoxy-3-[(trans-4-methylcyclohexyl)methyl]-3H-imidazo[4,5-c]pyridin-6-yl}-1,2,4-oxadiazol-5(4H)-one;

3-{4-(5-chloropyridin-3-yl)-2-[(4aR,7aR)-hexahydrocyclopenta[b][1,4]oxazin-4(4aH)-yl]-7-methyl-3-[(trans-4-methylcyclohexyl)methyl]-3H-imidazo[4,5-c]pyridin-6-yl}-1,2,4-oxadiazol-5(4H)-one;

4-(5-chloropyridin-3-yl)-7-(dimethylamino)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridine-6-carboxylic acid;

3-{4-(5-chloropyridin-3-yl)-2-[(2R or S)-1-methoxypropan-2-yl]-3-[(1R or S)-1-(trans-4-methylcyclohexyl)ethyl]-3H-imidazo[4,5-c]pyridin-6-yl}-1,2,4-oxadiazol-5(4H)-one;

4-(5-chloropyridin-3-yl)-2-[(4aR,7aR)-hexahydrocyclopenta[b][1,4]oxazin-4(4aH)-yl]-3-[(trans-4-methylcyclohexyl)methyl]-N-(methylsulfonyl)-3H-imidazo[4,5-c]pyridine-6-carboxamide;

4-(5-chloropyridin-3-yl)-N-(dimethylsulfamoyl)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridine-6-carboxamide;

4-(5-chloropyridin-3-yl)-N-methyl-3-[(trans-4-methylcyclohexyl)methyl]-2-[(3R)-3-phenylmorpholin-4-yl]-3H-imidazo[4,5-c]pyridine-6-carboxamide;

4-(5-chloropyridin-3-yl)-N,N-dimethyl-3-[(trans-4-methylcyclohexyl)methyl]-2-[(3R)-3-phenylmorpholin-4-yl]-3H-imidazo[4,5-c]pyridine-6-carboxamide;

N-{4-(5-chloropyridin-3-yl)-3-[(trans-4-methylcyclohexyl)methyl]-2-[(3R)-3-phenylmorpholin-4-yl]-3H-imidazo[4,5-c]pyridin-6-yl}methanesulfonamide;

4-(5-chloropyridin-3-yl)-3-[(trans-4-methylcyclohexyl)methyl]-6-(1H-tetrazol-5-yl)-2-[(2S)-2-(trifluoromethyl)pyrrolidin-1-yl]-3H-imidazo[4,5-c]pyridine;

5-{4-(5-chloropyridin-3-yl)-2-[(2S)-2-(fluoromethyl)pyrrolidin-1-yl]-3-[(trans-4-methylcyclohexyl)methyl]-3H-imidazo[4,5-c]pyridin-6-yl}-2-methyl-1,2-dihydro-3H-1,2,4-triazol-3-one;

5-{4-(5-chloropyridin-3-yl)-2-[(2S)-2-(fluoromethyl)pyrrolidin-1-yl]-3-[(trans-4-methylcyclohexyl)methyl]-3H-imidazo[4,5-c]pyridin-6-yl}-2,4-dihydro-3H-1,2,4-triazol-3-one;

4-(5-chloropyridin-3-yl)-2-[(4aR,7aR)-hexahydrocyclopenta[b][1,4]oxazin-4(4aH)-yl]-3-[(trans-4-methylcyclohexyl)methyl]-6-(1H-tetrazol-5-yl)-3H-imidazo[4,5-c]pyridine;

methyl 4-(5-chloropyridin-3-yl)-3-[(trans-4-methylcyclohexyl)methyl]-2-[(3R)-3-phenylmorpholin-4-yl]-3H-imidazo[4,5-c]pyridine-6-carboxylate;

ethyl 4-(5-chloropyridin-3-yl)-3-[(trans-4-methylcyclohexyl)methyl]-2-[(3R)-3-phenylmorpholin-4-yl]-3H-imidazo[4,5-c]pyridine-6-carboxylate;

3-{4-(5-chloropyridin-3-yl)-2-[(1S or R)cyclopropyl(ethoxy)methyl]-3-[(1R or S)-1-(trans-4-methylcyclohexyl)ethyl]-3H-imidazo[4,5-c]pyridin-6-yl}-1,2,4-oxadiazol-5(4H)-one;

3-{4-(5-chloropyridin-3-yl)-2-[(1S or R)-1-ethoxyethyl]-3-[(1R or S)-1-(trans-4-methylcyclohexy)ethyl]-3H-imidazo[4,5-c]pyridin-6-yl}-1,2,4-oxadiazol-5(4H)-one;

3-{4-(5-chloropyridin-3-yl)-2-[(1R or S)-1-ethoxy-2-methoxyethyl]-3-[(1R or S)-1-(trans-4-methylcyclohexyl)ethyl]-3H-imidazo[4,5-c]pyridin-6-yl}-1,2,4-oxadiazol-5(4H)-one;

3-{4-(5-chloropyridin-3-yl)-2-{(2R)-4-[(1-fluorocyclopropyl)carbonyl]-2-methylpiperazin-1-yl}-3-[(1R or S)-1-(trans-4-methylcyclohexyl)ethyl]-3H-imidazo[4,5-c]pyridin-6-yl}-1,2,4-oxadiazol-5(4H)-one;

3-{4-(5-chloropyridin-3-yl)-2-[(trans)-hexahydrocyclopenta[b][1,4]oxazin-4(4aH)-yl]-3-[4-(trifluoromethyl)benzyl]-3H-imidazo[4,5-c]pyridin-6-yl}-1,2,4-oxadiazol-5(4H)-one;

3-{4-(5-chloropyridin-3-yl)-3-[(trans-4-ethylcyclohexyl)methyl]-2-[(trans)-hexahydrocyclopenta[b][1,4]oxazin-4(4aH)-yl]-3H-imidazo[4,5-c]pyridin-6-yl}-1,2,4-oxadiazol-5(4H)-one;

5-{4-(5-chloropyridin-3-yl)-3-[(trans-4-ethylcyclohexyl)methyl]-2-[(trans)-hexahydrocyclopenta[b][1,4]oxazin-4(4aH)-yl]-3H-imidazo[4,5-c]pyridin-6-yl}-1,3,4-oxadiazol-2(3H)-one;

3-{4-(5-chloropyridin-3-yl)-3-[3-fluoro-4-(trifluoromethyl)benzyl]-2-[(trans)-hexahydrocyclopenta[b][1,4]oxazin-4(4aH)-yl]-3H-imidazo[4,5-c]pyridin-6-yl}-1,2,4-oxadiazol-5(4H)-one;

3-[4-(5-chloropyridin-3-yl)-2-[(trans)-hexahydrocyclopenta[b][1,4]oxazin-4(4aH)-yl]-3-{[trans-4-(trifluoromethyl)cyclohexyl]methyl}-3H-imidazo[4,5-c]pyridin-6-yl]-1,2,4-oxadiazol-5(4H)-one;

3-{4-(5-chloropyridin-3-yl)-3-[(3-ethylcyclopentyl)methyl]-2-[(4aR,7aR)-hexahydrocyclopenta[b][1,4]oxazin-4(4aH)-yl]-3H-imidazo[4,5-c]pyridin-6-yl}-1,2,4-oxadiazol-5(4H)-one;

3-{4-[5-chloro-2-(dimethylamino)pyridin-3-yl]-2-[(trans)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one;

3-{4-(5-chloro-2-methylpyridin-3-yl)-2-[(4aS,7aS)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one;

3-{4-(5-chloro-2-methylpyridin-3-yl)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one;

3-{4-[5-chloro-2-(2-hydroxyethoxy)pyridin-3-yl]-2-[(trans)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one;

3-{4-(5-chloro-2-methoxypyridin-3-yl)-2-[(4aS,7aS)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one;

3-{4-(5-chloro-2-methoxypyridin-3-yl)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one;

3-{4-[5-chloro-2-(2-methoxyethoxy)pyridin-3-yl]-2-[(4aR,7aR)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one;

3-{4-[5-chloro-2-(2-methoxyethoxy)pyridin-3-yl]-2-[(4aS,7aS)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one;

5-chloro-3-{2-[(4aR,7aR)-hexahydrocyclopenta[b][1,4]oxazin-4(4aH)-yl]-3-[(trans-4-methylcyclohexyl)methyl]-6-(5-oxo-4,5-dihydro-1,2,4-oxadiazol-3-yl)-3H-imidazo[4,5-c]pyridin-4-yl}pyridin-2(1H)-one;

3-{2-[(4aR,7aR)-hexahydrocyclopenta[b][1,4]oxazin-4(4aH)-yl]-3-[(trans-4-methylcyclohexyl)methyl]-4-(5-methylpyridin-3-yl)-3H-imidazo[4,5-c]pyridin-6-yl}-1,2,4-oxadiazol-5(4H)-one;

3-{2-[(4aS,7aS)-hexahydrocyclopenta[b][1,4]oxazin-4(4aH)-yl]-3-[(trans-4-methylcyclohexyl)methyl]-4-(5-methylpyridin-3-yl)-3H-imidazo[4,5-c]pyridin-6-yl}-1,2,4-oxadiazol-5(4H)-one;

3-{4-[5-chloro-2-(methylamino)pyridin-3-yl]-2-[(trans)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one;

5-chloro-3-{3-[(trans-4-methylcyclohexyl)methyl]-6-(5-oxo-4,5-dihydro-1,2,4-oxadiazol-3-yl)-2-[(3R)-3-phenylmorpholin-4-yl]-3H-imidazo[4,5-c]pyridin-4-yl}pyridin-2(1H)-one;

3-{3-[(trans-4-methylcyclohexyl)methyl]-2-[(3R)-3-phenylmorpholin-4-yl]-4-pyrimidin-5-yl-3H-imidazo[4,5-c]pyridin-6-yl}-1,2,4-oxadiazol-5(4H)-one;

3-{3-[(trans-4-methylcyclohexyl)methyl]-2-[(3R)-3-phenylmorpholin-4-yl]-4-(pyrazin-2-yl)-3H-imidazo[4,5-c]pyridin-6-yl}-1,2,4-oxadiazol-5(4H)-one;

3-{3-[(trans-4-methylcyclohexyl)methyl]-2-[(3R)-3-phenylmorpholin-4-yl]-4-(pyridazin-4-yl)-3H-imidazo[4,5-c]pyridin-6-yl}-1,2,4-oxadiazol-5(4H)-one;

3-{3-[(trans-4-methylcyclohexyl)methyl]-2-[(3R)-3-phenylmorpholin-4-yl]-4-(pyridazin-3-yl)-3H-imidazo[4,5-c]pyridin-6-yl}-1,2,4-oxadiazol-5(4H)-one;

3-{4-(5-chloropyridin-3-yl)-3-[(trans-4-methylcyclohexyl)methyl]-2-[1-methyl-2-(methylsulfanyl)ethyl]-3H-imidazo[4,5-c]pyridin-6-yl}-1,2,4-oxadiazol-5(4H)-one;

3-{4-(5-chloropyridin-3-yl)-3-[(trans-4-methylcyclohexyl)methyl]-2-[1-methyl-2-(methylsulfonyl)ethyl]-3H-imidazo[4,5-c]pyridin-6-yl}-1,2,4-oxadiazol-5(4H)-one;

3-[4-(5-chloropyridin-3-yl)-3-[(trans-4-methylcyclohexyl)methyl]-2-{1-[(methylsulfanyl)methyl]propyl}-3H-imidazo[4,5-c]pyridin-6-yl]-1,2,4-oxadiazol-5(4H)-one;

3-[4-(5-chloropyridin-3-yl)-3-[(trans-4-methylcyclohexyl)methyl]-2-{1-[(methylsulfonyl)methyl]propyl}-3H-imidazo[4,5-c]pyridin-6-yl]-1,2,4-oxadiazol-5(4H)-one;

3-[4-(5-chloropyridin-3-yl)-3-[(trans-4-methylcyclohexyl)methyl]-2-{2-methyl-1-[(methylsulfonyl)methyl]propyl}-3H-imidazo[4,5-c]pyridin-6-yl]-1,2,4-oxadiazol-5(4H)-one;

6-{4-(5-chloropyridin-3-yl)-3-[(trans-4-methylcyclohexyl)methyl]-2-[(3R)-3-phenylmorpholin-4-yl]-3H-imidazo[4,5-c]pyridin-6-yl}pyridin-2(1H)-one;

3-{4-(cyclobutylmethoxy)-3-[(trans-4-methylcyclohexyl)methyl]-2-[(3R)-3-phenylmorpholin-4-yl]-3H-imidazo[4,5-c]pyridin-6-yl}-1,2,4-oxadiazol-5(4H)-one;

3-{4-(1-cyclobutylethoxy)-3-[(trans-4-methylcyclohexyl)methyl]-2-[(3R)-3-phenylmorpholin-4-yl]-3H-imidazo[4,5-c]pyridin-6-yl}-1,2,4-oxadiazol-5(4H)-one;

or a stereoisomer thereof;
or a pharmaceutically acceptable salt thereof;
or a pharmaceutically acceptable salt of the stereoisomer thereof.

CHEMICAL DEFINITIONS

As used herein, "alkyl" is intended to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on.

When used in the phrases "alkylaryl", "alkylcycloalkyl" and "alkylheterocyclyl" the term "alkyl" refers to the alkyl portion of the moiety and does not describe the number of atoms in the heterocyclyl portion of the moiety. In an embodiment, if the number of carbon atoms is not specified, the "alkyl" of "alkylaryl", "alkylcycloalkyl" and "alkylheterocyclyl" refers to $C_1$-$C_{12}$ alkyl and in a further embodiment, refers to $C_1$-$C_6$ alkyl.

The term "cycloalkyl" means a monocyclic, bicyclic or spirocyclic saturated aliphatic hydrocarbon group having the specified number of carbon atoms. The cycloalkyl is optionally bridged (i.e., forming a bicyclic moiety), for example with a methylene, ethylene or propylene bridge. The cycloalkyl may be fused with an aryl group such as phenyl, and it is understood that the cycloalkyl substituent is attached via the cycloalkyl group. For example, "cycloalkyl" includes cyclopropyl, methyl-cyclopropyl, 2,2-dimethyl-cyclobutyl, 2-ethyl-cyclopentyl, cyclohexyl, and so on. "cycloalkyl" also includes cycloalkyl rings as described above wherein $=CH_2$ replaces two available hydrogens on the same ring carbon atom.

The term "cyclenyl" means a monocyclic, bicyclic or spirocyclic unsaturated aliphatic hydrocarbon group having the specified number of carbon atoms. The cyclenyl is optionally bridged (i.e., forming a bicyclic moiety), for example with a methylene, ethylene or propylene bridge. The cyclenyl may be fused with an aryl group such as phenyl, and it is understood that the cyclenyl substituent is attached via the cyclenyl group. For example, "cyclenyl" includes cyclopentenyl, cyclohexenyl and so on. "Cyclenyl" also includes cyclenyl rings as described above wherein $=CH_2$ replaces two available hydrogens on the same ring carbon atom.

In an embodiment, if the number of carbon atoms is not specified, "alkyl" refers to $C_1$-$C_{12}$ alkyl and in a further embodiment, "alkyl" refers to $C_1$-$C_6$ alkyl. In an embodiment, if the number of carbon atoms is not specified, "cycloalkyl" refers to $C_3$-$C_{10}$ cycloalkyl and in a further embodiment, "cycloalkyl" refers to $C_3$-$C_7$ cycloalkyl. In an embodiment, if the number of carbon atoms is not specified, "cyclenyl" refers to $C_5$-$C_{10}$ cyclenyl and in a further embodiment, "cyclenyl" refers to $C_5$-$C_7$ cyclenyl. In an embodiment, examples of "alkyl" include methyl, ethyl, n-propyl, i-propyl, n-butyl, t-butyl and i-butyl.

The term "alkylene" means a hydrocarbon diradical group having the specified number of carbon atoms. For example, "alkylene" includes —CH$_2$—, —CH$_2$CH$_2$— and the like. In an embodiment, if the number of carbon atoms is not specified, "alkylene" refers to C$_1$-C$_{12}$ alkylene and in a further embodiment, "alkylene" refers to C$_1$-C$_6$ alkylene.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "C$_2$-C$_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

"Alkenylene" means a diradical group of an alkenyl group that is defined above. For example, "alkenylene" includes —CH$_2$—CH$_2$—CH=CH—CH$_2$,—CH=CH—CH$_2$ and the like.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "C$_2$-C$_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as (C$_0$-C$_6$)alkylene-aryl. If aryl is taken to be phenyl, this definition would include phenyl itself as well as —CH$_2$Ph, —CH$_2$CH$_2$Ph, CH(CH$_3$) CH$_2$CH(CH$_3$)Ph, and so on.

"Aryl" is intended to mean any stable monocyclic, bicyclic or tricyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

In one embodiment, "aryl" is an aromatic ring of 6 to 14 carbon atoms, and includes a carbocyclic aromatic group fused with a 5- or 6-membered cycloalkyl group such as indan. Examples of carbocyclic aromatic groups include, but are not limited to, phenyl, naphthyl, e.g. 1-naphthyl and 2-naphthyl; anthracenyl, e.g. 1-anthracenyl, 2-anthracenyl; phenanthrenyl; fluorenonyl, e.g. 9-fluorenonyl, indanyl and the like.

The term heteroaryl, as used herein, represents a stable monocyclic, bicyclic or tricyclic ring of up to 7 atoms in each ring, wherein at least one ring is aromatic and contains carbon and from 1 to 4 heteroatoms selected from the group consisting of O, N and S. In another embodiment, the term heteroaryl refers to a monocyclic, bicyclic or tricyclic aromatic ring of 5- to 14-ring atoms of carbon and from one to four heteroatoms selected from O, N, or S. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, in one embodiment, the attachment is via the heteroatom containing aromatic ring, respectively.

Heteroaryl groups within the scope of this definition include but are not limited to acridinyl, carbazolyl, cinnolinyl, quinoxalinyl, pyrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. Additional examples of heteroaryl include, but are not limited to pyridyl, e.g., 2-pyridyl (also referred to as α-pyridyl), 3-pyridyl (also referred to as β-pyridyl) and 4-pyridyl (also referred to as (γ-pyridyl); thienyl, e.g., 2-thienyl and 3-thienyl; furanyl, e.g., 2-furanyl and 3-furanyl; pyrimidyl, e.g., 2-pyrimidyl and 4-pyrimidyl; imidazolyl, e.g., 2-imidazolyl; pyranyl, e.g., 2-pyranyl and 3-pyranyl; pyrazolyl, e.g., 4-pyrazolyl and 5-pyrazolyl; thiazolyl, e.g., 2-thiazolyl, 4-thiazolyl and 5-thiazolyl; thiadiazolyl; isothiazolyl; oxazolyl, e.g., 2-oxazolyl, 4-oxazolyl and 5-oxazolyl; isoxazolyl; pyrrolyl; pyridazinyl; pyrazinyl and the like.

In an embodiment, "heteroaryl" may also include a "fused polycyclic aromatic", which is a heteroaryl fused with one or more other heteroaryl or nonaromatic heterocyclic ring. Examples include, quinolinyl and isoquinolinyl, e.g. 2-quinolinyl, 3-quinolinyl, 4-quinolinyl, 5-quinolinyl, 6-quinolinyl, 7-quinolinyl and 8-quinolinyl, 1-isoquinolinyl, 3-quinolinyl, 4-isoquinolinyl, 5-isoquinolinyl, 6-isoquinolinyl, 7-isoquinolinyl and 8-isoquinolinyl; benzofuranyl, e.g. 2-benzofuranyl and 3-benzofuranyl; dibenzofuranyl, e.g. 2,3-dihydrobenzofuranyl; dibenzothiophenyl; benzothienyl, e.g. 2-benzothienyl and 3-benzothienyl; indolyl, e.g. 2-indolyl and 3-indolyl; benzothiazolyl, e.g., 2-benzothiazolyl; benzooxazolyl, e.g., 2-benzooxazolyl; benzimidazolyl, e.g. 2-benzoimidazolyl; isoindolyl, e.g. 1-isoindolyl and 3-isoindolyl; benzotriazolyl; purinyl; thionaphthenyl, pyrazinyl and the like.

"Heterocyclyl" means a non-aromatic saturated monocyclic, bicyclic, tricyclic or spirocyclic ring system comprising up to 7 atoms in each ring, or contains 3 to 14, or 5 to 10 ring atoms, in which one or more of the atoms in the ring system is an element other than carbon, for example, nitrogen, oxygen, phosphor or sulfur, alone or in combination. There are no adjacent oxygen and/or sulfur atoms present in the ring system. Preferred heterocyclyls contain about 5 to about 6 ring atoms. The heterocycle may be fused with an aromatic aryl group such as phenyl or heterocyclenyl. The heterocyclyl is optionally bridged (i.e., forming a bicyclic moiety), for example with a methylene, ethylene or propylene bridge. The prefix aza, oxa or thia before the heterocyclyl root name means that at least a nitrogen, oxygen or sulfur atom, respectively, is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes heterocyclyl rings as described above wherein =O replaces two available hydrogens on the same ring carbon atom. An example of such a moiety is pyrrolidone:

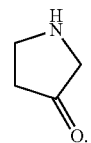

In describing the heteroatoms contained in a specified heterocyclyl group, the expression, "having one to x heteroatoms selected from the group of N, O, P and S" (wherein x is a specified integer), for example, means that each heteroatom in the specified heterocyclyl is independently selected from the specified selection of heteroatoms. Attachment of a heterocyclyl substituent can occur via a carbon atom or via a heteroatom. In cases where the heterocyclyl substituent is bicyclic and one ring is aromatic, unsaturated and/or contains no heteroatoms, in one embodiment, the attachment is via the heteroatom containing non-aromatic saturated ring.

"Heterocyclenyl" means a non-aromatic unsaturated monocyclic, bicyclic, tricyclic or spirocyclic ring system comprising up to 7 atoms in each ring. Preferably, the heterocyclenyl contains 3 to 14, or 5 to 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The heterocyclenyl is optionally bridged (i.e., forming a bicyclic moiety), for example with a methylene, ethylene or propylene bridge. The prefix aza, oxa or thia before the heterocyclenyl root name means that at least a nitrogen, oxygen, phosphor or sulfur atom respectively is present as a ring atom. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes heterocyclenyl rings as described above wherein =O replaces two available hydrogens on the same ring carbon atom. An example of such a moiety is pyrrolidinone:

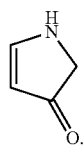

In describing the heteroatoms contained in a specified heterocyclenyl group, the expression, "having one to x heteroatoms selected from the group of N, O, P and S" (wherein x is an specified integer), for example, means that each heteroatom in the specified heterocyclenyl is independently selected from the specified selection of heteroatoms. In cases where the heterocyclenyl substituent is bicyclic and one ring is aromatic, saturated and/or contains no heteroatoms, in one embodiment, the attachment is via the heteroatom containing non-aromatic unsaturated ring.

It should also be noted that tautomeric forms such as, for example, the moieties:

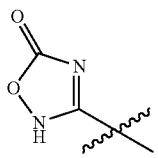 and 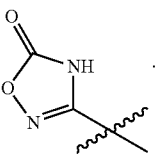

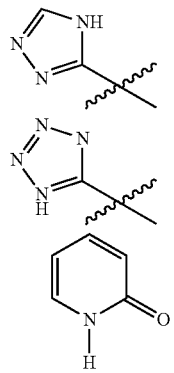 and 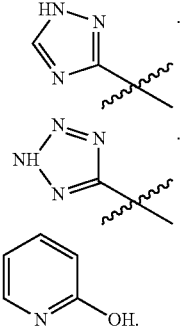

are considered equivalent in certain embodiments of this invention.

An "alkylaryl group" is an alkyl group substituted with an aryl group, for example, a phenyl group. Suitable aryl groups are described herein and suitable alkyl groups are described herein. The bond to the parent moiety is through the aryl group.

An "alkylheteroaryl group" is an alkyl group substituted with a heteroaryl group. Suitable heteroaryl groups are described herein and suitable alkyl groups are described herein. The bond to the parent moiety is through the heteroaryl group.

An "alkylheterocyclyl group" is an alkyl group substituted with a heterocyclyl group. Suitable heterocyclyl groups are described herein and suitable alkyl groups are described herein. The bond to the parent moiety is through the heterocyclyl group.

An "alkylheterocyclenyl group" is an alkyl group substituted with a heterocyclenyl group. Suitable heterocyclenyl groups are described herein and suitable alkyl groups are described herein. The bond to the parent moiety is through the heterocyclenyl group.

An "alkylcycloalkyl group" is an alkyl group substituted with a cycloalkyl group. Suitable cycloalkyl groups are described herein and suitable alkyl groups are described herein. The bond to the parent moiety is through the cycloalkyl group.

An "arylalkyl group" is an aryl group substituted with an alkyl group. Suitable aryl groups are described herein and suitable alkyl groups are described herein. The bond to the parent moiety is through the alkyl group.

A "heteroarylalkyl group" is a heteroaryl group substituted with an alkyl group. Suitable heteroaryl groups are described herein and suitable alkyl groups are described herein. The bond to the parent moiety is through the alkyl group.

A "heterocyclylalkyl group" is a heterocyclyl group substituted with an alkyl group. Suitable heterocyclyl groups are described herein and suitable alkyl groups are described herein. The bond to the parent moiety is through the alkyl group.

A "heterocyclenylalkyl group" is a heterocyclenyl group substituted with an alkyl group. Suitable heterocyclenyl groups are described herein and suitable alkyl groups are described herein. The bond to the parent moiety is through the alkyl group.

A "cycloalkylalkyl group" is a cycloalkyl group substituted with an alkyl group. Suitable cycloalkyl groups are described herein and suitable alkyl groups are described herein. The bond to the parent moiety is through the alkyl group.

An "aryloxy group" is an aryl group that is attached to a compound via an oxygen (e.g., phenoxy).

An "alkoxy group" (alkyloxy), as used herein, is a straight chain or branched $C_1$-$C_{12}$ or cyclic $C_3$-$C_{12}$ alkyl group that is connected to a compound via an oxygen atom. Examples of alkoxy groups include but are not limited to methoxy, ethoxy and propoxy.

An "arylalkoxy group" (arylalkyloxy) is an arylalkyl group that is attached to a compound via an oxygen on the alkyl portion of the arylalkyl (e.g., phenylmethoxy).

An "arylamino group" as used herein, is an aryl group that is attached to a compound via a nitrogen.

An "alkylamino group" as used herein, is an alkyl group that is attached to a compound via a nitrogen.

A "dialkylamino group" as used herein, is two alkyl groups that are attached to a compound via a nitrogen.

As used herein, an "arylalkylamino group" is an arylalkyl group that is attached to a compound via a nitrogen on the alkyl portion of the arylalkyl.

An "alkylsulfonyl group" as used herein, is an alkyl group that is attached to a compound via the sulfur of a sulfonyl group.

A "haloalkyl group" as used herein, is an alkyl group substituted with a halo group, which is attached to a compound via the alkyl group.

A "hydroxyalkyl group" as used herein, is an alkyl group substituted with a hydroxy group, which is attached to a compound via the alkyl group.

When a moiety is referred to as "unsubstituted" or not referred to as "substituted" or "optionally substituted", it means that the moiety does not have any substituents. When a moiety is referred to as substituted, it denotes that any portion of the moiety that is known to one skilled in the art as being available for substitution can be substituted. The phrase a group "optionally substituted with" substituent1, etc., or substituent2; substituent selected from the group consisting of substituent1, etc., and substituent2, means the group can be optionally substituted with one or more of the substituents, one substituent, two substituents, three substituents, four substituents or five substituents. For example, the substitutable group can be a hydrogen atom that is replaced with a group other than hydrogen (i.e., a substituent group). Multiple substituent groups can be present. When multiple substituents are present, the substituents can be the same or different and substitution can be at any of the substitutable sites. Such means for substitution are well known in the art. For purposes of exemplification, which should not be construed as limiting the scope of this invention, some examples of groups that are substituents are: alkyl, alkenyl or alkynyl groups (which can also be substituted, with one or more substituents), alkoxy groups (which can be substituted), a halogen or halo group (F, Cl, Br, I), hydroxy, nitro, oxo, —CN, —COH, —COOH, amino, azido, N-alkylamino or N,N-dialkylamino (in which the alkyl groups can also be substituted), N-arylamino or N,N-diarylamino (in which the aryl groups can also be substituted), esters (—C(O)—OR, where R can be a group such as alkyl, aryl, etc., which can be substituted), ureas (—NHC(O)—NHR, where R can be a group such as alkyl, aryl, etc., which can be substituted), carbamates (—NHC(O)—OR, where R can be a group such as alkyl, aryl, etc., which can be substituted), sulfonamides (—NHS(O)$_2$R, where R can be a group such as alkyl, aryl, etc., which can be substituted), alkylsulfonyl (which can be substituted), aryl (which can be substituted), cycloalkyl (which can be substituted) alkylaryl (which can be substituted), alkylheterocyclyl (which can be substituted), alkylcycloalkyl (which can be substituted), and aryloxy.

It should also be noted that any carbon as well as heteroatom with unsatisfied valences in the text, schemes, examples and Tables herein is assumed to have the sufficient number of hydrogen atom(s) to satisfy the valences.

Although symbols/letters (i.e., B, F, K, U, W and Y) for substituents under Formula I may coincide with the abbreviated name for a chemical element, the definitions for the substituents under Formula I should be used.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, "a," "an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

As used herein, the term "composition" is intended to encompass a product comprising the specified ingredients in the specified amounts, as well as any product which results, directly or indirectly, from combination of the specified ingredients in the specified amounts.

Isotopes

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Certain isotopically-labelled compounds of Formula (I) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Certain isotopically-labelled compounds of Formula (I) can be useful for medical imaging purposes. For instance those compounds labeled with positron-emitting isotopes like $^{11}$C or $^{18}$F can be useful for application in Positron Emission Tomography (PET) and those labeled with gamma ray emitting isotopes like $^{123}$I can be useful for application in Single Photon Emission Computed Tomography (SPECT). Additionally, isotopic substitution of a compound at a site where epimerization occurs may slow or reduce the epimerization process and thereby retain the more active or efficacious form of the compound for a longer period of time.

Stereochemistry

When structures of the same constitution differ in respect to the spatial arrangement of certain atoms or groups, they are stereoisomers, and the considerations that are significant in analyzing their interrelationships are topological. If the relationship between two stereoisomers is that of an object and its nonsuperimposable mirror image, the two structures are enantiomeric, and each structure is said to be chiral. Stereoisomers also include diastereomers, cis-trans isomers and conformational isomers. Diastereoisomers can be chiral or achiral, and are not mirror images of one another. Cis-trans isomers differ only in the positions of atoms relative to a specified planes in cases where these atoms are, or are considered as if they were, parts of a rigid structure. Conformational isomers are isomers that can be interconverted by rotations about formally single bonds. Examples of such conformational isomers include cyclohexane conformations with chair and boat conformers, carbohydrates, linear alkane conformations with staggered, eclipsed and gauche conformers, etc. See J. Org. Chem. 35, 2849 (1970).

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, enantiomers are identical except that they are non-superimposable mirror images of one another. A mixture of enantiomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the Formulas of the invention, it is understood that both the (R) and (S) configurations of the chiral carbon, and hence both enantiomers and mixtures thereof, are embraced within the Formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines (bonds to atoms below the plane). The Cahn-Inglod-Prelog system can be used to assign the (R) or (S) configuration to a chiral carbon.

When the compounds of the present invention contain one chiral center, the compounds exist in two enantiomeric forms and the present invention includes both enantiomers and mixtures of enantiomers, such as the specific 50:50 mixture referred to as a racemic mixtures. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

Designation of a specific absolute configuration at a chiral carbon of the compounds of the invention is understood to mean that the designated enantiomeric form of the compounds is in enantiomeric excess (ee) or in other words is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50%. In a particular embodiment when a specific absolute configuration is designated, the enantiomeric excess of depicted compounds is at least about 90%.

When a compound of the present invention has two or more chiral carbons it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs may be separated by methods known to those skilled in the art, for example chromatography or crystallization and the individual enantiomers within each pair may be separated as described above. The present invention includes each diastereoisomer of such compounds and mixtures thereof.

Solvates

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. Solvents to prepare solvates include but are not limited to acetic acid, acetone, anisole, 1-butanol, 2-butanol, butyl acetate, tert-butylmethyl ether, cumene, heptane, isobutyl acetate, methyl acetate, 3-methyl-1-butanol, methylethyl ketone, methylisobutyl ketone, 2-methyl-1-propanol, dimethyl sulfoxide, ethanol, ethyl acetate, ethyl ether, ethyl formate, formic acid, pentane, 1-pentanol, 1-propanol, 2-propanol, propyl acetate and propylene glycol. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al,

*AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The active compounds disclosed can also be prepared in any solid or liquid physical form. For example, the compound can be in a crystalline form, in amorphous form, and have any particle size. Furthermore, the compound particles may be micronized, or may be agglomerated, particulate granules, powders, oils, oily suspensions or any other form of solid or liquid physical form.

The compounds of the present invention may also exhibit polymorphism. This invention further includes different polymorphs of the compounds of the present invention. The term "polymorph" refers to a particular crystalline state of a substance, having particular physical properties such as X-ray diffraction, IR spectra, melting point, and the like.

Pharmaceutically acceptable Salts

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates), and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in The Orange Book (Food & Drug Administration, Washington, D.C. on their website).

Exemplary basic salts include ammonium salts, alkali metal salts such as sodium, lithium, and potassium salts, alkaline earth metal salts such as calcium and magnesium salts, zinc salts, salts with organic bases (for example, organic amines) such as N-Me-D-glucamine, Choline, tromethamine, dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention.

Compounds of Formula I, and salts, solvates thereof, may exist in their tautomeric form (for example, as an amide or imino ether). All such tautomeric forms are contemplated herein as part of the present invention.

Pharmaceutical Compositions

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described potential method of treating a patient by administering a pharmaceutical composition of the present invention is also intended to encompass the administration of the afore-said bulk composition and individual dosage units.

Isolation of the compound at various stages of the reaction may be achieved by standard techniques such as, for example, filtration, evaporation of solvent and the like. Purification of the product and the like, may also be performed by standard techniques such as recrystallization, distillation, sublimation, chromatography, conversion to a suitable derivative. Such techniques are well known to those skilled in the art. The compounds of this invention may be analyzed for their composition and purity as well as characterized by standard analytical techniques such as, for example, elemental analysis, NMR, mass spectroscopy, and IR spectra.

In another embodiment, this invention provides pharmaceutical compositions comprising the compounds of the invention as an active ingredient. The pharmaceutical compositions generally additionally comprise a pharmaceutically acceptable carrier diluent, excipient or carrier (collectively referred to herein as carrier materials).

In yet another embodiment, the present invention discloses methods for preparing pharmaceutical compositions comprising the compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture.

Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Lubricants in these dosage forms include boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. For example, water or water-propylene glycol solutions may be included for parenteral injections or sweeteners and pacifiers may be added for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool to solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Another aspect of this invention is a kit comprising a therapeutically effective amount of at least one compound of Formula I, or a pharmaceutically acceptable salt or solvate of said compound and a pharmaceutically acceptable carrier, vehicle or diluent.

Yet another aspect of this invention is a kit comprising an amount of at least one compound of Formula I, or a pharmaceutically acceptable salt or solvate of said compound and an amount of at least one anticancer therapy and/or anti-cancer agent described below, wherein the amounts of the two or more ingredients result in desired therapeutic effect.

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gels—refer to the active ingredients dispersed or solubilized in a hydrophillic semi-solid matrix.

Powders for constitution refer to powder blends containing the active ingredients and suitable diluents which can be suspended in water or juices.

Diluent—refers to substances that usually make up the major portion of the composition or dosage form. Suitable diluents include but are not limited to sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition.

Disintegrants—refers to materials added to the composition to help it break apart (disintegrate) and release the medicaments. Suitable disintegrants include but are not limited to modified starches such as sodium carboxymethyl starch; methylcellulose, microcrystalline celluloses and sodium croscarmellose; and sodium alginate. The amount of disintegrant in the composition can range from about 2 to about 10% by weight of the composition.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as high molecular weight polyethylene glycols and d,l-leucine. Lubricants are usually added at the very last step before compression, since they must be present on the surfaces of the granules and in between them and the parts of the tablet press. The amount of lubricant in the composition can range from about 0.2 to about 5% by weight of the composition.

Glidents—materials that prevent caking and improve the flow characteristics of granulations, so that flow is smooth and uniform. Suitable glidents include silicon dioxide and talc. The amount of glident in the composition can range from about 0.1% to about 5% by weight of the total composition.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Method of Treatment

HDM2, Hdm2, hDM2, and hdm2 are all equivalent representations of the Human Double Minute 2 protein. Likewise, MDM2, Mdm2, mDM2, and mdm2 are all equivalent representations mouse Double Minute 2 protein.

The compounds of Formula I can be inhibitors or antagonists of the Human or Mouse Double Minute 2 protein interaction with p53 protein and it can be activators of the p53 protein in cells. Furthermore, the pharmacological properties of the compounds of Formula I may be useful to treat or prevent cancer, treat or prevent other disease states associated with abnormal cell proliferation, and treat or prevent diseases resulting from inadequate levels of p53 protein in cells.

Those skilled in the art will realize that the term "cancer" to be the name for diseases in which the body's cells become abnormal and divide without control.

Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) colorectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

In one embodiment, cancers that may be treated by the compounds, compositions and methods of the invention include, but are not limited to: lung cancer, pancreatic cancer, colon cancer, colorectal cancer, myeloid leukemias, acute myelogenous leukemia, chronic myelogenous leukemia, chronic myelomonocytic leukemia, thyroid cancer, myelodysplastic syndrome, bladder carcinoma, epidermal carcinoma, melanoma, breast cancer, prostate cancer, head and neck cancers, ovarian cancer, brain cancers, cancers of mesenchymal origin, sarcomas, tetracarcinomas, neuroblastomas, kidney carcinomas, hepatomas, non-Hodgkin's lymphoma, multiple myeloma, and anaplastic thyroid carcinoma.

In another embodiment, cancers that may be treated by the compounds, compositions and methods of the invention include, but are not limited to: breast, prostate, colon, colorectal, lung, brain, testicular, stomach, pancrease, skin, small intestine, large intestine, throat, head and neck, oral, bone, liver, bladder, kidney, thyroid and blood.

In another embodiment, cancers that may be treated by the compounds, compositions and methods of the invention include breast, prostate, colon, ovary, endometrium and thyroid.

In another embodiment, cancers that may be treated by the compositions and methods of the invention include acute myeloid leukemia (AML), liposarcoma, colorectal cancer, gastric cancer and melanoma.

In a further embodiment, cancers that may be treated by the compositions and methods of the invention include hematological malignancies, for example acute myeloid leukemia.

In a further embodiment, cancers that may be treated by the compositions and methods of the invention include acute lymphoblastic leukemia (ALL), lymphoma, lung, breast and glioblastoma.

The compounds of the invention are also useful in preparing a medicament that may be useful in treating cancer. In one embodiment, the compounds of the invention are for the potential treatment of cancer.

The compounds of Formula I may be useful to the treatment of a variety of cancers, including, but not limited to: carcinoma, including, but not limited to, of the bladder, breast, colon, rectum, endometrium, kidney, liver, lung, head and neck, esophagus, gall bladder, cervix, pancreas, prostrate, larynx, ovaries, stomach, uterus, sarcoma and thyroid cancer;

hematopoietic tumors of the lymphoid lineage, including leukemia, acute lymphocytic leukemia, chronic lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma;

hematopoetic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma, and schwannomas; and other tumors, including melanoma, skin (non-melanomal) cancer, mesothelioma (cells), seminoma, teratocarcinoma, osteosarcoma, xenoderoma pigmentosum, keratoctanthoma, thyroid follicular cancer and Kaposi's sarcoma.

Due to the key role of p53 in the regulation of cellular apoptosis (cell death), the compounds of Formula I could act as agent to induce cell death which may be useful in the treatment of any disease process which features abnormal cellular proliferation eg, cancers of various origin and tissue types, inflammation, immunological disorders.

Due to the key role of HDM2 and p53 in the regulation of cellular proliferation, the compounds of Formula I could act as reversible cytostatic agents which may be useful in the treatment of any disease process which features abnormal cellular proliferation, inhibitors could act as reversible cytostatic agents which may be useful in the treatment of any disease process which features abnormal cell proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty, or vascular surgery, hypertrophic scar formation, inflammatory bowel disease, transplantation rejection, endotoxic shock, and fungal infections.

Compounds of Formula I may also be useful in the chemoprevention of cancer. Chemoprevention is defined as inhibiting the development of invasive cancer by either blocking the initiating mutagenic event by blocking the progression of pre-malignant cells that have already suffered an insult or inhibiting tumor relapse.

Compounds of Formula I may also be useful in inhibiting tumor angiogenesis and metastasis.

Another aspect of this invention is a potential method of treating a mammal (e.g., human) having a disease or condition associated with HDM2 by administering a therapeutically effective amount of at least one compound of Formula I, or a pharmaceutically acceptable salt or solvate of said compound to the mammal.

The invention also provides a potential method of inhibiting one or more HDM2 proteins in a patient in need thereof, comprising administering to the patient a therapeutically effective amount of at least one compound of claim 1 or a pharmaceutically acceptable salt or solvate thereof.

Another aspect of the present invention is a potential method of treating, or slowing the progression of a disease associated with one or more HDM2 proteins in a patient, comprising administering to a patient in need thereof, a therapeutically effective amount of at least one compound of the present invention or a pharmaceutically acceptable salt or solvate thereof.

Another aspect of the present invention is a potential method of treating, or slowing the progression of a disease associated with inadequate p53 levels in a patient, comprising administering to a patient in need thereof, a therapeutically effective amount of at least one compound of the present invention or a pharmaceutically acceptable salt or solvate thereof.

Yet another aspect of the present invention is a potential method of treating one or more diseases associated with HDM2, comprising administering to a mammal in need of such treatment an amount of a first compound, which is a compound of the present invention, or a pharmaceutically acceptable salt or solvate thereof; and an amount of at least one second compound, the second compound being an anti-cancer agent, wherein the amounts of the first compound and the second compound result in a therapeutic effect.

Another aspect of the present invention is a potential method of treating one or more diseases associated with inadequate p53 levels, comprising administering to a mammal in need of such treatment an amount of a first compound, which is a compound of the present invention, or a pharmaceutically acceptable salt or solvate thereof; and an amount of at least one second compound, the second compound being an anti-cancer agent, wherein the amounts of the first compound and the second compound result in a therapeutic effect.

Another aspect of the present invention is a potential method of treating, or slowing the progression of, a disease associated with a HDM2 protein comprising administering to a patient in need thereof, a therapeutically effective amount of a pharmaceutical composition comprising in combination at least one pharmaceutically acceptable carrier and at least one compound according to the present invention, or a pharmaceutically acceptable salt or solvate thereof.

Another aspect of the present invention is a potential method of treating, or slowing the progression of, a disease associated with inadequate p53 levels in a patient, comprising administering to a patient in need thereof, a therapeutically effective amount of a pharmaceutical composition comprising in combination at least one pharmaceutically acceptable carrier and at least one compound according to the present invention, or a pharmaceutically acceptable salt or solvate thereof.

In one embodiment, the dosage is about 0.001 to 500 mg/kg of body weight/day of the compound of Formula I. In another embodiment, the dosage is about 0.01 to 25 mg/kg of body weight/day of a compound of Formula I, or a pharmaceutically acceptable salt or solvate of said compound.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

"Patient" includes both human and animals.

"Mammal" means humans and other mammalian animals.

Combination Therapy

The instant compounds may also be useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds may also be useful when co-administered with radiation therapy. The compounds of the present invention can be present in the same dosage unit as the anticancer agent or in separate dosage units.

Another aspect of the present invention is a potential method of treating one or more diseases associated with HDM2, comprising administering to a mammal in need of such treatment an amount of a first compound, which is a compound of the present invention, or a pharmaceutically acceptable salt or solvate thereof; and an amount of at least one second compound, the second compound being an anti-cancer agent different from the compounds of the present invention, wherein the amounts of the first compound and the second compound result in a therapeutic effect.

Non-limiting examples of suitable anti-cancer agents include cytostatic agents, cytotoxic agents, targeted therapeutic agents (small molecules, biologics, siRNA and microRNA) against cancer and neoplastic diseases, 1) anti-metabolites (such as methoxtrexate, 5-fluorouracil, gemcitabine, fludarabine, capecitabine);
2) alkylating agents, such as temozolomide, cyclophosphamide,
3) DNA interactive and DNA damaging agents, such as cisplatin, oxaliplatin, doxorubicin,
4) Ionizing irradiation, such as radiation therapy,
5) topoisomerase II inhibitors, such as etoposide, doxorubicin,
6) topoisomerase I inhibitors, such as irinotecan, topotecan,
7) tubulin interacting agents, such as paclitaxel, docetaxel, Abraxane, epothilones,
8) kinesin spindle protein inhibitors,
9) spindle checkpoint inhibitors,
10) Poly(ADP-ribose) polymerase (PARP) inhibitors, such as olaparib, MK-4827 and veliparib
11) Matrix metalloprotease (MMP) inhibitors
12) Protease inhibitors, such as cathepsin D and cathepsin K inhibitors
13) Proteosome or ubiquitination inhibitors, such as bortezomib,
14) Activator of mutant p53 to restore its wild-type p53 activity
15) Adenoviral-p53
16) Bcl-2 inhibitors, such as ABT-263
17) Heat shock protein (HSP) modulators, such as geldanamycin and 17-AAG
18) Histone deacetylase (HDAC) inhibitors, such as vorinostat (SAHA),
19) sex hormone modulating agents,
   a. anti-estrogens, such as tamoxifen, fulvestrant,
   b. selective estrogen receptor modulators (SERM), such as raloxifene,
   c. anti-androgens, such as bicalutamide, flutamide
   d. LHRH agonists, such as leuprolide,
   e. 5α-reductase inhibitors, such as finasteride,
   f. Cytochrome P450 C17 lyase (CYP450c17, also called 17α-hydroxylase/17,20 lysase) inhibitors, such as Abiraterone acetate, VN/124-1, TAK-700
   g. aromatase inhibitors, such as letrozole, anastrozole, exemestane,
20) EGFR kinase inhibitors, such as geftinib, erlotinib, laptinib
21) dual erbB1 and erbB2 inhibitors, such as Lapatinib
22) multi-targeted kinases (serine/threonine and/or tyrosine kinase) inhibitors,
   a. ABL kinase inhibitors, imatinib and nilotinib, dasatinib
   b. VEGFR-1, VEGFR-2, PDGFR, KDR, FLT, c-Kit, Tie2, Raf, MEK and ERK inhibitors, such as sunitinib, sorafenib, Vandetanib, pazopanib, PLX-4032, Axitinib, PTK787, GSK-1120212
   c. Polo-like kinase inhibitors
   d. Aurora kinase inhibitors
   e. JAK inhibitor
   f. c-MET kinase inhibitors
   g. Cyclin-dependent kinase inhibitors, such as CDK1 and CDK2 inhibitor SCH 727965
   h. PI3K and mTOR inhibitors, such as GDC-0941, BEZ-235, BKM-120 and AZD-8055
   i. Rapamycin and its analogs, such as Temsirolimus, everolimus, and deforolimus
23) and other anti-cancer (also know as anti-neoplastic) agents include but are not limited to ara-C, adriamycin, cytoxan, Carboplatin, Uracil mustard, Clormethine, Ifosfsmide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, Pentostatine, Vinblastine, Vincristine, Vindesine, Vinorelbine, Navelbine, Bleomycin, Dactinomycin, Daunorubicin, Doxorubicin, Epirubicin, teniposide, cytarabine, pemetrexed, Idarubicin, Mithramycin, Deoxycoformycin, Mitomycin-C, L-Asparaginase, Teniposide, Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Flutamerol, Medroxyprogesteroneacetate, Toremifene, goserelin, Carboplatin, Hydroxyurea, Amsacrine, Procarbazine, Mitotane, Mitoxantrone, Levamisole, Drolloxafine, Hexamethylmelamine, Bexxar, Zevalin, Trisenox, Profimer, Thiotepa, Altretamine, Doxil, Ontak, Depocyt, Aranesp, Neupogen, Neulasta, Kepivance.

24) Farnesyl protein transferase inhibitors, such as, SARASAR™ (4-[2-[4-[(11R)-3,10-dibromo-8-chloro-6,11-dihydro-5H-benzo[5,6]cyclohepta[1,2-b]pyridin-11-yl-]-1-piperidinyl]-2-oxoethyl]-piperidinecarboxamide, tipifarnib
25) interferons, such as Intron A, Peg-Intron,
26) anti-erbB1 antibodies, such as cetuximab, panitumumab,
27) anti-erbB2 antibodies, such as trastuzumab,
28) anti-CD52 antibodies, such as Alemtuzumab,
29) anti-CD20 antibodies, such as Rituximab
30) anti-CD33 antibodies, such as Gemtuzumab ozogamicin
31) anti-VEGF antibodies, such as Avastin,
32) TRIAL ligands, such as Lexatumumab, mapatumumab, and AMG-655
33) Anti-CTLA-4 antibodies, such as ipilimumab
34) antibodies against CTA1, CEA, CD5, CD19, CD22, CD30, CD44, CD44V6, CD55, CD56, EpCAM, FAP,

MHCII, HGF, IL-6, MUC1, PSMA, TALE, TAG-72, TRAILR, VEGFR, IGF-2, FGF, 35) anti-IGF-1R antibodies, such as dalotuzumab (MK-0646) and robatumumab (SCH 717454).

If formulated as a fixed dose such combination products employ the compounds of this invention within the dosage range described herein and the other pharmaceutically active agent or treatment within its dosage range. Compounds of Formula I may also be administered sequentially with known anticancer or cytotoxic agents when a combination formulation is inappropriate. The invention is not limited in the sequence of administration; compounds of Formula I may be administered either concurrent with, prior to or after administration of the known anticancer or cytotoxic agent. Such techniques are within the skills of the persons skilled in the art as well as attending physicians.

Accordingly, in an aspect, this invention includes combinations comprising an amount of at least one compound of Formula I, or a pharmaceutically acceptable salt or solvate thereof, and an amount of one or more anti-cancer treatments and anti-cancer agents listed above wherein the amounts of the compounds/treatments result in potential therapeutic effect.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, platinum coordinator compounds, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine (chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, 4-demethoxy-3-deamino-3-aziridinyl-4-methylsulphonyl-daunorubicin (see WO 00/50032).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include taxanes in general. Specific compounds include paclitaxel (Taxol®), vindesine sulfate, 3',4'-didehydro-4'-deoxy-8'-norvincaleukoblastine, docetaxol (Taxotere®), rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino] ethyl]-5-[4-hydroOxy-3,5-dimethoxyphenyl]-5,5a,6,8,8a,9-hexahydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,1'-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidot-riazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other examples of angiogenesis inhibitors include, but are not limited to, endostatin, ukrain, ranpirnase, IM862,5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

Other therapeutic agents that modulate or inhibit angiogenesis and may also be used in combination with the compounds of the instant invention include agents that modulate or inhibit the coagulation and fibrinolysis systems (see review in *Clin.*

Chem. La. Med. 38:679-692 (2000)). Examples of such agents that modulate or inhibit the coagulation and fibrinolysis pathways include, but are not limited to, heparin (see Thromb. Haemost. 80:10-23 (1998)), low molecular weight heparins and carboxypeptidase U inhibitors (also known as inhibitors of active thrombin activatable fibrinolysis inhibitor [TAFIa]) (see Thrombosis Res. 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK11 and CHK12 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, Nature, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670, 469), inhibitors of Raf kinase (for example PLX-4032), inhibitors of MEK (for example Arry-162, RO-4987655 and GSK-1120212), inhibitors of mTOR (for example AZD-8055, BEZ-235 and everolimus), and inhibitors of PI3K (for example GDC-0941, BKM-120).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 µM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over 1050 for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550, 142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633, 272 and U.S. Pat. No. 5,932,598.

Inhibitors of COX-2 that may be useful in the instant method of treatment are: 3-phenyl-4-(4-(methylsulfonyl) phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and therefore may be useful in the present invention include, but are not limited to, the following: parecoxib, BEXTRA® and CELEBREX® or a pharmaceutically acceptable salt thereof.

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo [3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations of the instantly claimed compounds with PPAR-γ (i.e., PPAR-gamma) agonists and PPAR-δ (i.e., PPAR-delta) agonists may be useful in the treatment of certain malignancies. PPAR-γ and PPAR-δ are the nuclear peroxisome proliferator-activated receptors γ and ∂. The expression of PPAR-γ on endothelial cells and its involvement in angiogenesis has been reported in the literature (see J. Cardiovasc. Pharmacol. 1998; 31:909-913; J. Biol. Chem. 1999; 274:9116-9121; Invest. Ophthalmol. Vis. Sci. 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (Arch. Ophthamol. 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-6-yl)oxy]-2-methylpropionic acid, and 2(R)-7-(3-(2-chloro-4-(4-fluorophenoxy)phenoxy)propoxy)-2-ethylchromane-2-carboxylic acid.

Another embodiment of the instant invention is the use of the presently disclosed compounds in combination with gene therapy for the potential treatment of cancer. For an overview of genetic strategies to treating cancer see Hall et al (Am. J. Hum. Genet. 61:785-789, 1997) and Kufe et al (Cancer Medicine, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous erythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir.

A compound of the instant invention may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, 011033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

Inhibitors of Akt, as disclosed in the following publications; WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469, and including compounds of the instant invention, may also be useful in combination with potassium salts, magnesium salts, beta-blockers (such as atenolol) and endothelin-a (ETa)antagonists with the goal of maintaining cardiovascular homeostasis.

Inhibitors of Akt, as disclosed in the following publications; WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469, and including compounds of the instant invention, may also be useful in combination with insulin, insulin secretagogues, PPAR-gamma agonists, metformin, somatostatin receptor agonists such as octreotide, DPP4 inhibitors, sulfonylureas and alpha-glucosidase inhibitors with the goal of maintaining glucose homeostasis.

A compound of the instant invention may also be useful for treating or preventing cancer in combination with PARP inhibitors: olaparib, MK-4827 and veliparib.

A compound of the instant invention may also be useful for treating cancer in combination with the following chemotherapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bendamustine hydrochloride (Treanda®); bevacuzimab (Avastin®); bexarotene capsules (Targretin®); bexarotene gel (Targretin®); bleomycin (Blenoxane®); bortezomib (Velcade®); brefeldin A; busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); dalteparin sodium injection (Fragmin®); Darbepoetin alfa (Aranesp®); dasatinib (Sprycel®); daunorubicin liposomal (DanuoXome®); daunorubicin, daunomycin (Daunorubicin®); daunorubicin, daunomycin (Cerubidine®); degarelix (Firmagon®); Denileukin diftitox (Ontak®); dexrazoxane (Zinecard®); dexrazoxane hydrochloride (Totect®); didemnin B; 17-DMAG; docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); eculizumab injection (Soliris®); Elliott's B Solution (Elliott's B Solution®); eltrombopag (Promacta®); epirubicin (Ellence®); Epoetin alfa (Epogen®); erlotinib (Tarceva®); estramustine (Emcyt®); ethinyl estradiol; etoposide phosphate (Etopophos®); etoposide, VP-16 (Vepesid®); everolimus tablets (Afinitor®); exemestane (Aromasin®); ferumoxytol (Feraheme Injection®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); geldanamycin; gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); iobenguane I 123 injection (AdreView®); irinotecan (Camptosar®); ixabepilone (Ixempra®); lapatinib tablets (Tykerb®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); 8-methoxypsoralen; mitomycin C (Mutamycin®); mitotane (Lysodren®); mitoxantrone (Novantrone®); mitramycin; nandrolone phenpropionate (Durabolin-50®); nelarabine (Arranon®); nilotinib (Tasigna®); Nofetumomab (Verluma®); ofatumumab (Arzerra®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); panitumumab (Vectibix®);

pazopanib tablets (Votrienttm®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plerixafor (Mozobil®); plicamycin, mithramycin (Mithracin®); porfimer sodium (Photofrin®); pralatrexate injection (Folotyn®); procarbazine (Matulane®); quinacrine (Atabrine®); rapamycin; Rasburicase (Elitek®); raloxifene hydrochloride (Evista®); Rituximab (Rituxan®); romidepsin (Istodax®); romiplostim (Nplate®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); temsirolimus (Torisel®); teniposide, VM-26 (Vumon®); testolactone (Teslac®); thioguanine, 6-TG (Thioguanine®); thiopurine; thiotepa (Thioplex®); topotecan (Hycamtin®); toremifene (Fareston®); Tositumomab (Bexxar®); Tositumomab/I-131 tositumomab (Bexxar®); trans-retinoic acid; Trastuzumab (Herceptin®); tretinoin, ATRA (Vesanoid®); triethylenemelamine; Uracil Mustard (Uracil Mustard Capsules®); valrubicin (Valstar®); vinblastine (Velban®); vincristine (Oncovin®); vinorelbine (Navelbine®); vorinostat (Zolinza®); wortmannin; and zoledronate (Zometa®).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physician's Desk Reference, 56$^{th}$ Edition, 2002 (published by Medical Economics company, Inc. Montvale, N.J. 07645-1742), and the Physician's Desk Reference, 57$^{th}$ Edition, 2003 (published by Thompson PDR, Montvale, N.J. 07645-1742).

The invention disclosed herein is exemplified by the following preparations and examples which should not be construed to limit the scope of the disclosure.

EXAMPLES

Example 1

Methods of Preparing the Compounds of Formula (I)

The compounds of this invention may be made by a variety of methods, including standard chemistry. Any previously defined variable will continue to have the previously defined meaning unless otherwise indicated. Illustrative general synthetic methods are set out below, and then specific compounds of the Formula (I) are prepared in the Examples.

Compounds of general Formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of protecting groups as well as the reaction conditions and order of reaction steps shall be consistent with the preparation of compounds of Formula (I). Those skilled in the art will recognize whether a stereocenter exists in compounds of Formula (I). Accordingly, the present invention includes all possible stereoisomers and includes not only mixtures of stereoisomers (such as racemic compounds) but the individual stereoisomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994).

The following solvents, reagents, protecting groups, moieties, and other designations may be referred to by their abbreviations:

Me=methyl; Et=ethyl; Pr=propyl; iPr=isopropyl, Bu=butyl; t-Bu=tert-butyl; Ph=phenyl, and Ac=acetyl
μl=microliters
AcOH or HOAc=acetic acid
ACN=acetonitrile
Ad=adamantyl
APCI or APC=atmospheric-pressure chemical ionization
aq=aqueous
BINAP=2,2'-Bis(diphenylphosphino)-1,1'-binaphthalene
Bn=benzyl
Boc or BOO=tert-butoxycarbonyl
Bz=benzoyl
Cbz=benyzloxycarbonyl
CDI=1,1'-Carbonyldiimidazole
DAST=diethylaminosulfur trifluoride
dba=dibenzylideneacetone
DBU=1,8-Diaza-7-bicyclo[5.4.0]undecene
DCM=dichloromethane
DMAP=4-Dimethylaminopyridine
DIBAL or DIBALH=diisobutylaluminum hydride
DIEA or Hünig's Base=N,N-diisopropylethylamine
DMA=N,N-dimethylacetamide
DMF=dimethylformamide
DMSO=dimethyl sulfoxide
dppf=1,1'-Bis(diphenylphosphino)ferrocene
DMT=Dimercaptotriazine
DTT=dithiothreitol
EDC=1-ethyl-3-(3-dimethylaminopropyl)carbodiimide
EDTA=ethylenediamine tetraacetic acid
ESI or ES=Electrospray ionization
EtOAc=ethyl acetate
g=grams
GST=glutathione S-transferase
h=hour
HMDS=1,1,1,3,3,3-hexamethyldisilazane
HATU=N,N,N',N'-tetramethyl-O-(7-azabenzotriazol-1-yl)uronium hexafluorophosphate
HPLC=high-performance liquid chromatography
HOBt=1-hydroxybenzotriazole
LAH=lithium aluminium hydride
LDA=lithium diisopropylamide
LC=liquid chromatography
LCMS=liquid chromatography mass spectrometry
min=minute
mg=milligrams
mL=milliliters
mmol=millimoles
mCPBA=meta-Chloroperoxybenzoic acid
Me=methyl
MeOH=methanol
MS=mass spectrometry
MTBE=methyl tert-butyl ether
NBS=N-bromosuccinimide
NMP=N-methylpyrrolidone
NMR=nuclear magnetic resonance spectroscopy
PTLC=preparative thin layer chromatography
rac=racemic mixture
R$_f$=retardation factor
RT or rt=room temperature (ambient, about 25° C.)
sat=saturated
SFC=supercritical fluid chromatography
TBAF=tetrabutylammonium fluoride
TBSCI=t-butyldimethylsilyl chloride
TBS=t-butyldimethylsilyl
TEA=triethylamine (Et$_3$N)
TFA=trifluoroacetic acid
TFAA=trifluoroacetic anhydride
THF=tetrahydrofuran
TLC=thin layer chromatography
TMS=trimethylsilyl
Tris=tris(hydroxymethyl)aminomethane
Xantphos=4,5-Bis(diphenylphosphino)-9,9-dimethylxanthene Scheme 1

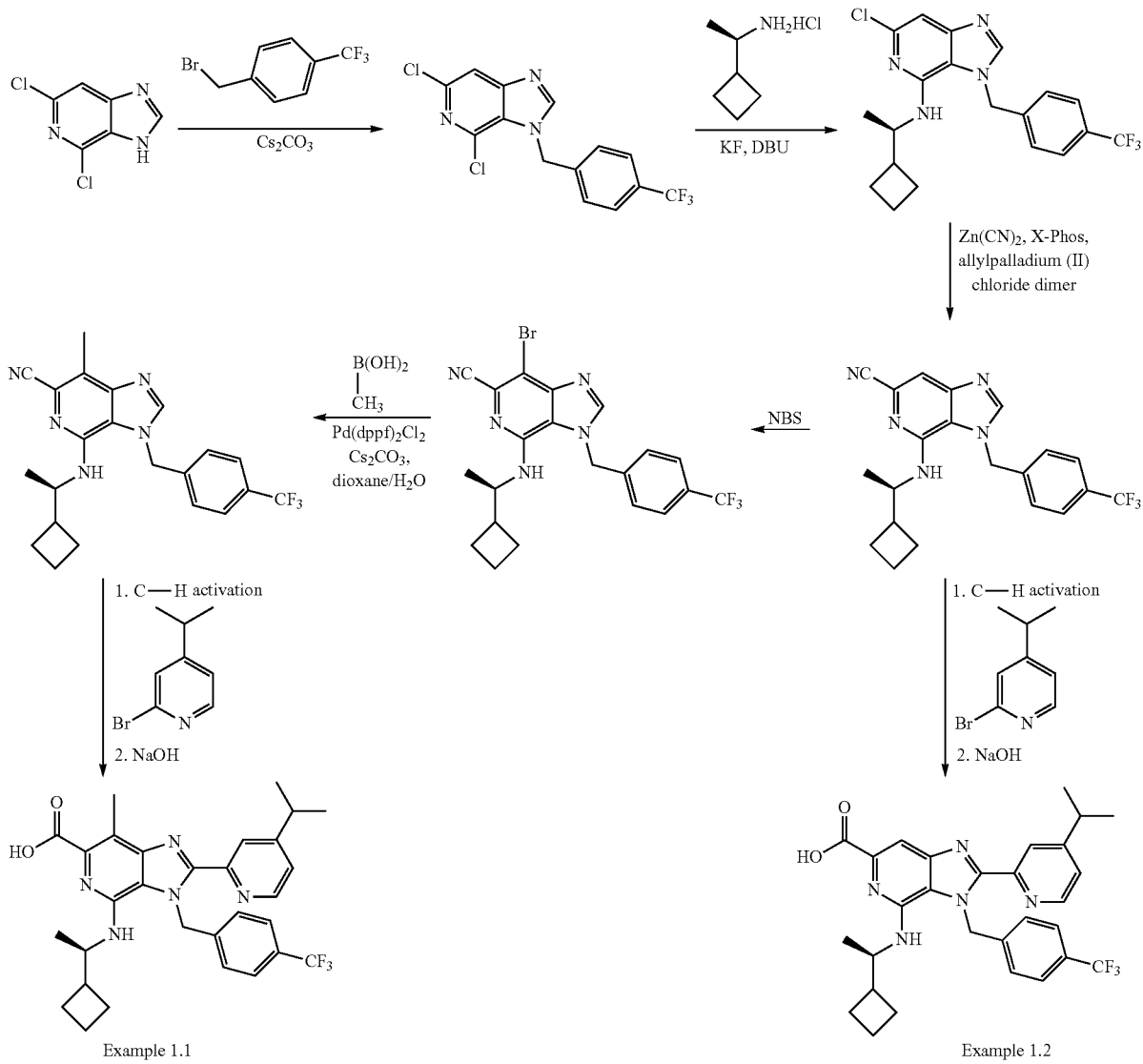

Example 1.1

Example 1.2

Preparative Example 1.1

(R)-6-chloro-N-(1-cyclobutylethyl)-3-(4-(trifluoromethyl)benzyl)-3H-imidazo[4,5-c]pyridin-4-amine

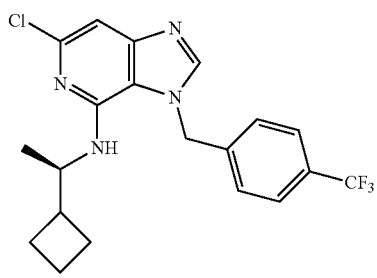 [SMILES: C[C@@H](Nc1nc(Cl)cc2ncn(Cc3ccc(C(F)(F)F)cc3)c12)C1CCC1]

Step 1: 1-(Bromomethyl)-4-(trifluoromethyl)benzene (6.36 g, 26.6 mmol) was added to a stirred solution of 4,6-dichloro-3H-imidazo[4,5-c]pyridine (5.0 g, 26.6 mmol) and cesium carbonate (10.40 g, 31.9 mmol) in DMA (30.0 ml) at room temperature and was stirred for 2 h. Water was added, and the solids were filtered and dried overnight. Crude $^1$H NMR showed ~4:1 ratio of undesired 4,6-dichloro-1-(4-(trifluoromethyl)benzyl)-1H-imidazo[4,5-c]pyridine:desired 4,6-dichloro-3-(4-(trifluoromethyl)benzyl)-3H-imidazo[4,5-c]pyridine. The crude residue was purified by silica gel chromatography (EtOAc/DCM, 0% to 20%) to afford the desired 4,6-dichloro-3-(4-(trifluoromethyl)benzyl)-3H-imidazo[4,5-c]pyridine (fraction 1) and the undesired 4,6-dichloro-1-(4-(trifluoromethyl)benzyl)-1H-imidazo[4,5-c]pyridine (fraction 2). 4,6-dichloro-3-(4-(trifluoromethyl)benzyl)-3H-imidazo[4,5-c]pyridine: MS ESI calc'd for $C_{14}H_8Cl_2F_3N_3$ [M+H]$^+$ 346. found 346.

Step 2: Potassium fluoride (0.940 g, 16.18 mmol) was added to a stirred solution of 4,6-dichloro-3-(4-(trifluoromethyl)benzyl)-3H-imidazo[4,5-c]pyridine (2.8 g, 8.09 mmol) in DMA (22.40 ml). The solution was stirred at room temperature for 5 min. (R)-1-cyclobutylethanamine hydrochloride (2.194 g, 16.18 mmol) and DBU (3.66 ml, 24.27 mmol) were added and the reaction mixture was heated at 120° C. overnight. The reaction mixture was cooled to room temperature and diluted with water and EtOAc. The aqueous layer was extracted with EtOAc (2×). The organic layers were combined, dried and concentrated. The residue was purified by silica gel chromatography (0-100% ethyl acetate/hexanes, linear gradient) to afford (R)-6-chloro-N-(1-cyclobutylethyl)-3-(4-(trifluoromethyl)benzyl)-3H-imidazo[4,5-c]pyridin-4-amine. MS ESI calc'd for $C_{20}H_{20}ClF_3N_4$ [M+H]$^+$ 409. found 409.

Preparative Example 1.2

(R)-1-cyclobutylethanamine hydrochloride

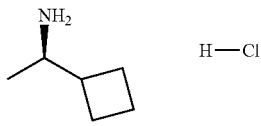

Step 1: Into a 20-L 4-necked round-bottom flask was placed a solution of cyclobutylmethanol (1000 g, 11.61 mol) in dichloromethane (10 L). This was followed by the addition of Dess-Martin periodinane (4683 g, 11.04 mol) in several batches at 10-15° C. over 120 min. The resulting solution was stirred for 2 h at room temperature and then quenched by the addition of 20 L of cold, saturated aqueous sodium bicarbonate solution. Solids were removed by filtration and washed with 5 L of dichloromethane. The filtrate was extracted with dichloromethane. The organic layers were combined, dried over anhydrous sodium sulfate and concentrated under vacuum. The residue was applied onto a silica gel column and eluted with DCM:PE (2:1). This resulted in 100 L of cyclobutanecarbaldehyde in dichloromethane and petroleum ether solution. Step 2: Into a 50-L barrel was placed cyclobutanecarbaldehyde in dichloromethane and petroleum ether (33 L of the solution described at the end of Step 1), (S)-2-methylpropane-2-sulfinamide (500 g, 4.13 mol) and copper sulfate (2 kg, 13.33 mol). The resulting solution was stirred for 2 days at room temperature. Solids were removed by filtration. The filtrate was concentrated under vacuum. The residue was applied onto a silica gel column and eluted with ethyl acetate/petroleum ether (1:5) to afford (S)—N-[(1E)-cyclobutylmethylidene]-2-methylpropane-2-sulfinamide.

Step 3: Into a 10-L 4-neck round-bottom flask purged and maintained with an inert atmosphere of nitrogen was placed a solution of (S)—N-[(1E)-cyclobutylmethylidene]-2-methylpropane-2-sulfinamide (200 g, 1.07 mol) in tetrahydrofuran (3000 mL). This was followed by the addition of methylmagnesium bromide in ether (1070 mL, 3.00 equiv) dropwise with stirring at −78° C. over 1 hr. The resulting solution was stirred for 1 h at −70° C., 1 h at −60° C., 1 h at −50° C. and 2 h at −40° C. The reaction was then quenched by the addition of 10 L of saturated aqueous NH$_4$Cl solution. The resulting solution was extracted with 2×3 L of ether. The organic layers were combined, washed with 2×3 L of brine, dried over anhydrous sodium sulfate, and concentrated under vacuum. The residue was diluted with 250 mL of n-hexane. The resulting solid was collected and washed with 2×100 mL of cold n-hexane to afford (S)—N-[(1R)-1-cyclobutylethyl]-2-methylpropane-2-sulfinamide.

Step 4: Into a 10-L 4-neck round-bottom flask was placed a solution of (S)—N-[(1R)-1-cyclobutylethyl]-2-methylpropane-2-sulfinamide (400 g, 1.97 mol) in methanol (2800 mL). This was followed by the addition of HCl/p-dioxane (5M, 1.6 L) dropwise with stirring at 0° C. over 60 min. The resulting solution was stirred for 60 min at room temperature. The solution was then concentrated under vacuum. The residue was diluted with 4 L of n-hexane and stirred for 30 min at room temperature. The solid was collected by filtration. The filtrate was diluted with 1200 mL of CH$_3$CN and stirred for 30 min at room temperature. The solid was collected by filtration. The combined solids were dried in an oven under reduced pressure to afford (1R)-1-cyclobutylethan-1-amine as a hydrogen chloride salt. MS ESI calc'd for $C_6H_{13}N$ [M+H]$^+$ 100. found 100. $^1$H NMR (400 MHz, DMSO-d$_6$): δ 7.95 (s, 3H), 3.11 (s, 1H), 2.32-2.42 (m, 1H), 1.75-2.01 (m, 6H), 1.10 (s, 3H).

Example 1.1

(R)-4-((1-cyclobutylethyl)amino)-2-(4-isopropylpyridin-2-yl)-7-methyl-3-(4-(trifluoromethyl)benzyl)-3H-imidazo[4,5-c]pyridine-6-carboxylic acid

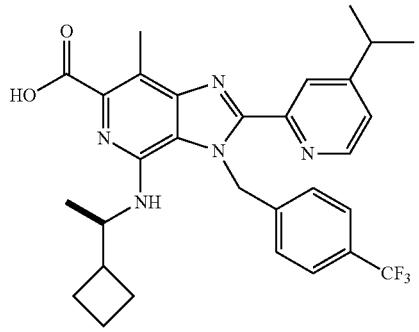 [SMILES: Cc1c(C(=O)O)nc(N[C@H](C)C2CCC2)c2c1nc(-c1cc(C(C)C)ccn1)n2Cc1ccc(C(F)(F)F)cc1]

Step 1: A vial containing 2-dicyclohexylphosphino-2',4',6'-triisopropylbiphenyl (67.6 mg, 0.142 mmol) and allylpalladium(II) chloride dimer (26 mg, 0.071 mmol) in DMA (400 ul) was evacuated and refilled with Ar (3×). The resulting solution was warmed to 70° C. for 20 minutes. In a separate vial was added zinc cyanide (92 mg, 0.78 mmol), (R)-6-chloro-N-(1-cyclobutylethyl)-3-(4-(trifluoromethyl)benzyl)-3H-imidazo[4,5-c]pyridin-4-amine (290 mg, 0.71 mmol) and DMA (500 uL). The mixture was degassed with Ar for 15 minutes, and the catalyst solution was added to the mixture. The resulting mixture was stirred at 120° C. overnight. The mixture was cooled to room temperature and concentrated. The residue was dissolved in DCM purified by silica gel chromatography (0-100% ethyl acetate/hexanes, linear gradient) to give (R)-4-((1-cyclobutylethyl)amino)-3-(4-(trifluoromethyl)benzyl)-3H-imidazo[4,5-c]pyridine-6-carbonitrile. MS ESI calc'd for $C_{21}H_{20}F_3N_5$ [M+H]$^+$ 400. found 400.

Step 2: NBS (73.5 mg, 0.413 mmol) was added to a stirred, room temperature mixture of (R)-4-((1-cyclobutylethyl)amino)-3-(4-(trifluoromethyl)benzyl)-3H-imidazo[4,5-c]pyridine-6-carbonitrile (150 mg, 0.376 mmol) in degassed chloroform (3 ml) in a sealed tube. The mixture was heated to 45° C. and stirred under Ar for 1 hour. The mixture was cooled to room temperature and diluted with DCM. The mixture was then transferred to a separatory funnel, washed with saturated sodium bicarbonate, dried over sodium sulfate, filtered, and concentrated in vacuo. The resulting dark orange oil was purified by silica gel chromatography (0-100% ethyl acetate/ hexanes, linear gradient) to afford (R)-7-bromo-4-((1-cyclobutylethyl)amino)-3-(4-(trifluoromethyl)benzyl)-3H-imidazo[4,5-c]pyridine-6-carbonitrile. MS ESI calc'd for $C_{21}H_{19}BrF_3N_5$ [M+H]$^+$ 479. found 479.

Step 3: To a vial containing (R)-7-bromo-4-((1-cyclobutylethyl)amino)-3-(4-(trifluoromethyl)benzyl)-3H-imidazo[4,5-c]pyridine-6-carbonitrile (65 mg, 0.14 mmol), methylboronic acid (16.3 mg, 0.3 mmol), 1,1'-Bis(diphenylphosphino)ferrocene-palladium(II)dichloride-chloroform adduct (11.1 mg, 0.014 mmol) and potassium phosphate (87 mg, 0.41 mmol) was added 1,4-dioxane (800 ul) and water (200 uL). The vial was evacuated and refilled with Ar (3×). The solution was heated to 120° C. for 10 minutes under microwave irradiation. The mixture was cooled to room temperature and quenched with saturated sodium bicarbonate and ethyl acetate. The organic layer was collected and concentrated. The residue was dissolved in DCM and purified by silica gel chromatography (0-100% ethyl acetate/hexanes, linear gradient) to give (R)-4-((1-cyclobutylethyl)amino)-7-methyl-3-(4-(trifluoromethyl)benzyl)-3H-imidazo[4,5-c]pyridine-6-carbonitrile. MS ESI calc'd for $C_{22}H_{22}F_3N_5$ [M+H]$^+$ 414. found 414.

Step 4: To a vial containing palladium(II) acetate (4.3 mg, 0.019 mmol) and butyldi-1-adamantylphosphine (13.9 mg, 0.039 mmol) was added 1,4-dioxane (300 ul). The vial was evacuated and refilled with Ar (3×). The solution was warmed to 70° C. for 20 minutes. In a separate vial were combined pivalic acid (9.9 mg, 0.097 mmol), cesium fluoride (44 mg, 0.29 mmol), 2-bromo-4-isopropylpyridine (purchased from CombiPhos Catalysts, Inc.) (29 mg, 0.15 mmol), (R)-4-((1-cyclobutylethyl)amino)-7-methyl-3-(4-(trifluoromethyl)benzyl)-3H-imidazo[4,5-c]pyridine-6-carbonitrile (40 mg, 0.097 mmol) and 1,4-dioxane (0.5 mL). The mixture was degassed with Ar for 15 minutes, and the catalyst solution was added to the mixture. The resulting mixture was stirred at 130° C. for 3 days. The mixture was cooled to room temperature and concentrated. The residue was dissolved in DCM and purified by silica gel chromatography (0-100% ethyl acetate/hexanes, linear gradient) to give (R)-4-((1-cyclobutylethyl)amino)-2-(4-isopropylpyridin-2-yl)-7-methyl-3-(4-(trifluoromethyl)benzyl)-3H-imidazo[4,5-c]pyridine-6-carbonitrile. MS ESI calc'd for $C_{30}H_{31}F_3N_6$ [M+H]$^+$ 533. found 533.

Step 5: To (R)-4-((1-cyclobutylethyl)amino)-2-(4-isopropylpyridin-2-yl)-7-methyl-3-(4-(trifluoromethyl)benzyl)-3H-imidazo[4,5-c]pyridine-6-carbonitrile (26 mg, 0.049 mmol) dissolved in ethanol (1 ml) was added sodium hydroxide (5.0 M in water, 1 mL, 5.0 mmol). The reaction was heated to 110° C. and stirred overnight. The solution was cooled to room temperature, concentrated, and then diluted with EtOAc. It was washed with 1N HCl, then dried over sodium sulfate, filtered and concentrated. The residue was purified by mass triggered, reverse phase (C-18) preparative HPLC (acetonitrile:water: 0.1% v/v trifluoroacetic acid modifier) to afford (R)-4-((1-cyclobutylethyl)amino)-2-(4-isopropylpyridin-2-yl)-7-methyl-3-(4-(trifluoromethyl)benzyl)-3H-imidazo[4,5-c]pyridine-6-carboxylic acid (as a TFA salt). MS ESI calc'd for $C_{30}H_{32}F_3N_5O_2$ [M+H]$^+$ 552. found 552. $^1$H NMR (500 MHz, CDCl$_3$): δ 0.99 (d, J=6.1 Hz, 3H); 1.32-1.25 (m, 1H); 1.35 (d, J=6.9 Hz, 6H); 1.50-1.42 (m, 1H); 1.63-1.54 (m, 2H); 1.78-1.67 (m, 1H); 1.92-1.85 (m, 1H); 2.06-1.99 (m, 1H); 2.89 (s, 3H); 3.08-3.02 (m, 1H); 3.81 (s, 1H); 5.30 (s, 1H); 6.36 (d, J=17.1 Hz, 1H); 6.59 (d, J=16.8 Hz, 1H); 7.29-7.27 (m, 1H); 7.33 (d, J=8.0 Hz, 2H); 7.68 (d, J=8.0 Hz, 2H); 8.33 (s, 1H); 8.45 (d, J=5.0 Hz, 1H).

Example 1.2, Example 1.3 and Example 1.4 in Table 1 were prepared using procedures which are analogous to those described above in Example 1.1 (Step 1, Step 4 and Step 5). Example 1.2 and Example 1.3 were prepared from (R)-6-chloro-N-(1-cyclobutylethyl)-3-(4-(trifluoromethyl)benzyl)-3H-imidazo[4,5-c]pyridin-4-amine (Preparative Example 1.1). Example 1.4 was prepared from 4,6-dichloro-3-((trans-4-methylcyclohexyl)methyl)-3H-imidazo[4,5-c]pyridine (Preparative Example 2.3).

TABLE 1

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.1 | 60 | 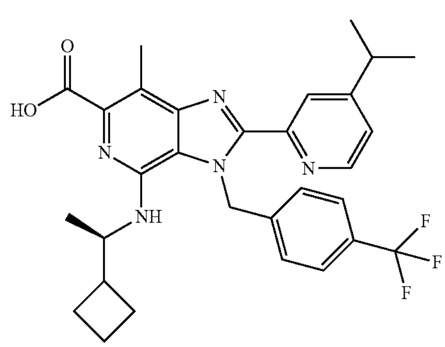 [SMILES: Cc1c(C(=O)O)nc(N[C@H](C)C2CCC2)c2c1nc(-c1cc(C(C)C)ccn1)n2Cc1ccc(C(F)(F)F)cc1] | (R)-4-((1-cyclobutylethyl)amino)-2-(4-isopropylpyridin-2-yl)-7-methyl-3-(4-(trifluoromethyl)benzyl)-3H-imidazo[4,5-c]pyridine-6-carboxylic acid | TFA | 552 | 552 |

TABLE 1-continued

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 1.2 | 29 | 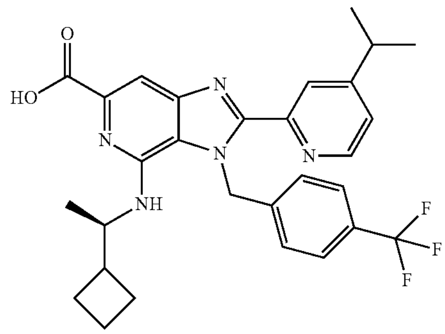 [SMILES: CC(C)c1ccnc(-c2nc3cc(C(=O)O)nc(N[C@H](C)C4CCC4)c3n2Cc2ccc(C(F)(F)F)cc2)c1] | 4-{[(1R)-1-cyclobutylethyl]amino}-2-[4-(1-methylethyl)pyridin-2-yl]-3-[4-(trifluoromethyl)benzyl]-3H-imidazo[4,5-c]pyridine-6-carboxylic acid | TFA | 538 | 538 |
| 1.3 | 122 | 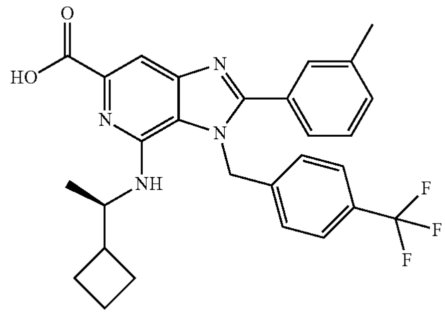 [SMILES: Cc1cccc(-c2nc3cc(C(=O)O)nc(N[C@H](C)C4CCC4)c3n2Cc2ccc(C(F)(F)F)cc2)c1] | 4-{[(1R)-1-cyclobutylethyl]amino}-2-(3-methylphenyl)-3-[4-(trifluoromethyl)benzyl]-3H-imidazo[4,5-c]pyridine-6-carboxylic acid | TFA | 509 | 509 |
| 1.4 | 4 | 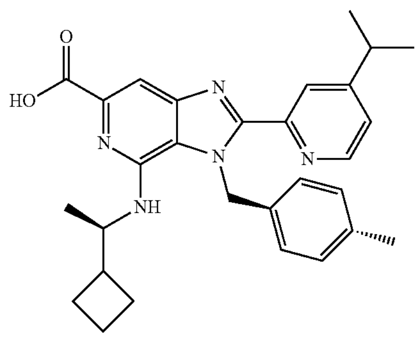 | 4-{[(1R)-1-cyclobutylethyl]amino}-3-[(trans-4-methylcyclohexyl)methyl]-2-[4-(1-methylethyl)pyridin-2-yl]-3H-imidazo[4,5-c]pyridine-6-carboxylic acid | TFA | 490 | 490 |

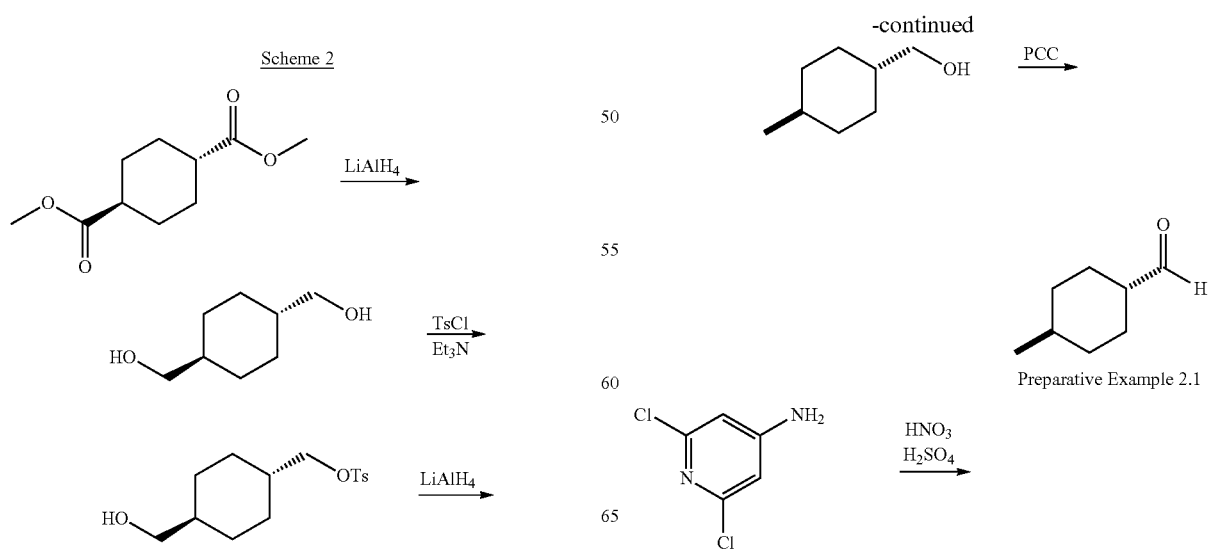

Preparative Example 2.1

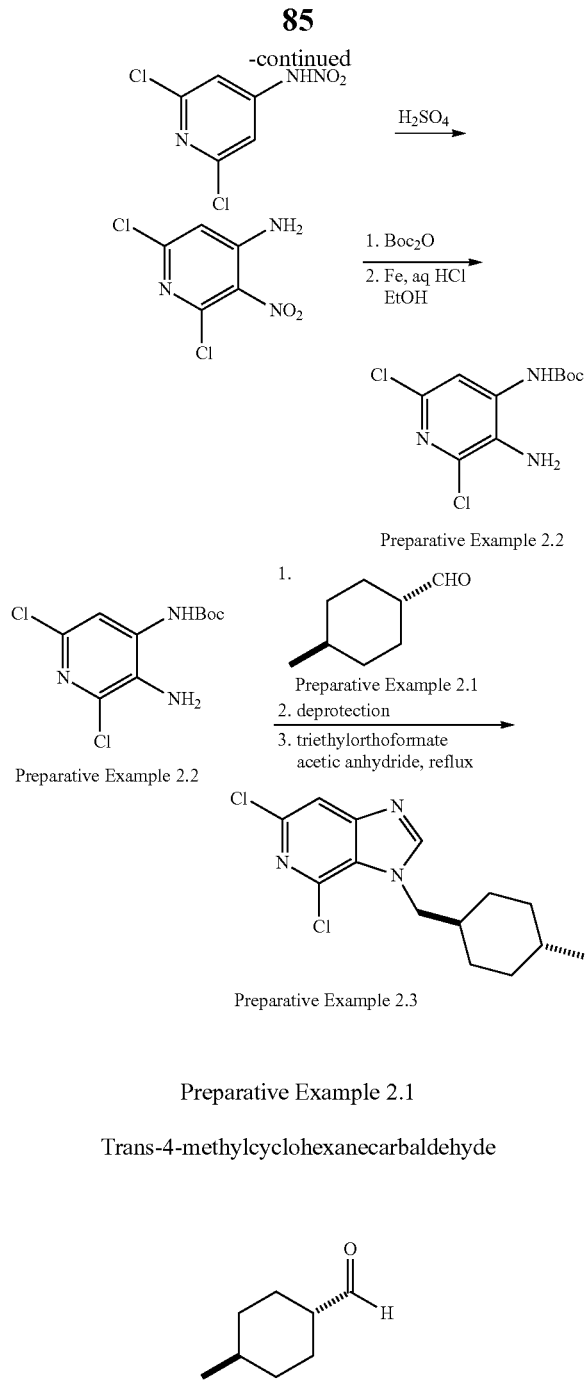

Preparative Example 2.1

Trans-4-methylcyclohexanecarbaldehyde

Step 1: To a solution of trans-dimethyl cyclohexane-1,4-dicarboxylate (1000 g, 5 mol) in THF (3000 mL) cooled to −20° C. was added LiAlH$_4$ (570 g, 15 mol). The mixture was stirred at room temperature for 3 h, quenched with water (10 L), and filtered. The filtrate was concentrated in vacuo to give trans-cyclohexane-1,4-diyldimethanol as white solid. $^1$H NMR (CDCl$_3$, 400 MHz): δ 3.48-3.46 (m, 4H), 1.86-1.84 (m, 4H), 1.47-1.42 (m, 4H), 1.01-0.96 (m, 4H).

Step 2: 4-Toluenesulfonyl chloride (742.5 g, 3.75 mol) was added to a solution of trans-cyclohexane-1,4-diyldimethanol (500 g, 4.17 mol) and Et$_3$N (695 g, 5 mol) in DCM (6000 mL) at −20° C. The mixture was stirred at room temperature for 10 h and then quenched with water (10 L). The organic layer was separated, the aqueous layer was extracted with DCM (2×3 L), and the combined organic layer was dried over sodium sulfate, filtered, and concentrated in vacuo to give trans-4-(hydroxymethyl)cyclohexylmethyl 4-methylbenzenesulfonate as a yellow oil.

Step 3: LiAlH$_4$ (153 g, 4 mol) was added to a solution of trans-4-(hydroxymethyl)cyclohexylmethyl 4-methylbenzenesulfonate (400 g, 1.34 mol) in THF (3000 mL) at −20° C. The mixture was stirred at room temperature for 3 h. It was quenched with water (10 L) and filtered. The filtrate was concentrated in vacuo to give trans-(4-methylcyclohexyl)methanol.

Step 4: To a solution of trans-(4-methylcyclohexyl)methanol (160 g, 1.25 mol) in DCM (1500 mL) was added pyridinium chlorochromate (405 g, 1.88 mol) at 0° C., and the mixture was stirred at room temperature for 2 h. It was filtered and the filtrate was concentrated in vacuo to give trans-4-methylcyclohexanecarbaldehyde.

Preparative Example 2.2

Tert-butyl (3-amino-2,6-dichloropyridin-4-yl)carbamate

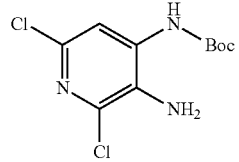 [SMILES: CC(C)(C)OC(=O)Nc1cc(Cl)nc(Cl)c1N]

Step 1: A solution of 2,6-dichloropyridin-4-amine (500 g, 3.08 mol) in sulfuric acid (5 L) was cooled to 0° C. Nitric acid (2 L, 15 mol) was slowly added dropwise to the above resulting solution. The starting 2,6-dichloropyridin-4-amine was consumed after 3 hr. The reaction mixture was added to water (20 L), and the solid was filtered to give N-(2,6-dichloropyridin-4-yl)nitramide. This material was used directly in the next step. $^1$H NMR (CDCl$_3$, 400 MHz): δ 7.11-7.14 (m, 1H), 7.09-7.09 (s, 1H).

Step 2: N-(2,6-dichloropyridin-4-yl)nitramide (610 g, 10.8 mol) in sulfuric acid (5 L) was heated to 100° C. and stirred for 3 h. The resulting mixture was slowly added to ice water (20 L). The solid was filtered to give crude 2,6-dichloro-3-nitropyridin-4-amine. $^1$H NMR (CDCl$_3$ 400 MHz): δ 6.95 (s, 1H), 5.78 (s, 2H).

Step 3: To a solution of 2,6-dichloro-3-nitropyridin-4-amine (580 g, 2.8 mol) and di-tert-butyl dicarbonate (2431 g, 11.2 mol) in THF (3000 mL) cooled to −20° C. was added LiHMDS (1 M in THF, 11.2 L, 11.2 mol). The mixture was stirred at room temperature for 3 h. It was quenched with ammonium chloride (6 L) and extracted with EtOAc (2×2 L). The organic layer was washed with saturated sodium bicarbonate (1 L) and brine, dried with anhydrous sodium sulfate, and concentrated in vacuo to give crude tert-butyl (2,6-dichloro-3-nitropyridin-4-yl)carbamate.

Step 4: A mixture of tert-butyl (2,6-dichloro-3-nitropyridin-4-yl)carbamate (700 g, 2.27 mol) and iron (1272.7 g, 22.7 mol) in ethanol (5 L) and water (1 L) was stirred at room temperature for 10 h. The mixture was filtered, the filtrate was concentrated in vacuo, and the crude product was crystallized using EtOAc to give tert-butyl (3-amino-2,6-dichloropyridin-4-yl)carbamate.

Preparative Example 2.3

4,6-dichloro-3-((trans-4-methylcyclohexyl)methyl)-3H-imidazo[4,5-c]pyridine

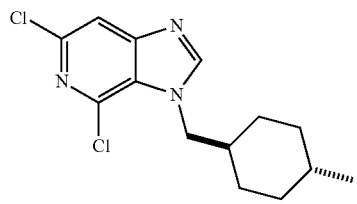

Step 1: To a solution of tert-butyl (3-amino-2,6-dichloropyridin-4-yl)carbamate (353 g, 1.27 mol) and trans-4-methylcyclohexanecarbaldehyde (160 g, 1.27 mol) in DCM (8.0 L) and acetic acid (2 ml) was added sodium triacetoxyborohydride (807.7 g, 3.81 mol) at 0° C. The mixture was stirred for 15 min, and then warmed to room temperature. The mixture was stirred for 15 h at room temperature and then quenched with water (10 L). The mixture was filtered, the filtrate was separated, and the organic layer was concentrated under reduced pressure to give crude product. The crude product was purified over a silica gel column, eluting with EtOAc: petroleum ether (0-1:10), to give tert-butyl (2,6-dichloro-3-(((trans-4-methylcyclohexyl)methyl)amino)pyridin-4-yl)carbamate.

Step 2: A solution of tert-butyl (2,6-dichloro-3-(((trans-4-methylcyclohexyl)methyl)amino)pyridin-4-yl)carbamate (150 g, 0.386 mol) in HCl/1,4-dioxane (4 M, 3.0 L) was stirred at 45° C. for 15 h. The mixture was concentrated under reduced pressure to give crude 2,6-dichloro-$N^3$-((trans-4-methylcyclohexyl)methyl)pyridine-3,4-diamine.

Step 3: A solution of 2,6-dichloro-$N^3$-((trans-4-methylcyclohexyl)methyl)pyridine-3,4-diamine (126 g, 0.386 mol) in triethylorthoformate (1.0 L) and acetic anhydride (1.0 L) was stirred at 90° C. for 3 h. The solution was concentrated in vacuo, and the residue was dissolved in DCM/10% NaOH (2.0 L/1.0 L). The organic layer was separated and concentrated. The crude product was purified by a silica gel column, eluting with DCM/petroleum ether (1:1), to give 4,6-dichloro-3-((trans-4-methylcyclohexyl)methyl)-3H-imidazo[4,5-c]pyridine. MS ESI calc'd. for $C_{14}H_{17}Cl_2N_3$ [M+H]$^+$ 298. found 298. $^1$H NMR (400 MHz, CDCl$_3$): 7.96 (s, 1H); 7.66 (m, 1H); 4.28-4.26 (d, 2H); 1.85-1.79 (m, 1H); 1.73-1.71 (d, 2H), 1.70-1.61 (d, 2H), 1.34-1.33 (m, 1H) 1.12-1.02 (m, 2H), 0.94-0.84 (m, 5H).

Scheme 3

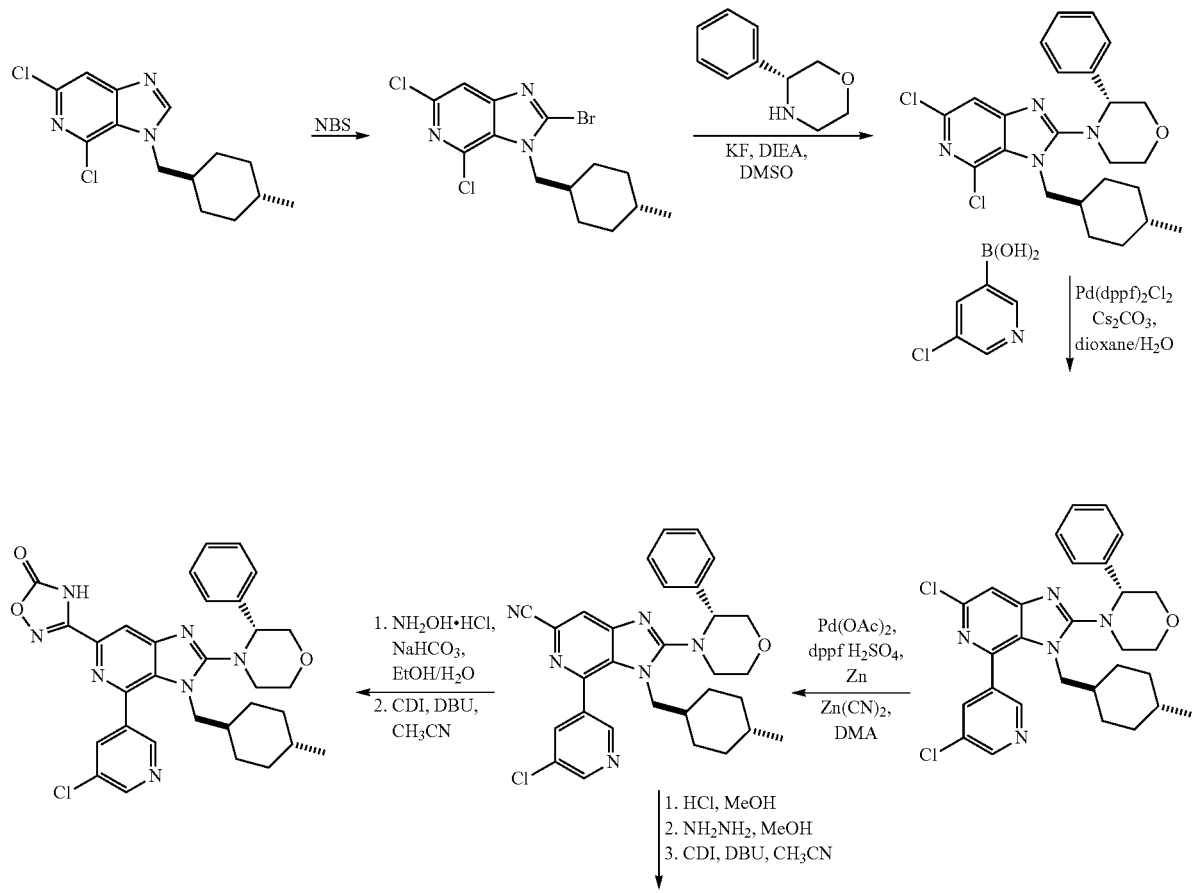

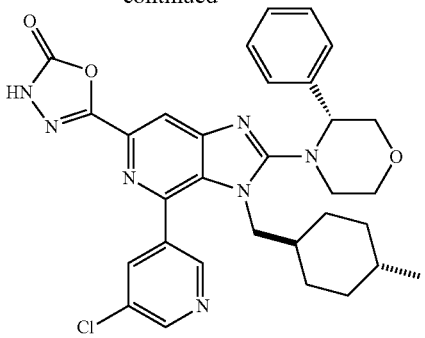

Example 2.2

Example 2.1

3-{4-(5-chloropyridin-3-yl)-3-[(trans-4-methylcyclohexyl)methyl]-2-[(3R)-3-phenylmorpholin-4-yl]-3H-imidazo[4,5-c]pyridin-6-yl}-1,2,4-oxadiazol-5(4H)-one

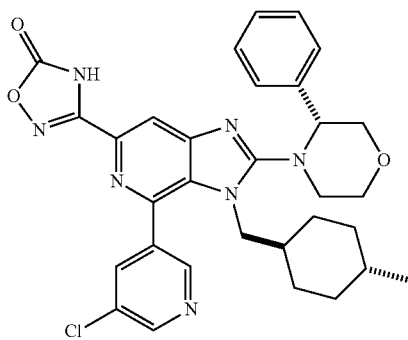

Step 1: N-bromosuccinimide (3.28 g, 18.4 mmol) was added to a solution of 4,6-dichloro-3-[(trans-4-methylcyclohexyl)methyl]-3H-imidazo[4,5-c]pyridine (Preparative Example 2.3, 5 g, 16.8 mmol) stirring in degassed chloroform (168 mL) at room temperature. The reaction was heated to reflux for 1 hour. The mixture was cooled to room temperature, diluted with dichloromethane, and washed with saturated aqueous sodium thiosulfate (2×) and brine. The organic layer was dried over sodium sulfate, filtered, and concentrated under reduced pressure. The residue was purified by silica gel chromatography (0-100% ethyl acetate/hexanes, linear gradient) to afford 2-bromo-4,6-dichloro-3-[(trans-4-methylcyclohexyl)methyl]-3H-imidazo[4,5-c]pyridine. MS ESI calc'd. for $C_{14}H_{16}BrCl_2N_3$ [M+H]$^+$ 378. found 378.

Alternatively, Step 1 could be performed as follows:

4,6-dichloro-3-[(trans-4-methylcyclohexyl)methyl]-3H-imidazo[4,5-c]pyridine (1 g, 3.35 mmol) was dissolved in THF (10 mL). Disodium hydrogen phosphate (1.43 g, 10.1 mmol) was added, and the reaction was warmed to 35° C. with stirring. 1,3-dibromo-5,5-dimethylhydantoin (1.15 g, 4.02 mmol) was added in 1 portion, and the reaction was continued with stirring at 35° C. After 45 minutes, the reaction was diluted with EtOAc (100 mL) and washed with aqueous $NaHSO_3$ and brine. The organic layer was dried over $Na_2SO_4$, filtered, and concentrated. Purification of the residue on a silica gel column with 0 to 50% EtOAc/hexanes provided 2-bromo-4,6-dichloro-3-[(trans-4-methylcyclohexyl)methyl]-3H-imidazo[4,5-c]pyridine.

Step 2: To a vial were added 2-bromo-4,6-dichloro-3-[(trans-4-methylcyclohexyl)methyl]-3H-imidazo[4,5-c]pyridine (3.13 g, 8.30 mmol), (R)-3-phenylmorpholine (purchased from Beyond Pharmatech) (2.71 g, 16.6 mmol), potassium fluoride (2.41 g, 41.5 mmol), DMSO (25.5 mL), and N,N-diisopropylethylamine (7.25 mL, 41.5 mmol). The vial was sealed and heated to 100° C. for 16 hours. The reaction mixture was cooled to room temperature, diluted with ethyl acetate, and washed with water and then brine. The organic layer was dried over sodium sulfate, filtered, and concentrated under reduced pressure. The residue was purified by silica gel chromatography (0-60% ethyl acetate/hexanes, linear gradient) to afford 4,6-dichloro-3-[(trans-4-methylcyclohexyl)methyl]-2-[(3R)-3-phenylmorpholin-4-yl]-3H-imidazo[4,5-c]pyridine. MS ESI calc'd. for $C_{24}H_{28}Cl_2N_4O$ [M+H]$^+$ 459. found 459.

Step 3: 4,6-dichloro-3-[(trans-4-methylcyclohexyl)methyl]-2-[(3R)-3-phenylmorpholin-4-yl]-3H-imidazo[4,5-c]pyridine (3.44 g, 7.49 mmol), 5-chloropyridine-3-boronic acid (1.32 g, 08.39 mmol), cesium carbonate (12.2 g, 37.4 mmol), and 1,1'-Bis(diphenylphosphino)ferrocene-palladium(II)dichloride (1.1 g, 1.49 mmol) were combined in a vial that had been oven-dried and flushed with nitrogen. Dioxane (75 mL) was added, and the vial was sealed and heated to 90° C. for 4 hours. The reaction mixture was cooled to room temperature, filtered over celite, and the filtrate was concentrated under reduced pressure. The residue was purified by silica gel chromatography (0-100% ethyl acetate/hexanes, linear gradient) to afford 6-chloro-4-(5-chloropyridin-3-yl)-3-[(trans-4-methylcyclohexyl)methyl]-2-[(3R)-3-phenylmorpholin-4-yl]-3H-imidazo[4,5-c]pyridine. MS ESI calc'd. for $C_{29}H_{31}Cl_2N_5O$ [M+H]$^+$ 536. found 536.

Step 4: In an oven-dried, nitrogen cooled flask were combined palladium(II) acetate (70 mg, 0.312 mmol) and (R)-(+)-2,2'-bis(diphenylphosphino)-1,1'-binaphthyl (195 mg, 0.313 mmol). N,N-dimethylacetamide (18.7 mL) was added, and the mixture was degassed for three minutes with nitrogen (sparge). Sulfuric acid (0.017 mL) was added, and the mixture was degassed for three minutes with nitrogen (sparge). The flask was sealed and heated to 80° C. for 30 minutes. The mixture was cooled to room temperature and added to a separate nitrogen purged flask containing 6-chloro-4-(5-chloropyridin-3-yl)-3-[(trans-4-methylcyclohexyl)methyl]-2-[(3R)-3-phenylmorpholin-4-yl]-3H-imidazo[4,5-c]pyridine (1.68 g, 3.14 mmol), zinc cyanide (0.184 g, 1.57 mmol), and zinc (21 mg, 0.32 mmol). The flask was purged with nitrogen for five minutes and sealed and heated to 100° C. for 3.5 hours. The reaction mixture was cooled to room temperature, filtered, diluted with ethyl acetate, and washed with water and brine. The organic layer was dried over sodium sulfate, filtered, and concentrated under reduced pressure. The residue was purified by silica gel chromatography (0-100% ethyl acetate/hexanes, linear gradient) to afford 4-(5-chloropyridin-3-yl)-3-[(trans-4-methylcyclohexyl)methyl]-2-[(3R)-3-phenylmorpholin-4-yl]-3H-imidazo[4,5-c]pyridine-6-carbonitrile. MS ESI calc'd. for $C_{30}H_{31}ClN_6O$ [M+H]$^+$ 527. found 527.

Step 5: Hydroxylamine hydrochloride (5.4 mg, 0.08 mmol), sodium bicarbonate (9.9 mg, 0.12 mmol), and water (0.12 mL) were combined in a vial and stirred for 15 minutes. This solution was added to a vial containing 4-(5-chloropyridin-3-yl)-3-[(trans-4-methylcyclohexyl)methyl]-2-[(3R)-3-phenylmorpholin-4-yl]-3H-imidazo[4,5-c]pyridine-6-carbonitrile (20.6 mg, 0.04 mmol) dissolved in ethanol (0.3 mL). The mixture was sealed and heated at 100° C. for 1 hour. The reaction was cooled to room temperature, quenched with water, and extracted with ethyl acetate (2×). The combined organic layers were dried over sodium sulfate, filtered, and concentrated to afford 4-(5-chloropyridin-3-yl)-N'-hydroxy-3-[(trans-4-methylcyclohexyl)methyl]-2-[(3R)-3-phenylmorpholin-4-yl]-3H-imidazo[4,5-c]pyridine-6-carboximidamide. MS ESI calc'd. for $C_{30}H_{34}ClN_7O_2$ [M+H]$^+$ 560. found 560.

Step 6: To a solution of 4-(5-chloropyridin-3-yl)-N'-hydroxy-3-[(trans-4-methylcyclohexyl)methyl]-2-[(3R)-3-phenylmorpholin-4-yl]-3H-imidazo[4,5-c]pyridine-6-carboximidamide (21 mg, 0.04 mmol) and 1,1'-carbonyldiimidazole (6.1 mg, 0.04 mmol) dissolved in acetonitrile (1 mL) was added 1,8-diazabicyclo[5.4.0]undec-7-ene (0.022 mL, 0.15 mmol). The reaction mixture was stirred at room temperature for 1 hour. The reaction was washed with water and extracted with dichloromethane. The organic layer was dried over sodium sulfate, filtered, and concentrated under reduced pressure. The residue was purified by mass triggered, reverse phase (C-18) preparative HPLC (acetonitrile:water: 0.1% v/v trifluoroacetic acid modifier) to afford 3-{4-(5-chloropyridin-3-yl)-3-[(trans-4-methylcyclohexyl)methyl]-2-[(3R)-3-phenylmorpholin-4-yl]-3H-imidazo[4,5-c]pyridin-6-yl}-1,2,4-oxadiazol-5(4H)-one (as a TFA salt). MS ESI calc'd. for $C_{31}H_{32}ClN_7O_3$ [M+H]$^+$ 586. found 586. $^1$H NMR (500 MHz, DMSO-d$_6$) δ 12.85 (s, 1H), 8.88 (d, J=1.6, 1H), 8.79 (d, J=2.3, 1H), 8.41 (t, J=2.0, 1H), 7.92 (s, 1H), 7.44 (d, J=7.4, 2H), 7.27 (t, J=7.5, 2H), 7.20 (t, J=7.2, 1H), 4.88-4.81 (m, 1H), 4.05-3.74 (m, 5H), 3.65-3.52 (m, 3H), 1.42-1.30 (m, 2H), 1.11-0.99 (m, 1H), 0.87-0.77 (m, 1H), 0.74-0.58 (m, 5H), 0.57-0.51 (m, 1H), 0.49-0.42 (m, 1H), 0.41-0.26 (m, 2H).

Example 2.2

5-{4-(5-chloropyridin-3-yl)-3-[(trans-4-methylcyclohexyl)methyl]-2-[(3R)-3-phenylmorpholin-4-yl]-3H-imidazo[4,5-c]pyridin-6-yl}-1,3,4-oxadiazol-2(3H)-one

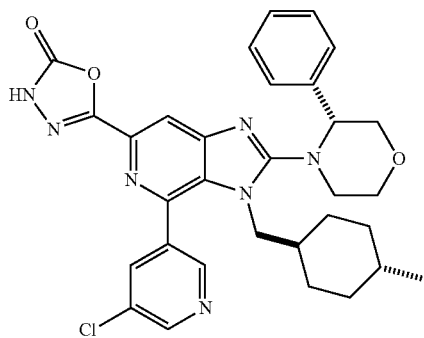

Step 1: Hydrochloric acid (3.0 M in methanol, 102 mL, 307 mmol) was added to 4-(5-chloropyridin-3-yl)-3-[(trans-4-methylcyclohexyl)methyl]-2-[(3R)-3-phenylmorpholin-4-yl]-3H-imidazo[4,5-c]pyridine-6-carbonitrile (4.04 g, 7.67 mmol), and the mixture was stirred at 75° C. for 3.5 hours. The reaction was cooled to room temperature, diluted with dichloromethane, and washed with saturated aqueous sodium bicarbonate and brine. The organic layer was dried over sodium sulfate, filtered, and concentrated under reduced pressure to afford methyl 4-(5-chloropyridin-3-yl)-3-[(trans-4-methylcyclohexyl)methyl]-2-[(3R)-3-phenylmorpholin-4-yl]-3H-imidazo[4,5-c]pyridine-6-carboxylate. MS ESI calc'd. for $O_{31}H_{34}ClN_5O_3$ [M+H]$^+$ 560. found 560.

Step 2: Hydrazine (9.2 mL, 293 mmol) was added to methyl 4-(5-chloropyridin-3-yl)-3-[(trans-4-methylcyclohexyl)methyl]-2-[(3R)-3-phenylmorpholin-4-yl]-3H-imidazo[4,5-c]pyridine-6-carboxylate (4.11 g, 7.33 mmol) dissolved in methanol (36.6 mL), and the solution was stirred at room temperature for 30 minutes. The mixture was diluted with dichloromethane and washed with water and brine. The organic layer was dried over sodium sulfate, filtered, and concentrated under reduced pressure to afford 4-(5-chloropyridin-3-yl)-3-[(trans-4-methylcyclohexyl)methyl]-2-[(3R)-3-phenylmorpholin-4-yl]-3H-imidazo[4,5-c]pyridine-6-carbohydrazide. MS ESI calc'd. for $C_{30}H_{34}ClN_7O_2$ [M+H]$^+$ 560. found 560.

Step 3: To a solution of 4-(5-chloropyridin-3-yl)-3-[(trans-4-methylcyclohexyl)methyl]-2-[(3R)-3-phenylmorpholin-4-yl]-3H-imidazo[4,5-c]pyridine-6-carbohydrazide (4.5 g, 8.03 mmol) and 1,1'-carbonyldiimidazole (1.43 g, 8.84 mmol) dissolved in acetonitrile (53.6 mL) was added 1,8-diazabicyclo[5.4.0]undec-7-ene (4.8 mL, 32.1 mmol). The reaction mixture was stirred at room temperature for 1 hour. The reaction was washed with water and extracted with dichloromethane. The organic layer was dried over sodium sulfate, filtered, and concentrated under reduced pressure. The residue was purified by silica gel chromatography (0-10% methanol/dichloromethane, and then 0-100% ethyl acetate/hexanes, linear gradient) to afford 5-{4-(5-chloropyridin-3-yl)-3-[(trans-4-methylcyclohexyl)methyl]-2-[(3R)-3-phenylmorpholin-4-yl]-3H-imidazo[4,5-c]pyridin-6-yl}-1,3,4-oxadiazol-2(3H)-one. MS ESI calc'd. for $O_{31}H_{32}ClN_7O_3$ [M+H]$^+$ 586. found 586. $^1$H NMR (500 MHz, DMSO-d$_6$) δ 12.62 (s, 1H), 8.79 (d, J=8.3, 2H), 8.27 (s, 1H), 7.87 (s, 1H), 7.42 (t, J=10.0, 2H), 7.25 (t, J=7.2, 2H), 7.22-7.17 (m, 1H), 4.76 (s, 1H), 4.05-3.81 (m, 4H), 3.80-3.69 (m, 1H), 3.67-3.47 (m, 2H), 3.27 (s, 1H), 1.37 (t, J=13.0, 2H), 1.03 (broad, 1H), 0.83 (broad, 1H), 0.68 (d, J=6.2, 4H), 0.64-0.52 (m, 2H), 0.51-0.27 (m, 3H).

The following compounds in Table 2 (other than Example 2.1 and 2.2) were prepared using procedures which were analogous to those described above in Example 2.1 and Example 2.2

TABLE 2

| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.1 | <1 | 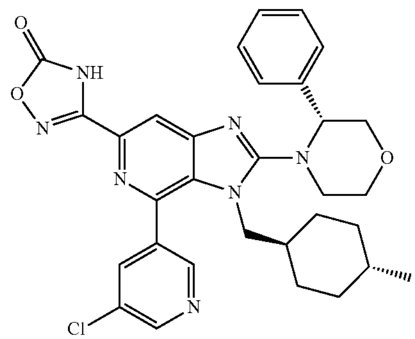 [SMILES: C[C@H]1CC[C@H](Cn2c(N3CCOC[C@H]3c3ccccc3)nc3cc(-c4noc(=O)[nH]4)nc(-c4cncc(Cl)c4)c32)CC1] | 3-{4-(5-chloropyridin-3-yl)-3-[(trans-4-methylcyclohexyl)methyl]-2-[(3R)-3-phenylmorpholin-4-yl]-3H-imidazo[4,5-c]pyridin-6-yl}-1,2,4-oxadiazol-5(4H)-one | TFA | 586 | 586 |
| 2.2 | 1 | 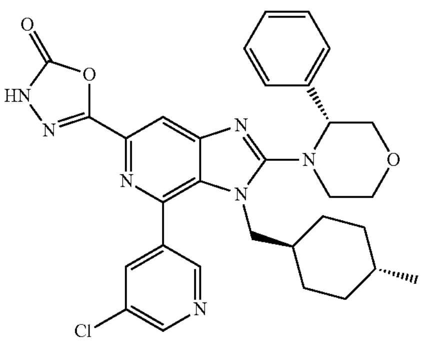 [SMILES: C[C@H]1CC[C@H](Cn2c(N3CCOC[C@H]3c3ccccc3)nc3cc(-c4n[nH]c(=O)o4)nc(-c4cncc(Cl)c4)c32)CC1] | 5-{4-(5-chloropyridin-3-yl)-3-[(trans-4-methylcyclohexyl)methyl]-2-[(3R)-3-phenylmorpholin-4-yl]-3H-imidazo[4,5-c]pyridin-6-yl}-1,3,4-oxadiazol-2(3H)-one | TFA | 586 | 586 |
| 2.3 | 3 | 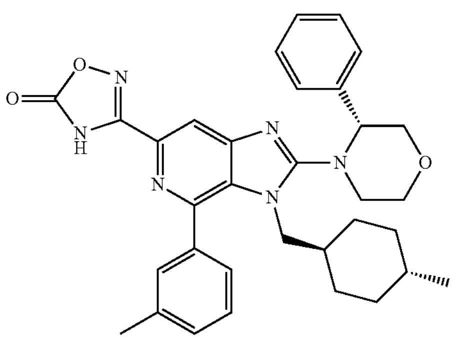 [SMILES: Cc1cccc(-c2nc(-c3noc(=O)[nH]3)cc3nc(N4CCOC[C@H]4c4ccccc4)n(C[C@H]4CC[C@H](C)CC4)c23)c1] | 3-{3-[(trans-4-methylcyclohexyl)methyl]-4-(3-methylphenyl)-2-[(3R)-3-phenylmorpholin-4-yl]-3H-imidazo[4,5-c]pyridin-6-yl}-1,2,4-oxadiazol-5(4H)-one | TFA | 565 | 565 |
| 2.4 | 3 | 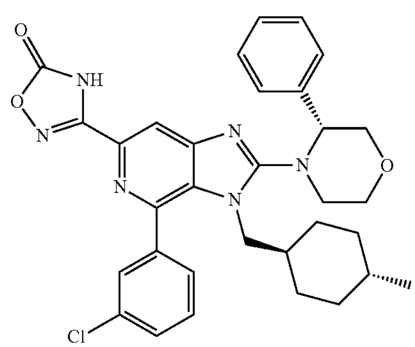 [SMILES: C[C@H]1CC[C@H](Cn2c(N3CCOC[C@H]3c3ccccc3)nc3cc(-c4noc(=O)[nH]4)nc(-c4cccc(Cl)c4)c32)CC1] | 3-{4-(3-chlorophenyl)-3-[(trans-4-methylcyclohexyl)methyl]-2-[(3R)-3-phenylmorpholin-4-yl]-3H-imidazo[4,5-c]pyridin-6-yl}-1,2,4-oxadiazol-5(4H)-one | TFA | 585 | 585 |

TABLE 2-continued
| Ex. | FRET IC$_{50}$ (nM) | Structure | Chemical Name | Salt Form | [M + H]$^+$ Calc'd | [M + H]$^+$ Obsv'd |
|---|---|---|---|---|---|---|
| 2.5 | 9 | 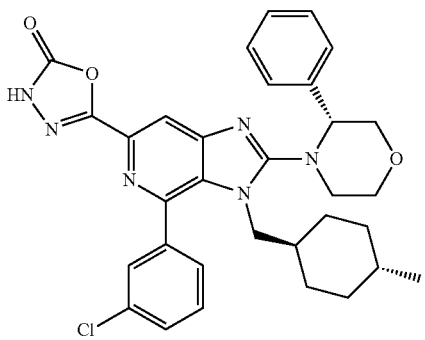 [SMILES: C[C@H]1CC[C@H](Cn2c(N3CCOC[C@H]3c3ccccc3)nc3cc(-c4n[nH]c(=O)o4)nc(-c4cccc(Cl)c4)c32)CC1] | 5-{4-(3-chlorophenyl)-3-[(trans-4-methylcyclohexyl)methyl]-2-[(3R)-3-phenylmorpholin-4-yl]-3H-imidazo[4,5-c]pyridin-6-yl}-1,3,4-oxadiazol-2(3H)-one | TFA | 585 | 585 |
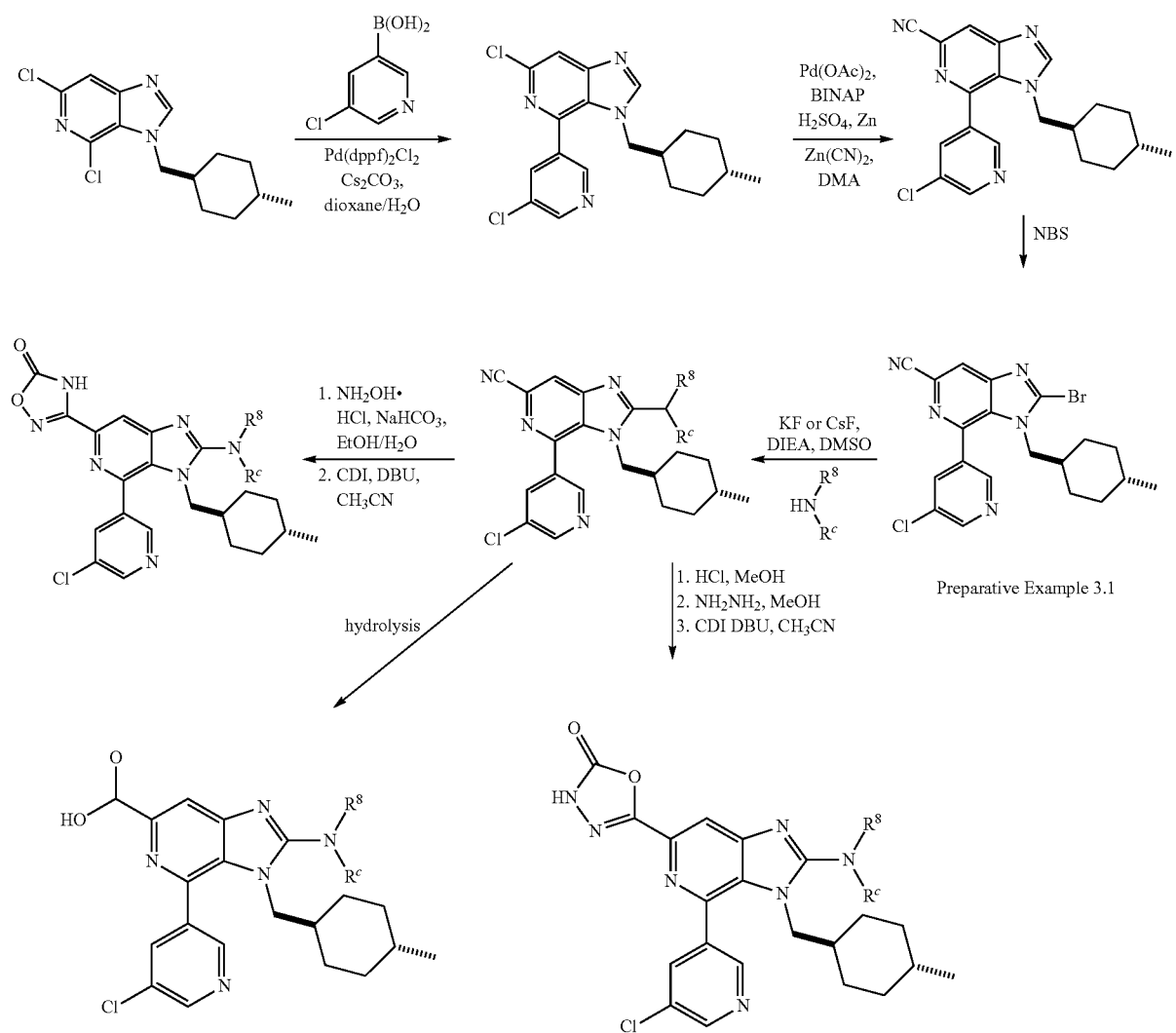
Scheme 4
Preparative Example 3.1

Preparative Example 3.1

2-bromo-4-(5-chloropyridin-3-yl)-3-[(trans-4-methylcyclohexyl)methyl]-3H-imidazo[4,5-c]pyridine-6-carbonitrile

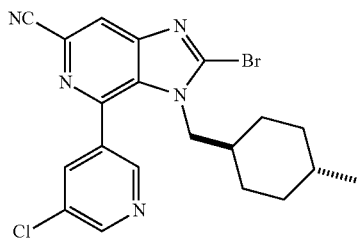

Step 1: 4,6-dichloro-3-[(trans-4-methylcyclohexyl)methyl]-3H-imidazo[4,5-c]pyridine (6.8 g, 22.8 mmol), 5-chloropyridine-3-boronic acid (3.95 g, 25.1 mmol), cesium carbonate (22.3 g, 68.4 mmol), and 1,1'-Bis(diphenylphosphino)ferrocene-palladium(II)dichloride (1.67 g, 2.28 mmol) were combined in a vial that had been oven-dried and flushed with nitrogen. Dioxane (73 mL) and water (18 mL) were added, and the vial was sealed and heated to 90° C. for 3 hours. The reaction mixture was cooled to room temperature, diluted with ethyl acetate, and washed with water. The organic layer was washed with brine, dried over sodium sulfate, filtered, and concentrated under reduced pressure. The residue was purified by silica gel chromatography (0-100% ethyl acetate/hexanes, linear gradient) to afford 6-chloro-4-(5-chloropyridin-3-yl)-3-[(trans-4-methylcyclohexyl)methyl]-3H-imidazo[4,5-c]pyridine. MS ESI calc'd. for $C_{19}H_{20}Cl_2N_4$ [M+H]$^+$ 375. found 375.

Step 2: In an oven-dried, nitrogen cooled flask were placed palladium(II) acetate (438 mg, 1.95 mmol) and (R)-(+)-2,2'-Bis(diphenylphosphino)-1,1'-binaphthyl (1.22 g, 1.95 mmol). N,N-dimethylacetamide (98 mL) was added, and the flask was degassed for three minutes with nitrogen (sparge). Sulfuric acid (0.104 mL, 1.95 mmol) was added, and the flask was degassed for three minutes with nitrogen (sparge). The flask was sealed and heated to 80° C. for 30 minutes. The mixture was cooled to room temperature and added to a separate nitrogen purged flask containing 6-chloro-4-(5-chloropyridin-3-yl)-3-[(trans-4-methylcyclohexyl)methyl]-3H-imidazo[4,5-c]pyridine (7.33 g, 19.5 mmol), zinc cyanide (1.15 g, 9.77 mmol), and zinc (128 mg, 1.95 mmol). The flask was purged with nitrogen for five minutes, then sealed and heated to 100° C. for 3.5 hours. The reaction mixture was cooled to room temperature, filtered, diluted with ethyl acetate, and washed with water and brine. The organic layer was dried over sodium sulfate, filtered, and concentrated under reduced pressure. The residue was purified by silica gel chromatography (0-100% ethyl acetate/hexanes, linear gradient) to afford 4-(5-chloropyridin-3-yl)-3-[(trans-4-methylcyclohexyl)methyl]-3H-imidazo[4,5-c]pyridine-6-carbonitrile. MS ESI calc'd. for $C_{20}H_{20}ClN_5$ [M+H]$^+$ 366. found 366.

Step 3: N-bromosuccinimide (5.84 g, 32.8 mmol) was added to a room temperature solution of 4-(5-chloropyridin-3-yl)-3-[(trans-4-methylcyclohexyl)methyl]-3H-imidazo[4,5-c]pyridine-6-carbonitrile (4 g, 10.9 mmol) stirring in degassed chloroform (54.7 mL). The reaction was heated to reflux for 1 hour. The mixture was cooled to room temperature, diluted with dichloromethane, and washed with saturated aqueous sodium thiosulfate (2×) and brine. The organic layer was dried over sodium sulfate, filtered, and concentrated under reduced pressure. The residue was purified by silica gel chromatography (0-100% ethyl acetate/hexanes, linear gradient) to afford 2-bromo-4-(5-chloropyridin-3-yl)-3-[(trans-4-methylcyclohexyl)methyl]-3H-imidazo[4,5-c]pyridine-6-carbonitrile. MS ESI calc'd. for $C_{20}H_{19}BrClN_5$ [M+H]$^+$ 444. found 444. $^1$H NMR (500 MHz, DMSO-d$_6$) δ 8.87 (s, 1H), 8.84 (s, 1H), 8.57 (s, 1H), 8.40 (s, 1H), 3.86 (d, J=6.1, 2H), 1.44 (d, J=12.1, 2H), 1.15-1.05 (broad, 1H), 1.00-0.85 (broad, 1H), 0.85-0.73 (m, 4H), 0.72 (d, J=6.1, 3H), 0.56-0.43 (m 2H).

Alternatively, Step 3 could be performed as follows:
4-(5-chloropyridin-3-yl)-3-[(trans-4-methylcyclohexyl)methyl]-3H-imidazo[4,5-c]pyridine-6-carbonitrile (1 g, 2.73 mmol) was dissolved in THF (10 mL). Disodium hydrogen phosphate (1.16 g, 8.20 mmol) was added and the reaction was warmed to 35° C. with stirring. 1,3-dibromo-5,5-dimethylhydantoin (0.938 g, 3.28 mmol) was added in 1 portion and the reaction was continued with stirring at 35° C. After 1 hour, the reaction was diluted with EtOAc (100 mL) and washed with aqueous NaHSO$_3$ and brine. The organic layer was dried over Na$_2$SO$_4$, filtered, and concentrated. Purification of the residue on a silica gel column with 0 to 75% EtOAc/hexanes provided 2-bromo-4-(5-chloropyridin-3-yl)-3-[(trans-4-methylcyclohexyl)methyl]-3H-imidazo[4,5-c]pyridine-6-carbonitrile.

Preparative Example 3.2

Benzyl (4aR,8aR)-octahydro-6H-pyrido[3,4-b][1,4]oxazine-6-carboxylate

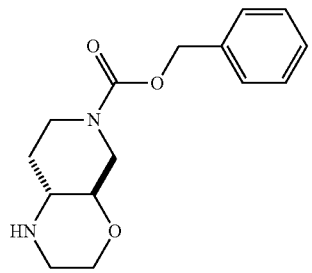

Step 1: To N-Boc-4-hydroxypiperidine (2200 g, 10.95 mol) in anhydrous DCM (8 L) was added triethylamine (2284 mL, 16.42 mol) in one portion at 0° C., then MsCl (1316 g, 11.49 mol) was added drop wise into the mixture at 0° C. The mixture was stirred at room temperature for 2 h. Water (2 L) was added to the mixture and the organic phase was separated, and then the organic phase was washed with 1 M hydrochloride solution (4 L), saturated NaHCO$_3$ solution (4 L), brine (1 L), and dried over anhydrous Na$_2$SO$_4$. The organic layer was concentrated to afford tert-butyl 4-[(methylsulfonyl)oxy]piperidine-1-carboxylate, which was used for the next step without further purification.

Step 2: A solution of tert-butyl 4-[(methylsulfonyl)oxy]piperidine-1-carboxylate (312 g, 1.12 mol) and DBU (400 g, 2.24 mol) in THF (4.5 L) was heated to reflux overnight. The mixture was poured into ice-water (2 L) and then extracted with EtOAc (2 L). The combined organic phase was washed with 1 M HCl solution (4 L×2), aq. NaHCO$_3$ (4 L), and dried over anhydrous sodium sulfate. The residue was concentrated to afford tert-butyl 3,6-dihydropyridine-1(2H)-carboxylate, which was used in the next step without further purification.

Step 3: To a solution of tert-butyl 3,6-dihydropyridine-1 (2H)-carboxylate (617 g, 3.37 mol) in anhydrous DCM (10 L) was added m-CPBA (989 g, 5.73 mol) in portions at 0° C. The mixture was stirred at room temperature for 1 hour. Saturated $Na_2S_2O_3$ (1 L) was added and the organic layer was separated. The organic layer was washed with 5% aqueous $K_2CO_3$ (5 L×2), brine (4 L), dried over sodium sulfate, and concentrated under reduced pressure. The residue was purified by column chromatography (petroleum ether:ethyl acetate=100:1-20:1) to obtain pure tert-butyl 7-oxa-3-azabicyclo[4.1.0]heptane-3-carboxylate.

Step 4: To a solution of tert-butyl 7-oxa-3-azabicyclo [4.1.0]heptane-3-carboxylate (500 g, 2.5 mol) in $H_2O$ (5 L) was added $BnNH_2$ (294 g, 2.75 mol) at room temperature. The mixture was heated to reflux overnight. The mixture was extracted with DCM (1 L), dried over sodium sulfate, and concentrated under reduced pressure to give tert-butyl-4-(benzylamino)-3-hydroxypiperidine-1-carboxylate and tert-butyl-3-(benzylamino)-4-hydroxypiperidine-1-carboxylate, which were used in the next step without further purification.

Step 5: To a solution of tert-butyl-4-(benzylamino)-3-hydroxypiperidine-1-carboxylate and tert-butyl-3-(benzylamino)-4-hydroxypiperidine-1-carboxylate (153 g, 0.42 mol, crude) and triethylamine (126 g, 1.25 mol) in DCM (800 mL) was added drop wise chloroacetyl chloride (33 g, 0.45 mol) at room temperature. The mixture was stirred at room temperature overnight. The mixture was quenched with water (300 mL) at 0° C., and extracted with DCM (500 mL×3). The organic layer was washed with brine (1 L), dried over sodium sulfate, and concentrated under reduced pressure. The residue was purified by silica gel chromatography to afford tert-butyl 4-[benzyl(chloroacetyl)amino]-3-hydroxypiperidine-1-carboxylate as a mixture of trans diastereomers which was used directly in the next step.

Step 6: To a solution of trans-tert-butyl 4-[benzyl(chloroacetyl)amino]-3-hydroxypiperidine-1-carboxylate (144 g, 376 mmol) in $CH_3CN$ (2 L) was added NaI (56.4 g, 376 mmol) in one portion. The mixture was stirred at reflux for 1 h and then concentrated. The residue was dissolved in DCM (1 L) and filtered. The filtrate was concentrated under reduced pressure to afford trans-tert-butyl 4-[benzyl(iodoacetyl)amino]-3-hydroxypiperidine-1-carboxylate, which was used directly in the next step without further purification.

Step 7: To a solution of trans-tert-butyl 4-[benzyl(iodoacetyl)amino]-3-hydroxypiperidine-1-carboxylate (172 g, 363 mmol) in THF (1500 mL) was added t-BuOK (48.72 g, 435 mmol) in portions at 0° C. The mixture was stirred at room temperature for 2 h. The mixture was poured into ice-water (400 mL) and extracted with EtOAc (200 mL×2). The organic layer was washed with brine (200 mL), dried over sodium sulfate, and concentrated under reduced pressure to give tert-butyl 1-benzyl-2-oxooctahydro-6H-pyrido[3,4-b][1,4]oxazine-6-carboxylate as a mixture of trans diastereomers, which was used in the next step without further purification.

Step 8: To a solution of trans-tert-butyl 1-benzyl-2-oxooctahydro-6H-pyrido[3,4-b][1,4]oxazine-6-carboxylate (126 g, 346 mmol) in anhydrous THF (2 L) was added borane methylsulfide complex (109 mL, 1.038 mol) drop wise at 0° C. The mixture was stirred at room temperature overnight. Methanol (300 mL) was added to the mixture at room temperature and heated to reflux for 1 h. The mixture was washed with saturated $NaHCO_3$ and brine, dried over sodium sulfate, and concentrated under reduced pressure. The residue was purified by silica gel chromatography to afford tert-butyl 1-benzyloctahydro-6H-pyrido[3,4-b][1,4]oxazine-6-carboxylate as a mixture of trans diastereomers.

Step 9: To a mixture of trans-tert-butyl 1-benzyloctahydro-6H-pyrido[3,4-b][1,4]oxazine-6-carboxylate (82 g, 246 mmol) in EtOAc (500 mL) at 0° C. was added HCl in EtOAc (1500 mL, 4 M) dropwise. The reaction was stirred at room temperature for 2 hours. The mixture was concentrated to afford 1-benzyloctahydro-1H-pyrido[3,4-b][1,4]oxazine as a mixture of trans diastereomers.

Step 10: To a solution of trans-1-benzyloctahydro-1H-pyrido[3,4-b][1,4]oxazine (79 g, 0.34 mol) and TEA (72.1 g, 0.714 mol) in DCM (1 L) was added TFAA (78.5 g, 0.37 mol) dropwise at 0° C. The mixture was stirred at room temperature overnight till the reaction was complete. The mixture was poured into water and extracted with DCM (500 mL×3). The combined organic layers were dried over sodium sulfate and concentrated to afford 1-(1-benzyloctahydro-6H-pyrido[3,4-b][1,4]oxazin-6-yl)-2,2,2-trifluoroethanone as a mixture of trans diastereomers, which was used in next step without further purification.

Step 11: A mixture of trans-1-(1-benzyloctahydro-6H-pyrido[3,4-b][1,4]oxazin-6-yl)-2,2,2-trifluoroethanone (51.6 g, 0.15 mol), Pd/C (20 g) and $(Boc)_2O$ (38.4 g, 0.176 mol) in MeOH (100 mL) was stirred at room temperature under $H_2$ (20 psi) for 6 h. The mixture was filtered, and the filtrate was concentrated under reduced pressure to give tert-butyl 6-(trifluoroacetyl)octahydro-1H-pyrido[3,4-b][1,4]oxazine-1-carboxylate as a mixture of trans diastereomers.

Step 12: To a solution of trans-tert-butyl 6-(trifluoroacetyl) octahydro-1H-pyrido[3,4-b][1,4]oxazine-1-carboxylate (70 g, 0.20 mol) in MeOH (160 mL) and water (600 mL) was added $K_2CO_3$ (34.2 g, 0.24 mol) in one portion at room temperature. The mixture was stirred for 2 h at room temperature, and then extracted with DCM (200 mL×5). The combined organic layers were concentrated to give tert-butyl octahydro-1H-pyrido[3,4-b][1,4]oxazine-1-carboxylate as a mixture of trans diastereomers. SFC purification afforded the pure S,S diastereomer tert-butyl (4aS,8aS)-octahydro-1H-pyrido[3,4-b][1,4]oxazine-1-carboxylate (peak 1) $^1H$ NMR: ($CDCl_3$) δ 3.88-3.80 (m, 2H), 3.77-3.67 (m, 1H), 3.35-3.34 (m, 2H), 3.29-3.27 (m, 2H), 3.10-3.11 (d, 1H), 2.54-2.42 (m, 3H), 1.76 (s, 1H), 1.70-1.60 (m, 1H), 1.45 (s, 9H) LCMS (M+H)=243 and R,R diastereomer tert-butyl (4aR,8aR)-octahydro-1H-pyrido[3,4-b][1,4]oxazine-1-carboxylate (peak 2)$^1H$ NMR: ($CDCl_3$) δ 3.89-3.80 (m, 2H), 3.77-3.67 (m, 1H), 3.35-3.34 (m, 2H), 3.29-3.27 (m, 2H), 3.10-3.11 (d, 1H), 2.54-2.42 (m, 3H), 1.76 (s, 1H), 1.70-1.60 (m, 1H), 1.44 (s, 9H) LCMS (M+H)=243.

Step 13: To tert-butyl (4aR,8aR)-octahydro-1H-pyrido[3, 4-b][1,4]oxazine-1-carboxylate (250 mg, 1.03 mmol) dissolved in DCM (2 mL) was added benzyl chloroformate (0.21 mL, 1.44 mmol). Triethylamine (0.4 mL, 2.89 mmol) was added slowly and stirred for 3 hours at room temperature. The reaction was quenched with saturated aqueous sodium bicarbonate. The aqueous layer was extracted with DCM, and the combined organic layers were dried over sodium sulfate, filtered, and concentrated to afford (4aR,8aR)-6-benzyl 1-tert-butyl hexahydro-1H-pyrido[3,4-b][1,4]oxazine-1,6 (7H)-dicarboxylate. $^1H$ NMR (500 MHz, $CDCl_3$) δ 7.40-7.30 (m, 5H), 5.12 (s, 2H), 4.40-4.15 (m, 1H), 3.93-3.87 (m, 1H), 3.86-3.79 (m, 1H), 3.77-3.71 (m, 1H), 3.42-3.29 (m, 2H), 3.19-3.13 (m, 1H), 2.81-2.48 (m, 2H), 1.76-1.66 (m, 1H), 1.58 (s, 2H), 1.45 (s, 9H).

Step 14: To (4aR,8aR)-6-benzyl 1-tert-butyl hexahydro-1H-pyrido[3,4-b][1,4]oxazine-1,6(7H)-dicarboxylate (388 mg, 1.03 mmol) dissolved in DCM (2.8 mL) was added TFA (0.57 mL). The reaction was stirred at room temperature for 16 hours. The mixture was concentrated to afford benzyl (4aR,8aR)-octahydro-6H-pyrido[3,4-b][1,4]oxazine-6-carboxylate as a TFA salt. MS ESI calc'd. for $C_{15}H_{20}N_2O_3$ [M+H]+ 277. found 277.

Preparative Example 3.3

7-azabicyclo[2.2.1]heptan-2-ol

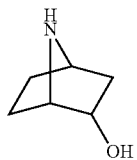

Step 1: Into a 20-L 3-necked round-bottom flask were placed 1H-pyrrole (670.9 g, 10.00 mol, 1.00 equiv), $CH_2Cl_2$ (6000 ml), DMAP (61.09 g, 500.04 mmol, 0.05 equiv) and $Et_3N$ (1011.9 g, 10.00 mol, 1.00 equiv). Added a solution of $(Boc)_2O$ (2400 g, 11.00 mol, 1.10 equiv) in $CH_2Cl_2$ (2500 mL) dropwise with stirring at room temperature over 30 min. The resulting solution was stirred for 5 hr at room temperature, then washed with 2×500 mL of HCl (3%) and 2×500 mL of $H_2O$. The organic layer was dried over anhydrous sodium sulfate and concentrated under vacuum. The crude product was purified by distillation under reduced pressure (20 mm Hg), and a fraction was collected at 50° C. This resulted in tert-butyl 1H-pyrrole-1-carboxylate as a yellow liquid.

Step 2: Into a 2000-mL 3-necked round-bottom flask was placed methyl 3-bromopropiolate (120 g, 736.33 mmol, 1.00 equiv) and tert-butyl 1H-pyrrole-1-carboxylate (615.61 g, 3.68 mol, 5.00 equiv). The resulting solution was stirred for 30 hr at 95° C. in an oil bath. The reaction mixture was cooled and distilled under reduced pressure (20 mm Hg). The fraction collected at 55° C. was purified by silica gel chromatography (ethyl acetate/petroleum ether, 1:20) to afford 7-tert-butyl 2-methyl 3-bromo-7-azabicyclo[2.2.1]hepta-2,5-diene-2,7-dicarboxylate as a yellow liquid.

Step 3: Into a 2000-mL 3-necked round-bottom flask purged and maintained with an inert atmosphere of nitrogen was placed 7-tert-butyl 2-methyl 3-bromo-7-azabicyclo [2.2.1]hepta-2,5-diene-2,7-dicarboxylate (70 g, 212.01 mmol, 1.00 equiv), acetonitrile (700 mL) and triethylamine (107.26 g, 1.06 mol, 5.00 equiv). Diethylamine (17.06 g, 233.25 mmol, 1.10 equiv) was added dropwise with stirring at room temperature over 60 min, followed by addition of HCl (700 mL) dropwise with stirring at room temperature over 30 min. The resulting solution was stirred for 4 hr at room temperature, then quenched by the addition of 700 mL of water. The resulting solution was extracted with 3×700 mL of dichloromethane. The organic layers were combined, dried, and concentrated under vacuum to afford 7-tert-butyl 2-methyl 3-oxo-7-azabicyclo[2.2.1]hept-5-ene-2,7-dicarboxylate.

Step 4: A mixture of 7-tert-butyl 2-methyl 3-oxo-7-azabicyclo[2.2.1]hept-5-ene-2,7-dicarboxylate (50 g, 187.07 mmol, 1.00 equiv), MeOH (500 mL), and Pd/C (5 g, 10%) was stirred overnight at room temperature under a hydrogen atmosphere. The reaction was filtered, and the filtrate was concentrated under vacuum to afford 7-tert-butyl 2-methyl 3-oxo-7-azabicyclo[2.2.1]heptane-2,7-dicarboxylate.

Step 5: Into a 2000-mL 3-necked round-bottom flask purged and maintained with an inert atmosphere of nitrogen was placed 7-tert-butyl 2-methyl 3-oxo-7-azabicyclo[2.2.1] heptane-2,7-dicarboxylate (121.82 g, 452.37 mmol, 1.00 equiv) and HCl (1200 mL, 10%). The resulting solution was stirred for 3 hr at 105° C. in an oil bath, then cooled and concentrated under vacuum to afford 7-aza-bicyclo[2.2.1] heptan-2-one.

Step 6: Into a 2000-mL 3-necked round-bottom flask purged and maintained with an inert atmosphere of nitrogen was placed 7-aza-bicyclo[2.2.1]heptan-2-one (39.72 g, 357.39 mmol, 1.00 equiv), DCM (400 mL), triethylamine (146.47 g, 1.45 mol, 4.05 equiv), and $(Boc)_2O$ (156.01 g, 714.82 mmol, 2.00 equiv). The resulting solution was stirred for 2 h at room temperature. The resulting mixture was washed with 1×400 mL of $Na_2CO_3$ solution and 1×400 mL of $H_2O$. The organic layer was dried over anhydrous sodium sulfate and concentrated under vacuum. The residue was purified by silica gel chromatograpy (ethyl acetate/petroleum ether, 10:1) to afford tert-butyl 2-oxo-7-azabicyclo[2.2.1] heptane-7-carboxylate.

Step 7: To a solution of tert-butyl 2-oxo-7-azabicyclo [2.2.1]heptane-7-carboxylate (500 mg, 2.37 mmol) in methanol (4.7 mL) at 0° C. was added sodium borohydride (134 mg, 3.55 mmol). The reaction mixture was stirred at 0° C. for 1 hour and then stirred for 16 hours at room temperature. The mixture was quenched with saturated aqueous ammonium chloride and concentrated. The resulting residue was extracted with DCM (3×) and the combined extracts were dried over sodium sulfate, filtered, and concentrated to afford tert-butyl 2-hydroxy-7-azabicyclo[2.2.1]heptane-7-carboxylate. $^1$H NMR (500 MHz, $CDCl_3$) δ 4.35 (broad, 1H), 4.13 (s, 2H), 2.28-2.19 (m, 1H), 2.18-2.12 (m, 1H), 1.83-1.75 (m, 1H), 1.71-1.68 (m, 1H), 1.66-1.56 (m, 1H), 1.56-1.48 (m, 1H), 1.44 (s, 9H), 1.05 (dd, J=3.4, 12.7, 1H).

Step 8: To tert-butyl 2-hydroxy-7-azabicyclo[2.2.1]heptane-7-carboxylate (505 mg, 2.37 mmol) dissolved in DCM (5.9 mL) was added TFA (1.9 mL). The reaction was stirred for 16 hours at room temperature. The mixture was concentrated to give 7-azabicyclo[2.2.1]heptan-2-ol.

Preparative Example 3.4

(3R,5S)-5-(propan-2-yl)pyrrolidin-3-ol

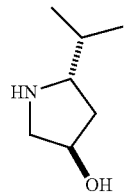

Step 1: Thionyl chloride (270 mL) was added dropwise to methanol (1500 mL) over 1 hour, followed by the addition of (4R)-4-hydroxy-L-proline (150 g). The mixture was stirred at reflux for 36 hours, and then concentrated under reduced pressure. Methanol (1500 mL) was added, followed by a slow addition of triethylamine (310 mL). The mixture was cooled to 0° C., filtered, and the filtrate was concentrated to afford methyl (4R)-4-hydroxy-L-prolinate. The residue was used directly without further purification.

Step 2: To a solution of methyl (4R)-4-hydroxy-L-prolinate (120 g) in tetrahydrofuran (500 mL) at 0° C. was added triethylamine (180 mL) dropwise. The solution was stirred at 0° C. for 15 minutes, then di-tert-butyl dicarbonate (130 g)

dissolved in tetrahydrofuran (100 mL) was added at 0° C. over 1 hour. The mixture was stirred at 0° C. for 1 hour. Upon completion the mixture was filtered. The filtrate was concentrated, dissolved in ethyl acetate, and washed with water. The aqueous layer was extracted with ethyl acetate (2×), and the combined organic layers were washed with brine, dried over sodium sulfate, filtered, and concentrated to give 1-tert-butyl 2-methyl (2S,4R)-4-hydroxypyrrolidine-1,2-dicarboxylate. The residue was used directly without further purification.

Step 3: To a solution of 1-tert-butyl 2-methyl (2S,4R)-4-hydroxypyrrolidine-1,2-dicarboxylate (970 g) in N,N-dimethylformamide (1000 mL) was added imidazole (591 g) at 0° C. Upon dissolution of the imidazole, tert-butyldimethylsilyl chloride (652 g) was added at 0° C. The reaction was stirred for 16 hours at room temperature, cooled to 0° C., and quenched with water (2.25 L). The mixture was extracted with ethyl acetate (4×), and the combined organic layer was washed with brine (3×), dried over magnesium sulfate, filtered, and concentrated to give 1-tert-butyl 2-methyl (2S,4R)-4-{[tert-butyl(dimethyl)silyl]oxy}pyrrolidine-1,2-dicarboxylate. The residue was used directly without further purification.

Step 4: To magnesium (76 g) in a three-neck flask was added ether to cover the solid. Iodomethane (200 mL) was added dropwise to maintain reflux of the ether, and the mixture was stirred at 30° C. for 1 hour. A solution of 1-tert-butyl 2-methyl (2S,4R)-4-{[tert-butyl(dimethyl)silyl]oxy}pyrrolidine-1,2-dicarboxylate (280 g) in ether (200 mL) was added dropwise over 3 hours at 0° C. The mixture was stirred at room temperature for 1 hour, and then it was poured into a solution of saturated aqueous ammonium chloride slowly. The organic layer was separated and the aqueous layer was extracted with ethyl acetate (2×). The combined organic layer was washed with brine, dried over sodium sulfate, filtered, and concentrated to give tert-butyl (2S,4R)-4-{[tert-butyl(dimethyl)silyl]oxy}-2-(2-hydroxypropan-2-yl)pyrrolidine-1-carboxylate. The residue was used directly without further purification.

Step 5: To a solution of tert-butyl (2S,4R)-4-{[tert-butyl(dimethyl)silyl]oxy}-2-(2-hydroxypropan-2-yl)pyrrolidine-1-carboxylate (98 g) dissolved in toluene (900 mL) at −78° C. was added triethylamine (310 mL). The mixture was stirred at −78° C. for 10 minutes, and then thionyl chloride (60 mL) in toluene (100 mL) was added dropwise over 1.5 hours. The mixture was stirred at −78° C. for 2 hours and then quenched with saturated ammonium chloride. The aqueous layer was extracted with ethyl acetate, and the organic layer was washed with saturated aqueous sodium bicarbonate and brine. The organic layer was dried over sodium sulfate, filtered, and concentrated to give tert-butyl (2S,4R)-4-{[tert-butyl(dimethyl)silyl]oxy}-2-(prop-1-en-2-yl)pyrrolidine-1-carboxylate. The residue was used directly without further purification.

Step 6: To a solution of tert-butyl (2S,4R)-4-{[tert-butyl(dimethyl)silyl]oxy}-2-(prop-1-en-2-yl)pyrrolidine-1-carboxylate (90 g) dissolved in methanol (250 mL) was added Raney Nickel (24 g). The reaction mixture was stirred under hydrogen (40 atm) at 60° C. for 3 hours. The mixture was filtered and concentrated under reduced pressure. The residue was dissolved in ethyl acetate, washed with brine (2×50 mL), dried over magnesium sulfate, filtered and concentrated to give tert-butyl (2S,4R)-4-{[tert-butyl(dimethyl)silyl]oxy}-2-(propan-2-yl)pyrrolidine-1-carboxylate. The residue was used directly without further purification.

Step 7: To a solution of tert-butyl (2S,4R)-4-{[tert-butyl(dimethyl)silyl]oxy}-2-(propan-2-yl)pyrrolidine-1-carboxylate (50 g) dissolved in tetrahydrofuran was added tetra-N-butylammonium fluoride (95 g) dissolved in tetrahydrofuran (250 mL) at 0° C. The mixture was stirred for 16 h at room temperature and then quenched with water (100 mL). The solution was washed with hydrochloric acid (6 N), extracted with ethyl acetate (3×100 mL), dried over magnesium sulfate, filtered, and concentrated. The residue was purified by silica gel chromatography (2/1 petroleum ether/ethyl acetate) to afford tert-butyl (2S,4R)-4-hydroxy-2-(propan-2-yl)pyrrolidine-1-carboxylate.

Step 8: To a solution of tert-butyl (2S,4R)-4-hydroxy-2-(propan-2-yl)pyrrolidine-1-carboxylate (500 mg, 2.180 mmol) dissolved in dichloromethane (5.4 mL) was added trifluoroacetic acid (1.8 mL). The reaction was stirred for 16 hours at room temperature. The mixture was concentrated to afford (3R,5S)-5-(propan-2-yl)pyrrolidin-3-ol as a TFA salt. $^1$H NMR (500 MHz, CDCl$_3$) δ 3.91-3.62 (m, 1H), 3.60-3.36 (m, 2H), 2.47-2.10 (m, 2H), 2.05-1.79 (m, 2H), 1.07 (d, J=6.6, 3H), 1.01 (d, J=6.7, 3H).

Preparative Example 3.5

(5S)-3-methyl-5-(propan-2-yl)pyrrolidin-3-ol

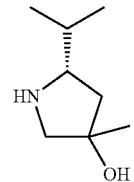

Step 1: Oxalyl chloride (16 mL) dissolved in DCM (200 mL) was placed in a three-neck flask equipped with a stirrer and two addition funnels. One funnel contained DMSO (23 mL) in DCM (100 mL) and the other tert-butyl (2S,4R)-4-hydroxy-2-(propan-2-yl)pyrrolidine-1-carboxylate (37 g) in DCM (100 mL). The contents of the flask were cooled to −78° C., and the DMSO solution was added dropwise. After 15 minutes, tert-butyl (2S,4R)-4-hydroxy-2-(propan-2-yl)pyrrolidine-1-carboxylate was added. The reaction mixture was stirred for 30 minutes, and triethylamine (110 mL) was added. The cooling bath was removed, and water (100 mL) was added at room temperature and stirred for 10 minutes. The organic layer was separated, and the aqueous layer was extracted with DCM (3×100 mL). The combined organic layers were washed with brine (3×50 mL), dried over magnesium sulfate, filtered, and concentrated. The material was purified by silica gel chromatography (petroleum ether/ethyl acetate, 15/1) to afford tert-butyl (2S)-4-oxo-2-(propan-2-yl)pyrrolidine-1-carboxylate.

Step 2: To a solution of tert-butyl (2S)-4-oxo-2-(propan-2-yl)pyrrolidine-1-carboxylate (500 mg, 2.2 mmol) in THF (10 mL) at −78° C. was added methylmagnesium bromide (1.65 mL, 4.95 mmol) dropwise. The reaction was stirred at −78° C. for 2 hours before warming to room temperature and stirring for an additional 2 hours. The reaction was quenched by slowly adding saturated aqueous ammonium chloride at 0° C. The mixture was acidified with HCl (1 N) and extracted with ethyl acetate (2×). The combined organic layers were washed with brine, dried over sodium sulfate, filtered, and concentrated. The residue was purified by silica gel chromatography (0-80% ethylacete/hexanes, linear gradient) to afford tert-butyl (2S)-4-hydroxy-4-methyl-2-(propan-2-yl)pyrrolidine-1-carboxylate.

Step 3: To tert-butyl (2S)-4-hydroxy-4-methyl-2-(propan-2-yl)pyrrolidine-1-carboxylate (532.2 mg, 2.18 mmol) dissolved in DCM (5.5 mL) was added TFA (1.8 mL). The mixture was stirred for 16 hours. The mixture was concentrated to give (5S)-3-methyl-5-(propan-2-yl)pyrrolidin-3-ol as a TFA salt. $^1$H NMR (500 MHz, CDCl$_3$) δ 3.76 (s, 1H), 3.49-3.34 (m, 2H), 2.29-2.17 (m, 1H), 2.06-1.95 (m, 2H), 1.51 (s, 3H), 1.07-0.97 (m, 7H).

Preparative Example 3.6

(3R,5S)-5-(hydroxymethyl)pyrrolidin-3-ol

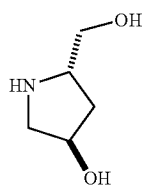

Step 1: Into a 20000-mL 4-necked round-bottom flask, was placed a solution of methyl (2S,4R)-4-hydroxypyrrolidine-2-carboxylate hydrochloride (1000 g, 5.51 mol, 1.00 equiv) in dichloromethane (8000 mL). This was followed by the addition of triethylamine (1680 g, 16.60 mol, 3.00 equiv) dropwise with stirring at <20° C. The resulting solution was stirred for 1 h at room temperature. To this was added di-tert-butyl dicarbonate (1446 g, 1.20 equiv) in several batches at 0° C. The resulting solution was stirred overnight at room temperature. The resulting solution was washed with 3×5000 mL of water, 2×5000 mL of hydrogen chloride (1 N), 2×5000 mL of sodium bicarbonate(aq) and 2×5000 mL of brine. The mixture was dried over anhydrous sodium sulfate and concentrated under vacuum. The crude product was purified by recrystallization from petroleum ether (3000 mL). This resulted in 1-tert-butyl 2-methyl (2S,4R)-4-hydroxypyrrolidine-1,2-dicarboxylate as a white solid.

Step 2: Into a 3000-mL 4-necked round-bottom flask, purged and maintained with an inert atmosphere of nitrogen, was placed a solution of LiBH$_4$ (16.2 g, 736.36 mmol, 1.50 equiv) in tetrahydrofuran (500 mL). This was followed by the addition of a solution of 1-tert-butyl 2-methyl (2S,4R)-4-hydroxypyrrolidine-1,2-dicarboxylate (120 g, 489.25 mmol, 1.00 equiv) in tetrahydrofuran (700 mL) dropwise with stirring at <5° C. The resulting solution was stirred overnight at room temperature. The reaction was then quenched by the addition of 2000 mL of water. The resulting solution was extracted with 2×500 mL of ethyl acetate. The combined organic layers were washed with 2×500 mL of brine. The organic layer was dried over anhydrous sodium sulfate and concentrated under vacuum. The crude product was purified by re-crystallization from hexane. This resulted in tert-butyl (2S,4R)-4-hydroxy-2-(hydroxymethyl)pyrrolidine-1-carboxylate as a white solid.

$^1$H NMR (300 MHz, DMSO-d$_6$) δ 4.84 (s, 1H), 4.64-4.66 (d, 1H, J=5.7 Hz), 4.18-4.23 (m, 1H), 3.75 (s, 1H), 3.36-3.45 (m, 2H), 3.21-3.24 (t, 2H, J=5.1 Hz), 1.87-2.02 (m, 2H), 1.39 (s, 9H).

Step 3: To tert-butyl (2S,4R)-4-hydroxy-2-(hydroxymethyl)pyrrolidine-1-carboxylate (498.5 mg, 2.29 mmol) dissolved in DCM (6.8 mL) was added TFA (0.85 mL). The mixture was stirred for 16 hours. The mixture was concentrated to give (3R,5S)-5-(hydroxymethyl)pyrrolidin-3-ol as a TFA salt.

Preparative Example 3.7

4-methoxy-2-(1-methoxycyclopropyl)pyrrolidine

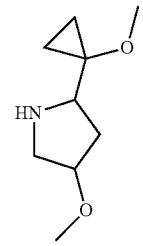

Step 1: To a mixture of 1-benzyl 2-methyl (2S,4R)-4-hydroxypyrrolidine-1,2-dicarboxylate (500 mg, 1.79 mmol) in THF (6 mL) was added methyl iodide (0.385 mL) followed by sodium hydride (95 mg, 3.94 mmol). The reaction was stirred for 1 hour, then quenched with ice and diluted with diethyl ether. The organic layer was washed with water and brine, dried over sodium sulfate, filtered, and concentrated under reduced pressure to afford 1-benzyl 2-methyl 4-methoxypyrrolidine-1,2-dicarboxylate. MS ESI calc'd. for C$_{15}$H$_{19}$NO$_5$ [M+H]$^+$ 294. found 294.

Step 2: A 3M solution of ethylmagnesium bromide (1.43 mL, 4.30 mmol) was added over a period of 40-60 minutes under stirring to a room temperature solution of 1-benzyl 2-methyl 4-methoxypyrrolidine-1,2-dicarboxylate (420 mg, 1.43 mmol) and titanium (IV) isopropoxide (0.086 mL, 0.286 mmol) in diethyl ether. The mixture was stirred for 1 hour at room temperature. The reaction was cooled to 0° C., treated with a few drops of saturated aqueous ammonium chloride, filtered through celite, and washed with diethyl ether. The organic layer was dried over sodium sulfate, filtered, and concentrated under reduced pressure to afford benzyl 241-hydroxycyclopropyl)-4-methoxypyrrolidine-1-carboxylate. MS ESI calc'd. for C$_{16}$H$_{21}$NO$_4$ [M+H]$^+$ 292. found 292.

Step 3: To a mixture of benzyl 2-(1-hydroxycyclopropyl)-4-methoxypyrrolidine-1-carboxylate (312 mg, 1.07 mmol) dissolved in THF (3.6 mL) at 0° C. was added methyl iodide (0.23 mL, 3.68 mmol) followed by sodium hydride (56.5 mg, 2.36 mmol). The mixture was stirred for 2 hours at room temperature. The reaction was quenched with ice, and diluted with diethyl ether. The organic layer was washed with water and brine, dried over sodium sulfate, filtered and concentrated under reduced pressure. The residue was purified by silica gel chromatography (0-20% methanol/dichloromethane, linear gradient) to afford benzyl 4-methoxy-2-(1-methoxycyclopropyl)pyrrolidine-1-carboxylate. MS ESI calc'd. for C$_{17}$H$_{23}$NO$_4$ [M+H]$^+$ 306. found 306.

Step 4: To benzyl 4-methoxy-2-(1-methoxycyclopropyl) pyrrolidine-1-carboxylate (141 mg, 0.462 mmol) dissolved in ethyl acetate (3.1 mL) was added palladium on carbon (49.1 mg, 0.05 mmol). Hydrogen gas was added via balloon and the reaction was stirred at room temperature for 3 hours. The mixture was filtered over celite and concentrated under reduced pressure to afford 4-methoxy-2-(1-methoxycyclopropyl)pyrrolidine.

Preparative Example 3.8

Decahydroquinolin-3-ol

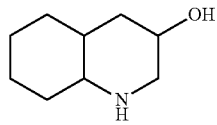 [SMILES: OC1CNC2CCCCC2C1]

3-Quinolinol (10 g) was dissolved in THF (180 ml) and hydrogenated over Raney—Ni (3.0 g) with an initial pressure of 110 kg/cm². The reaction was heated to 150° C. during which time the pressure rose to 120 kg/cm² and these conditions were maintained for 24 hr. After cooling, the solution was filtered through Celite, and the solvent was removed in vacuo leaving 10 g of oil. After standing, the oil solidified. A small amount of EtOAc was added, and the solid was removed by filtration and washed with EtOAc to give decahydroquinolin-3-ol as a white solid. $^1$H-NMR (300 MHz, CDCl$_3$): δ1.07-1.33 (m, 5H), 1.57-2.05 (m, 7H), 2.39-2.47 (t, 1H), 3.18-3.24 (m, 1H), 3.63-3.73 (m, 1H)

Preparative Example 3.9

2-(1-methoxyethyl)pyrrolidine

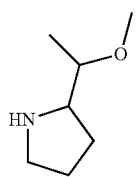

Step 1: To a mixture of tert-butyl 2-(1-hydroxyethyl)pyrrolidine-1-carboxylate (750 mg, 3.48 mmol) in DMF (12 mL) at 0° C. was added methyl iodide (0.75 mL, 11.98 mmol) followed by sodium hydride (184 mg, 7.66 mmol). The mixture was stirred for 2 hours at room temperature. The reaction was quenched with ice and diluted with diethyl ether. The organic layer was washed with water and brine, dried over sodium sulfate, and filtered and concentrated under reduced pressure to afford tert-butyl 2-(1-methoxyethyl)pyrrolidine-1-carboxylate. $^1$H NMR (500 MHz, CDCl$_3$) δ 3.92-3.45 (m, 2H), 3.45-3.23 (m, 4H), 2.11-1.66 (m, 4H), 1.63 (s, 1H), 1.46 (s, 9H), 1.04 (dd, J=6.3, 30.8, 3H).

Step 2: To tert-butyl 2-(1-methoxyethyl)pyrrolidine-1-carboxylate (827 mg, 3.61 mmol) dissolved in DCM (15 mL) was added TFA (0.83 mL). The mixture was stirred for 16 hours. The reaction was concentrated, diluted with DCM, and washed with HCl (1 N). The combined organic layers were dried over sodium sulfate, filtered, and concentrated under reduced pressure to afford 2-(1-methoxyethyl)pyrrolidine.

Preparative Example 3.10

(2S,4R)-2-(fluoromethyl)-4-methoxypyrrolidine

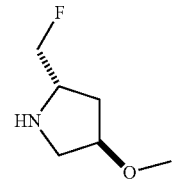

Step 1: To a solution of benzyl (2S,4R)-2-(fluoromethyl)-4-hydroxypyrrolidine-1-carboxylate (500 mg, 1.97 mmol) in THF (6.6 mL) at 0° C. was added methyl iodide (0.43 mL, 3.44 mmol) followed by sodium hydride (104 mg, 4.34 mmol). The mixture was stirred for 2 hours at room temperature. The reaction was quenched with ice, and diluted with diethyl ether. The organic layer was washed with water and brine, dried over sodium sulfate, filtered and concentrated under reduced pressure to afford benzyl (2S,4R)-2-(fluoromethyl)-4-methoxypyrrolidine-1-carboxylate. MS ESI calc'd. for C$_{14}$H$_{18}$FNO$_3$ [M+H]$^+$ 268. found 268.

Step 2: To benzyl (2S,4R)-2-(fluoromethyl)-4-methoxypyrrolidine-1-carboxylate (529 mg, 1.98 mmol) dissolved in ethyl acetate (12.9 mL) was added palladium on carbon (211 mg, 0.2 mmol). Hydrogen gas was added via balloon, and the reaction was stirred at room temperature for 3 hours. The mixture was filtered over celite and concentrated under reduced pressure to afford (2S,4R)-2-(fluoromethyl)-4-methoxypyrrolidine. $^1$H NMR (500 MHz, CDCl$_3$) δ 4.44-4.19 (m, 2H), 3.29 (s, 3H), 3.09-2.93 (m, 2H), 2.02-1.92 (m, 1H), 1.78 (s, 2H), 1.62-1.56 (m, 1H), 1.25 (s, 1H).

Preparative Example 3.11

(2R)-5-methoxy-2-methylpiperidine

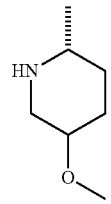

Step 1: To a solution of 6-methylpyridin-3-ol (20.0 g, 0.183 mol) in MeOH (200 mL) were added concentrated HCl (15.43 mL, 0.1850 mol) and PtO$_2$ (2.40 g, 0.011 mol). The resulting mixture was heated to 70° C. at 50 PSI overnight. The reaction was filtered to remove the PtO$_2$ and concentrated to a solid to provide ±trans-6-methylpiperidin-3-ol hydrochloride. The crude solid was taken on without further purification.

Step 2: A mixture of ±trans-6-methylpiperidin-3-ol hydrochloride (14.0 g, 0.092 mol) in CH$_2$Cl$_2$ (150 mL) was cooled to 0° C. Triethylamine (51.5 mL, 0.369 mol) was added slowly. CbzCl (13.59 mL, 0.092 mol) was added dropwise, keeping the temperature below 20° C. The reaction was allowed to warm overnight to room temperature. The reaction was quenched by addition of water and diluted further with additional $CH_2Cl_2$. The layers were separated and the organics were dried over $MgSO_4$ and concentrated. The crude material was purified by silica gel gradient chromatography (0-75% ethyl acetate in hexanes), providing ±Benzyl trans-5-hydroxy-2-methylpiperidine-1-carboxylate.

Step 3: To a solution of oxalyl chloride (13.17 mL, 0.150 mol) in $CH_2Cl_2$ (250 mL) at −78° C. was added DMSO (14.23 mL, 0.201 mol) dropwise. The reaction was aged for 20 min at −78° C., then ±Benzyl trans-5-hydroxy-2-methylpiperidine-1-carboxylate (25.0 g, 0.100 mol) was added dropwise over 10 min and aged for an additional 10 min before triethylamine (41.9 mL, 0.301 mol) was added dropwise over 5 min at −78° C. The reaction was warmed to room temperature, then quenched with addition of half-saturated, aqueous $NaHCO_3$ and additional $CH_2Cl_2$. The layers were separated, and the organics were dried with $MgSO_4$ and concentrated. The crude material was purified by silica gel gradient chromatography (0-50% ethyl acetate in hexanes), providing ±benzyl 2-methyl-5-oxopiperidine-1-carboxylate.

Step 4: To a solution of THF (200 mL) and MeOH (11 mL) was added $LiBH_4$ (2 M, 89 mL, 0.18 mol). Some gas evolution and a small exotherm were observed. The reaction was aged at room temperature for 30 min before being cooled to −10° C. ±benzyl 2-methyl-5-oxopiperidine-1-carboxylate (22.0 g, 0.089 mol) was then added dropwise, keeping the temperature below −5° C. The reaction was then aged at −10° C. for 30 min. The reaction was quenched by adding half-saturated, aqueous $NaHCO_3$, then extracted with EtOAc. The layers were separated and the organics dried with $MgSO_4$. The organics were concentrated to give crude ±benzyl-5-hydroxy-2-methylpiperidine-1-carboxylate as a crude, colorless oil.

Step 5: Chiral separation (SFC, IC 30×250 mm, 15% MeOH/$CO_2$, 70 ml/min, 115 mg/ml in MeOH) of the crude ±benzyl-5-hydroxy-2-methylpiperidine-1-carboxylate provided benzyl (2R,5S)-5-hydroxy-2-methylpiperidine-1-carboxylate as enantiopure material.

Step 6: Benzyl (2R,5S)-5-hydroxy-2-methylpiperidine-1-carboxylate (6.8 g, 27.3 mmol) was dissolved in DCM (100 mL) containing crushed molecular sieves. N-methylmorpholine N-oxide (4.15 g, 35.5 mmol) and tetrapropylammonium perruthenate (0.48 g, 1.36 mmol) were added, and the reaction was stirred at room temperature for 1.5 hours. The mixture was filtered through a celite pad and concentrated. The residue was purified by silica gel chromatography (0-30% ethyl acetate/hexanes, linear gradient) to afford benzyl (2R)-2-methyl-5-oxopiperidine-1-carboxylate. MS ESI calc'd. for $C_{14}H_{17}NO_3$ [M+H]$^+$ 248. found 248.

Step 7: To a solution of benzyl (2R)-2-methyl-5-oxopiperidine-1-carboxylate (365 mg, 1.47 mmol) in methanol (2.9 mL) at 0° C. was added sodium borohydride (84 mg, 2.21 mmol). The reaction mixture was stirred at 0° C. for 1 hour and then stirred for 16 hours at room temperature. The mixture was quenched with saturated aqueous ammonium chloride and concentrated. The resulting residue was extracted with DCM (3×) and the combined extracts were dried over sodium sulfate, filtered, and concentrated to afford benzyl (2R)-5-hydroxy-2-methylpiperidine-1-carboxylate. MS ESI calc'd. for $C_{14}H_{19}NO_3$ [M+H]$^+$ 250. found 250.

Step 8: To a mixture of benzyl (2R)-5-hydroxy-2-methylpiperidine-1-carboxylate (368 mg, 1.47 mmol) dissolved in THF (4.9 mL) at 0° C. was added methyl iodide (0.32 mL, 5.08 mmol) followed by sodium hydride (78 mg, 3.25 mmol). The mixture was stirred for 2 hours at room temperature. The reaction was quenched with ice, and diluted with diethyl ether. The organic layer was washed with water and brine, dried over sodium sulfate, filtered and concentrated under reduced pressure to afford benzyl (2R)-5-methoxy-2-methylpiperidine-1-carboxylate. MS ESI calc'd. for $C_{15}H_{21}NO_3$ [M+H]$^+$ 264. found 264.

Step 9: To benzyl (2R)-5-methoxy-2-methylpiperidine-1-carboxylate (345 mg, 1.31 mmol) dissolved in ethyl acetate (6.5 mL) was added palladium on carbon (139 mg, 0.13 mmol). Hydrogen gas was added via balloon, and the reaction was stirred at room temperature for 3 hours. The mixture was filtered over celite and concentrated under reduced pressure to afford (2R)-5-methoxy-2-methylpiperidine. $^1$H NMR (500 MHz, DMSO-d$_6$) δ 3.33 (s, 3H), 3.23-3.13 (m, 2H), 2.66-2.59 (m, 1H), 2.03-1.97 (m, 1H), 1.47-1.40 (m, 1H), 1.39-1.28 (m, 2H), 1.08-1.04 (m, 3H), 0.91-0.79 (m, 2H).

Preparative Example 3.12

Trans-5,5-difluorooctahydrocyclopenta[b][1,4]oxazine hydrochloride

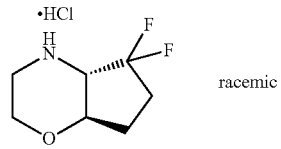 [SMILES: Cl ; FC1(F)CC[C@H]2OCCN[C@@H]21]

racemic

Step 1: To a stirred solution of cyclopent-2-enone (1.70 g, 20.7 mmol) in $CH_2Cl_2$ (20 mL), bromine (3.27 g, 20.7 mmol) in $CH_2Cl_2$ (10 mL) and $Et_3N$ (3.29 g, 31.1 mmol) in $CH_2Cl_2$ (10 mL) were added at 0° C. under a nitrogen atmosphere. The reaction mixture was gradually warmed to room temperature and stirred for 2 hours. The reaction mixture was filtered through celite, washing with $CH_2Cl_2$, and the filtrate was concentrated in vacuo. Purification of the residue on a silica gel column with 0 to 20% EtOAc/Hexanes afforded 2-bromocyclopent-2-enone.

Step 2: To a stirred solution of 2-bromocyclopent-2-enone (1.00 g, 6.21 mmol) in $H_2O$ (25 mL), tetrabutylammonium bromide (400 mg, 1.24 mmol) and benzyl amine (790 mg, 7.45 mmol) were added at room temperature. The reaction mixture was stirred for 24 hours and then extracted with EtOAc (100 mL). The organic layer was separated, washed with brine, and dried over anhydrous $Na_2SO_4$, filtered and concentrated in vacuo. Purification of the residue on a silica gel column with 0 to 30% EtOAc/Hexanes afforded 6-benzyl-6-azabicyclo[3.1.0]hexan-2-one. MS ESI calc'd. for $C_{12}H_{13}NO$ [M+H]$^+$ 188. found 188.

Step 3: 6-benzyl-6-azabicyclo[3.1.0]hexan-2-one (50 mg, 0.26 mmol) was dissolved in toluene (1.0 mL) and DAST (215 mg, 1.33 mmol) was added dropwise. The reaction was then heated at 60° C. for 5 hours, cooled to 0° C. and quenched by adding saturated aqueous $NaHCO_3$ solution (2 mL). The layers were separated, and the aqueous layer was extracted using EtOAc (10 mL). The combined organic layers were washed with brine, dried over anhydrous $Na_2SO_4$, filtered and concentrated in vacuo. Purification of the residue on a silica gel column with 0 to 20% EtOAc/Hexanes afforded 6-benzyl-2,2-difluoro-6-azabicyclo[3.1.0]hexane. MS ESI calc'd. for $C_{12}H_{13}F_2N$ [M+H]$^+$ 210. found 210.

Step 4: To a stirred solution of 6-benzyl-2,2-difluoro-6-azabicyclo[3.1.0]hexane (25 mg, 0.11 mmol) in $CH_3CN$ (1 mL), acetic acid (1 mL) was added at room temperature. The reaction mixture was heated to 80° C. for 16 h, cooled to room temperature and concentrated in vacuo. Purification of the residue on a silica gel column with 0 to 20% EtOAc/Hexanes afforded trans-2-(benzylamino)-3,3-difluorocyclopentyl acetate. MS ESI calc'd. for $C_{14}H_{17}F_2NO_2$ [M+H]$^+$ 270. found 270.

Step 5: To a stirred solution of trans-2-(benzylamino)-3,3-difluorocyclopentyl acetate (100 mg, 0.37 mmol) in $CH_3OH$ (2 mL), $K_2CO_3$ (52 mg, 0.37 mmol) was added at room temperature. The reaction mixture was stirred at room temperature for 1 hour and concentrated in vacuo. The residue was dissolved in $CH_2Cl_2$, washed with brine, dried over anhydrous $Na_2SO_4$, filtered and concentrated in vacuo to afford trans-2-(benzylamino)-3,3-difluorocyclopentanol. MS ESI calc'd. for $C_{12}H_{15}F_2NO$ [M+H]$^+$ 228. found 228.

Step 6: Triethylamine (1.84 mL, 13.2 mmol) was added to a solution of trans-2-(benzylamino)-3,3-difluorocyclopentanol (500 mg, 2.2 mmol) in dichloromethane (20 mL) at −40° C., followed by the addition of 2-chloroacetyl chloride (547 mg, 4.8 mmol) dropwise to the reaction. The reacton mixture was stirred at −40° C. for 3 hours and then warmed to 0° C.; this temperature was maintained for 2 hours. The reaction mixture was quenched with saturated aqueous $NaHCO_3$ solution. The layers were separated, and the aqueous layer was extracted with dichloromethane (3×20 mL). The combined organic layers were washed with brine, dried over anhydrous $Na_2SO_4$, filtered and concentrated in vacuo. Purification of the residue on a silica gel column (0 to 30% EtOAc/hexanes) afforded trans-2-(N-benzyl-2-chloroacetamido)-3,3-difluorocyclopentyl 2-chloroacetate. MS ESI calc'd. for $C_{16}H_{17}Cl_2F_2NO_3$ [M+H]$^+$ 380. found 380.

Step 7: To a stirred solution of trans-2-(N-benzyl-2-chloroacetamido)-3,3-difluorocyclopentyl 2-chloroacetate (480 mg, 1.26 mmol) in $CH_3OH$ (15 mL), $K_2CO_3$ (175 mg, 1.26 mmol) was added at room temperature. The reaction mixture was stirred at room temperature for 3 hours and then concentrated in vacuo. The residue was dissolved in $CH_2Cl_2$, washed with brine, dried over anhydrous $Na_2SO_4$, filtered and concentrated in vacuo to afford trans-N-benzyl-2-chloro-N-(2,2-difluoro-5-hydroxycyclopentyl)acetamide. MS ESI calc'd. for $C_{14}H_{16}ClF_2NO_2$ [M+H]$^+$ 304. found 304.

Step 8: To a stirred solution of trans-N-benzyl-2-chloro-N-(2,2-difluoro-5-hydroxycyclopentyl)acetamide (750 mg, 2.46 mmol) in t-BuOH (20 mL) was added a 1M solution of KOtBu in THF (4.93 mL, 4.93 mmol) at 20° C. The reaction mixture was stirred at 20° C. for 2 hours and then the solvent was evaporated under reduced pressure. The residue was dissolved in EtOAc (20 mL), washed with brine (10 mL), dried over anhydrous $Na_2SO_4$, and concentrated under reduced pressure. Purification of the residue on a silica gel column (0 to 40% EtOAc/hexanes) afforded trans-4-benzyl-5,5-difluorohexahydrocyclopenta[b][1,4]oxazin-3(2H)-one. MS ESI calc'd. for $C_{14}H_{15}F_2NO_2$ [M+H]$^+$ 268. found 268.

Step 9: LiAlH$_4$ (176 mg, 4.63 mmol) was added to a solution of trans-4-benzyl-5,5-difluorohexahydrocyclopenta[b][1,4]oxazin-3(2H)-one (550 mg, 2.05 mmol) in THF (15 mL) at 0° C. The reaction mixture was heated at 70° C. for 2 hours and then cooled to room temperature. 5 mL of water was added slowly to quench the reaction and then the reaction was extracted with EtOAc (100 mL). The organic layer was washed with brine (50 mL), dried over anhydrous $Na_2SO_4$, and concentrated under reduced pressure. Purification of the residue on a silica gel column (0 to 40% EtOAc/hexanes) afforded trans-4-benzyl-5,5-difluorooctahydrocyclopenta[b][1,4]oxazine. MS ESI calc'd. for $C_{14}H_{17}F_2NO$ [M+H]$^+$ 254. found 254.

Step 10: Trans-4-benzyl-5,5-difluorooctahydrocyclopenta[b][1,4]oxazine (350 mg, 1.38 mmol) was dissolved in MeOH (10 mL). 3M HCl in MeOH (1.5 mL) was added and the solution was stirred for 1 hour. The solvent was evaporated and further azeotroped using toluene. The residue was then dissolved in MeOH (10 mL), and 20% Pd(OH)$_2$/C (20% by wt, 50 mg) added. Hydrogen was purged through the reaction for 10 minutes and stirring was continued at room temperature under 1 atm of hydrogen for 16 hours. The reaction was filtered through celite, and the filtrate was concentrated to afford trans-5,5-difluorooctahydrocyclopenta[b][1,4]oxazine hydrochloride. $^1$H NMR (400 MHz, CD$_3$OD) δ 4.16 (dd, J=13.6, 4.0 Hz, 1H), 3.78-3.92 (m, 2H), 3.65 (m, 1H), 3.43 (dd, J=13.2, 2.4 Hz, 1H), 3.28-3.31 (m, 2H), 2.15-2.55 (m, 2H), 1.89 (m, 1H). MS ESI calc'd. for $C_7H_{11}F_2NO$ [M+H]$^+$ 164. found 164.

Preparative Example 3.13

Trans-3-methyloctahydrocyclopenta[b][1,4]oxazine hydrochloride

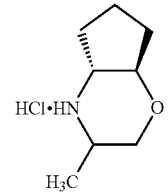

Step 1: Cyclopentene oxide (5.0 g, 59.1 mmol), benzylamine (7.0 g, 65.3 mmol) and titanium isopropoxide (3.40 g, 12.0 mmol) were taken in a microwave vial and microwaved at 150° C. for 3 hours. The reaction mixture was then cooled and diluted with EtOAc (100 mL). The organic layer was washed with water and dried over anhydrous $Na_2SO_4$. Evaporation of the solvent in vacuo and purification on a silica gel column (0 to 20% MeOH/CH$_2$Cl$_2$) afforded trans-2-(benzylamino)cyclopentanol. MS APCl calc'd for $C_{12}H_{17}NO$ [M+H]$^+$ 192. found 192.

Step 2: To a suspension of NaH (6.0 g of 60% w/w in oil, 150 mmol) in THF (300 mL) cooled at 0° C., trans-2-(benzylamino)cyclopentanol (9.6 g, 50 mmol) was added slowly. After stirring for 15 minutes at 0° C., ethyl bromoacetate (10 g, 60 mmol) was added slowly. The reaction mixture was then warmed to room temperature and stirred for 2 hours. Methanol (5.0 mL) was added slowly to the reaction followed by addition of saturated aqueous NH$_4$Cl (100 mL). The reaction mixture was then extracted with EtOAc (2×300 mL), and the combined organic layers were washed with water (100 mL) and dried over anhydrous $Na_2SO_4$. Evaporation of solvent in vacuo followed by purification on a silica gel column (0 to 50% EtOAc/Hexanes) afforded trans-4-benzylhexahydrocyclopenta[b][1,4]oxazin-3(2H)-one. MS APCl calc'd for $C_{14}H_{17}NO_2$ [M+H]$^+$ 232. found 232.

Step 3: To −78° C. solution of trans-4-benzylhexahydrocyclopenta[b][1,4]oxazin-3(2H)-one (5.0 g, 21.6 mmol) in THF (200.0 mL), methyl lithium (11.0 mL of 3.00 M solution in dimethoxyethane, 33.0 mmol) was added. The reaction mixture was slowly warmed to 0° C. and stirred at that temperature for 2 hours. Acetic acid (2.00 mL, 2.00 g, 33.3 mmol) was added to the reaction dropwise at 0° C. and stirred for 10 minutes. Then BH$_3$ (33.0 mL, 1.0 M solution in THF, 33.0 mmol) was added to the reaction at 0° C. and stirred for 30 minutes. After slow addition of methanol (5.0 mL), saturated aqueous NH$_4$Cl (50.0 mL) solution was added. The reaction mixture was then extracted with EtOAc (2×200 mL), and the combined organic layers were washed with water (100 mL) and dried over anhydrous $Na_2SO_4$. Evaporation of solvent in vacuo and purification on a silica gel column (0 to 20% EtOAc/Hexanes) afforded trans-4-benzyl-3-methyloctahydrocyclopenta[b][1,4]oxazine as a mixture of diastereomers.

Step 4: To a solution of trans-4-benzyl-3-methyloctahydrocyclopenta[b][1,4]oxazine (1.0 g, 4.3 mmol) in methanol (20 mL), palladium hydroxide (50 mg of 10% w/w in carbon) was added. The reaction mixture was flushed with hydrogen and then stirred under an atmosphere of hydrogen for two hours at room temperature. Aqueous HCl (2.0 mL of a 2.0 M solution) was added to the reaction, and the reaction mixture was filtered through a pad of celite, rinsing with MeOH. The filtrate was concentrated in vacuo to afford trans-3-methyloctahydrocyclopenta[b][1,4]oxazine hydrochloride (mixture of diastereomers).

Preparative Example 3.14

(2R,3R)-3-ethyl-2-methylmorpholine hydrochloride

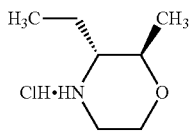

Step 1: To a solution of (2R,3R)-3-aminopentan-2-ol hydrochloride (1.00 g, 7.2 mmol) in DCM (20 mL) at rt was added sodium bicarbonate solution (604 mg, 7.2 mmol dissolved in 3.0 mL of water), dropwise. The reaction mixture was stirred for 1 hour, and the solvent was evaporated under reduced pressure. The residue and sodium cyanoborohydride (600 mg, 10.7 mmol) were added to a solution of benzaldehyde 877 mg, 8.6 mmol) in DCM (20 mL). The reaction mixture was stirred at room temperature overnight and then concentrated in vacuo. 30.0 mL water was added to this mixture, and the aqueous layer was extracted with dichloromethane (3×10 mL). The combined organic layers were washed with brine, dried over anhydrous $Na_2SO_4$, filtered and concentrated in vacuo. Purification of the residue on a silica gel column (0 to 50% EtOAc/hexanes) afforded (2R,3R)-3-(benzylamino)pentan-2-ol. MS APCl calc'd for $C_{12}H_{19}NO$ $[M+H]^+$ 194. found 194.

Step 2: Triethylamine (0.43 mL, 3.4 mmol) was added to a −40° C. solution of (2R,3R)-3-(benzylamino)pentan-2-ol (220 mg, 1.1 mmol) in dichloromethane (100 mL), followed by the addition of 2-chloroacetyl chloride (0.10 mL, 1.1 mmol) dropwise. The reaction mixture was stirred at −40° C. for 1 hour and then quenched with saturated $NaHCO_3$ solution. The layers were separated, and the aqueous layer was extracted with dichloromethane (3×10 mL). The combined organic layers were washed with brine, dried over anhydrous $Na_2SO_4$, filtered and concentrated in vacuo. Purification of the residue on a silica gel column (0 to 50% EtOAc/hexanes) afforded N-benzyl-2-chloro-N-((2R,3R)-2-hydroxypentan-3-yl)acetamide. MS APCl calc'd for $C_{14}H_{20}ClNO_2$ $[M+H]^+$ 270. found 270.

Step 3: A solution of N-benzyl-2-chloro-N-((2R,3R)-2-hydroxypentan-3-yl)acetamide (210 mg, 0.7 mmol) in THF (5 mL) was added to a suspension of NaH (89 mg, 3.7 mmol) in THF (5 mL) at 0° C. The reaction mixture was stirred at 0° C. for 1 hour and then quenched with saturated $NH_4Cl$ solution. The layers were separated and the aqueous layer was extracted with EtOAc (2×10 mL). The combined organic layers were washed with brine, dried over anhydrous $Na_2SO_4$, filtered and concentrated in vacuo. Purification of the residue on a silica gel column (0 to 50% EtOAc/hexanes) afforded (5R,6R)-4-benzyl-5-ethyl-6-methylmorpholin-3-one. MS APCl calc'd for $C_{14}H_{19}NO_2$ $[M+H]^+$ 234. found 234.

Step 4: $LiAlH_4$ (217 mg, 37.95 mmol) was added to a solution of (5R,6R)-4-benzyl-5-ethyl-6-methylmorpholin-3-one (200 mg, 0.85 mmol) in THF (10 mL). The reaction mixture was heated at 70° C. for 3 hours and then cooled to 0° C. At 0° C. was added aqueous sodium sulfate (15 mL). The mixture was stirred at room temperature for 10 minutes, and the white solid was removed by filtration. The filtrate was extracted with EtOAc (3×15 mL), dried over anhydrous $Na_2SO_4$, filtered and concentrated in vacuo. Purification of the residue on a silica gel column (0 to 30% EtOAc/hexanes) afforded (2R,3R)-4-benzyl-3-ethyl-2-methylmorpholine. MS APCl calc'd for $C_{14}H_{21}NO$ $[M+H]^+$ 220. found 220.

Step 5: $Pd(OH)_2$ (15.0 mg, 10% on carbon) was added to a solution of (2R,3R)-4-benzyl-3-ethyl-2-methylmorpholine (110 mg, 0.50 mmol) in MeOH (10 mL) under $N_2$. Hydrogen was bubbled through the reaction mixture for one minute and then the reaction was stirred at rt under hydrogen (1 atm) for 2 hours. Then, $N_2$ was bubbled through the reaction for 1 minute. A solution of HCl (3M, 3 mL, 9 mmol) in methanol was added. The reaction mixture was stirred at room temperature for 30 minutes and concentrated in vacuo to afford (2R,3R)-3-ethyl-2-methylmorpholine hydrochloride. $^1H$ NMR (300 MHz, DMSO-$d_6$) δ 9.45-9.34 (br s, 1H), 3.84-3.91 (m, 1H), 3.68-3.78 (m, 1H), 3.53-3.61 (m, 1H), 3.08-3.21 (m, 1H), 2.93-3.01 (m, 1H), 2.70-2.85 (m, 1H), 1.45-1.81 (m, 2H), 1.13 (d, J=6.3 Hz, 3H), 0.90-1.05 (m, 3H). MS APCl calc'd for $C_7H_{15}NO$ $[M+H]^+$ 130. found 130.

Preparative Example 3.15

(Trans)-6,6-difluorooctahydrocyclopenta[b][1,4]oxazine (racemic HCl salt)

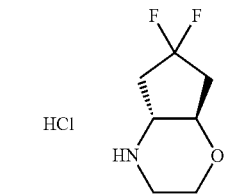

racemate

Step 1: To a solution of cyclopent-3-enol (500 mg, 6.0 mmol) in $CH_2Cl_2$ (30 mL) at 0° C. was added imidazole (1.06 g, 15.6 mmol) and TBDPS-Cl (2.1 g, 7.8 mmol). The reaction was gradually warmed to room temperature and stirred for 16 hours. The reaction was then diluted with water (40 mL) and extracted using EtOAc (100 mL). The organic layer was separated, washed with brine, dried over anhydrous $Na_2SO_4$, filtered, and concentrated in vacuo. Purification of the residue on a silica gel column with 0 to 5% EtOAc/Hexanes afforded tert-butyl(cyclopent-3-en-1-yloxy)diphenylsilane, which was then dissolved in $CH_2Cl_2$ (30 mL). 70% m-CPBA (830 mg, 6.9 mmol) was added at 0° C. The reaction was gradually warmed to room temperature while stirring for 16 hours. The reaction was then diluted with a saturated aqueous solution of $NaHCO_3$ (40 mL) and extracted using $CH_2Cl_2$ (100 mL). The organic layer was separated, washed with brine, dried over anhydrous Na$_2$SO$_4$, filtered, and concentrated in vacuo. Purification of the residue on a silica gel column with 0 to 20% EtOAc/Hexanes afforded (6-oxabicyclo[3.1.0]hexan-3-yloxy)(tert-butyl)diphenylsilane.

Step 2: Ti(OiPr)$_4$ (100 mg, 0.35 mmol) was added to a solution of (6-oxabicyclo[3.1.0]hexan-3-yloxy)(tert-butyl)diphenylsilane (1.0 g, 3.0 mmol) in benzylamine (1.5 mL). The mixture was heated in a microwave at 130° C. for 3 h and then cooled to room temperature. 16 mL of MeOH/water (1:8) was added to the reaction, and the mixture was stirred for 10 minutes. The gummy precipitate that formed was filtered off, and this solid was dissolved in acetonitrile (30 mL). The solution was filtered again, and the filtrate was evaporated to dryness. The residue was loaded onto a C-18 column and purified using 0-100% CH$_3$CN/water to afford (trans)-2-(benzylamino)-4-((tert-butyldiphenylsilyl)oxy)cyclopentanol. MS APCI calc'd for C$_{28}$H$_{35}$NO$_2$Si [M+H]$^+$ 446. found 446.5tep 3: Triethylamine (0.90 mL, 6.42 mmol) was added to a solution of (trans)-2-(benzylamino)-4-((tert-butyldiphenylsilyl)oxy)cyclopentanol (950 mg, 2.1 mmol) in dichloromethane (10 mL) at –40° C., followed by dropwise addition of 2-chloroacetyl chloride (264 mg, 2.3 mmol) to the reaction. The reacton mixture was stirred at –40° C. for 1 hour and was quenched with saturated aqueous NaHCO$_3$ solution. The layers were separated and the aqueous layer was extracted with dichloromethane (3×20 mL). The combined organic layers were washed with brine, dried over anhydrous Na$_2$SO$_4$, filtered, and concentrated in vacuo. Purification of the residue on a silica gel column (0 to 20% EtOAc/hexanes) afforded (trans)-N-benzyl-N-(4-((tert-butyldiphenylsilyl)oxy)-2-hydroxycyclopentyl)-2-chloroacetamide.

Step 4: To a solution of (trans)-N-benzyl-N-(4-((tert-butyldiphenylsilyl)oxy)-2-hydroxycyclopentyl)-2-chloroacetamide (260 mg, 0.5 mmol) in t-BuOH (5 mL) was added a solution of KOtBu (0.75 mL, 0.75 mmol) in THF (10 mL) at 15° C. The reaction mixture was stirred at 15° C. for 1 hour and then the solvent was evaporated under reduced pressure. The residue was dissolved in EtOAc (20 mL), washed with brine (10 mL), dried over anhydrous Na$_2$SO$_4$, and concentrated under reduced pressure. Purification of the residue on a C-18 column (0 to 100% CH$_3$CN/water) afforded (trans)-4-benzyl-6-((tert-butyldiphenylsilyl)oxy)hexahydrocyclopenta[b][1,4]oxazin-3(2H)-one.

Step 5: LiAlH$_4$ (176 mg, 4.63 mmol) was added to a solution of (trans)-4-benzyl-6-((tert-butyldiphenylsilyl)oxy)hexahydrocyclopenta[b][1,4]oxazin-3(2H)-one (48 mg, 0.1 mmol) in THF (1.0 mL). The reaction mixture was heated at 70° C. for 2 hours and then cooled to room temperature. Water was added to quench the reaction. The reaction mixture was stirred at room temperature for 15 minutes, and the white solids were removed by filtration. The filtrate was dried over anhydrous Na$_2$SO$_4$, filtered and concentrated in vacuo. Purification of the residue on a silica gel column (0 to 50% EtOAc/hexanes) afforded (trans)-4-benzyl-6-((tert-butyldiphenylsilyl)oxy)octahydrocyclopenta [b][1,4]oxazine. MS APCI calc'd for C$_{30}$H$_{37}$NO$_2$Si [M+H]$^+$ 472. found 472.

Step 6: (Trans)-4-benzyl-6-((tert-butyldiphenylsilyl)oxy) octahydrocyclopenta [b][1,4]oxazine (1.0 g, 2.1 mmol) was suspended in 3M HCl in MeOH (8.0 mL) and heated in a sealed tube at 45° C. for 16 hours. Solid NaHCO$_3$ was added to the reaction until the pH was neutral. Solids were filtered off and the solvent was evaporated under reduced pressure. Purification of the residue on a silica gel column with 0 to 20% MeOH/CH$_2$Cl$_2$ afforded (trans)-4-benzyloctahydrocyclopenta[b][1,4]oxazin-6-ol, which was dissolved in anhydrous CH$_2$Cl$_2$ (20 mL). The solution was cooled to 0° C. and Dess-Martin periodinane (1.40 g, 3.2 mmol) was added in several portions. The reaction was warmed to 10° C. over 2 hours and then quenched by adding a mixture (1:1) of saturated aqueous NaHCO$_3$ and Na$_2$S$_2$O$_3$ solution. The layers were separated, and the aqueous layer was extracted using CH$_2$Cl$_2$ (20 mL). The combined organics were dried over Na$_2$SO$_4$, filtered, and concentrated under reduced pressure. Purification of the residue on a silica gel column with 0 to 20% MeOH/CH$_2$Cl$_2$ afforded (trans)-4-benzylhexahydrocyclo penta[b][1,4]oxazin-6(2H)-one. MS APCI calc'd for C$_{14}$H$_{17}$NO$_2$ [M+H]$^+$ 232. found 232.

Step 7: (trans)-4-benzylhexahydrocyclo penta[b][1,4]oxazin-6(2H)-one (150 mg, 0.64 mmol) was dissolved in toluene (3.0 mL) and DAST (522 mg, 3.2 mmol) was added dropwise. The reaction was then heated at 90° C. for 2 hours, cooled to 0° C., and quenched by adding saturated aqueous NaHCO$_3$ solution (2 mL). The layers were separated and the aqueous layer was extracted using CH$_2$Cl$_2$ (10 mL). The combined organics were concentrated under reduced pressure. Purification of the residue on a silica gel column with 0 to 60% EtOAc/hexanes afforded (trans)-4-benzyl-6,6-difluorooctahydrocyclopenta[b][1,4]oxazine, which was then dissolved in MeOH (2 mL). 3M HCl in MeOH (0.3 mL) was added to the above solution and it was stirred for 1 hour. The solvent was evaporated and the residue was further azeotroped using toluene. The residue was then dissolved in MeOH (2.0 mL) and Pd(OH)$_2$/C (8.0 mg) was added. Hydrogen was purged through the reaction for 10 minutes and then the reaction was stirred at room temperature under 1 atm of hydrogen for 16 hours. The reaction was filtered through celite, and the filtrate was concentrated to afford (trans)-6,6-difluorooctahydrocyclopenta[b][1,4]oxazine hydrochloride (racemic). MS APCI calc'd for C$_7$H$_{11}$F$_2$NO [M+H]$^+$ 164. found 164.

Preparative Example 3.16

(Trans)-6-fluorooctahydrocyclopenta[b][1,4]oxazine (HCl salt)

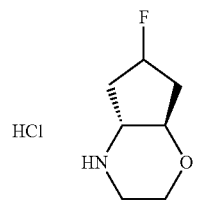

Step 1: (trans)-4-benzyloctahydrocyclopenta[b][1,4]oxazin-6-ol (Intermediate 3.15, Step 6) (250 mg, 1.07 mmol) was dissolved in CH$_2$Cl$_2$(10 mL), and DAST (518 mg, 3.2 mmol) was added dropwise. The reaction was stirred for 3 hours and quenched by adding saturated aqueous NaHCO$_3$ (15 mL). The layers were separated, and the aqueous layer was extracted using CH$_2$Cl$_2$ (2×20 mL). The combined organic layers were dried over anhydrous Na$_2$SO$_4$, filtered, and concentrated in vacuo. The residue was purified on a silica gel column (0 to 50% EtOAc/hexanes) to afford a slower eluting and a faster eluting diastereomer (both racemic) of (trans)-4-benzyl-6-fluorooctahydrocyclopenta[b][1,4]oxazine. Faster eluting diastereomer: $^1$H NMR (400 MHz, CDCl$_3$) δ 7.21-7.35 (m, 5H), 5.11 (m, 1H), 3.80-3.89 (m, 2H), 3.64-3.75 (m, 2H), 3.11 (d, J=13.2 Hz, 1H), 2.63 (m, 1H), 2.52 (m, 1H), 2.23 (m, 1H), 0.57-2.21 (m, 4H). MS APCI calc'd for C$_{14}$H$_{18}$FNO [M+H]$^+$ 236. found 236. Slower eluting diastereomer: $^1$H NMR (400 MHz, CDCl$_3$) δ 7.22-7.33 (m, 5H), 5.09 (m, 1H), 3.80-3.91 (m, 2H), 3.66 (m, 1H), 3.27 (m, 1H), 3.20 (d, J=12.8 Hz, 1H), 2.48-3.15 (m, 4H), 2.15 (m, 1H), 1.88 (m, 1H), 1.60 (m, 1H). MS APCI calc'd for C$_{14}$H$_{18}$FNO [M+H]$^+$ 236. found 236.

Step 2: (Trans)-4-benzyl-6-fluorooctahydrocyclopenta[b][1,4]oxazine (racemic faster eluting diastereomer) (200 mg, 0.85 mmol) was dissolved in MeOH (10 mL). 3M HCl in MeOH (1.5 mL) was added, and the solution was stirred for 1 hour. The solvent was evaporated, and the residue was further azeotroped using toluene. The residue was then dissolved in MeOH (10 mL), and 20% Pd(OH)$_2$/C (20% by wt, 40 mg) was added. Hydrogen was purged through the reaction for 10 minutes, and then the reaction was stirred at room temperature under 1 atm of hydrogen for 16 hours. The reaction was filtered through celite, and the filtrate was concentrated to afford (trans)-6-fluorooctahydrocyclopenta[b][1,4]oxazine hydrochloride (racemic, diastereomer 1). MS ES calc'd for $C_7H_{12}FNO$ [M+H]$^+$ 146. found 146. A similar procedure was carried out starting from the slower eluting diastereomer of step 1 to produce a second racemic diastereomer of product.

Preparative Intermediate 3.17 (trans)-hexahydro-2H-furo[3,4-b][1,4]oxazine (HCl salt, racemic)

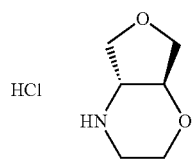

racemate

Step 1: Ti(O$^i$Pr)$_4$ (1.0 mL, 3.48 mmol) was added to a solution of 3,6-dioxabicyclo[3.1.0]hexane (1.5 g, 17.4 mmol) in benzylamine (2.0 mL). The mixture was irradiated in a microwave reactor at 130° C. for 2 hours. It was cooled to room temperature, and 50 mL of saturated aqueous NH$_4$Cl solution and 20 mL of EtOAc were added to the reaction. The mixture was stirred for 10 minutes. The resulting gummy precipitate was filtered over a celite bed, and the filtrate was extracted using EtOAc (100 mL). The organic layer was separated, washed with brine, dried over anhydrous Na$_2$SO$_4$, filtered, and concentrated in vacuo. The residue was purified by reverse phase chromatography on a C-18 column (0-100% CH$_3$CN/water) to afford trans-4-(benzylamino)tetrahydrofuran-3-ol. MS APCl calc'd for $C_{11}H_{15}NO_2$ [M+H]$^+$ 194. found 194.

Step 2: To a solution of trans-4-(benzylamino)tetrahydrofuran-3-ol (4.1 g, 21.2 mmol) in CH$_2$Cl$_2$ (40 mL) at −40° C. was added triethylamine (5.9 mL, 42.4 mmol) followed by dropwise addition of 2-chloroacetyl chloride (1.6 mL, 21.2 mmol). The reaction was stirred at −40° C. for 2 hours. The reaction was quenched with saturated aqueous NaHCO$_3$ (40 mL) and extracted using CH$_2$Cl$_2$ (100 mL). The organic layer was separated, washed with brine, dried over anhydrous Na$_2$SO$_4$, filtered, and concentrated in vacuo. Purification of the residue on a silica gel column with 0 to 100% EtOAc/hexanes afforded trans-N-benzyl-2-chloro-N-(4-hydroxytetrahydrofuran-3-yl)acetamide. MS APCl calc'd for $C_{13}H_{16}ClNO_3$ [M+H]$^+$ 270. found 270.

Step 3: To a solution of trans-N-benzyl-2-chloro-N-(4-hydroxytetrahydrofuran-3-yl)acetamide (4.7 g, 17.4 mmol) in t-BuOH (40 mL) was added KOt-Bu (1.0 M in THF; 34.8 mL, 34.8 mmol) solution at 25° C. The reaction mixture was stirred at 25° C. for 2 hours and then the solvent was evaporated under reduced pressure. The residue was dissolved in water and extracted with EtOAc (100 mL). The organic extract was washed with brine (40 mL), dried over anhydrous Na$_2$SO$_4$, and concentrated under reduced pressure to afford trans-4-benzyltetrahydro-2H-furo[3,4-b][1,4]oxazin-3(4H)-one. MS APCl calc'd for $C_{13}H_{15}NO_3$ [M+H]$^+$ 234. found 234.

Step 4: To a solution of trans-4-benzyltetrahydro-2H-furo[3,4-b][1,4]oxazin-3(4H)-one (3.1 g, 13.2 mmol) in THF (35 mL) at 0° C. was added BH$_3$:THF (1.0 M in THF; 39.7 mL, 39.7 mmol). The reaction mixture was stirred at 0° C. for 16 hours. The reaction was quenched with aqueous 1 N NaOH solution, adjusting to pH 13, and extracted with EtOAc (100 mL). The organic extract was washed with brine (40 mL), dried over anhydrous Na$_2$SO$_4$, and concentrated under reduced pressure to afford trans-4-benzylhexahydro-2H-furo[3,4-b][1,4]oxazine. $^1$H NMR (400 MHz, CDCl$_3$) δ 7.29-7.31 (m, 5H), 3.96 (t, J=7.2 Hz, 1H), 3.92 (ddd, J=11.6, 3.6, 1.2 Hz, 1H), 3.86 (m, 1H), 3.67-3.77 (m, 2H), 3.52-3.66 (m, 3H), 3.45 (dd, J=12.0, 9.0 Hz, 1H), 3.34 (d, J=13.2 Hz, 1H), 2.71 (ddd, J=12.0, 2.8, 1.2 Hz, 1H), 2.42 (ddd, J=15.6, 8.8, 6.8 Hz, 1H). MS APCl calc'd for $C_{13}H_{17}NO_2$ [M+H]$^+$ 220. found 220.

Step 5: To a solution of trans-4-benzylhexahydro-2H-furo[3,4-b][1,4]oxazine (600 mg, 2.73 mmol) in MeOH (10 mL) at room temperature was added Pd(OH)$_2$/C (250 mg). Hydrogen was purged through the reaction for 10 minutes and then the reaction was stirred at room temperature under 1 atm of hydrogen for 2 hours. Concentrated HCl (0.3 mL) was added, and the solution was stirred for 15 minutes. The reaction was filtered through celite, and the solvent was evaporated to afford (trans)-hexahydro-2H-furo[3,4-b][1,4]oxazine (HCl salt, racemic). $^1$H NMR (400 MHz, CD$_3$OD) δ 3.72-4.29 (m, 6H), 3.41-3.69 (m, 3H), 3.23-3.35 (m, 1H).

Preparative Example 3.18
(trans)-2-methyloctahydrocyclopenta[b][1,4]oxazine (HCl salt) (mixture of diastereomers)

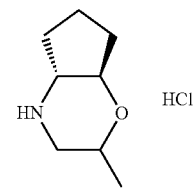

mixture of diastereomers
(Trans)-2-methyloctahydrocyclopenta[b][1,4]oxazine (HCl salt) (mixture of diastereomers) was prepared using chemistry similar to that described for Preparative Example 3.17. In step 1, 3,6-dioxabicyclo[3.1.0]hexane was replaced with cyclopentene oxide, and in step 2, 2-chloroacetyl chloride was replaced with 2-chloropropanoyl chloride.

Example 3.1

3-{4-(5-chloropyridin-3-yl)-2-[(2S)-2-(fluoromethyl) pyrrolidin-1-yl]-3-[(trans-4-methylcyclohexyl)methyl]-3H-imidazo[4,5-c]pyridin-6-yl}-1,2,4-oxadiazol-5(4H)-one

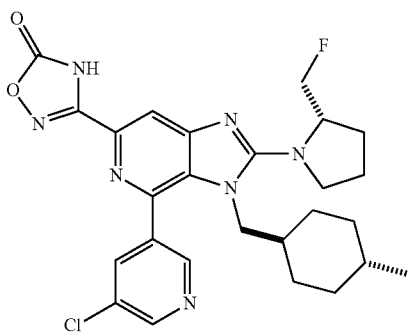 [SMILES: C[C@H]1CC[C@H](Cn2c(N3CCC[C@H]3CF)nc3cc(-c4noc(=O)[nH]4)nc(-c4cncc(Cl)c4)c32)CC1]

Step 1: To a vial was added 2-bromo-4-(5-chloropyridin-3-yl)-3-[(trans-4-methylcyclohexyl)methyl]-3H-imidazo[4,5-c]pyridine-6-carbonitrile (Preparative Example 3.1, 382.2 mg, 0.86 mmol), (S)-2-(fluoromethyl)pyrrolidine hydrochloride (240 mg, 1.72 mmol), potassium fluoride (250 mg, 4.30 mmol), DMSO (2.6 mL), and N,N-diisopropylethylamine (0.75 mL, 4.30 mmol). The vial was sealed and heated to 100° C. for 16 hours. The reaction mixture was cooled to room temperature, diluted with ethyl acetate, and washed with water and then brine. The organic layer was dried over sodium sulfate, filtered, and concentrated under reduced pressure. The residue was purified by silica gel chromatography (0-100% ethyl acetate/hexanes, linear gradient) to afford 4-(5-chloropyridin-3-yl)-2-[(2S)-2-(fluoromethyl)pyrrolidin-1-yl]-3-[(trans-4-methylcyclohexyl)methyl]-3H-imidazo[4,5-c]pyridine-6-carbonitrile. MS ESI calc'd. for $C_{25}H_{28}ClFN_6$ [M+H]$^+$ 467. found 467.

Step 2: Hydroxylamine hydrochloride (108 mg, 1.56 mmol), sodium bicarbonate (196 mg, 2.34 mmol), and water (1.56 mL) were combined in a vial and stirred for 15 minutes. This solution was added to a vial containing 4-[5-chloropyridin-3-yl)-2-(2S)-2-(fluoromethyl)pyrrolidin-1-yl]-3-[(trans-4-methylcyclohexyl)methyl]-3H-imidazo[4,5-c]pyridine-6-carbonitrile (364 mg, 0.78 mmol) dissolved in ethanol (3.6 mL). The mixture was sealed and heated at 100° C. for 1 hour. The reaction was cooled to room temperature, quenched with water, and extracted with ethyl acetate (2×). The combined organic layers were dried over sodium sulfate, filtered, and concentrated to afford 4-(5-chloropyridin-3-yl)-2-[(2S)-2-(fluoromethyl)pyrrolidin-1-yl]-N'-hydroxy-3-[(trans-4-methylcyclohexyl)methyl]-3H-imidazo[4,5-c]pyridine-6-carboximidamide. MS ESI calc'd. for $C_{25}H_{31}ClFN_7O$ [M+H]$^+$ 500. found 500.

Step 3: To a solution of 4-(5-chloropyridin-3-yl)-2-[(2S)-2-(fluoromethyl)pyrrolidin-1-yl]-N'-hydroxy-3-[(trans-4-methylcyclohexyl)methyl]-3H-imidazo[4,5-c]pyridine-6-carboximidamide (408 mg, 0.82 mmol) and 1,1'-carbonyldiimidazole (146 mg, 0.90 mmol) dissolved in acetonitrile (8.2 mL) was added 1,8-diazabicyclo[5.4.0]undec-7-ene (0.488 mL, 3.26 mmol). The reaction mixture was stirred at room temperature for 1 hour. The reaction was washed with water and extracted with dichloromethane. The organic layer was dried over sodium sulfate, filtered, and concentrated under reduced pressure. The residue was purified by silica gel chromatography (0-100% ethyl acetate/hexanes, linear gradient) to afford 3-{4-(5-chloropyridin-3-yl)-2-[(2S)-2-(fluoromethyl)pyrrolidin-1-yl]-3-[(trans-4-methylcyclohexyl)methyl]-3H-imidazo[4,5-c]pyridin-6-yl}-1,2,4-oxadiazol-5(4H)-one. MS ESI calc'd. for $C_{26}H_{29}ClFN_7O_2$ [M+H]$^+$ 526. found 526. $^1$H NMR (500 MHz, DMSO-$d_6$) δ 12.83 (s, 1H), 8.93 (s, 1H), 8.78 (s, 1H), 8.48 (s, 1H), 7.83 (s, 1H), 4.67-4.42 (m, 3H), 3.91-3.81 (m, 1H), 3.79-3.64 (m, 2H), 3.53-3.45 (m, 1H), 2.20-2.12 (broad, 1H), 2.06-1.98 (broad, 1H), 1.94-1.78 (m, 2H), 1.40-1.31 (broad, 2H), 1.17-1.07 (broad, 1H), 1.06-0.96 (broad, 1H), 0.89 (d, J=12.5, 1H), 0.67 (d, J=6.4, 3H), 0.63-0.36 (m, 5H).

Example 3.2

3-{4-(5-chloropyridin-3-yl)-2-(4aR,7aR)-hexahydrocyclopenta[b][1,4]oxazin-4(4aH)-yl)-3-[(trans-4-methylcyclohexyl)methyl]-3H-imidazo[4,5-c]pyridin-6-yl}-1,2,4-oxadiazol-5(4H)-one

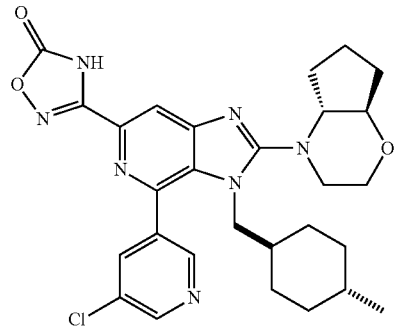

Step 1: To octahydrocyclopenta[b][1,4]oxazine hydrochloride (purchased from Enamine) (300 mg, 1.83 mmol) dissolved in dichloromethane (2.4 mL) was added benzyl chloroformate (0.44 mL, 2.57 mmol). Triethylamine (0.72 mL, 5.13 mmol) was added slowly to the reaction mixture, and the reaction was stirred for 16 hours at room temperature. The mixture was quenched with saturated aqueous sodium bicarbonate and extracted with dichloromethane (2×). The combined organic layers were dried over sodium sulfate, filtered, and concentrated under reduced pressure. The residue was purified by silica gel chromatography (0-100% ethyl acetate/hexanes, linear gradient), and then purified by chiral supercritical fluid chromatography (Chiralpak AZ-H, 21×250 mm, 10% methanol in $CO_2$) to afford the trans stereoisomers of benzyl hexahydrocyclopenta[b][1,4]oxazine-4(4aH)-carboxylate. (4aS,7aS)-Benzyl hexahydrocyclopenta[b][1,4]oxazine-4(4aH)-carboxylate (faster eluting enantiomer): MS ESI calc'd. for $C_{15}H_{19}NO_3$ [M+H]$^+$ 262. found 262; (4aR,7aR)-Benzyl hexahydrocyclopenta[b][1,4]oxazine-4(4aH)-carboxylate (slower eluting enantiomer): MS ESI calc'd. for $C_{15}H_{19}NO_3$ [M+H]$^+$ 262. found 262.

Step 2: To (4aR,7aR)-benzyl hexahydrocyclopenta[b][1,4]oxazine-4(4aH)-carboxylate (199.5 mg, 0.76 mmol) dissolved in ethyl acetate (5 mL) was added palladium (10 weight % on carbon, 81 mg, 0.076 mmol). Added hydrogen gas via balloon, and the reaction was stirred under a hydrogen atmosphere for two hours at room temperature. The mixture was filtered over celite and concentrated under reduced pressure to afford (4aR,7aR)-octahydrocyclopenta[b][1,4]oxazine. $^1$H NMR (500 MHz, CDCl$_3$) δ 3.90 (d, J=11.5, 1H), 3.64 (t, J=11.6, 1H), 3.17 (dd, J=9.2, 18.3, 1H), 2.96 (t, J=11.9, 1H), 2.88 (d, J=12.2, 1H), 2.59-2.47 (m, 1H), 1.89 (dd, J=9.1, 18.4, 1H), 1.84-1.61 (m, 4H), 1.57-1.44 (m, 1H), 1.38-1.26 (m, 1H).

Step 3: To a vial was added 2-bromo-4-(5-chloropyridin-3-yl)-3-[(trans-4-methylcyclohexyl)methyl]-3H-imidazo[4,5-c]pyridine-6-carbonitrile (Preparative Example 3.1, 90 mg, 0.202 mmol), (4aR,7aR)-octahydrocyclopenta[b][1,4]oxazine (51.5 mg, 0.405 mmol), potassium fluoride (58.8 mg, 1.01 mmol), DMSO (0.62 mL), and N,N-diisopropylethylamine (0.18 mL, 1.01 mmol). The vial was sealed to 100° C. for 16 hours. The reaction mixture was cooled to room temperature, diluted with ethyl acetate, and washed with water and then brine. The organic layer was dried over sodium sulfate, filtered, and concentrated under reduced pressure. The residue was purified by silica gel chromatography and heated (0-100% ethyl acetate/hexanes, linear gradient) to afford 4-(5-chloropyridin-3-yl)-2-((4aR,7aR)-hexahydrocyclopenta[b][1,4]oxazin-4(4aH)-yl)-3-[(trans-4-methylcyclohexyl)methyl]-3H-imidazo[4,5-c]pyridine-6-carbonitrile. MS ESI calc'd. for $C_{27}H_{31}ClN_6O$ [M+H]$^+$ 491. found 491.

Step 4: Hydroxylamine hydrochloride (24.3 mg, 0.35 mmol), sodium bicarbonate (44 mg, 0.52 mmol), and water (0.52 mL) were combined in a vial and stirred for 15 minutes. This solution was added to a vial containing 4-(5-chloropyridin-3-yl)-2-((4aR,7aR)-hexahydrocyclopenta[b][1,4]oxazin-4(4aH)-yl)-3-[(trans-4-methylcyclohexyl)methyl]-3H-imidazo[4,5-c]pyridine-6-carbonitrile (85.8 mg, 0.175 mmol) dissolved in ethanol (1.2 mL). The mixture was sealed and heated at 100° C. for 1 hour. The reaction was cooled to room temperature, quenched with water, and extracted with ethyl acetate (2×). The combined organic layers were dried over sodium sulfate, filtered, and concentrated to afford 4-(5-chloropyridin-3-yl)-2-((4aR,7aR)-hexahydrocyclopenta[b][1,4]oxazin-4(4aH)-yl)-N'-hydroxy-3-[(trans-4-methylcyclohexyl)methyl]-3H-imidazo[4,5-c]pyridine-6-carboximidamide. MS ESI calc'd. for $C_{27}H_{34}ClN_7O_2$ [M+H]$^+$ 524. found 524.

Step 5: To a solution of 4-(5-chloropyridin-3-yl)-2-((4aR,7aR)-hexahydrocyclopenta[b][1,4]oxazin-4(4aH)-yl)-N'-hydroxy-3-[(trans-4-methylcyclohexyl)methyl]-3H-imidazo[4,5-c]pyridine-6-carboximidamide (86.7 mg, 0.165 mmol) and 1,1'-carbonyldiimidazole (29.5 mg, 0.18 mmol) dissolved in acetonitrile (1.1 mL) was added 1,8-diazabicyclo[5.4.0]undec-7-ene (0.099 mL, 0.66 mmol). The reaction mixture was stirred at room temperature for 1 hour. The reaction was washed with water and extracted with dichloromethane. The organic layer was dried over sodium sulfate, filtered, and concentrated under reduced pressure. The residue was purified by silica gel chromatography (0-10% methanol/dichloromethane, and then 0-100% ethyl acetate/hexanes, linear gradient) to afford 3-{4-(5-chloropyridin-3-yl)-2-(4aR,7aR)-hexahydrocyclopenta[b][1,4]oxazin-4(4aH)-yl)-3-[(trans-4-methylcyclohexyl)methyl]-3H-imidazo[4,5-c]pyridin-6-yl}-1,2,4-oxadiazol-5(4H)-one. MS ESI calc'd. for $C_{28}H_{32}ClN_7O_3$ [M+H]$^+$ 550. found 550. $^1$H NMR (500 MHz, DMSO-d$_6$) δ 12.89 (s, 1H), 8.93 (s, 1H), 8.82 (s, 1H), 8.46 (s, 1H), 8.07 (s, 1H), 3.96 (d, J=10.8, 1H), 3.92-3.78 (m, 2H), 3.62 (d, J=14.4, 1H), 3.56 (d, J=12.8, 1H), 3.44-3.35 (m, 1H), 3.07-2.98 (m, 1H), 2.89-2.79 (m, 1H), 2.33-2.24 (m, 1H), 1.92-1.82 (m, 1H), 1.77-1.49 (m, 3H), 1.40 (d, J=12.8, 1H), 1.34 (d, J=12.7, 1H), 1.19-0.95 (m, 2H), 0.89-0.78 (m, 1H), 0.77-0.69 (m, 2H), 0.67 (d, J=6.4, 3H), 0.65-0.60 (m, 1H), 0.50 (d, J=11.6, 1H), 0.44-0.31 (m, 2H).

Example 3.3

3-{4-(5-chloropyridin-3-yl)-3-[(trans-4-methylcyclohexyl)methyl]-2-[(2S)-2-(trifluoromethyl)pyrrolidin-1-yl]-3H-imidazo[4,5-c]pyridin-6-yl}-1,2,4-oxadiazol-5(4H)-one

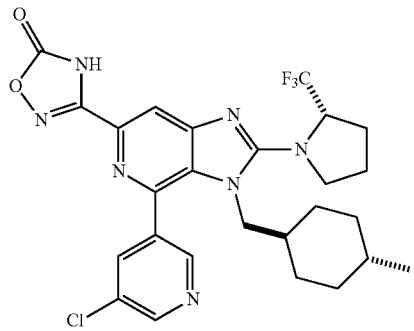 [SMILES: C[C@H]1CC[C@H](Cn2c(N3CCC[C@H]3C(F)(F)F)nc3cc(-c4noc(=O)[nH]4)nc(-c4cncc(Cl)c4)c32)CC1]

Step 1: To a vial was added 2-bromo-4-(5-chloropyridin-3-yl)-3-[(trans-4-methylcyclohexyl)methyl]-3H-imidazo[4,5-c]pyridine-6-carbonitrile (Preparative Example 3.1, 350 mg, 0.79 mmol), (S)-2-(trifluoromethyl)pyrrolidine (purchased from Sigma Aldrich) (219 mg, 1.57 mmol), potassium fluoride (229 mg, 3.93 mmol), DMSO (2.4 mL), and N,N-diisopropylethylamine (0.69 mL, 3.93 mmol). The vial was sealed and heated to 100° C. for 16 hours. The reaction mixture was cooled to room temperature, diluted with ethyl acetate, and washed with water and then brine. The organic layer was dried over sodium sulfate, filtered, and concentrated under reduced pressure. The residue was purified by silica gel chromatography (0-100% ethyl acetate/hexanes, linear gradient) to afford 4-(5-chloropyridin-3-yl)-3-[(trans-4-methylcyclohexyl)methyl]-2-[(2S)-2-(trifluoromethyl)pyrrolidin-1-yl]-3H-imidazo[4,5-c]pyridine-6-carbonitrile. MS ESI calc'd. for $C_{25}H_{26}ClF_3N_6$ [M+H]$^+$ 503. found 503.

Step 2: Hydroxylamine hydrochloride (44.5 mg, 0.64 mmol), sodium bicarbonate (81 mg, 0.96 mmol), and water (0.64 mL) were combined in a vial and stirred for 15 minutes. This solution was added to a vial containing 4-(5-chloropyridin-3-yl)-3-[(trans-4-methylcyclohexyl)methyl]-2-[(2S)-2-(trifluoromethyl)pyrrolidin-1-yl]-3H-imidazo[4,5-c]pyridine-6-carbonitrile (161 mg, 0.32 mmol) dissolved in ethanol (1.5 mL). The mixture was sealed and heated at 100° C. for 1 hour. The reaction was cooled to room temperature, quenched with water, and extracted with ethyl acetate (2×). The combined organic layers were dried over sodium sulfate, filtered, and concentrated to afford 4-(5-chloropyridin-3-yl)-N'-hydroxy-3-[(trans-4-methylcyclohexyl)methyl]-2-[(2S)-2-(trifluoromethyl)pyrrolidin-1-yl]-3H-imidazo[4,5-c]pyridine-6-carboximidamide. MS ESI calc'd. for $C_{25}H_{29}ClF_3N_7O$ [M+H]$^+$ 536. found 536.

Step 3: To a solution of 4-(5-chloropyridin-3-yl)-N'-hydroxy-3-[(trans-4-methylcyclohexyl)methyl]-2-[(2S)-2-(trifluoromethyl)pyrrolidin-1-yl]-3H-imidazo[4,5-c]pyridine-6-carboximidamide (169 mg, 0.315 mmol) and 1,1'-carbonyldiimidazole (56.2 mg, 0.35 mmol) dissolved in acetonitrile (3.2 mL) was added 1,8-diazabicyclo[5.4.0]undec-7-ene (0.188 mL, 1.26 mmol). The reaction mixture was stirred at room temperature for 1 hour. The reaction was washed with water and extracted with dichloromethane. The organic layer was dried over sodium sulfate, filtered, and concentrated under reduced pressure. The residue was purified by silica gel chromatography (0-100% ethyl acetate/hexanes, linear gradient) to afford 3-{4-(5-chloropyridin-3-yl)-3-[(trans-4-methylcyclohexyl)methyl]-2-[(2S)-2-(trifluoromethyl)pyrrolidin-1-yl]-3H-imidazo[4,5-c]pyridin-6-yl}-1,2,4-oxadiazol-5(4H)-one. MS ESI calc'd. for $C_{26}H_{27}ClF_3N_7O_2$ [M+H]$^+$ 562. found 562. $^1$H NMR (500 MHz, DMSO-d$_6$) δ 12.87 (s, 1H), 8.95 (s, 1H), 8.80 (s, 1H), 8.49 (s, 1H), 7.94 (s, 1H), 5.40-5.31 (m, 1H), 3.95-3.85 (m, 1H), 3.80-3.72 (m, 2H), 3.59-3.51 (m, 1H), 2.44-2.33 (m, 1H), 2.11-1.95 (m, 2H), 1.95-1.83 (m, 1H), 1.42-1.32 (broad, 2H), 1.11-0.98 (broad, 2H), 0.89 (d, J=12.1, 1H), 0.67 (d, J=6.3, 3H), 0.65-0.53 (m, 2H), 0.53-0.34 (m, 3H).

Example 3.90

3-{4-(5-chloropyridin-3-yl)-2-[(2S,4R)-4-methoxy-2-(propan-2-yl)pyrrolidin-1-yl]-3-[(trans-4-methylcyclohexyl)methyl]-3H-imidazo[4,5-d]pyridin-6-yl}-1,2,4-oxadiazol-5(4H)-one

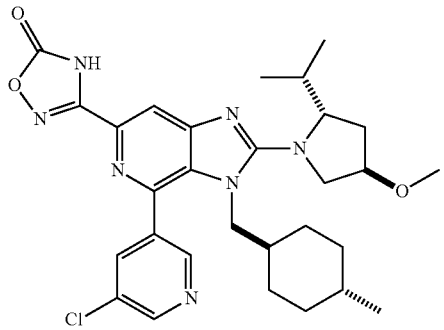

Step 1: To a vial was added 2-bromo-4-(5-chloropyridin-3-yl)-3-[(trans-4-methylcyclohexyl)methyl]-3H-imidazo[4,5-c]pyridine-6-carbonitrile (150 mg, 0.337 mmol), (3R,5S)-5-(propan-2-yl)pyrrolidin-3-ol(TFA salt, 164 mg, 0.675 mmol), potassium fluoride (98 mg, 1.68 mmol), DMSO (1 mL), and N,N-diisopropylethylamine (0.589 mL, 3.37 mmol). The vial was sealed and heated to 100° C. for 16 hours. The reaction mixture was cooled to room temperature, diluted with ethyl acetate, and washed with water and then brine. The organic layer was dried over sodium sulfate, filtered, and concentrated under reduced pressure. The residue was purified by silica gel chromatography (0-100% ethyl acetate/hexanes, linear gradient) to afford 4-(5-chloropyridin-3-yl)-2-[(2S,4R)-4-hydroxy-2-(propan-2-yl)pyrrolidin-1-yl]-3-[(trans-4-methylcyclohexyl)methyl]-3H-imidazo[4,5-c]pyridine-6-carbonitrile. MS ESI calc'd. for $C_{27}H_{33}ClN_6O$ [M+H]$^+$ 493. found 493.

Step 2: To a mixture of 4-(5-chloropyridin-3-yl)-2-[(2S,4R)-4-hydroxy-2-(propan-2-yl)pyrrolidin-1-yl]-3-[(trans-4-methylcyclohexyl)methyl]-3H-imidazo[4,5-c]pyridine-6-carbonitrile (71.4 mg, 0.145 mmol) in THF (0.483 mL) at 0° C. was added methyl iodide (31.1 μl, 0.498 mmol) followed by sodium hydride (7.65 mg, 0.319 mmol). The mixture was stirred for 3 hours at room temperature, quenched with ice, and diluted with dichloromethane. The organic layer was washed with water and brine, dried over sodium sulfate, filtered, and concentrated to afford 4-(5-chloropyridin-3-yl)-2-[(2S,4R)-4-methoxy-2-(propan-2-yl)pyrrolidin-1-yl]-3-[(trans-4-methylcyclohexyl)methyl]-3H-imidazo[4,5-c]pyridine-6-carbonitrile. MS ESI calc'd. for $C_{28}H_{35}ClN_6O$ [M+H]$^+$ 507. found 507.

Step 3: Hydroxylamine hydrochloride (20.2 mg, 0.29 mmol), sodium bicarbonate (36.6 mg, 0.44 mmol), and water (0.436 mL) were combined in a vial and stirred for 15 minutes. This solution was added to a vial containing 4-(5-chloropyridin-3-yl)-2-[(2S,4R)-4-methoxy-2-(propan-2-yl)pyrrolidin-1-yl]-3-[(trans-4-methylcyclohexyl)methyl]-3H-imidazo[4,5-c]pyridine-6-carbonitrile (73.7 mg, 0.145 mmol) dissolved in ethanol (1 mL). The mixture was sealed and heated at 100° C. for 1 hour. The reaction was cooled to room temperature, quenched with water, and extracted with ethyl acetate (2×). The combined organic layers were dried over sodium sulfate, filtered, and concentrated to afford 4-(5-chloropyridin-3-yl)-N'-hydroxy-2-[(2S,4R)-4-methoxy-2-(propan-2-yl)pyrrolidin-1-yl]-3-[(trans-4-methylcyclohexyl)methyl]-3H-imidazo[4,5-c]pyridine-6-carboximidamide. MS ESI calc'd. for $C_{28}H_{38}ClN_7O_2$ [M+H]$^+$ 540. found 540.

Step 4: To a solution of 4-(5-chloropyridin-3-yl)-N'-hydroxy-2-[(2S,4R)-4-methoxy-2-(propan-2-yl)pyrrolidin-1-yl]-3-[(trans-4-methylcyclohexyl)methyl]-3H-imidazo[4,5-c]pyridine-6-carboximidamide (79 mg, 0.146 mmol) and 1,1'-carbonyldiimidazole (26.1 mg, 0.161 mmol) dissolved in acetonitrile (1 mL) was added 1,8-diazabicyclo[5.4.0]undec-7-ene (0.087 mL, 0.585 mmol). The reaction mixture was stirred at room temperature for 1 hour. The reaction was washed with water and extracted with dichloromethane. The organic layer was dried over sodium sulfate, filtered, and concentrated under reduced pressure. The residue was purified by silica gel chromatography (0-10% methanol/dichloromethane, and then 0-100% ethyl acetate/hexanes, linear gradient) to afford 3-{4-(5-chloropyridin-3-yl)-2-[(2S,4R)-4-methoxy-2-(propan-2-yl)pyrrolidin-1-yl]-3-[(trans-4-methylcyclohexyl)ethyl]-3H-imidazo[4,5-d]pyridin-6-yl}-1,2,4-oxadiazol-5(4H)-one. MS ESI calc'd. for $C_{29}H_{36}ClN_7O_3$ [M+H]$^+$ 566. found 566. $^1$H NMR (500 MHz, DMSO-$d_6$) δ 12.82 (s, 1H), 8.96 (d, J=1.8, 1H), 8.78 (d, J=2.4, 1H), 8.50 (t, J=2.1, 1H), 7.82 (s, 1H), 4.39-4.34 (m, 1H), 3.98 (s, 1H), 3.85-3.81 (m, 1H), 3.77 (s, 2H), 3.53 (dd, J=5.9, 15.1, 1H), 3.20 (s, 3H), 2.31-2.27 (m, 1H), 2.09-2.00 (m, 1H), 1.80-1.72 (m, 1H), 1.37 (d, J=10.5, 2H), 1.12-1.05 (m, 1H), 1.05-0.96 (m, 1H), 0.89 (d, J=7.0, 3H), 0.87 (s, 1H), 0.76 (d, J=6.8, 3H), 0.6 (d, J=6.5, 3H), 0.61-0.55 (m, 1H), 0.54-0.48 (m, 1H), 0.48-0.44 (m, 1H), 0.40-0.34 (m, 2H).

Example 3.91

3-{4-(5-chloropyridin-3-yl)-2-[(2S,4R)-4-hydroxy-2-(propan-2-yl)pyrrolidin-1-yl]-3-[(trans-4-methylcyclohexyl)methyl]-3H-imidazo[4,5-d]pyridin-6-yl}-1,2,4-oxadiazol-5(4H)-one

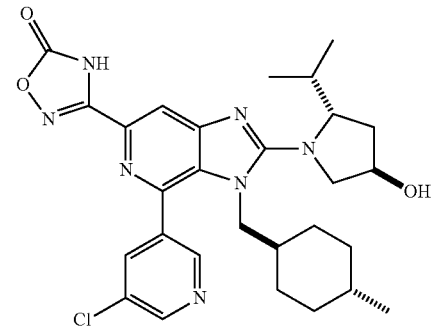

Using a procedure analogous to that described in Example 3.90 (Step 3 and Step 4), and starting with 4-(5-chloropyridin-3-yl)-2-[(2S,4R)-4-hydroxy-2-(propan-2-yl)pyrrolidin-1-yl]-3-[(trans-4-methylcyclohexyl)methyl]-3H-imidazo[4,5-c]pyridine-6-carbonitrile (product in Step 1, Example 3.90), 3-{4-(5-chloropyridin-3-yl)-2-[(2S,4R)-4-hydroxy-2-(propan-2-yl)pyrrolidin-1-yl]-3-[(trans-4-methylcyclohexyl)methyl]-3H-imidazo[4,5-c]pyridin-6-yl}-1,2,4-oxadiazol-5(4H)-one was prepared. MS ESI calc'd. for $C_{28}H_{34}ClN_7O_3$ [M+H]$^+$ 552. found 552. $^1$H NMR (500 MHz, DMSO-$d_6$) δ 12.81 (s, 1H), 8.92 (d, J=1.8, 1H), 8.77 (d, J=2.4, 1H), 8.47 (t, J=2.1, 1H), 7.82 (s, 1H), 4.90 (d, J=2.5, 1H), 4.52-4.46 (m, 1H), 4.33 (s, 1H), 3.85-3.73 (m, 2H), 3.56 (d, J=10.4, 1H), 3.48 (dd, J=5.8, 14.9, 1H), 2.36-2.26 (m, 1H), 1.88-1.74 (m, 2H), 1.36 (d, J=10.5, 2H), 1.16-1.05 (m, 1H), 1.05-0.95 (m, 1H), 0.89 (d, J=6.9, 3H), 0.86-0.79 (m, 1H), 0.75 (d, J=6.8, 3H), 0.66 (d, J=6.5, 3H), 0.64-0.54 (m, 1H), 0.53-0.49 (m, 1H), 0.49-0.41 (m, 1H), 0.41-0.32 (m, 2H).

Example 3.94

3-(4-(5-chloropyridin-3-yl)-2-(methyl(2,2,2-trifluoroethyl)amino)-3-((trans-4-methylcyclohexyl)methyl)-3H-imidazo[4,5-c]pyridin-6-yl)-1,2,4-oxadiazol-5(4H)-one

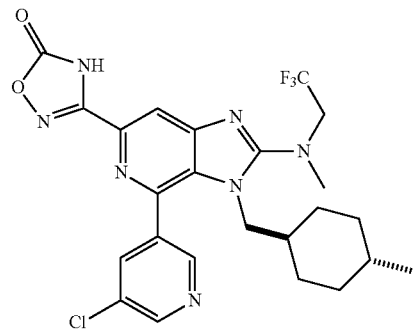 [SMILES: CN(CC(F)(F)F)c1nc2cc(-c3noc(=O)[nH]3)nc(-c3cncc(Cl)c3)c2n1C[C@H]1CC[C@H](C)CC1]

Step 1: To a sealed reaction vessel was added cesium fluoride (0.085 g, 0.56 mmol). The reaction vessel was heated to 150° C. for 3 hours with stirring, under high vacuum. The vial was cooled to ambient temperature under high vacuum. The reaction vessel was backfilled with argon, and next was added a solution of 2,2,2-trifluoro-N-methylethanamine (purchased from Enamine) (0.019 g, 0.17 mmol) and 2-bromo-4-(5-chloropyridin-3-yl)-3-((trans-4-methylcyclohexyl)methyl)-3H-imidazo[4,5-c]pyridine-6-carbonitrile (Preparative Example 3.1, 0.025 g, 0.056 mmol) in DMSO (0.30 mL). The reaction was heated to 100° C. for 12 hours. The reaction was cooled, diluted with H$_2$O (2.0 mL) and extracted with EtOAc (2×5.0 mL). The combined organics were dried over anhydrous MgSO$_4$, filtered and concentrated in vacuo to afford 4-(5-chloropyridin-3-yl)-2-(methyl(2,2,2-trifluoroethyl)amino)-3-((trans-4-methylcyclohexyl)methyl)-3H-imidazo[4,5-c]pyridine-6-carbonitrile as a crude residue. MS ESI calc'd. for C$_{23}$H$_{24}$ClF$_3$N$_6$ [M+H]$^+$ 477. found 477.

Step 2: To a reaction vessel containing the residue of 4-(5-chloropyridin-3-yl)-2-(methyl(2,2,2-trifluoroethyl)amino)-3-((trans-4-methylcyclohexyl)methyl)-3H-imidazo[4,5-c]pyridine-6-carbonitrile (0.027 g, 0.056 mmol) suspended in EtOH (1.0 mL) was added hydroxylamine (0.10 mL, 50% w/w in H$_2$O). The reaction was stirred at ambient temperature for 3 hours. To the reaction was then added benzene (2.0 mL), and the reaction was concentrated in vacuo to afford 4-(5-chloropyridin-3-yl)-N-hydroxy-2-(methyl(2,2,2-trifluoroethyl)amino)-3-((trans-4-methylcyclohexyl)methyl)-3H-imidazo[4,5-c]pyridine-6-carboximidamide as a crude residue. MS ESI calc'd. for C$_{23}$H$_{27}$ClF$_3$N$_7$O [M+H]$^+$ 510. found 510.

Step 3: To a reaction vessel containing the residue of 4-(5-chloropyridin-3-yl)-N-hydroxy-2-(methyl(2,2,2-trifluoroethypamino)-3-((trans-4-methylcyclohexyl)methyl)-3H-imidazo[4,5-c]pyridine-6-carboximidamide (0.028 g, 0.056 mmol) suspended in acetonitrile (1.0 mL) was added DBU (0.025 mL, 0.17 mmol) and 1,1'-carbonyldiimidazole (0.020 g, 0.12 mmol). The reaction was allowed to stir at ambient temperature for 3 hours. The reaction was concentrated in vacuo and taken up in DMSO (1.0 mL) and was passed through a syringe filter. The filtrate was purified by reverse phase preparative HPLC (0:100 to 95:5 acetonitrile:water: 0.1% v/v TFA modifier) to afford 3-(4-(5-chloropyridin-3-yl)-2-(methyl (2,2,2-trifluoroethyl)amino)-3-((trans-4-methylcyclohexyl)methyl)-3H-imidazo[4,5-c]pyridin-6-yl)-1,2,4-oxadiazol-5(4H)-one, TFA salt. MS ESI calc'd. for C$_{24}$H$_{25}$ClF$_3$N$_7$O$_2$ [M+H]$^+$ 536. found 536. $^1$H NMR (500 MHz, DMSO-d$_6$) δ 12.89 (s, 1H), 8.98 (s, 1H), 8.80 (m, 1H), 8.52 (s, 1H), 7.93 (s, 1H), 4.55 (m, 3H), 3.30 (s, 3H), 1.38 (m, 2H), 1.02 (m, 2H), 0.67 (d, J=6.5, 3H), 0.48 (m, 7H).

Example 3.95

3-(4-(5-chloropyridin-3-yl)-2-((trans-4-methoxytetrahydrofuran-3-yl)(methyl)amino)-3-((trans-4-methylcyclohexyl)methyl)-3H-imidazo[4,5-c]pyridin-6-yl)-1,2,4-oxadiazol-5(4H)-one

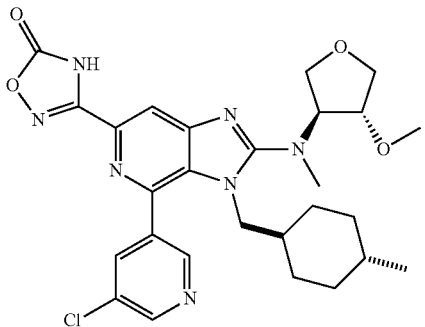 [SMILES: CO[C@H]1COC[C@@H]1N(C)c1nc2cc(-c3noc(=O)[nH]3)nc(-c3cncc(Cl)c3)c2n1C[C@H]1CC[C@H](C)CC1]

Step 1: Using a procedure analogous to that described in Example 3.94 (Step 1), starting with 2-bromo-4-(5-chloropyridin-3-yl)-3-((trans-4-methylcyclohexyl)methyl)-3H-imidazo[4,5-c]pyridine-6-carbonitrile (Preparative Example 3.1) and trans-4-aminotetrahydrofuran-3-ol (purchased from Chembridge Corporation), 4-(5-chloropyridin-3-yl)-2-((trans-4-hydroxytetrahydrofuran-3-yl)amino)-3-((trans-4-methylcyclohexyl)methyl)-3H-imidazo[4,5-c]pyridine-6-carbonitrile was prepared. MS ESI calc'd. for C$_{24}$H$_{27}$ClN$_6$O$_2$ [M+H]$^+$ 467. found 467.

Step 2: To a reaction vessel containing the residue of 4-(5-chloropyridin-3-yl)-2-((trans-4-hydroxytetrahydrofuran-3-yl)amino)-3-((trans-4-methylcyclohexyl)methyl)-3H-imidazo[4,5-c]pyridine-6-carbonitrile (0.010 g, 0.021 mmol) suspended in THF (0.5 mL) was added NaH (0.0043 g, 0.11 mmol, 60% dispersion in mineral oil). The reaction was allowed to stir at ambient temperature for 15 minutes. To the reaction vessel was then added iodomethane (0.025 mL, 0.40 mmol). The reaction vessel was sealed and warmed to 60° C. for 4 hours. The reaction was cooled to ambient temperature and quenched with H$_2$O (2.0 mL) and was extracted with EtOAc (2×5.0 mL). The collected organics were concentrated in vacuo to afford 4-(5-chloropyridin-3-yl)-2-((trans-4-methoxytetrahydrofuran-3-yl)(methyl)amino)-3-((trans-4-methylcyclohexyl)methyl)-3H-imidazo[4,5-c]pyridine-6-carbonitrile as a crude residue. MS ESI calc'd. for C$_{26}$H$_{31}$ClN$_6$O$_2$ [M+H]$^+$ 495. found 495.

Step 3: Using a procedure analogous to that described in Example 3.94 (Step 2) and starting with 4-(5-chloropyridin-3-yl)-2-((trans-4-methoxytetrahydrofuran-3-yl)(methyl)amino)-3-((trans-4-methylcyclohexyl)methyl)-3H-imidazo[4,5-c]pyridine-6-carbonitrile, 4-(5-chloropyridin-3-yl)-N-hydroxy-2-((trans-4-methoxytetrahydrofuran-3-yl)(methyl)amino)-3-((trans-4-methylcyclohexyl)methyl)-3H-imidazo[4,5-c]pyridine-6-carboximidamide was prepared. MS ESI calc'd. for C$_{26}$H$_{34}$ClN$_7$O$_3$ [M+H]$^+$ 528. found 528.

Step 4: Using a procedure analogous to that described in Example 3.94 (Step 3) and starting with 4-(5-chloropyridin-3-yl)-N-hydroxy-2-((trans-4-methoxytetrahydrofuran-3-yl)(methyl)amino)-3-((trans-4-methylcyclohexyl)methyl)-3H-imidazo[4,5-c]pyridine-6-carboximidamide, 3-(4-(5-chloropyridin-3-yl)-2-((trans-4-methoxytetrahydrofuran-3-yl)(methyl)amino)-3-((trans-4-methylcyclohexyl)methyl)-3H-imidazo[4,5-c]pyridin-6-yl)-1,2,4-oxadiazol-5(4H)-one (TFA salt, racemic) was prepared. MS ESI calc'd. for C$_{27}$H$_{32}$ClN$_7$O$_4$ [M+H]$^+$ 554. found 554. $^1$H NMR (500 MHz, d6-dmso): δ 12.87 (s, 1H); 8.96 (s, 1H); 8.80 (d, J=2.3 Hz, 1H); 8.50 (s, 1H); 7.93 (s, 1H); 4.35 (s, 1H); 4.20 (s, 1H); 4.03 (dd, J=9.9, 6.1 Hz, 2H); 3.82-3.84 (m, 1H); 3.69-3.72 (m, 3H); 3.63-3.65 (m, 2H); 3.07 (s, 3H); 1.36 (d, J=12.6 Hz, 2H); 0.93-1.03 (m, 2H); 0.67 (d, J=6.5 Hz, 3H); 0.54-0.61 (m, 5H); 0.38-0.43 (m, 2H).

Example 3.96

3-(4-(5-chloropyridin-3-yl)-2-(2-(1-methyl-1H-1,2,3-triazol-4-yl)pyrrolidin-1-yl)-3-((trans-4-methylcyclohexyl)methyl)-3H-imidazo[4,5-c]pyridin-6-yl)-1,2,4-oxadiazol-5(4H)-one

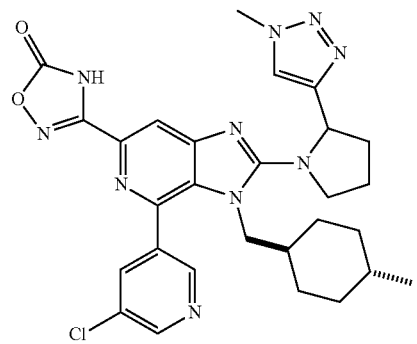 [SMILES: Cn1cc(C2CCCN2c2nc3cc(-c4noc(=O)[nH]4)nc(-c4cncc(Cl)c4)c3n2C[C@H]2CC[C@H](C)CC2)nn1]

Step 1: Using a procedure analogous to that described in Example 3.94 (Step 1), starting with 2-bromo-4-(5-chloropyridin-3-yl)-3-((trans-4-methylcyclohexyl)methyl)-3H-imidazo[4,5-c]pyridine-6-carbonitrile (Preparative Example 3.1) and 2-ethynylpyrrolidine, 4-(5-chloropyridin-3-yl)-2-(2-ethynylpyrrolidin-1-yl)-3-((trans-4-methylcyclohexyl)methyl)-3H-imidazo[4,5-c]pyridine-6-carbonitrile was prepared. MS ESI calc'd. for $C_{26}H_{27}ClN_6$ [M+H]$^+$ 459. found 459.

Step 2: Using a procedure analogous to that described in Example 3.94 (Step 2), and starting with 4-(5-chloropyridin-3-yl)-2-(2-ethynylpyrrolidin-1-yl)-3-((trans-4-methylcyclohexyl)methyl)-3H-imidazo[4,5-c]pyridine-6-carbonitrile, 4-(5-chloropyridin-3-yl)-2-(2-ethynyl pyrrolidin-1-yl)-N-hydroxy-3-((trans-4-methylcyclohexyl)methyl)-3H-imidazo[4,5-c]pyridine-6-carboximidam ide was prepared. MS ESI calc'd. for $C_{26}H_{30}ClN_7O$ [M+H]$^+$ 492. found 492.

Step 3: Using a procedure analogous to that described in Example 3.94 (Step 3), and starting with 4-(5-chloropyridin-3-yl)-2-(2-ethynylpyrrolidin-1-yl)-N-hydroxy-3-((trans-4-methylcyclohexyl)methyl)-3H-imidazo[4,5-c]pyridine-6-carboximidamide, 3-(4-(5-chloropyridin-3-yl)-2-(2-ethynylpyrrolidin-1-yl)-3-((trans-4-methylcyclohexyl)methyl)-3H-imidazo[4,5-c]pyridin-6-yl)-1,2,4-oxadiazol-5(4H)-one was prepared. MS ESI calc'd. for $C_{27}H_{28}ClN_7O_2$ [M+H]$^+$ 518. found 518.

Step 4: To a reaction vessel were added DMSO (0.4 mL), sodium azide (0.005 g, 0.080 mmol) and iodomethane (0.006 mL, 0.085 mmol). The reaction vessel was sealed and stirred at 50° C. for 12 hours. To the reaction was then added 3-(4-(5-chloropyridin-3-yl)-2-(2-ethynylpyrrolidin-1-yl)-3-((trans-4-methylcyclohexyl)methyl)-3H-imidazo[4,5-c]pyridin-6-yl)-1,2,4-oxadiazol-5(4H)-one (0.020 g, 0.039 mmol), CuI (0.004 g, 0.019 mmol), and DIEA (0.015 mL, 0.086 mmol). The reaction vessel was sealed and further stirred at 50° C. for 6 hours. To the reaction was added DMSO (0.6 mL), and the solution was passed through a syringe filter. The filtrate was purified by reverse phase preparative HPLC (0:100 to 95:5 acetonitrile:water: 0.1% v/v TFA modifier) to afford 3-(4-(5-chloropyridin-3-yl)-2-(2-(1-methyl-1H-1,2,3-triazol-4-yl)pyrrolidin-1-yl)-3-((trans-4-methylcyclohexyl)methyl)-3H-imidazo[4,5-c]pyridin-6-yl)-1,2,4-oxadiazol-5(4H)-one (TFA salt). MS ESI calc'd. for $C_{28}H_{31}ClN_{10}O_2$ [M+H]$^+$ 575. found 575. $^1$H NMR (500 MHz, DMSO-d6): δ 12.81 (s, 1H); 8.85 (s, 1H); 8.77 (d, J=2.3 Hz, 1H); 8.41 (s, 1H); 7.94 (s, 1H); 7.79 (s, 1H); 5.50 (t, J=7.1 Hz, 1H); 3.94 (s, 3H); 3.80-3.86 (m, 3H); 3.43-3.46 (m, 1H); 2.37-2.39 (m, 1H); 2.12-2.18 (m, 2H); 1.95-2.00 (m, 1H); 1.28-1.30 (m, 2H); 0.96-1.03 (m, 2H); 0.66 (d, J=6.5 Hz, 4H); 0.41-0.44 (m, 3H); 0.30-0.36 (m, 2H).

Example 3.97

(S)-1-(4-(5-chloropyridin-3-yl)-3-((trans-4-methylcyclohexyl)methyl)-6-(5-oxo-4,5-dihydro-1,2,4-oxadiazol-3-yl)-3H-imidazo[4,5-c]pyridin-2-yl)-N-ethyl-N-methylpyrrolidine-2-carboxamide

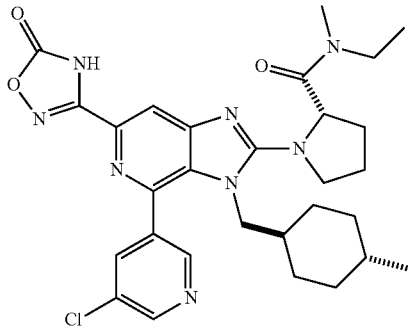 [SMILES: CCN(C)C(=O)[C@@H]1CCCN1c1nc2cc(-c3noc(=O)[nH]3)nc(-c3cncc(Cl)c3)c2n1C[C@H]1CC[C@H](C)CC1]

Step 1: (S)-1-(4-(5-chloropyridin-3-yl)-6-cyano-3-((trans-4-methylcyclohexyl)methyl)-3H-imidazo[4,5-c]pyridin-2-yl)pyrrolidine-2-carboxylic acid was prepared using a procedure analogous to that described in Example 3.94 (Step 1) using 2-bromo-4-(5-chloropyridin-3-yl)-3-((trans-4-methylcyclohexyl)methyl)-3H-imidazo[4,5-c]pyridine-6-carbonitrile (Preparative Example 3.1) and L-proline. MS ESI calc'd. for $C_{25}H_{27}ClN_6O_2$ [M+H]$^+$ 479. found 479.

Step 2: To a reaction vessel was added the crude residue of (S)-1-(4-(5-chloropyridin-3-yl)-6-cyano-3-((trans-4-methylcyclohexyl)methyl)-3H-imidazo[4,5-c]pyridin-2-yl)pyrrolidine-2-carboxylic acid (0.030 g, 0.063 mmol), propylphosphonic anhydride (0.10 mL, 50% w/w in DMF), and N-methylethanamine (0.0037 g, 0.063 mmol) suspended in DMF (0.5 mL). The reaction was stirred at ambient temperature for 6 hours. The reaction was diluted with $H_2O$ (2.0 mL) and was extracted with EtOAc (2×5 mL). The combined organics were concentrated in vacuo to afford (S)-1-(4-(5-chloropyridin-3-yl)-6-cyano-3-((trans-4-methylcyclohexyl)methyl)-3H-imidazo[4,5-c]pyridin-2-yl)-N-ethyl-N-methylpyrrolidine-2-carboxamide as a crude residue. MS ESI calc'd. for $C_{28}H_{34}ClN_7O$ [M+H]$^+$ 520. found 520.

Step 3: Using a procedure analogous to that described in Example 3.94 (Step 2), and starting with (S)-1-(4-(5-chloropyridin-3-yl)-6-cyano-3-((trans-4-methylcyclohexyl)methyl)-3H-imidazo[4,5-c]pyridin-2-yl)-N-ethyl-N-methylpyrrolidine-2-carboxamide, (S)-1-(4-(5-chloropyridin-3-yl)-6-(N-hydroxycarbamimidoyl)-3-((trans-4-methylcyclohexyl)methyl)-3H-imidazo[4,5-c]pyridin-2-yl)-N-ethyl-N-methylpyrrolidine-2-carboxamide was prepared. MS ESI calc'd. for $C_{28}H_{37}ClN_8O_2$ [M+H]$^+$ 553. found 553.

Step 4: Using a procedure analogous to that described in Example 3.94 (Step 3), and starting with (S)-1-(4-(5-chloropyridin-3-yl)-6-(N-hydroxycarbamimidoyl)-3-((trans-4-methylcyclohexyl)methyl)-3H-imidazo[4,5-c]pyridin-2-yl)-N-ethyl-N-methylpyrrolidine-2-carboxamide, (S)-1-(4-(5-chloropyridin-3-yl)-3-((trans-4-methylcyclohexyl)methyl)-6-(5-oxo-4,5-dihydro-1,2,4-oxadiazol-3-yl)-3H-imidazo[4,5-c]pyridin-2-yl)-N-ethyl-N-methylpyrrolidine-2-carboxamide (TFA salt) was prepared. MS ESI calc'd. for $C_{29}H_{35}ClN_8O_3$ [M+H]$^+$ 579. found 579. $^1$H NMR (500 MHz, DMSO-d6) δ 12.79 (s, 1H), 8.89 (m, J=7.9, 1H), 8.77 (d, J=2.3, 1H), 8.46 (m, 1H), 7.69 (d, J=17.4, 1H), 5.14 (m, 1H), 3.88 (m, 1H), 3.72 (m, 1H), 3.53 (m, 2H), 3.27 (m, 1H), 3.15 (s, 2H), 2.79 (s, 2H), 2.35 (m, 1H), 2.06 (m, 1H), 1.93 (m, 1H), 1.78 (m, 1H), 1.30 (m, J=7.1, 5H), 1.07 (m, J=7.1, 3H), 0.69 (d, J=6.5, 3H), 0.55 (m, 5H).

Example 3.98

3-(4-(5-chloropyridin-3-yl)-2-((2-fluorophenyl)amino)-3-((trans-4-methylcyclohexyl)methyl)-3H-imidazo[4,5-c]pyridin-6-yl)-1,2,4-oxadiazol-5(4H)-one

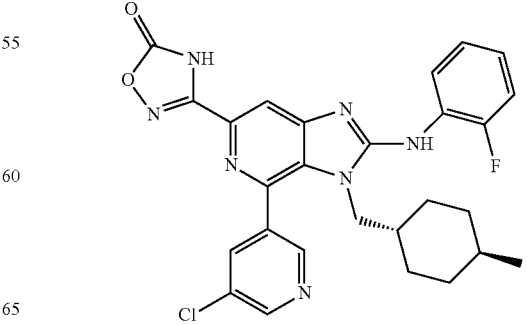

Step 1: To a sealed tube were added 2-bromo-4-(5-chloropyridin-3-yl)-3-((trans-4-methylcyclohexyl)methyl)-3H-imidazo[4,5-c]pyridine-6-carbonitrile (Preparative Example 3.1) (0.010 g, 0.045 mmol), 2-fluoroaniline (0.0050 g, 0.045 mmol), Cs$_2$CO$_3$ (0.022 g, 0.067 mmol), chloro[(4,5-bis(diphenylphosphino)-9,9-dimethylxanthene)-2-(2'-amino-1,1'-biphenyl)]palladium(11) (0.0050 g, 0.0056 mmol), and dioxane (0.5 mL). The reaction vessel was purged with argon, sealed and warmed to 75° C. for 8 hours with stirring. The reaction was cooled and diluted with dioxane (1.0 mL) and was passed through a syringe filter. The collected eluent was concentrated in vacuo to afford 4-(5-chloropyridin-3-yl)-2-((2-fluorophenyl)amino)-3-((trans-4-methylcyclohexyl)methyl)-3H-imidazo[4,5-c]pyridine-6-carbonitrile as a crude residue. MS ESI calc'd. for C$_{26}$H$_{24}$ClFN$_6$ [M+H]$^+$ 475. found 475.

Step 2: Using a procedure analogous to that described in Example 3.94 (Step 2), and starting with 4-(5-chloropyridin-3-yl)-2-((2-fluorophenyl)amino)-3-((trans-4-methylcyclohexyl)methyl)-3H-imidazo[4,5-c]pyridine-6-carbonitrile, 4-(5-chloropyridin-3-yl)-2-((2-fluorophenyl)amino)-N-hydroxy-3-((trans-4-methylcyclohexyl)methyl)-3H-imidazo[4,5-c]pyridine-6-carboximidamide was prepared. MS ESI calc'd. for O$_{26}$H$_{27}$ClFN$_7$O [M+H]$^+$ 508. found 508.

Step 3: Using a procedure analogous to that described in Example 3.94 (Step 3), and starting with 4-(5-chloropyridin-3-yl)-2-((2-fluorophenyl)amino)-N-hydroxy-3-((trans-4-methylcyclohexyl)methyl)-3H-imidazo[4,5-c]pyridine-6-carboximidamide, 3-(4-(5-chloropyridin-3-yl)-2-(2-fluorophenyl)amino)-3-((trans-4-methylcyclohexyl)methyl)-3H-imidazo[4,5-c]pyridin-6-yl)-1,2,4-oxadiazol-5(4H)-one (TFA salt) was prepared. MS ESI calc'd. for C$_{27}$H$_{25}$ClFNγO$_2$ [M+H]$^+$ 534. found 534. $^1$H NMR (500 MHz, DMSO-d$_6$) δ 12.83 (s, 1H), 9.27 (s, 1H), 8.83 (m, J=20.7, 2H), 8.39 (s, 1H), 7.81 (s, 1H), 7.65 (m, 1H), 7.26 (m, 3H), 3.85 (s, 2H), 1.44 (d, 2H), 1.07 (m, 2H), 0.71 (m, J=6.5, 7H), 0.54 (m, 2H)

Example 3.120

(4aS,7aS)-4-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-1-methyloctahydro-2H-cyclopenta[b]pyrazin-2-one

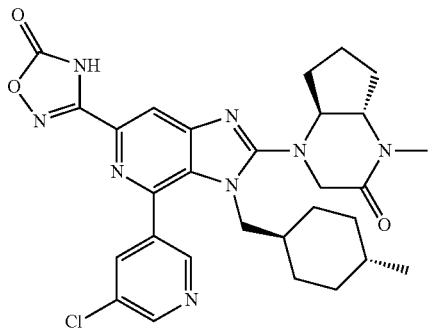 [SMILES: CN1C(=O)CN(c2nc3cc(-c4noc(=O)[nH]4)nc(-c4cncc(Cl)c4)c3n2C[C@H]2CC[C@H](C)CC2)[C@H]2CCC[C@@H]21]

Step 1: tert-Butyl [(1S,2S)-2-aminocyclopentyl]carbamate (900 mg, 4.49 mmol) (purchased from Sigma Aldrich) was taken up in acetonitrile (13 mL). Potassium carbonate (932 mg, 6.74 mmol) and ethyl chloroacetate (0.577 mL, 5.39 mmol) were added, and the resulting mixture was heated to 55° C. overnight. The resulting mixture was cooled to room temperature and concentrated under reduced pressure. The residue was taken up in EtOAc, washed with water and brine, dried over magnesium sulfate, filtered, and concentrated under reduced pressure. The resulting residue was purified by silica gel chromatography (0-100% EtOAc/hexanes) to afford ethyl N-{(1S,2S)-2-[(tert-butoxycarbonyl)amino]cyclopentyl}glycinate.

Step 2: Ethyl N-{(1S,2S)-2-[(tert-butoxycarbonyl)amino]cyclopentyl}glycinate (910 mg, 3.18 mmol) was taken up in dioxane (16 mL) and HCl (7.5 mL of 4 M in dioxane, 30.0 mmol) was added. The resulting mixture was stirred at room temperature overnight. The mixture was concentrated under reduced pressure to afford ethyl N-[(1S,2S)-2-aminocyclopentyl]glycinate (HCl salt) which was used without further purification.

Step 3: Ethyl N-[(1S,2S)-2-aminocyclopentyl]glycinate (HCl salt) (708 mg, 3.18 mmol) was dissolved in ethanol (16 mL), and triethylamine (4.43 mL, 31.8 mmol) was added. The resulting mixture was stirred and heated at 85° C. for 24 hours. The mixture was then cooled and concentrated under reduced pressure. Ethyl acetate was added to the residue, and the resulting slurry was filtered. The filtrate was concentrated under reduced pressure to afford (4aS,7aS)-octahydro-2H-cyclopenta[b]pyrazin-2-one, which was used without further purification. $^1$H NMR (500 MHz, CDCl$_3$) δ 6.31 (s, 1H), 3.68-3.67 (m, 2H), 3.23-3.17 (m, 1H), 2.86-2.81 (m, 1H), 1.97-1.82 (m, 5H), 1.49-1.40 (m, 2H).

Step 4: A vial was charged with potassium fluoride (163 mg, 2.81 mmol), 2-bromo-4-(5-chloropyridin-3-yl)-3-[(trans-4-methylcyclohexyl)methyl]-3H-imidazo[4,5-c]pyridine-6-carbonitrile (Preparative Example 3.1, 250 mg, 0.562 mmol), (4aS,7aS)-octahydro-2H-cyclopenta[b]pyrazin-2-one (189 mg, 1.349 mmol), DMSO (1730 μl) and DIEA (491 μl, 2.81 mmol). The vial was capped and heated to 100° C. overnight. The mixture was then cooled to room temperature, diluted with ethyl acetate and washed with water and brine. The organic layer was dried over magnesium sulfate, filtered, and concentrated. Purification by silica gel chromatography (0-20% MeOH in DCM) afforded 4-(5-chloropyridin-3-yl)-3-[(trans-4-methylcyclohexyl)methyl]-2-[(4aS,7aS)-3-oxooctahydro-1H-cyclopenta[b]pyrazin-1-yl]-3H-imidazo[4,5-c]pyridine-6-carbonitrile. MS ESI calc'd. for C$_{27}$H$_{30}$ClN$_7$O [M+H]$^+$ 504. found 504.

Step 5: 4-(5-chloropyridin-3-yl)-3-[(trans-4-methylcyclohexyl)methyl]-2-[(4aS,7aS)-3-oxooctahydro-1H-cyclopenta[b]pyrazin-1-yl]-3H-imidazo[4,5-c]pyridine-6-carbonitrile (282 mg, 0.559 mmol) was taken up in DMF (5595 μl), and sodium hydride (22.38 mg, 0.559 mmol) and iodomethane (87 μl, 1.399 mmol) were added. The mixture was stirred for 1 hour, quenched via the addition of saturated aqueous ammonium chloride and extracted with ethyl acetate. The organic layer was dried over magnesium sulfate, filtered, and concentrated under reduced pressure. The resulting residue was purified via silica gel chromatography (0-20% MeOH/DCM) to afford 4-(5-chloropyridin-3-yl)-3-[(trans-4-methylcyclohexyl)methyl]-2-[(4aS,7aS)-4-methyl-3-oxooctahydro-1H-cyclopenta[b]pyrazin-1-yl]-3H-imidazo[4,5-c]pyridine-6-carbonitrile as a brown foam. MS ESI calc'd. for C$_{28}$H$_{32}$ClN$_7$O [M+H]$^+$ 518. found 518.

Step 6: 4-(5-Chloropyridin-3-yl)-N'-hydroxy-3-[(trans-4-methylcyclohexyl)methyl]-2-[(4aS,7aS)-4-methyl-3-oxooctahydro-1H-cyclopenta[b]pyrazin-1-yl]-3H-imidazo[4,5-c]pyridine-6-carboximidamide was prepared in analogy to Example 3.1, Step 2 using 4-(5-chloropyridin-3-yl)-3-[(trans-4-methylcyclohexyl)methyl]-2-[(4aS,7aS)-4-methyl-3-oxooctahydro-1H-cyclopenta[b]pyrazin-1-yl]-3H-imidazo[4,5-c]pyridine-6-carbonitrile (185 mg, 0.357 mmol) as starting material. MS ESI calc'd. for C$_{28}$H$_{35}$ClN$_8$O$_2$ [M+H]$^+$ 551. found 551.

Step 7: (4aS,7aS)-4-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-1-methyloctahydro-2H-cyclopenta[b]pyrazin-2-one was prepared in analogy to Example 3.1, Step 3 using 4-(5-chloropyridin-3-yl)-N'-hydroxy-3-[(trans-4-methylcyclohexyl)methyl]-2-[(4aS,7aS)-4-methyl-3-oxooctahydro-1H-cyclopenta[b]pyrazin-1-yl]-3H-imidazo[4,5-c]pyridine-6-carboximidamide (197 mg, 0.357 mmol) as starting material and 0-20% methanol in DCM as eluant for chromatography. MS ESI calc'd. for $C_{29}H_{33}ClN_8O_3$ [M+H]$^+$ 577. found 577. $^1$H NMR (500 MHz, DMSO-d$_6$) δ 12.89 (s, 1H), 8.98 (d, J=2.0 Hz, 1H), 8.81 (d, J=2.0 Hz, 1H), 8.49 (t, J=2.0 Hz, 1H), 8.04 (s, 1H), 4.31-4.28 (m, 1H), 3.88-3.84 (m, 2H), 3.69-3.61 (m, 3H), 2.88 (s, 3H), 2.34-2.24 (m, 1H), 2.31-2.04 (m, 1H), 1.89-1.75 (m, 2H), 1.70-1.61 (m, 1H), 1.47-1.33 (m, 3H), 1.25-1.20 (m, 2H), 1.08-0.98 (m, 1H), 0.85-0.82 (m, 1H), 0.73-0.60 (m, 5H), 0.62-0.33 (m, 2H).

Examples 3.127 and 3.128

3-{4-(5-chloropyridin-3-yl)-3-[(trans-4-methylcyclohexyl)methyl]-2-[(4aR,8aR)-octahydro-1H-pyrido[3,4-b][1,4]oxazin-1-yl]-3H-imidazo[4,5-c]pyridin-6-yl}-1,2,4-oxadiazol-5(4H)-one and 3-{2-[(4aR,8aR)-6-benzyloctahydro-1H-pyrido[3,4-b][1,4]oxazin-1-yl]-4-(5-chloropyridin-3-yl)-3-[(trans-4-methylcyclohexyl)methyl]-3H-imidazo[4,5-c]pyridin-6-yl}-1,2,4-oxadiazol-5(4H)-one

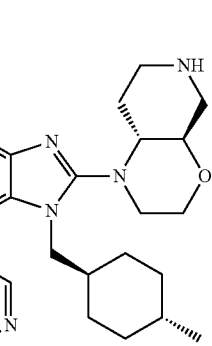

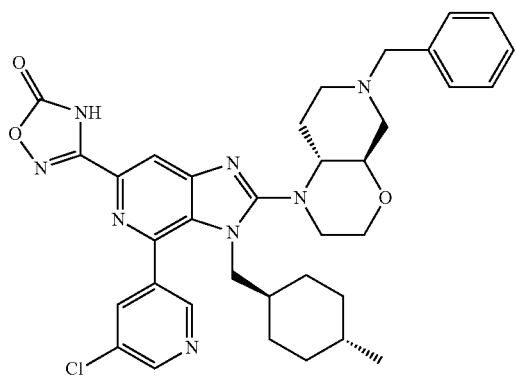 [SMILES: C[C@H]1CC[C@H](Cn2c(N3CCO[C@@H]4CN(Cc5ccccc5)CC[C@H]43)nc3cc(-c4noc(=O)[nH]4)nc(-c4cncc(Cl)c4)c32)CC1]

To benzyl (4aR,8aR)-1-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]octahydro-6H-pyrido[3,4-b][1,4]oxazine-6-carboxylate (Example 3.126, prepared in analogy to Example 3.1, starting with Preparative Example 3.1 and Preparative Example 3.2, 58.7 mg, 0.08 mmol) dissolved in DCM (3.2 mL) at 0° C. under an argon atmosphere was added iodotrimethylsilane (60 μL, 0.42 mmol). The reaction was stirred for 1 hour at room temperature. Isopropanol (1.5 mL) and aqueous sodium carbonate solution (2 M, 3 mL) were added, and the biphasic reaction was stirred for 1 hour. The organic layer was separated, and the aqueous layer was extracted with DCM (3×). The combined organic layers were dried over sodium sulfate, filtered, and concentrated. The residue was purified by mass triggered, reverse phase (C-18) preparative HPLC (acetonitrile:water: 0.1% v/v trifluoroacetic acid modifier) to afford 3-{4-(5-chloropyridin-3-yl)-3-[(trans-4-methylcyclohexyl)methyl]-2-[(4aR,8aR)-octahydro-1H-pyrido[3,4-b][1,4]oxazin-1-yl]-3H-imidazo[4,5-c]pyridin-6-yl}-1,2,4-oxadiazol-5(4H)-one as a TFA salt. MS ESI calc'd. for $C_{28}H_{33}ClN_8O_3$ [M+H]$^+$ 565. found 565. $^1$H NMR (500 MHz, DMSO-d$_6$) δ 12.94 (s, 1H), 8.95 (s, 1H), 8.83 (d, J=2.0, 1H), 8.63 (s, 1H), 8.47 (s, 1H), 8.13 (s, 1H), 4.01-3.86 (m, 3H), 3.72-3.57 (m, 3H), 3.54-3.48 (m, 2H), 3.10-2.92 (m, 3H), 2.74 (s, 1H), 1.46-1.39 (m, 1H), 1.37-1.29 (m, 2H), 1.06 (s, 1H), 0.81 (s, 1H), 0.76-0.67 (m, 6H), 0.53 (s, 1H), 0.48-0.31 (m, 3H). Also isolated was 3-{2-[(4aR,8aR)-6-benzyloctahydro-1H-pyrido[3,4-b][1,4]oxazin-1-yl]-4-(5-chloropyridin-3-yl)-3-[(trans-4-methylcyclohexyl)methyl]-3H-imidazo[4,5-c]pyridin-6-yl}-1,2,4-oxadiazol-5(4H)-one MS ESI calc'd. for $C_{35}H_{39}ClN_8O_3$ [M+H]$^+$ 655. found 655.

Example 3.141

3-(4-(5-chloropyridin-3-yl)-2-((2S,4R)-2-(difluoromethyl)-4-methoxypyrrolidin-1-yl)-3-((trans-4-methylcyclohexyl)methyl)-3H-imidazo[4,5-c]pyridin-6-yl)-1,2,4-oxadiazol-5(4H)-one

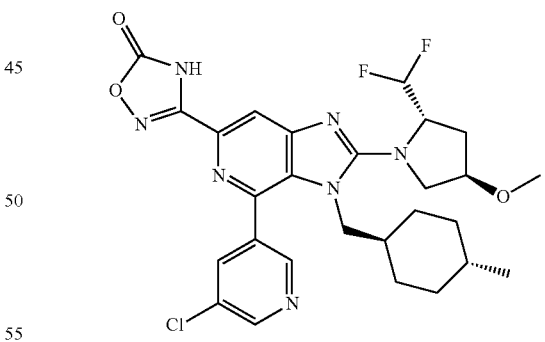

Step 1: To a vial were added ((2S,4R)-4-methoxypyrrolidin-2-yl)methanol, HCl (0.303 g, 1.81 mmol), 2-bromo-4-(5-chloropyridin-3-yl)-3-((trans-4-methylcyclohexyl)methyl)-3H-imidazo[4,5-c]pyridine-6-carbonitrile (Preparative Example 3.1) (0.805 g, 1.810 mmol), potassium fluoride (0.210 g, 3.62 mmol), DMSO (4 ml) and DIEA (0.948 ml, 5.43 mmol). The reaction vial was capped and heated to 100° C. for 8 h. The reaction mixture was cooled to room temperature, diluted with ethyl acetate, and washed with water and then brine. The organic layer was dried over sodium sulfate, filtered, and concentrated under reduced pressure. The residue was purified by silica gel chromatography (0-100% ethyl acetate/hexanes, linear gradient) to afford 4-(5-chloropyridin-3-yl)-2-((2S,4R)-2-(hydroxymethyl)-4-methoxypyrrolidin-1-yl)-3-((trans-4-methylcyclohexyl)methyl)-3H-imidazo[4,5-c]pyridine-6-carbonitrile. MS ESI calc'd. for $C_{26}H_{31}ClN_6O_2$ [M+H]$^+$ 495. found 495.

Step 2: A solution of oxalyl chloride (0.160 ml, 1.826 mmol) in dichloromethane (5 ml) was cooled to −78° C., and a solution of DMSO (0.259 ml, 3.65 mmol) in dichloromethane (2.5 ml) was slowly added. The reaction was warmed to −60° C. After 10 min of stirring, a solution of 4-(5-chloropyridin-3-yl)-2-((2S,4R)-2-(hydroxymethyl)-4-methoxypyrrolidin-1-yl)-3-((trans-4-methylcyclohexyl)methyl)-3H-imidazo[4,5-c]pyridine-6-carbonitrile (452 mg, 0.913 mmol) in dichloromethane (5 ml) was slowly added. The reaction was stirred for 30 min at −40° C. Then triethylamine (0.764 ml, 5.48 mmol) was added, and the reaction was warmed to room temperature and stirred overnight. The reaction mixture was quenched with saturated aqueous NaHCO$_3$ (30 mL). The dichloromethane layer was separated. The aqueous layer was extracted with dichloromethane (20 mL). The combined dichloromethane layers were washed with brine (50 mL), dried over Na$_2$SO$_4$, filtered, and concentrated in vacuo. The residue was purified by column chromatography on silica gel, eluting with EtOAc/isohexane to give 4-(5-chloropyridin-3-yl)-2-(2S,4R)-2-formyl-4-methoxypyrrolidin-1-yl)-3-((trans-4-methylcyclohexyl)methyl)-3H-imidazo[4,5-c]pyridine-6-carbonitrile. MS ESI calc'd. for $C_{26}H_{29}ClN_6O_2$ [M+H]$^+$ 493. found 493.

Step 3: To a solution of 4-(5-chloropyridin-3-yl)-2-((2S, 4R)-2-formyl-4-methoxypyrrolidin-1-yl)-3-((trans-4-methylcyclohexyl)methyl)-3H-imidazo[4,5-c]pyridine-6-carbonitrile (360 mg, 0.730 mmol) in dichloromethane (10 ml) was added dropwise deoxofluor (0.296 ml, 1.606 mmol) at −60° C. The resulting mixture was stirred at room temperature overnight. The reaction mixture was quenched with 5% aqueous Na$_2$CO$_3$ (30 mL) at 0° C. The dichloromethane layer was separated. The aqueous layer was extracted with dichloromethane (20 mL). The combined dichloromethane layers were washed with brine (50 mL), dried over Na$_2$SO$_4$, filtered, and concentrated in vacuo. The crude residue containing 4-(5-chloropyridin-3-yl)-2-((2S,4R)-2-(difluoromethyl)-4-methoxypyrrolidin-1-yl)-3-((trans-4-methylcyclohexyl)methyl)-3H-imidazo[4,5-c]pyridine-6-carbonitrile was used in the next step. MS ESI calc'd. for $C_{26}H_{29}ClF_2N_6O$ [M+H]$^+$ 515. found 515.

Steps 4 & 5: Using a procedure analogous to that described in Example 3.1 (Step 2 and Step 3), and starting with 4-(5-chloropyridin-3-yl)-2-(2S,4R)-2-(difluoromethyl)-4-methoxypyrrolidin-1-yl)-3-((trans-4-methylcyclohexyl)methyl)-3H-imidazo[4,5-c]pyridine-6-carbonitrile, 3-(4-(5-chloropyridin-3-yl)-2-((2S,4R)-2-(difluoromethyl)-4-methoxypyrrolidin-1-yl)-3-((trans-4-methylcyclohexyl)methyl)-3H-imidazo[4,5-c]pyridin-6-yl)-1,2,4-oxadiazol-5(4H)-one, TFA salt was prepared. MS ESI calc'd. for $C_{27}H_{30}ClF_2N_7O_3$ [M+H]$^+$ 574. found 574. $^1$H NMR (500 MHz, DMSO-d6) δ 8.97 (s, 1H); 8.79 (s, 1H); 8.50 (s, 1H); 7.90 (s, 1H); 6.17 (t, J=56.1 Hz, 1H); 4.85 (br s, 1H); 4.08 (s, 1H); 3.79-3.85 (m, 3H); 3.52-3.60 (m, 1H); 3.21 (s, 3H); 2.31 (dd, J=13.8, 7.6 Hz, 1H); 2.00-2.06 (m, 1H); 1.36 (br s, 3H); 1.02 (br s, 3H); 0.86 (d, J=12.5 Hz, 1H); 0.67 (d, J=6.5 Hz, 3H); 0.39-0.67 (m, 4H).

Example 3.172

3-[4-(5-chloropyridin-3-yl)-3-[(trans-4-methylcyclohexyl)methyl]-2-(pyridin-2-ylamino)-3H-imidazo[4,5-c]pyridin-6-yl]-1,2,4-oxadiazol-5(4H)-one

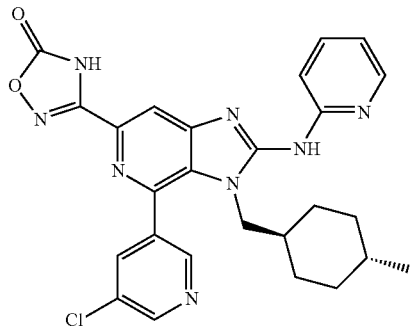 [SMILES: C[C@H]1CC[C@H](Cn2c(Nc3ccccn3)nc3cc(-c4noc(=O)[nH]4)nc(-c4cncc(Cl)c4)c32)CC1]

Step 1: To a solution of 2-bromo-4-(5-chloropyridin-3-yl)-3-((trans-4-methylcyclohexyl)methyl)-3H-imidazo[4,5-c]pyridine-6-carbonitrile (Preparative Example 3.1) (0.5 g, 1.128 mmol) in toluene (5 mL) in a pyrex tube, 2-aminopyridine (0.127 g, 1.35 mmol), and BINAP (35 mg, 0.056 mmol) were added, and the reaction mixture was degassed with argon for 5 minutes. Pd$_2$(dba)$_3$ (51 mg, 0.056 mmol) and potassium tert-butoxide (0.189 g, 1.69 mmol) were added, and the tube was capped and heated to 100° C. for 17 h. The reaction mixture was cooled to room temperature, and the solvent was removed under reduced pressure. The residue was dissolved in ethyl acetate (20 mL), washed with water (5 mL) and brine (5 mL), dried over anhydrous Na$_2$SO$_4$, filtered, and concentrated under reduced pressure. The residue was purified on a silica gel column using 40% ethyl acetate/petroleum ether as eluent to give 4-(5-chloropyridin-3-yl)-3-[(trans-4-methylcyclohexyl)methyl]-2-(pyridin-2-ylamino)-3H-imidazo[4,5-c]pyridine-6-carbonitrile. MS ES/APCl calc'd. for $C_{25}H_{24}ClN_7$ [M+H]$^+$ 458. found 458.

Steps 2 & 3: Using procedures analogous to those described in Example 3.1 (Steps 2 and 3), 4-(5-chloropyridin-3-yl)-3-[(trans-4-methylcyclohexyl)methyl]-2-(pyridin-2-ylamino)-3H-imidazo[4,5-c]pyridine-6-carbonitrile was converted to 3-[4-(5-chloropyridin-3-yl)-3-[(trans-4-methylcyclohexyl)methyl]-2-(pyridin-2-ylamino)-3H-imidazo[4,5-c]pyridin-6-yl]-1,2,4-oxadiazol-5(4H)-one (TFA salt). $^1$H NMR (400 MHz, CD$_3$OD): δ 8.81 (s, 1H), 8.33 (s, 1H), 8.26 (d, J=4.4 Hz, 1H), 8.20 (t, J=8.8 Hz, 1H), 8.11 (s, 1H), 7.66 (d, J=8.8 Hz, 1H), 7.28-7.11 (m, 2H), 3.92 (d, J=6.4 Hz, 2H), 1.55 (d, J=12.4 Hz, 2H), 1.26-1.04 (m, 4H), 0.97-0.84 (m, 2H), 0.79 (d, J=6.4 Hz, 3H), 0.71-0.55 (m, 2H). MS ES/APCl calc'd. for $C_{26}H_{25}ClN_8O_2$ [M+H]$^+$ 517. found 517.

Example 3.173

4-(5-chloropyridin-3-yl)-3-[(trans-4-methylcyclohexyl)methyl]-2-(pyridin-2-ylamino)-3H-imidazo[4,5-c]pyridine-6-carboxylic acid

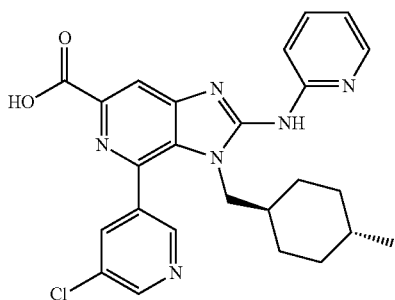 [SMILES: C[C@H]1CC[C@H](Cn2c(Nc3ccccn3)nc3cc(C(=O)O)nc(-c4cncc(Cl)c4)c32)CC1]

4-(5-chloropyridin-3-yl)-3-[(trans-4-methylcyclohexyl)methyl]-2-(pyridin-2-ylamino)-3H-imidazo[4,5-c]pyridine-6-carbonitrile (Example 3.172, Step 1) (60 mg, 0.131 mmol) was placed in a pyrex tube, and conc. HCl (2 mL) was added. The tube was capped and heated to 80° C. for 2 h. The reaction mixture was concentrated and the residue obtained was purified by reverse phase prep-HPLC (Kromasil C18, water/acetonitrile+0.1% TFA) to give 4-(5-chloropyridin-3-yl)-3-[(trans-4-methylcyclohexyl)methyl]-2-(pyridin-2-ylamino)-3H-imidazo[4,5-c]pyridine-6-carboxylic acid (TFA salt). $^1$H NMR (400 MHz, CDCl$_3$): δ 8.83 (s, 1H), 8.82 (s, 1H), 8.74 (s, 1H), 8.51 (s, 1H), 8.26-8.22 (m, 2H), 7.99 (s, 1H), 7.33-7.32 (m, 1H), 4.07 (d, J=6.4 Hz, 2H), 1.52 (d, J=12.1 Hz, 2H), 1.20-1.09 (m, 2H), 0.94-0.80 (m, 4H), 0.77 (d, J=6.5 Hz, 3H), 0.62-0.56 (m, 2H). MS ES/APCl calc'd. for $C_{25}H_{25}ClN_6O_2$ [M+H]$^+$ 477. found 477.

Example 3.174

3-{4-(5-chloropyridin-3-yl)-3-[(trans-4-methylcyclohexyl)methyl]-2-[methyl(phenyl)amino]-3H-imidazo[4,5-c]pyridin-6-yl}-1,2,4-oxadiazol-5(4H)-one

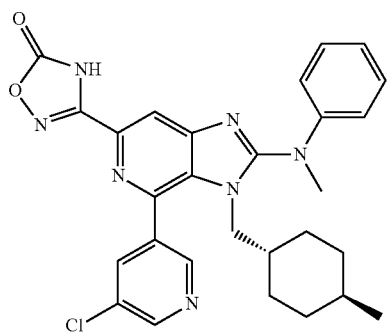 [SMILES: CN(c1ccccc1)c1nc2cc(-c3noc(=O)[nH]3)nc(-c3cncc(Cl)c3)c2n1C[C@H]1CC[C@H](C)CC1]

Step 1: To a solution of 2-bromo-4-(5-chloropyridin-3-yl)-3-((trans-4-methylcyclohexyl)methyl)-3H-imidazo[4,5-c]pyridine-6-carbonitrile (Preparative Example 3.1, 500 mg, 1.35 mmol) in toluene (5 mL), was added aniline (0.13 mL, 1.48 mmol) and chloro[2-(dicyclohexylphosphino)-3,6-dimethoxy-2',4',6'-triisopropyl-1,1'-biphenyl][2-(2-aminoethyl)phenyl]palladium(II) (BrettPhos precatalyst, 107 mg, 0.135 mmol), and the reaction was deoxygenated by purging with nitrogen for 10 minutes. Sodium tert-butoxide (194 mg, 2.02 mmol) in THF (2 mL) was added, and the reaction was again purged with nitrogen for 5 minutes. The reaction flask was sealed, and the mixture was stirred at room temperature for 2 hours. The reaction mixture was diluted with EtOAc (100 mL) and the layers were separated. The organic layer was washed with water (2×25 mL) followed by saturated brine solution (25 mL). The organic layer was dried over anhydrous Na$_2$SO$_4$ and concentrated. The crude product was purified on a silica gel column (30% EtOAc/petroleum ether) to afford 4-(5-chloropyridin-3-yl)-3-[(trans-4-methylcyclohexyl)methyl]-2-(phenylamino)-3H-imidazo[4,5-c]pyridine-6-carbonitrile. MS ES/APCl calc'd. for $C_{26}H_{25}ClN_6$ [M+H]$^+$ 457. found 457.

Step 2: DMF (4 mL) was added to a vial containing 4-(5-chloropyridin-3-yl)-3-[(trans-4-methylcyclohexyl)methyl]-2-(phenylamino)-3H-imidazo[4,5-c]pyridine-6-carbonitrile (200 mg, 0.438 mmol), followed by methyl iodide (68 mg, 0.481 mmol) and potassium carbonate (121 mg, 0.877 mmol), and the vial was sealed and heated to 60° C. for 2 hours. The reaction mixture was cooled to room temperature, diluted with ethyl acetate, and washed with water and brine. The organic layer was dried over anhydrous sodium sulfate, filtered, and concentrated under reduced pressure. The residue was purified by silica gel column chromatography using 15% ethyl acetate/petroleum ether as eluent to afford 4-(5-chloropyridin-3-yl)-3-[(trans-4-methylcyclohexyl)methyl]-2-[methyl(phenyl)amino]-3H-imidazo[4,5-c]pyridine-6-carbonitrile. MS ES/APCl calc'd. for $C_{27}H_{27}ClN_6$ [M+H]$^+$ 471. found 471.

Step 3 & 4: Using procedures similar to those described in Example 3.1 (Steps 2 and 3), 4-(5-chloropyridin-3-yl)-3-[(trans-4-methylcyclohexyl)methyl]-2-[methyl(phenyl)amino]-3H-imidazo[4,5-c]pyridine-6-carbonitrile was converted to 3-{4-(5-chloropyridin-3-yl)-3-[(trans-4-methylcyclohexyl)methyl]-2-[methyl(phenyl)amino]-3H-imidazo[4,5-c]pyridin-6-yl}-1,2,4-oxadiazol-5(4H)-one (TFA salt). MS ES/APCl calc'd. for $C_{28}H_{28}ClN_7O_2$ [M+H]$^+$ 530. found 530. $^1$H NMR (400 MHz, DMSO-d$_6$): δ 12.95 (s, 1H), 8.82 (d, J=3.5 Hz, 2H), 8.40 (bs, 1H), 7.96 (s, 1H), 7.35 (t, J=7.1 Hz, 2H), 7.10-7.00 (m, 3H), 3.45 (s, 2H), 3.35 (bs, 3H), 1.42-1.40 (m, 2H), 1.02-0.97 (m, 2H), 0.85-0.83 (m, 2H), 0.70 (d, J=6.4 Hz, 3H), 0.59-0.53 (m, 4H).

Example 3.175

4-(5-chloropyridin-3-yl)-3-[(trans-4-methylcyclohexyl)methyl]-2-[methyl(phenyl)amino]-3H-imidazo[4,5-c]pyridine-6-carboxylic acid

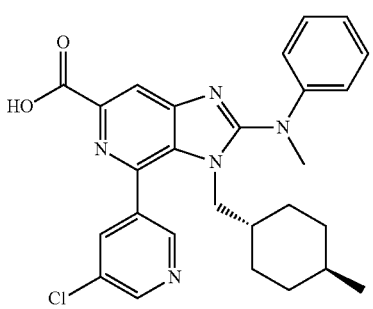 [SMILES: CN(c1ccccc1)c1nc2cc(C(=O)O)nc(-c3cncc(Cl)c3)c2n1C[C@H]1CC[C@H](C)CC1]

To a solution of 4-(5-chloropyridin-3-yl)-3-[(trans-4-methyl-cyclohexyl)methyl]-2-[methyl(phenyl)amino]-3H-imidazo[4,5-c]pyridine-6-carbonitrile (Example 3.174 step 2, 160 mg, 0.339 mmol) in methanol (2 mL) in a sealable tube was added 30% sodium hydroxide solution (4 mL). The tube was sealed and heated to 80° C. for 14 hours. The reaction mixture was cooled to room temperature and neutralized with the addition of 1.5 M HCl solution. The solution was extracted with ethyl acetate (4×25 mL). The organic layer was dried over sodium sulfate, filtered, and concentrated under reduced pressure. The residue was purified by preparative HPLC (Kromasil C18, water/acetonitrile+0.1% TFA modifier) to afford 4-(5-chloropyridin-3-yl)-3-[(trans-4-methylcyclohexyl)methyl]-2-[methyl(phenyl)amino]-3H-imidazo[4,5-c]pyridine-6-carboxylic acid (TFA salt). MS ES/APCl calc'd. for $C_{27}H_{28}ClN_6O_2$ [M+H]$^+$ 490. found 490. $^1$H NMR (400 MHz, DMSO-d$_6$): δ 12.79 (bs, 1H), 8.78 (d, J=12.8 Hz, 2H), 8.30 (s, 1H), 7.82 (s, 1H), 7.26 (t, J=7.6 Hz, 2H), 6.96-6.87 (m, 3H), 3.40-3.30 (m, 2H), 3.21 (s, 3H), 1.46-1.42 (m, 2H), 1.26-1.01 (m, 4H), 0.86-0.84 (m, 3H), 0.73-0.71 (m, 4H).

The compounds in Table 3 were prepared as described above or using procedures which were analogous to those described above. In some cases, enantiomers or diastereomers were separated by chromatography on chiral columns using standard techniques. Amines used to displace the bromide of Preparative Example 3.1 are described above, commercially available, known in the literature, or can be prepared using methods readily available in the literature.

TABLE 3

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.1 | 1 | 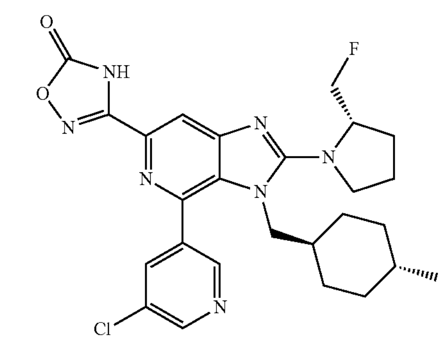 [SMILES: C[C@H]1CC[C@H](Cn2c(N3CCC[C@H]3CF)nc3cc(-c4noc(=O)[nH]4)nc(-c4cncc(Cl)c4)c32)CC1] | 3-{4-(5-chloropyridin-3-yl)-2-[(2S)-2-(fluoromethyl)-pyrrolidin-1-yl]-3-[(trans-4-methylcyclohexyl)methyl]-3H-imidazo[4,5-c]pyridin-6-yl}-1,2,4-oxadiazol-5(4H)-one | | 526 | 526 |
| 3.2 | 1 | 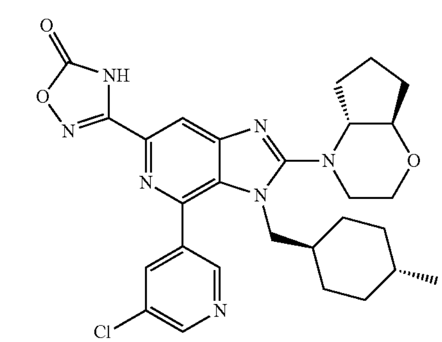 [SMILES: C[C@H]1CC[C@H](Cn2c(N3CCO[C@@H]4CCC[C@H]43)nc3cc(-c4noc(=O)[nH]4)nc(-c4cncc(Cl)c4)c32)CC1] | 3-{4-(5-chloropyridin-3-yl)-2-((4aR,7aR)-hexahydrocyclopenta[b][1,4]-oxazin-4(4aH)-yl)-3-[(trans-4-methylcyclohexyl)methyl]-3H-imidazo[4,5-c]pyridin-6-yl}-1,2,4-oxadiazol-5(4H)-one | | 550 | 550 |
| 3.3 | 1 | 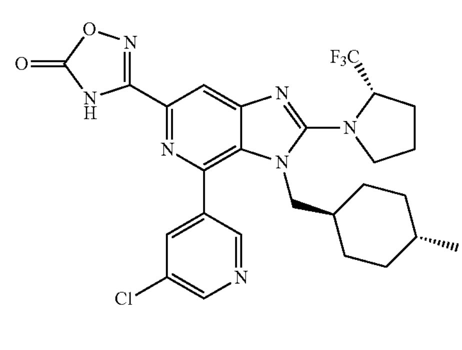 [SMILES: C[C@H]1CC[C@H](Cn2c(N3CCC[C@H]3C(F)(F)F)nc3cc(-c4noc(=O)[nH]4)nc(-c4cncc(Cl)c4)c32)CC1] | 3-(4-(5-chloropyridin-3-yl)-3-((trans-4-methylcyclohexyl)methyl)-2-((S)-2-(trifluoromethyl)pyrrolidin-1-yl)-3H-imidazo[4,5-c]pyridin-6-yl)-1,2,4-oxadiazol-5(4H)-one | | 562 | 562 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.4 | 2 | 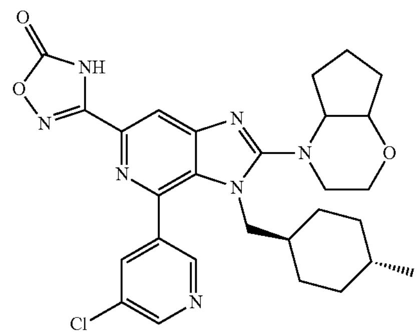 [SMILES: C[C@H]1CC[C@H](Cn2c(N3CCOC4CCCC43)nc3cc(-c4noc(=O)[nH]4)nc(-c4cncc(Cl)c4)c32)CC1] | 3-{4-(5-chloropyridin-3-yl)-2-(hexahydrocyclopenta[b][1,4]-oxazin-4(4aH)-yl)-3-[(trans-4-methylcyclohex-yl)methyl]-3H-imidazo[4,5-c]pyridin-6-yl}-1,2,4-oxadiazol-5(4H)-one (racemic) | | 550 | 550 |
| 3.5 | 4 | 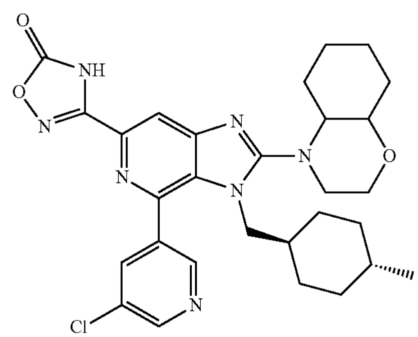 [SMILES: C[C@H]1CC[C@H](Cn2c(N3CCOC4CCCCC43)nc3cc(-c4noc(=O)[nH]4)nc(-c4cncc(Cl)c4)c32)CC1] | 3-[4-(5-chloropyridin-3-yl)-3-[(trans-4-methylcyclohex-yl)methyl]-2-(octahydro-4H-1,4-benzoxazin-4-yl)-3H-imidazo[4,5-c]pyridin-6-yl]-1,2,4-oxadiazol-5(4H)-one (racemic) | | 564 | 564 |
| 3.6 | 4 | 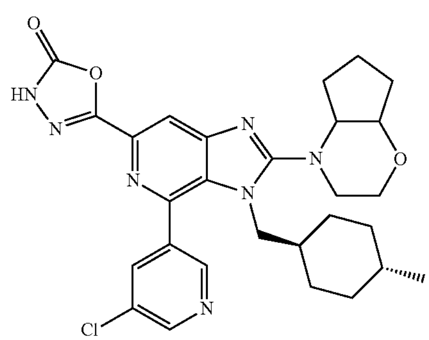 [SMILES: C[C@H]1CC[C@H](Cn2c(N3CCOC4CCCC43)nc3cc(-c4n[nH]c(=O)o4)nc(-c4cncc(Cl)c4)c32)CC1] | 5-{4-(5-chloropyridin-3-yl)-2-(hexahydrocyclopenta[b][1,4]-oxazin-4(4aH)-yl)-3-[(trans-4-methylcyclohex-yl)methyl]-3H-imidazo[4,5-c]pyridin-6-yl}-1,3,4-oxadiazol-2(3H)-one (racemic) | TFA | 550 | 550 |
| 3.7 | 1 | 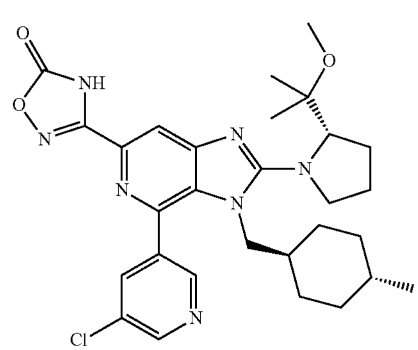 [SMILES: COC(C)(C)[C@@H]1CCCN1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(2S)-2-(1-methoxy-1-methylethyl)-pyrrolidin-1-yl]-3-[(trans-4-methylcyclohex-yl)methyl]-3H-imidazo[4,5-c]pyridin-6-yl}-1,2,4-oxadiazol-5(4H)-one | TFA | 566 | 566 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.8 | 4 | 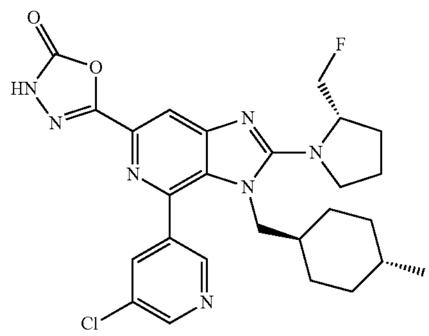 [SMILES: C[C@H]1CC[C@H](Cn2c(N3CCC[C@H]3CF)nc3cc(-c4n[nH]c(=O)o4)nc(-c4cncc(Cl)c4)c32)CC1] | 5-{4-(5-chloropyridin-3-yl)-2-[(2S)-2-(fluoromethyl)-pyrrolidin-1-yl]-3-[(trans-4-methylcyclohex-yl)methyl]-3H-imidazo[4,5-c]pyridin-6-yl}-1,3,4-oxadiazol-2(3H)-one | TFA | 526 | 526 |
| 3.9 | 59 | 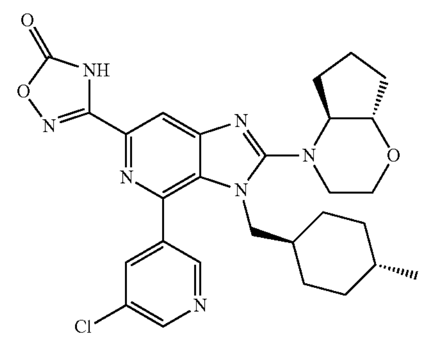 [SMILES: C[C@H]1CC[C@H](Cn2c(N3CCO[C@H]4CCC[C@@H]43)nc3cc(-c4noc(=O)[nH]4)nc(-c4cncc(Cl)c4)c32)CC1] | 3-{4-(5-chloropyridin-3-yl)-2-((4aS,7aS)-hexahydrocyclo-penta[b][1,4]-oxazin-4(4aH)-yl)-3-[(trans-4-methylcyclohex-yl)methyl]-3H-imidazo[4,5-c]pyridin-6-yl}-1,2,4-oxadiazol-5(4H)-one | | 550 | 550 |
| 3.10 | 1 | 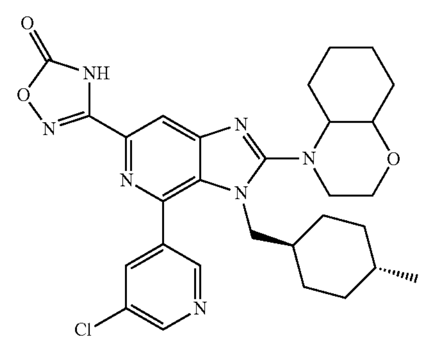 [SMILES: C[C@H]1CC[C@H](Cn2c(N3CCOC4CCCCC43)nc3cc(-c4noc(=O)[nH]4)nc(-c4cncc(Cl)c4)c32)CC1] | 3-[4-(5-chloropyridin-3-yl)-3-[(trans-4-methylcyclohex-yl)methyl]-2-(octahydro-4H-1,4-benzoxazin-4-yl)-3H-imidazo[4,5-c]pyridin-6-yl]-1,2,4-oxadiazol-5(4H)-one (enantiomer 1) | | 564 | 564 |
| 3.11 | 17 | 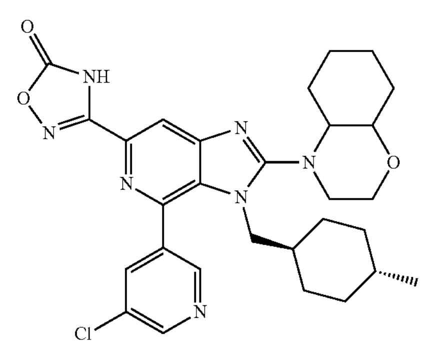 [SMILES: C[C@H]1CC[C@H](Cn2c(N3CCOC4CCCCC43)nc3cc(-c4noc(=O)[nH]4)nc(-c4cncc(Cl)c4)c32)CC1] | 3-[4-(5-chloropyridin-3-yl)-3-[(trans-4-methylcyclohex-yl)methyl]-2-(octahydro-4H-1,4-benzoxazin-4-yl)-3H-imidazo[4,5-c]pyridin-6-yl]-1,2,4-oxadiazol-5(4H)-one (enantiomer 2) | | 564 | 564 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.12 | 7 | 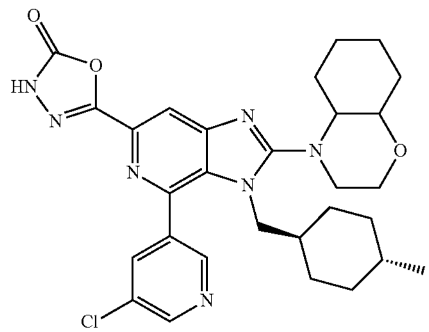 [SMILES: C[C@H]1CC[C@H](Cn2c(N3CCOC4CCCCC43)nc3cc(-c4n[nH]c(=O)o4)nc(-c4cncc(Cl)c4)c32)CC1] | 5-[4-(5-chloropyridin-3-yl)-3-[(trans-4-methylcyclohex-yl)methyl]-2-(octahydro-4H-1,4-benzoxazin-4-yl)-3H-imidazo[4,5-c]pyridin-6-yl]-1,3,4-oxadiazol-2(3H)-one (racemic) | TFA | 564 | 564 |
| 3.13 | 2 | 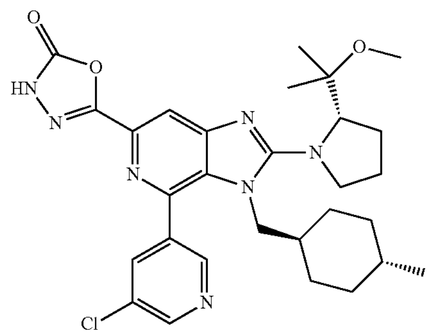 [SMILES: COC(C)(C)[C@@H]1CCCN1c1nc2cc(-c3n[nH]c(=O)o3)nc(-c3cncc(Cl)c3)c2n1C[C@H]1CC[C@H](C)CC1] | 5-{4-(5-chloropyridin-3-yl)-2-[(2S)-2-(1-methoxy-1-methylethyl)-pyrrolidin-1-yl]-3-[(trans-4-methylcyclohex-yl)methyl]-3H-imidazo[4,5-c]pyridin-6-yl}-1,3,4-oxadiazol-2(3H)-one | TFA | 566 | 566 |
| 3.14 | 164 | 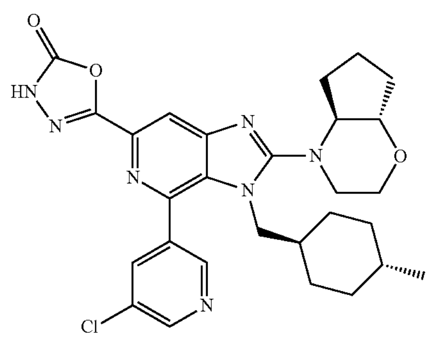 [SMILES: C[C@H]1CC[C@H](Cn2c(N3CCO[C@H]4CCC[C@@H]43)nc3cc(-c4n[nH]c(=O)o4)nc(-c4cncc(Cl)c4)c32)CC1] | 5-{4-(5-chloropyridin-3-yl)-2-((4aS,7aS)-hexahydrocyclo-penta[b][1,4]-oxazin-4(4aH)-yl)-3-[(trans-4-methylcyclohex-yl)methyl]-3H-imidazo[4,5-c]pyridin-6-yl}-1,3,4-oxadiazol-2(3H)-one | | 550 | 550 |
| 3.15 | 2 | 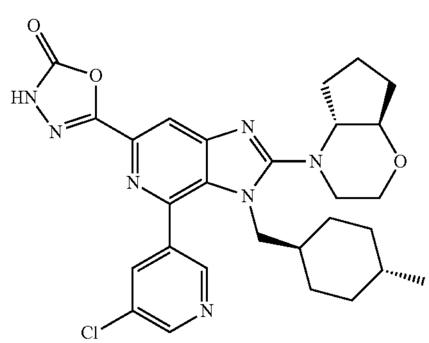 [SMILES: C[C@H]1CC[C@H](Cn2c(N3CCO[C@@H]4CCC[C@H]43)nc3cc(-c4n[nH]c(=O)o4)nc(-c4cncc(Cl)c4)c32)CC1] | 5-{4-(5-chloropyridin-3-yl)-2-((4aR,7aR)-hexahydrocyclo-penta[b][1,4]-oxazin-4(4aH)-yl)-3-[(trans-4-methylcyclohex-yl)methyl]-3H-imidazo[4,5-c]pyridin-6-yl}-1,3,4-oxadiazol-2(3H)-one | | 550 | 550 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.16 | 2 | 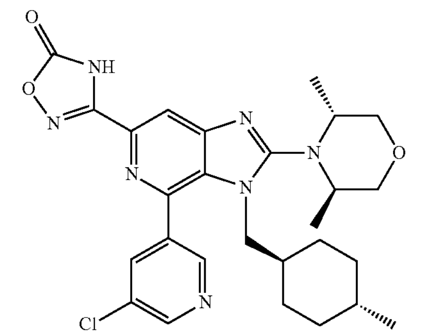 [SMILES: C[C@@H]1COC[C@@H](C)N1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(3R,5R)-3,5-dimethyl-morpholin-4-yl]-3-[(trans-4-methylcyclohex-yl)methyl]-3H-imidazo[4,5-c]pyridin-6-yl}-1,2,4-oxadiazol-5(4H)-one | | 538 | 538 |
| 3.18 | 62 | 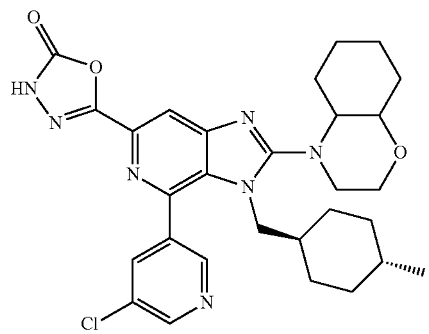 [SMILES: C[C@H]1CC[C@H](Cn2c(N3CCOC4CCCCC43)nc3cc(-c4n[nH]c(=O)o4)nc(-c4cncc(Cl)c4)c32)CC1] | 5-[4-(5-chloropyridin-3-yl)-3-[(trans-4-methylcyclohex-yl)methyl]-2-(octahydro-4H-1,4-benzoxazin-4-yl)-3H-imidazo[4,5-c]pyridin-6-yl]-1,3,4-oxadiazol-2(3H)-one (enantiomer 1) | | 564 | 564 |
| 3.19 | 4 | 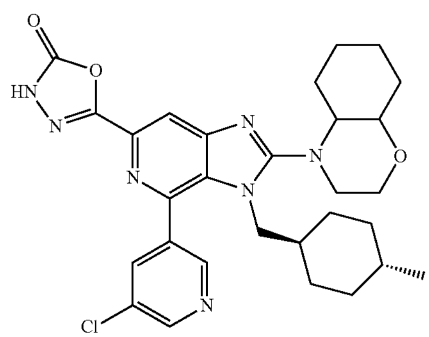 [SMILES: C[C@H]1CC[C@H](Cn2c(N3CCOC4CCCCC43)nc3cc(-c4n[nH]c(=O)o4)nc(-c4cncc(Cl)c4)c32)CC1] | 5-[4-(5-chloropyridin-3-yl)-3-[(trans-4-methylcyclohex-yl)methyl]-2-(octahydro-4H-1,4-benzoxazin-4-yl)-3H-imidazo[4,5-c]pyridin-6-yl]-1,3,4-oxadiazol-2(3H)-one (enantiomer 2) | | 564 | 564 |
| 3.20 | 7 | 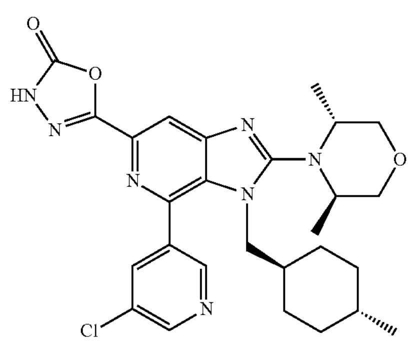 [SMILES: C[C@@H]1COC[C@@H](C)N1c1nc2cc(-c3n[nH]c(=O)o3)nc(-c3cncc(Cl)c3)c2n1C[C@H]1CC[C@H](C)CC1] | 5-{4-(5-chloropyridin-3-yl)-2-[(3R,5R)-3,5-dimethyl-morpholin-4-yl]-3-[(trans-4-methylcyclohex-yl)methyl]-3H-imidazo[4,5-c]pyridin-6-yl}-1,3,4-oxadiazol-2(3H)-one | TFA | 538 | 538 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.21 | 2 | 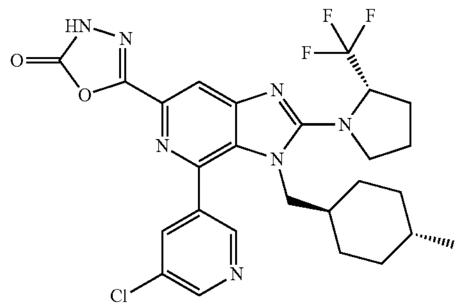 [SMILES: C[C@H]1CC[C@H](Cn2c(N3CCC[C@H]3C(F)(F)F)nc3cc(-c4n[nH]c(=O)o4)nc(-c4cncc(Cl)c4)c32)CC1] | 5-{4-(5-chloropyridin-3-yl)-3-[(trans-4-methylcyclohex-yl)methyl]-2-[(2S)-2-(trifluoromethyl)pyrrolidin-1-yl]-3H-imidazo[4,5-c]pyridin-6-yl}-1,3,4-oxadiazol-2(3H)-one | TFA | 562 | 562 |
| 3.22 | 1 | 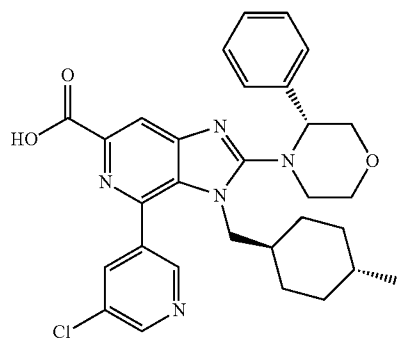 [SMILES: C[C@H]1CC[C@H](Cn2c(N3CCOC[C@H]3c3ccccc3)nc3cc(C(=O)O)nc(-c4cncc(Cl)c4)c32)CC1] | 4-(5-chloropyridin-3-yl)-3-[(trans-4-methylcyclohex-yl)methyl]-2-[(3R)-3-phenylmorpholin-4-yl]-3H-imidazo[4,5-c]pyridine-6-carboxylic acid | TFA | 546 | 546 |
| 3.23 | 4 | 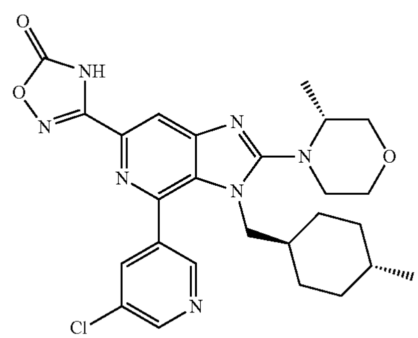 [SMILES: C[C@@H]1COCCN1c1nc2cc(-c3noc(=O)[nH]3)nc(-c3cncc(Cl)c3)c2n1C[C@H]1CC[C@H](C)CC1] | 3-{4-(5-chloropyridin-3-yl)-3-[(trans-4-methylcyclohex-yl)methyl]-2-[(3R)-3-methylmorpholin-4-yl]-3H-imidazo[4,5-c]pyridin-6-yl}-1,2,4-oxadiazol-5(4H)-one | TFA | 524 | 524 |
| 3.24 | 157 | 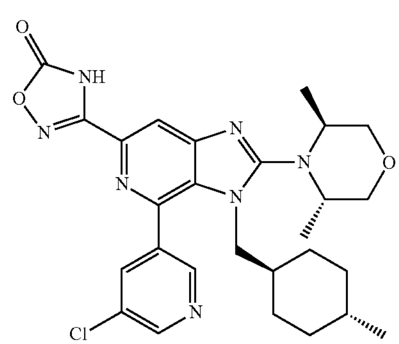 [SMILES: C[C@H]1COC[C@H](C)N1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(3S,5S)-3,5-dimethyl-morpholin-4-yl]-3-[(trans-4-methylcyclohex-yl)methyl]-3H-imidazo[4,5-c]pyridin-6-yl}-1,2,4-oxadiazol-5(4H)-one | TFA | 538 | 538 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.26 | 2 | 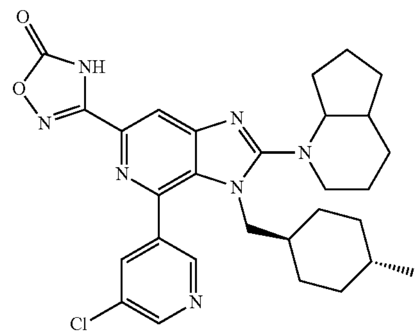 | 3-[4-(5-chloropyridin-3-yl)-3-[(trans-4-methylcyclohex-yl)methyl]-2-(octahydro-1H-cyclopenta[b]-pyridin-1-yl)-3H-imidazo[4,5-c]pyridin-6-yl]-1,2,4-oxadiazol-5(4H)-one (mixture of stereoisomers) | | 548 | 548 |
| 3.27 | 2 | 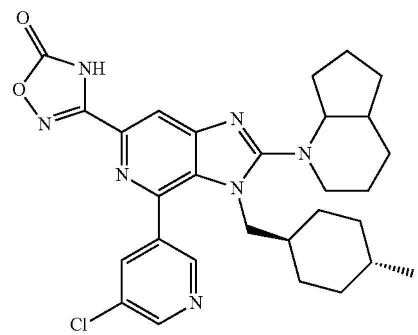 [SMILES: C[C@H]1CC[C@H](Cn2c(N3CCCC4CCCC43)nc3cc(-c4noc(=O)[nH]4)nc(-c4cncc(Cl)c4)c32)CC1] | 3-[4-(5-chloropyridin-3-yl)-3-[(trans-4-methylcyclohex-yl)methyl]-2-(octahydro-1H-cyclopenta[b]-pyridin-1-yl)-3H-imidazo[4,5-c]pyridin-6-yl]-1,2,4-oxadiazol-5(4H)-one (stereoisomer 1) | | 548 | 548 |
| 3.28 | 63 | 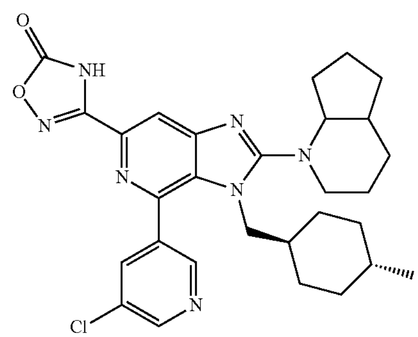 | 3-[4-(5-chloropyridin-3-yl)-3-[(trans-4-methylcyclohex-yl)methyl]-2-(octahydro-1H-cyclopenta[b]-pyridin-1-yl)-3H-imidazo[4,5-c]pyridin-6-yl]-1,2,4-oxadiazol-5(4H)-one (stereoisomer 2) | | 548 | 548 |
| 3.29 | 58 | 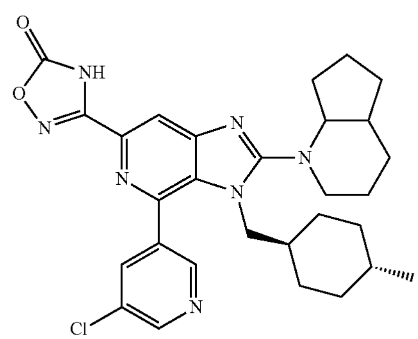 | 3-[4-(5-chloropyridin-3-yl)-3-[(trans-4-methylcyclohex-yl)methyl]-2-(octahydro-1H-cyclopenta[b]-pyridin-1-yl)-3H-imidazo[4,5-c]pyridin-6-yl]-1,2,4-oxadiazol-5(4H)-one (stereoisomer 3) | | 548 | 548 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.30 | 1 | 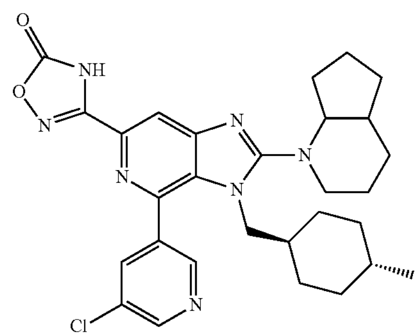 | 3-[4-(5-chloropyridin-3-yl)-3-[(trans-4-methylcyclohex-yl)methyl]-2-(octahydro-1H-cyclopenta[b]-pyridin-1-yl)-3H-imidazo[4,5-c]pyridin-6-yl]-1,2,4-oxadiazol-5(4H)-one (stereoisomer 4) | | 548 | 548 |
| 3.31 | 32 | 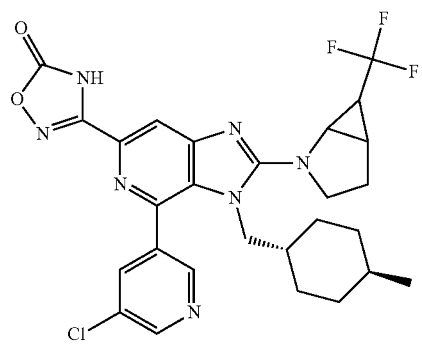 [SMILES: C[C@H]1CC[C@H](Cn2c(N3CCC4C3C4C(F)(F)F)nc3cc(-c4noc(=O)[nH]4)nc(-c4cncc(Cl)c4)c32)CC1] | 3-{4-(5-chloropyridin-3-yl)-3-[(trans-4-methylcyclohex-yl)methyl]-2-[6-(trifluoromethyl)-2-azabicyclo[3.1.0]-hex-2-yl]-3H-imidazo[4,5-c]pyridin-6-yl}-1,2,4-oxadiazol-5(4H)-one | TFA | 574 | 574 |
| 3.32 | 3 | 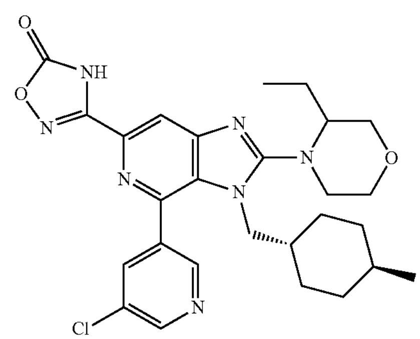 [SMILES: CCC1COCCN1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-(3-ethylmorpholin-4-yl)-3-[(trans-4-methylcyclohex-yl)methyl]-3H-imidazo[4,5-c]pyridin-6-yl}-1,2,4-oxadiazol-5(4H)-one | TFA | 538 | 538 |
| 3.33 | 43 | 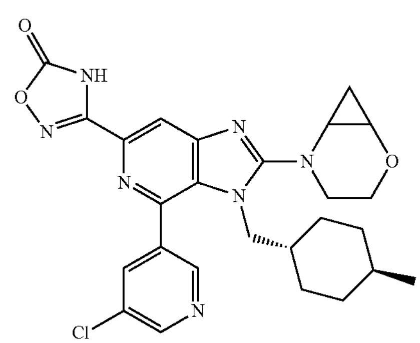 [SMILES: C[C@H]1CC[C@H](Cn2c(N3CCOC4CC43)nc3cc(-c4noc(=O)[nH]4)nc(-c4cncc(Cl)c4)c32)CC1] | 3-[4-(5-chloropyridin-3-yl)-3-[(trans-4-methylcyclohex-yl)methyl]-2-(2-oxa-5-azabicyclo[4.1.0]-hept-5-yl)-3H-imidazo[4,5-c]pyridin-6-yl]-1,2,4-oxadiazol-5(4H)-one | TFA | 522 | 522 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.34 | 156 | 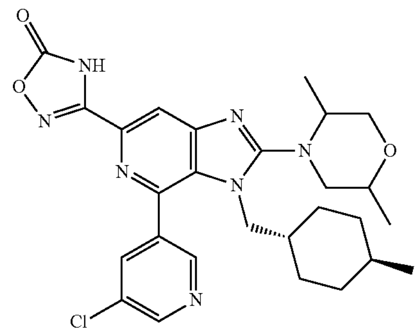 [SMILES: CC1CN(c2nc3cc(-c4noc(=O)[nH]4)nc(-c4cncc(Cl)c4)c3n2C[C@H]2CC[C@H](C)CC2)C(C)CO1] | 3-{4-(5-chloropyridin-3-yl)-2-(2,5-dimethylmorpholin-4-yl)-3-[(trans-4-methylcyclohex-yl)methyl]-3H-imidazo[4,5-c]pyridin-6-yl}-1,2,4-oxadiazol-5(4H)-one (diastereoisomer 1) | TFA | 538 | 538 |
| 3.35 | 16 | 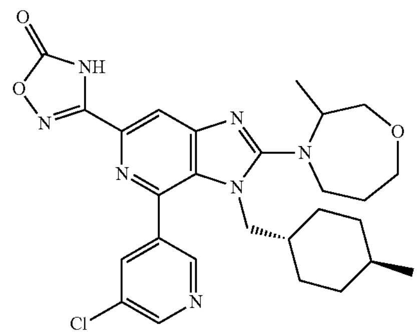 [SMILES: CC1COCCCN1c1nc2cc(-c3noc(=O)[nH]3)nc(-c3cncc(Cl)c3)c2n1C[C@H]1CC[C@H](C)CC1] | 3-[4-(5-chloropyridin-3-yl)-3-[(trans-4-methylcyclohex-yl)methyl]-2-(3-methyl-1,4-oxazepan-4-yl)-3H-imidazo[4,5-c]pyridin-6-yl]-1,2,4-oxadiazol-5(4H)-one | TFA | 538 | 538 |
| 3.36 | 1 | 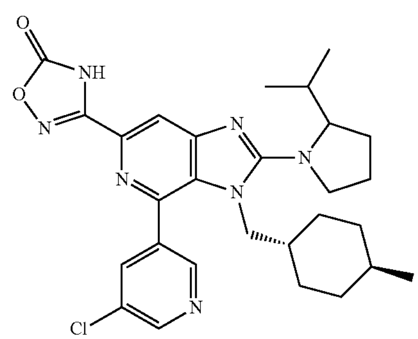 [SMILES: CC(C)C1CCCN1c1nc2cc(-c3noc(=O)[nH]3)nc(-c3cncc(Cl)c3)c2n1C[C@H]1CC[C@H](C)CC1] | 3-{4-(5-chloropyridin-3-yl)-3-[(trans-4-methylcyclohex-yl)methyl]-2-[2-(1-methylethyl)-pyrrolidin-1-yl]-3H-imidazo[4,5-c]pyridin-6-yl}-1,2,4-oxadiazol-5(4H)-one | TFA | 536 | 536 |
| 3.37 | 2 | 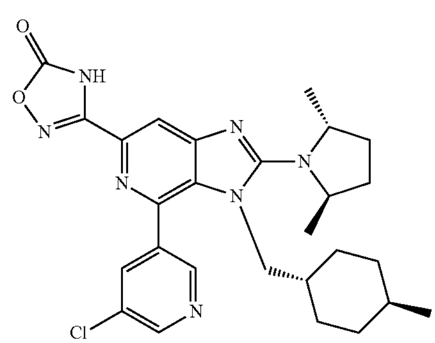 [SMILES: C[C@@H]1CC[C@@H](C)N1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(2R,5R)-2,5-dimethylpyrrolidin-1-yl]-3-[(trans-4-methylcyclohex-yl)methyl]-3H-imidazo[4,5-c]pyridin-6-yl}-1,2,4-oxadiazol-5(4H)-one | TFA | 522 | 522 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.38 | 20 | 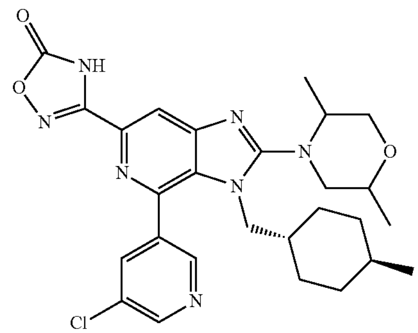 [SMILES: CC1CN(c2nc3cc(-c4noc(=O)[nH]4)nc(-c4cncc(Cl)c4)c3n2C[C@H]2CC[C@H](C)CC2)C(C)CO1] | 3-{4-(5-chloropyridin-3-yl)-2-(2,5-dimethylmorpholin-4-yl)-3-[(trans-4-methylcyclohexyl)methyl]-3H-imidazo[4,5-c]pyridin-6-yl}-1,2,4-oxadiazol-5(4H)-one (diastereoisomer 2) | TFA | 538 | 538 |
| 3.39 | 1 | 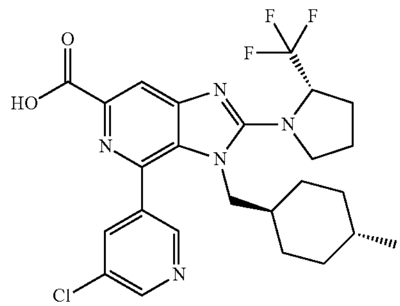 [SMILES: C[C@H]1CC[C@H](Cn2c(N3CCC[C@H]3C(F)(F)F)nc3cc(C(=O)O)nc(-c4cncc(Cl)c4)c32)CC1] | 4-(5-chloropyridin-3-yl)-3-[(trans-4-methylcyclohexyl)methyl]-2-[(2S)-2-(trifluoromethyl)pyrrolidin-1-yl]-3H-imidazo[4,5-c]pyridine-6-carboxylic acid | TFA | 522 | 522 |
| 3.40 | 1 | 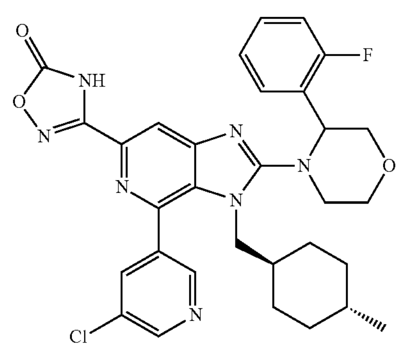 [SMILES: C[C@H]1CC[C@H](Cn2c(N3CCOCC3c3ccccc3F)nc3cc(-c4noc(=O)[nH]4)nc(-c4cncc(Cl)c4)c32)CC1] | 3-{4-(5-chloropyridin-3-yl)-2-[3-(2-fluorophenyl)-morpholin-4-yl]-3-[(trans-4-methylcyclohexyl)methyl]-3H-imidazo[4,5-c]pyridin-6-yl}-1,2,4-oxadiazol-5(4H)-one (racemic) | | 604 | 604 |
| 3.41 | 961 | 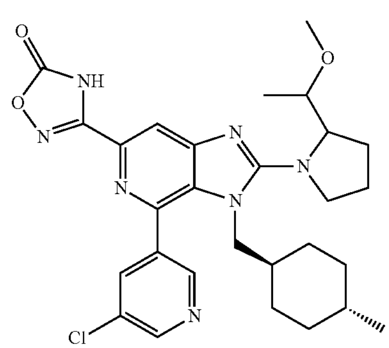 [SMILES: COC(C)C1CCCN1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[2-(1-methoxyethyl)-pyrrolidin-1-yl]-3-[(trans-4-methylcyclohexyl)methyl]-3H-imidazo[4,5-c]pyridin-6-yl}-1,2,4-oxadiazol-5(4H)-one (stereoisomer 1) | TFA | 552 | 552 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.42 | 3 | 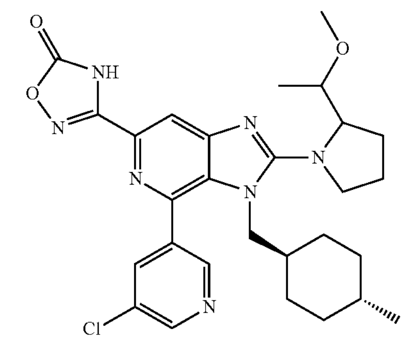 [SMILES: COC(C)C1CCCN1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[2-(1-methoxyethyl)-pyrrolidin-1-yl]-3-[(trans-4-methylcyclohex-yl)methyl]-3H-imidazo[4,5-c]pyridin-6-yl}-1,2,4-oxadiazol-5(4H)-one (stereoisomer 2) | TFA | 552 | 552 |
| 3.43 | <1 | 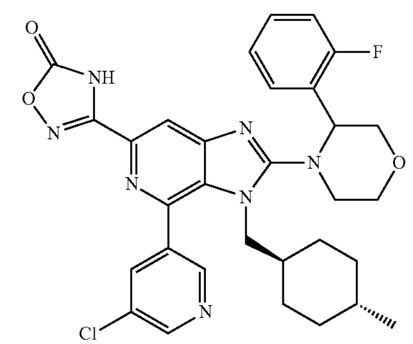 [SMILES: C[C@H]1CC[C@H](Cn2c(N3CCOCC3c3ccccc3F)nc3cc(-c4noc(=O)[nH]4)nc(-c4cncc(Cl)c4)c32)CC1] | 3-{4-(5-chloropyridin-3-yl)-2-[3-(2-fluorophenyl)-morpholin-4-yl]-3-[(trans-4-methylcyclohex-yl)methyl]-3H-imidazo[4,5-c]pyridin-6-yl}-1,2,4-oxadiazol-5(4H)-one (enantiomer 1) | | 604 | 604 |
| 3.44 | 8 | 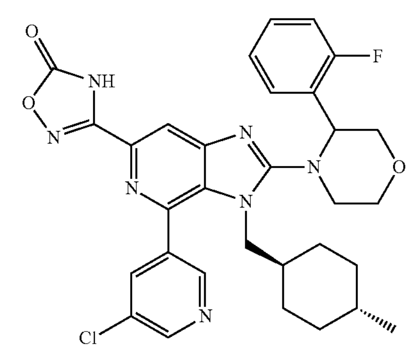 [SMILES: C[C@H]1CC[C@H](Cn2c(N3CCOCC3c3ccccc3F)nc3cc(-c4noc(=O)[nH]4)nc(-c4cncc(Cl)c4)c32)CC1] | 3-{4-(5-chloropyridin-3-yl)-2-[3-(2-fluorophenyl)-morpholin-4-yl]-3-[(trans-4-methylcyclohex-yl)methyl]-3H-imidazo[4,5-c]pyridin-6-yl}-1,2,4-oxadiazol-5(4H)-one (enantiomer 2) | | 604 | 604 |
| 3.45 | 9 | 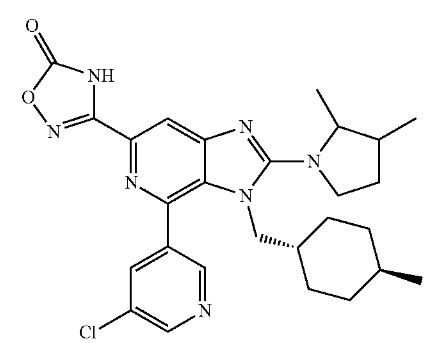 [SMILES: CC1CCN(c2nc3cc(-c4noc(=O)[nH]4)nc(-c4cncc(Cl)c4)c3n2C[C@H]2CC[C@H](C)CC2)C1C] | 3-{4-(5-chloropyridin-3-yl)-2-(2,3-dimethylpyrrolidin-1-yl)-3-[(trans-4-methylcyclohex-yl)methyl]-3H-imidazo[4,5-c]pyridin-6-yl}-1,2,4-oxadiazol-5(4H)-one | TFA | 522 | 522 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.46 | 1 | 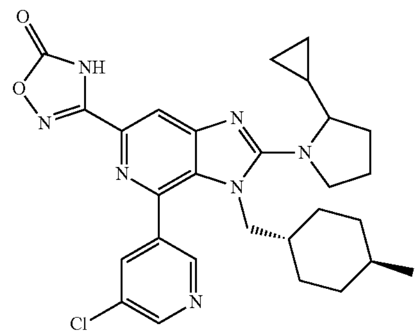 [SMILES: C[C@H]1CC[C@H](Cn2c(N3CCCC3C3CC3)nc3cc(-c4noc(=O)[nH]4)nc(-c4cncc(Cl)c4)c32)CC1] | 3-{4-(5-chloropyridin-3-yl)-2-(2-cyclopropylpyrrolidin-1-yl)-3-[(trans-4-methylcyclohexyl)methyl]-3H-imidazo[4,5-c]pyridin-6-yl}-1,2,4-oxadiazol-5(4H)-one | TFA | 534 | 534 |
| 3.47 | 3 | 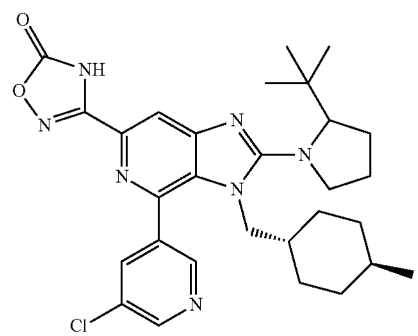 [SMILES: CC(C)(C)C1CCCN1c1nc2cc(-c3noc(=O)[nH]3)nc(-c3cncc(Cl)c3)c2n1C[C@H]1CC[C@H](C)CC1] | 3-{2-(2-tert-butylpyrrolidin-1-yl)-4-(5-chloropyridin-3-yl)-3-[(trans-4-methylcyclohexyl)methyl]-3H-imidazo[4,5-c]pyridin-6-yl}-1,2,4-oxadiazol-5(4H)-one | TFA | 550 | 550 |
| 3.48 | 8 | 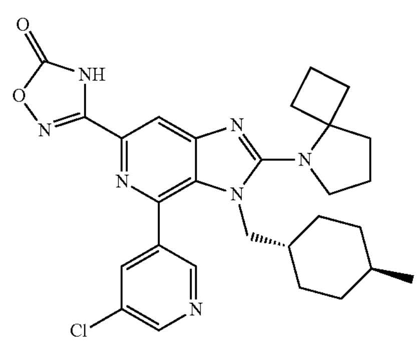 [SMILES: C[C@H]1CC[C@H](Cn2c(N3CCCC34CCC4)nc3cc(-c4noc(=O)[nH]4)nc(-c4cncc(Cl)c4)c32)CC1] | 3-{2-(5-azaspiro[3.4]oct-5-yl)-4-(5-chloropyridin-3-yl)-3-[(trans-4-methylcyclohexyl)methyl]-3H-imidazo[4,5-c]pyridin-6-yl}-1,2,4-oxadiazol-5(4H)-one | TFA | 534 | 534 |
| 3.49 | 2 | 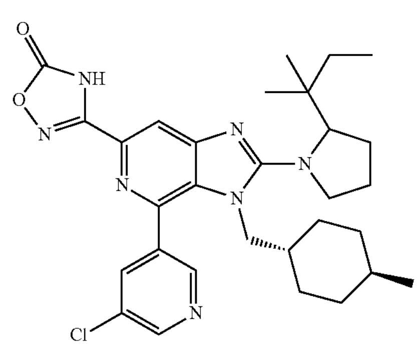 [SMILES: CCC(C)(C)C1CCCN1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[2-(1,1-dimethylpropyl)pyrrolidin-1-yl]-3-[(trans-4-methylcyclohexyl)methyl]-3H-imidazo[4,5-c]pyridin-6-yl}-1,2,4-oxadiazol-5(4H)-one | TFA | 564 | 564 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.50 | 1 | 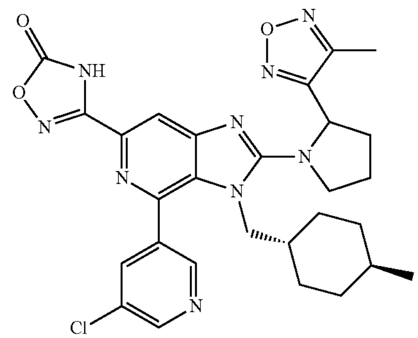 [SMILES: Cc1nonc1C1CCCN1c1nc2cc(-c3noc(=O)[nH]3)nc(-c3cncc(Cl)c3)c2n1C[C@H]1CC[C@H](C)CC1] | 3-{4-(5-chloropyridin-3-yl)-3-[(trans-4-methylcyclohexyl)methyl]-2-[2-(4-methyl-1,2,5-oxadiazol-3-yl)pyrrolidin-1-yl]-3H-imidazo[4,5-c]pyridin-6-yl}-1,2,4-oxadiazol-5(4H)-one | TFA | 576 | 576 |
| 3.51 | 4 | 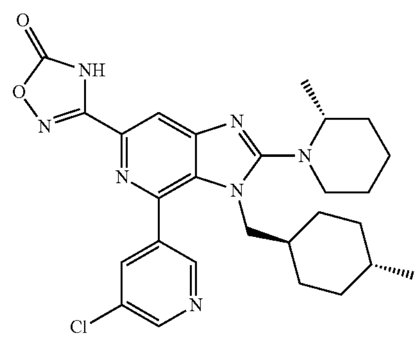 | 3-{4-(5-chloropyridin-3-yl)-3-[(trans-4-methylcyclohexyl)methyl]-2-[(2R)-2-methylpiperidin-1-yl]-3H-imidazo[4,5-c]pyridin-6-yl}-1,2,4-oxadiazol-5(4H)-one | TFA | 522 | 522 |
| 3.52 | 6 | 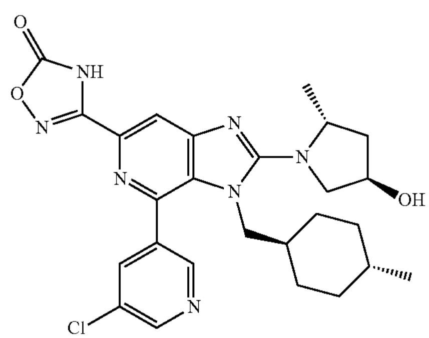 [SMILES: C[C@@H]1C[C@@H](O)CN1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(2R,4R)-4-hydroxy-2-methylpyrrolidin-1-yl]-3-[(trans-4-methylcyclohexyl)methyl]-3H-imidazo[4,5-c]pyridin-6-yl}-1,2,4-oxadiazol-5(4H)-one | TFA | 524 | 524 |
| 3.53 | 1 | 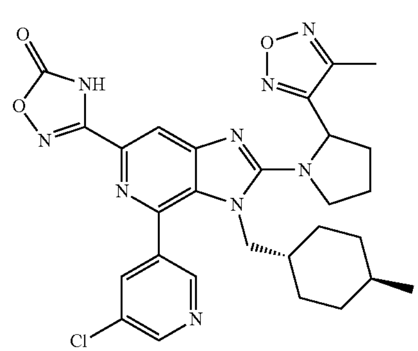 [SMILES: Cc1nonc1C1CCCN1c1nc2cc(-c3noc(=O)[nH]3)nc(-c3cncc(Cl)c3)c2n1C[C@H]1CC[C@H](C)CC1] | 3-{4-(5-chloropyridin-3-yl)-3-[(trans-4-methylcyclohexyl)methyl]-2-[2-(4-methyl-1,2,5-oxadiazol-3-yl)pyrrolidin-1-yl]-3H-imidazo[4,5-c]pyridin-6-yl}-1,2,4-oxadiazol-5(4H)-one (enantiomer 1) | TFA | 576 | 576 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.54 | 80 | 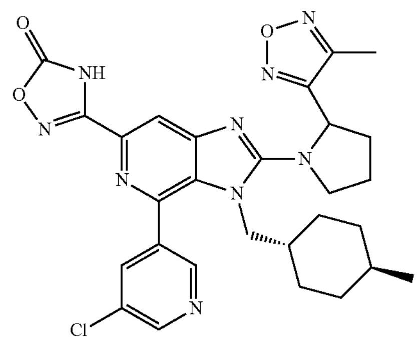 [SMILES: Cc1nonc1C1CCCN1c1nc2cc(-c3noc(=O)[nH]3)nc(-c3cncc(Cl)c3)c2n1C[C@H]1CC[C@H](C)CC1] | 3-{4-(5-chloropyridin-3-yl)-3-[(trans-4-methylcyclohexyl)methyl]-2-[2-(4-methyl-1,2,5-oxadiazol-3-yl)pyrrolidin-1-yl]-3H-imidazo[4,5-c]pyridin-6-yl}-1,2,4-oxadiazol-5(4H)-one (enantiomer 2) | TFA | 576 | 576 |
| 3.55 | 2 | 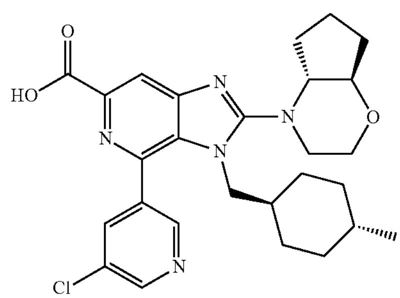 [SMILES: C[C@H]1CC[C@H](Cn2c(N3CCO[C@@H]4CCC[C@H]43)nc3cc(C(=O)O)nc(-c4cncc(Cl)c4)c32)CC1] | 4-(5-chloropyridin-3-yl)-2-((4aR,7aR)-hexahydrocyclopenta[b][1,4]oxazin-4(4aH)-yl)-3-((trans-4-methylcyclohexyl)methyl)-3H-imidazo[4,5-c]pyridine-6-carboxylic acid | TFA | 510 | 510 |
| 3.56 | 3 | 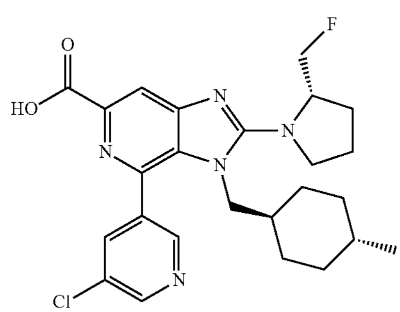 [SMILES: C[C@H]1CC[C@H](Cn2c(N3CCC[C@H]3CF)nc3cc(C(=O)O)nc(-c4cncc(Cl)c4)c32)CC1] | 4-(5-chloropyridin-3-yl)-2-[(2S)-2-(fluoromethyl)pyrrolidin-1-yl]-3-[(trans-4-methylcyclohexyl)methyl]-3H-imidazo[4,5-c]pyridine-6-carboxylic acid | TFA | 486 | 486 |
| 3.57 | 2 | 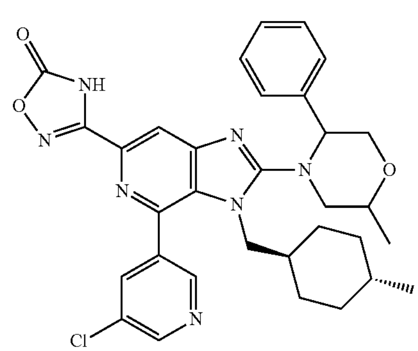 [SMILES: CC1CN(c2nc3cc(-c4noc(=O)[nH]4)nc(-c4cncc(Cl)c4)c3n2C[C@H]2CC[C@H](C)CC2)C(c2ccccc2)CO1] | 3-[4-(5-chloropyridin-3-yl)-3-[(trans-4-methylcyclohexyl)methyl]-2-(trans-2-methyl-5-phenylmorpholin-4-yl)-3H-imidazo[4,5-c]pyridin-6-yl]-1,2,4-oxadiazol-5(4H)-one (racemic) | TFA | 600 | 600 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.58 | 4 | 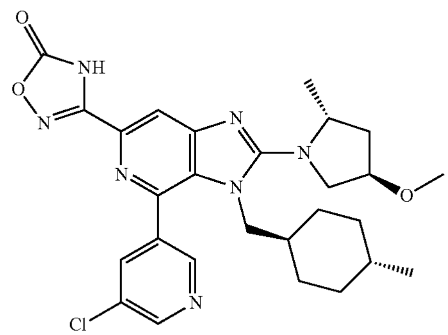 [SMILES: CO[C@@H]1C[C@@H](C)N(c2nc3cc(-c4noc(=O)[nH]4)nc(-c4cncc(Cl)c4)c3n2C[C@H]2CC[C@H](C)CC2)C1] | 3-{4-(5-chloropyridin-3-yl)-2-[(2R,4R)-4-methoxy-2-methylpyrrolidin-1-yl]-3-[(trans-4-methylcyclohex-yl)methyl]-3H-imidazo[4,5-c]pyridin-6-yl}-1,2,4-oxadiazol-5(4H)-one | TFA | 538 | 538 |
| 3.59 | 1 | 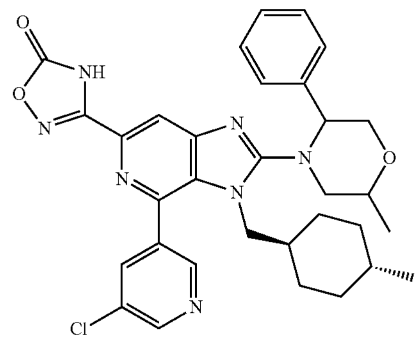 [SMILES: CC1CN(c2nc3cc(-c4noc(=O)[nH]4)nc(-c4cncc(Cl)c4)c3n2C[C@H]2CC[C@H](C)CC2)C(c2ccccc2)CO1] | 3-[4-(5-chloropyridin-3-yl)-3-[(trans-4-methylcyclohex-yl)methyl]-2-(trans-2-methyl-5-phenylmorpholin-4-yl)-3H-imidazo[4,5-c]pyridin-6-yl]-1,2,4-oxadiazol-5(4H)-one (enantiomer 1) | TFA | 600 | 600 |
| 3.60 | 16 | 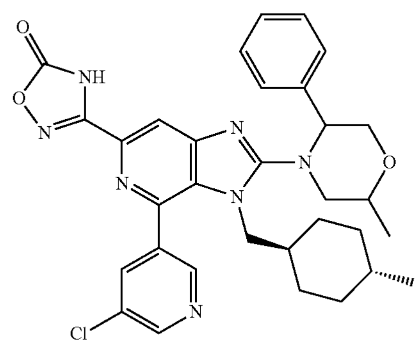 [SMILES: CC1CN(c2nc3cc(-c4noc(=O)[nH]4)nc(-c4cncc(Cl)c4)c3n2C[C@H]2CC[C@H](C)CC2)C(c2ccccc2)CO1] | 3-[4-(5-chloropyridin-3-yl)-3-[(trans-4-methylcyclohex-yl)methyl]-2-(trans-2-methyl-5-phenylmorpholin-4-yl)-3H-imidazo[4,5-c]pyridin-6-yl]-1,2,4-oxadiazol-5(4H)-one (enantiomer 2) | TFA | 600 | 600 |
| 3.61 | 29 | 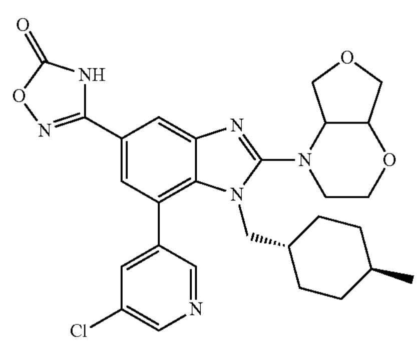 [SMILES: C[C@H]1CC[C@H](Cn2c(N3CCOC4COCC43)nc3cc(-c4noc(=O)[nH]4)cc(-c4cncc(Cl)c4)c32)CC1] | 3-{4-(5-chloropyridin-3-yl)-2-(hexahydro-4H-furo[3,4-b][1,4]oxazin-4-yl)-3-[(trans-4-methylcyclohex-yl)methyl]-3H-imidazo[4,5-c]pyridin-6-yl}-1,2,4-oxadiazol-5(4H)-one | TFA | 552 | 552 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.62 | 54 | 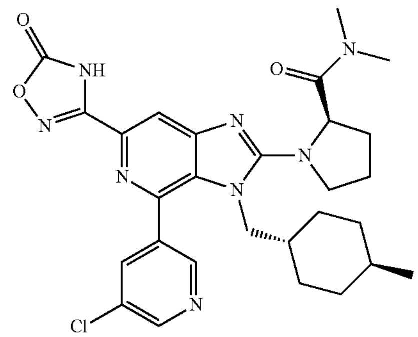 [SMILES: CN(C)C(=O)[C@H]1CCCN1c1nc2cc(-c3noc(=O)[nH]3)nc(-c3cncc(Cl)c3)c2n1C[C@H]1CC[C@H](C)CC1] | 1-[4-(5-chloropyridin-3-yl)-3-[(trans-4-methylcyclohex-yl)methyl]-6-(5-oxo-4,5-dihydro-1,2,4-oxadiazol-3-yl)-3H-imidazo[4,5-c]pyridin-2-yl]-N,N-dimethyl-D-prolinamide | TFA | 565 | 565 |
| 3.63 | 35 | 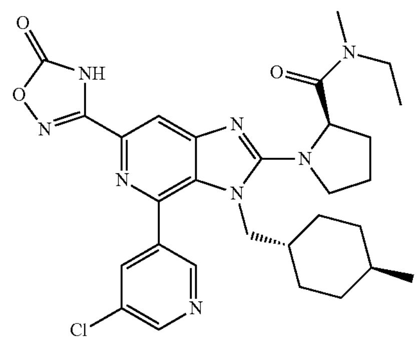 [SMILES: CCN(C)C(=O)[C@H]1CCCN1c1nc2cc(-c3noc(=O)[nH]3)nc(-c3cncc(Cl)c3)c2n1C[C@H]1CC[C@H](C)CC1] | 1-[4-(5-chloropyridin-3-yl)-3-[(trans-4-methylcyclohex-yl)methyl]-6-(5-oxo-4,5-dihydro-1,2,4-oxadiazol-3-yl)-3H-imidazo[4,5-c]pyridin-2-yl]-N-ethyl-N-methyl-D-prolinamide | TFA | 579 | 579 |
| 3.64 | 17 | 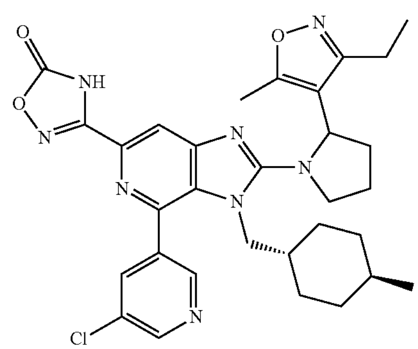 [SMILES: CCc1noc(C)c1C1CCCN1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[2-(3-ethyl-5-methylisoxazol-4-yl)pyrrolidin-1-yl]-3-[(trans-4-methylcyclohex-yl)methyl]-3H-imidazo[4,5-c]pyridin-6-yl}-1,2,4-oxadiazol-5(4H)-one | TFA | 603 | 603 |
| 3.65 | 2 | 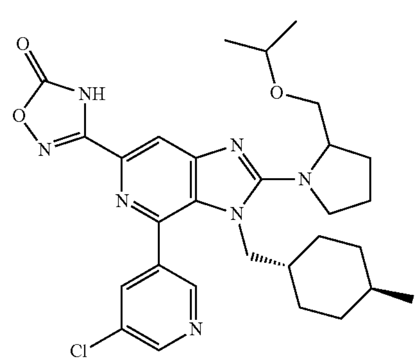 [SMILES: CC(C)OCC1CCCN1c1nc2cc(-c3noc(=O)[nH]3)nc(-c3cncc(Cl)c3)c2n1C[C@H]1CC[C@H](C)CC1] | 3-[4-(5-chloropyridin-3-yl)-3-[(trans-4-methylcyclohex-yl)methyl]-2-{2-[(1-methylethoxy)-methyl]pyrrolidin-1-yl}-3H-imidazo[4,5-c]pyridin-6-yl]-1,2,4-oxadiazol-5(4H)-one (enantiomer 1) | TFA | 566 | 566 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.66 | 7 | 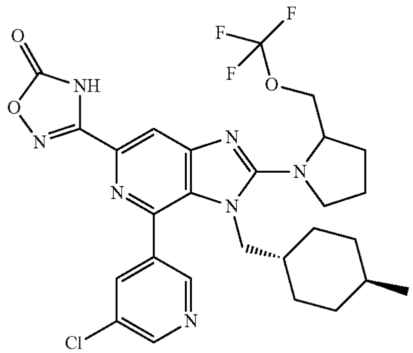 [SMILES: C[C@H]1CC[C@H](Cn2c(N3CCCC3COC(F)(F)F)nc3cc(-c4noc(=O)[nH]4)nc(-c4cncc(Cl)c4)c32)CC1] | 3-[4-(5-chloropyridin-3-yl)-3-[(trans-4-methylcyclohex-yl)methyl]-2-{2-[(trifluoromethoxy)-methyl]pyrrolidin-1-yl}-3H-imidazo[4,5-pyridin-6-yl]-1,2,4-oxadiazol-5(4H)-one | TFA | 592 | 592 |
| 3.67 | 4 | 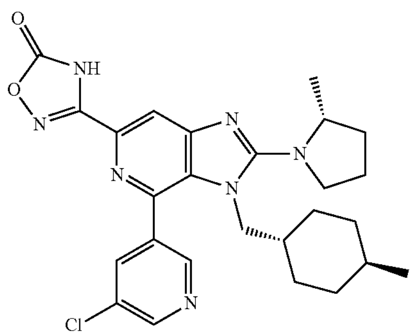 [SMILES: C[C@@H]1CCCN1c1nc2cc(-c3noc(=O)[nH]3)nc(-c3cncc(Cl)c3)c2n1C[C@H]1CC[C@H](C)CC1] | 3-{4-(5-chloropyridin-3-yl)-3-[(trans-4-methylcyclohex-yl)methyl]-2-[(2R)-2-methylpyrrolidin-1-yl]-3H-imidazo[4,5-c]pyridin-6-yl}-1,2,4-oxadiazol-5(4H)-one | TFA | 508 | 508 |
| 3.68 | 3 | 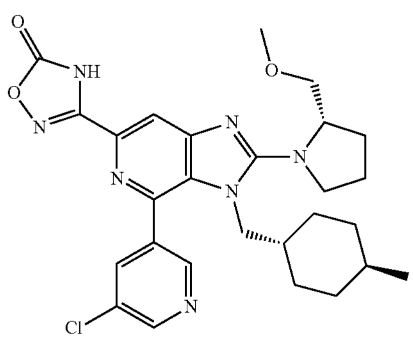 [SMILES: COC[C@@H]1CCCN1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(2S)-2-(methoxymethyl)-pyrrolidin-1-yl]-3-[(trans-4-methylcyclohex-yl)methyl]-3H-imidazo[4,5-c]pyridin-6-yl}-1,2,4-oxadiazol-5(4H)-one | TFA | 538 | 538 |
| 3.69 | 47 | 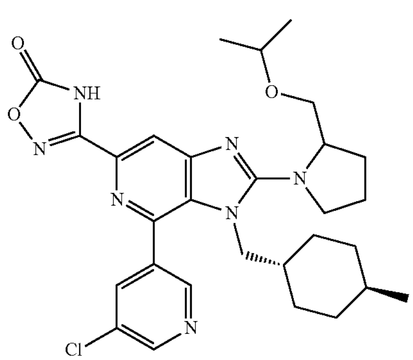 [SMILES: CC(C)OCC1CCCN1c1nc2cc(-c3noc(=O)[nH]3)nc(-c3cncc(Cl)c3)c2n1C[C@H]1CC[C@H](C)CC1] | 3-[4-(5-chloropyridin-3-yl)-3-[(trans-4-methylcyclohex-yl)methyl]-2-{2-[(1-methylethoxy)-methyl]pyrrolidin-1-yl}-3H-imidazo[4,5-c]pyridin-6-yl]-1,2,4-oxadiazol-5(4H)-one (enantiomer 2) | TFA | 566 | 566 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.70 | 1 | 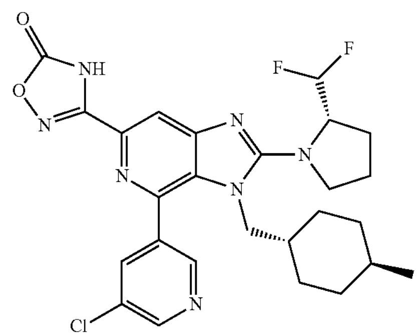 [SMILES: C[C@H]1CC[C@H](Cn2c(N3CCC[C@H]3C(F)F)nc3cc(-c4noc(=O)[nH]4)nc(-c4cncc(Cl)c4)c32)CC1] | 3-{4-(5-chloropyridin-3-yl)-2-[(2S)-2-(difluoromethyl)pyrrolidin-1-yl]-3-[(trans-4-methylcyclohex-yl)methyl]-3H-imidazo[4,5-c]pyridin-6-yl}-1,2,4-oxadiazol-5(4H)-one | TFA | 544 | 544 |
| 3.72 | 5 | 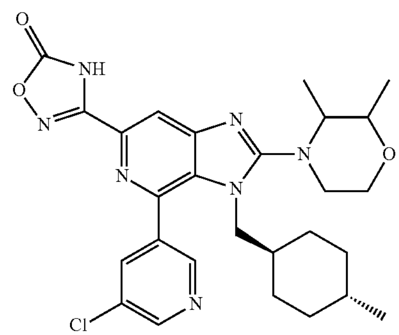 [SMILES: CC1OCCN(c2nc3cc(-c4noc(=O)[nH]4)nc(-c4cncc(Cl)c4)c3n2C[C@H]2CC[C@H](C)CC2)C1C] | 3-{4-(5-chloropyridin-3-yl)-2-(trans-2,3-dimethylmorpholin-4-yl)-3-[(trans-4-methylcyclohex-yl)methyl]-3H-imidazo[4,5-c]pyridin-6-yl}-1,2,4-oxadiazol-5(4H)-one (racemic) | TFA | 538 | 538 |
| 3.73 | 6 | 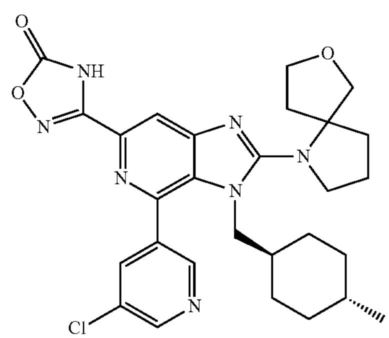 [SMILES: C[C@H]1CC[C@H](Cn2c(N3CCCC34CCOC4)nc3cc(-c4noc(=O)[nH]4)nc(-c4cncc(Cl)c4)c32)CC1] | 3-[4-(5-chloropyridin-3-yl)-3-[(trans-4-methylcyclohex-yl)methyl]-2-(7-oxa-1-azaspiro[4.4]non-1-yl)-3H-imidazo[4,5-c]pyridin-6-yl]-1,2,4-oxadiazol-5(4H)-one | TFA | 550 | 550 |
| 3.74 | 3 | 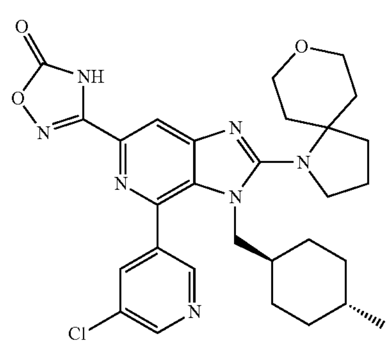 [SMILES: C[C@H]1CC[C@H](Cn2c(N3CCCC34CCOCC4)nc3cc(-c4noc(=O)[nH]4)nc(-c4cncc(Cl)c4)c32)CC1] | 3-[4-(5-chloropyridin-3-yl)-3-[(trans-4-methylcyclohex-yl)methyl]-2-(8-oxa-1-azaspiro[4.5]dec-1-yl)-3H-imidazo[4,5-c]pyridin-6-yl]-1,2,4-oxadiazol-5(4H)-one | TFA | 564 | 564 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.75 | 1 | 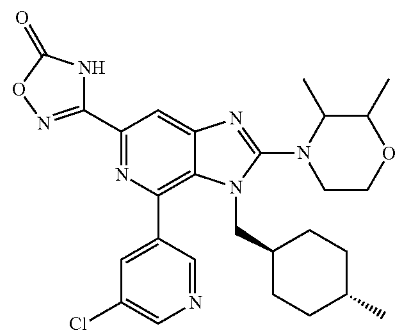 [SMILES: CC1OCCN(c2nc3cc(-c4noc(=O)[nH]4)nc(-c4cncc(Cl)c4)c3n2C[C@H]2CC[C@H](C)CC2)C1C] | 3-{4-(5-chloropyridin-3-yl)-2-(trans-2,3-dimethylmorpholin-4-yl)-3-[(trans-4-methylcyclohex-yl)methyl]-3H-imidazo[4,5-c]pyridin-6-yl}-1,2,4-oxadiazol-5(4H)-one (enantiomer 1) | TFA | 538 | 538 |
| 3.76 | 25 | 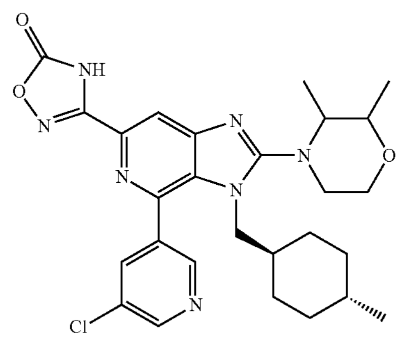 [SMILES: CC1OCCN(c2nc3cc(-c4noc(=O)[nH]4)nc(-c4cncc(Cl)c4)c3n2C[C@H]2CC[C@H](C)CC2)C1C] | 3-{4-(5-chloropyridin-3-yl)-2-(trans-2,3-dimethylmorpholin-4-yl)-3-[(trans-4-methylcyclohex-yl)methyl]-3H-imidazo[4,5-c]pyridin-6-yl}-1,2,4-oxadiazol-5(4H)-one (enantiomer 2) | TFA | 538 | 538 |
| 3.77 | 10 | 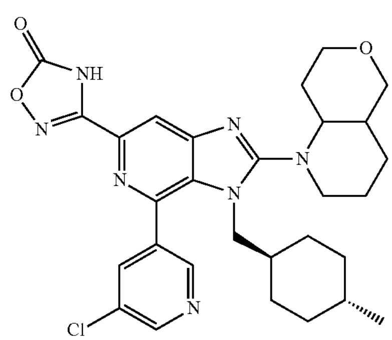 [SMILES: C[C@H]1CC[C@H](Cn2c(N3CCCC4COCCC43)nc3cc(-c4noc(=O)[nH]4)nc(-c4cncc(Cl)c4)c32)CC1] | 3-{4-(5-chloropyridin-3-yl)-2-(hexahydro-2H-pyrano[4,3-b]pyridin-1(5H)-yl)-3-[(trans-4-methylcyclohex-yl)methyl]-3H-imidazo[4,5-c]pyridin-6-yl}-1,2,4-oxadiazol-5(4H)-one | TFA | 564 | 564 |
| 3.78 | 1 | 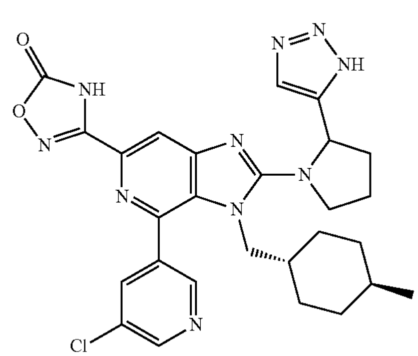 [SMILES: C[C@H]1CC[C@H](Cn2c(N3CCCC3c3cnn[nH]3)nc3cc(-c4noc(=O)[nH]4)nc(-c4cncc(Cl)c4)c32)CC1] | 3-{4-(5-chloropyridin-3-yl)-3-[(trans-4-methylcyclohex-yl)methyl]-2-[2-(1H-1,2,3-triazol-5-yl)pyrrolidin-1-yl]-3H-imidazo[4,5-c]pyridin-6-yl}-1,2,4-oxadiazol-5(4H)-one | TFA | 561 | 561 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.79 | 12 | 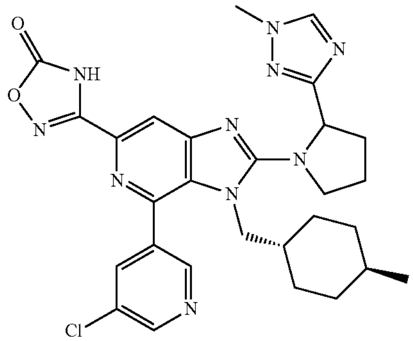 [SMILES: Cn1cnc(C2CCCN2c2nc3cc(-c4noc(=O)[nH]4)nc(-c4cncc(Cl)c4)c3n2C[C@H]2CC[C@H](C)CC2)n1] | 3-{4-(5-chloropyridin-3-yl)-3-[(trans-4-methylcyclohex-yl)methyl]-2-[2-(1-methyl-1H-1,2,4-triazol-3-yl)pyrrolidin-1-yl]-3H-imidazo[4,5-c]pyridin-6-yl}-1,2,4-oxadiazol-5(4H)-one | TFA | 575 | 575 |
| 3.80 | 21 | 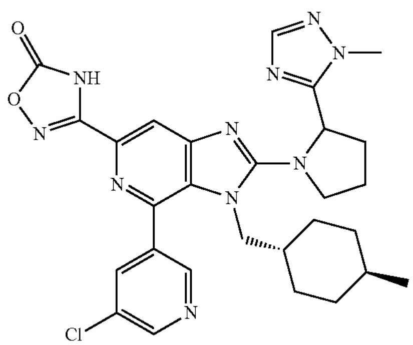 [SMILES: Cn1ncnc1C1CCCN1c1nc2cc(-c3noc(=O)[nH]3)nc(-c3cncc(Cl)c3)c2n1C[C@H]1CC[C@H](C)CC1] | 3-{4-(5-chloropyridin-3-yl)-3-[(trans-4-methylcyclohex-yl)methyl]-2-[2-(1-methyl-1H-1,2,4-triazol-5-yl)pyrrolidin-1-yl]-3H-imidazo[4,5-c]pyridin-6-yl}-1,2,4-oxadiazol-5(4H)-one | TFA | 575 | 575 |
| 3.81 | <1 | 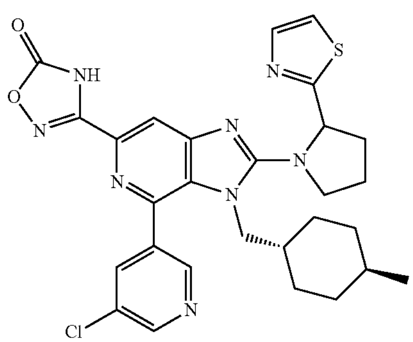 [SMILES: C[C@H]1CC[C@H](Cn2c(N3CCCC3c3nccs3)nc3cc(-c4noc(=O)[nH]4)nc(-c4cncc(Cl)c4)c32)CC1] | 3-{4-(5-chloropyridin-3-yl)-3-[(trans-4-methylcyclohex-yl)methyl]-2-[(2S)-2-(1,3-thiazol-2-yl)pyrrolidin-1-yl]-3H-imidazo[4,5-c]pyridin-6-yl}-1,2,4-oxadiazol-5(4H)-one | TFA | 577 | 577 |
| 3.82 | 2 | 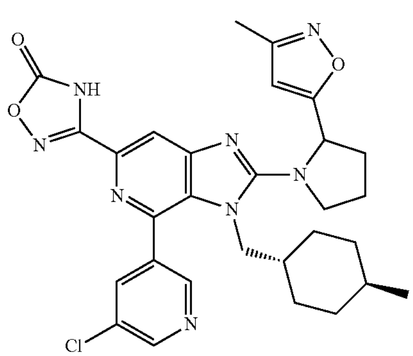 | 3-{4-(5-chloropyridin-3-yl)-3-[(trans-4-methylcyclohex-yl)methyl]-2-[2-(3-methylisoxazol-5-yl)pyrrolidin-1-yl]-3H-imidazo[4,5-c]pyridin-6-yl}-1,2,4-oxadiazol-5(4H)-one | TFA | 575 | 575 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.83 | 11 | 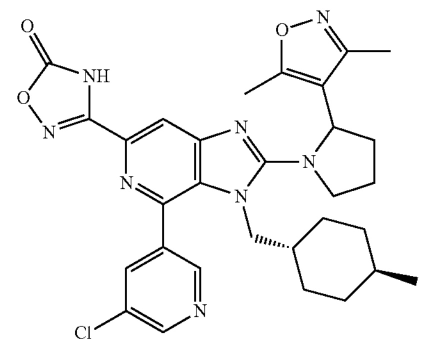 [SMILES: Cc1noc(C)c1C1CCCN1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[2-(3,5-dimethylisoxazol-4-yl)pyrrolidin-1-yl]-3-[(trans-4-methylcyclohexyl)methyl]-3H-imidazo[4,5-c]pyridin-6-yl}-1,2,4-oxadiazol-5(4H)-one | TFA | 589 | 589 |
| 3.84 | 1 | 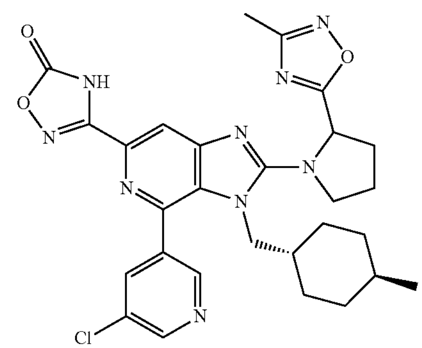 [SMILES: Cc1noc(C2CCCN2c2nc3cc(-c4noc(=O)[nH]4)nc(-c4cncc(Cl)c4)c3n2C[C@H]2CC[C@H](C)CC2)n1] | 3-{4-(5-chloropyridin-3-yl)-3-[(trans-4-methylcyclohexyl)methyl]-2-[2-(3-methyl-1,2,4-oxadiazol-5-yl)pyrrolidin-1-yl]-3H-imidazo[4,5-c]pyridin-6-yl}-1,2,4-oxadiazol-5(4H)-one | TFA | 576 | 576 |
| 3.85 | 144 | 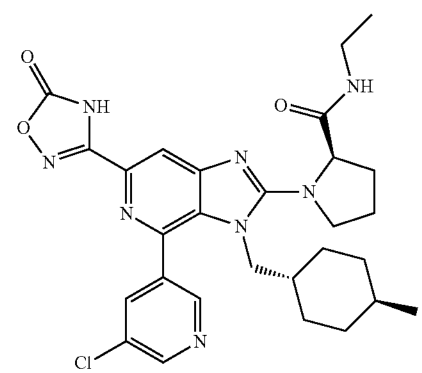 [SMILES: CCNC(=O)[C@H]1CCCN1c1nc2cc(-c3noc(=O)[nH]3)nc(-c3cncc(Cl)c3)c2n1C[C@H]1CC[C@H](C)CC1] | 1-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-N-ethyl-D-prolinamide | TFA | 565 | 565 |
| 3.86 | 11 | 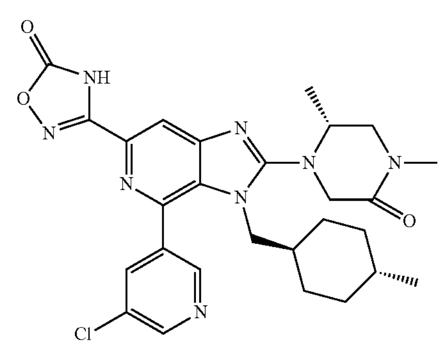 [SMILES: C[C@@H]1CN(C)C(=O)CN1c1nc2cc(-c3noc(=O)[nH]3)nc(-c3cncc(Cl)c3)c2n1C[C@H]1CC[C@H](C)CC1] | (5R)-4-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-1,5-dimethylpiperazin-2-one | TFA | 551 | 551 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.87 | 3 | 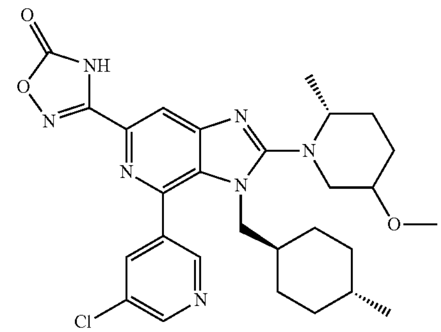 [SMILES: COC1CC[C@@H](C)N(c2nc3cc(-c4noc(=O)[nH]4)nc(-c4cncc(Cl)c4)c3n2C[C@H]2CC[C@H](C)CC2)C1] | 3-{4-(5-chloropyridin-3-yl)-2-[(2R)-5-methoxy-2-methylpiperidin-1-yl]-3-[(trans-4-methylcyclohex-yl)methyl]-3H-imidazo[4,5-c]pyridin-6-yl}-1,2,4-oxadiazol-5(4H)-one | TFA | 552 | 552 |
| 3.88 | 8 | 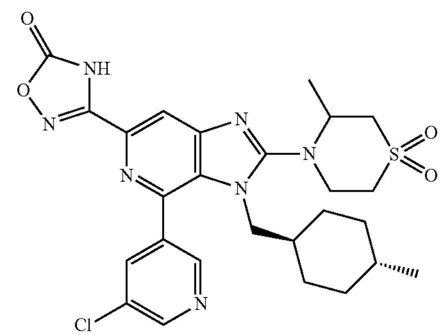 [SMILES: CC1CS(=O)(=O)CCN1c1nc2cc(-c3noc(=O)[nH]3)nc(-c3cncc(Cl)c3)c2n1C[C@H]1CC[C@H](C)CC1] | 3-[4-(5-chloropyridin-3-yl)-3-[(trans-4-methylcyclohex-yl)methyl]-2-(3-methyl-1,1-dioxidothio-morpholin-4-yl)-3H-imidazo[4,5-c]pyridin-6-yl]-1,2,4-oxadiazol-5(4H)-one | TFA | 572 | 572 |
| 3.89 | 9 | 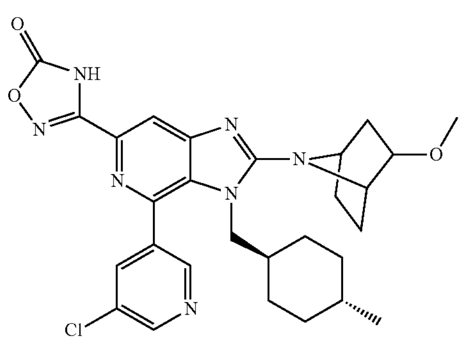 | 3-{4-(5-chloropyridin-3-yl)-2-(2-methoxy-7-azabicyclo[2.2.1]-hept-7-yl)-3-[(trans-4-methylcyclohex-yl)methyl]-3H-imidazo[4,5-c]pyridin-6-yl}-1,2,4-oxadiazol-5(4H)-one | TFA | 550 | 550 |
| 3.90 | <1 | 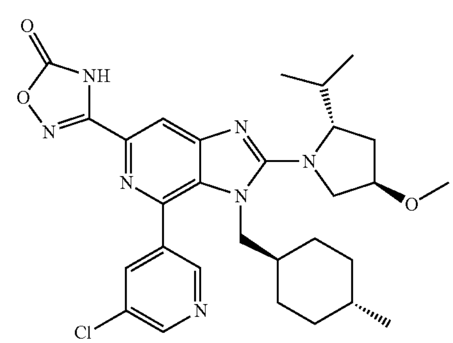 [SMILES: CO[C@@H]1C[C@@H](C(C)C)N(c2nc3cc(-c4noc(=O)[nH]4)nc(-c4cncc(Cl)c4)c3n2C[C@H]2CC[C@H](C)CC2)C1] | 3-{4-(5-chloropyridin-3-yl)-2-[(2S,4R)-4-methoxy-2-(1-methylethyl)-pyrrolidin-1-yl]-3-[(trans-4-methylcyclohex-yl)methyl]-3H-imidazo[4,5-c]pyridin-6-yl}-1,2,4-oxadiazol-5(4H)-one | TFA | 566 | 566 |

TABLE 3-continued

| Ex. | FRET IC$_{50}$ (nM) | Chemical Name | Salt | [M + H]$^+$ Calc'd | [M + H]$^+$ Obsv'd |
|---|---|---|---|---|---|
| 3.91 | 1 | 3-{4-(5-chloropyridin-3-yl)-2-[(2S,4R)-4-hydroxy-2-(1-methylethyl)-pyrrolidin-1-yl]-3-[(trans-4-methylcyclohex-yl)methyl]-3H-imidazo[4,5-c]pyridin-6-yl}-1,2,4-oxadiazol-5(4H)-one | TFA | 552 | 552 |
| 3.92 | 1 | 3-{4-(5-chloropyridin-3-yl)-2-[(2S,4R)-2-(fluoromethyl)-4-methoxy-pyrrolidin-1-yl]-3-[(trans-4-methylcyclohex-yl)methyl]-3H-imidazo[4,5-c]pyridin-6-yl}-1,2,4-oxadiazol-5(4H)-one | | 556 | 556 |
| 3.93 | 353 | 3-{4-(5-chloropyridin-3-yl)-2-[(2R,4R)-2-(fluoromethyl)-4-methoxy-pyrrolidin-1-yl]-3-[(trans-4-methylcyclohex-yl)methyl]-3H-imidazo[4,5-c]pyridin-6-yl}-1,2,4-oxadiazol-5(4H)-one | | 556 | 556 |
| 3.94 | 1 | 3-{4-(5-chloropyridin-3-yl)-3-[(trans-4-methylcyclohex-yl)methyl]-2-[methyl(2,2,2-trifluoroethyl)-amino]-3H-imidazo[4,5-c]pyridin-6-yl}-1,2,4-oxadiazol-5(4H)-one | TFA | 536 | 536 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.95 | 26 | 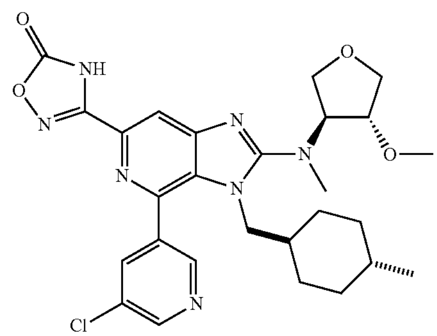 [SMILES: CO[C@H]1COC[C@@H]1N(C)c1nc2cc(-c3noc(=O)[nH]3)nc(-c3cncc(Cl)c3)c2n1C[C@H]1CC[C@H](C)CC1] | 3-(4-(5-chloropyridin-3-yl)-2-((trans-4-methoxytetrahydrofuran-3-yl)(methyl)amino)-3-((trans-4-methylcyclohexyl)methyl)-3H-imidazo[4,5-c]pyridin-6-yl)-1,2,4-oxadiazol-5(4H)-one (racemic) | TFA | 554 | 554 |
| 3.96 | 13 | 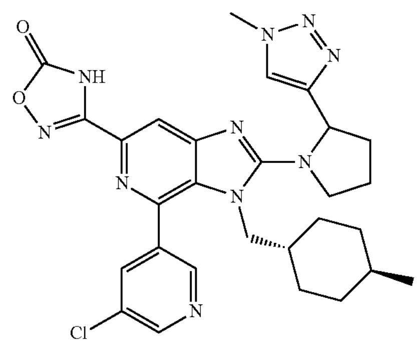 [SMILES: Cn1cc(C2CCCN2c2nc3cc(-c4noc(=O)[nH]4)nc(-c4cncc(Cl)c4)c3n2C[C@H]2CC[C@H](C)CC2)nn1] | 3-{4-(5-chloropyridin-3-yl)-3-[(trans-4-methylcyclohexyl)methyl]-2-[2-(1-methyl-1H-1,2,3-triazol-4-yl)pyrrolidin-1-yl]-3H-imidazo[4,5-c]pyridin-6-yl}-1,2,4-oxadiazol-5(4H)-one | TFA | 575 | 575 |
| 3.97 | 7 | 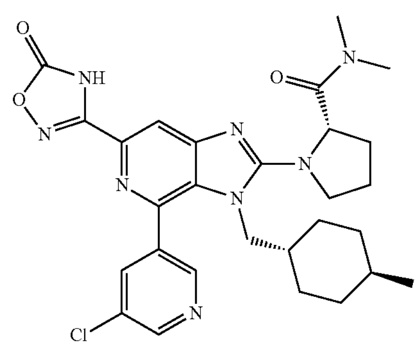 [SMILES: CN(C)C(=O)[C@@H]1CCCN1c1nc2cc(-c3noc(=O)[nH]3)nc(-c3cncc(Cl)c3)c2n1C[C@H]1CC[C@H](C)CC1] | 1-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-N-ethyl-N-methyl-L-prolinamide | TFA | 579 | 579 |
| 3.98 | 1 | 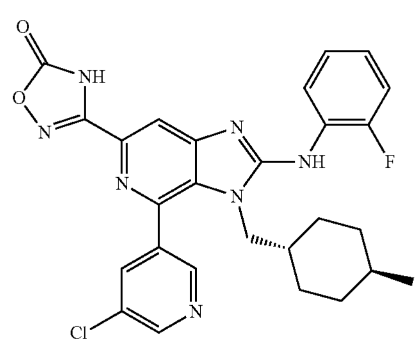 [SMILES: C[C@H]1CC[C@H](Cn2c(Nc3ccccc3F)nc3cc(-c4noc(=O)[nH]4)nc(-c4cncc(Cl)c4)c32)CC1] | 3-{4-(5-chloropyridin-3-yl)-2-[(2-fluorophenyl)amino]-3-[(trans-4-methylcyclohexyl)methyl]-3H-imidazo[4,5-c]pyridin-6-yl}-1,2,4-oxadiazol-5(4H)-one | | 534 | 534 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.99 | 3 | 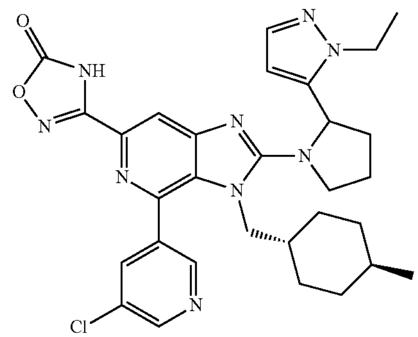 [SMILES: CCn1nccc1C1CCCN1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[2-(1-ethyl-1H-pyrazol-5-yl)pyrrolidin-1-yl]-3-[(trans-4-methylcyclohexyl)methyl]-3H-imidazo[4,5-c]pyridin-6-yl}-1,2,4-oxadiazol-5(4H)-one | TFA | 588 | 588 |
| 3.100 | 7 | 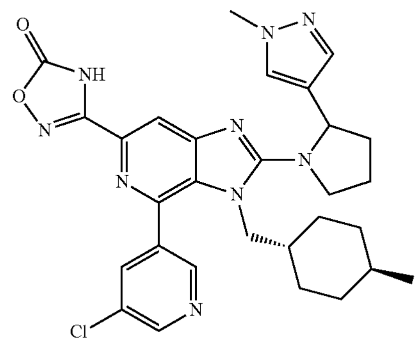 [SMILES: Cn1cc(C2CCCN2c2nc3cc(-c4noc(=O)[nH]4)nc(-c4cncc(Cl)c4)c3n2C[C@H]2CC[C@H](C)CC2)cn1] | 3-{4-(5-chloropyridin-3-yl)-3-[(trans-4-methylcyclohexyl)methyl]-2-[2-(1-methyl-1H-pyrazol-4-yl)pyrrolidin-1-yl]-3H-imidazo[4,5-c]pyridin-6-yl}-1,2,4-oxadiazol-5(4H)-one | TFA | 574 | 574 |
| 3.101 | 1 | 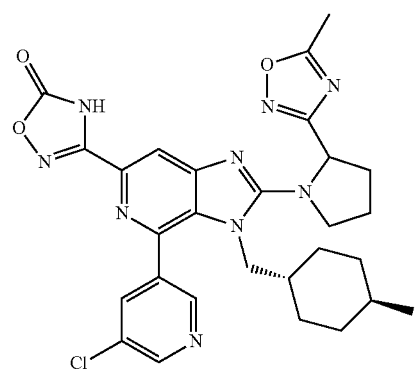 [SMILES: Cc1nc(C2CCCN2c2nc3cc(-c4noc(=O)[nH]4)nc(-c4cncc(Cl)c4)c3n2C[C@H]2CC[C@H](C)CC2)no1] | 3-{4-(5-chloropyridin-3-yl)-3-[(trans-4-methylcyclohexyl)methyl]-2-[2-(5-methyl-1,2,4-oxadiazol-3-yl)pyrrolidin-1-yl]-3H-imidazo[4,5-c]pyridin-6-yl}-1,2,4-oxadiazol-5(4H)-one | TFA | 576 | 576 |
| 3.102 | <1 | 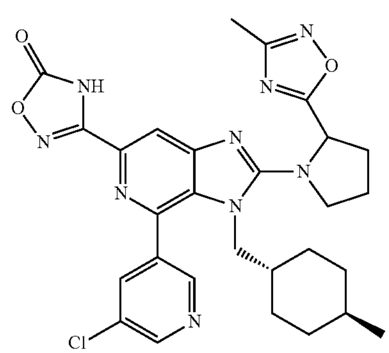 [SMILES: Cc1noc(C2CCCN2c2nc3cc(-c4noc(=O)[nH]4)nc(-c4cncc(Cl)c4)c3n2C[C@H]2CC[C@H](C)CC2)n1] | 3-{4-(5-chloropyridin-3-yl)-3-[(trans-4-methylcyclohexyl)methyl]-2-[2-(3-methyl-1,2,4-oxadiazol-5-yl)pyrrolidin-1-yl]-3H-imidazo[4,5-c]pyridin-6-yl}-1,2,4-oxadiazol-5(4H)-one (enantiomer 1) | | 576 | 576 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.103 | 116 | 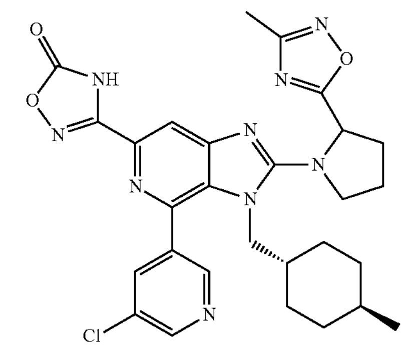 [SMILES: Cc1noc(C2CCCN2c2nc3cc(-c4noc(=O)[nH]4)nc(-c4cncc(Cl)c4)c3n2C[C@H]2CC[C@H](C)CC2)n1] | 3-{4-(5-chloropyridin-3-yl)-3-[(trans-4-methylcyclohexyl)methyl]-2-[2-(3-methyl-1,2,4-oxadiazol-5-yl)pyrrolidin-1-yl]-3H-imidazo[4,5-c]pyridin-6-yl}-1,2,4-oxadiazol-5(4H)-one (enantiomer 2) | | 576 | 576 |
| 3.104 | 19 | 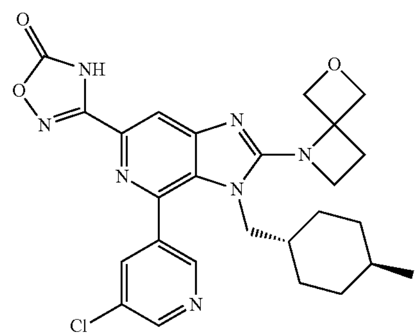 [SMILES: C[C@H]1CC[C@H](Cn2c(N3CCC34COC4)nc3cc(-c4noc(=O)[nH]4)nc(-c4cncc(Cl)c4)c32)CC1] | 3-[4-(5-chloropyridin-3-yl)-3-[(trans-4-methylcyclohexyl)methyl]-2-(6-oxa-1-azaspiro[3.3]hept-1-yl)-3H-imidazo[4,5-c]pyridin-6-yl]-1,2,4-oxadiazol-5(4H)-one | TFA | 522 | 522 |
| 3.105 | 9 | 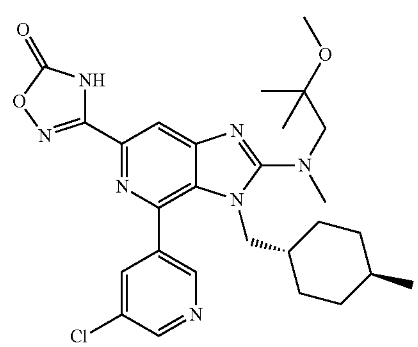 [SMILES: COC(C)(C)CN(C)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(2-methoxy-2-methylpropyl)-(methyl)amino]-3-[(trans-4-methylcyclohexyl)methyl]-3H-imidazo[4,5-c]pyridin-6-yl}-1,2,4-oxadiazol-5(4H)-one | TFA | 540 | 540 |
| 3.106 | 1 | 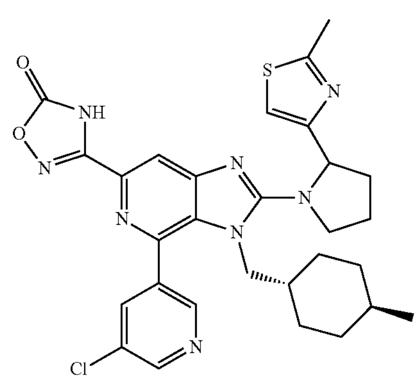 [SMILES: Cc1nc(C2CCCN2c2nc3cc(-c4noc(=O)[nH]4)nc(-c4cncc(Cl)c4)c3n2C[C@H]2CC[C@H](C)CC2)cs1] | 3-{4-(5-chloropyridin-3-yl)-3-[(trans-4-methylcyclohexyl)methyl]-2-[2-(2-methyl-1,3-thiazol-4-yl)pyrrolidin-1-yl]-3H-imidazo[4,5-c]pyridin-6-yl}-1,2,4-oxadiazol-5(4H)-one | TFA | 591 | 591 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.107 | 41 | 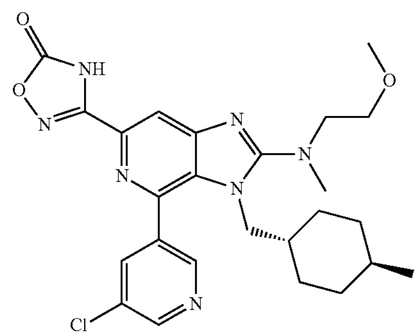 [SMILES: COCCN(C)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(2-methoxyethyl)-(methyl)amino]-3-[(trans-4-methylcyclohex-yl)methyl]-3H-imidazo[4,5-c]pyridin-6-yl}-1,2,4-oxadiazol-5(4H)-one | TFA | 512 | 512 |
| 3.108 | 11 | 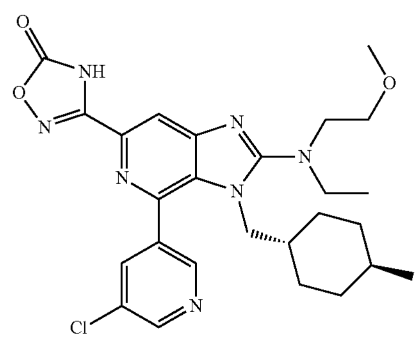 [SMILES: CCN(CCOC)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[ethyl(2-methoxyethyl)-amino]-3-[(trans-4-methylcyclohex-yl)methyl]-3H-imidazo[4,5-c]pyridin-6-yl}-1,2,4-oxadiazol-5(4H)-one | TFA | 526 | 526 |
| 3.109 | 14 | 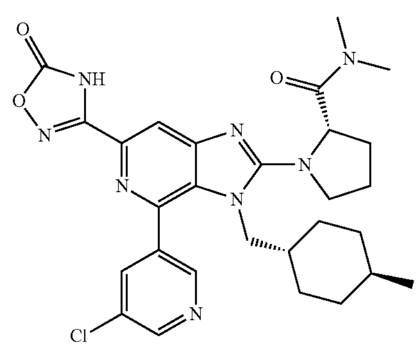 [SMILES: CN(C)C(=O)[C@@H]1CCCN1c1nc2cc(-c3noc(=O)[nH]3)nc(-c3cncc(Cl)c3)c2n1C[C@H]1CC[C@H](C)CC1] | 1-[4-(5-chloropyridin-3-yl)-3-[(trans-4-methylcyclohex-yl)methyl]-6-(5-oxo-4,5-dihydro-1,2,4-oxadiazol-3-yl)-3H-imidazo[4,5-c]pyridin-2-yl]-N,N-dimethyl-L-prolinamide | TFA | 565 | 565 |
| 3.110 | 9 | 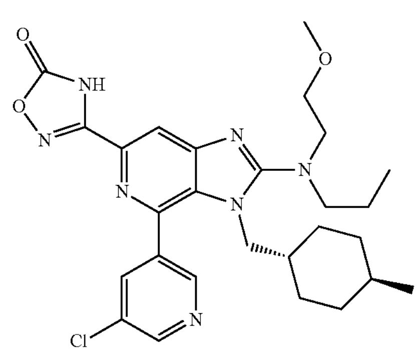 [SMILES: CCCN(CCOC)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(2-methoxyethyl)-(propyl)amino]-3-[(trans-4-methylcyclohex-yl)methyl]-3H-imidazo[4,5-c]pyridin-6-yl}-1,2,4-oxadiazol-5(4H)-one | TFA | 540 | 540 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.111 | 2 | 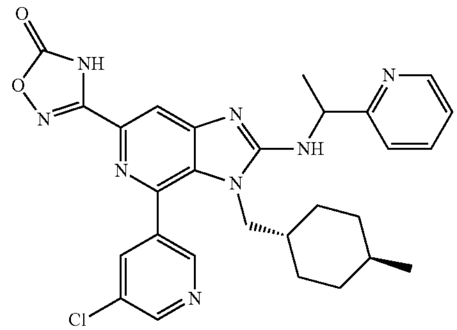 [SMILES: CC(Nc1nc2cc(-c3noc(=O)[nH]3)nc(-c3cncc(Cl)c3)c2n1C[C@H]1CC[C@H](C)CC1)c1ccccn1] | 3-{4-(5-chloropyridin-3-yl)-3-[(trans-4-methylcyclohex-yl)methyl]-2-[(1-pyridin-2-ylethyl)amino]-3H-imidazo[4,5-c]pyridin-6-yl}-1,2,4-oxadiazol-5(4H)-one | TFA | 545 | 545 |
| 3.112 | 50 | 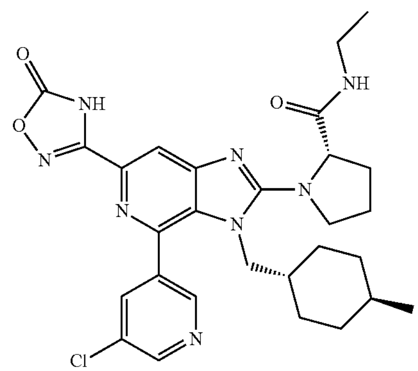 [SMILES: CCNC(=O)[C@@H]1CCCN1c1nc2cc(-c3noc(=O)[nH]3)nc(-c3cncc(Cl)c3)c2n1C[C@H]1CC[C@H](C)CC1] | 1-[4-(5-chloropyridin-3-yl)-3-[(trans-4-methylcyclohex-yl)methyl]-6-(5-oxo-4,5-dihydro-1,2,4-oxadiazol-3-yl)-3H-imidazo[4,5-c]pyridin-2-yl]-N-ethyl-L-prolinamide | TFA | 565 | 565 |
| 3.113 | 2 | 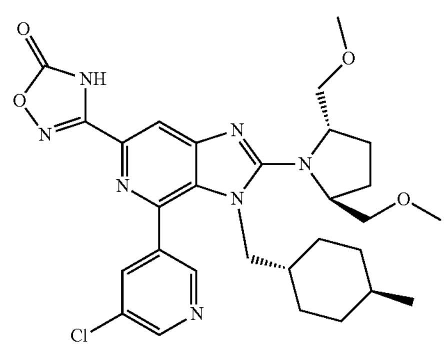 [SMILES: COC[C@@H]1CC[C@@H](COC)N1c1nc2cc(-c3noc(=O)[nH]3)nc(-c3cncc(Cl)c3)c2n1C[C@H]1CC[C@H](C)CC1] | 3-{2-[(2S,5S)-2,5-bis(methoxy-methyl)pyrrolidin-1-yl]-4-(5-chloropyridin-3-yl)-3-[(trans-4-methylcyclohex-yl)methyl]-3H-imidazo[4,5-c]pyridin-6-yl}-1,2,4-oxadiazol-5(4H)-one | TFA | 582 | 582 |
| 3.114 | 16 | 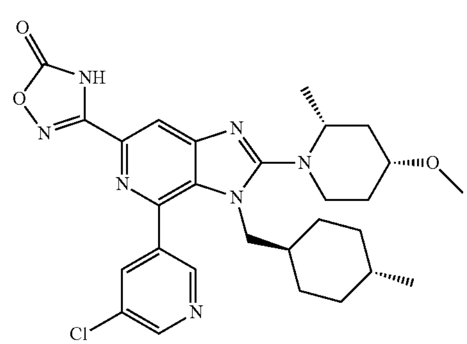 [SMILES: CO[C@@H]1CCN(c2nc3cc(-c4noc(=O)[nH]4)nc(-c4cncc(Cl)c4)c3n2C[C@H]2CC[C@H](C)CC2)[C@H](C)C1] | 3-{4-(5-chloropyridin-3-yl)-2-[cis-4-methoxy-2-methylpiperidin-1-yl]-3-[(trans-4-methylcyclohex-yl)methyl]-3H-imidazo[4,5-c]pyridin-6-yl}-1,2,4-oxadiazol-5(4H)-one (racemic) | | 552 | 552 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.115 | 9 | 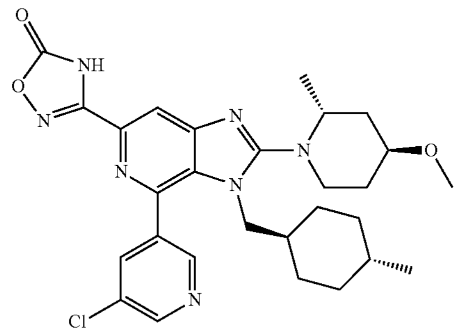 [SMILES: CO[C@H]1CCN(c2nc3cc(-c4noc(=O)[nH]4)nc(-c4cncc(Cl)c4)c3n2C[C@H]2CC[C@H](C)CC2)[C@H](C)C1] | 3-{4-(5-chloropyridin-3-yl)-2-[trans-4-methoxy-2-methylpiperidin-1-yl]-3-[(trans-4-methylcyclohexyl)methyl]-3H-imidazo[4,5-c]pyridin-6-yl}-1,2,4-oxadiazol-5(4H)-one (racemic) | | 552 | 552 |
| 3.116 | 5 | 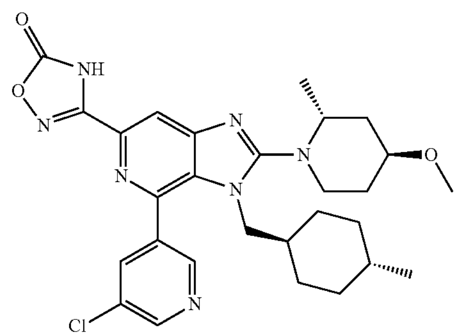 [SMILES: CO[C@H]1CCN(c2nc3cc(-c4noc(=O)[nH]4)nc(-c4cncc(Cl)c4)c3n2C[C@H]2CC[C@H](C)CC2)[C@H](C)C1] | 3-{4-(5-chloropyridin-3-yl)-2-[trans-4-methoxy-2-methylpiperidin-1-yl]-3-[(trans-4-methylcyclohexyl)methyl]-3H-imidazo[4,5-c]pyridin-6-yl}-1,2,4-oxadiazol-5(4H)-one (enantiomer 1) | | 552 | 552 |
| 3.117 | 18 | 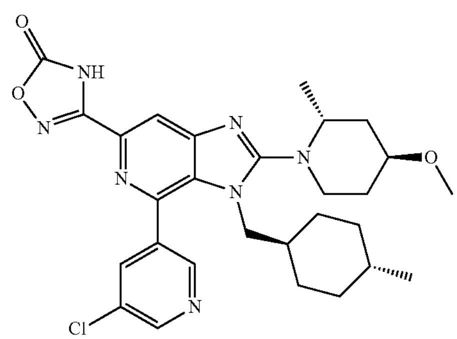 [SMILES: CO[C@H]1CCN(c2nc3cc(-c4noc(=O)[nH]4)nc(-c4cncc(Cl)c4)c3n2C[C@H]2CC[C@H](C)CC2)[C@H](C)C1] | 3-{4-(5-chloropyridin-3-yl)-2-[trans-4-methoxy-2-methylpiperidin-1-yl]-3-[(trans-4-methylcyclohexyl)methyl]-3H-imidazo[4,5-c]pyridin-6-yl}-1,2,4-oxadiazol-5(4H)-one (enantiomer 2) | | 552 | 552 |
| 3.118 | 13 | 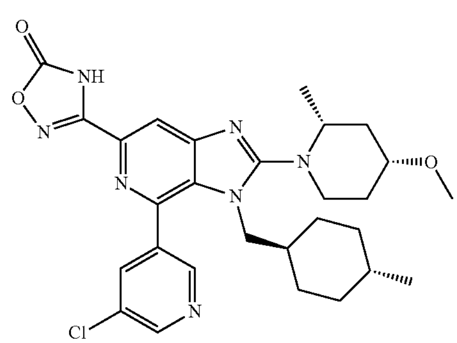 [SMILES: CO[C@@H]1CCN(c2nc3cc(-c4noc(=O)[nH]4)nc(-c4cncc(Cl)c4)c3n2C[C@H]2CC[C@H](C)CC2)[C@H](C)C1] | 3-{4-(5-chloropyridin-3-yl)-2-[cis-4-methoxy-2-methylpiperidin-1-yl]-3-[(trans-4-methylcyclohexyl)methyl]-3H-imidazo[4,5-c]pyridin-6-yl}-1,2,4-oxadiazol-5(4H)-one (enantiomer 1) | | 552 | 552 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.119 | 31 | 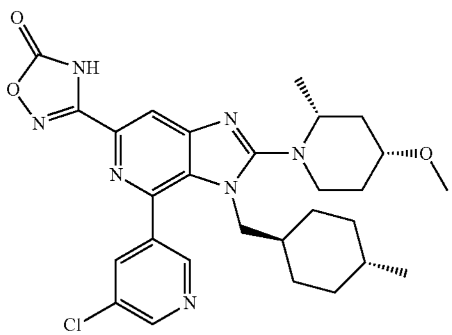 [SMILES: CO[C@@H]1CCN(c2nc3cc(-c4noc(=O)[nH]4)nc(-c4cncc(Cl)c4)c3n2C[C@H]2CC[C@H](C)CC2)[C@H](C)C1] | 3-{4-(5-chloropyridin-3-yl)-2-[cis-4-methoxy-2-methylpiperidin-1-yl]-3-[(trans-4-methylcyclohex-yl)methyl]-3H-imidazo[4,5-c]pyridin-6-yl}-1,2,4-oxadiazol-5(4H)-one (enantiomer 2) | | 552 | 552 |
| 3.120 | 32 | 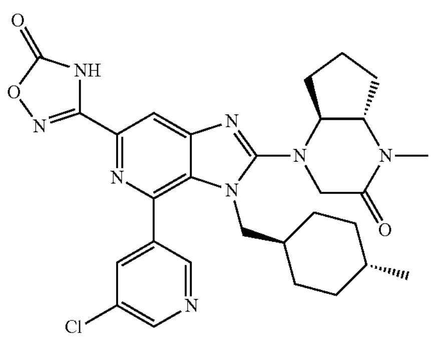 [SMILES: CN1C(=O)CN(c2nc3cc(-c4noc(=O)[nH]4)nc(-c4cncc(Cl)c4)c3n2C[C@H]2CC[C@H](C)CC2)[C@H]2CCC[C@@H]21] | (4aS,7aS)-4-[4-(5-chloropyridin-3-yl)-3-[(trans-4-methylcyclohex-yl)methyl]-6-(5-oxo-4,5-dihydro-1,2,4-oxadiazol-3-yl)-3H-imidazo[4,5-c]pyridin-2-yl]-1-methyloctahydro-2H-cyclopenta[b]-pyrazin-2-one | | 577 | 577 |
| 3.121 | 9 | 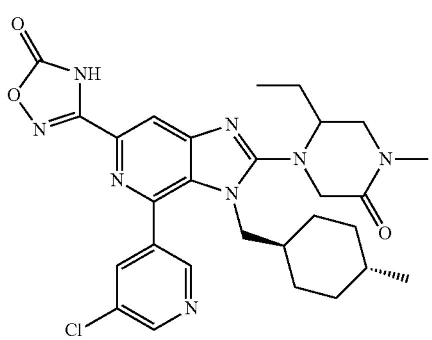 [SMILES: CCC1CN(C)C(=O)CN1c1nc2cc(-c3noc(=O)[nH]3)nc(-c3cncc(Cl)c3)c2n1C[C@H]1CC[C@H](C)CC1] | 4-[4-(5-chloropyridin-3-yl)-3-[(trans-4-methylcyclohex-yl)methyl]-6-(5-oxo-4,5-dihydro-1,2,4-oxadiazol-3-yl)-3H-imidazo[4,5-c]pyridin-2-yl]-5-ethyl-1-methylpiperazin-2-one (racemic) | | 565 | 565 |
| 3.122 | 6 | 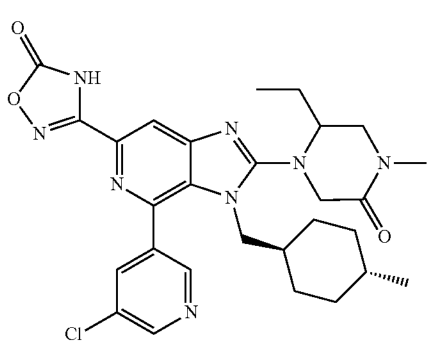 [SMILES: CCC1CN(C)C(=O)CN1c1nc2cc(-c3noc(=O)[nH]3)nc(-c3cncc(Cl)c3)c2n1C[C@H]1CC[C@H](C)CC1] | 4-[4-(5-chloropyridin-3-yl)-3-[(trans-4-methylcyclohex-yl)methyl]-6-(5-oxo-4,5-dihydro-1,2,4-oxadiazol-3-yl)-3H-imidazo[4,5-c]pyridin-2-yl]-5-ethyl-1-methylpiperazin-2-one (enantiomer 1) | | 565 | 565 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.123 | 25 | 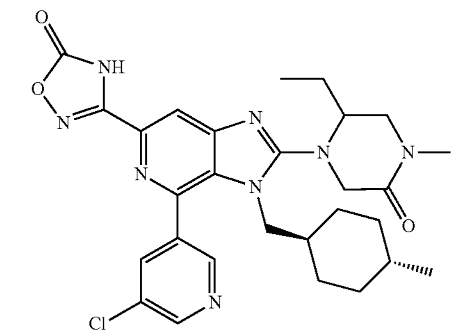 [SMILES: CCC1CN(C)C(=O)CN1c1nc2cc(-c3noc(=O)[nH]3)nc(-c3cncc(Cl)c3)c2n1C[C@H]1CC[C@H](C)CC1] | 4-[4-(5-chloropyridin-3-yl)-3-[(trans-4-methylcyclohex-yl)methyl]-6-(5-oxo-4,5-dihydro-1,2,4-oxadiazol-3-yl)-3H-imidazo[4,5-c]pyridin-2-yl]-5-ethyl-1-methylpiperazin-2-one (enantiomer 2) | | 565 | 565 |
| 3.124 | 29 | 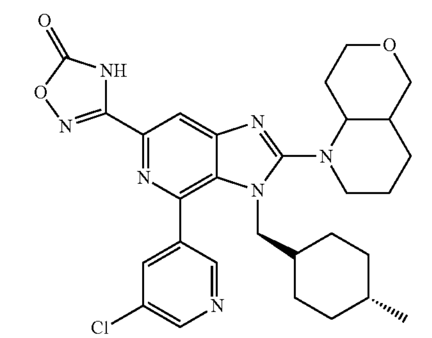 | 3-{4-(5-chloropyridin-3-yl)-2-(hexahydro-2H-pyrano[4,3-b]pyridin-1(5H)-yl)-3-[(trans-4-methylcyclohex-yl)methyl]-3H-imidazo[4,5-c]pyridin-6-yl}-1,2,4-oxadiazol-5(4H)-one (enantiomer 1) | | 564 | 564 |
| 3.125 | 8 | 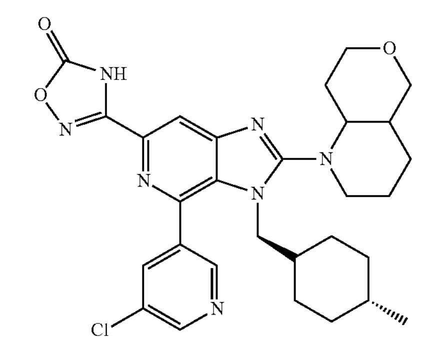 | 3-{4-(5-chloropyridin-3-yl)-2-(hexahydro-2H-pyrano[4,3-b]pyridin-1(5H)-yl)-3-[(trans-4-methylcyclohex-yl)methyl]-3H-imidazo[4,5-c]pyridin-6-yl}-1,2,4-oxadiazol-5(4H)-one (enantiomer 2) | | 564 | 564 |
| 3.126 | 250 | 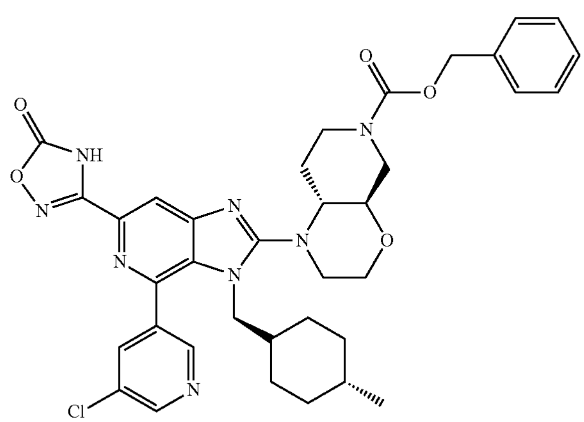 | benzyl (4aR,8aR)-1-[4-(5-chloropyridin-3-yl)-3-[(trans-4-methylcyclohex-yl)methyl]-6-(5-oxo-4,5-dihydro-1,2,4-oxadiazol-3-yl)-3H-imidazo[4,5-c]pyridin-2-yl]octahydro-6H-pyrido[3,4-b][1,4]oxazine-6-carboxylate | | 699 | 699 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.127 | 512 | 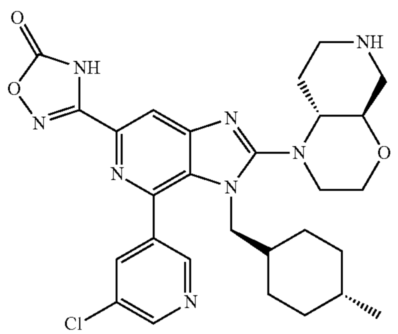 | 3-{4-(5-chloropyridin-3-yl)-3-[(trans-4-methylcyclohex-yl)methyl]-2-[(4aR,8aR)-octahydro-1H-pyrido[3,4-b][1,4]oxazin-1-yl]-3H-imidazo[4,5-c]pyridin-6-yl}-1,2,4-oxadiazol-5(4H)-one | TFA | 565 | 565 |
| 3.128 | 129 | 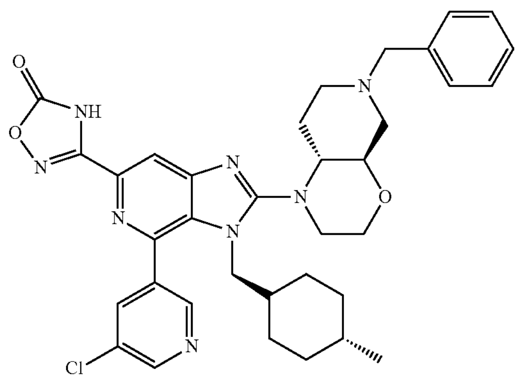 | 3-{2-[(4aR,8aR)-6-benzyloctahydro-1H-pyrido[3,4-b][1,4]oxazin-1-yl]-4-(5-chloropyridin-3-yl)-3-[(trans-4-methylcyclohex-yl)methyl]-3H-imidazo[4,5-c]pyridin-6-yl}-1,2,4-oxadiazol-5(4H)-one | TFA | 655 | 655 |
| 3.129 | 14 | 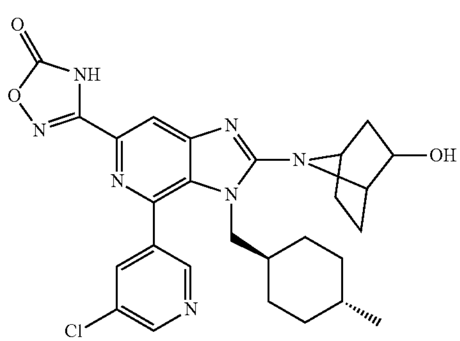 [SMILES: C[C@H]1CC[C@H](Cn2c(N3C4CCC3C(O)C4)nc3cc(-c4noc(=O)[nH]4)nc(-c4cncc(Cl)c4)c32)CC1] | 3-{4-(5-chloropyridin-3-yl)-2-(2-hydroxy-7-azabicyclo[2.2.1]hept-7-yl)-3-[(trans-4-methylcyclohex-yl)methyl]-3H-imidazo[4,5-c]pyridin-6-yl}-1,2,4-oxadiazol-5(4H)-one | TFA | 536 | 536 |
| 3.130 | 14 | 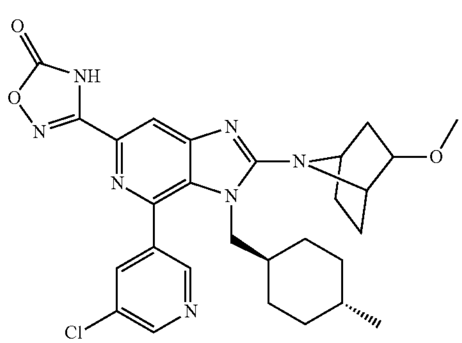 [SMILES: COC1CC2CCC1N2c1nc2cc(-c3noc(=O)[nH]3)nc(-c3cncc(Cl)c3)c2n1C[C@H]1CC[C@H](C)CC1] | 3-{4-(5-chloropyridin-3-yl)-2-(2-methoxy-7-azabicyclo[2.2.1]hept-7-yl)-3-[(trans-4-methylcyclohex-yl)methyl]-3H-imidazo[4,5-c]pyridin-6-yl}-1,2,4-oxadiazol-5(4H)-one (enantiomer 1) | | 550 | 550 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.131 | 9 | 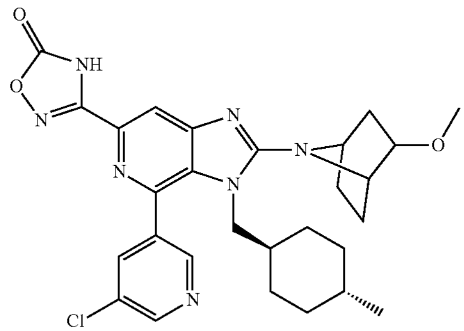 | 3-{4-(5-chloropyridin-3-yl)-2-(2-methoxy-7-azabicyclo[2.2.1]-hept-7-yl)-3-[(trans-4-methylcyclohex-yl)methyl]-3H-imidazo[4,5-c]pyridin-6-yl}-1,2,4-oxadiazol-5(4H)-one (enantiomer 2) | | 550 | 550 |
| 3.132 | 1 | 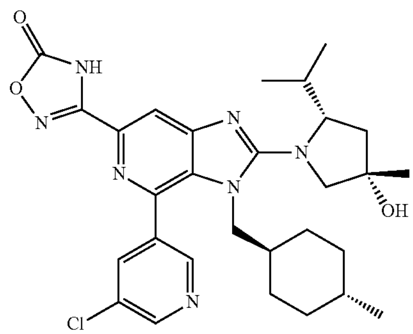 [SMILES: CC(C)[C@@H]1C[C@](C)(O)CN1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(2S,4S)-4-hydroxy-4-methyl-2-(1-methylethyl)-pyrrolidin-1-yl]-3-[(trans-4-methylcyclohex-yl)methyl]-3H-imidazo[4,5-c]pyridin-6-yl}-1,2,4-oxadiazol-5(4H)-one | | 566 | 566 |
| 3.133 | 3 | 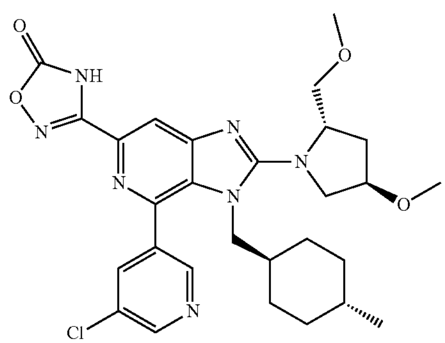 [SMILES: COC[C@@H]1C[C@@H](OC)CN1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(2S,4R)-4-methoxy-2-(methoxymethyl)-pyrrolidin-1-yl]-3-[(trans-4-methylcyclohex-yl)methyl]-3H-imidazo[4,5-c]pyridin-6-yl}-1,2,4-oxadiazol-5(4H)-one | TFA | 568 | 568 |
| 3.134 | 28 | 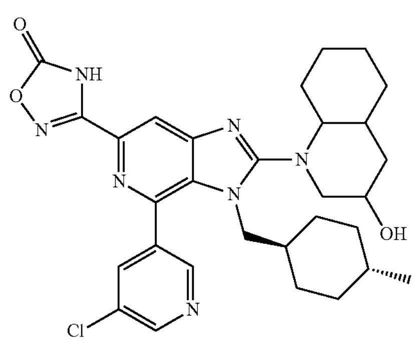 [SMILES: C[C@H]1CC[C@H](Cn2c(N3CC(O)CC4CCCCC43)nc3cc(-c4noc(=O)[nH]4)nc(-c4cncc(Cl)c4)c32)CC1] | 3-{4-(5-chloropyridin-3-yl)-2-(3-hydroxyoctahydro-quinolin-1(2H)-yl)-3-[(trans-4-methylcyclohex-yl)methyl]-3H-imidazo[4,5-c]pyridin-6-yl}-1,2,4-oxadiazol-5(4H)-one (stereoisomer 1) | TFA | 578 | 578 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.135 | 3 | 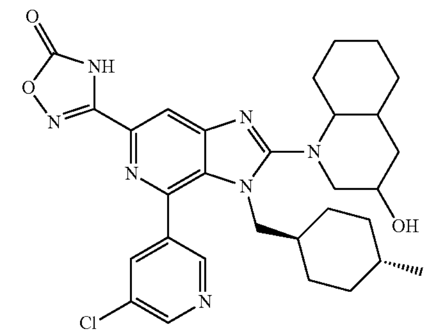 [SMILES: C[C@H]1CC[C@H](Cn2c(N3CC(O)CC4CCCCC43)nc3cc(-c4noc(=O)[nH]4)nc(-c4cncc(Cl)c4)c32)CC1] | 3-{4-(5-chloropyridin-3-yl)-2-(3-hydroxyoctahydroquinolin-1(2H)-yl)-3-[(trans-4-methylcyclohexyl)methyl]-3H-imidazo[4,5-c]pyridin-6-yl}-1,2,4-oxadiazol-5(4H)-one (stereoisomer 2) | TFA | 578 | 578 |
| 3.136 | <1 | 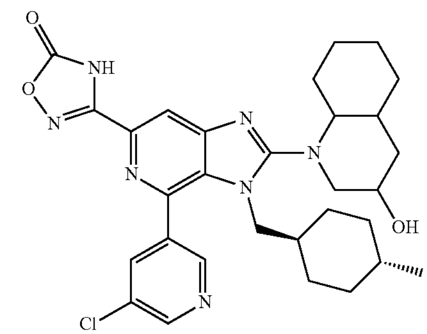 [SMILES: C[C@H]1CC[C@H](Cn2c(N3CC(O)CC4CCCCC43)nc3cc(-c4noc(=O)[nH]4)nc(-c4cncc(Cl)c4)c32)CC1] | 3-{4-(5-chloropyridin-3-yl)-2-(3-hydroxyoctahydroquinolin-1(2H)-yl)-3-[(trans-4-methylcyclohexyl)methyl]-3H-imidazo[4,5-c]pyridin-6-yl}-1,2,4-oxadiazol-5(4H)-one (stereoisomer 3) | TFA | 578 | 578 |
| 3.137 | 5 | 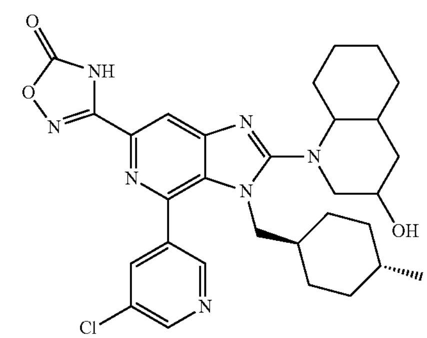 [SMILES: C[C@H]1CC[C@H](Cn2c(N3CC(O)CC4CCCCC43)nc3cc(-c4noc(=O)[nH]4)nc(-c4cncc(Cl)c4)c32)CC1] | 3-{4-(5-chloropyridin-3-yl)-2-(3-hydroxyoctahydroquinolin-1(2H)-yl)-3-[(trans-4-methylcyclohexyl)methyl]-3H-imidazo[4,5-c]pyridin-6-yl}-1,2,4-oxadiazol-5(4H)-one (stereoisomer 4) | TFA | 578 | 578 |
| 3.138 | 2 | 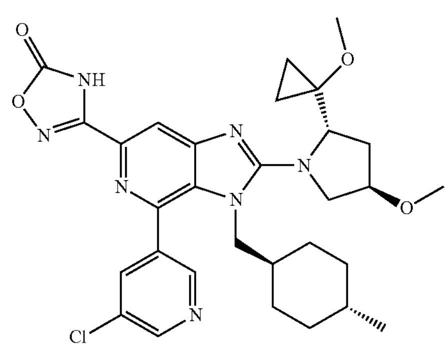 [SMILES: CO[C@@H]1C[C@@H](C2(OC)CC2)N(c2nc3cc(-c4noc(=O)[nH]4)nc(-c4cncc(Cl)c4)c3n2C[C@H]2CC[C@H](C)CC2)C1] | 3-{4-(5-chloropyridin-3-yl)-2-[(2S,4R)-4-methoxy-2-(1-methoxycyclopropyl)-pyrrolidin-1-yl]-3-[(trans-4-methylcyclohexyl)methyl]-3H-imidazo[4,5-c]pyridin-6-yl}-1,2,4-oxadiazol-5(4H)-one | TFA | 594 | 594 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.139 | 10 | 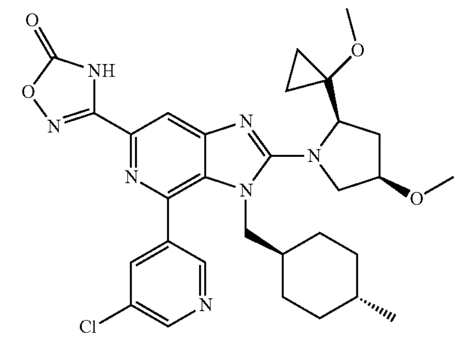 [SMILES: CO[C@@H]1C[C@H](C2(OC)CC2)N(c2nc3cc(-c4noc(=O)[nH]4)nc(-c4cncc(Cl)c4)c3n2C[C@H]2CC[C@H](C)CC2)C1] | 3-{4-(5-chloropyridin-3-yl)-2-[(2R,4R)-4-methoxy-2-(1-methoxycyclopropyl)-pyrrolidin-1-yl]-3-[(trans-4-methylcyclohex-yl)methyl]-3H-imidazo[4,5-c]pyridin-6-yl}-1,2,4-oxadiazol-5(4H)-one | TFA | 594 | 594 |
| 3.140 | 9 | 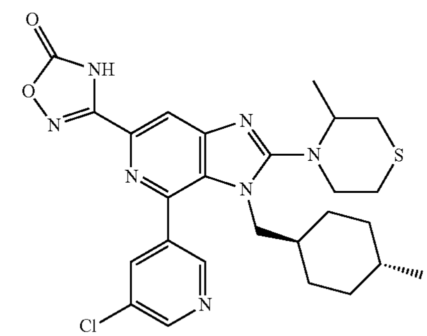 [SMILES: CC1CSCCN1c1nc2cc(-c3noc(=O)[nH]3)nc(-c3cncc(Cl)c3)c2n1C[C@H]1CC[C@H](C)CC1] | 3-[4-(5-chloropyridin-3-yl)-3-[(trans-4-methylcyclohex-yl)methyl]-2-(3-methylthio-morpholin-4-yl)-3H-imidazo[4,5-c]pyridin-6-yl]-1,2,4-oxadiazol-5(4H)-one (racemic) | TFA | 540 | 540 |
| 3.141 | 1 | 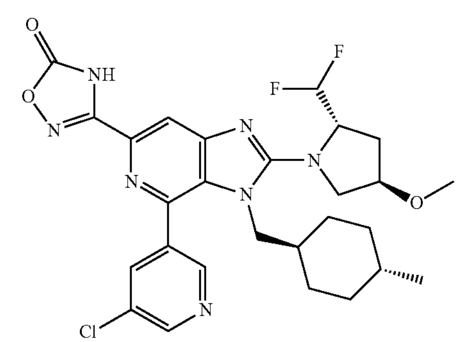 [SMILES: CO[C@@H]1C[C@@H](C(F)F)N(c2nc3cc(-c4noc(=O)[nH]4)nc(-c4cncc(Cl)c4)c3n2C[C@H]2CC[C@H](C)CC2)C1] | 3-{4-(5-chloropyridin-3-yl)-2-[(2S,4R)-2-(difluoromethyl)-4-methoxypyrrolidin-1-yl]-3-[(trans-4-methylcyclohex-yl)methyl]-3H-imidazo[4,5-c]pyridin-6-yl}-1,2,4-oxadiazol-5(4H)-one | TFA | 574 | 574 |
| 3.142 | 1 | 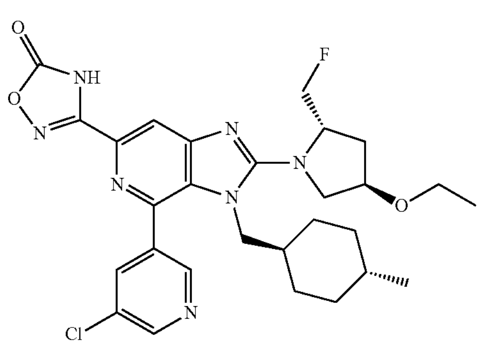 [SMILES: CCO[C@@H]1C[C@@H](CF)N(c2nc3cc(-c4noc(=O)[nH]4)nc(-c4cncc(Cl)c4)c3n2C[C@H]2CC[C@H](C)CC2)C1] | 3-{4-(5-chloropyridin-3-yl)-2-[(2S,4R)-4-ethoxy-2-(fluoromethyl)-pyrrolidin-1-yl]-3-[(trans-4-methylcyclohex-yl)methyl]-3H-imidazo[4,5-c]pyridin-6-yl}-1,2,4-oxadiazol-5(4H)-one | TFA | 570 | 570 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.143 | 4 | 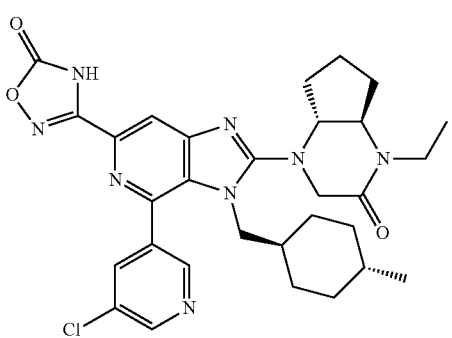 [SMILES: CCN1C(=O)CN(c2nc3cc(-c4noc(=O)[nH]4)nc(-c4cncc(Cl)c4)c3n2C[C@H]2CC[C@H](C)CC2)[C@@H]2CCC[C@H]21] | (4aR,7aR)-4-[4-(5-chloropyridin-3-yl)-3-[(trans-4-methylcyclohex-yl)methyl]-6-(5-oxo-4,5-dihydro-1,2,4-oxadiazol-3-yl)-3H-imidazo[4,5-c]pyridin-2-yl]-1-ethyloctahydro-2H-cyclopenta[b]-pyrazin-2-one | TFA | 591 | 591 |
| 3.144 | <1 | 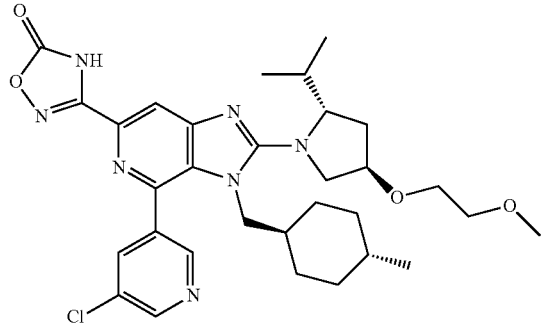 [SMILES: COCCO[C@@H]1C[C@@H](C(C)C)N(c2nc3cc(-c4noc(=O)[nH]4)nc(-c4cncc(Cl)c4)c3n2C[C@H]2CC[C@H](C)CC2)C1] | 3-{4-(5-chloropyridin-3-yl)-2-[(2S,4R)-4-(2-methoxyethoxy)-2-(1-methylethyl)-pyrrolidin-1-yl]-3-[(trans-4-methylcyclohex-yl)methyl]-3H-imidazo[4,5-c]pyridin-6-yl}-1,2,4-oxadiazol-5(4H)-one | TFA | 610 | 610 |
| 3.145 | 1 | 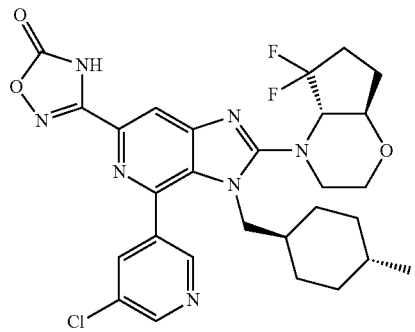 [SMILES: C[C@H]1CC[C@H](Cn2c(N3CCO[C@@H]4CCC(F)(F)[C@H]43)nc3cc(-c4noc(=O)[nH]4)nc(-c4cncc(Cl)c4)c32)CC1] | 3-{4-(5-chloropyridin-3-yl)-2-[(trans)-5,5-difluorohexa-hydrocyclo-penta[b][1,4]oxazin-4(4aH)-yl]-3-[(trans-4-methylcyclohex-yl)methyl]-3H-imidazo[4,5-c]pyridin-6-yl}-1,2,4-oxadiazol-5(4H)-one (racemic) | TFA | 586 | 586 |
| 3.146 | 1 | 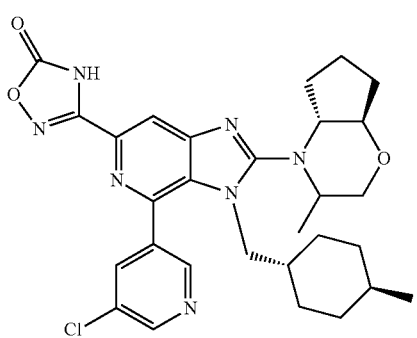 [SMILES: CC1CO[C@@H]2CCC[C@H]2N1c1nc2cc(-c3noc(=O)[nH]3)nc(-c3cncc(Cl)c3)c2n1C[C@H]1CC[C@H](C)CC1] | 3-{4-(5-chloro pyridin-3-yl)-3-[(trans-4-methylcyclohex-yl)methyl]-2-[(trans)-3-methylhexahydro-cyclopenta[b]-[1,4]oxazin-4(4aH)-yl]-3H-imidazo[4,5-c]pyridin-6-yl}-1,2,4-oxadiazol-5(4H)-one (racemic; major diastereomer) | TFA | 564 | 564 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.147 | 1 | 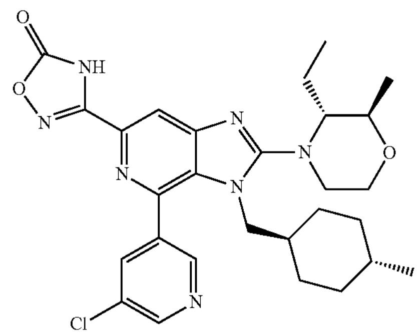 [SMILES: CC[C@@H]1[C@@H](C)OCCN1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(2R,3R)-3-ethyl-2-methylmorpholin-4-yl]-3-[(trans-4-methylcyclohex-yl)methyl]-3H-imidazo[4,5-c]pyridin-6-yl}-1,2,4-oxadiazol-5(4H)-one | | 552 | 552 |
| 3.148 | 2 | 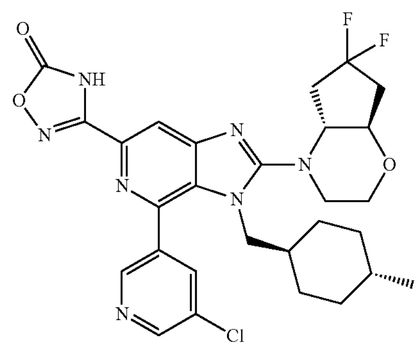 [SMILES: C[C@H]1CC[C@H](Cn2c(N3CCO[C@@H]4CC(F)(F)C[C@H]43)nc3cc(-c4noc(=O)[nH]4)nc(-c4cncc(Cl)c4)c32)CC1] | 3-{4-(5-chloropyridin-3-yl)-2-[(trans)-6,6-difluorohexa-hydrocyclopenta[b]-[1,4]oxazin-4(4aH)-yl]-3-[(trans-4-methylcyclohex-yl)methyl]-3H-imidazo[4,5-c]pyridin-6-yl}-1,2,4-oxadiazol-5(4H)-one (enantiomer 1) | | 586 | 586 |
| 3.149 | 130 | 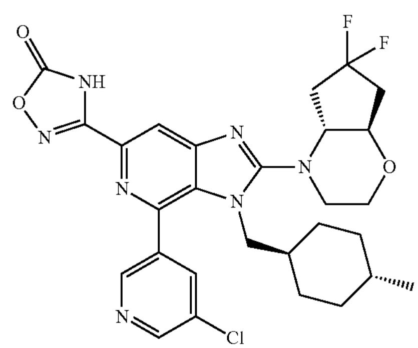 [SMILES: C[C@H]1CC[C@H](Cn2c(N3CCO[C@@H]4CC(F)(F)C[C@H]43)nc3cc(-c4noc(=O)[nH]4)nc(-c4cncc(Cl)c4)c32)CC1] | 3-{4-(5-chloropyridin-3-yl)-2-[(trans)-6,6-difluorohexa-hydrocyclopenta[b]-[1,4]oxazin-4(4aH)-yl]-3-[(trans-4-methylcyclohex-yl)methyl]-3H-imidazo[4,5-c]pyridin-6-yl}-1,2,4-oxadiazol-5(4H)-one (enantiomer 2) | | 586 | 586 |
| 3.150 | 1 | 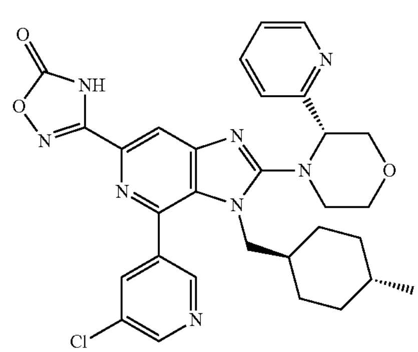 [SMILES: C[C@H]1CC[C@H](Cn2c(N3CCOC[C@H]3c3ccccn3)nc3cc(-c4noc(=O)[nH]4)nc(-c4cncc(Cl)c4)c32)CC1] | 3-{4-(5-chloropyridin-3-yl)-3-[(trans-4-methylcyclohex-yl)methyl]-2-[(3R)-3-pyridin-2-ylmorpholin-4-yl]-3H-imidazo[4,5-c]pyridin-6-yl}-1,2,4-oxadiazol-5(4H)-one | | 587 | 587 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.151 | 21 | 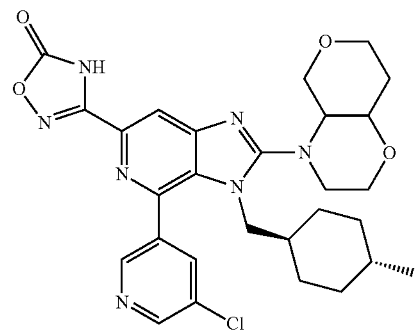 [SMILES: C[C@H]1CC[C@H](Cn2c(N3CCOC4CCOCC43)nc3cc(-c4noc(=O)[nH]4)nc(-c4cncc(Cl)c4)c32)CC1] | 3-{4-(5-chloropyridin-3-yl)-2-(hexahydro-4H,5H-pyrano[4,3-b][1,4]oxazin-4-yl)-3-[(trans-4-methylcyclohex-yl)methyl]-3H-imidazo[4,5-c]pyridin-6-yl}-1,2,4-oxadiazol-5(4H)-one | | 566 | 566 |
| 3.152 | 18 | 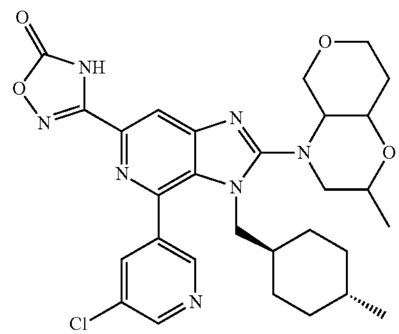 [SMILES: CC1CN(c2nc3cc(-c4noc(=O)[nH]4)nc(-c4cncc(Cl)c4)c3n2C[C@H]2CC[C@H](C)CC2)C2COCCC2O1] | 3-[4-(5-chloropyridin-3-yl)-3-[(trans-4-methylcyclohex-yl)methyl]-2-(2-methylhexahydro-4H,5H-pyrano[4,3-b][1,4]oxazin-4-yl)-3H-imidazo[4,5-c]pyridin-6-yl]-1,2,4-oxadiazol-5(4H)-one (stereoisomer 1) | | 580 | 580 |
| 3.153 | 63 | 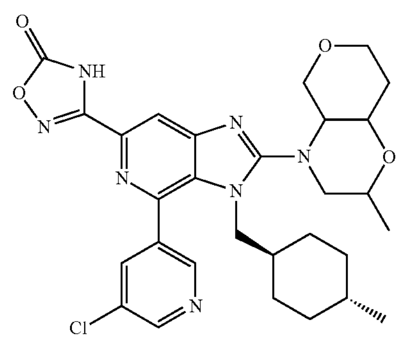 [SMILES: CC1CN(c2nc3cc(-c4noc(=O)[nH]4)nc(-c4cncc(Cl)c4)c3n2C[C@H]2CC[C@H](C)CC2)C2COCCC2O1] | 3-[4-(5-chloropyridin-3-yl)-3-[(trans-4-methylcyclohex-yl)methyl]-2-(2-methylhexahydro-4H,5H-pyrano[4,3-b][1,4]oxazin-4-yl)-3H-imidazo[4,5-c]pyridin-6-yl]-1,2,4-oxadiazol-5(4H)-one (stereoisomer 2) | | 580 | 580 |
| 3.154 | 3 | 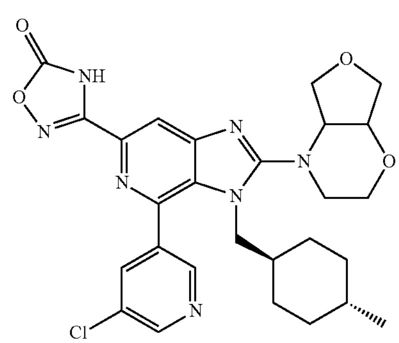 [SMILES: C[C@H]1CC[C@H](Cn2c(N3CCOC4COCC43)nc3cc(-c4noc(=O)[nH]4)nc(-c4cncc(Cl)c4)c32)CC1] | 3-{4-(5-chloropyridin-3-yl)-2-[(trans)-hexahydro-4H-furo[3,4-b][1,4]oxazin-4-yl]-3-[(trans-4-methylcyclohex-yl)methyl]-3H-imidazo[4,5-c]pyridin-6-yl}-1,2,4-oxadiazol-5(4H)-one (enantiomer 1) | | 552 | 552 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.155 | 131 | 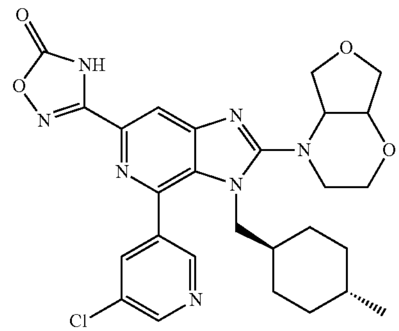 [SMILES: C[C@H]1CC[C@H](Cn2c(N3CCOC4COCC43)nc3cc(-c4noc(=O)[nH]4)nc(-c4cncc(Cl)c4)c32)CC1] | 3-{4-(5-chloropyridin-3-yl)-2-[(trans)-hexahydro-4H-furo[3,4-b][1,4]oxazin-4-yl]-3-[(trans-4-methylcyclohex-yl)methyl]-3H-imidazo[4,5-c]pyridin-6-yl}-1,2,4-oxadiazol-5(4H)-one (enantiomer 2) | | 552 | 552 |
| 3.156 | 1 | 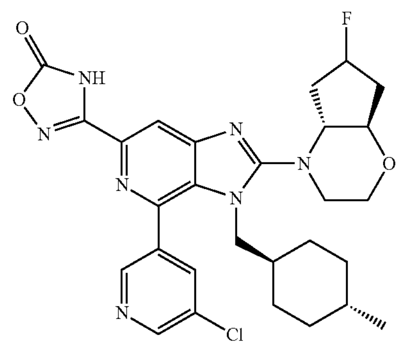 | 3-{4-(5-chloropyridin-3-yl)-2-[(trans)-6-fluorohexahydro-cyclopenta[b]-[1,4]oxazin-4(4aH)-yl]-3-[(trans-4-methylcyclohex-yl)methyl]-3H-imidazo[4,5-c]pyridin-6-yl}-1,2,4-oxadiazol-5(4H)-one (stereoisomer 1) | | 568 | 568 |
| 3.157 | 113 | 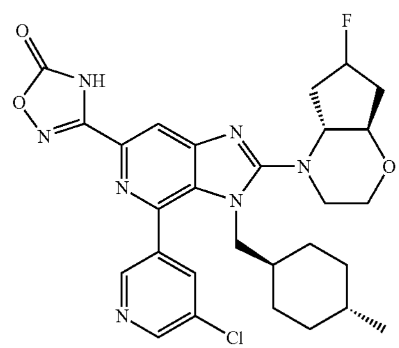 | 3-{4-(5-chloropyridin-3-yl)-2-[(trans)-6-fluorohexahydro-cyclopenta[b]-[1,4]oxazin-4(4aH)-yl]-3-[(trans-4-methylcyclohex-yl)methyl]-3H-imidazo[4,5-c]pyridin-6-yl}-1,2,4-oxadiazol-5(4H)-one (stereoisomer 2) | | 568 | 568 |
| 3.158 | 4 | 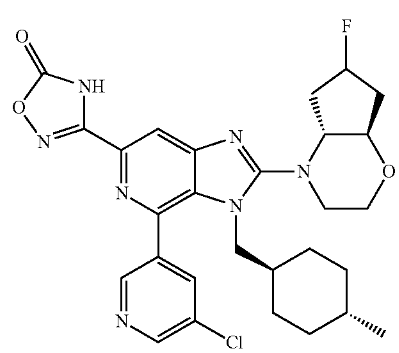 | 3-{4-(5-chloropyridin-3-yl)-2-[(trans)-6-fluorohexahydro-cyclopenta[b]-[1,4]oxazin-4(4aH)-yl]-3-[(trans-4-methylcyclohex-yl)methyl]-3H-imidazo[4,5-c]pyridin-6-yl}-1,2,4-oxadiazol-5(4H)-one (stereoisomer 3) | | 568 | 568 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.159 | 48 | 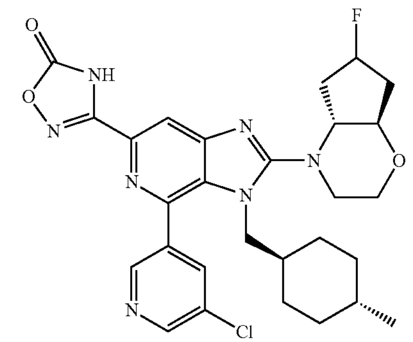 | 3-{4-(5-chloropyridin-3-yl)-2-[(trans)-6-fluorohexahydro-cyclopenta[b]-[1,4]oxazin-4(4aH)-yl]-3-[(trans-4-methylcyclohex-yl)methyl]-3H-imidazo[4,5-c]pyridin-6-yl}-1,2,4-oxadiazol-5(4H)-one (stereoisomer 4) | | 568 | 568 |
| 3.160 | 80 | 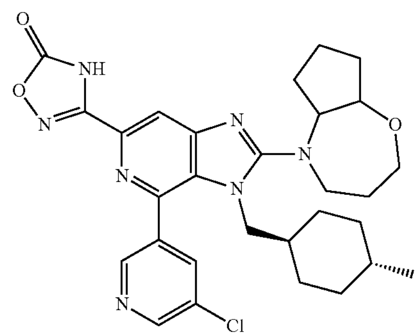 [SMILES: C[C@H]1CC[C@H](Cn2c(N3CCCOC4CCCC43)nc3cc(-c4noc(=O)[nH]4)nc(-c4cncc(Cl)c4)c32)CC1] | 3-{4-(5-chloropyridin-3-yl)-2-(hexahydro-2H-cyclopenta[b]-[1,4]oxazepin-5(5aH)-yl)-3-[(trans-4-methylcyclohex-yl)methyl]-3H-imidazo[4,5-c]pyridin-6-yl}-1,2,4-oxadiazol-5(4H)-one (enantiomer 1) | | 564 | 564 |
| 3.161 | 1 | 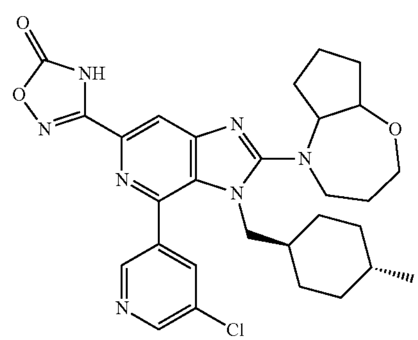 [SMILES: C[C@H]1CC[C@H](Cn2c(N3CCCOC4CCCC43)nc3cc(-c4noc(=O)[nH]4)nc(-c4cncc(Cl)c4)c32)CC1] | 3-{4-(5-chloropyridin-3-yl)-2-(hexahydro-2H-cyclopenta[b]-[1,4]oxazepin-5(5aH)-yl)-3-[(trans-4-methylcyclohex-yl)methyl]-3H-imidazo[4,5-c]pyridin-6-yl}-1,2,4-oxadiazol-5(4H)-one (enantiomer 2) | | 564 | 564 |
| 3.162 | 17 | 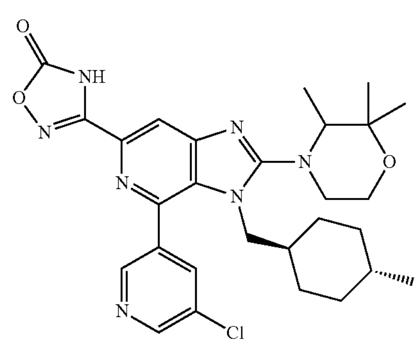 [SMILES: CC1N(c2nc3cc(-c4noc(=O)[nH]4)nc(-c4cncc(Cl)c4)c3n2C[C@H]2CC[C@H](C)CC2)CCOC1(C)C] | 3-[4-(5-chloropyridin-3-yl)-3-[(trans-4-methylcyclohex-yl)methyl]-2-(2,2,3-trimethyl-morpholin-4-yl)-3H-imidazo[4,5-c]pyridin-6-yl]-1,2,4-oxadiazol-5(4H)-one (racemic) | | 552 | 552 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.163 | 3 | 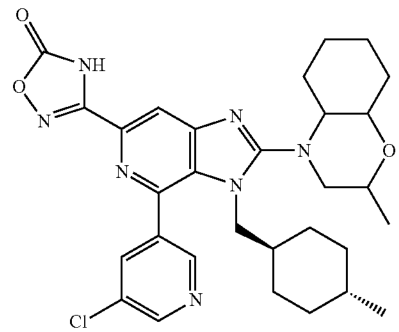 [SMILES: CC1CN(c2nc3cc(-c4noc(=O)[nH]4)nc(-c4cncc(Cl)c4)c3n2C[C@H]2CC[C@H](C)CC2)C2CCCCC2O1] | 3-[4-(5-chloropyridin-3-yl)-3-[(trans-4-methylcyclohex-yl)methyl]-2-(2-methyloctahydro-4H-1,4-benzoxazin-4-yl)-3H-imidazo[4,5-c]pyridin-6-yl]-1,2,4-oxadiazol-5(4H)-one | | 578 | 578 |
| 3.164 | 5 | 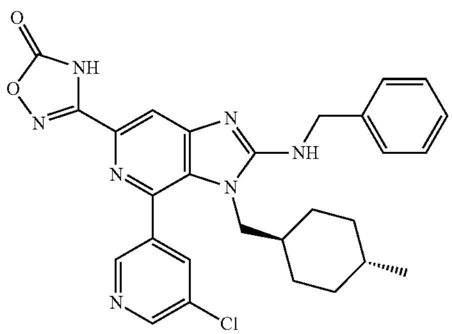 [SMILES: C[C@H]1CC[C@H](Cn2c(NCc3ccccc3)nc3cc(-c4noc(=O)[nH]4)nc(-c4cncc(Cl)c4)c32)CC1] | 3-{2-(benzylamino)-4-(5-chloropyridin-3-yl)-3-[(trans-4-methylcyclohex-yl)methyl]-3H-imidazo[4,5-c]pyridin-6-yl}-1,2,4-oxadiazol-5(4H)-one | | 530 | 530 |
| 3.165 | 14 | 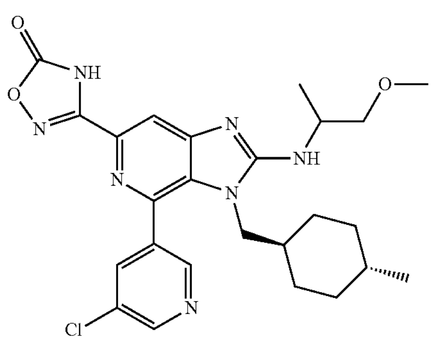 [SMILES: COCC(C)Nc1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(2-methoxy-1-methylethyl)-amino]-3-[(trans-4-methylcyclohex-yl)methyl]-3H-imidazo[4,5-c]pyridin-6-yl}-1,2,4-oxadiazol-5(4H)-one | | 512 | 512 |
| 3.166 | 19 | 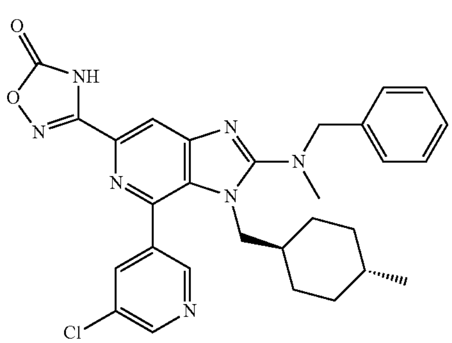 [SMILES: CN(Cc1ccccc1)c1nc2cc(-c3noc(=O)[nH]3)nc(-c3cncc(Cl)c3)c2n1C[C@H]1CC[C@H](C)CC1] | 3-{2-[benzyl(methyl)amino]-4-(5-chloropyridin-3-yl)-3-[(trans-4-methylcyclohex-yl)methyl]-3H-imidazo[4,5-c]pyridin-6-yl}-1,2,4-oxadiazol-5(4H)-one | | 544 | 544 |

TABLE 3-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.167 | 8 | 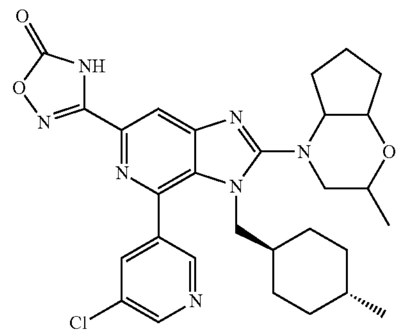 [SMILES: CC1CN(c2nc3cc(-c4noc(=O)[nH]4)nc(-c4cncc(Cl)c4)c3n2C[C@H]2CC[C@H](C)CC2)C2CCCC2O1] | 3-[4-(5-chloropyridin-3-yl)-3-[(trans-4-methylcyclohex-yl)methyl]-2-(2-methylhexahydro-cyclopenta[b]-[1,4]oxazin-4(4aH)-yl)-3H-imidazo[4,5-c]pyridin-6-yl]-1,2,4-oxadiazol-5(4H)-one (stereoisomer 1) | | 564 | 564 |
| 3.168 | 1 | 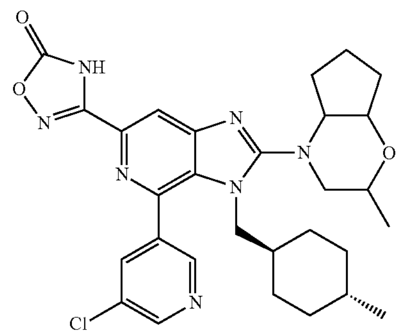 [SMILES: CC1CN(c2nc3cc(-c4noc(=O)[nH]4)nc(-c4cncc(Cl)c4)c3n2C[C@H]2CC[C@H](C)CC2)C2CCCC2O1] | 3-[4-(5-chloropyridin-3-yl)-3-[(trans-4-methylcyclohex-yl)methyl]-2-(2-methylhexahydro-cyclopenta[b]-[1,4]oxazin-4(4aH)-yl)-3H-imidazo[4,5-c]pyridin-6-yl]-1,2,4-oxadiazol-5(4H)-one (stereoisomer 2) | | 564 | 564 |
| 3.169 | 17 | 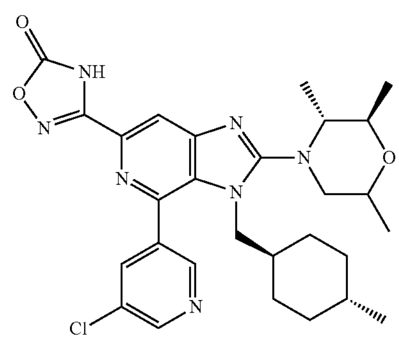 [SMILES: CC1CN(c2nc3cc(-c4noc(=O)[nH]4)nc(-c4cncc(Cl)c4)c3n2C[C@H]2CC[C@H](C)CC2)[C@H](C)[C@@H](C)O1] | 3-{4-(5-chloropyridin-3-yl)-3-[(trans-4-methylcyclohex-yl)methyl]-2-[(2R,3R)-2,3,6-trimethylmorpholin-4-yl]-3H-imidazo[4,5-c]pyridin-6-yl}-1,2,4-oxadiazol-5(4H)-one (diastereomer 1) | | 552 | 552 |
| 3.170 | 1 | 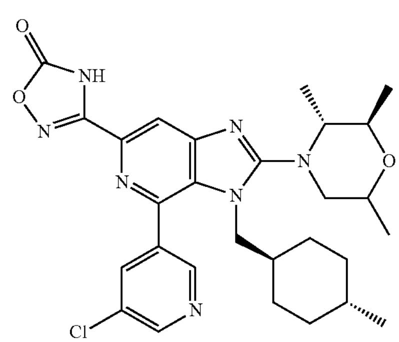 [SMILES: CC1CN(c2nc3cc(-c4noc(=O)[nH]4)nc(-c4cncc(Cl)c4)c3n2C[C@H]2CC[C@H](C)CC2)[C@H](C)[C@@H](C)O1] | 3-{4-(5-chloropyridin-3-yl)-3-[(trans-4-methylcyclohex-yl)methyl]-2-[(2R,3R)-2,3,6-trimethylmorpholin-4-yl]-3H-imidazo[4,5-c]pyridin-6-yl}-1,2,4-oxadiazol-5(4H)-one (diastereomer 2) | | 552 | 552 |

TABLE 3-continued

| Ex. | FRET IC$_{50}$ (nM) | Chemical Name | Salt | [M + H]$^+$ Calc'd | [M + H]$^+$ Obsv'd |
|---|---|---|---|---|---|
| 3.171 | 42 | 3-{4-(5-chloropyridin-3-yl)-2-[(2-methoxy-1-methylethyl)-(methyl)amino]-3-[(trans-4-methylcyclohex-yl)methyl]-3H-imidazo[4,5-c]pyridin-6-yl}-1,2,4-oxadiazol-5(4H)-one (racemic) | | 526 | 526 |
| 3.172 | 23 | 3-[4-(5-chloropyridin-3-yl)-3-[(trans-4-methylcyclohex-yl)methyl]-2-(pyridin-2-ylamino)-3H-imidazo[4,5-c]pyridin-6-yl]-1,2,4-oxadiazol-5(4H)-one | TFA | 517 | 517 |
| 3.173 | 40 | 4-(5-chloropyridin-3-yl)-3-[(trans-4-methylcyclohex-yl)methyl]-2-(pyridin-2-ylamino)-3H-imidazo[4,5-c]pyridine-6-carboxylic acid | TFA | 477 | 477 |
| 3.174 | 132 | 3-{4-(5-chloropyridin-3-yl)-3-[(trans-4-methylcyclohex-yl)methyl]-2-[methyl(phenyl)amino]-3H-imidazo[4,5-c]pyridin-6-yl}-1,2,4-oxadiazol-5(4H)-one | TFA | 530 | 530 |

TABLE 3-continued
| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 3.175 | 86 | 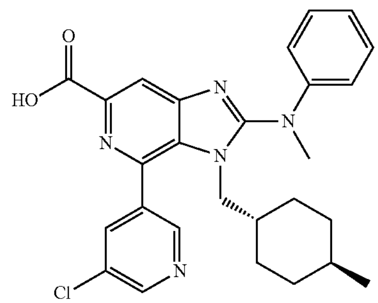 [SMILES: CN(c1ccccc1)c1nc2cc(C(=O)O)nc(-c3cncc(Cl)c3)c2n1C[C@H]1CC[C@H](C)CC1] | 4-(5-chloropyridin-3-yl)-3-[(trans-4-methylcyclohexyl)methyl]-2-[methyl(phenyl)amino]-3H-imidazo[4,5-c]pyridine-6-carboxylic acid | TFA | 490 | 490 |
| 3.176 | 18 | 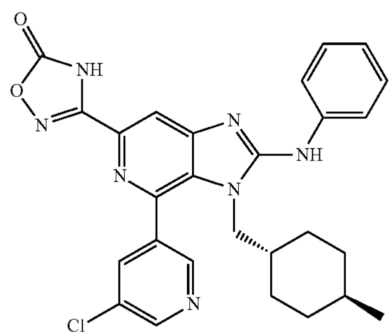 [SMILES: C[C@H]1CC[C@H](Cn2c(Nc3ccccc3)nc3cc(-c4noc(=O)[nH]4)nc(-c4cncc(Cl)c4)c32)CC1] | 3-[4-(5-chloropyridin-3-yl)-3-[(trans-4-methylcyclohexyl)methyl]-2-(phenylamino)-3H-imidazo[4,5-c]pyridin-6-yl]-1,2,4-oxadiazol-5(4H)-one | | 516 | 516 |
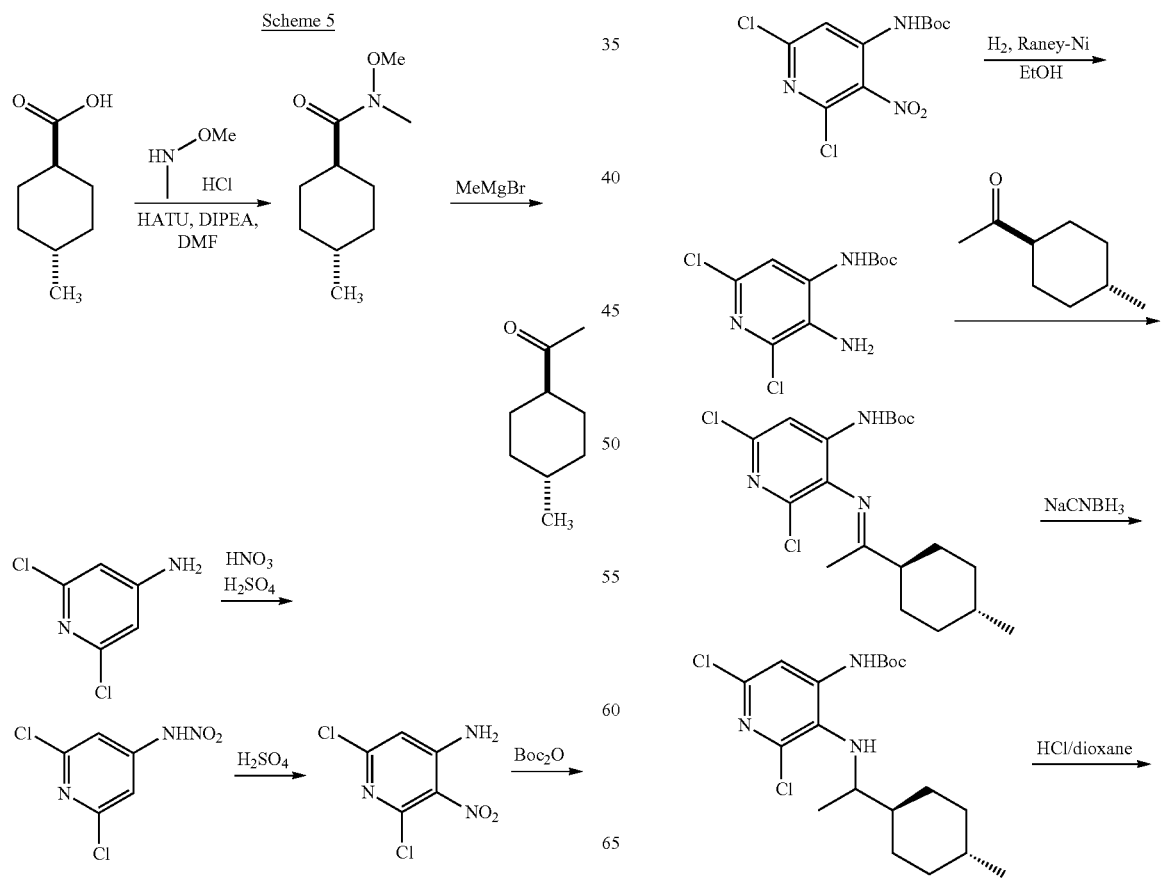
Scheme 5

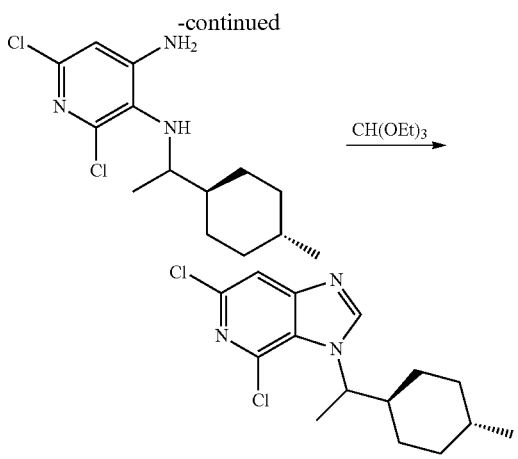

was added slowly. The mixture was stirred at room temperature for 3 h. TLC (petroleum ether/ethyl acetate=5:1) showed the reaction was complete. The reaction was diluted with water and extracted with ethyl acetate. The organic layer was washed with water twice, washed with brine, dried over Na$_2$SO$_4$ and concentrated to give crude trans-N-methoxy-N,4-dimethylcyclohexanecarboxamide, which was used for the next step without further purification.

Step 2: MeMgBr (352 mL, 1.1 mol, 3 mol/L) was added dropwise slowly to a stirred solution of trans-N-methoxy-N,4-dimethylcyclohexanecarboxamide (130 g, 0.7 mol) in THF (1.2 L) at 0° C. The mixture was stirred at room temperature for 2 hours. TLC showed no starting material (petroleum ether/ethyl acetate=5:1) left. The mixture was cooled to 0-5° C., and quenched by the addition of saturated NH$_4$Cl (0.1 L) and H$_2$O (2 L). The mixture was extracted with ethyl acetate twice. The combined organic layer was washed with brine and dried over Na$_2$SO$_4$, filtered and concentrated under reduced pressure to give crude 1-(trans-4-methylcyclohexyl)

Scheme 6

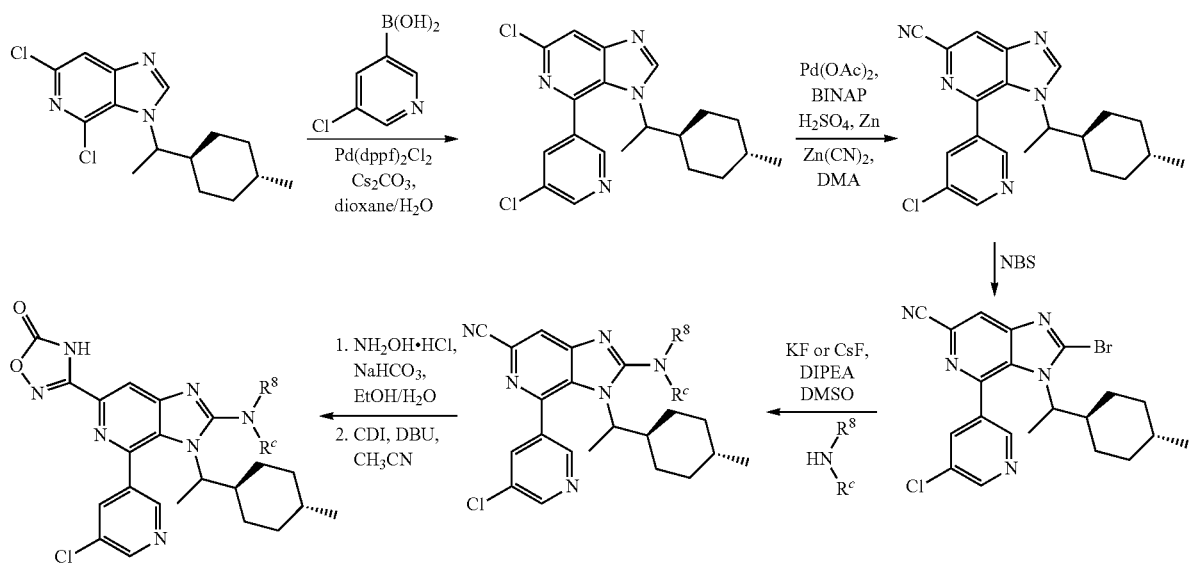

ethanone, which was used for the next step without further purification. $^1$H NMR (400 MHz, CDCl$_3$) δ: 2.27-2.19 (m, 1H), 2.10 (s, 3H), 1.90 (d, J=12.8 Hz, 2H), 1.70 (d, J=12.8 Hz, 2H), 1.35-1.23 (m, 3H), 0.96-0.85 (m, 5H).

Preparative Example 4.1

1-(trans-4-methylcyclohexyl)ethanone

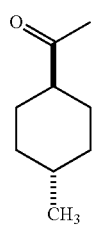

Step 1: To a solution of trans-4-methylcyclohexanecarboxylic acid (100 g, 0.70 mol) in DMF (1.2 L) were added HATU (294 g, 0.77 mol) and DIPEA (273 g, 2.1 mol) at room temperature. After stirring for 0.5 h, TLC showed no starting material left (petroleum ether/ethyl acetate=5:1). Then N,O-dimethylhydroxylamine hydrochloride (75.5 g, 0.77 mol)

Preparative Example 4.2 tert-butyl (3-amino-2,6-dichloropyridin-4-yl)carbamate

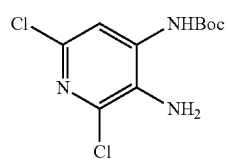 [SMILES: CC(C)(C)OC(=O)Nc1cc(Cl)nc(Cl)c1N]

Step 1: 2,6-dichloropyridin-4-amine (100 g, 0.617 mol) was added slowly to conc. H$_2$SO$_4$ (415 mL) by portion while cooled with an ice bath. The mixture was cooled to 0° C., and nitric acid (250 mL) was added dropwise at 0° C. The mixture was stirred at room temperature for 2 h. TLC (petroleum ether/ethyl acetate=2:1) showed the reaction was complete. The mixture was poured into crushed ice and stirred for 30 min. The resulting precipitate was collected by filtration and washed with water to give crude N-(2,6-dichloropyridin-4-yl)nitramide as a yellow solid, which was used for the next step without further purification.

Step 2: N-(2,6-dichloropyridin-4-yl)nitramide (205 g crude, 0.617 mol) was added carefully to conc. $H_2SO_4$ (800 mL) at room temperature. Then the reaction mixture was stirred at 80° C. for 2 h. TLC (Petroleum ether/ethyl acetate=2:1) showed the reaction was complete. The mixture was cooled to room temperature and poured into crushed ice. The mixture was cooled to 0° C. and neutralized with NaOH and $NH_4OH$. The resulting precipitate was collected by filtration and washed with water. The resulting precipitate was dissolved in ethyl acetate, dried over $Na_2SO_4$ and concentrated to give crude 2,6-dichloro-3-nitropyridin-4-amine, which was used for the next step without further purification. $^1H$ NMR (400 MHz, $CDCl_3$) δ: 7.64 (s, 2H), 6.86 (s, 1H).

Step 3: 2,6-dichloro-3-nitropyridin-4-amine (50 g, 0.24 mol) and $(Boc)_2O$ (78.5 g, 0.36 mol) were dissolved in tetrahydrofuran (0.4 L). Then the mixture was cooled to −70° C. NaHMDS in THF (725 mL, 0.725 mol, 1 mol/L) was added dropwise to the mixture. The resulting mixture was stirred for 2 h at −70° C. TLC (petroleum/ethyl acetate=5:1) showed the reaction was complete. The mixture was poured into ice water and extracted with ethyl acetate. The combined organic layers were washed with water and brine, dried over $Na_2SO_4$, filtered and concentrated under reduced pressure to give crude tert-butyl (2,6-dichloro-3-nitropyridin-4-yl)carbamate as a yellow solid, which was used for the next step without further purification. $^1H$ NMR (400 MHz, $CDCl_3$) δ: 8.27 (s, 1H), 7.78 (s, 1H), 1.38 (s, 9H)

Step 4: tert-Butyl (2,6-dichloro-3-nitropyridin-4-yl)carbamate (65 g, 0.212 mol) was added to a mixture of Raney-Ni (12.5 g) in ethanol (1.5 L) under $H_2$. The mixture was stirred at 50° C. for 3 h. TLC (petroleum/ethyl acetate=5:1) showed that most of the tert-butyl (2,6-dichloro-3-nitropyridin-4-yl)carbamate was consumed. The mixture was filtered, and the filtrate was concentrated to give crude tert-butyl (3-amino-2,6-dichloropyridin-4-yl)carbamate, which was used for the next step without further purification. $^1H$ NMR (400 MHz, $CDCl_3$) δ: 7.84 (s, 1H), 6.85 (s, 1H), 1.54 (s, 9H).

Preparative Example 4.3 4,6-dichloro-3-[1-(trans-4-methylcyclohexyl)ethyl]-3H-imidazo[4,5-c]pyridine

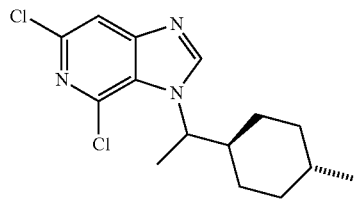 [SMILES: CC([C@H]1CC[C@H](C)CC1)n1cnc2cc(Cl)nc(Cl)c21]

Step 1: p-TsOH.$H_2O$ (3.4 g, 0.018 mol) was added to a mixture of tert-butyl (3-amino-2,6-dichloropyridin-4-yl)carbamate (85 g, 0.306 mol) and 1-(trans-4-methylcyclohexyl)ethanone (64 g, 0.46 mol) in toluene (1.3 L). The mixture was heated to reflux with a Dean-Stark trap for 14 h. TLC (petroleum/ethyl acetate=5:1) showed about ⅔ of tert-butyl (3-amino-2,6-dichloropyridin-4-yl)carbamate was consumed. The solvent was removed under reduced pressure. The residue was purified by column chromatography (petroleum ether) to give crude tert-butyl (2,6-dichloro-3-((1-(trans-4-methylcyclohexyl)ethylidene)amino)pyridin-4-yl)carbamate.

Step 2: $NaCNBH_3$ (100 g, 1.59 mol) was added to a mixture of tert-butyl (2,6-dichloro-3-((1-(trans-4-methylcyclohexyl)ethylidene)amino)pyridin-4-yl)carbamate (80 g, 0.2 mol) and acetic acid (60 mL) in ethanol (1.2 L). The mixture was heated to 50° C. for 4 h. TLC (petroleum ether/ethyl acetate=8:1) showed the reaction was complete. The reaction mixture was cooled down, poured into ice water, and then extracted with ethyl acetate. The combined organic layer was washed with brine, dried over $Na_2SO_4$, filtered and concentrated to give crude tert-butyl (2,6-dichloro-3-((1-(trans-4-methylcyclohexyl)ethyl)amino)pyridin-4-yl)carbamate, which was used for the next step without further purification.

Step 3: Crude tert-butyl (2,6-dichloro-3-((1-(trans-4-methylcyclohexyl)ethyl)amino)pyridin-4-yl)carbamate (70 g, 0.17 mol) was dissolved in a solution of HCl in dioxane (550 mL, 4 mol/L). The mixture was heated to 50° C. for 12 h. TLC (petroleum ether/ethyl acetate=5:1) showed the reaction was complete. White solid appeared. The solvent was removed under reduced pressure. The residue was washed with methyl tertiary butyl ether to give crude 2,6-dichloro-$N^3$-(1-(trans-4-methylcyclohexyl)ethyl)pyridine-3,4-diamine, which was used for the next step without further purification. $^1H$ NMR (400 MHz, DMSO-$d_6$) δ: 6.63 (s, 1H), 3.16-3.13 (m, 1H), 1.84-1.76 (m, 2H), 1.67 (bs, 2H), 1.39 (bs, 1H), 1.25 (bs, 1H), 1.10-0.96 (m, 5H), 0.89-0.81 (m, 5H).

Step 4: A suspension of 2,6-dichloro-$N^3$-(1-(trans-4-methylcyclohexyl)ethyl)pyridine-3,4-diamine (35 g, 0.116 mol) in triethylorthoformate (200 mL, 1.16 mol) was stirred at 100° C. for 3 h. TLC (petroleum ether/ethyl acetate=3/1) showed the reaction was complete. The solvent was removed under reduced pressure. The residue was purified by column chromatography (petroleum ether/ethyl acetate=10:1) to give the crude product, which was washed with a mixture of petroleum ether/ethyl acetate=10:1 to afford 4,6-dichloro-3-[1-(trans-4-methylcyclohexyl)ethyl]-3H-imidazo[4,5-c]pyridine. $^1H$ NMR (400 MHz, DMSO-$d_6$) δ: 8.85 (s, 1H), 7.86 (s, 1H), 4.98 (bs, 1H), 1.76-1.67 (m, 3H), 1.58-1.56 (m, 4H), 1.23-1.20 (m, 2H), 1.07-0.99 (m, 2H), 0.84-0.79 (m, 5H). MS ESI calc'd. for $C_{15}H_{19}Cl_2N_3$ [M+H]$^+$ 312. found 312.

Example 4.1 and Example 4.2

3-{4-(5-chloropyridin-3-yl)-2-[(4aR,7aR)-hexahydrocyclopenta[b][1,4]oxazin-4(4aH)-yl]-3-[(1R)-1-(trans-4-methylcyclohexyl)ethyl]-3H-imidazo[4,5-c]pyridin-6-yl}-1,2,4-oxadiazol-5(4H)-one and 3-{4-(5-chloropyridin-3-yl)-2-[(4aR,7aR)-hexahydrocyclopenta[b][1,4]oxazin-4(4aH)-yl]-3-[(1S)-1-(trans-4-methylcyclohexyl)ethyl]-3H-imidazo[4,5-c]pyridin-6-yl}-1,2,4-oxadiazol-5(4H)-one (diastereoisomer 1 and diastereoisomer 2)

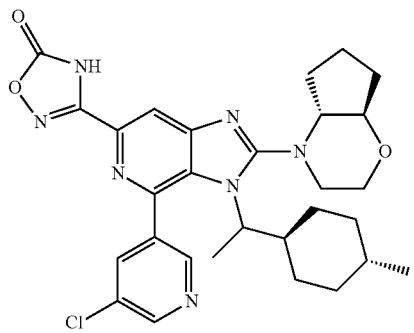

enantiopure diastereomer 1 and

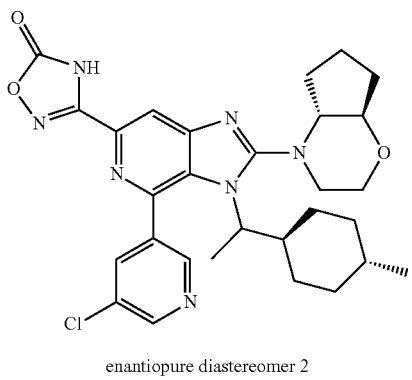 [SMILES: CC([C@H]1CC[C@H](C)CC1)n1c(N2CCO[C@@H]3CCC[C@H]32)nc2cc(-c3noc(=O)[nH]3)nc(-c3cncc(Cl)c3)c21]

enantiopure diastereomer 2

Step 1: Racemic 4,6-dichloro-3-[1-(trans-4-methylcyclohexyl)ethyl]-3H-imidazo[4,5-c]pyridine (Preparative Example 4.3) (5 g, 16 mmol), 5-chloropyridine-3-boronic acid (2.77 g, 17.61 mmol), cesium carbonate (15.65 g, 48 mmol), and 1,1'-Bis(diphenylphosphino)ferrocene-palladium(II)dichloride (1.17 g, 1.6 mmol) were combined in a flask that had been oven-dried and flushed with nitrogen. Dioxane (43 mL) and water (10.6 mL) were added, and the vial was capped and heated to 90° C. for 3 hours. The reaction mixture was cooled to room temperature, diluted with ethyl acetate, and washed with water. The organic layer was washed with brine, dried over sodium sulfate, filtered, and concentrated under reduced pressure. The residue was purified by silica gel chromatography (0-100% ethyl acetate/hexanes, linear gradient) to afford racemic 6-chloro-4-(5-chloropyridin-3-yl)-3-[1-(trans-4-methylcyclohexyl)ethyl]-3H-imidazo[4,5-c]pyridine. MS ESI calc'd. for $C_{20}H_{22}Cl_2N_4$ [M+H]$^+$ 389. found 389.

Step 2: In an oven-dried, nitrogen cooled flask were placed palladium(II) acetate (286 mg, 1.27 mmol) and (R)-(+)-2,2'-Bis(diphenylphosphino)-1,1'-binaphthyl (793 mg, 1.27 mmol). N,N-dimethylacetamide (76 mL) was added and degassed for three minutes with nitrogen (sparge). Sulfuric acid (0.068 mL, 1.27 mmol) was added and degassed for three minutes with nitrogen (sparge). The flask was sealed and heated to 80° C. for 30 minutes. The mixture was cooled to room temperature and added to a separate nitrogen purged flask containing racemic 6-chloro-4-(5-chloropyridin-3-yl)-3-[1-(trans-4-methylcyclohexyl)ethyl]-3H-imidazo[4,5-c]pyridine (4.96 g, 12.7 mmol), zinc cyanide (748 mg, 6.37 mmol), and zinc (83 mg, 1.27 mmol). The flask was purged with nitrogen for five minutes and sealed and heated to 80° C. for 16 hours. The reaction mixture was cooled to room temperature, filtered, diluted with ethyl acetate, and washed with water and brine. The organic layer was dried over sodium sulfate, filtered, and concentrated under reduced pressure. The residue was purified by silica gel chromatography (0-100% ethyl acetate/hexanes, linear gradient) to afford racemic 4-(5-chloropyridin-3-yl)-3-[1-(trans-4-methylcyclohexyl)ethyl]-3H-imidazo[4,5-c]pyridine-6-carbonitrile. MS ESI calc'd. for $C_{21}H_{22}ClN_5$ [M+H]$^+$ 380. found 380.

Step 3: N-bromosuccinimide (4.07 g, 22.9 mmol) was added to a room temperature solution of racemic 4-(5-chloropyridin-3-yl)-3-[1-(trans-4-methylcyclohexyl)ethyl]-3H-imidazo[4,5-c]pyridine-6-carbonitrile (4.14 g, 7.63 mmol) stirring in degassed chloroform (38 mL). The reaction was heated to reflux for 1.5 hours. The mixture was cooled to room temperature, diluted with dichloromethane, and washed with saturated aqueous sodium thiosulfate (2×) and brine. The organic layer was dried over sodium sulfate, filtered, and concentrated under reduced pressure. The residue was purified by silica gel chromatography (0-80% ethyl acetate/hexanes, linear gradient) to afford racemic 2-bromo-4-(5-chloropyridin-3-yl)-3-[1-(trans-4-methylcyclohexyl)ethyl]-3H-imidazo[4,5-c]pyridine-6-carbonitrile. The racemic material was then purified by chiral supercritical fluid chromatography (Chiralpak IB, 21×250 mm, 25% methanol in CO$_2$) to afford 2-bromo-4-(5-chloropyridin-3-yl)-3-[(1S)-1-(trans-4-methylcyclohexypethyl]-3H-imidazo[4,5-d]pyridine-6-carbonitrile and 2-bromo-4-(5-chloropyridin-3-yl)-3-[(1R)-1-(trans-4-methylcyclohexyl)ethyl]-3H-imidazo[4,5-c]pyridine-6-carbonitrile. Faster eluting enantiomer 1: MS ESI calc'd. for $C_{21}H_{21}BrClN_5$ [M+H]$^+$ 458. found 458. Slower eluting enantiomer 2: MS ESI calc'd. for $C_{21}H_{21}BrClN_5$ [M+H]$^+$ 458. found 458.

Alternatively, racemic 4-(5-chloropyridin-3-yl)-3-[1-(trans-4-methylcyclohexyl)ethyl]-3H-imidazo[4,5-c]pyridine-6-carbonitrile (Step 2) was resolved into its enantiomers as described in Preparative Example 15.1 and brominated using the conditions described above or using the alternative conditions (disodium hydrogen phosphate and 1,3-dibromo-5,5-dimethylhydantoin in THF at 35° C., described in Example 2.1, Step 1 and Preparative Example 3.1, Step 3) to afford 2-bromo-4-(5-chloropyridin-3-yl)-3-[(1S)-1-(trans-4-methylcyclohexyl)ethyl]-3H-imidazo[4,5-c]pyridine-6-carbonitrile and 2-bromo-4-(5-chloropyridin-3-yl)-3-[(1R)-1-(trans-4-methylcyclohexyl)ethyl]-3H-imidazo[4,5-c]pyridine-6-carbonitrile.

Step 4: To a vial was added faster eluting enantiomer 1 2-bromo-4-(5-chloropyridin-3-yl)-3-[(1R or S)-1-(trans-4-methylcyclohexyl)ethyl]-3H-imidazo[4,5-c]pyridine-6-carbonitrile (150 mg, 0.327 mmol), (4aR,7aR)-octahydrocyclopenta[b][1,4]oxazine (83 mg, 0.654 mmol), potassium fluoride (95 mg, 1.64 mmol), DMSO (1 mL), and N,N-diisopropylethylamine (0.286 mL, 1.64 mmol). The vial was sealed and heated to 100° C. for 16 hours. The reaction mixture was cooled to room temperature, diluted with ethyl acetate, and washed with water and then brine. The organic layer was dried over sodium sulfate, filtered, and concentrated under reduced pressure. The residue was purified by silica gel chromatography (0-100% ethyl acetate/hexanes, linear gradient) to afford 4-(5-chloropyridin-3-yl)-2-[(4aR,7aR)-hexahydrocyclopenta[b][1,4]oxazin-4(4aH)-yl]-3-[(1R or S)-1-(trans-4-methylcyclohexyl)ethyl]-3H-imidazo[4,5-c]pyridine-6-carbonitrile. MS ESI calc'd. for $C_{28}H_{33}ClN_6O$ [M+H]$^+$ 505. found 505.

Step 5: Hydroxylamine hydrochloride (27.2 mg, 0.39 mmol), sodium bicarbonate (49.4 mg, 0.59 mmol), and water (0.392 mL) were combined in a vial and stirred for 15 minutes. This solution was added to a vial containing 4-(5-chloropyridin-3-yl)-2-[(4aR,7aR)-hexahydrocyclopenta[b][1,4]oxazin-4(4aH)-yl]-3-[(1R or S)-1-(trans-4-methylcyclohexyl)ethyl]-3H-imidazo[4,5-c]pyridine-6-carbonitrile (99 mg, 0.196 mmol), dissolved in ethanol (0.915 mL). The mixture was sealed and heated at 100° C. for 1 hour. The reaction was cooled to room temperature, quenched with water, and extracted with ethyl acetate (2×). The combined organic layers were dried over sodium sulfate, filtered, and concentrated to afford 4-(5-chloropyridin-3-yl)-2-[(4aR,7aR)-hexahydrocyclopenta[b][1,4]oxazin-4(4aH)-yl]-N-hydroxy-3-[(1R or S)-1-(trans-4-methylcyclohexyl)ethyl]-3H-imidazo[4,5-c]pyridine-6-carboximidamide. MS ESI calc'd. for $C_{28}H_{36}ClN_7O_2$ [M+H]$^+$ 538. found 538.

Step 6: To a solution of 4-(5-chloropyridin-3-yl)-2-[(4aR,7aR)-hexahydrocyclopenta[b][1,4]oxazin-4(4aH)-yl]-N-hydroxy-3-[(1R or S)-1-(trans-4-methylcyclohexyl)ethyl]-3H-imidazo[4,5-c]pyridine-6-carboximidamide (105 mg, 0.195 mmol), and 1,1'-carbonyldiimidazole (34.8 mg, 0.215 mmol) dissolved in acetonitrile (1.9 mL) was added 1,8-diazabicyclo[5.4.0]undec-7-ene (0.117 mL, 0.781 mmol). The reaction mixture was stirred at room temperature for 1 hour. The reaction was washed with water and extracted with dichloromethane. The organic layer was dried over sodium sulfate, filtered, and concentrated under reduced pressure. The residue was purified by silica gel chromatography (0-10% methanol/dichloromethane, and then 0-100% ethyl acetate/hexanes, linear gradient) to afford 3-{4-(5-chloropyridin-3-yl)-2-[(4aR,7aR)-hexahydrocyclopenta[b][1,4]oxazin-4(4aH)-yl]-3-[(1R or S)-1-(trans-4-methylcyclohexyl)ethyl]-3H-imidazo[4,5-c]pyridin-6-yl}-1,2,4-oxadiazol-5(4H)-one. MS ESI calc'd. for $C_{29}H_{34}ClN_7O_3$ [M+H]$^+$ 564. found 564. $^1$H NMR (500 MHz, DMSO-d$_6$) δ 12.90 (s, 1H), 8.92 (d, J=1.7, 1H), 8.81 (d, J=2.4, 1H), 8.45 (t, J=2.1, 1H), 8.14 (s, 1H), 4.04-3.93 (m, 1H), 3.76 (dd, J=9.8, 11.8, 1H), 3.61 (s, 1H), 3.45 (q, J=7.8, 2H), 3.16-3.05 (m, 1H), 2.74 (dd, J=9.5, 12.0, 1H), 2.11 (s, 1H), 1.94-1.85 (m, 1H), 1.71-1.64 (m, 2H), 1.63-1.48 (m, 5H), 1.31-1.16 (m, 2H), 1.15-1.05 (m, 1H), 0.98 (broad, 1H), 0.92 (d, J=6.5, 1H), 0.87-0.72 (m, 2H), 0.69 (d, J=6.5, 3H), 0.55-0.40 (m, 1H), 0.35-0.20 (m, 1H), 0.18-0.10 (m, 1H).

Diastereoisomer 2, 3-{4-(5-chloropyridin-3-yl)-2-[(4aR,7aR)-hexahydrocyclopenta[b][1,4]oxazin-4(4aH)-yl]-3-[(1S or R)-1-(trans-4-methylcyclohexyl)ethyl]-3H-imidazo[4,5-c]pyridin-6-yl}-1,2,4-oxadiazol-5(4H)-one, was obtained using the same chemistry as described in steps 4-6, starting with slower eluting enantiomer 2 produced in Step 3 above. MS ESI calc'd. for $C_{29}H_{34}ClN_7O_3$ [M+H]$^+$ 564. found 564. $^1$H NMR (500 MHz, DMSO-d$_6$) δ 12.86 (s, 1H), 8.83 (d, J=2.4, 1H), 8.75 (d, J=1.6, 1H), 8.30 (t, J=2.0, 1H), 8.13 (s, 1H), 4.03-3.91 (m, 2H), 3.77 (dd, J=9.5, 11.8, 1H), 3.47 (dd, J=9.5, 17.7, 1H), 3.06 (dd, J=8.0, 19.3, 2H), 2.89 (dd, J=9.2, 12.0, 1H), 1.97 (s, 1H), 1.91-1.81 (m, 1H), 1.70-1.43 (m, 6H), 1.39-1.31 (m 1H), 1.24-1.14 (m, 4H), 1.11-0.96 (m, 1H), 0.92 (d, J=6.5, 1H), 0.86-0.77 (m, 1H), 0.74 (d, J=6.5, 3H), 0.63-0.43 (m, 3H).

The following compounds in Table 4 (other than Example 4.1 and 4.2) were prepared using procedures which were analogous to those described above.

TABLE 4

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 4.1 | 2 | 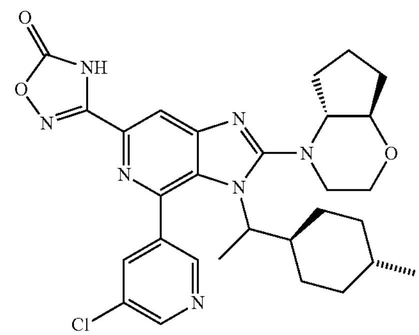 [SMILES: CC([C@H]1CC[C@H](C)CC1)n1c(N2CCO[C@@H]3CCC[C@H]32)nc2cc(-c3noc(=O)[nH]3)nc(-c3cncc(Cl)c3)c21] | 3-{4-(5-chloropyridin-3-yl)-2-[(4aR,7aR)-hexahydrocyclopenta[b][1,4]oxazin-4(4aH)-yl]-3-[(1R or S)-1-(trans-4-methylcyclohexyl)ethyl]-3H-imidazo[4,5-c]pyridin-6-yl}-1,2,4-oxadiazol-5(4H)-one (diastereoisomer 1) | TFA | 564 | 564 |
| 4.2 | 1 | 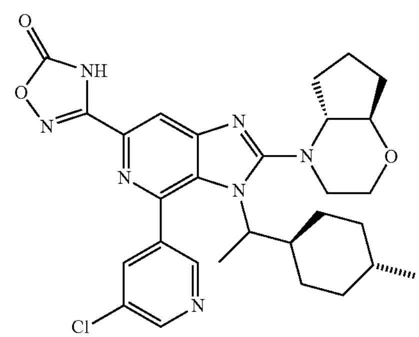 [SMILES: CC([C@H]1CC[C@H](C)CC1)n1c(N2CCO[C@@H]3CCC[C@H]32)nc2cc(-c3noc(=O)[nH]3)nc(-c3cncc(Cl)c3)c21] | 3-{4-(5-chloropyridin-3-yl)-2-[(4aR,7aR)-hexahydrocyclopenta[b][1,4]oxazin-4(4aH)-yl]-3-[(1S or R)-1-(trans-4-methylcyclohexyl)ethyl]-3H-imidazo[4,5-c]pyridin-6-yl}-1,2,4-oxadiazol-5(4H)-one (diastereoisomer 2) | TFA | 564 | 564 |
| 4.3 | 3 | 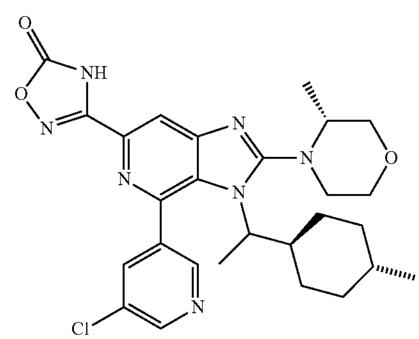 [SMILES: CC([C@H]1CC[C@H](C)CC1)n1c(N2CCOC[C@H]2C)nc2cc(-c3noc(=O)[nH]3)nc(-c3cncc(Cl)c3)c21] | 3-(4-(5-chloropyridin-3-yl)-3-(1-(trans-4-methylcyclohexyl)ethyl)-2-((R)-3-methylmorpholino)-3H-imidazo[4,5-c]pyridin-6-yl)-1,2,4-oxadiazol-5(4H)-one (diastereoisomer 1) | TFA | 538 | 538 |

TABLE 4-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 4.4 | 1 | 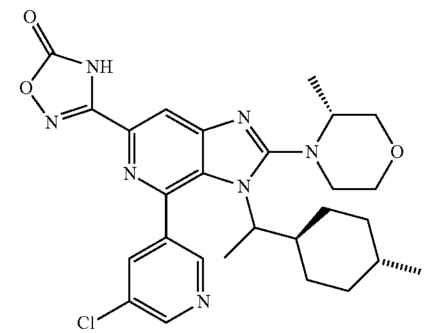 [SMILES: CC([C@H]1CC[C@H](C)CC1)n1c(N2CCOC[C@H]2C)nc2cc(-c3noc(=O)[nH]3)nc(-c3cncc(Cl)c3)c21] | 3-(4-(5-chloropyridin-3-yl)-3-(1-(trans-4-methylcyclohexyl)ethyl)-2-((R)-3-methylmorpholino)-3H-imidazo[4,5-c]pyridin-6-yl)-1,2,4-oxadiazol-5(4H)-one (diastereoisomer 2) | TFA | 538 | 538 |
| 4.5 | 4 | 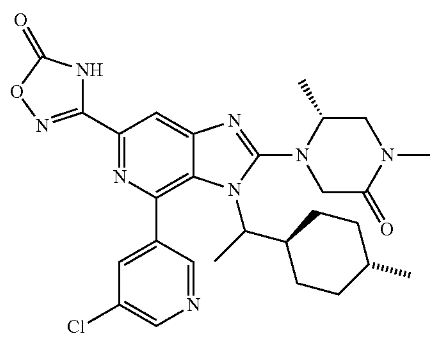 [SMILES: CC([C@H]1CC[C@H](C)CC1)n1c(N2CC(=O)N(C)C[C@H]2C)nc2cc(-c3noc(=O)[nH]3)nc(-c3cncc(Cl)c3)c21] | (5R)-4-[4-(5-chloropyridin-3-yl)-3-[1-(trans-4-methylcyclohexyl)ethyl]-6-(5-oxo-4,5-dihydro-1,2,4-oxadiazol-3-yl)-3H-imidazo[4,5-c]pyridin-2-yl]-1,5-dimethylpiperazin-2-one (diastereoisomer 1) | TFA | 565 | 565 |
| 4.6 | 13 | 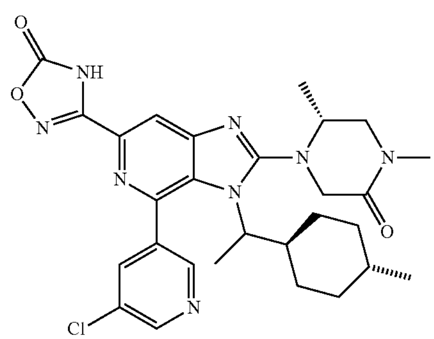 [SMILES: CC([C@H]1CC[C@H](C)CC1)n1c(N2CC(=O)N(C)C[C@H]2C)nc2cc(-c3noc(=O)[nH]3)nc(-c3cncc(Cl)c3)c21] | (5R)-4-[4-(5-chloropyridin-3-yl)-3-[1-(trans-4-methylcyclohexyl)ethyl]-6-(5-oxo-4,5-dihydro-1,2,4-oxadiazol-3-yl)-3H-imidazo[4,5-c]pyridin-2-yl]-1,5-dimethylpiperazin-2-one (diastereoisomer 2) | TFA | 565 | 565 |
| 4.7 | 1 | 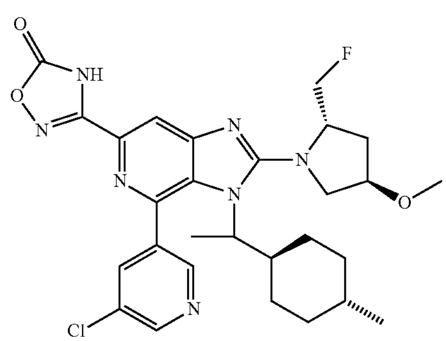 [SMILES: CO[C@@H]1C[C@@H](CF)N(c2nc3cc(-c4noc(=O)[nH]4)nc(-c4cncc(Cl)c4)c3n2C(C)[C@H]2CC[C@H](C)CC2)C1] | 3-{4-(5-chloropyridin-3-yl)-2-[(2S,4R)-2-(fluoromethyl)-4-methoxypyrrolidin-1-yl]-3-[1-(trans-4-methylcyclohexyl)ethyl]-3H-imidazo[4,5-c]pyridin-6-yl}-1,2,4-oxadiazol-5(4H)-one (diastereoisomer 1) | TFA | 570 | 570 |

TABLE 4-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 4.8 | 1 | 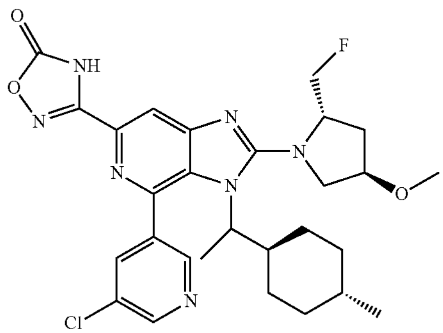 [SMILES: CO[C@@H]1C[C@@H](CF)N(c2nc3cc(-c4noc(=O)[nH]4)nc(-c4cncc(Cl)c4)c3n2C(C)[C@H]2CC[C@H](C)CC2)C1] | 3-{4-(5-chloropyridin-3-yl)-2-[(2S,4R)-2-(fluoromethyl)-4-methoxypyrrolidin-1-yl]-3-[1-(trans-4-methylcyclohexyl)ethyl]-3H-imidazo[4,5-c]pyridin-6-yl}-1,2,4-oxadiazol-5(4H)-one (diastereoisomer 2) | TFA | 570 | 570 |
| 4.9 | 1 | 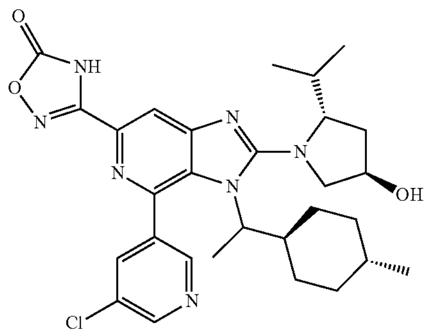 [SMILES: CC(C)[C@@H]1C[C@@H](O)CN1c1nc2cc(-c3noc(=O)[nH]3)nc(-c3cncc(Cl)c3)c2n1C(C)[C@H]1CC[C@H](C)CC1] | 3-{4-(5-chloropyridin-3-yl)-2-[(2S,4R)-4-hydroxy-2-(propan-2-yl)pyrrolidin-1-yl]-3-[1-(trans-4-methylcyclohexyl)ethyl]-3H-imidazo[4,5-c]pyridin-6-yl}-1,2,4-oxadiazol-5(4H)-one (diastereoisomer 1) | TFA | 566 | 566 |
| 4.10 | 1 | 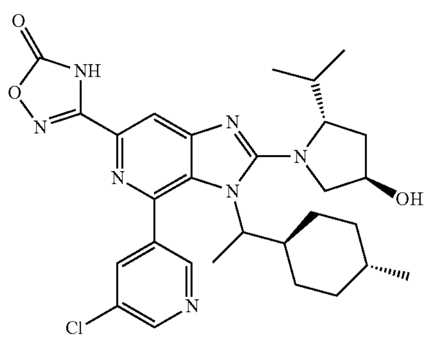 [SMILES: CC(C)[C@@H]1C[C@@H](O)CN1c1nc2cc(-c3noc(=O)[nH]3)nc(-c3cncc(Cl)c3)c2n1C(C)[C@H]1CC[C@H](C)CC1] | 3-{4-(5-chloropyridin-3-yl)-2-[(2S,4R)-4-hydroxy-2-(propan-2-yl)pyrrolidin-1-yl]-3-[1-(trans-4-methylcyclohexyl)ethyl]-3H-imidazo[4,5-c]pyridin-6-yl}-1,2,4-oxadiazol-5(4H)-one (diastereoisomer 2) | TFA | 566 | 566 |
| 4.11 | 3 | 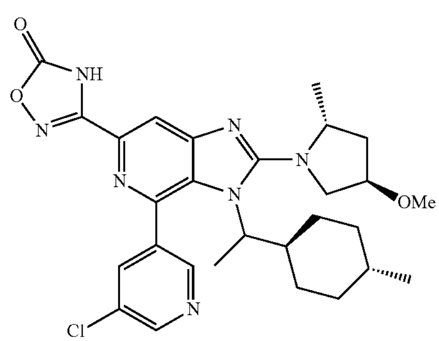 [SMILES: CO[C@@H]1C[C@@H](C)N(c2nc3cc(-c4noc(=O)[nH]4)nc(-c4cncc(Cl)c4)c3n2C(C)[C@H]2CC[C@H](C)CC2)C1] | 3-{4-(5-chloropyridin-3-yl)-2-[(2R,4R)-4-methoxy-2-methylpyrrolidin-1-yl]-3-[1-(trans-4-methylcyclohexyl)ethyl]-3H-imidazo[4,5-c]pyridin-6-yl}-1,2,4-oxadiazol-5(4H)-one (diastereomer 1) | TFA | 552 | 552 |

TABLE 4-continued

| Ex. | FRET IC$_{50}$ (nM) | Structure | Chemical Name | Salt | [M + H]$^+$ Calc'd | [M + H]$^+$ Obsv'd |
|---|---|---|---|---|---|---|
| 4.12 | 4 | 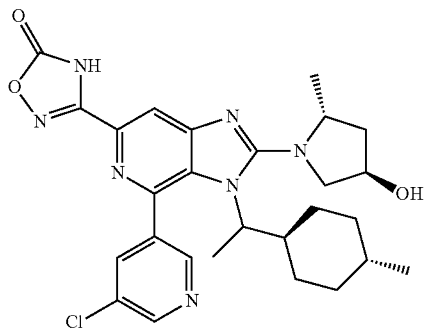 [SMILES: CC([C@H]1CC[C@H](C)CC1)n1c(N2C[C@H](O)C[C@H]2C)nc2cc(-c3noc(=O)[nH]3)nc(-c3cncc(Cl)c3)c21] | 3-{4-(5-chloropyridin-3-yl)-2-[(2R,4R)-4-hydroxy-2-methylpyrrolidin-1-yl]-3-[1-(trans-4-methylcyclohexyl)ethyl]-3H-imidazo[4,5-c]pyridin-6-yl}-1,2,4-oxadiazol-5(4H)-one (diastereomer 1) | TFA | 538 | 538 |
| 4.13 | 3 | 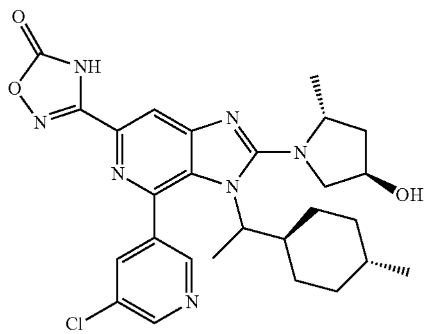 [SMILES: CC([C@H]1CC[C@H](C)CC1)n1c(N2C[C@H](O)C[C@H]2C)nc2cc(-c3noc(=O)[nH]3)nc(-c3cncc(Cl)c3)c21] | 3-{4-(5-chloropyridin-3-yl)-2-[(2R,4R)-4-hydroxy-2-methylpyrrolidin-1-yl]-3-[1-(trans-4-methylcyclohexyl)ethyl]-3H-imidazo[4,5-c]pyridin-6-yl}-1,2,4-oxadiazol-5(4H)-one (diastereomer 2) | TFA | 538 | 538 |
| 4.14 | 2 | 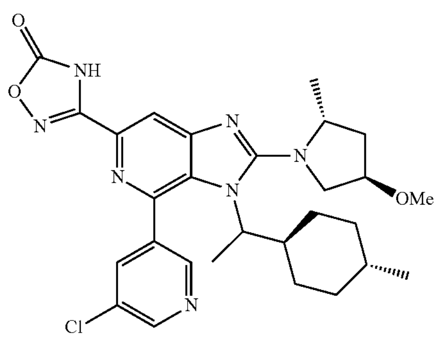 [SMILES: CO[C@@H]1C[C@@H](C)N(c2nc3cc(-c4noc(=O)[nH]4)nc(-c4cncc(Cl)c4)c3n2C(C)[C@H]2CC[C@H](C)CC2)C1] | 3-{4-(5-chloropyridin-3-yl)-2-[(2R,4R)-4-methoxy-2-methylpyrrolidin-1-yl]-3-[1-(trans-4-methylcyclohexyl)ethyl]-3H-imidazo[4,5-c]pyridin-6-yl}-1,2,4-oxadiazol-5(4H)-one (diastereomer 2) | TFA | 552 | 552 |

Scheme 7

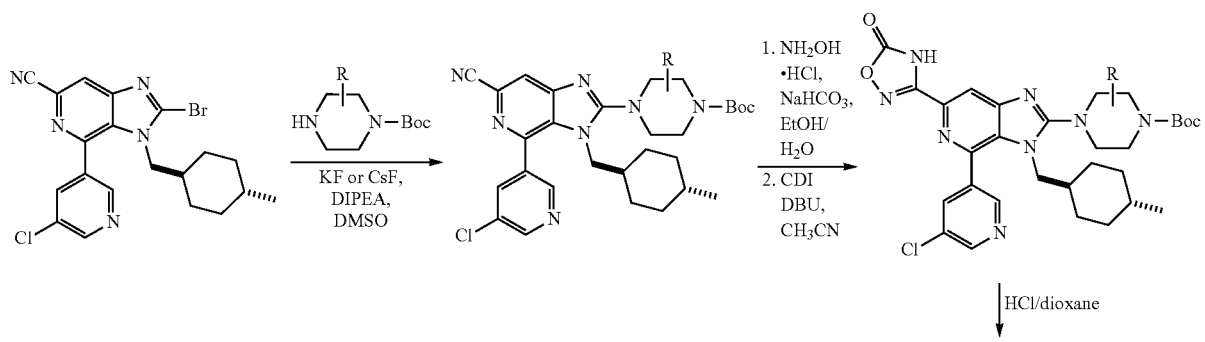

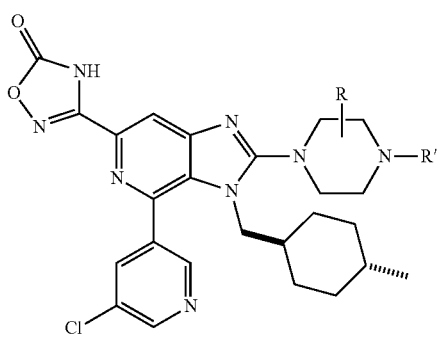 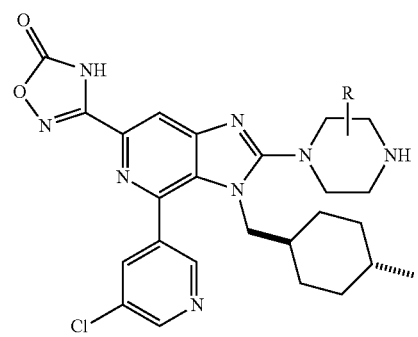

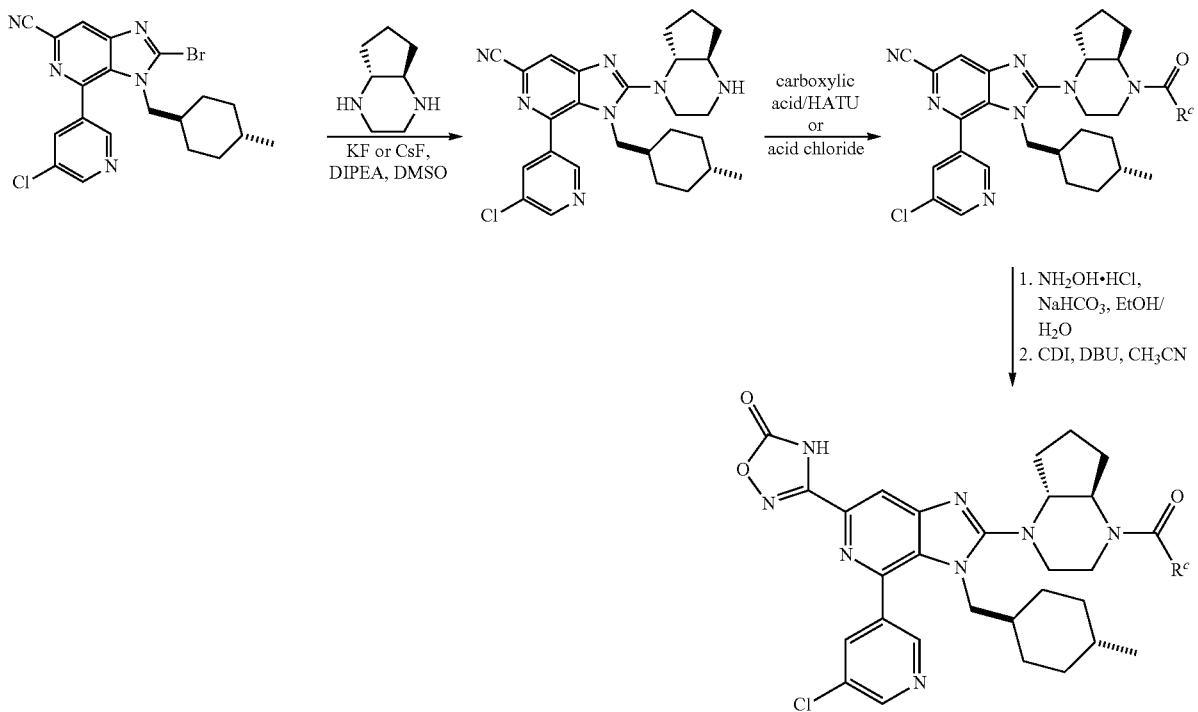

Preparative Example 5.1

3-(4-(5-chloropyridin-3-yl)-3-((trans-4-methylcyclohexyl)methyl)-2-(R)-2-methylpiperazin-1-yl)-3H-imidazo[4,5-c]pyridin-6-yl)-1,2,4-oxadiazol-5(4H)-one

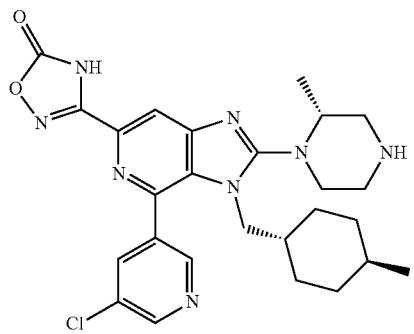 [SMILES: C[C@@H]1CNCCN1c1nc2cc(-c3noc(=O)[nH]3)nc(-c3cncc(Cl)c3)c2n1C[C@H]1CC[C@H](C)CC1]

Step 1: To a microwave vial was added (R)-tert-butyl 3-methylpiperazine-1-carboxylate (purchased from Astatech) (180 mg, 0.899 mmol), 2-bromo-4-(5-chloropyridin-3-yl)-3-((trans-4-methylcyclohexyl)methyl)-3H-imidazo[4,5-c]pyridine-6-carbonitrile (200 mg, 0.450 mmol, Preparative Example 3.1), potassium fluoride (78 mg, 1.349 mmol), DMSO (1 ml) and DIEA (0.236 ml, 1.349 mmol). The reaction vial was capped and heated to 100° C. overnight. The mixture was cooled to room temperature and diluted with EtOAc. The mixture was washed with water and brine, then dried over sodium sulfate, filtered, and concentrated. The residue was purified by column chromatography on silica gel, eluting with EtOAc/isohexane to give (R)-tert-butyl 4-(4-(5-chloropyridin-3-yl)-6-cyano-3-((trans-4-methylcyclohexyl)methyl)-3H-imidazo[4,5-c]pyridin-2-yl)-3-methylpiperazine-1-carboxylate. MS ESI calc'd. for $C_{30}H_{38}ClN_7O_2$ [M+H]$^+$ 564. found 564.

Step 2: Using a procedure analogous to that described in Example 2.1 (Step 5), and starting with (R)-tert-butyl 4-(4-(5-chloropyridin-3-yl)-6-cyano-3-((trans-4-methylcyclohexyl)methyl)-3H-imidazo[4,5-c]pyridin-2-yl)-3-methylpiperazine-1-carboxylate, (R)-tert-butyl 4-(4-(5- chloropyridin-3-yl)-6-(N'-hydroxycarbamimidoyl)-3-((trans-4-methylcyclohexyl)methyl)-3H-imidazo[4,5-c]pyridin-2-yl)-3-methylpiperazine-1-carboxylate was prepared. MS ESI calc'd. for $C_{30}H_{41}ClN_8O_3$ [M+H]$^+$ 597. found 597.

Step 3: Using a procedure analogous to that described in Example 2.1 (Step 6), and starting with (R)-tert-butyl 4-(4-(5-chloropyridin-3-yl)-6-(N'-hydroxycarbamimidoyl)-3-((trans-4-methylcyclohexyl)methyl)-3H-imidazo[4,5-c]pyridin-2-yl)-3-methylpiperazine-1-carboxylate, (R)-tert-butyl 4-(4-(5-chloropyridin-3-yl)-3-((trans-4-methylcyclohexyl)methyl)-6-(5-oxo-4,5-dihydro-1,2,4-oxadiazol-3-yl)-3H-imidazo[4,5-c]pyridin-2-yl)-3-methylpiperazine-1-carboxylate was prepared. MS ESI calc'd. for $O_{31}H_{39}ClN_8O_4$ [M+H]$^+$ 623. found 623.

Step 4: HCl solution in 1,4-Dioxane (4.0 M, 1.0 ml, 4.0 mmol) was added to a stirred solution of (R)-tert-butyl 4-(4-(5-chloropyridin-3-yl)-3-((trans-4-methylcyclohexyl)methyl)-6-(5-oxo-4,5-dihydro-1,2,4-oxadiazol-3-yl)-3H-imidazo[4,5-c]pyridin-2-yl)-3-methylpiperazine-1-carboxylate (164 mg, 0.263 mmol) in 1,4-dioxane (1 ml) at room temperature, and the mixture was stirred at room temperature overnight. The solvent was evaporated under reduced pressure to give 3-(4-(5-chloropyridin-3-yl)-3-((trans-4-methylcyclohexyl)methyl)-2-((R)-2-methylpiperazin-1-yl)-3H-imidazo[4,5-c]pyridin-6-yl)-1,2,4-oxadiazol-5(4H)-one (HCl salt). MS ESI calc'd. for $C_{26}H_{31}ClN_8O_2$ [M+H]$^+$ 523. found 523.

Preparative Example 5.2

(4aR,7aR)-octahydro-1H-cyclopenta[b]pyrazine

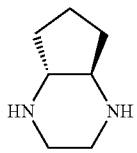

To a cooled (0° C.) solution of (4aR,7aR)-octahydro-2H-cyclopenta[b]pyrazin-2-one (prepared in analogy to Example 3.120, Steps 1-3) (570 mg, 4.07 mmol) in THF (27 mL) was added dropwise LAH (4.07 mL of a 2.0M solution in THF, 8.14 mmol) over 5 minutes. After the addition was complete, the mixture was capped with a reflux condenser and heated to 65° C. for 14 hours. The resulting mixture was then cooled to room temperature and carefully quenched by the addition of sodium sulfate decahydrate (1.3 g). The reaction mixture was filtered through Celite®, and the filter cake was washed with ethyl acetate. The combined filtrate was dried over magnesium sulfate, filtered, evaporated under reduced pressure and dried in vacuo to give (4aR,7aR)-octahydro-1H-cyclopenta[b]pyrazine. $^1$H NMR (500 MHz, DMSO-d$_6$) δ 2.75-2.69 (m, 2H), 2.55-2.50 (m, 2H), 2.13-2.07 (m, 4H), 1.66-1.59 (m, 2H), 1.57-1.51 (m, 2H), 1.22-1.12 (m, 2H). Example 5.1 3-(2-((R)-4-acetyl-2-methylpiperazin-1-yl)-4-(5-chloropyridin-3-yl)-3-((trans-4-methyl cyclohexyl)methyl)-3H-imidazo[4,5-c]pyridin-6-yl)-1,2,4-oxadiazol-5(4H)-one

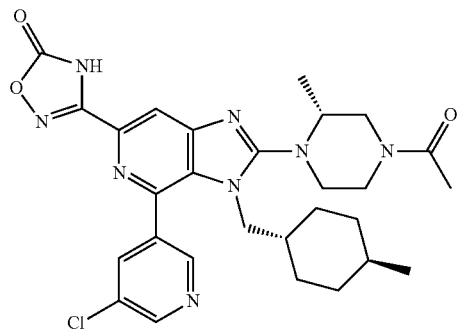 [SMILES: CC(=O)N1CCN(c2nc3cc(-c4noc(=O)[nH]4)nc(-c4cncc(Cl)c4)c3n2C[C@H]2CC[C@H](C)CC2)[C@H](C)C1]

Acetic acid (6.73 mg, 0.112 mmol), N,N-diisopropylethylamine (29.0 mg, 0.224 mmol) and HATU (42.6 mg, 0.112 mmol) were added to a stirred, cooled 0° C. solution of 3-(4-(5-chloropyridin-3-yl)-3-((trans-4-methylcyclohexyl)methyl)-2-((R)-2-methylpiperazin-1-yl)-3H-imidazo[4,5-c]pyridin-6-yl)-1,2,4-oxadiazol-5(4H)-one (HCl salt, 31.3 mg, 0.056 mmol) in DMF (1 ml), and the mixture was stirred at room temperature overnight. The reaction mixture was concentrated under reduced pressure. The residue was purified by preparative Reverse phase HPLC(C-18), eluting with acetonitrile/water+0.1% TFA, to give 3-(2-((R)-4-acetyl-2-methylpiperazin-1-yl)-4-(5-chloropyridin-3-yl)-3-((trans-4-methylcyclohexyl)methyl)-3H-imidazo[4,5-c]pyridin-6-yl)-1,2,4-oxadiazol-5(4H)-one, TFA salt. MS ESI calc'd. for $C_{28}H_{33}ClN_8O_3$ [M+H]$^+$ 565. found 565. $^1$H NMR (500 MHz, DMSO-d$_6$) δ 12.88 (br s, 1H), 8.96 (d, J=1.8 Hz, 1H), 8.81 (d, J=2.3 Hz, 1H), 8.50 (s, 1H), 7.99 (d, J=1.8 Hz, 1H), 4.00-3.57 (m, 5H), 3.53-3.16 (m, 4H), 2.05 (d, J=22.2 Hz, 3H), 1.38-1.32 (m, 2H), 1.20-1.12 (m, 3H), 1.04-0.87 (m, 2H), 0.67-0.50 (m, 7H), 0.44-0.33 (m, 2H).

Example 5.5

3-(4-(5-chloropyridin-3-yl)-2-((2R,6R)-2,6-dimethyl-4-(methylsulfonyl)piperazin-1-yl)-3-((trans-4-methylcyclohexyl)methyl)-3H-imidazo[4,5-c]pyridin-6-yl)-1,2,4-oxadiazol-5(4H)-one

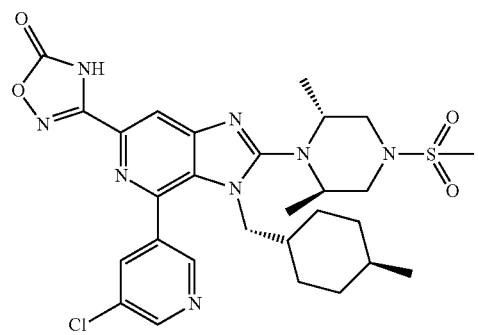

To a reaction vessel was added 3-(4-(5-chloropyridin-3-yl)-2-((2R,6R)-2,6-dimethylpiperazin-1-yl)-3-((trans-4-methylcyclohexyl)methyl)-3H-imidazo[4,5-c]pyridin-6-yl)-1,2,4-oxadiazol-5(4H)-one (prepared in the same manner as Preparative Example 5.1, starting with 2-bromo-4-(5-chloropyridin-3-yl)-3-((trans-4-methylcyclohexyl)methyl)-3H-imidazo[4,5-c]pyridine-6-carbonitrile, Preparative Example 3.1, and tert-butyl (3R,5R)-3,5-dimethylpiperazine-1-carboxylate, purchased from Enamine, 0.025 g, 0.047 mmol) suspended in DMF (1.0 mL). To the reaction was then added methanesulfonyl chloride (0.011 g, 0.093 mmol). The reaction was allowed to stir at ambient temperature for 2 hours. The reaction was passed through a syringe filter, and the filtrate was purified by reverse phase preparative HPLC (0:100 to 95:5 acetonitrile:water: 0.1% v/v TFA modifier) to afford 3-(4-(5-chloropyridin-3-yl)-2-((2R,6R)-2,6-dimethyl-4-(methylsulfonyl)piperazin-1-yl)-3-((trans-4-methylcyclohexyl)methyl)-3H-imidazo[4,5-c]pyridin-6-yl)-1,2,4-oxadiazol-5(4H)-one, TFA salt. MS ESI calc'd. for $C_{28}H_{36}ClN_8O_4S$ [M+H]$^+$ 615. found 615. $^1$H NMR (600 MHz, DMSO) δ 8.94 (d, J=1.7, 1H), 8.80 (d, J=2.3, 1H), 8.47 (s, 1H), 8.11 (s, 1H), 3.81 (m, 3H), 3.70 (m, 1H), 2.92 (s, 3H), 1.36 (m, 3H), 1.05 (m, 8H), 0.80 (m, 1H), 0.75 (m, J=6.5, 8H), 0.50 (m, 1H), 0.33 (m, 2H).

Example 5.6

(3R,5R)-ethyl 4-(4-(5-chloropyridin-3-yl)-3-((trans-4-methylcyclohexyl)methyl)-6-(5-oxo-4,5-dihydro-1,2,4-oxadiazol-3-yl)-3H-imidazo[4,5-c]pyridin-2-yl)-3,5-dimethylpiperazine-1-carboxylate

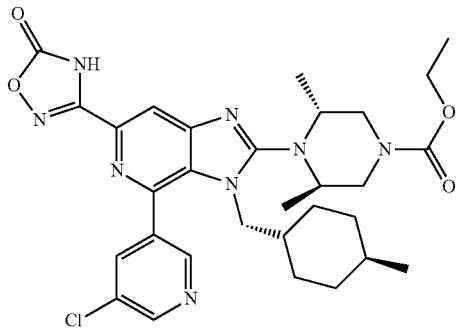

To a reaction vessel was added ethanol (0.009 g, 0.195 mmol), DMSO (0.14 mL), DIEA (0.065 mL, 0.37 mmol) and N,N'-Disuccinimidyl carbonate (0.047 g, 0.18 mmol). The reaction vial was sealed and allowed to stir for 12 hours at ambient temperature. To the reaction was then added 3-(4-(5-chloropyridin-3-yl)-2-((2R,6R)-2,6-dimethylpiperazin-1-yl)-3-((trans-4-methylcyclohexyl)methyl)-3H-imidazo[4,5-c]pyridin-6-yl)-1,2,4-oxadiazol-5(4H)-one (prepared in the same manner as Preparative Example 5.1, starting with 2-bromo-4-(5-chloropyridin-3-yl)-3-((trans-4-methylcyclohexyl)methyl)-3H-imidazo[4,5-c]pyridine-6-carbonitrile, Preparative Example 3.1, and tert-butyl (3R,5R)-3,5-dimethylpiperazine-1-carboxylate, purchased from Enamine; 0.015 g, 0.028 mmol) and DMSO (0.14 mL). The reaction vial was sealed and allowed to stir for 12 hours at ambient temperature. The reaction was passed through a syringe filter, and the filtrate was purified by reverse phase preparative HPLC (0:100 to 95:5 acetonitrile:water: 0.1% v/v TFA modifier) to afford (3R,5R)-ethyl 4-(4-(5-chloropyridin-3-yl)-3-((trans-4-methylcyclohexyl)methyl)-6-(5-oxo-4,5-dihydro-1,2,4-oxadiazol-3-yl)-3H-imidazo[4,5-c]pyridin-2-yl)-3,5-dimethylpiperazine-1-carboxylate, TFA salt. MS ESI calc'd. for $C_{30}H_{37}ClN_8O_4$ [M+H]$^+$ 609. found 609. $^1$H NMR (500 MHz, DMSO-d$_6$): δ 12.89 (s, 1H), 8.96 (s, 1H), 8.82 (s, 1H), 8.49 (s, 1H), 8.12 (s, 1H), 4.03-4.10 (m, 2H), 3.84-3.89 (m, 2H), 3.71 (s, 4H), 3.60-3.63 (m, 2H), 1.37 (dd, J=28.9, 12.7 Hz, 2H), 1.19 (t, J=7.1 Hz, 3H), 0.99-1.05 (m, 7H), 0.80-0.90 (m, 1H), 0.65-0.72 (m, 6H), 0.52 (d, J=12.3 Hz, 1H), 0.36 (m, 2H).

Example 5.7

(3R,5R)-4-(4-(5-chloropyridin-3-yl)-3-((trans-4-methylcyclohexyl)methyl)-6-(5-oxo-4,5-dihydro-1,2,4-oxadiazol-3-yl)-3H-imidazo[4,5-c]pyridin-2-yl)-N-ethyl-3,5-dimethylpiperazine-1-carboxamide

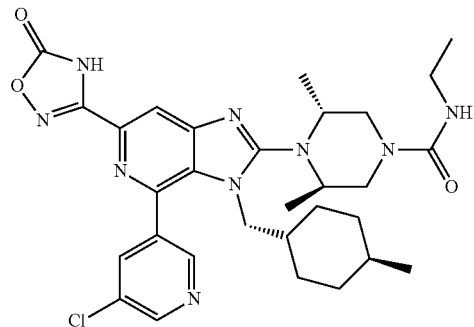

To a reaction vessel was added 3-(4-(5-chloropyridin-3-yl)-2-((2R,6R)-2,6-dimethylpiperazin-1-yl)-3-((trans-4-methylcyclohexyl)methyl)-3H-imidazo[4,5-c]pyridin-6-yl)-1,2,4-oxadiazol-5(4H)-one (prepared in the same manner as Preparative Example 5.1, starting with 2-bromo-4-(5-chloropyridin-3-yl)-3-((trans-4-methylcyclohexyl)methyl)-3H-imidazo[4,5-c]pyridine-6-carbonitrile, Preparative Example 3.1, and tert-butyl (3R,5R)-3,5-dimethylpiperazine-1-carboxylate, purchased from Enamine; 0.015 g, 0.028 mmol), DMF (0.5 mL), DIEA (0.009 g, 0.052 mmol) and isocyanatoethane (0.0013 mL, 0.026 mmol). The reaction vial was sealed and allowed to stir at ambient temperature for 2 hours. The reaction was diluted with DMSO (0.5 mL) and passed through a syringe filter. The filtrate was purified by reverse phase preparative HPLC (0:100 to 95:5 acetonitrile:water/ 0.1% v/v TFA modifier) to afford (3R,5R)-4-(4-(5-chloropyridin-3-yl)-3-((trans-4-methylcyclohexyl)methyl)-6-(5-oxo-4,5-dihydro-1,2,4-oxadiazol-3-yl)-3H-imidazo[4,5-c]pyridin-2-yl)-N-ethyl-3,5-dimethylpiperazine-1-carboxamide, TFA salt. MS ESI calc'd. for $C_{30}H_{38}ClN_9O_3$ [M+H]$^+$ 608. found 608. $^1$H NMR (500 MHz, DMSO-d$_6$) δ 12.88 (s, 1H), 8.96 (s, 1H), 8.82 (s, 1H), 8.49 (d, 1H), 8.16 (d, 1H), 6.58 (s, 1H), 3.91 (m, 1H), 3.67 (m, 4H), 3.19 (m, 3H), 1.38 (dd, 2H), 1.01 (m, 11H), 0.83 (m, 1H), 0.67 (m, 7H), 0.53 (m, 1H), 0.36 (m, 2H).

Example 5.19

3-{2-[(4aR,7aR)-4-acetyloctahydro-1H-cyclopenta[b]pyrazin-1-yl]-4-(5-chloropyridin-3-yl)-3-[(trans-4-methylcyclohexyl)methyl]-3H-imidazo[4,5-c]pyridin-6-yl}-1,2,4-oxadiazol-5(4H)-one

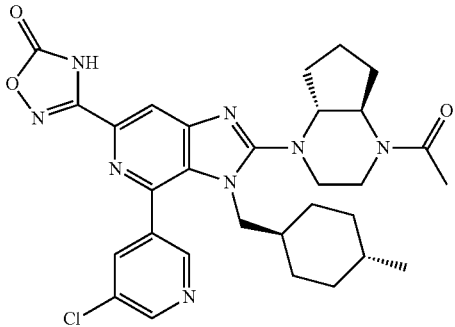 [SMILES: CC(=O)N1CCN(c2nc3cc(-c4noc(=O)[nH]4)nc(-c4cncc(Cl)c4)c3n2C[C@H]2CC[C@H](C)CC2)[C@@H]2CCC[C@H]21]

Step 1: To a microwave vial was added (4aR,7aR)-octahydro-1H-cyclopenta[b]pyrazine (Preparative Example 5.2, 295 mg, 2.338 mmol), 2-bromo-4-(5-chloropyridin-3-yl)-3-((trans-4-methylcyclohexyl)methyl)-3H-imidazo[4,5-c]pyridine-6-carbonitrile (Preparative Example 3.1, 800 mg, 1.799 mmol), potassium fluoride (209 mg, 3.60 mmol), DMSO (8 ml), and DIEA (0.942 ml, 5.40 mmol). The reaction vial was capped and heated to 100° C. overnight. The mixture was then cooled to room temperature and diluted with EtOAc. The solution was washed with water and brine, dried over sodium sulfate, filtered, and concentrated to give crude 4-(5-chloropyridin-3-yl)-3-[(trans-4-methylcyclohexyl)methyl]-2-[(4aR,7aR)-octahydro-1H-cyclopenta[b]pyrazin-1-yl]-3H-imidazo[4,5-c]pyridine-6-carbonitrile. MS ESI calc'd. for $C_{27}H_{32}ClN_7$ [M+H]$^+$ 490. found 490.

Step 2: Acetic acid (60.7 mg, 1.01 mmol), N,N-diisopropylethylamine (174 mg, 1.348 mmol) and HATU (513 mg, 1.348 mmol) were added to 4-(5-chloropyridin-3-yl)-3-[(trans-4-methylcyclohexyl)methyl]-2-[(4aR,7aR)-octahydro-1H-cyclopenta[b]pyrazin-1-yl]-3H-imidazo[4,5-c]pyridine-6-carbonitrile (177 mg, 0.33 mmol) in DMSO (1.5 ml), and the mixture was stirred at room temperature overnight. The reaction was then diluted with EtOAc, washed with water and brine, dried over sodium sulfate, filtered, and concentrated under reduced pressure. The residue was purified by column chromatography on silica gel, eluting with EtOAc/isohexane to give 2-[(4aR,7aR)-4-acetyloctahydro-1H-cyclopenta[b]pyrazin-1-yl]-4-(5-chloropyridin-3-yl)-3-[(trans-4-methylcyclohexyl)methyl]-3H-imidazo[4,5-c]pyridine-6-carbonitrile. MS ESI calc'd. for $C_{29}H_{34}ClN_7O$ [M+H]$^+$ 532. found 532.

Step 3 & 4: Using a procedure analogous to that described in Example 2.1 (Steps 5 and 6), and starting with 2-[(4aR,7aR)-4-acetyloctahydro-1H-cyclopenta[b]pyrazin-1-yl]-4-(5-chloropyridin-3-yl)-3-[(trans-4-methylcyclohexyl)methyl]-3H-imidazo[4,5-c]pyridine-6-carbonitrile, 3-{2-[(4aR,7aR)-4-acetyloctahydro-1H-cyclopenta[b]pyrazin-1-yl]-4-(5-chloropyridin-3-yl)-3-[(trans-4-methylcyclohexyl)methyl]-3H-imidazo[4,5-c]pyridin-6-yl}-1,2,4-oxadiazol-5(4H)-one (TFA salt) was prepared. MS ESI calc'd. for $C_{30}H_{35}ClN_8O_3$ [M+H]$^+$ 591. found 591. 1H NMR (500 MHz, DMSO-$d_6$) δ 12.86 (s, 1H), 8.96 (d, J=1.8 Hz, 1H), 8.80 (d, J=2.4 Hz, 1H), 8.48 (t, J=2.1 Hz, 1H), 7.97 (s, 1H), 3.90 (m, 2H), 3.78 (dd, J=14.5, 9.8 Hz, 2H), 3.52-3.61 (m, 4H), 2.02 (s, 3H), 1.68 (m, 3H), 1.36 (m, 2H); 1.15 (m, 1H), 1.02-1.04 (m, 1H), 0.92-0.94 (m, 1H), 0.66-0.67 (m, 7H), 0.38-0.48 (m, 4H).

The following compounds in Table 5 (other than Examples 5.1, 5.5, 5.6, 5.7, and 5.19) were prepared using procedures that were analogous to those described above.

TABLE 5

| Ex. | FRET IC$_{50}$ (nM) | Structure | Chemical Name | Salt | [M + H]+ Calc'd | [M + H]+ Obsv'd |
|---|---|---|---|---|---|---|
| 5.1 | 6 | 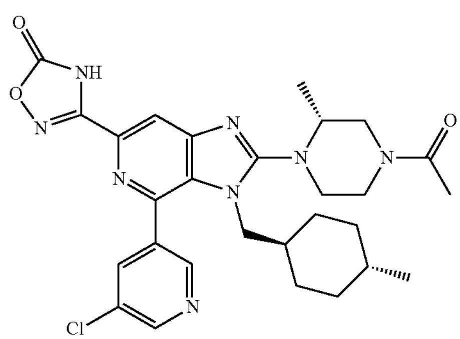 [SMILES: CC(=O)N1CCN(c2nc3cc(-c4noc(=O)[nH]4)nc(-c4cncc(Cl)c4)c3n2C[C@H]2CC[C@H](C)CC2)[C@H](C)C1] | 3-{2-[(2R)-4-acetyl-2-methylpiperazin-1-yl]-4-(5-chloropyridin-3-yl)-3-[(trans-4-methylcyclohexyl)methyl]-3H-imidazo[4,5-c]pyridin-6-yl}-1,2,4-oxadiazol-5(4H)-one | TFA | 565 | 565 |
| 5.2 | 5 | 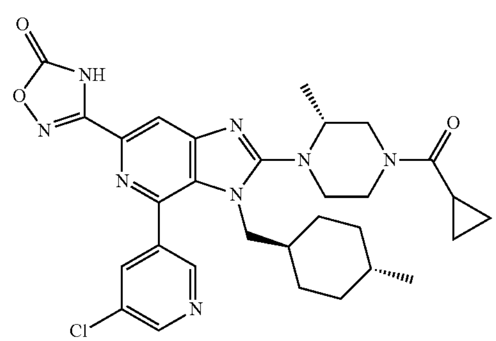 [SMILES: C[C@@H]1CN(C(=O)C2CC2)CCN1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(2R)-4-(cyclopropylcarbonyl)-2-methylpiperazin-1-yl]-3-[(trans-4-methylcyclohexyl)methyl]-3H-imidazo[4,5-c]pyridin-6-yl}-1,2,4-oxadiazol-5(4H)-one | TFA | 591 | 591 |

TABLE 5-continued

| Ex. | FRET IC$_{50}$ (nM) | Structure | Chemical Name | Salt | [M + H]+ Calc'd | [M + H]+ Obsv'd |
|---|---|---|---|---|---|---|
| 5.3 | 1 | 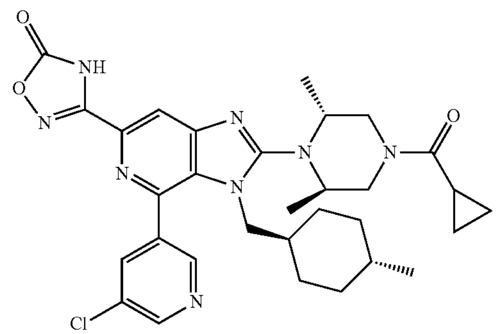 [SMILES: C[C@@H]1CN(C(=O)C2CC2)C[C@@H](C)N1c1nc2cc(-c3noc(=O)[nH]3)nc(-c3cncc(Cl)c3)c2n1C[C@H]1CC[C@H](C)CC1] | 3-{2-[(2R,6R)-4-acetyl-2,6-dimethylpiperazin-1-yl]-4-(5-chloropyridin-3-yl)-3-[(trans-4-methylcyclohexyl)methyl]-3H-imidazo[4,5-c]pyridin-6-yl}-1,2,4-oxadiazol-5(4H)-one | TFA | 579 | 579 |
| 5.4 | 1 | 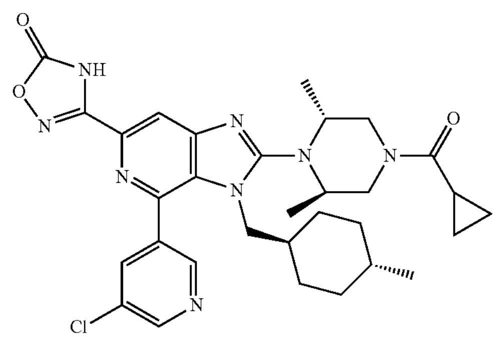 [SMILES: C[C@@H]1CN(C(=O)C2CC2)C[C@@H](C)N1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(2R,6R)-4-(cyclopropylcarbonyl)-2,6-dimethylpiperazin-1-yl]-3-[(trans-4-methylcyclohexyl)methyl]-3H-imidazo[4,5-c]pyridin-6-yl}-1,2,4-oxadiazol-5(4H)-one | TFA | 605 | 605 |
| 5.5 | 3 | 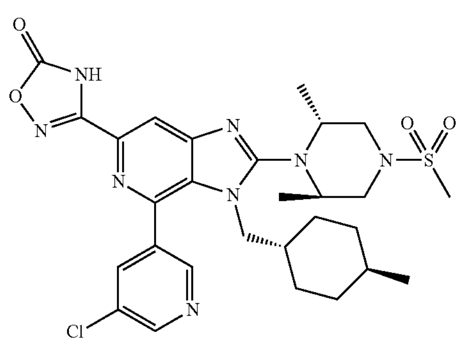 [SMILES: C[C@@H]1CN(S(C)(=O)=O)C[C@@H](C)N1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(2R,6R)-2,6-dimethyl-4-(methylsulfonyl)piperazin-1-yl]-3-[(trans-4-methylcyclohexyl)methyl]-3H-imidazo[4,5-c]pyridin-6-yl}-1,2,4-oxadiazol-5(4H)-one | TFA | 615 | 615 |
| 5.6 | 2 | 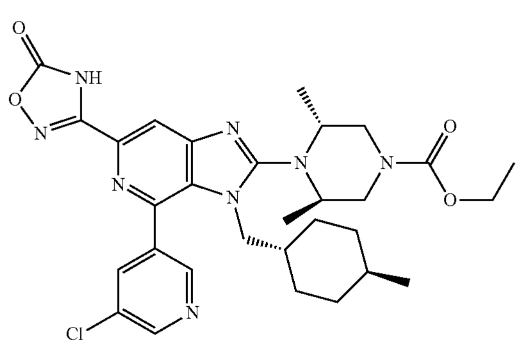 [SMILES: CCOC(=O)N1C[C@@H](C)N(c2nc3cc(-c4noc(=O)[nH]4)nc(-c4cncc(Cl)c4)c3n2C[C@H]2CC[C@H](C)CC2)[C@H](C)C1] | ethyl (3R,5R)-4-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-3,5-dimethylpiperazine-1-carboxylate | TFA | 609 | 609 |

TABLE 5-continued

| Ex. | FRET IC$_{50}$ (nM) | Structure | Chemical Name | Salt | [M + H]+ Calc'd | [M + H]+ Obsv'd |
|---|---|---|---|---|---|---|
| 5.7 | 3 | 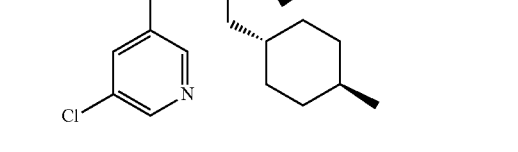 | (3R,5R)-4-[4-(5-chloropyridin-3-yl)-3-[(trans-4-methylcyclohexyl)methyl]-6-(5-oxo-4,5-dihydro-1,2,4-oxadiazo-3-yl)-3H-imidazo[4,5-c]pyridin-2-yl]-N-ethyl-3,5-dimethylpiperazine-1-carboxamide | TFA | 608 | 608 |
| 5.8 | 3 | 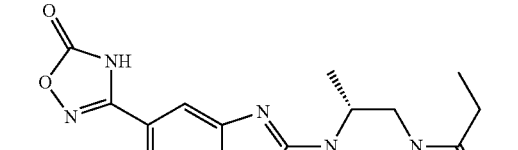 | 3-{4-(5-chloropyridin-3-yl)-2-[(2R,6R)-2,6-dimethyl-4-propanoylpiperazin-1-yl]-3-[(trans-4-methylcyclohexyl)methyl]-3H-imidazo[4,5-c]pyridin-6-yl}-1,2,4-oxadiazol-5(4H)-one | TFA | 593 | 593 |
| 5.9 | 1 | 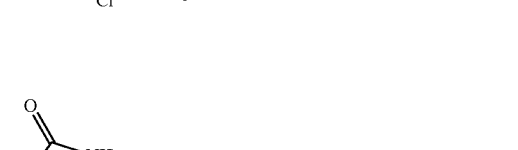 | 3-{4-(5-chloropyridin-3-yl)-2-[(2R,6R)-4-(cyclobutylcarbonyl)-2,6-dimethylpiperazin-1-yl]-3-[(trans-4-methylcyclohexyl)methyl]-3H-imidazo[4,5-c]pyridin-6-yl}-1,2,4-oxadiazol-5(4H)-one | TFA | 619 | 619 |
| 5.10 | 3 | 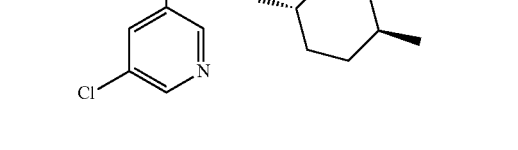 | 3-{2-[(2R,6R)-4-butanoyl-2,6-dimethylpiperazin-1-yl]-4-(5-chloropyridin-3-yl)-3-[(trans-4-methylcyclohexyl)methyl]-3H-imidazo[4,5-c]pyridin-6-yl}-1,2,4-oxadiazol-5(4H)-one | TFA | 607 | 607 |

TABLE 5-continued

| Ex. | FRET IC$_{50}$ (nM) | Structure | Chemical Name | Salt | [M + H]+ Calc'd | [M + H]+ Obsv'd |
|---|---|---|---|---|---|---|
| 5.11 | 2 | 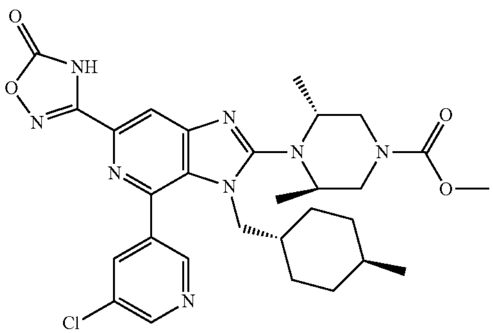 [SMILES: COC(=O)N1C[C@@H](C)N(c2nc3cc(-c4noc(=O)[nH]4)nc(-c4cncc(Cl)c4)c3n2C[C@H]2CC[C@H](C)CC2)[C@H](C)C1] | methyl (3R,5R)-4-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-3,5-dimethylpiperazine-1-carboxylate | TFA | 595 | 595 |
| 5.12 | 3 | 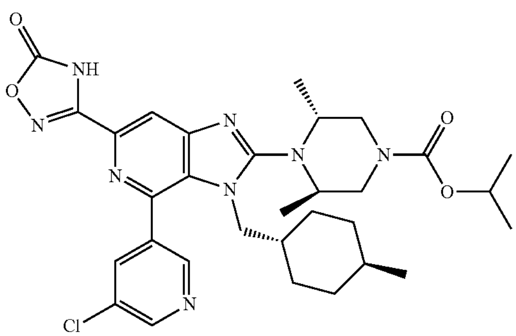 [SMILES: CC(C)OC(=O)N1C[C@@H](C)N(c2nc3cc(-c4noc(=O)[nH]4)nc(-c4cncc(Cl)c4)c3n2C[C@H]2CC[C@H](C)CC2)[C@H](C)C1] | 1-methylethyl (3R,5R)-4-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-3,5-dimethylpiperazine-1-carboxylate | TFA | 623 | 623 |
| 5.13 | 2 | 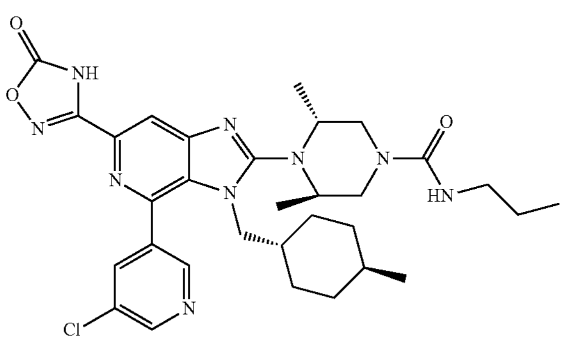 [SMILES: CCCNC(=O)N1C[C@@H](C)N(c2nc3cc(-c4noc(=O)[nH]4)nc(-c4cncc(Cl)c4)c3n2C[C@H]2CC[C@H](C)CC2)[C@H](C)C1] | (3R,5R)-4-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-3,5-dimethyl-N-propylpiperazine-1-carboxamide | TFA | 622 | 622 |
| 5.14 | 3 | 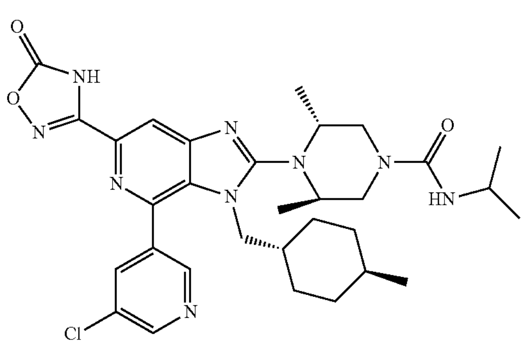 [SMILES: CC(C)NC(=O)N1C[C@@H](C)N(c2nc3cc(-c4noc(=O)[nH]4)nc(-c4cncc(Cl)c4)c3n2C[C@H]2CC[C@H](C)CC2)[C@H](C)C1] | (3R,5R)-4-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-3,5-dimethyl-N-(1-methylethyl)piperazine-1-carboxamide | TFA | 622 | 622 |

TABLE 5-continued

| Ex. | FRET IC$_{50}$ (nM) | Structure | Chemical Name | Salt | [M + H]+ Calc'd | [M + H]+ Obsv'd |
|---|---|---|---|---|---|---|
| 5.15 | 82 | 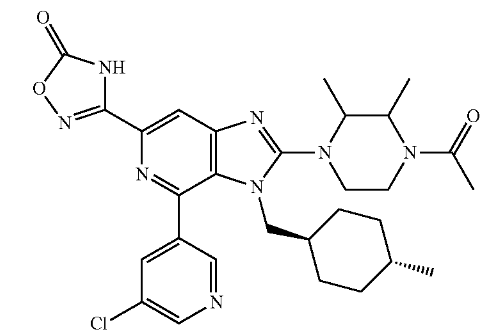 [SMILES: CC(=O)N1CCN(c2nc3cc(-c4noc(=O)[nH]4)nc(-c4cncc(Cl)c4)c3n2C[C@H]2CC[C@H](C)CC2)C(C)C1C] | 3-{2-(4-acetyl-2,3-dimethylpiperazin-1-yl)-4-(5-chloropyridin-3-yl)-3-[(trans-4-methylcyclohexyl)methyl]-3H-imidazo[4,5-c]pyridin-6-yl}-1,2,4-oxadiazol-5(4H)-one | TFA | 579 | 579 |
| 5.16 | 68 | 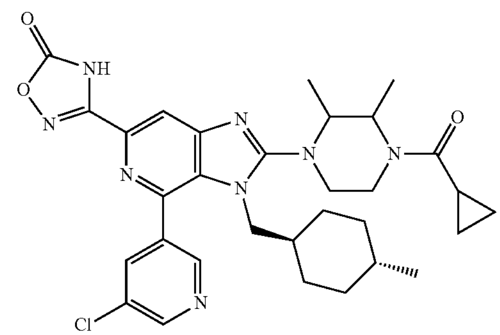 [SMILES: CC1C(C)N(c2nc3cc(-c4noc(=O)[nH]4)nc(-c4cncc(Cl)c4)c3n2C[C@H]2CC[C@H](C)CC2)CCN1C(=O)C1CC1] | 3-{4-(5-chloropyridin-3-yl)-2-[4-(cyclopropylcarbonyl)-2,3-dimethylpiperazin-1-yl]-3-[(trans-4-methylcyclohexyl)methyl]-3H-imidazo[4,5-c]pyridin-6-yl}-1,2,4-oxadiazol-5(4H)-one | TFA | 605 | 605 |
| 5.17 | 3 | 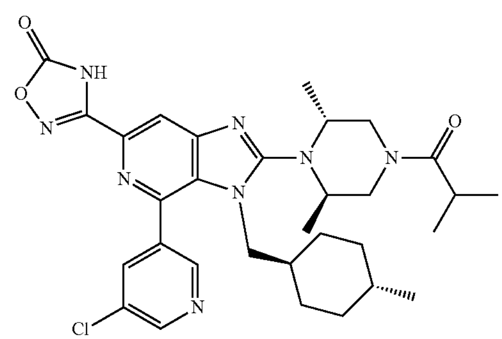 [SMILES: CC(C)C(=O)N1C[C@@H](C)N(c2nc3cc(-c4noc(=O)[nH]4)nc(-c4cncc(Cl)c4)c3n2C[C@H]2CC[C@H](C)CC2)[C@H](C)C1] | 3-{4-(5-chloropyridin-3-yl)-2-[(2R,6R)-2,6-dimethyl-4-(2-methylpropanoyl)piperazin-1-yl]-3-[(trans-4-methylcyclohexyl)methyl]-3H-imidazo[4,5-pyridin-6-yl}-1,2,4-oxadiazol-5(4H)-one | TFA | 607 | 607 |
| 5.18 | 5 | 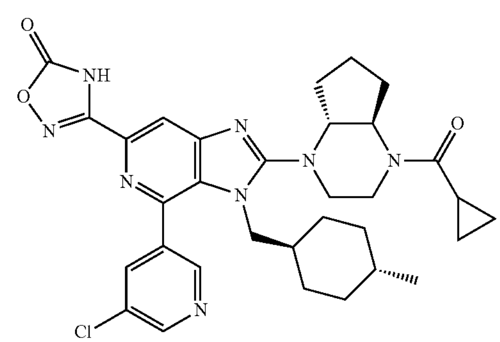 [SMILES: C[C@H]1CC[C@H](Cn2c(N3CCN(C(=O)C4CC4)[C@@H]4CCC[C@H]43)nc3cc(-c4noc(=O)[nH]4)nc(-c4cncc(Cl)c4)c32)CC1] | 3-{4-(5-chloropyridin-3-yl)-2-[(4aR,7aR)-4-(cyclopropylcarbonyl)octahydro-1H-cyclopenta[b]pyrazin-1-yl]-3-[(trans-4-methylcyclohexyl)methyl]-3H-imidazo[4,5-c]pyridin-6-yl}-1,2,4-oxadiazol-5(4H)-one | TFA | 617 | 617 |

TABLE 5-continued

| Ex. | FRET IC$_{50}$ (nM) | Structure | Chemical Name | Salt | [M + H]+ Calc'd | [M + H]+ Obsv'd |
|---|---|---|---|---|---|---|
| 5.19 | 4 | 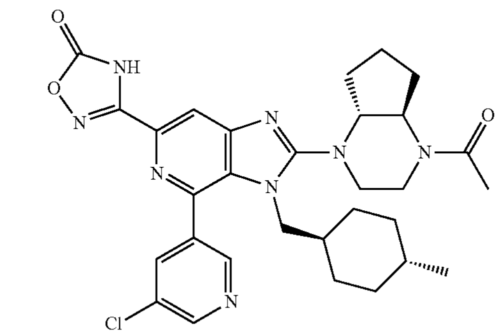 [SMILES: CC(=O)N1CCN(c2nc3cc(-c4noc(=O)[nH]4)nc(-c4cncc(Cl)c4)c3n2C[C@H]2CC[C@H](C)CC2)[C@@H]2CCC[C@H]21] | 3-{2-[(4aR,7aR)-4-acetyloctahydro-1H-cyclopenta[b]pyrazin-1-yl]-4-(5-chloropyridin-3-yl)-3-[(trans-4-methylcyclohexyl)methyl]-3H-imidazo[4,5-c]pyridin-6-yl}-1,2,4-oxadiazol-5(4H)-one | TFA | 591 | 591 |
| 5.20 | 3 | 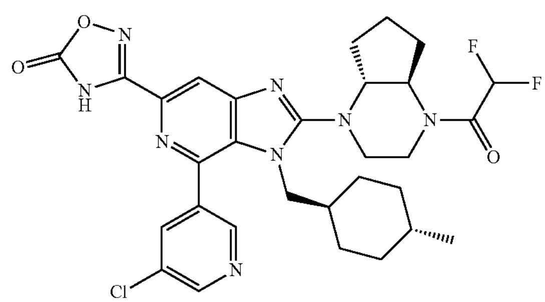 [SMILES: C[C@H]1CC[C@H](Cn2c(N3CCN(C(=O)C(F)F)[C@@H]4CCC[C@H]43)nc3cc(-c4noc(=O)[nH]4)nc(-c4cncc(Cl)c4)c32)CC1] | 3-{4-(5-chloropyridin-3-yl)-2-[(4aR,7aR)-4-(difluoroacetyl)octahydro-1H-cyclopenta[b]pyrazin-1-yl]-3-[(trans-4-methylcyclohexyl)methyl]-3H-imidazo[4,5-c]pyridin-6-yl}-1,2,4-oxadiazol-5(4H)-one | TFA | 627 | 627 |
| 5.21 | 5 | 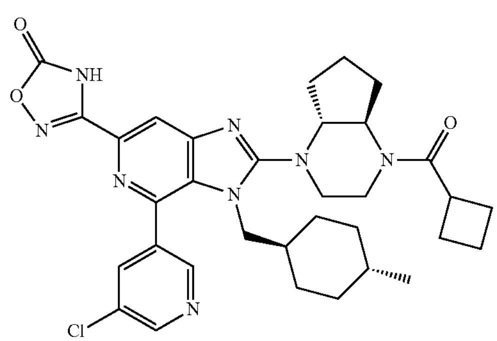 [SMILES: C[C@H]1CC[C@H](Cn2c(N3CCN(C(=O)C4CCC4)[C@@H]4CCC[C@H]43)nc3cc(-c4noc(=O)[nH]4)nc(-c4cncc(Cl)c4)c32)CC1] | 3-{4-(5-chloropyridin-3-yl)-2-[(4aR,7aR)-4-(cyclobutylcarbonyl)octahydro-1H-cyclopenta[b]pyrazin-1-yl]-3-[(trans-4-methylcyclohexyl)methyl]-3H-imidazo[4,5-c]pyridin-6-yl}-1,2,4-oxadiazol-5(4H)-one | TFA | 631 | 631 |
| 5.22 | 1 | 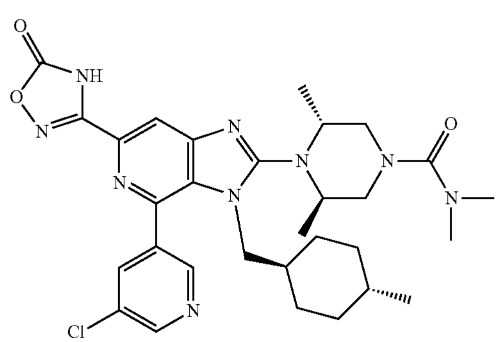 [SMILES: C[C@@H]1CN(C(=O)N(C)C)C[C@@H](C)N1c1nc2cc(-c3noc(=O)[nH]3)nc(-c3cncc(Cl)c3)c2n1C[C@H]1CC[C@H](C)CC1] | (3R,5R)-4-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-N,N,3,5-tetramethylpiperazine-1-carboxamide | TFA | 608 | 608 |

TABLE 5-continued

| Ex. | FRET IC$_{50}$ (nM) | Structure | Chemical Name | Salt | [M + H]+ Calc'd | [M + H]+ Obsv'd |
|---|---|---|---|---|---|---|
| 5.23 | 1 | 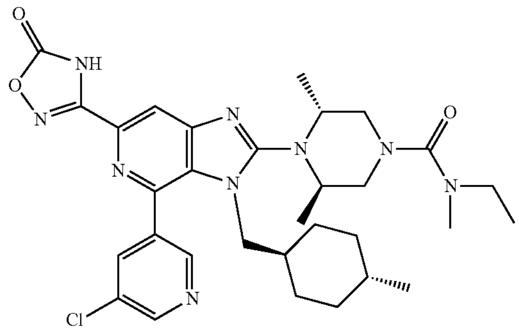 [SMILES: CCN(C)C(=O)N1C[C@@H](C)N(c2nc3cc(-c4noc(=O)[nH]4)nc(-c4cncc(Cl)c4)c3n2C[C@H]2CC[C@H](C)CC2)[C@H](C)C1] | (3R,5R)-4-[4-(5-chloropyridin-3-yl)-3-[(trans-4-methylcyclohexyl)methyl]-6-(5-oxo-4,5-dihydro-1,2,4-oxadiazol-3-yl)-3H-imidazo[4,5-c]pyridin-2-yl]-N-ethyl-N,3,5-trimethylpiperazine-1-carboxamide | TFA | 622 | 622 |
| 5.24 | 1 | 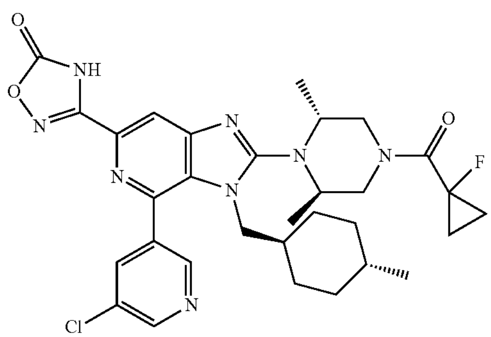 [SMILES: C[C@@H]1CN(C(=O)C2(F)CC2)C[C@@H](C)N1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-{(2R,6R)-4-[(1-fluorocyclopropyl)carbonyl]-2,6-dimethylpiperazin-1-yl}-3-[(trans-4-methylcyclohexyl)methyl]-3H-imidazo[4,5-c]pyridin-6-yl}-1,2,4-oxadiazol-5(4H)-one | TFA | 623 | 623 |
| 5.25 | 4 | 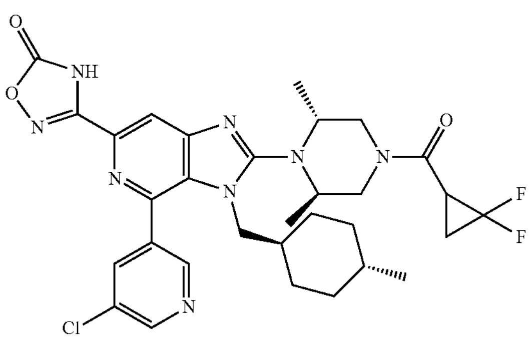 [SMILES: C[C@@H]1CN(C(=O)C2CC2(F)F)C[C@@H](C)N1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-{(2R,6R)-4-[(2,2-difluorocyclopropyl)carbonyl]-2,6-dimethylpiperazin-1-yl}-3-[(trans-4-methylcyclohexyl)methyl]-3H-imidazo[4,5-c]pyridin-6-yl}-1,2,4-oxadiazol-5(4H)-one | TFA | 641 | 641 |
| 5.26 | 4 | 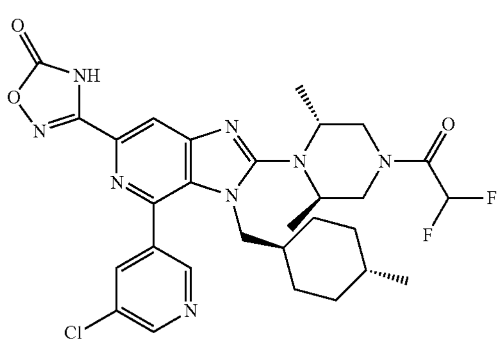 [SMILES: C[C@@H]1CN(C(=O)C(F)F)C[C@@H](C)N1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(2R,6R)-4-(difluoroacetyl)-2,6-dimethylpiperazin-1-yl]-3-[(trans-4-methylcyclohexyl)methyl]-3H-imidazo[4,5-c]pyridin-6-yl}-1,2,4-oxadiazol-5(4H)-one | TFA | 615 | 615 |

TABLE 5-continued

| Ex. | FRET IC$_{50}$ (nM) | Structure | Chemical Name | Salt | [M + H]+ Calc'd | [M + H]+ Obsv'd |
|---|---|---|---|---|---|---|
| 5.27 | 11 | 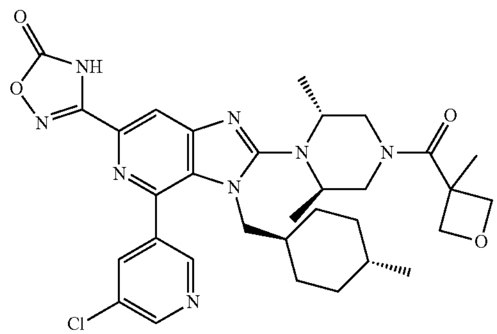 [SMILES: C[C@@H]1CN(C(=O)C2(C)COC2)C[C@@H](C)N1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-{(2R,6R)-2,6-dimethyl-4-[(3-methyloxetan-3-yl)carbonyl]piperazin-1-yl}-3-[(trans-4-methylcyclohexyl)methyl]-3H-imidazo[4,5-c]pyridin-6-yl}-1,2,4-oxadiazol-5(4H)-one | TFA | 635 | 635 |
| 5.28 | 10 | 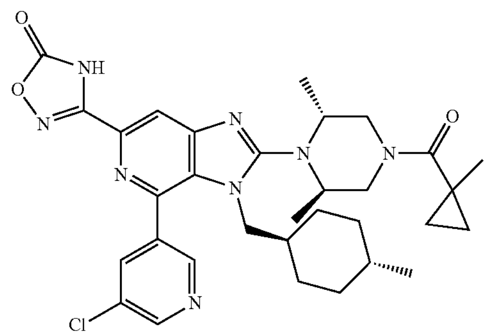 [SMILES: C[C@@H]1CN(C(=O)C2(C)CC2)C[C@@H](C)N1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-{(2R,6R)-2,6-dimethyl-4-[(1-methylcyclopropyl)carbonyl]piperazin-1-yl}-3-[(trans-4-methylcyclohexyl)methyl]-3H-imidazo[4,5-c]pyridin-6-yl}-1,2,4-oxadiazol-5(4H)-one | | 619 | 619 |
| 5.29 | 4 | 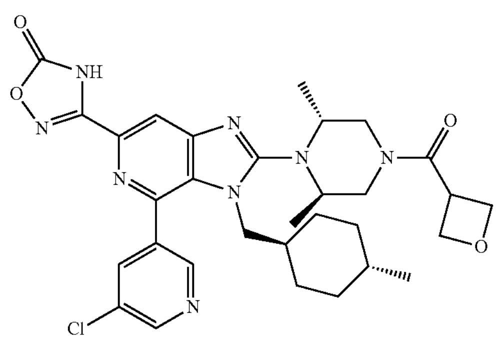 [SMILES: C[C@@H]1CN(C(=O)C2COC2)C[C@@H](C)N1c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(2R,6R)-2,6-dimethyl-4-(oxetan-3-ylcarbonyl)piperazin-1-yl]-3-[(trans-4-methylcyclohexyl)methyl]-3H-imidazo[4,5-c]pyridin-6-yl}-1,2,4-oxadiazol-5(4H)-one | TFA | 621 | 621 |
| 5.30 | 10 | 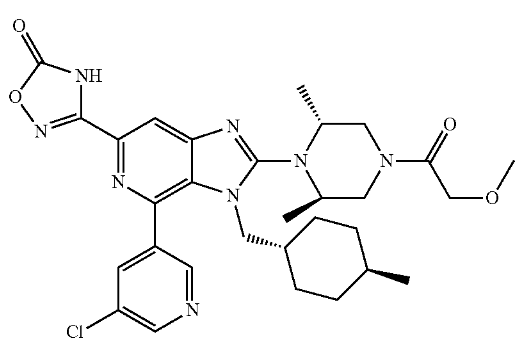 [SMILES: COCC(=O)N1C[C@@H](C)N(c2nc3cc(-c4noc(=O)[nH]4)nc(-c4cncc(Cl)c4)c3n2C[C@H]2CC[C@H](C)CC2)[C@H](C)C1] | 3-{4-(5-chloropyridin-3-yl)-2-[(2R,6R)-4-(methoxyacetyl)-2,6-dimethylpiperazin-1-yl]-3-[(trans-4-methylcyclohexyl)methyl]-3H-imidazo[4,5-c]pyridin-6-yl}-1,2,4-oxadiazol-5(4H)-one | | 609 | 609 |

Scheme 9

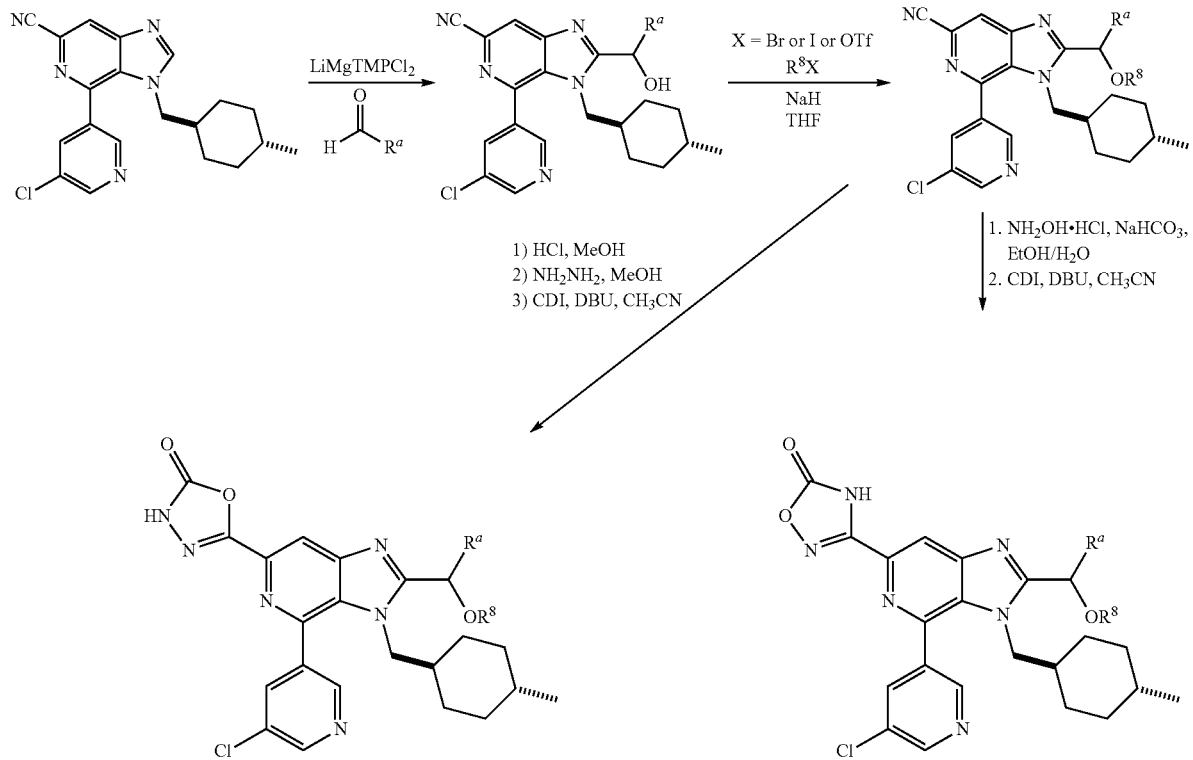

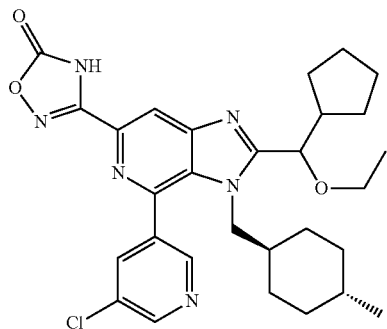 [SMILES: CCOC(c1nc2cc(-c3noc(=O)[nH]3)nc(-c3cncc(Cl)c3)c2n1C[C@H]1CC[C@H](C)CC1)C1CCCC1]

Example 6.1

3-(4-(5-chloropyridin-3-yl)-2-((R or S)-cyclopentyl (ethoxy)methyl)-3-((trans-4-methylcyclohexyl)methyl)-3H-imidazo[4,5-c]pyridin-6-yl)-1,2,4-oxadiazol-5(4H)-one Step 1: 4-(5-chloropyridin-3-yl)-3-((trans-4-methylcyclohexyl)methyl)-3H-imidazo[4,5-c]pyridine-6-carbonitrile (product of Step 2, Preparative Example 3.1) (500 mg, 1.367 mmol) was dissolved in THF (13.7 mL) and cooled to −78° C. in a flask under nitrogen before adding lithium magnesium 2,2,6,6-tetramethylpiperidin-1-ide dichloride, 1.0 M in THF (3.01 mL, 3.01 mmol). After stirring at −78° C. for 45 minutes, cyclopentanecarbaldehyde (321 μL, 3.01 mmol) was added, and the reaction was allowed to stir at −78° C. for 30 minutes before removing the cooling bath. After warming to room temperature over 1 hr, the reaction mixture was quenched with sat. aqueous ammonium chloride and extracted with ethyl acetate. The organic layer was dried over sodium sulfate, filtered, and concentrated. The residue was purified by silica gel chromatography (hexanes/0-65% EtOAc) to afford 4-(5-chloropyridin-3-yl)-2-(cyclopentyl (hydroxy)methyl)-3-((trans-4-methylcyclohexyl)methyl)-3H-imidazo[4,5-c]pyridine-6-carbonitrile. MS ESI calc'd. for $C_{26}H_{30}ClN_5O$ [M+H]$^+$ 464. found 464. $^1$H NMR (600 MHz, CD$_3$OD) δ 8.78 (d, J=2.1, 1H), 8.74 (d, J=1.3, 1H), 8.27-8.24 (m, 1H), 8.23 (s, 1H), 4.68 (d, J=9.1, 1H), 4.15-3.88 (m, 2H), 2.73 (dd, J=8.0, 16.0, 1H), 1.99-1.91 (m, 1H), 1.76-1.54 (m, 6H), 1.50 (d, J=13.3, 2H), 1.31-1.22 (m, 1H), 1.19-1.09 (m, 1H), 1.02-0.96 (m, 1H), 0.92-0.77 (m, 4H), 0.75 (d, J=6.5, 3H), 0.60-0.47 (m, 2H).

Step 2: 4-(5-chloropyridin-3-yl)-2-(cyclopentyl(hydroxy) methyl)-3-((trans-4-methylcyclohexyl)methyl)-3H-imidazo [4,5-c]pyridine-6-carbonitrile (240 mg, 0.517 mmol) was dissolved in THF (5.2 mL) and cooled to 0° C. in a flask under nitrogen before adding sodium hydride (41.4 mg, 1.034 mmol). Upon cessation of gas evolution, iodoethane (0.125 μL, 1.552 mmol) was added, and the reaction was allowed to warm to room temperature overnight. The reaction mixture was quenched with sat. aqueous ammonium chloride and extracted with ethyl acetate. The organic layer was dried over sodium sulfate, filtered, and concentrated. The residue was purified by silica gel chromatography (hexanes/0-40% EtOAc) to afford racemic 4-(5-chloropyridin-3-yl)-2-(cyclopentyl(ethoxy)methyl)-3-((trans-4-methylcyclohexyl)methyl)-3H-imidazo[4,5-c]pyridine-6-carbonitrile. The racemic material was then purified by chiral supercritical fluid chromatography (Chiralpak IC, 21×250 mm, 2-Propanol+ 0.25% Dimethyl Ethyl Amine in CO$_2$) to afford 4-(5-chloropyridin-3-yl)-2- ((R)-cyclopentyl(ethoxy)methyl)-3-((trans- 4-methylcyclohexyl)methyl)-3H-imidazo[4,5-c]pyridine-6-carbonitrile and 4-(5-chloropyridin-3-yl)-2-(S)-cyclopentyl(ethoxy)methyl)-3-((trans-4-methylcyclohexyl)methyl)-3H-imidazo[4,5-c]pyridine-6-carbonitrile. $^1$H NMR (600 MHz, CD$_3$OD) δ 8.78 (d, J=2.3, 1H), 8.75 (d, J=1.5, 1H), 8.29 (t, J=2.0, 1H), 8.24 (s, 1H), 4.65 (d, J=8.5, 1H), 4.08-3.97 (m, 2H), 3.59-3.34 (m, 2H), 2.65-2.54 (m, 1H), 1.88-1.77 (m, 1H), 1.73-1.54 (m, 6H), 1.49 (d, J=13.2, 2H), 1.30-1.25 (m, 1H), 1.17 (t, J=7.0, 3H), 1.15-1.08 (m, 1H), 1.01-0.95 (m, 1H), 0.91-0.76 (m, 4H), 0.75 (d, J=6.6, 3H), 0.56-0.45 (m, 2H). MS ESI calc'd. for C$_{28}$H$_{34}$ClN$_5$O [M+H]$^+$ 492. found 492.

Step 3: Using a procedure analogous to that described in Example 2.1 (Step 5), and starting with 4-(5-chloropyridin-3-yl)-2-((R or S)-cyclopentyl(ethoxy)methyl)-3-((trans-4-methylcyclohexyl)methyl)-3H-imidazo[4,5-c]pyridine-6-carbonitrile, 4-(5-chloropyridin-3-yl)-2-((R or S)-cyclopentyl(ethoxy)methyl)-N'-hydroxy-3-((trans-4-methylcyclohexyl)methyl)-3H-imidazo[4,5-c]pyridine-6-carboximidamide was prepared.

Step 4: Using a procedure analogous to that described in Example 2.1 (Step 6), and starting with 4-(5-chloropyridin-3-yl)-2-((R or S)-cyclopentyl(ethoxy)methyl)-N'-hydroxy-3-((trans-4-methylcyclohexyl)methyl)-3H-imidazo[4,5-c]pyridine-6-carboximidamide, 3-(4-(5-chloropyridin-3-yl)-2-((R or S)-cyclopentyl(ethoxy)methyl)-3-((trans-4-methylcyclohexyl)methyl)-3H-imidazo[4,5-c]pyridin-6-yl)-1,2,4-oxadiazol-5(4H)-one (enantiomer 1) was prepared. $^1$H NMR (600 MHz, CD$_3$OD) δ 8.80 (d, J=1.7, 1H), 8.77 (d, J=2.3, 1H), 8.35-8.34 (m, 2H), 4.68 (d, J=8.3, 1H), 4.12-4.01 (m, 2H), 3.62-3.53 (m, 1H), 3.47-3.35 (m, 1H), 2.63-2.54 (m, 1H), 1.87-1.77 (m, 1H), 1.76-1.52 (m, 6H), 1.50 (d, J=11.2, 2H), 1.36-1.25 (m, 1H), 1.21-1.15 (m, 3H), 1.16-1.08 (m, 1H), 1.05-0.96 (m, 1H), 0.95-0.77 (m, 4H), 0.75 (d, J=6.6, 3H), 0.55-0.44 (m, 2H). MS ESI calc'd. for C$_{29}$H$_{35}$ClN$_6$O$_3$ [M+H]$^+$ 551. found 551.

3-(4-(5-chloropyridin-3-yl)-2-((S or R)-cyclopentyl(ethoxy)methyl)-3-((trans-4-methylcyclohexyl)methyl)-3H-imidazo[4,5-c]pyridin-6-yl)-1,2,4-oxadiazol-5(4H)-one (enantiomer 2, Example 6.2) was prepared in analogous manner.

Example 6.3

5-(4-(5-chloropyridin-3-yl)-2-((R or S)-cyclopentyl(ethoxy)methyl)-3-((trans-4-methylcyclohexyl)methyl)-3H-imidazo[4,5-c]pyridin-6-yl)-1,3,4-oxadiazol-2(3H)-one

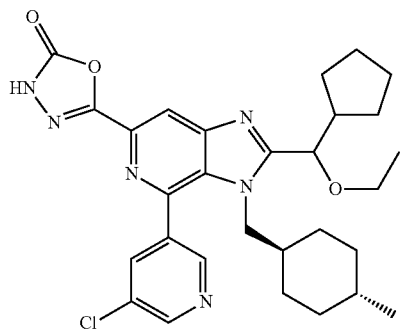 [SMILES: CCOC(c1nc2cc(-c3n[nH]c(=O)o3)nc(-c3cncc(Cl)c3)c2n1C[C@H]1CC[C@H](C)CC1)C1CCCC1]

Using a procedure analogous to that described in Example 2.2 (Step 1 to Step 3), and starting with 4-(5-chloropyridin-3-yl)-2-((R or S)-cyclopentyl(ethoxy)methyl)-3-((trans-4-methylcyclohexyl)methyl)-3H-imidazo[4,5-c]pyridine-6-carbonitrile, 5-(4-(5-chloropyridin-3-yl)-2-((R or S)cyclopentyl(ethoxy)methyl)-3-((trans-4-methylcyclohexyl)methyl)-3H-imidazo[4,5-c]pyridin-6-yl)-1,3,4-oxadiazol-2(3H)-one (enantiomer 1) was prepared. $^1$H NMR (600 MHz, CD$_3$OD) δ 8.77 (d, J=2.1, 2H), 8.30 (t, J=2.1, 1H), 8.26 (s, 1H), 4.69 (d, J=8.2, 1H), 4.03 (d, J=6.8, 2H), 3.64-3.51 (m, 1H), 3.47-3.35 (m, 1H), 2.64-2.47 (m, 1H), 1.85-1.76 (m, 1H), 1.75-1.53 (m, 6H), 1.50 (d, J=11.3, 2H), 1.36-1.28 (m, 1H), 1.19 (d, J=7.0, 3H), 1.17-1.09 (m, 1H), 1.07-0.97 (m, 1H), 0.96-0.77 (m, 4H), 0.75 (d, J=6.6, 3H), 0.58-0.45 (m, 2H). MS ESI calc'd. for C$_{29}$H$_{35}$ClN$_6$O$_3$ [M+H]$^+$ 551. found 551.5-(4-(5-chloropyridin-3-yl)-2-((S or R)cyclopentyl(ethoxy)methyl)-3-((trans-4-methylcyclohexyl)methyl)-3H-imidazo[4,5-c]pyridin-6-yl)-1,3,4-oxadiazol-2(3H)-one (enantiomer 2, Example 6.4) was prepared in analogous manner.

Example 6.13

3-(4-(5-chloropyridin-3-yl)-2-(1-ethoxy-2-hydroxyethyl)-3-((trans-4-methylcyclohexyl)methyl)-3H-imidazo[4,5-c]pyridin-6-yl)-1,2,4-oxadiazol-5(4H)-one

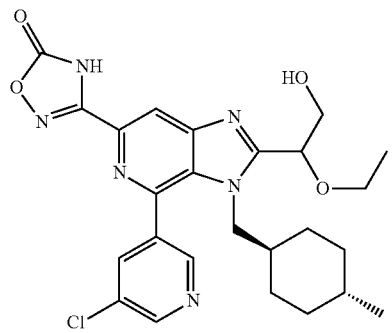 [SMILES: CCOC(CO)c1nc2cc(-c3noc(=O)[nH]3)nc(-c3cncc(Cl)c3)c2n1C[C@H]1CC[C@H](C)CC1]

Step 1: Using a procedure analogous to that described in Example 6.1 (Step 1), and starting with 4-(5-chloropyridin-3-yl)-3-((trans-4-methylcyclohexyl)methyl)-3H-imidazo[4,5-c]pyridine-6-carbonitrile (Step 2, Preparative Example 3.1) and {[tert-butyl(dimethyl)silyl]oxy}acetaldehyde, 2-(2-((tert-butyldimethylsilyl)oxy)-1-hydroxyethyl)-4-(5-chloropyridin-3-yl)-3-((trans-4-methylcyclohexyl)methyl)-3H-imidazo[4,5-c]pyridine-6-carbonitrile was prepared.

Step 2: Using a procedure analogous to that described in Example 6.1 (Step 2), and starting with 2-(2-((tert-butyldimethylsilyl)oxy)-1-hydroxyethyl)-4-(5-chloropyridin-3-yl)-3-((trans-4-methylcyclohexyl)methyl)-3H-imidazo[4,5-c]pyridine-6-carbonitrile, 2-(2-((tert-butyldimethylsilyl)oxy)-1-ethoxyethyl)-4-(5-chloropyridin-3-yl)-3-((trans-4-methylcyclohexyl)methyl)-3H-imidazo[4,5-c]pyridine-6-carbonitrile was prepared.

Step 3: 2-(2-((tert-butyldimethylsilyl)oxy)-1-ethoxyethyl)-4-(5-chloropyridin-3-yl)-3-((trans-4-methylcyclohexyl)methyl)-3H-imidazo[4,5-c]pyridine-6-carbonitrile was dissolved in THF (3.9 mL) and cooled to 0° C. before adding TBAF (1M in THF, 1.5 mL). After stirring at 0° C. for 25 minutes, the reaction mixture was diluted with ethyl acetate and washed with water followed by brine. The organic layer was dried over sodium sulfate, filtered, and concentrated. The residue was purified by silica gel chromatography (DCM/0-10% MeOH) to afford 4-(5-chloropyridin-3-yl)-2-(1-ethoxy-2-hydroxyethyl)-3-((trans-4-methylcyclohexyl)methyl)-3H-imidazo[4,5-c]pyridine-6-carbonitrile. MS ESI calc'd. for C$_{24}$H$_{28}$ClN$_5$O$_2$ [M+H]$^+$ 454. found 454.

Step 4: Using a procedure analogous to that described in Example 2.1 (Step 5), and starting with 4-(5-chloropyridin-3-yl)-2-(1-ethoxy-2-hydroxyethyl)-3-((trans-4-methylcyclohexyl)methyl)-3H-imidazo[4,5-c]pyridine-6-carbonitrile, 4-(5-chloropyridin-3-yl)-2-(1-ethoxy-2-hydroxyethyl)-N'-hydroxy-3-((trans-4-methylcyclohexyl)methyl)-3H-imidazo[4,5-c]pyridine-6-carboximidamide was prepared.

Step 5: Using a procedure analogous to that described in Example 2.1 (Step 6), and starting with 4-(5-chloropyridin-3-yl)-2-(1-ethoxy-2-hydroxyethyl)-N'-hydroxy-3-((trans-4-methylcyclohexyl)methyl)-3H-imidazo[4,5-c]pyridine-6-carboximidamide, 3-(4-(5-chloropyridin-3-yl)-2-(1-ethoxy-2-hydroxyethyl)-3-((trans-4-methylcyclohexyl)methyl)-3H-imidazo[4,5-c]pyridin-6-yl)-1,2,4-oxadiazol-5(4H)-one was prepared. MS ESI calc'd. for $C_{25}H_{29}ClN_6O_4$ [M+H]$^+$ 513. found 513. $^1$H NMR (600 MHz, CD$_3$OD) δ 8.80 (s, 1H), 8.77 (d, J=2.2, 1H), 8.35 (s, 1H), 8.32 (s, 1H), 4.93 (t, J=6.0, 1H), 4.08-3.90 (m, 4H), 3.62 (q, J=7.0, 2H), 1.51 (d, J=11.8, 2H), 1.23 (t, J=7.0, 3H), 1.20-1.11 (m, 1H), 1.10-0.99 (m, 1H), 0.99-0.91 (m, 1H), 0.90-0.78 (m, 3H), 0.76 (d, J=6.5, 3H), 0.60-0.47 (m, 2H).

Example 6.14

3-(4-(5-chloropyridin-3-yl)-2-(1-ethoxy-2-methoxyethyl)-3-(((1r,4r)-4-methylcyclohexyl)methyl)-3H-imidazo[4,5-c]pyridin-6-yl)-1,2,4-oxadiazol-5(4H)-one

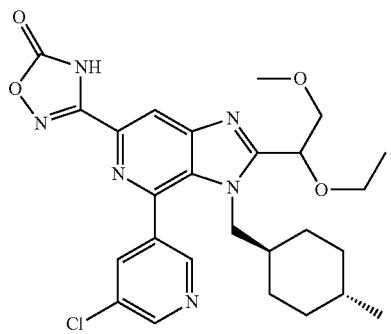 [SMILES: CCOC(COC)c1nc2cc(-c3noc(=O)[nH]3)nc(-c3cncc(Cl)c3)c2n1C[C@H]1CC[C@H](C)CC1]

Step 1: Using a procedure analogous to that described in Example 6.1 (Step 2), and starting with 4-(5-chloropyridin-3-yl)-2-(1-ethoxy-2-hydroxyethyl)-3-((trans-4-methylcyclohexyl)methyl)-3H-imidazo[4,5-c]pyridine-6-carbonitrile (Example 6.13, Step 3) and iodomethane, 4-(5-chloropyridin-3-yl)-2-(1-ethoxy-2-methoxyethyl)-3-((trans-4-methylcyclohexyl)methyl)-3H-imidazo[4,5-c]pyridine-6-carbonitrile was prepared. MS ESI calc'd. for $C_{25}H_{30}ClN_5O_2$ [M+H]$^+$ 468. found 468.

Step 2: Using a procedure analogous to that described in Example 2.1 (Step 5), and starting with 4-(5-chloropyridin-3-yl)-2-(1-ethoxy-2-methoxyethyl)-3-((trans-4-methylcyclohexyl)methyl)-3H-imidazo[4,5-c]pyridine-6-carbonitrile, 4-(5-chloropyridin-3-yl)-2-(1-ethoxy-2-methoxyethyl)-N'-hydroxy-3-((trans-4-methylcyclohexyl)methyl)-3H-imidazo[4,5-c]pyridine-6-carboximidamide was prepared.

Step 3: Using a procedure analogous to that described in Example 2.1 (Step 6), and starting with 4-(5-chloropyridin-3-yl)-2-(1-ethoxy-2-methoxyethyl)-N'-hydroxy-3-((trans-4-methylcyclohexyl)methyl)-3H-imidazo[4,5-c]pyridine-6-carboximidamide, 3-(4-(5-chloropyridin-3-yl)-2-(1-ethoxy-2-methoxyethyl)-3-((trans-4-methylcyclohexyl)methyl)-3H-imidazo[4,5-c]pyridin-6-yl)-1,2,4-oxadiazol-5(4H)-one was prepared. MS ESI calc'd. for $C_{26}H_{31}ClN_6O_4$ [M+H]$^+$ 527. found 527. $^1$H NMR (600 MHz, CD$_3$OD) δ 8.79 (s, 1H), 8.77 (d, J=2.2, 1H), 8.35 (s, 1H), 8.32 (s, 1H), 5.06 (t, J=6.0, 1H), 4.02 (d, J=7.4, 2H), 3.97-3.81 (m, 2H), 3.68-3.56 (m, 2H), 3.37 (s, 3H), 1.51 (d, J=11.2, 2H), 1.21 (t, J=7.0, 3H), 1.18-1.11 (m, 1H), 1.09-1.00 (m, 1H), 0.97-0.88 (m, 1H), 0.88-0.78 (m, 3H), 0.76 (d, J=6.5, 3H), 0.58-0.47 (m, 2H).

The following compounds in Table 6 (other than Examples 6.1-6.4, 6.13, and 6.14) were prepared using procedures which were analogous to those described above.

TABLE 6

| Ex. | FRET IC$_{50}$ (nM) | Structure | Chemical Name | Salt | [M + H]+ Calc'd | [M + H]+ Obsv'd |
|---|---|---|---|---|---|---|
| 6.1 | 2 | 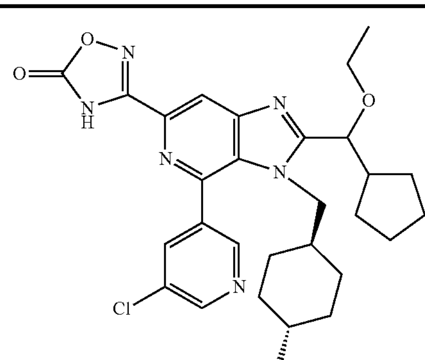 | 3-{4-(5-chloropyridin-3-yl)-2-[cyclopentyl(ethoxy)methyl]-3-[(trans-4-methylcyclohexyl)methyl]-3H-imidazo[4,5-c]pyridin-6-yl}-1,2,4-oxadiazol-5(4H)-one (enantiomer 1) | TFA | 551 | 551 |

TABLE 6-continued

| Ex. | FRET IC$_{50}$ (nM) | Structure | Chemical Name | Salt | [M + H]+ Calc'd | [M + H]+ Obsv'd |
|---|---|---|---|---|---|---|
| 6.2 | 3 | 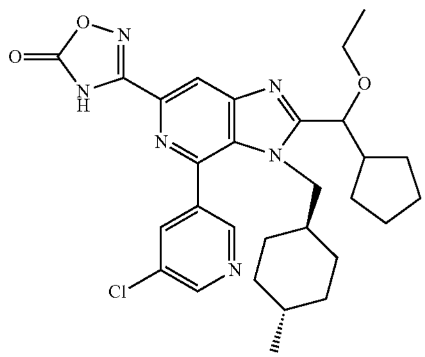 [SMILES: CCOC(c1nc2cc(-c3noc(=O)[nH]3)nc(-c3cncc(Cl)c3)c2n1C[C@H]1CC[C@H](C)CC1)C1CCCC1] | 3-{4-(5-chloropyridin-3-yl)-2-[cyclopentyl(ethoxy)methyl]-3-[(trans-4-methylcyclohexyl)methyl]-3H-imidazo[4,5-c]pyridin-6-yl}-1,2,4-oxadiazol-5(4H)-one (enantiomer 2) | TFA | 551 | 551 |
| 6.3 | 6 | 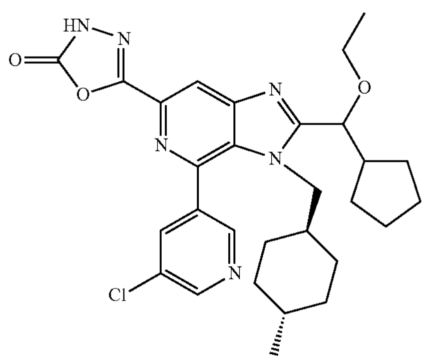 [SMILES: CCOC(c1nc2cc(-c3n[nH]c(=O)o3)nc(-c3cncc(Cl)c3)c2n1C[C@H]1CC[C@H](C)CC1)C1CCCC1] | 5-{4-(5-chloropyridin-3-yl)-2-[cyclopentyl(ethoxy)methyl]-3-[(trans-4-methylcyclohexyl)methyl]-3H-imidazo[4,5-c]pyridin-6-yl}-1,3,4-oxadiazol-2(3H)-one (enantiomer 1) | TFA | 551 | 551 |
| 6.4 | 10 | 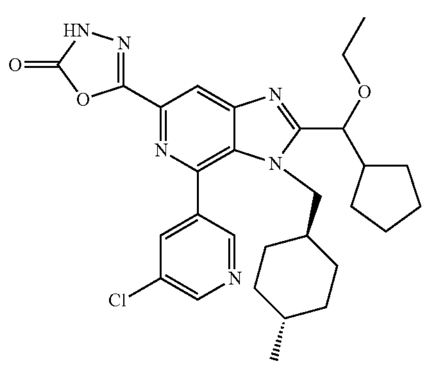 [SMILES: CCOC(c1nc2cc(-c3n[nH]c(=O)o3)nc(-c3cncc(Cl)c3)c2n1C[C@H]1CC[C@H](C)CC1)C1CCCC1] | 5-{4-(5-chloropyridin-3-yl)-2-[cyclopentyl(ethoxy)methyl]-3-[(trans-4-methylcyclohexyl)methyl]-3H-imidazo[4,5-c]pyridin-6-yl}-1,3,4-oxadiazol-2(3H)-one (enantiomer 2) | TFA | 551 | 551 |
| 6.5 | 9 | 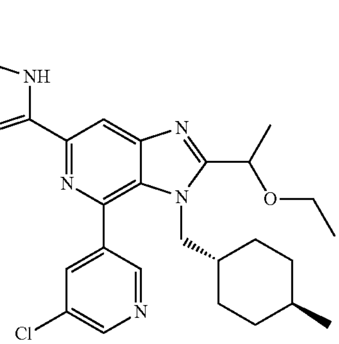 | 3-(4-(5-chloropyridin-3-yl)-2-(1-ethoxyethyl)-3-((trans-4-methylcyclohexyl)methyl)-3H-imidazo[4,5-c]pyridin-6-yl)-1,2,4-oxadiazol-5(4H)-one (enantiomer 1) | TFA | 497 | 497 |

TABLE 6-continued

| Ex. | FRET IC$_{50}$ (nM) | Structure | Chemical Name | Salt | [M + H]+ Calc'd | [M + H]+ Obsv'd |
|---|---|---|---|---|---|---|
| 6.6 | 18 | 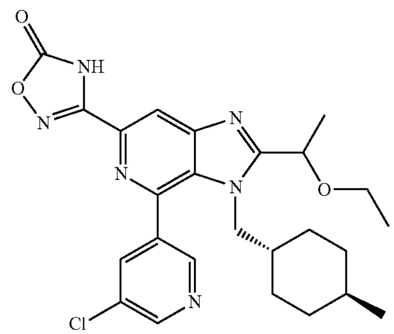 [SMILES: CCOC(C)c1nc2cc(-c3noc(=O)[nH]3)nc(-c3cncc(Cl)c3)c2n1C[C@H]1CC[C@H](C)CC1] | 3-(4-(5-chloropyridin-3-yl)-2-(1-ethoxyethyl)-3-((trans-4-methylcyclohexyl)methyl)-3H-imidazo[4,5-c]pyridin-6-yl)-1,2,4-oxadiazol-5(4H)-one (enantiomer 2) | TFA | 497 | 497 |
| 6.7 | 4 | 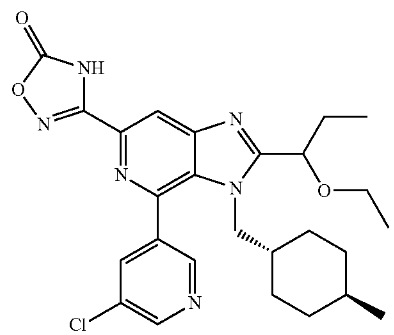 [SMILES: CCOC(CC)c1nc2cc(-c3noc(=O)[nH]3)nc(-c3cncc(Cl)c3)c2n1C[C@H]1CC[C@H](C)CC1] | 3-(4-(5-chloropyridin-3-yl)-2-(1-ethoxypropyl)-3-((trans-4-methylcyclohexyl)methyl)-3H-imidazo[4,5-c]pyridin-6-yl)-1,2,4-oxadiazol-5(4H)-one (enantiomer 1) | TFA | 511 | 511 |
| 6.8 | 8 | 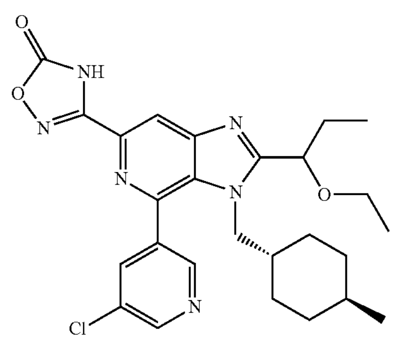 [SMILES: CCOC(CC)c1nc2cc(-c3noc(=O)[nH]3)nc(-c3cncc(Cl)c3)c2n1C[C@H]1CC[C@H](C)CC1] | 3-(4-(5-chloropyridin-3-yl)-2-(1-ethoxypropyl)-3-((trans-4-methylcyclohexyl)methyl)-3H-imidazo[4,5-c]pyridin-6-yl)-1,2,4-oxadiazol-5(4H)-one (enantiomer 2) | TFA | 511 | 511 |
| 6.9 | 2 | 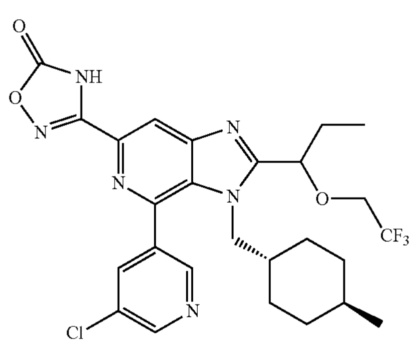 [SMILES: CCC(OCC(F)(F)F)c1nc2cc(-c3noc(=O)[nH]3)nc(-c3cncc(Cl)c3)c2n1C[C@H]1CC[C@H](C)CC1] | 3-(4-(5-chloropyridin-3-yl)-3-((trans-4-methylcyclohexyl)methyl)-2-(1-(2,2,2-trifluoroethoxy)propyl)-3H-imidazo[4,5-c]pyridin-6-yl)-1,2,4-oxadiazol-5(4H)-one (racemic) | TFA | 565 | 565 |

TABLE 6-continued

| Ex. | FRET IC$_{50}$ (nM) | Structure | Chemical Name | Salt | [M + H]+ Calc'd | [M + H]+ Obsv'd |
|---|---|---|---|---|---|---|
| 6.10 | 5 | 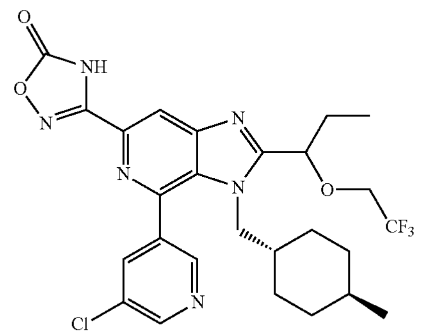 [SMILES: CCC(OCC(F)(F)F)c1nc2cc(-c3noc(=O)[nH]3)nc(-c3cncc(Cl)c3)c2n1C[C@H]1CC[C@H](C)CC1] | 3-(4-(5-chloropyridin-3-yl)-3-((trans-4-methylcyclohexyl)methyl)-2-(1-(2,2,2-trifluoroethoxy)propyl)-3H-imidazo[4,5-c]pyridin-6-yl)-1,2,4-oxadiazol-5(4H)-one (enantiomer 1) | | 565 | 565 |
| 6.11 | 2 | 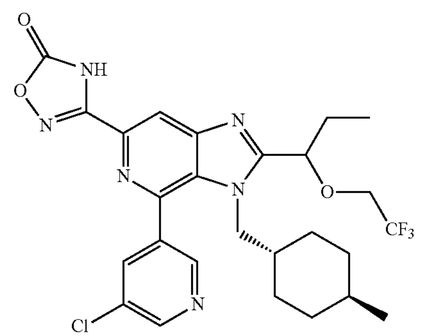 [SMILES: CCC(OCC(F)(F)F)c1nc2cc(-c3noc(=O)[nH]3)nc(-c3cncc(Cl)c3)c2n1C[C@H]1CC[C@H](C)CC1] | 3-(4-(5-chloropyridin-3-yl)-3-((trans-4-methylcyclohexyl)methyl)-2-(1-(2,2,2-trifluoroethoxy)propyl)-3H-imidazo[4,5-c]pyridin-6-yl)-1,2,4-oxadiazol-5(4H)-one (enantiomer 2) | | 565 | 565 |
| 6.12 | 3 | 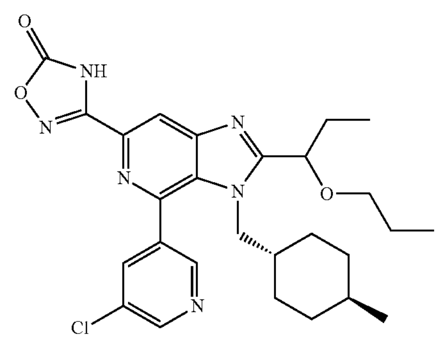 [SMILES: CCCOC(CC)c1nc2cc(-c3noc(=O)[nH]3)nc(-c3cncc(Cl)c3)c2n1C[C@H]1CC[C@H](C)CC1] | 3-(4-(5-chloropyridin-3-yl)-3-((trans-4-methylcyclohexyl)methyl)-2-(1-propoxypropyl)-3H-imidazo[4,5-c]pyridin-6-yl)-1,2,4-oxadiazol-5(4H)-one (racemic) | TFA | 525 | 525 |
| 6.13 | 15 | 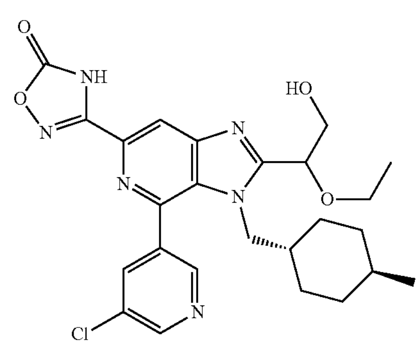 [SMILES: CCOC(CO)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-(1-ethoxy-2-hydroxyethyl)-3-[(trans-4-methylcyclohexyl)methyl]-3H-imidazo[4,5-c]pyridin-6-yl}-1,2,4-oxadiazol-5(4H)-one (racemic) | TFA | 513 | 513 |

| Ex. | FRET IC$_{50}$ (nM) | Structure | Chemical Name | Salt | [M + H]+ Calc'd | [M + H]+ Obsv'd |
|---|---|---|---|---|---|---|
| 6.14 | 9 | 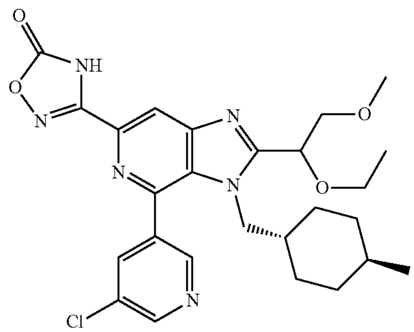 [SMILES: CCOC(COC)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-(1-ethoxy-2-methoxyethyl)-3-[(trans-4-methylcyclohexyl)methyl]-3H-imidazo[4,5-c]pyridin-6-yl}-1,2,4-oxadiazol-5(4H)-one (racemic) | TFA | 527 | 527 |
| 6.15 | 2 | 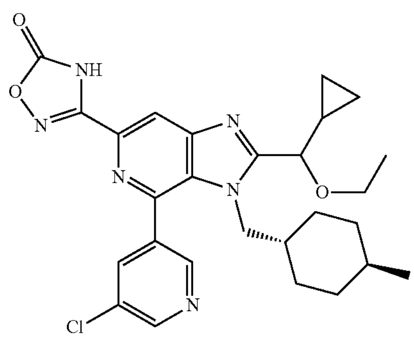 [SMILES: CCOC(c1nc2cc(-c3noc(=O)[nH]3)nc(-c3cncc(Cl)c3)c2n1C[C@H]1CC[C@H](C)CC1)C1CC1] | 3-{4-(5-chloropyridin-3-yl)-2-[cyclopropyl(ethoxy)methyl]-3-[(trans-4-methylcyclohexyl)methyl]-3H-imidazo[4,5-c]pyridin-6-yl}-1,2,4-oxadiazol-5(4H)-one (racemic) | TFA | 523 | 523 |
| 6.16 | 1 | 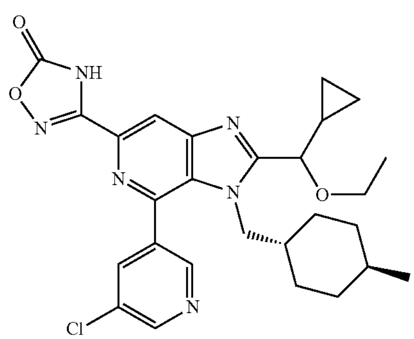 [SMILES: CCOC(c1nc2cc(-c3noc(=O)[nH]3)nc(-c3cncc(Cl)c3)c2n1C[C@H]1CC[C@H](C)CC1)C1CC1] | 3-{4-(5-chloropyridin-3-yl)-2-[cyclopropyl(ethoxy)methyl]-3-[(trans-4-methylcyclohexyl)methyl]-3H-imidazo[4,5-c]pyridin-6-yl}-1,2,4-oxadiazol-5(4H)-one (enantiomer 1) | | 523 | 523 |
| 6.17 | 4 | 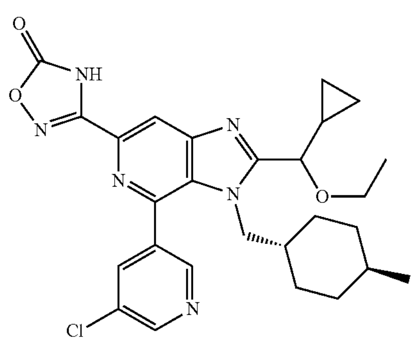 [SMILES: CCOC(c1nc2cc(-c3noc(=O)[nH]3)nc(-c3cncc(Cl)c3)c2n1C[C@H]1CC[C@H](C)CC1)C1CC1] | 3-{4-(5-chloropyridin-3-yl)-2-[cyclopropyl(ethoxy)methyl]-3-[(trans-4-methylcyclohexyl)methyl]-3H-imidazo[4,5-c]pyridin-6-yl}-1,2,4-oxadiazol-5(4H)-one (enantiomer 2) | | 523 | 523 |

TABLE 6-continued

| Ex. | FRET IC$_{50}$ (nM) | Structure | Chemical Name | Salt | [M + H]+ Calc'd | [M + H]+ Obsv'd |
|---|---|---|---|---|---|---|
| 6.18 | 2 | 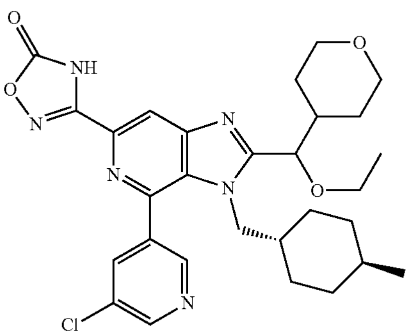 [SMILES: CCOC(c1nc2cc(-c3noc(=O)[nH]3)nc(-c3cncc(Cl)c3)c2n1C[C@H]1CC[C@H](C)CC1)C1CCOCC1] | 3-{4-(5-chloropyridin-3-yl)-2-[ethoxy(tetrahydro-2H-pyran-4-yl)methyl]-3-[(trans-4-methylcyclohexyl)methyl]-3H-imidazo[4,5-c]pyridin-6-yl}-1,2,4-oxadiazol-5(4H)-one (racemic) | TFA | 567 | 567 |
| 6.19 | 5 | 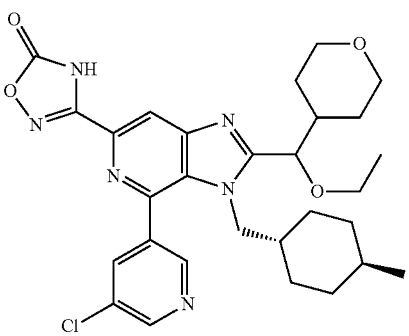 [SMILES: CCOC(c1nc2cc(-c3noc(=O)[nH]3)nc(-c3cncc(Cl)c3)c2n1C[C@H]1CC[C@H](C)CC1)C1CCOCC1] | 3-{4-(5-chloropyridin-3-yl)-2-[ethoxy(tetrahydro-2H-pyran-4-yl)methyl]-3-[(trans-4-methylcyclohexyl)methyl]-3H-imidazo[4,5-c]pyridin-6-yl}-1,2,4-oxadiazol-5(4H)-one (enantiomer 1) | | 567 | 567 |
| 6.20 | 3 | 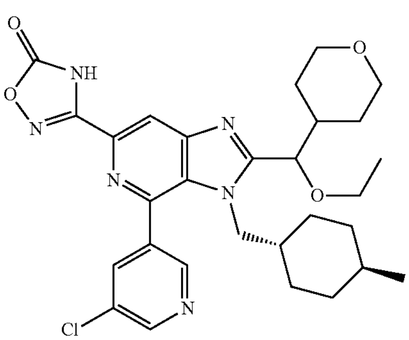 [SMILES: CCOC(c1nc2cc(-c3noc(=O)[nH]3)nc(-c3cncc(Cl)c3)c2n1C[C@H]1CC[C@H](C)CC1)C1CCOCC1] | 3-{4-(5-chloropyridin-3-yl)-2-[ethoxy(tetrahydro-2H-pyran-4-yl)methyl]-3-[(trans-4-methylcyclohexyl)methyl]-3H-imidazo[4,5-c]pyridin-6-yl}-1,2,4-oxadiazol-5(4H)-one (enantiomer 2) | | 567 | 567 |
| 6.21 | 2 | 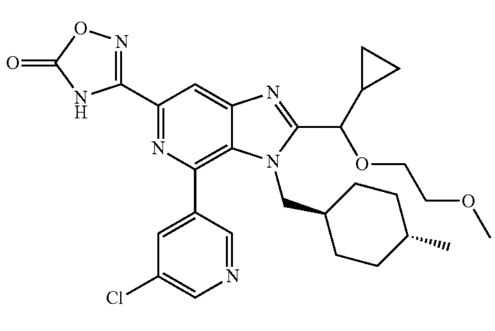 [SMILES: COCCOC(c1nc2cc(-c3noc(=O)[nH]3)nc(-c3cncc(Cl)c3)c2n1C[C@H]1CC[C@H](C)CC1)C1CC1] | 3-{4-(5-chloropyridin-3-yl)-2-[cyclopropyl(2-methoxyethoxy)methyl]-3-[(trans-4-methylcyclohexyl)methyl]-3H-imidazo[4,5-c]pyridin-6-yl}-1,2,4-oxadiazol-5(4H)-one (racemic) | TFA | 553 | 553 |

TABLE 6-continued

| Ex. | FRET IC$_{50}$ (nM) | Structure | Chemical Name | Salt | [M + H]+ Calc'd | [M + H]+ Obsv'd |
|---|---|---|---|---|---|---|
| 6.22 | 2 | 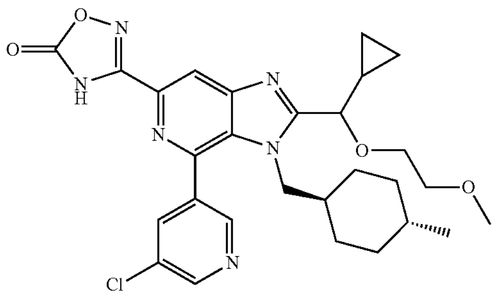 [SMILES: COCCOC(c1nc2cc(-c3noc(=O)[nH]3)nc(-c3cncc(Cl)c3)c2n1C[C@H]1CC[C@H](C)CC1)C1CC1] | 3-{4-(5-chloropyridin-3-yl)-2-[cyclopropyl(2-methoxyethoxy)methyl]-3-[(trans-4-methylcyclohexyl)methyl]-3H-imidazo[4,5-c]pyridin-6-yl}-1,2,4-oxadiazol-5(4H)-one (enantiomer 1) | | 553 | 553 |
| 6.23 | 7 | 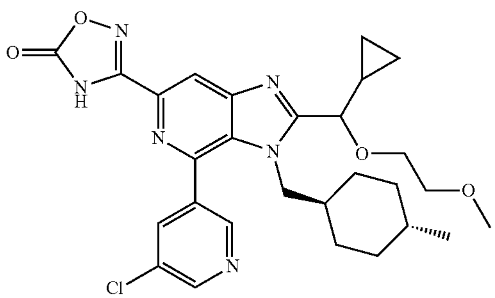 [SMILES: COCCOC(c1nc2cc(-c3noc(=O)[nH]3)nc(-c3cncc(Cl)c3)c2n1C[C@H]1CC[C@H](C)CC1)C1CC1] | 3-{4-(5-chloropyridin-3-yl)-2-[cyclopropyl(2-methoxyethoxy)methyl]-3-[(trans-4-methylcyclohexyl)methyl]-3H-imidazo[4,5-c]pyridin-6-yl}-1,2,4-oxadiazol-5(4H)-one (enantiomer 2) | | 553 | 553 |

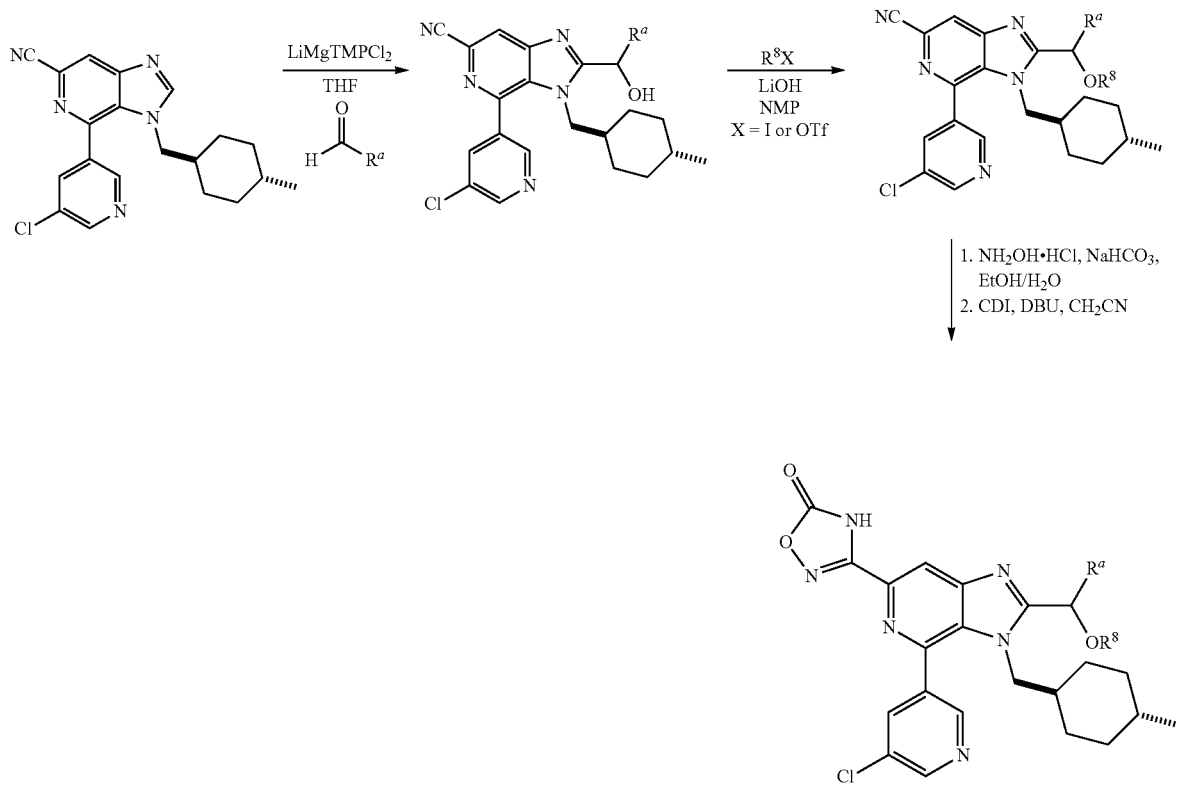

Scheme 10

Example 7.1

3-{4-(5-chloropyridin-3-yl)-2-[(R or S)-ethoxy(phenyl)methyl]-3-[(trans-4-methylcyclohexyl)methyl]-3H-imidazo[4,5-c]pyridin-6-yl}-1,2,4-oxadiazol-5(4H)-one

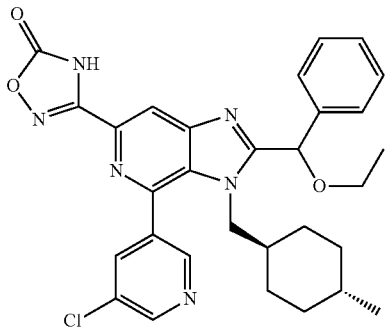 [SMILES: CCOC(c1ccccc1)c1nc2cc(-c3noc(=O)[nH]3)nc(-c3cncc(Cl)c3)c2n1C[C@H]1CC[C@H](C)CC1]

Step 1: 4-(5-chloropyridin-3-yl)-2-(hydroxy(phenyl)methyl)-3-((trans-4-methylcyclohexyl)methyl)-3H-imidazo[4,5-c]pyridine-6-carbonitrile was prepared using 4-(5-chloropyridin-3-yl)-3-((trans-4-methylcyclohexyl)methyl)-3H-imidazo[4,5-c]pyridine-6-carbonitrile (product of Step 2, Preparative Example 3.1) and benzaldehyde in a manner analogous to Example 6.1, Step 1. $^1$H NMR (600 MHz, CD$_3$OD) δ 8.75 (d, J=2.2, 1H), 8.69 (s, 1H), 8.26 (s, 1H), 8.21 (s, 1H), 7.48 (d, J=7.5, 2H), 7.37 (t, J=7.5, 2H), 7.34-7.28 (m, 1H), 6.22 (s, 1H), 3.94 (s, 2H), 1.40 (t, J=14.0, 2H), 1.06-0.98 (m, 1H), 0.83-0.77 (m, 1H), 0.75-0.68 (m, 5H), 0.64-0.56 (m, 1H), 0.51-0.36 (m, 3H). MS ESI calc'd. for C$_{27}$H$_{26}$ClN$_5$O [M+H]$^+$ 472. found 472.

Step 2: To a solution of 4-(5-chloropyridin-3-yl)-2-(hydroxy(phenyl)methyl)-3-((trans-4-methylcyclohexyl)methyl)-3H-imidazo[4,5-c]pyridine-6-carbonitrile (276 mg, 0.585 mmol) in NMP (3 mL) was added lithium hydroxide (28.0 mg, 1.170 mmol) and iodoethane (142 µL, 1.754 mmol), and the reaction mixture was allowed to stir at room temperature overnight. The reaction mixture was quenched with sat. aqueous ammonium chloride and extracted with ethyl acetate. The organic layer was dried over sodium sulfate, filtered, and concentrated. The residue was purified by silica gel chromatography (hexanes/0-50% EtOAc) to afford racemic 4-(5-chloropyridin-3-yl)-2-(ethoxy(phenyl)methyl)-3-((trans-4-methylcyclohexyl)methyl)-3H-imidazo[4,5-c]pyridine-6-carbonitrile. The racemic material was then purified by chiral supercritical fluid chromatography (Chiralpak OJ-H, 21×250 mm, MeOH in CO$_2$) to afford 4-(5-chloropyridin-3-yl)-2-((R)-ethoxy(phenyl)methyl)-3-((trans-4-methylcyclohexyl)methyl)-3H-imidazo[4,5-c]pyridine-6-carbonitrile and 4-(5-chloropyridin-3-yl)-2-(S)-ethoxy(phenyl)methyl)-3-((trans-4-methylcyclohexyl)methyl)-3H-imidazo[4,5-c]pyridine-6-carbonitrile. MS ESI calc'd. for C$_{29}$H$_{30}$ClN$_5$O [M+H]$^+$ 500. found 500. $^1$H NMR (600 MHz, CD$_3$OD) δ 8.75 (d, J=2.3, 1H), 8.70 (d, J=1.6, 1H), 8.27 (s, 1H), 8.23 (t, J=2.0, 1H), 7.49 (d, J=7.2, 2H), 7.38 (t, J=7.3, 2H), 7.36-7.31 (m, 1H), 5.94 (s, 1H), 4.01-3.85 (m, 2H), 3.68-3.59 (m, 2H), 1.44-1.36 (m, 2H), 1.27 (t, J=7.0, 3H), 1.07-0.98 (m, 1H), 0.89-0.78 (m, 1H), 0.76-0.66 (m, 5H), 0.64-0.54 (m, 1H), 0.54-0.46 (m, 1H), 0.46-0.36 (m, 2H).

Step 3: Using a procedure analogous to that described in Example 2.1 (Step 5 and Step 6), and starting with 4-(5-chloropyridin-3-yl)-2-((R or S)-ethoxy(phenyl)methyl)-3-((trans-4-methylcyclohexyl)methyl)-3H-imidazo[4,5-c]pyridine-6-carbonitrile, 3-{4-(5-chloropyridin-3-yl)-2-[(R or S)-ethoxy(phenyl)methyl]-3-[(trans-4-methylcyclohexyl)methyl]-3H-imidazo[4,5-c]pyridin-6-yl}-1,2,4-oxadiazol-5(4H)-one (enantiomer 1) was prepared. MS ESI calc'd. for C$_{30}$H$_{31}$ClN$_6$O$_3$ [M+H]$^+$ 559. found 559. $^1$H NMR (600 MHz, CD$_3$OD) δ 8.74 (t, J=2.1, 2H), 8.36 (s, 1H), 8.29 (t, J=2.0, 1H), 7.50 (d, J=7.3, 2H), 7.42-7.37 (m, 2H), 7.37-7.33 (m, 1H), 5.96 (s, 1H), 4.04-3.88 (m, 2H), 3.70-3.61 (m, 2H), 1.44-1.36 (m, 2H), 1.29 (t, J=7.0, 3H), 1.07-0.98 (m, 1H), 0.88-0.79 (m, 1H), 0.78-0.65 (m, 5H), 0.63-0.53 (m, 1H), 0.53-0.44 (m, 1H), 0.44-0.34 (m, 2H).

3-{4-(5-chloropyridin-3-yl)-2-[(S or R)-ethoxy(phenyl)methyl]-3-[(trans-4-methylcyclohexyl)methyl]-3H-imidazo[4,5-c]pyridin-6-yl}-1,2,4-oxadiazol-5(4H)-one (Example 7.2, enantiomer 2) was prepared in an analogous manner.

The following compounds in Table 7 (other than Example 7.1 and 7.2) were prepared using procedures which were analogous to those described above.

TABLE 7

| Ex. | FRET IC$_{50}$ (nM) | Structure | Chemical Name | Salt | [M+H]+ Calc'd | [M+H]+ Obsv'd |
|---|---|---|---|---|---|---|
| 7.1 | 1 | 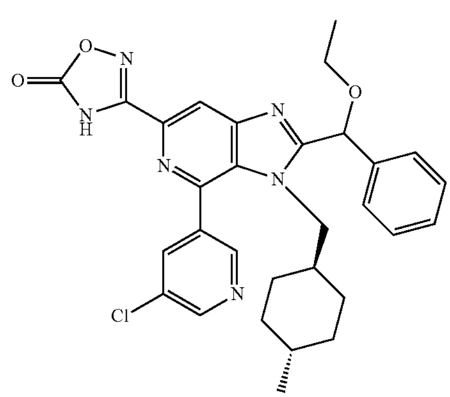 [SMILES: CCOC(c1ccccc1)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[ethoxy(phenyl)methyl]-3-[(trans-4-methylcyclohexyl)methyl]-3H-imidazol[4,5-c]pyridin-6-yl}-1,2,4-oxadiazol-5(4H)-one (enantiomer 1) | TFA | 559 | 559 |

TABLE 7-continued

| Ex. | FRET IC$_{50}$ (nM) | Structure | Chemical Name | Salt | [M+H]+ Calc'd | [M+H]+ Obsv'd |
|---|---|---|---|---|---|---|
| 7.2 | 4 | 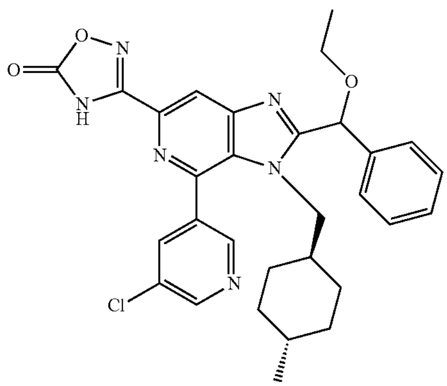 [SMILES: CCOC(c1ccccc1)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[ethoxy(phenyl)methyl]-3-[(trans-4-methylcyclohexyl)methyl]-3H-imidazo[4,5-c]pyridin-6-yl}-1,2,4-oxadiazol-5(4H)-one (enantiomer 2) | TFA | 559 | 559 |
| 7.3 | 19 | 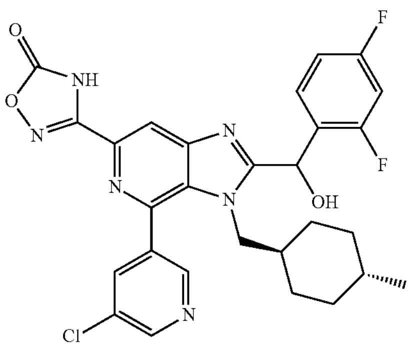 [SMILES: C[C@H]1CC[C@H](Cn2c(C(O)c3ccc(F)cc3F)nc3cc(-c4noc(=O)[nH]4)nc(-c4cncc(Cl)c4)c32)CC1] | 3-{4-(5-chloropyridin-3-yl)-2-[(2,4-difluorophenyl)(hydroxy)methyl]-3-[(trans-4-methylcyclohexyl)methyl]-3H-imidazo[4,5-c]pyridin-6-yl}-1,2,4-oxadiazol-5(4H)-one | TFA | 567 | 567 |
| 7.4 | 2 | 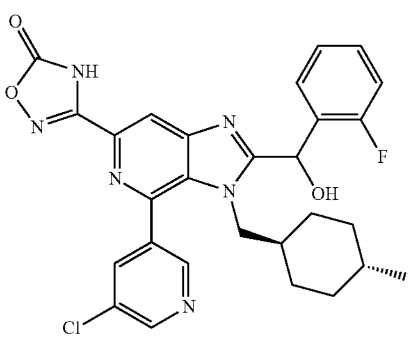 [SMILES: C[C@H]1CC[C@H](Cn2c(C(O)c3ccccc3F)nc3cc(-c4noc(=O)[nH]4)nc(-c4cncc(Cl)c4)c32)CC1] | 3-{4-(5-chloropyridin-3-yl)-2-[(2-fluorophenyl)(hydroxy)methyl]-3-[(trans-4-methylcyclohexyl)methyl]-3H-imidazo[4,5-c]pyridin-6-yl}-1,2,4-oxadiazol-5(4H)-one | TFA | 549 | 549 |
| 7.5 | 5 | 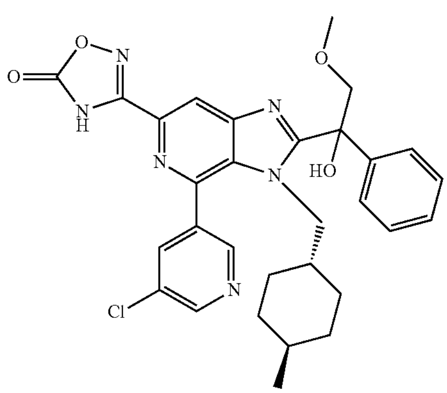 [SMILES: COCC(O)(c1ccccc1)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-(1-hydroxy-2-methoxy-1-phenylethyl)-3-[(trans-4-methylcyclohexyl)methyl]-3H-imidazol[4,5-c]pyridin-6-yl}-1,2,4-oxadiazol-5(4H)-one (racemic) | TFA | 575 | 575 |

TABLE 7-continued

| Ex. | FRET IC$_{50}$ (nM) | Structure | Chemical Name | Salt | [M+H]+ Calc'd | [M+H]+ Obsv'd |
|---|---|---|---|---|---|---|
| 7.6 | 2 | 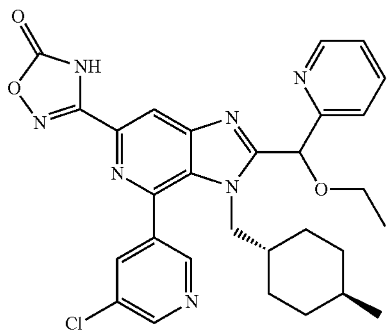 [SMILES: CCOC(c1ccccn1)c1nc2cc(-c3noc(=O)[nH]3)nc(-c3cncc(Cl)c3)c2n1C[C@H]1CC[C@H](C)CC1] | 3-(4-(5-chloropyridin-3-yl)-2-(ethoxy(pyridin-2-yl)methyl)-3-((trans-4-methylcyclohexyl)methyl)-3H-imidazo[4,5-c]pyridin-6-yl)-1,2,4-oxadiazol-5(4H)-one (racemic) | TFA | 560 | 560 |
| 7.7 | 5 | 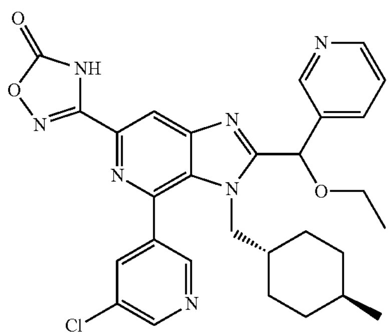 [SMILES: CCOC(c1cccnc1)c1nc2cc(-c3noc(=O)[nH]3)nc(-c3cncc(Cl)c3)c2n1C[C@H]1CC[C@H](C)CC1] | 3-(4-(5-chloropyridin-3-yl)-2-(ethoxy(pyridin-3-yl)methyl)-3-((trans-4-methylcyclohexyl)methyl)-3H-imidazo[4,5-c]pyridin-6-yl)-1,2,4-oxadiazol-5(4H)-one (racemic) | TFA | 560 | 560 |
| 7.8 | 6 | 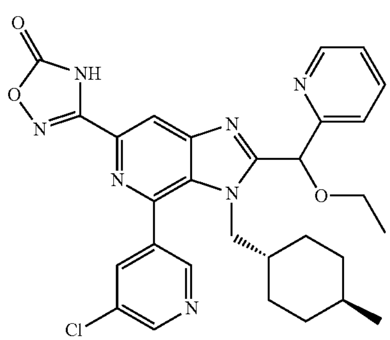 [SMILES: CCOC(c1ccccn1)c1nc2cc(-c3noc(=O)[nH]3)nc(-c3cncc(Cl)c3)c2n1C[C@H]1CC[C@H](C)CC1] | 3-(4-(5-chloropyridin-3-yl)-2-(ethoxy(pyridin-2-yl)methyl)-3-((trans-4-methylcyclohexyl)methyl)-3H-imidazo[4,5-c]pyridin-6-yl)-1,2,4-oxadiazol-5(4H)-one (enantiomer 1) | | 560 | 560 |
| 7.9 | 2 | 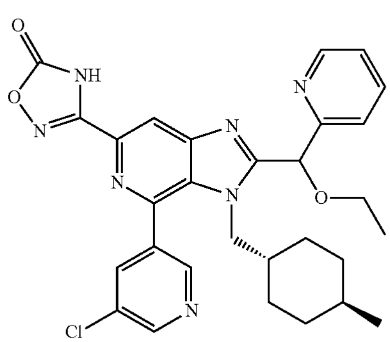 [SMILES: CCOC(c1ccccn1)c1nc2cc(-c3noc(=O)[nH]3)nc(-c3cncc(Cl)c3)c2n1C[C@H]1CC[C@H](C)CC1] | 3-(4-(5-chloropyridin-3-yl)-2-(ethoxy(pyridin-2-yl)methyl)-3-((trans-4-methylcyclohexyl)methyl)-3H-imidazo[4,5-c]pyridin-6-yl)-1,2,4-oxadiazol-5(4H)-one (enantiomer 2) | | 560 | 560 |

TABLE 7-continued

| Ex. | FRET IC$_{50}$ (nM) | Structure | Chemical Name | Salt | [M+H]+ Calc'd | [M+H]+ Obsv'd |
|---|---|---|---|---|---|---|
| 7.10 | 2 | 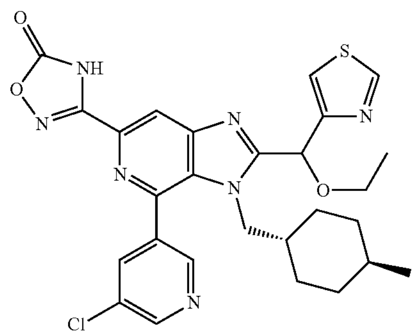 [SMILES: CCOC(c1cscn1)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[ethoxy(1,3-thiazol-4-yl)methyl]-3-[(trans-4-methylcyclohexyl)methyl]-3H-imidazo[4,5-c]pyridin-6-yl]-1,2,4-oxadiazol-5(4H)-one (racemic) | TFA | 566 | 566 |
| 7.11 | 3 | 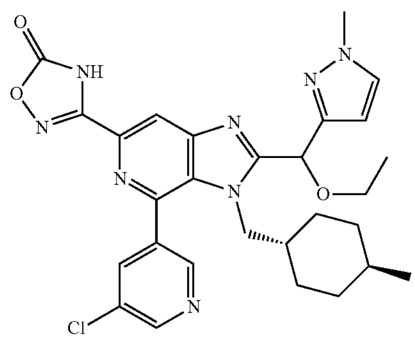 [SMILES: CCOC(c1ccn(C)n1)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[ethoxy(1-methyl-1H-pyrazol-3-yl)methyl]-3-[(trans-4-methylcyclohexyl)methyl]-3H-imidazo[4,5-c]pyridin-6-yl}-1,2,4-oxadiazol-5(4H)-one (racemic) | TFA | 563 | 563 |
| 7.12 | 3 | 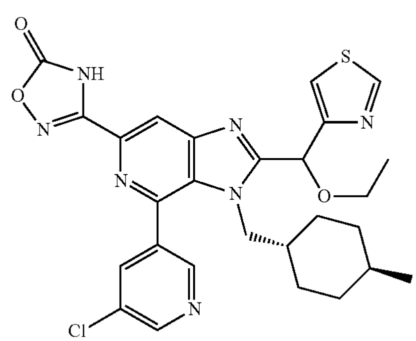 [SMILES: CCOC(c1cscn1)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[ethoxy(1,3-thiazol-4-yl)methyl]-3-[(trans-4-methylcyclohexyl)methyl]-3H-imidazo[4,5-c]pyridin-6-yl]-1,2,4-oxadiazol-5(4H)-one (enantiomer 1) | | 566 | 566 |
| 7.13 | 7 | 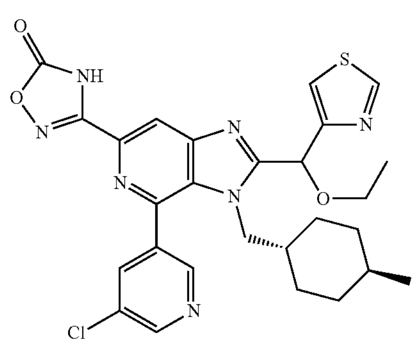 [SMILES: CCOC(c1cscn1)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[ethoxy(1,3-thiazol-4-yl)methyl]-3-[(trans-4-methylcyclohexyl)methyl]-3H-imidazo[4,5-c]pyridin-6-yl}-1,2,4-oxadiazol-5(4H)-one (enantiomer 2) | | 566 | 566 |

TABLE 7-continued
| Ex. | FRET IC$_{50}$ (nM) | Structure | Chemical Name | Salt | [M+H]+ Calc'd | [M+H]+ Obsv'd |
|---|---|---|---|---|---|---|
| 7.14 | 3 | 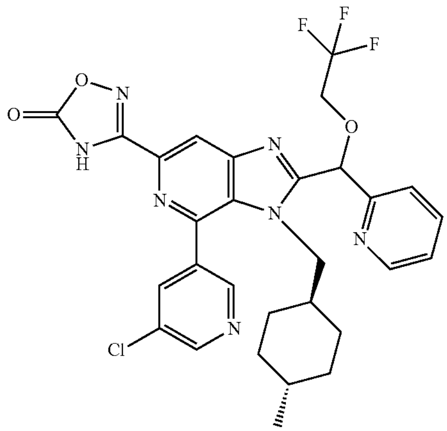 [SMILES: C[C@H]1CC[C@H](Cn2c(C(OCC(F)(F)F)c3ccccn3)nc3cc(-c4noc(=O)[nH]4)nc(-c4cncc(Cl)c4)c32)CC1] | 3-{4-(5-chloropyridin-3-yl)-3-[(trans-4-methylcyclohexyl)methyl]-2-[pyridin-2-yl(2,2,2-trifluoroethoxy)methyl]-3H-imidazo[4,5-c]pyridin-6-yl}-1,2,4-oxadiazol-5(4H)-one (racemic) | TFA | 614 | 614 |
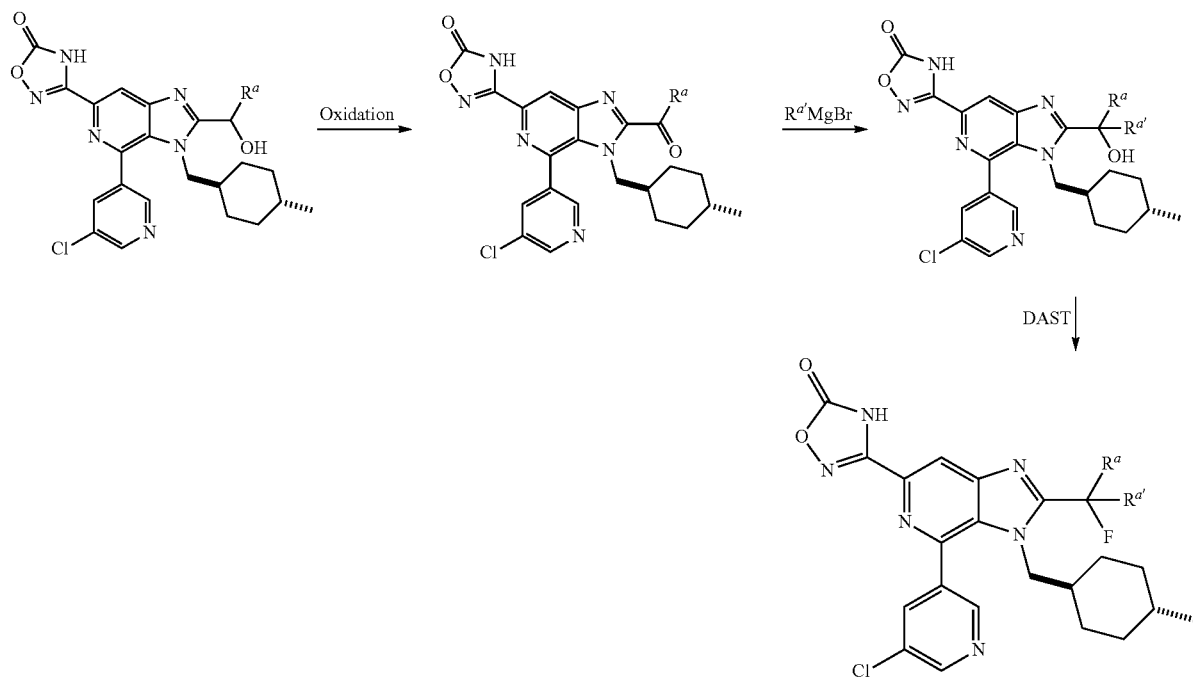
Scheme 11
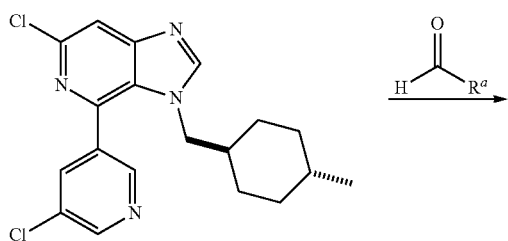
Scheme 12

289        290
-continued
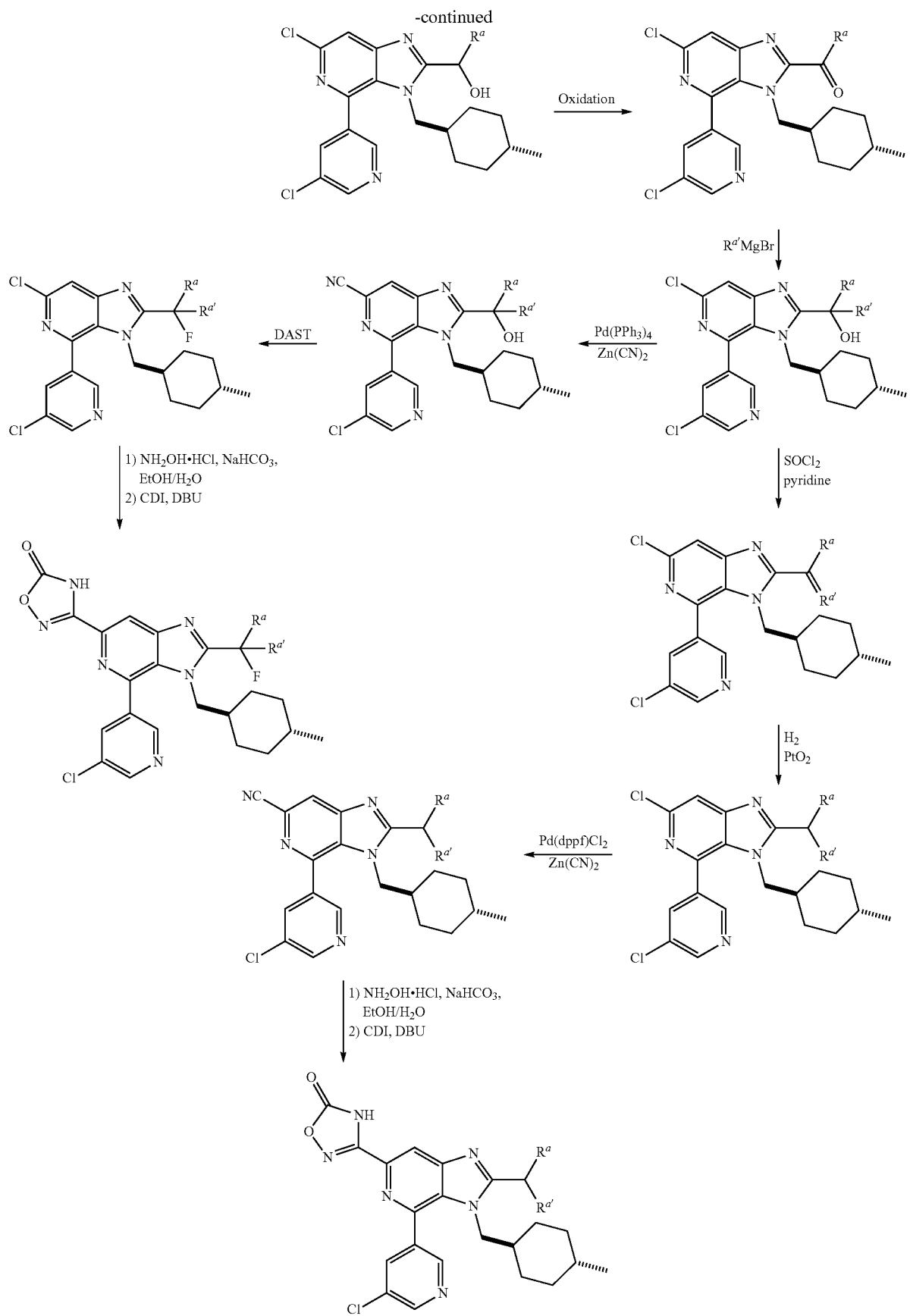

Example 8.1

3-{4-(5-chloropyridin-3-yl)-2-[(2-fluorophenyl)carbonyl]-3-[(trans-4-methylcyclohexyl)methyl]-3H-imidazo[4,5-d]pyridin-6-yl}-1,2,4-oxadiazol-5(4H)-one

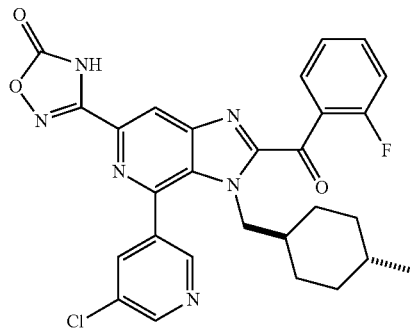

To a room temperature slurry of 3-{4-(5-chloropyridin-3-yl)-2-[(2-fluorophenyl)(hydroxy)methyl]-3-[(trans-4-methylcyclohexyl)methyl]-3H-imidazo[4,5-d]pyridin-6-yl}-1,2,4-oxadiazol-5(4H)-one (Example 7.4 in Table 7, 150 mg, 0.273 mmol) in dichloromethane (4 mL) was added 1,1,1-triacetoxy-1,1-dihydro-1,2-benziodoxol-3(1H)-one (127 mg, 0.301 mmol). The mixture was stirred at room temperature for 1 hour during which time it became a homogeneous solution. Saturated aqueous sodium thiosulfate was added, and the resulting mixture was extracted with ethyl acetate (2×). The combined organic layers were dried over sodium sulfate, filtered, and concentrated. Purification via mass guided reverse phase HPLC (acetonitrile/water+0.1% TFA modifier) afforded 3-{4-(5-chloropyridin-3-yl)-2-[(2-fluorophenyl)carbonyl]-3-[(trans-4-methylcyclohexyl)methyl]-3H-imidazo[4,5-c]pyridin-6-yl}-1,2,4-oxadiazol-5(4H)-one (TFA salt) as a white solid. MS ESI calcd. for $C_{28}H_{24}ClFN_6O_3$ [M+H]$^+$ 547. found 547. $^1$H NMR (500 MHz, DMSO-$d_6$) δ 13.01 (s, 1H), 8.96 (s, 1H), 8.89 (s, 1H), 8.51 (s, 1H), 8.45 (s, 1H), 7.85-7.87 (m, 2H), 7.45-7.41 (m, 2H), 4.25 (d, J=6.5 Hz, 2H), 1.43-1.40 (m, 2H), 1.15-1.02 (m, 2H), 0.86-0.80 (m, 2H), 0.73-0.65 (m, 5H), 0.55-0.50 (m, 2H).

Example 8.2

3-{4-(5-chloropyridin-3-yl)-2-[1-fluoro-1-(2-fluorophenyl)ethyl]-3-[(trans-4-methylcyclohexyl)methyl]-3H-imidazo[4,5-c]pyridin-6-yl}-1,2,4-oxadiazol-5(4H)-one Step 1: To a solution of 3-{4-(5-chloropyridin-3-yl)-2-[(2-fluorophenyl)carbonyl]-3-[(trans-4-methylcyclohexyl)methyl]-3H-imidazo[4,5-d]pyridin-6-yl}-1,2,4-oxadiazol-5(4H)-one (Example 8.1, 44 mg, 0.08 mmol) in tetrahydrofuran (0.8 mL) at −78° C. was added dropwise methyl magnesium bromide (0.054 mL of 3.0 M in diethyl ether, 0.161 mmol). The reaction was stirred and slowly warmed to −20° C. over 3 hours. The reaction was then quenched via the addition of saturated aqueous ammonium chloride and extracted with ethyl acetate (2×). The combined organics were dried over magnesium sulfate, filtered, and concentrated under reduced pressure. The resulting residue was purified via silica gel chromatography (0-10% methanol/DCM) to afford 3-{4-(5-chloropyridin-3-yl)-2-[1-(2-fluorophenyl)-1-hydroxyethyl]-3-[(trans-4-methylcyclohexyl)methyl]-3H-imidazo[4,5-d]pyridin-6-yl}-1,2,4-oxadiazol-5(4H)-one as a white solid. MS ESI calcd. for $C_{29}H_{28}ClFN_6O_3$ [M+H]$^+$ 563. found 563.

Step 2: To a room temperature slurry of 3-{4-(5-chloropyridin-3-yl)-2-[1-(2-fluorophenyl)-1-hydroxyethyl]-3-[(trans-4-methylcyclohexyl)methyl]-3H-imidazo[4,5-c]pyridin-6-yl}-1,2,4-oxadiazol-5(4H)-one (38 mg, 0.067 mmol) in dichloromethane (1.35 mL) was added N,N-diethylaminosulfur trifluoride (0.045 mL, 0.337 mmol). The mixture was stirred for one hour, then quenched with saturated aqueous sodium bicarbonate and extracted with dichloromethane (2×). The combined organic layers were washed with brine (1×), dried over magnesium sulfate, filtered, and concentrated under reduced pressure. The resulting residue was purified via silica gel chromatography (0-100% ethyl acetate/hexanes) to afford 3-{4-(5-chloropyridin-3-yl)-2-[1-fluoro-1-(2-fluorophenyl)ethyl]-3-[(trans-4-methylcyclohexyl)methyl]-3H-imidazo[4,5-c]pyridin-6-yl}-1,2,4-oxadiazol-5(4H)-one as a white solid. MS ESI calcd. for $C_{29}H_{27}ClF_2N_6O_2$ [M+H]$^+$ 565. found 565. $^1$H NMR (500 MHz, DMSO-$d_6$) δ 12.97 (s, 1H), 8.86 (s, 1H), 8.82 (s, 1H), 8.45 (s, 1H), 8.38 (s, 1H), 7.68-7.57 (m, 1H), 7.52-7.50 (m, 1H), 7.35-7.32 (m, 1H), 7.26-7.22 (m, 1H), 3.84-3.78 (m, 1H), 2.28 (d, J=23 Hz, 3H), 1.35-1.33 (m, 1H), 1.28-1.18 (m, 2H), 0.93-0.80 (m, 2H), 0.72-0.62 (m, 5H), 0.54-0.43 (m, 2H), 0.33-0.23 (m, 2H).

Examples 8.3 and 8.4

3-{4-(5-chloropyridin-3-yl)-2-[(1R or S)-1-fluoro-1-(2-fluorophenyl)ethyl]-3-[(trans-4-methylcyclohexyl)methyl]-3H-imidazo[4,5-c]pyridin-6-yl}-1,2,4-oxadiazol-5(4H)one and 3-{4-(5-chloropyridin-3-yl)-2-[(1S or R)-1-fluoro-1-(2-fluorophenyl)ethyl]-3-[(trans-4-methylcyclohexyl)methyl]-3H-imidazo[4,5-c]pyridin-6-yl}-1,2,4-oxadiazol-5(4H)-one

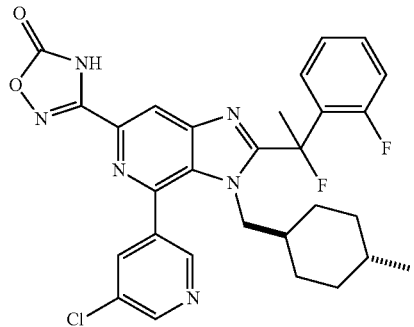

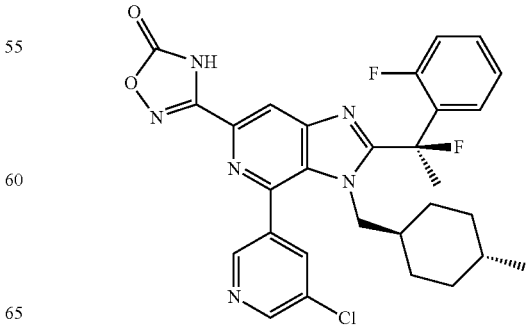

and

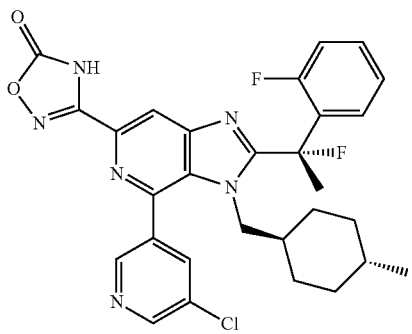 [SMILES: C[C@](F)(c1ccccc1F)c1nc2cc(-c3noc(=O)[nH]3)nc(-c3cncc(Cl)c3)c2n1C[C@H]1CC[C@H](C)CC1]

The enantiomers of 3-{4-(5-chloropyridin-3-yl)-2-[(2-fluorophenyl)carbonyl]-3-[(trans-4-methylcyclohexyl)methyl]-3H-imidazo[4,5-c]pyridin-6-yl}-1,2,4-oxadiazol-5(4H)-one (Example 8.2) were separated by chiral SFC chromatography (Chiralpak AS-H, 21×250 mm, 25% methanol in $CO_2$+0.25% dimethylethylamine modifier, flow rate=70 mL/min) to afford 3-{4-(5-chloropyridin-3-yl)-2-[(1R or S)-1-fluoro-1-(2-fluorophenyl)ethyl]-3-[(trans-4-methylcyclohexyl)methyl]-3H-imidazo[4,5-c]pyridin-6-yl}-1,2,4-oxadiazol-5(4H)-one and 3-{4-(5-chloropyridin-3-yl)-2-[(1S or R)-1-fluoro-1-(2-fluorophenyl)ethyl]-3-[(trans-4-methylcyclohexyl)methyl]-3H-imidazo[4,5-c]pyridin-6-yl}-1,2,4-oxadiazol-5(4H)-one both as white solids.

3-{4-(5-chloropyridin-3-yl)-2-[(1R or S)-1-fluoro-1-(2-fluorophenyl)ethyl]-3-[(trans-4-methylcyclohexyl)methyl]-3H-imidazo[4,5-c]pyridin-6-yl}-1,2,4-oxadiazol-5(4H)-one (enantiomer 1, Example 8.3): $T_R$=2.58 min. MS ESI calcd. for $C_{29}H_{27}ClF_2N_6O_2$ [M+H]$^+$ 565. found 565. $^1$H NMR (500 MHz, DMSO-$d_6$) δ 12.97 (s, 1H), 8.86 (s, 1H), 8.82 (s, 1H), 8.45 (s, 1H), 8.38 (s, 1H), 7.68-7.57 (m, 1H), 7.52-7.50 (m, 1H), 7.35-7.32 (m, 1H), 7.26-7.22 (m, 1H), 3.84-3.78 (m, 1H), 2.28 (d, J=23 Hz, 3H), 1.35-1.33 (m, 1H), 1.28-1.18 (m, 2H), 0.93-0.80 (m, 2H), 0.72-0.62 (m, 5H), 0.54-0.43 (m, 2H), 0.33-0.23 (m, 2H).

3-{4-(5-chloropyridin-3-yl)-2-[(1S or R)-1-fluoro-1-(2-fluorophenyl)ethyl]-3-[(trans-4-methylcyclohexyl)methyl]-3H-imidazo[4,5-c]pyridin-6-yl}-1,2,4-oxadiazol-5(4H)-one (enantiomer 2, Example 8.4): $T_R$=5.48 min. MS ESI calcd. for $C_{29}H_{27}ClF_2N_6O_2$ [M+H]$^+$ 565. found 565. $^1$H NMR (500 MHz, DMSO-$d_6$) δ 12.97 (s, 1H), 8.86 (s, 1H), 8.82 (s, 1H), 8.45 (s, 1H), 8.38 (s, 1H), 7.68-7.57 (m, 1H), 7.52-7.50 (m, 1H), 7.35-7.32 (m, 1H), 7.26-7.22 (m, 1H), 3.84-3.78 (m, 1H), 2.28 (d, J=23 Hz, 3H), 1.35-1.33 (m, 1H), 1.28-1.18 (m, 2H), 0.93-0.80 (m, 2H), 0.72-0.62 (m, 5H), 0.54-0.43 (m, 2H), 0.33-0.23 (m, 2H).

Examples 8.6 and 8.7

3-{4-(5-chloropyridin-3-yl)-2-[(1R or S)-1-fluoro-1-(3-fluoropyridin-2-yl)ethyl]-3-[(trans-4-methylcyclohexyl)methyl]-3H-imidazo[4,5-c]pyridin-6-yl}-1,2,4-oxadiazol-5(4H)-one and 3-{4-(5-chloropyridin-3-yl)-2-[(1S or R)-1-fluoro-1-(3-fluoropyridin-2-yl)ethyl]-3-[(trans-4-methylcyclohexyl)methyl]-3H-imidazo[4,5-c]pyridin-6-yl}-1,2,4-oxadiazol-5(4H)-one

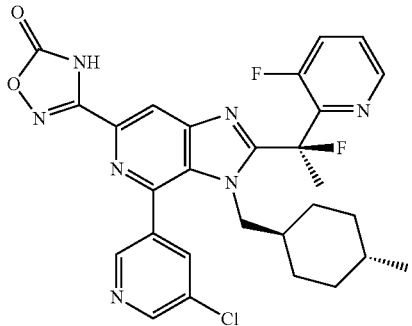 [SMILES: C[C@@](F)(c1ncccc1F)c1nc2cc(-c3noc(=O)[nH]3)nc(-c3cncc(Cl)c3)c2n1C[C@H]1CC[C@H](C)CC1]

and

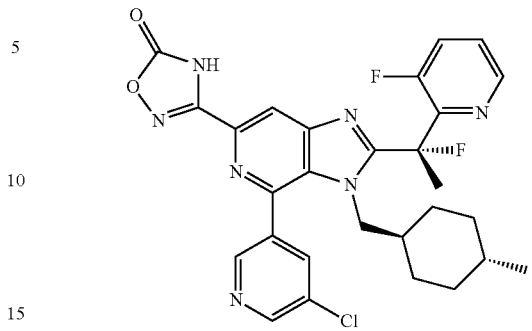

Step 1: To a stirred solution of 6-chloro-4-(5-chloropyridin-3-yl)-3-[(trans-4-methylcyclohexyl)methyl]-3H-imidazo[4,5-c]pyridine (Preparative Example 3.1, Step 1) (1.2 g, 3.19 mmol) in THF (20 mL) was added 2,2,6,6-tetramethylpiperidinylmagnesium chloride lithium chloride complex (Aldrich, 1M in THF/toluene) (5.11 mL, 5.11 mmol) at −78° C., and the reaction was stirred at −78° C. for 2 hours under a nitrogen atmosphere. 3-fluoropicolinaldehyde (1.1 g, 9.59 mmol) dissolved in THF (4.0 mL) was added dropwise at −78° C., and the reaction was stirred for an additional 2 hours at −78° C. The reaction was quenched with aqueous saturated $NH_4Cl$ solution (50 mL) and extracted with ethyl acetate (2×40 mL). The combined organic extracts were washed with brine (20 mL), dried over anhydrous $Na_2SO_4$, filtered, and concentrated. Purification of the residue on a silica gel column (0 to 100% EtOAc/hexanes) afforded {6-chloro-4-(5-chloropyridin-3-yl)-3-[(trans-4-methylcyclohexyl)methyl]-3H-imidazo[4,5-c]pyridin-2-yl}(3-fluoropyridin-2-yl)methanol. MS APCl calcd. for $C_{25}H_{24}Cl_2FN_5O$ [M+H]$^+$ 500. found 500.

Step 2: To a stirred solution of {6-chloro-4-(5-chloropyridin-3-yl)-3-[(trans-4-methylcyclohexyl)methyl]-3H-imidazo[4,5-c]pyridin-2-yl}(3-fluoropyridin-2-yl)methanol (807 mg, 1.61 mmol) in dichloromethane (15 mL) was added Dess-Martin periodinane (2.7 g, 6.45 mmoL) at 0° C. Then reaction was gradually warmed to room temperature and stirred for 2 hours. The reaction mixture was diluted with dichloromethane (15 mL), quenched with aqueous saturated $NaHCO_3$ solution (40 mL), and extracted with dichloromethane (2×30 mL). The combined organic extracts were washed with brine (10 mL), dried over anhydrous $Na_2SO_4$, filtered, and concentrated. Purification of the residue on a silica gel column (0 to 100% EtOAc/hexanes) afforded {6-chloro-4-(5-chloropyridin-3-yl)-3-[(trans-4-methylcyclohexyl)methyl]-3H-imidazo[4,5-d]pyridin-2-yl}(3-fluoropyridin-2-yl)methanone. MS APCl calcd. for $C_{25}H_{22}Cl_2FN_5O$ [M+H]$^+$ 498. found 498.

Step 3: To a stirred solution of {6-chloro-4-(5-chloropyridin-3-yl)-3-[(trans-4-methylcyclohexyl)methyl]-3H-imidazo[4,5-c]pyridin-2-yl}(3-fluoropyridin-2-yl)methanone (618 mg, 1.24 mmol) in THF (10 mL) was added methyl magnesium bromide (3 M in diethyl ether, 0.82 mL, 2.46 mmol) at −78° C., and the reaction mixture was stirred for 2 hours. The reaction mixture was quenched with aqueous saturated $NH_4Cl$ solution (40 mL) and extracted with ethyl acetate (2×35 mL). The combined organic extracts were washed with brine (20 mL), dried over anhydrous $Na_2SO_4$, filtered, and concentrated. Purification of the residue on a silica gel column (0 to 100% EtOAc/hexanes) afforded (1RS)-1-{6-chloro-4-(5-chloropyridin-3-yl)-3-[(trans-4-methylcyclohexyl)methyl]-3H-imidazo[4,5-c]pyridin-2-yl}-1-(3-fluoropyridin-2-yl)ethanol. MS APCl calcd. for $C_{26}H_{26}Cl_2FN_5O$ [M+H]+ 514. found 514.

Step 4: An oven-dried reaction vial was charged with (1RS)-1-{6-chloro-4-(5-chloropyridin-3-yl)-3-[(trans-4-methylcyclohexyl)methyl]-3H-imidazo[4,5-c]pyridin-2-yl}-1-(3-fluoropyridin-2-yl)ethanol (440 mg, 0.85 mmol, 1.0 equiv), $Zn(CN)_2$ (45 mg, 0.38 mmol, 0.45 equiv), $Pd(PPh_3)_4$ (246 mg, 0.21 mmol, 0.25 equiv) and degassed DMA (3.5 mL). The reaction mixture was degassed again and sealed. The reaction was heated at 100° C. for 6 hours. The reaction was then cooled to room temperature and diluted with water (15 mL). The mixture was extracted with ethyl acetate (3×20 mL). The organic layers were combined, washed with brine (2×10 m L), dried over anhydrous sodium sulfate, filtered, and concentrated under reduced pressure. The residue was loaded onto a C-18 column and purified using 0-100% acetonitrile/water to afford 4-(5-chloropyridin-3-yl)-2-[(1RS)-1-(3-fluoropyridin-2-yl)-1-hydroxyethyl]-3-[(trans-4-methylcyclohexyl)methyl]-3H-imidazo[4,5-c]pyridine-6-carbonitrile. MS APCl calcd. for $C_{27}H_{26}ClFN_6O$ [M+H]+ 505. found 505.

Step 5: To a solution of 4-(5-chloropyridin-3-yl)-2-[(1RS)-1-(3-fluoropyridin-2-yl)-1-hydroxyethyl]-3-[(trans-4-methylcyclohexyl)methyl]-3H-imidazo[4,5-c]pyridine-6-carbonitrile (156 mg, 0.31 mmol) in $CH_2Cl_2$ (10.0 mL) at −40° C. under a nitrogen atmosphere was added DAST (0.08 mL, 0.22 mmol), and the resulting solution was stirred at this temperature for 1 hour. The reaction mixture was then quenched with a saturated aqueous solution of $NaHCO_3$ (5 mL) and extracted with $CH_2Cl_2$ (2×15 mL). The combined organic layers were washed with brine (10 mL), dried over anhydrous $Na_2SO_4$, filtered, and concentrated. Purification of the resulting residue on a silica gel column (0 to 100% ethyl acetate/hexanes) afforded 4-(5-chloropyridin-3-yl)-2-[(1RS)-1-fluoro-1-(3-fluoropyridin-2-yl)ethyl]-3-[(trans-4-methylcyclohexyl)methyl]-3H-imidazo[4,5-c]pyridine-6-carbonitrile. MS APCl calcd. for $C_{27}H_{25}ClF_2N_6$ [M+H]+ 507. found 507. The two enantiomers were separated on a chiralpak-AD column (15% IPA/heptane) to afford faster eluting Enantiomer A and slower eluting Enantiomer B.

Steps 6 & 7: Using conditions similar to those described in Example 2.1, (Steps 5 and 6) 4-(5-chloropyridin-3-yl)-2-[(1R or S)-1-fluoro-1-(3-fluoropyridin-2-yl)ethyl]-3-[(trans-4-methylcyclohexyl)methyl]-3H-imidazo[4,5-c]pyridine-6-carbonitrile (Enantiomer A) and 4-(5-chloropyridin-3-yl)-2-[(1S or R)-1-fluoro-1-(3-fluoropyridin-2-yl)ethyl]-3-[(trans-4-methylcyclohexyl)methyl]-3H-imidazo[4,5-c]pyridine-6-carbonitrile (Enantiomer B) were converted to 3-{4-(5-chloropyridin-3-yl)-2-[(1R or S)-1-fluoro-1-(3-fluoropyridin-2-yl)ethyl]-3-[(trans-4-methylcyclohexyl)methyl]-3H-imidazo[4,5-c]pyridin-6-yl}-1,2,4-oxadiazol-5 (4H)-one and 3-{4-(5-chloropyridin-3-yl)-2-[(1S or R)-1-fluoro-1-(3-fluoropyridin-2-yl)ethyl]-3-[(trans-4-methylcyclohexyl)methyl]-3H-imidazo[4,5-c]pyridin-6-yl}-1,2,4-oxadiazol-5(4H)-one. MS ES calcd. for $C_{28}H_{26}ClF_2N_7O_2$ [M+H]+ 566. found 566. 1H NMR (400 MHz, $CD_3OD$) δ 8.77 (br s, 1H), 8.75 (d, J=2.4 Hz, 1H), 8.40 (d, J=4.4 Hz, 1H), 8.36 (s, 1H), 8.33 (m, 1H), 7.70 (m, 1H), 7.57 (m, 1H), 3.88-3.94 (m, 2H), 2.37 (d, J=21.6 Hz, 3H), 1.42-1.48 (m, 2H), 1.08 (m, 1H), 0.82-0.95 (m, 2H), 0.74 (d, J=6.8 Hz, 3H), 0.40-0.68 (m, 5H).

Example 8.14

3-{4-(5-chloropyridin-3-yl)-2-(1-fluoro-2-methoxy-1-methylethyl)-3-[(trans-4-methylcyclohexyl)methyl]-3H-imidazo[4,5-c]pyridin-6-yl}-1,2,4-oxadiazol-5(4H)-one (racemate)

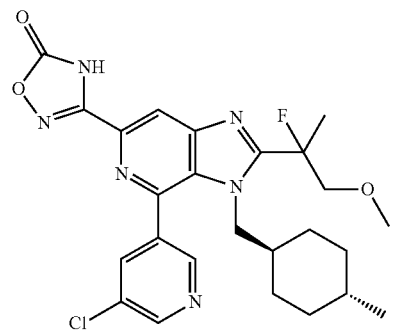 [SMILES: COCC(C)(F)c1nc2cc(-c3noc(=O)[nH]3)nc(-c3cncc(Cl)c3)c2n1C[C@H]1CC[C@H](C)CC1]

Step 1: 4-(5-chloropyridin-3-yl)-3-[(trans-4-methylcyclohexyl)methyl]-3H-imidazo[4,5-c]pyridine-6-carbonitrile (Preparative Example 3.1, Step 2) (350 mg, 0.95 mmol) was dissolved in THF (10 mL) and cooled to −78° C. 2,2,6,6-tetramethylpiperidinylmagnesium chloride lithium chloride complex (Aldrich, 1M in THF/toluene) (2.0 mL, 2.0 mmol) was added slowly to the solution at −78° C. The reaction was stirred at −78° C. for 2 hours. Then methoxyacetone (168 mg, 2.0 mmol) was added into the reaction mixture at −78° C. The reaction was allowed to warm to room temperature and stirred for 8 hours under a nitrogen atmosphere. The reaction was quenched with saturated $NH_4Cl$ solution (5 mL) at −78° C. and extracted with EtOAc (2×10 mL). The combined organic layers were dried over anhydrous $Na_2SO_4$, filtered, and concentrated under reduced pressure. The residue was purified on a silica gel column (0 to 100% EtOAc/hexanes) to afford 4-(5-chloropyridin-3-yl)-2-(2-hydroxy-1-methoxypropan-2-yl)-3-[(trans-4-methylcyclohexyl)methyl]-3H-imidazo[4,5-c]pyridine-6-carbonitrile. MS APCl calcd. for $C_{24}H_{28}ClN_5O_2$ [M+H]+ 454. found 454.

Steps 2, 3, & 4: Using procedures similar to those described in Example 8.6/8.7 (Step 5) and Example 2.1, (Steps 5 and 6), 4-(5-chloropyridin-3-yl)-2-(2-hydroxy-1-methoxypropan-2-yl)-3-[(trans-4-methylcyclohexyl)methyl]-3H-imidazo[4,5-c]pyridine-6-carbonitrile was converted to 3-{4-(5-chloropyridin-3-yl)-2-(1-fluoro-2-methoxy-1-methylethyl)-3-[(trans-4-methylcyclohexyl)methyl]-3H-imidazo[4,5-c]pyridin-6-yl}-1,2,4-oxadiazol-5(4H)-one (racemate). 1H NMR (400 MHz, $CD_3OD$) δ 8.74 (d, J=2.0 Hz, 1H), 8.51 (s, 1H), 8.47 (s, 1H), 8.22 (d, J=2.0 Hz, 1H), 4.14-4.22 (m, 1H), 3.92-3.97 (m, 3H), 3.42 (s, 3H), 1.85 (d, J=22 Hz, 3H), 1.52 (m, 2H), 1.20

(m, 3H), 0.95-0.98 (m, 3H), 0.78 (d, J=6.8 Hz, 3H) 0.54-0.64 (m, 2H). MS APCl calcd. for $C_{25}H_{28}ClFN_6O_3$ [M+H]$^+$ 515. found 515.

Example 8.15

3-{4-(5-chloropyridin-3-yl)-2-[1-(3-fluoropyridin-2-yl)ethyl]-3-[(trans-4-methylcyclohexyl)methyl]-3H-imidazo[4,5-c]pyridin-6-yl}-1,2,4-oxadiazol-5(4H)-one (racemate)

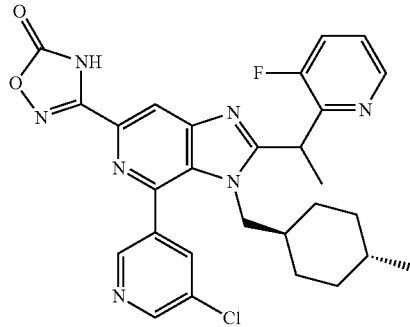 [SMILES: CC(c1ncccc1F)c1nc2cc(-c3noc(=O)[nH]3)nc(-c3cncc(Cl)c3)c2n1C[C@H]1CC[C@H](C)CC1]

Step 1: To a stirred solution of (1RS)-1-{6-chloro-4-(5-chloropyridin-3-yl)-3-[(trans-4-methylcyclohexyl)methyl]-3H-imidazo[4,5-c]pyridin-2-yl}-1-(3-fluoropyridin-2-yl) ethanol (Example 8.6/8.7, Step 3; 1.2 g, 2.33 mmol) and pyridine (1.88 mL, 23.3 mmol) in dichloromethane (20 mL) was added thionyl chloride (0.85 mL, 11.67 mmol) dropwise at 0° C., and the reaction was stirred at 0° C. for 1 h. The reaction was quenched with saturated NaHCO$_3$ solution and extracted with dichloromethane (2×25 mL). The combined organic extracts were washed with water (1×25 mL) and brine (1×25 mL), dried over anhydrous Na$_2$SO$_4$, filtered, and concentrated. The residue was purified on a silica gel column (eluting with 40-60% EtOAc/petroleum ether) to afford 6-chloro-4-(5-chloropyridin-3-yl)-2-[1-(3-fluoropyridin-2-yl)ethenyl]-3-[(trans-4-methylcyclohexyl)methyl]-3H-imidazo[4,5-c]pyridine. MS ES/APCl calcd. for $C_{26}H_{24}Cl_2FN_5$ [M+H]$^+$ 496. found 496.

Step 2: To a stirred solution of 6-chloro-4-(5-chloropyridin-3-yl)-2-[1-(3-fluoropyridin-2-yl)ethenyl]-3-[(trans-4-methylcyclohexyl)methyl]-3H-imidazo[4,5-c]pyridine (530 mg, 1.07 mmol) in EtOAc (12 mL) was added platinum(IV) oxide (53 mg). The reaction was placed under a H$_2$ atmosphere and stirred for 3 h. The reaction was filtered through celite, washing with MeOH, and the filtrate was concentrated. The residue was purified by silica gel chromatography (eluting with 38-50% EtOAc/petroleum ether) to yield 6-chloro-4-(5-chloropyridin-3-yl)-2-[1-(3-fluoropyridin-2-yl)ethyl]-3-[(trans-4-methylcyclohexyl)methyl]-3H-imidazo[4,5-c]pyridine. MS ES/APCl calcd. for $C_{26}H_{26}Cl_2FN_5$ [M+H]$^+$ 498. found 498.

Step 3: To a stirred solution of 6-chloro-4-(5-chloropyridin-3-yl)-2-[1-(3-fluoropyridin-2-yl)ethyl]-3-[(trans-4-methylcyclohexyl)methyl]-3H-imidazo[4,5-c]pyridine (400 mg, 0.80 mmol) in DMF (16 mL) was added zinc cyanide (37.7 mg, 0.32 mmol), and the reaction was deoxygenated by purging with nitrogen for 10 minutes. 1,1'-Bis(diphenylphosphino)ferrocene-palladium(II)dichloride dichloromethane complex (65.5 mg, 0.08 mmol) was added, and the reaction mixture was again deoxygenated for 5 minutes. The reaction was heated to 140° C. for 5 h under a nitrogen atmosphere. The reaction was then cooled to room temperature, diluted with water (25 mL), and extracted with ethyl acetate (2×25 mL). The combined organic extracts were washed with water (1×25 mL) and brine (1×25 mL), dried over anhydrous Na$_2$SO$_4$, filtered, and concentrated. The residue was purified by silica gel chromatography (eluting with 35% EtOAc/petroleum ether) to yield 4-(5-chloropyridin-3-yl)-2-[1-(3-fluoropyridin-2-yl)ethyl]-3-[(trans-4-methylcyclohexyl)methyl]-3H-imidazo[4,5-c]pyridine-6-carbonitrile. MS ES/APCl calcd. for $C_{27}H_{26}ClFN_6$ [M+H]$^+$ 489. found 489.

Steps 4 & 5: Using procedures similar to those described in Example 2.1, (Steps 5 and 6) 4-(5-chloropyridin-3-yl)-2-[1-(3-fluoropyridin-2-yl)ethyl]-3-[(trans-4-methylcyclohexyl)methyl]-3H-imidazo[4,5-c]pyridine-6-carbonitrile was converted to 3-{4-(5-chloropyridin-3-yl)-2-[1-(3-fluoropyridin-2-yl)ethyl]-3-[(trans-4-methylcyclohexyl)methyl]-3H-imidazo[4,5-c]pyridin-6-yl}-1,2,4-oxadiazol-5(4H)-one (racemate). MS ES/APCl calcd. for $C_{28}H_{27}ClFN_7O_2$ [M+H]$^+$ 548. found 548. $^1$H NMR (400 MHz, DMSO-d$_6$): δ 12.50 (bs, 1H), 8.83 (d, J=2.00 Hz, 1H), 8.80 (s, 1H), 8.42-8.38 (m, 2H), 8.14 (s, 1H), 7.75-7.70 (m, 1H), 7.47-7.43 (m, 1H), 4.97-4.95 (m, 1H), 3.81-3.57 (m, 2H), 1.78-1.74 (m, 3H), 1.45-1.35 (m, 2H), 1.29-1.04 (m, 3H), 0.89-0.84 (m, 2H), 0.76-0.70 (m, 3H), 0.56-0.43 (m, 3H).

Examples in Table 8 (other than Examples 8.1-8.4, 8.6-8.7 and 8.14-8.15) were prepared using procedures that were analogous to those described above.

TABLE 8

| Ex. | FRET IC$_{50}$ (nM) | Structure | Chemical Name | Salt | [M+H]+ Calc'd | [M+H]+ Obsv'd |
|---|---|---|---|---|---|---|
| 8.1 | 2 | (structure shown) | 3-{4-(5-chloropyridin-3-yl)-2-[(2-fluorophenyl)carbonyl]-3-[(trans-4-methylcyclohexyl)methyl]-3H-imidazo[4,5-c]pyridin-6-yl}-1,2,4-oxadiazol-5(4H)-one | TFA | 547 | 547 |

TABLE 8-continued

| Ex. | FRET IC$_{50}$ (nM) | Structure | Chemical Name | Salt | [M+H]+ Calc'd | [M+H]+ Obsv'd |
|---|---|---|---|---|---|---|
| 8.2 | 2 | 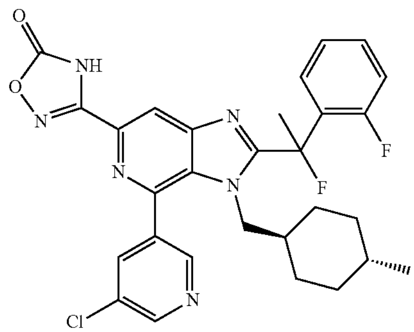 [SMILES: CC(F)(c1ccccc1F)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[1-fluoro-1-(2-fluorophenyl)-ethyl]-3-[(trans-4-methylcyclohexyl)methyl]-3H-imidazo[4,5-c]pyridin-6-yl}-1,2,4-oxadiazol-5(4H)-one (racemic) | TFA | 565 | 565 |
| 8.3 | 1 | 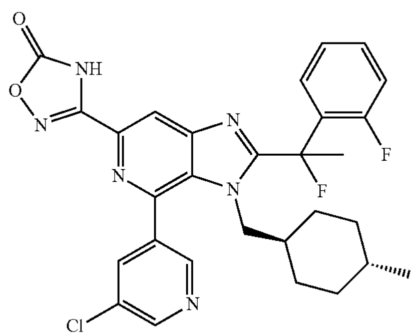 [SMILES: CC(F)(c1ccccc1F)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(1R or S)-1-fluoro-1-(2-fluorophenyl)ethyl]-3-[(trans-4-methylcyclohexyl)methyl]-3H-imidazo[4,5-c]pyridin-6-yl}-1,2,4-oxadiazol-5(4H)-one (enantiomer 1) | TFA | 565 | 565 |
| 8.4 | 20 | 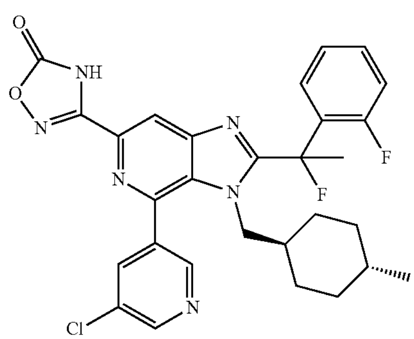 [SMILES: CC(F)(c1ccccc1F)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(1S or R)-1-fluoro-1-(2-fluorophenyl)ethyl]-3-[(trans-4-methylcyclohexyl)methyl]-3H-imidazo[4,5-c]pyridin-6-yl}-1,2,4-oxadiazol-5(4H)-one (enantiomer 2) | TFA | 565 | 565 |
| 8.5 | 2 | 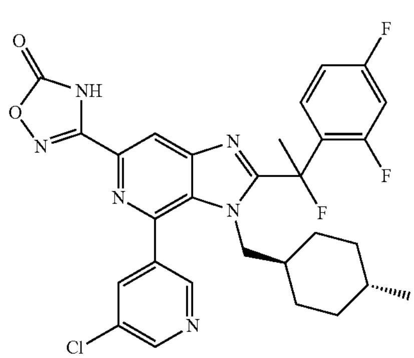 [SMILES: CC(F)(c1ccc(F)cc1F)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-1-(2,4-difluorophenyl)-1-fluoroethyl]-3-[(trans-4-methylcyclohexyl)methyl-[3H-imidazo[4,5-c]pyridin-6-yl}-1,2,4-oxadiazol-5(4H)-one (racemic) | TFA | 583 | 583 |

| Ex. | FRET IC$_{50}$ (nM) | Structure | Chemical Name | Salt | [M+H]+ Calc'd | [M+H]+ Obsv'd |
|---|---|---|---|---|---|---|
| 8.6 | 9 | 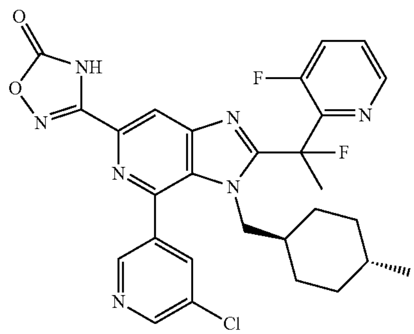 [SMILES: CC(F)(c1ncccc1F)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(1R or S)-1-fluoro-1-(3-fluoropyridin-2-yl)ethyl]-3-[(trans-4-methylcyclohexyl)methyl]-3H-imidazo[4,5-c]pyridin-6-yl}-1,2,4-oxadiazol-5(4H)-one (Enantiomer 1) | | 566 | 566 |
| 8.7 | <1 | 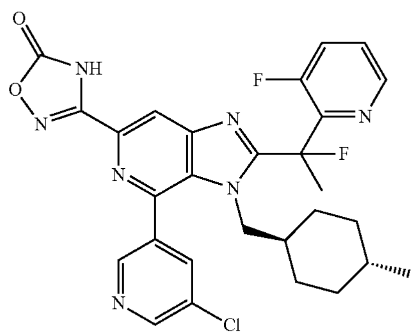 [SMILES: CC(F)(c1ncccc1F)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(1S or R)-1-fluoro-1-(3-fluoropyridin-2-yl)ethyl]-3-[(trans-4-methylcyclohexyl)methyl]-3H-imidazo[4,5-c]pyridin-6-yl}-1,2,4-oxadiazol-5(4H)-one (Enantiomer 2) | | 566 | 566 |
| 8.8 | 4 | 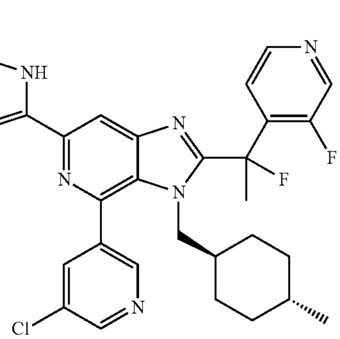 | 3-{4-(5-chloropyridin-3-yl)-2-[(1R or S)-1-fluoro-1-(3-fluoropyridin-4-yl)ethyl]-3-[(trans-4-methylcyclohexyl)methyl]-3H-imidazo[4,5-c]pyridin-6-yl}-1,2,4-oxadiazol-5(4H)-one (Enantiomer 1) | | 566 | 566 |
| 8.9 | 1 | 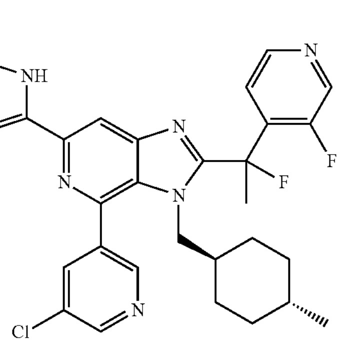 | 3-{4-(5-chloropyridin-3-yl)-2-[(1S or R)-1-fluoro-1-(3-fluoropyridin-4-yl)ethyl]-3-[(trans-4-methylcyclohexyl)methyl]-3H-imidazo[4,5-c]pyridin-6-yl}-1,2,4-oxadiazol-5(4H)-one (Enantiomer 2) | | 566 | 566 |

TABLE 8-continued

| Ex. | FRET IC$_{50}$ (nM) | Structure | Chemical Name | Salt | [M+H]+ Calc'd | [M+H]+ Obsv'd |
|---|---|---|---|---|---|---|
| 8.10 | 11 | 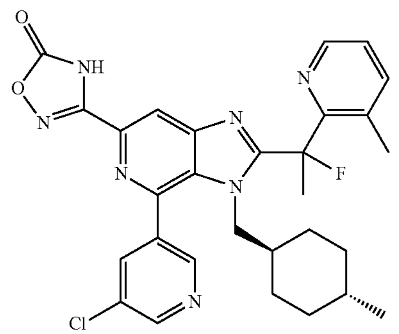 [SMILES: Cc1cccnc1C(C)(F)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(1 R or S)-1-fluoro-1-(3-methylpyridin-2-yl)ethyl]-3-[(trans-4-methylcyclohexyl)methyl]-3H-imidazo[4,5-c]pyridin-6-yl}-1,2,4-oxadiazol-5(4H)-one (Enantiomer 1) | | 562 | 562 |
| 8.11 | <1 | 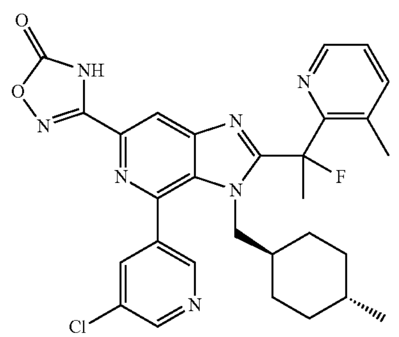 [SMILES: Cc1cccnc1C(C)(F)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(1S or R)-1-fluoro-1-(3-methylpyridin-2-yl)ethyl]-3-[(trans-4-methylcyclohexyl)methyl]-3H-imidazo[4,5-c]pyridin-6-yl}-1,2,4-oxadiazol-5(4H)-one (Enantiomer 2) | | 562 | 562 |
| 8.12 | 3 | 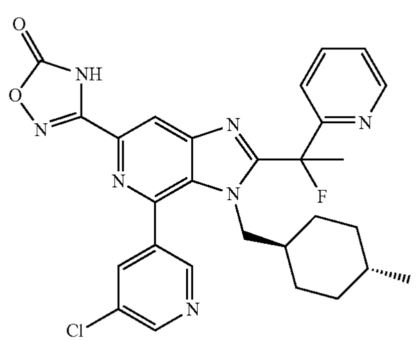 [SMILES: CC(F)(c1ccccn1)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(1 R or S)-1-fluoro-1-(pyridin-2-yl)ethyl]-3-[(trans-4-methylcyclohexyl)methyl]-3H-imidazo-[4,5-c]pyridin-6-yl}-1,2,4-oxadiazol-5(4H)-one (Enantiomer 1) | | 548 | 548 |
| 8.13 | 2 | 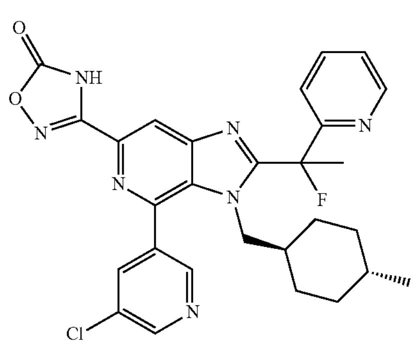 [SMILES: CC(F)(c1ccccn1)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[(1S or R)-1-fluoro-1-(pyridin-2-yl)ethyl]-3-[(trans-4-methylcyclohexyl)methyl]-3H-imidazo[4,5-c]pyridin-6-yl}-1,2,4-oxadiazol-5(4H)-one (Enantiomer 2) | | 548 | 548 |

TABLE 8-continued
| Ex. | FRET IC$_{50}$ (nM) | Structure | Chemical Name | Salt | [M+H]+ Calc'd | [M+H]+ Obsv'd |
|---|---|---|---|---|---|---|
| 8.14 | 21 | 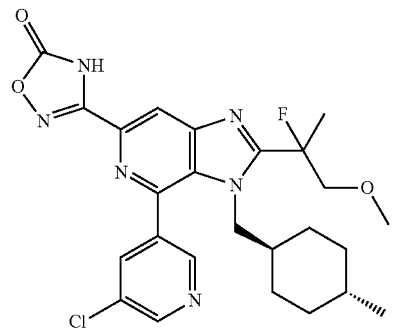 [SMILES: COCC(C)(F)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-(1-fluoro-2-methoxy-1-methylethyl)-3-[(trans-4-methylcyclohexyl)methyl]-3H-imidazo[4,5-c]pyridin-6-yl}-1,2,4-oxadiazol-5(4H)-one (racemate) | | 515 | 515 |
| 8.15 | 4 | 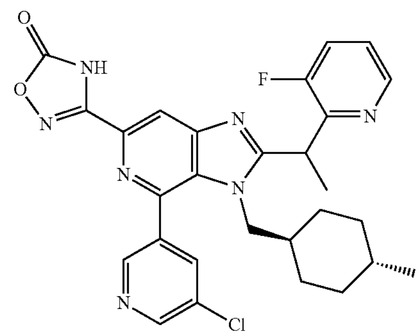 [SMILES: CC(c1ncccc1F)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[1-(3-fluoropyridin-2-yl)ethyl]-3-[(trans-4-methylcyclohexyl)methyl]-3H-imidazo[4,5-c]pyridin-6-yl}-1,2,4-oxadiazol-5(4H)-one (racemate) | | 548 | 548 |
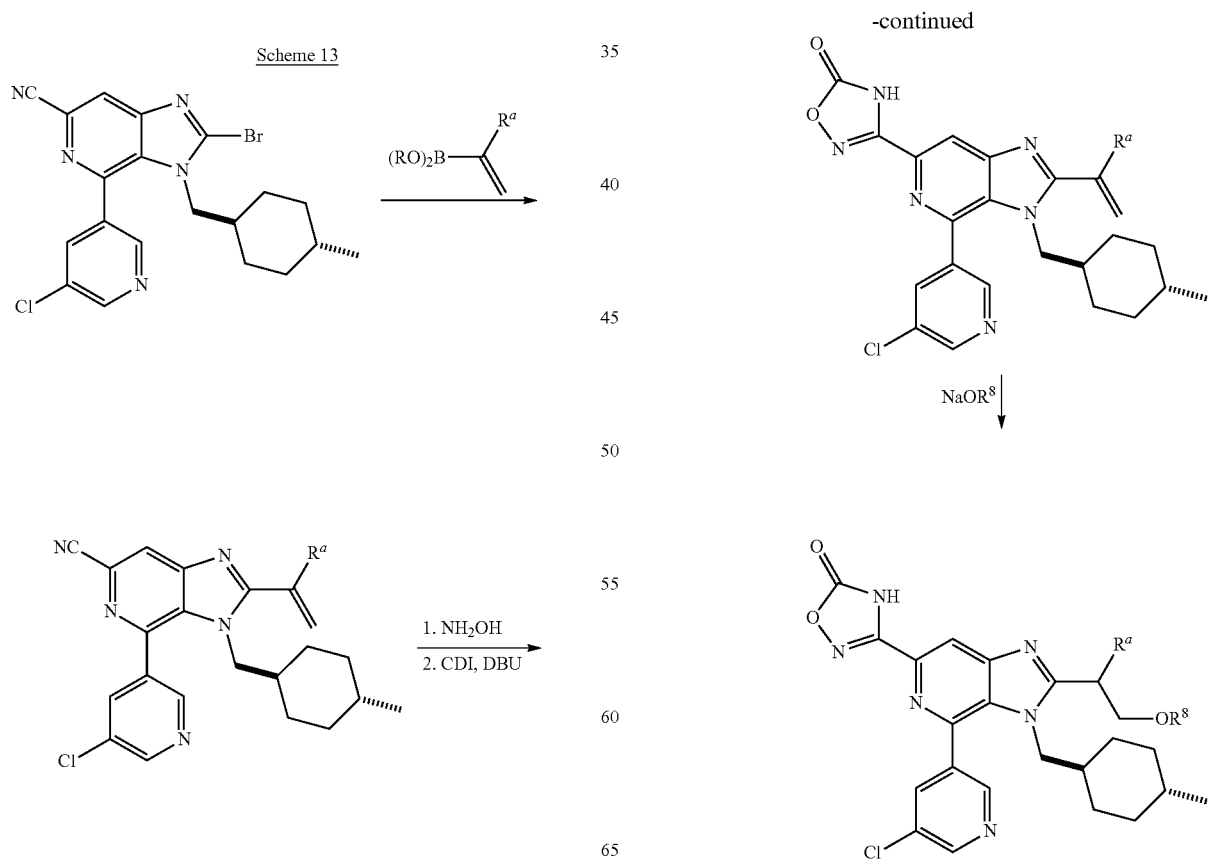
Scheme 13

307

Preparative Example 9.1 4,4,5,5-tetramethyl-2-(3-methylbut-1-en-2-yl)-1,3,2-dioxaborolane

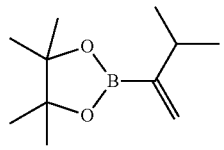

Step 1: A solution of 3-methylbut-1-yne (2 g, 29.3 mmol) in anhydrous n-pentane (5.0 mL) was cooled to −30° C. (dry ice/acetonitrile). Trifluoromethanesulfonic acid (2.2 g, 14.6 mmol) was slowly added dropwise, and the reaction was stirred at −30° C. for 2 h. The reaction mixture was quenched with saturated sodium bicarbonate (5 mL) and extracted with diethyl ether (2×5 mL). The combined organic layers were washed with sodium bicarbonate solution (10 mL) and brine (10 mL), dried over anhydrous $Na_2SO_4$, filtered, and concentrated under reduced pressure. The crude 3-methylbut-1-en-2-yl trifluoromethanesulfonate was taken into next step without further purification.

Step 2: To a stirred solution of 3-methylbut-1-en-2-yl trifluoromethanesulfonate (2.0 g, 29.3 mmol) in toluene (40 mL), sodium phenoxide (3.74 g, 32.23 mmol) and bis(pinacolato)diboron (8.18 g, 32.23 mmol) were added, and the mixture was degassed with argon for 10 minutes. Triphenylphospine (0.46 g, 1.758 mmol) and $PdCl_2(PPh_3)_2$ (1.02 g, 1.45 mmol) were added, and the reaction was heated to 60° C. for 12 h. The reaction mixture was quenched with ice and extracted with ethyl acetate (3×50 mL). The combined organic layers were washed with sodium bicarbonate solution (25 mL) and brine (25 mL), dried over anhydrous $Na_2SO_4$, filtered, and concentrated. The residue was purified by silica gel column chromatography using 15% ethyl acetate/petroleum ether as eluent to give 4,4,5,5-tetramethyl-2-(3-methyl-but-1-en-2-yl)-1,3,2-dioxaborolane. $^1H$ NMR (400 MHz, $CDCl_3$): δ 5.72 (d, J=3.0 Hz, 1H), 5.60 (d, J=3.0 Hz, 1H), 2.47-2.50 (m, 1H), 1.25-1.36 (m, 12H), 1.06 (d, J=6.8 Hz, 6H).

Example 9.1

3-[4-(5-chloropyridin-3-yl)-3-[(trans-4-methylcyclohexyl)methyl]-2-(1-phenylethenyl)-3H-imidazo[4,5-c]pyridin-6-yl]-1,2,4-oxadiazol-5(4H)-one

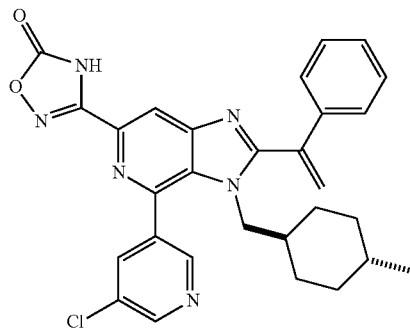

Step 1: A sealed tube was charged with 2-bromo-4-(5-chloropyridin-3-yl)-3-[(trans-4-methylcyclohexyl)methyl]-3H-imidazo[4,5-c]pyridine-6-carbonitrile (Preparative Example 3.1, 150 mg, 0.337 mmol), 4,4,5,5-tetramethyl-2-(1-phenylethenyl)-1,3,2-dioxaborolane (93 mg, 0.405 mmol), $PdCl_2$(dppf)-dichloromethane adduct (27.5 mg, 0.034 mmol), and potassium phosphate (215 mg, 1.012 mmol). The tube was evacuated and backfilled with argon (3×). Fully degassed dioxane (1.53 mL) and water (0.153 mL) were added. The vial was sealed and heated at 50° C. overnight. The mixture was then cooled to room temperature and directly purified via silica gel chromatography (0-100% ethyl acetate/hexanes) to afford 4-(5-chloropyridin-3-yl)-3-[(trans-4-methylcyclohexyl)methyl]-2-(1-phenylethenyl)-3H-imidazo[4,5-c]pyridine-6-carbonitrile as a yellow solid. MS ESI calcd. for $C_{28}H_{26}ClN_5$ [M+H]$^+$ 468. found 468.

Step 2: 4-(5-Chloropyridin-3-yl)-N'-hydroxy-3-[(trans-4-methylcyclohexyl)methyl]-2-(1-phenylethenyl)-3H-imidazo[4,5-c]pyridine-6-carboximidamide was prepared in analogy to Example 2.1, Step 5 and starting from 4-(5-chloropyridin-3-yl)-3-[(trans-4-methylcyclohexyl)methyl]-2-(1-phenylethenyl)-3H-imidazo[4,5-c]pyridine-6-carbonitrile. MS ESI calcd. for $C_{28}H_{29}ClN_6O$ [M+H]$^+$ 501. found 501.

Step 3: 3-[4-(5-Chloropyridin-3-yl)-3-[(trans-4-methylcyclohexyl)methyl]-2-(1-phenylethenyl)-3H-imidazo[4,5-c]pyridin-6-yl]-1,2,4-oxadiazol-5(4H)-one (TFA salt) was prepared in analogy to Example 2.1, Step 6 and starting from 4-(5-chloropyridin-3-yl)-N'-hydroxy-3-[(trans-4-methylcyclohexyl)methyl]-2-(1-phenylethenyl)-3H-imidazo[4,5-c]pyridine-6-carboximidamide. MS ESI calcd. for $C_{29}H_{27}ClN_6O_2$ [M+H]$^+$ 527. found 527. $^1H$ NMR (500 MHz, DMSO-$d_6$) δ 12.98 (s, 1H), 8.94 (s, 1H), 8.83 (s, 1H), 8.48 (s, 1H), 8.34 (s, 1H), 7.47-7.46 (m, 2H), 7.41-7.40 (m, 3H), 6.40 (s, 1H), 5.90 (s, 1H), 3.67 (d, J=6.5 Hz, 2H), 1.33-1.30 (m, 2H), 0.99-0.92 (m, 1H), 0.88-0.78 (m, 1H), 0.65-0.63 (m, 4H), 0.62-0.58 (m, 1H), 0.48-0.32 (m, 4H).

Example 9.2

3-{4-(5-chloropyridin-3-yl)-2-(2-methoxy-1-phenylethyl)-3-[(trans-4-methylcyclohexyl)methyl]-3H-imidazo[4,5-c]pyridin-6-yl}-1,2,4-oxadiazol-5(4H)-one

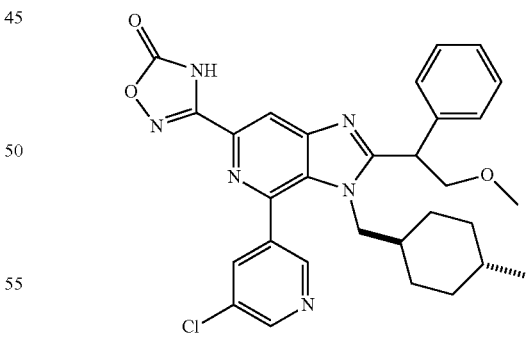

3-[4-(5-Chloropyridin-3-yl)-3-[(trans-4-methylcyclohexyl)methyl]-2-(1-phenylethenyl)-3H-imidazo[4,5-c]pyridin-6-yl]-1,2,4-oxadiazol-5(4H)-one (Example 9.1, 130 mg, 0.247 mmol) was taken up in methanol (1.644 mL) at room temperature, and sodium methoxide (1.2 mL of 25 wt % in methanol, 5.25 mmol) was added. The mixture was capped and heated to 75° C. for 24 hours. The mixture was cooled to room temperature, quenched with saturated aqueous ammonium chloride, and extracted with ethyl acetate. The organic layer was dried over magnesium sulfate, filtered, and concentrated under reduced pressure. The resulting residue was purified via automated reverse phase HPLC (methanol/water+ 0.1% TFA modifier) to afford 3-{4-(5-chloropyridin-3-yl)-2-(2-methoxy-1-phenylethyl)-3-[(trans-4-methylcyclohexyl)methyl]-3H-imidazo[4,5-c]pyridin-6-yl}-1,2,4-oxadiazol-5(4H)-one (TFA salt) as a white solid. MS ESI calcd. for $C_{30}H_{31}ClN_6O_3$ [M+H]$^+$ 559. found 559. $^1$H NMR (500 MHz, DMSO-$d_6$) δ 12.91 (s, 1H), 8.83 (s, 2H), 8.40 (s, 1H), 8.32 (s, 1H), 7.58-7.48 (m, 2H), 7.31-7.25 (m, 3H), 4.80-4.75 (m, 1H), 4.21-4.15 (m, 1H), 3.90-3.80 (m, 3H), 3.25 (s, 3H), 1.42-1.35 (m, 1H), 1.29-1.20 (m, 2H), 1.04-0.94 (m, 1H), 0.75-0.64 (m, 5H), 0.40-0.29 (m, 4H).

Example 9.15

3-{4-(5-chloropyridin-3-yl)-2-[2-methoxy-1-(methoxymethyl)ethyl]-3-[(trans-4-methylcyclohexyl)methyl]-3H-imidazo[4,5-c]pyridin-6-yl}-1,2,4-oxadiazol-5(4H)-one

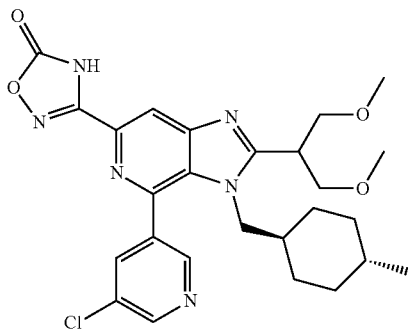 [SMILES: COCC(COC)c1nc2cc(-c3noc(=O)[nH]3)nc(-c3cncc(Cl)c3)c2n1C[C@H]1CC[C@H](C)CC1]

Step 1: A slurry of sodium iodide (20.07 g, 133.9 mmol) in acetonitrile (100 mL) was cooled to 0° C. Trimethylsilyl chloride (17 mL, 133.9 mmol) was added dropwise over a period of 5 minutes followed by water (1.0 mL, 53.56 mmol) and stirred for 10 minutes. Prop-2-yn-1-ol (5.0 g, 89.3 mmol) was added at 0° C. and the reaction mixture was slowly warmed to room temperature and stirred for 1 h. The reaction mixture was quenched with water and extracted with diethyl ether (15 mL). The organic layer was washed with saturated sodium thiosulphate solution (10 mL) followed by brine solution (10 mL). The organic layer was dried over anhydrous $Na_2SO_4$, filtered and concentrated under reduced pressure (water bath temperature <25° C.). The residue was purified by silica gel column chromatography using 10% diethyl ether/petroleum ether as eluent to yield 2-iodoprop-2-en-1-ol.

Step 2: A stirred solution of 2-iodoprop-2-en-1-ol (24 g, 130.4 mmol) in dry dichloromethane (500 mL) was cooled to 0° C. Imidazole (17.75 g, 260.9 mmol) was added in several portions, and the mixture was stirred for 10 minutes. Tert-butyldimethylsilyl chloride (29.49 g, 195.9 mmol) was added in several portions at 0° C., and the reaction mixture was slowly warmed to room temperature and stirred for 3 h. The reaction mixture was quenched with water (100 mL), and the organic phase was separated. The organic phase was washed with brine (100 mL), dried over anhydrous $Na_2SO_4$, filtered, and concentrated under reduced pressure (water bath temperature <25° C.). The residue was purified by column chromatography using 100% petroleum ether as eluent to afford tert-butyl((2-iodoallyl)oxy)dimethylsilane.

Step 3: To a stirred solution of tert-butyl((2-iodoallyl)oxy)dimethylsilane (35.0 g, 117.4 mmol) in dry toluene (1000 mL), potassium phenoxide (31.27 g, 234.8 mmol), bis(pinacolato)diboron (44.7 g, 176.2 mmol), and triphenylphospine (3.07 g, 11.7 mmol) were added, and the mixture was degassed with argon for 15 minutes. PdCl$_2$(Ph$_3$P) (4.94 g, 7.06 mmol) was added, and the mixture was degassed again for 10 minutes and then heated to 50° C. for 12 h. The reaction mixture was quenched with water (200 mL) and extracted with ethyl acetate (500 mL). The organic layer was washed with brine solution (250 mL), dried over anhydrous $Na_2SO_4$, filtered and concentrated. The residue was purified by silica gel column chromatography using 4% ethyl acetate/petroleum ether as eluent to yield tert-butyldimethyl((2-(4,4,5,5-tetramethyl-1,3,2-dioxaborolan-2-yl)allyl)oxy)silane.

$^1$H NMR (400 MHz, CDCl$_3$): δ 5.97 (d, J=1.7 Hz, 1H), 5.87 (d, J=1.7 Hz, 1H), 4.28 (s, 2H), 1.29 (s, 3H), 1.27 (s, 3H), 1.27 (s, 3H), 1.26 (s, 3H), 0.92 (s, 9H), 0.15 (s, 6H).

Step 4: To a stirred solution of 2-bromo-4-(5-chloropyridin-3-yl)-3-[(trans-4-methylcyclohexyl)methyl]-3H-imidazo[4,5-c]pyridine-6-carbonitrile (Preparative Example 3.1; 3.0 g, 6.93 mmol) in 1,4-dioxane (60 mL), tert-butyldimethyl((2-(4,4,5,5-tetramethyl-1,3,2-dioxaborolan-2-yl)allyl)oxy)silane (3.09 g 10.39 mmol), potassium phosphate (2.94 g, 13.86 mmol), and water (6 mL) were added, and the mixture was degassed with argon for 15 minutes. PdCl$_2$(dppf) (0.85 g, 1.04 mmol), was added, and the mixture was degassed with argon again for 5 minutes. The reaction was then heated at 100° C. for 16 h. The reaction mixture was cooled to room temperature, quenched with water (20 mL), and extracted with ethyl acetate (100 mL). The organic layer was separated, washed with brine (50 mL), dried over anhydrous $Na_2SO_4$, filtered, and concentrated under reduced pressure. The residue was purified by column chromatography using 15% ethyl acetate/petroleum ether as eluent to yield 2-(3-{[tert-butyl(dimethyl)silyl]oxy}prop-1-en-2-yl)-4-(5-chloropyridin-3-yl)-3-[(trans-4-methylcyclohexyl)methyl]-3H-imidazo[4,5-c]pyridine-6-carbonitrile. MS ES/APCl calcd. for $C_{29}H_{38}ClN_5OSi$ [M+H]$^+$ 536. found 536.

Steps 5 & 6: A stirred solution of 2-(3-{[tert-butyl(dimethyl)silyl]oxy}prop-1-en-2-yl)-4-(5-chloropyridin-3-yl)-3-[(trans-4-methylcyclohexyl)methyl]-3H-imidazo[4,5-c]pyridine-6-carbonitrile (1.2 g, 2.24 mmol) in THF (20 mL) was cooled to 0° C. Tetrabutylammonium fluoride (3.36 mL, 3.36 mmol, 1M solution in THF) was added dropwise over a period of 5 minutes, and the reaction mixture was warmed to room temperature and stirred for 1 h. The reaction mixture was quenched with water (10 mL) and extracted with ethyl acetate (15 mL). The organic phase was separated, washed with brine solution (10 mL), dried over anhydrous $Na_2SO_4$, filtered, and concentrated. The crude 4-(5-chloropyridin-3-yl)-2-(3-hydroxyprop-1-en-2-yl)-3-[(trans-4-methylcyclohexyl)methyl]-3H-imidazo[4,5-c]pyridine-6-carbonitrile (0.9 g, 2.14 mmol) was dissolved in dry THF (10 mL) and cooled to 0° C. NaH (0.123 g, 3.12 mmol, 60% in mineral oil) was added in several portions and stirred for 15 minutes. Methyl iodide (0.16 mL, 2.57 mmol) was added dropwise over a period of 5 minutes, and the reaction mixture was slowly warmed to room temperature and stirred for 1 h. The reaction mixture was quenched with ice and extracted with ethyl acetate (100 mL). The organic layer was separated, washed with brine (20 mL), dried over anhydrous $Na_2SO_4$, filtered, and concentrated under reduced pressure. The residue was purified by silica gel column chromatography using 15% ethyl acetate/petroleum ether as eluent to yield 4-(5-chloropyridin-3-yl)-2-(3-methoxyprop-1-en-2-yl)-3-[(trans- 4-methylcyclohexyl)methyl]-3H-imidazo[4,5-c]pyridine-6-carbonitrile. MS ES/APCl calcd. for $C_{24}H_{26}ClN_5O$ [M+H]$^+$ 436. found 436

Steps 7-9: Using procedures similar to those described in Example 2.1 (Step 5 and Step 6) and Example 9.2, 4-(5-chloropyridin-3-yl)-2-(3-methoxyprop-1-en-2-yl)-3-[(trans-4-methylcyclohexyl)methyl]-3H-imidazo[4,5-c]pyridine-6-carbonitrile was converted to 3-{4-(5-chloropyridin-3-yl)-2-[2-methoxy-1-(methoxymethyl)ethyl]-3-[(trans-4-methylcyclohexyl)methyl]-3H-imidazo[4,5 -c]pyridin-6-yl}-1,2,4-oxadiazol-5(4H)-one (TFA salt). MS ES/APCl calcd. for $C_{26}H_{31}ClN_6O_4$ [M+H]$^+$ 527. found 527. $^1$H NMR (400 MHz, CDCl$_3$): δ 9.90 (br s, 1H), 8.76 (s, 1H), 8.65 (s, 1H), δ 8.49 (s, 1H), 7.98 (s, 1H), 3.90-3.66 (m, 6H), 3.33 (s, 6H), 3.25-3.11 (m, 1H), 1.55 (d, J=11.6 Hz, 2H), 1.26-0.87 (m, 4H), 0.78 (d, J=6.4 Hz, 3H), 0.72-0.55 (m, 4H).

Examples in Table 9 (other than examples 9.1, 9.2, and 9.15) were prepared using procedures which were analogous to those described above.

TABLE 9

| Ex. | FRET IC$_{50}$ (nM) | Structure | Chemical Name | Salt | [M+H]+ Calc'd | [M+H]+ Obsv'd |
|---|---|---|---|---|---|---|
| 9.1 | 4 | 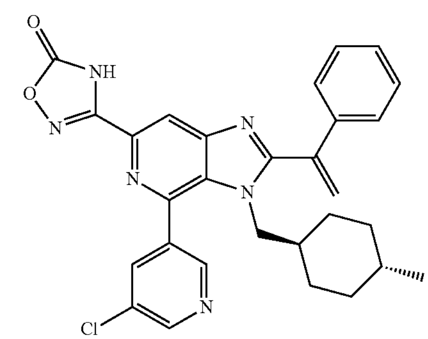 [SMILES: C=C(c1ccccc1)c1nc2cc(-c3noc(=O)[nH]3)nc(-c3cncc(Cl)c3)c2n1C[C@H]1CC[C@H](C)CC1] | 3-[4-(5-chloropyridin-3-yl)-3-[(trans-4-methylcyclohexyl)methyl]-2-(1-phenylethenyl)-3H-imidazo[4,5-c]pyridin-6-yl]-1,2,4-oxadiazol-5(4H)-one | TFA | 527 | 527 |
| 9.2 | 2 | 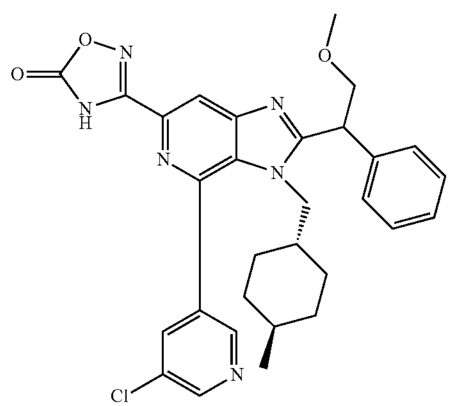 [SMILES: COCC(c1ccccc1)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-(2-methoxy-1-phenylethyl)-3-[(trans-4-methylcyclohexyl)methyl]-3H-imidazo[4,5-c]pyridin-6-yl}-1,2,4-oxadiazol-5(4H)-one (racemic) | TFA | 559 | 559 |
| 9.4 | 2 | 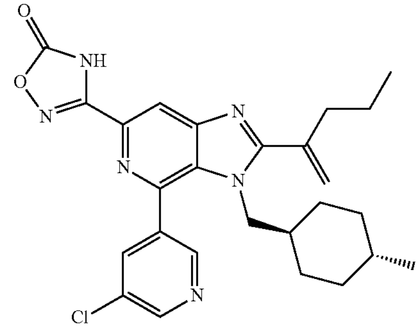 [SMILES: C=C(CCC)c1nc2cc(-c3noc(=O)[nH]3)nc(-c3cncc(Cl)c3)c2n1C[C@H]1CC[C@H](C)CC1] | 3-[4-(5-chloropyridin-3-yl)-3-[(trans-4-methylcyclohexyl)methyl]-2-(1-methylidenebutyl)-3H-imidazo[4,5-c]pyridin-6-yl]-1,2,4-oxadiazol-5(4H)-one | TFA | 493 | 493 |

TABLE 9-continued

| Ex. | FRET IC$_{50}$ (nM) | Structure | Chemical Name | Salt | [M+H]+ Calc'd | [M+H]+ Obsv'd |
|---|---|---|---|---|---|---|
| 9.5 | 2 | 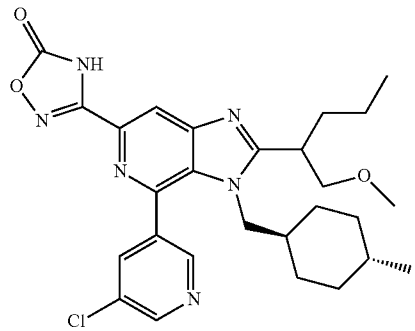 [SMILES: CCCC(COC)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[1-(methoxymethyl)butyl]-3-[(trans-4-methylcyclohexyl)methyl]-3H-imidazo[4,5-c]pyridin-6-yl}-1,2,4-oxadiazol-5(4H)-one (racemic) | | 525 | 525 |
| 9.6 | 2 | 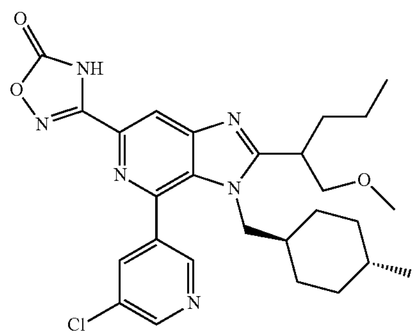 [SMILES: CCCC(COC)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[1-(methoxymethyl)butyl]-3-[(trans-4-methylcyclohexyl)methyl]-3H-imidazo[4,5-c]pyridin-6-yl}-1,2,4-oxadiazol-5(4H)-one (enantiomer 1) | | 525 | 525 |
| 9.7 | 3 | 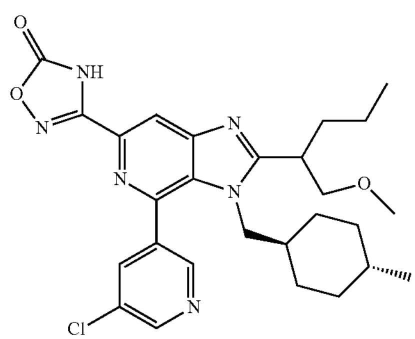 [SMILES: CCCC(COC)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[1-(methoxymethyl)butyl]-3-[(trans-4-methylcyclohexyl)methyl]-3H-imidazo[4,5-c]pyridin-6-yl}-1,2,4-oxadiazol-5(4H)-one (enantiomer 2) | | 525 | 525 |
| 9.8 | 7 | 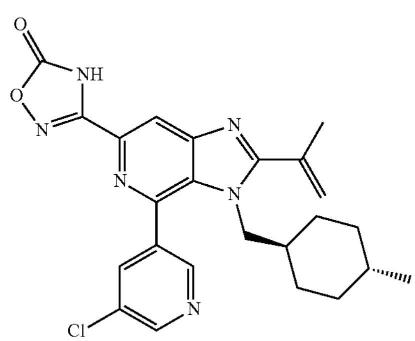 [SMILES: C=C(C)c1nc2cc(-c3noc(=O)[nH]3)nc(-c3cncc(Cl)c3)c2n1C[C@H]1CC[C@H](C)CC1] | 3-[4-(5-chloropyridin-3-yl)-3-[(trans-4-methylcyclohexyl)methyl]-2-(1-methylethenyl)-3H-imidazo[4,5-c]pyridin-6-yl]-1,2,4-oxadiazol-5(4H)-one | | 465 | 465 |

TABLE 9-continued

| Ex. | FRET IC$_{50}$ (nM) | Structure | Chemical Name | Salt | [M+H]+ Calc'd | [M+H]+ Obsv'd |
|---|---|---|---|---|---|---|
| 9.9 | 11 | 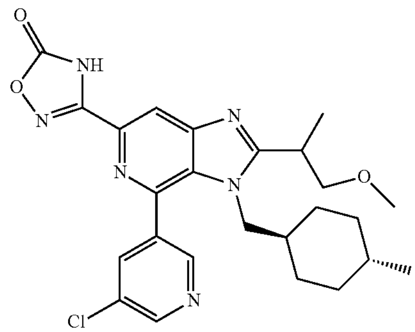 [SMILES: COCC(C)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-(2-methoxy-1-methylethyl)-3-[(trans-4-methylcyclohexyl) methyl]-3H-imidazo[4,5-c]pyridin-6-yl}-1,2,4-oxadiazol-5(4H)-one (racemic) | | 497 | 497 |
| 9.10 | 9 | 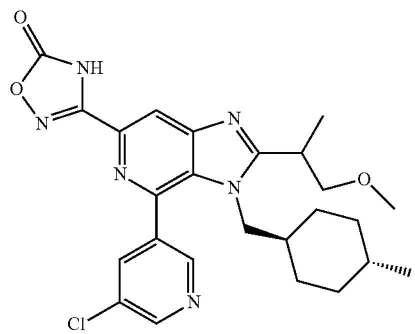 [SMILES: COCC(C)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[2-methoxy-1-methylethyl]-3-[(trans-4-methylcyclohexyl)m methyl]-3H-imidazo[4,5-c]pyridin-6-yl}-1,2,4-oxadiazol-5(4H)-one (enantiomer 1) | | 497 | 497 |
| 9.11 | 17 | 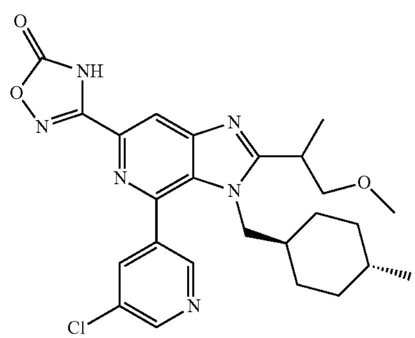 [SMILES: COCC(C)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[2-methoxy-1-methylethyl]-3-[(trans-4-methylcyclohexyl) methyl]-3H-imidazo[4,5-c]pyridin-6-yl}-1,2,4-oxadiazol-5(4H)-one (enantiomer 2) | | 497 | 497 |
| 9.12 | 8 | 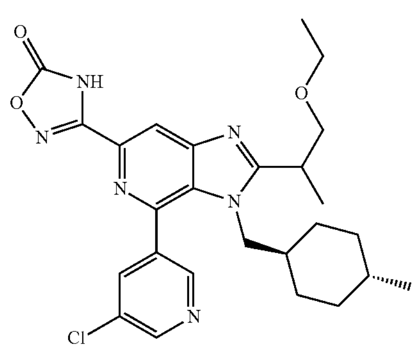 [SMILES: CCOCC(C)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-(2-ethoxy-1-methylethyl)-3-[(trans-4-methylcyclohexyl) methyl]-3H-imidazo[4,5-c]pyridin-6-yl}-1,2,4-oxadiazol-5(4H)-one (racemate) | | 511 | 511 |

TABLE 9-continued

| Ex. | FRET IC$_{50}$ (nM) | Structure | Chemical Name | Salt | [M+H]+ Calc'd | [M+H]+ Obsv'd |
|---|---|---|---|---|---|---|
| 9.13 | 8 | 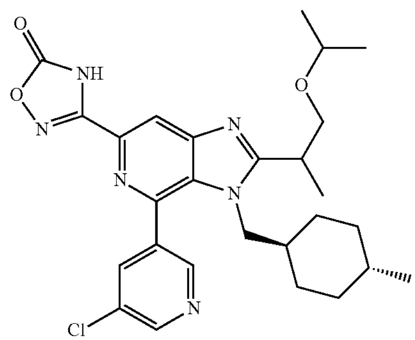 [SMILES: CC(C)OCC(C)c1nc2cc(-c3noc(=O)[nH]3)nc(-c3cncc(Cl)c3)c2n1C[C@H]1CC[C@H](C)CC1] | 3-{4-(5-chloropyridin-3-yl)-3-[(trans-4-methylcyclohexyl)methyl]-2-[1-methyl-2-(1-methylethoxy)ethyl]-3H-imidazo[4,5-c]pyridin-6-yl}-1,2,4-oxadiazol-5(4H)-one (racemate) | | 525 | 525 |
| 9.14 | 6 | 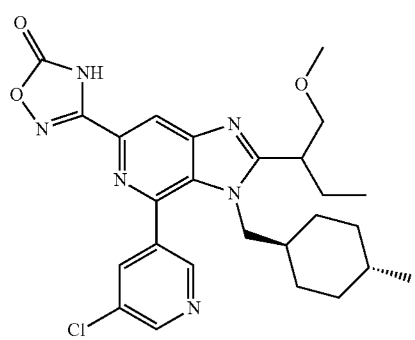 [SMILES: CCC(COC)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[1-(methoxymethyl)propyl]-3-[(trans-4-methylcyclohexyl)methyl]-3H-imidazo[4,5-c]pyridin-6-yl}-1,2,4-oxadiazol-5(4H)-one (racemate) | | 511 | 511 |
| 9.15 | 8 | 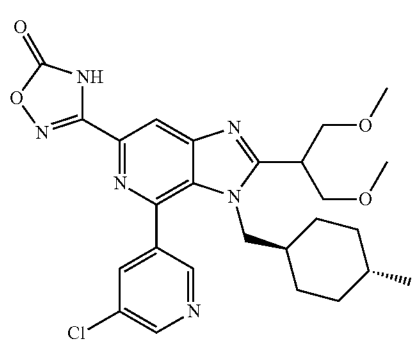 [SMILES: COCC(COC)c1nc2cc(-c3noc(=O)[nH]3)nc(-c3cncc(Cl)c3)c2n1C[C@H]1CC[C@H](C)CC1] | 3-{4-(5-chloropyridin-3-yl)-2-[2-methoxy-1-(methoxymethyl)ethyl]-3-[(trans-4-methylcyclohexyl)methyl]-3H-imidazo[4,5-c]pyridin-6-yl}-1,2,4-oxadiazol-5(4H)-one | TFA | 527 | 527 |

TABLE 9-continued

| Ex. | FRET IC$_{50}$ (nM) | Structure | Chemical Name | Salt | [M+H]+ Calc'd | [M+H]+ Obsv'd |
|---|---|---|---|---|---|---|
| 9.16 | 5 | 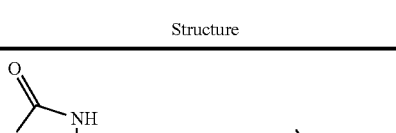 | 3-{4-(5-chloropyridin-3-yl)-2-[1-(methoxymethyl)-[2-methylpropyl]-3-[(trans-4-methylcyclohexyl)methyl]-3H-imidazo[4,5-c]pyridin-6-yl}-1,2,4-oxadiazol-5(4H)-one (racemate) | TFA | 525 | 525 |

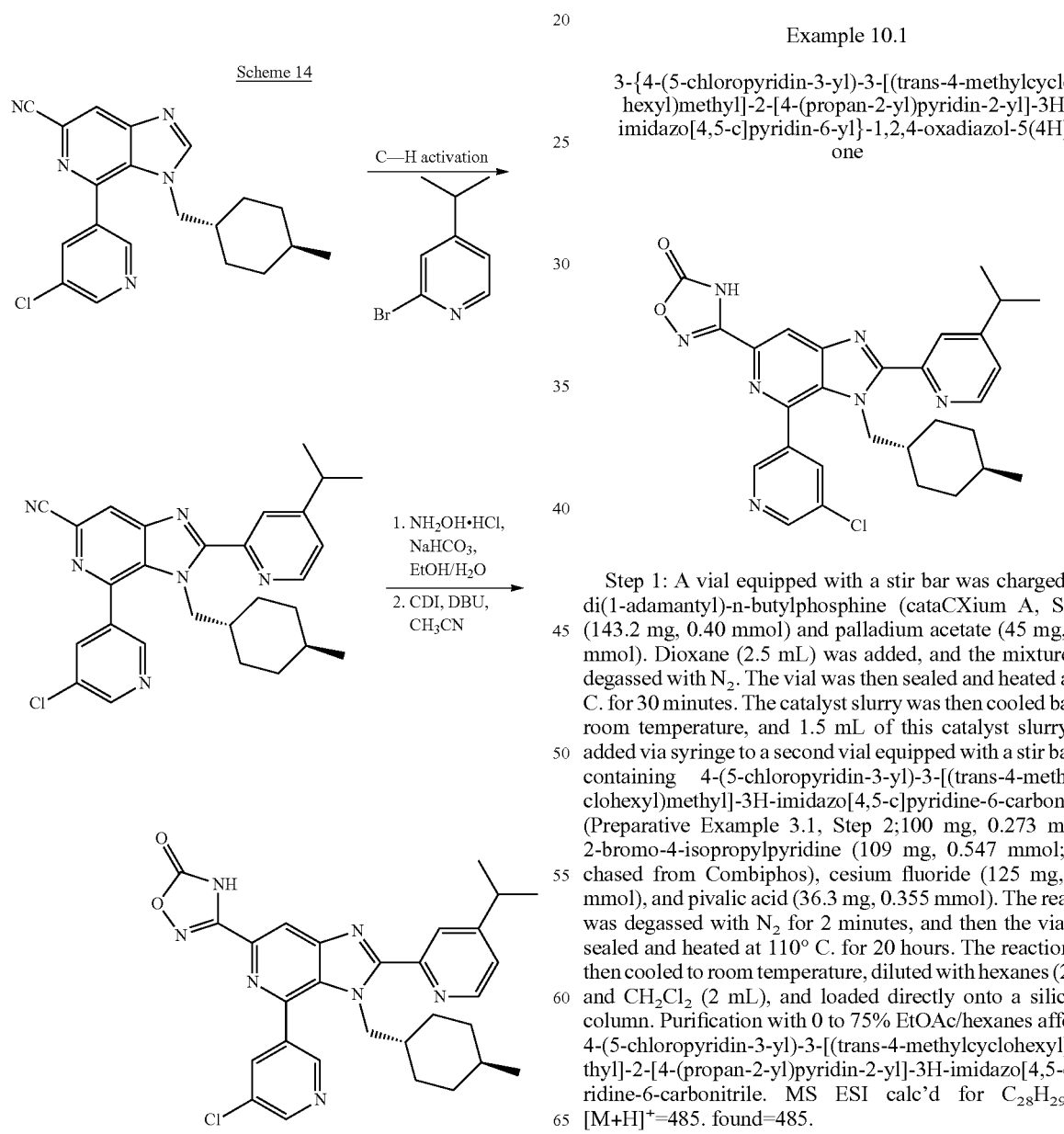

Scheme 14

Example 10.1

3-{4-(5-chloropyridin-3-yl)-3-[(trans-4-methylcyclohexyl)methyl]-2-[4-(propan-2-yl)pyridin-2-yl]-3H-imidazo[4,5-c]pyridin-6-yl}-1,2,4-oxadiazol-5(4H)-one Step 1: A vial equipped with a stir bar was charged with di(1-adamantyl)-n-butylphosphine (cataCXium A, Strem) (143.2 mg, 0.40 mmol) and palladium acetate (45 mg, 0.20 mmol). Dioxane (2.5 mL) was added, and the mixture was degassed with $N_2$. The vial was then sealed and heated at 50° C. for 30 minutes. The catalyst slurry was then cooled back to room temperature, and 1.5 mL of this catalyst slurry was added via syringe to a second vial equipped with a stir bar and containing 4-(5-chloropyridin-3-yl)-3-[(trans-4-methylcyclohexyl)methyl]-3H-imidazo[4,5-c]pyridine-6-carbonitrile (Preparative Example 3.1, Step 2;100 mg, 0.273 mmol), 2-bromo-4-isopropylpyridine (109 mg, 0.547 mmol; purchased from Combiphos), cesium fluoride (125 mg, 0.82 mmol), and pivalic acid (36.3 mg, 0.355 mmol). The reaction was degassed with $N_2$ for 2 minutes, and then the vial was sealed and heated at 110° C. for 20 hours. The reaction was then cooled to room temperature, diluted with hexanes (2 mL) and $CH_2Cl_2$ (2 mL), and loaded directly onto a silica gel column. Purification with 0 to 75% EtOAc/hexanes afforded 4-(5-chloropyridin-3-yl)-3-[(trans-4-methylcyclohexyl)methyl]-2-[4-(propan-2-yl)pyridin-2-yl]-3H-imidazo[4,5-c]pyridine-6-carbonitrile. MS ESI calc'd for $C_{28}H_{29}ClN_6$ [M+H]$^+$=485. found=485.

Steps 2 and 3: Using a procedure analogous to that described in Example 2.1 (Steps 5 and 6) and starting with 4-(5-chloropyridin-3-yl)-3-[(trans-4-methylcyclohexyl)methyl]-2-[4-(propan-2-yl)pyridin-2-yl]-3H-imidazo[4,5-c]pyridine-6-carbonitrile, 3-{4-(5-chloropyridin-3-yl)-3-[(trans-4-methylcyclohexyl)methyl]-2-[4-(propan-2-yl)pyridin-2-yl]-3H-imidazo[4,5-c]pyridin-6-yl}-1,2,4-oxadiazol-5(4H)-one (TFA salt) was prepared. MS ESI calc'd for $C_{29}H_{30}ClN_7O_2$ $[M+H]^+=544$. found=544. $^1$H NMR (600 MHz, d6-DMSO) δ 12.95 (s, 1H), 8.93 (s, 1H), 8.39 (s, 1H), 8.64 (d, J=5.4 Hz, 1H), 8.46 (s, 1H), 8.35 (s, 1H), 8.18 (s, 1H), 7.50 (d, J=5.4 Hz, 1H), 4.54 (bs, 2H), 3.05 (m, 1H), 1.24-1.30 (m, 8H), 0.92 (m, 2H), 0.55-0.63 (m, 5H), 0.36-0.45 (m, 4H).

Example 10.1

(Table 10) was Prepared as Described Above

TABLE 10

| Ex | FRET IC$_{50}$ (nM) | Structure | Chemical Name | Salt | [M+H]+ Calc'd | [M+H]+ Obsv'd |
|---|---|---|---|---|---|---|
| 10.1 | 4 | 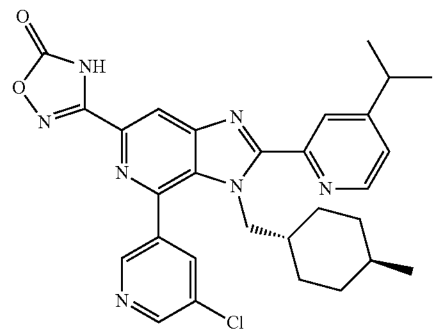 [SMILES: CC(C)c1ccnc(-c2nc3cc(-c4noc(=O)[nH]4)nc(-c4cncc(Cl)c4)c3n2C[C@H]2CC[C@H](C)CC2)c1] | 3-{4-(5-chloropyridin-3-yl)-3-[(trans-4-methylcyclohexyl)methyl]-2-[4-(1-methylethyl)pyridin-2-yl]-3H-imidazo[4,5-c]pyridin-6-yl}-1,2,4-oxadiazol-5(4H)-one | TFA | 544 | 544 |

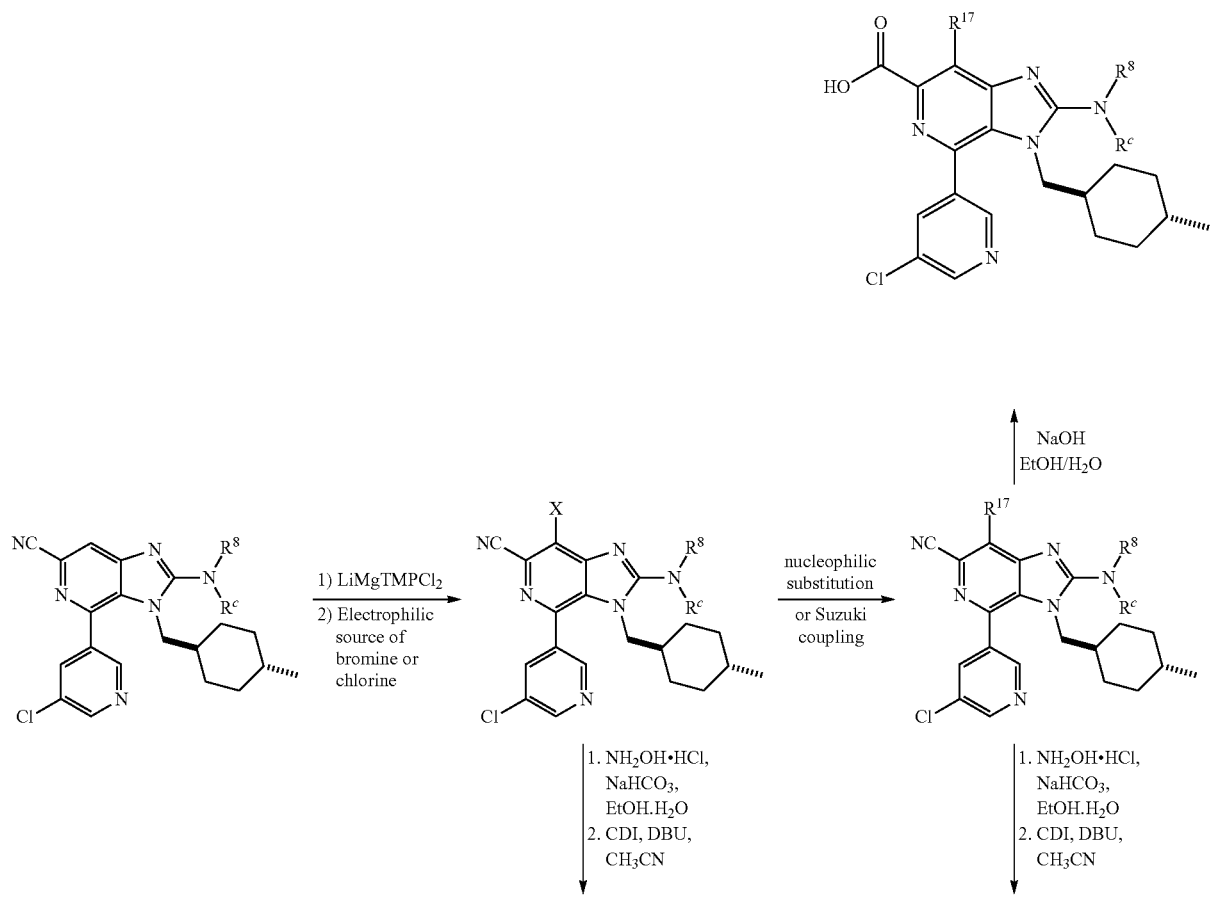

Scheme 15

-continued

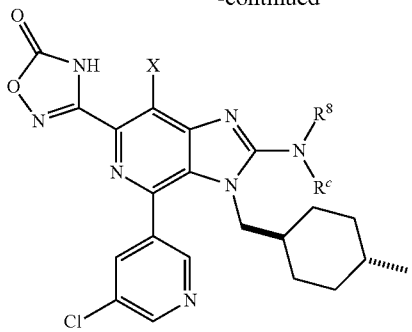

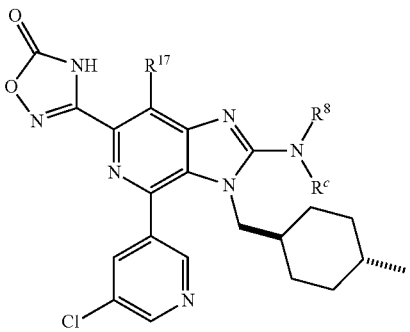

Example 11.1

3-{7-bromo-4-(5-chloropyridin-3-yl)-3-[(trans-4-methylcyclohexyl)methyl]-2-[(3R)-3-phenylmorpholin-4-yl]-3H-imidazo[4,5-c]pyridin-6-yl}-1,2,4-oxadiazol-5(4H)-one

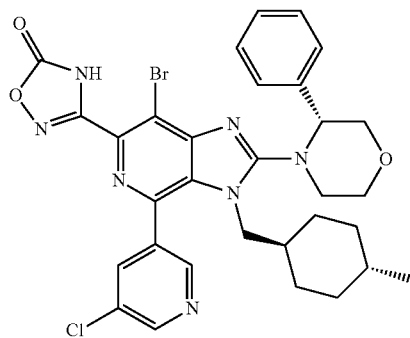 [SMILES: C[C@H]1CC[C@H](Cn2c(N3CCOC[C@H]3c3ccccc3)nc3c(Br)c(-c4noc(=O)[nH]4)nc(-c4cncc(Cl)c4)c32)CC1]

Step 1: 4-(5-Chloropyridin-3-yl)-3-[(trans-4-methylcyclohexyl)methyl]-2-[(3R)-3-phenylmorpholin-4-yl]-3H-imidazo[4,5-c]pyridine-6-carbonitrile (Example 2.1, Step 4; 180 mg, 0.342 mmol) was taken up in THF (3415 μl) and cooled to −78° C. Lithium magnesium 2,2,6,6-tetramethylpiperidin-1-ide dichloride (1M solution in THF/toluene, 683 μl, 0.683 mmol) was added, and the mixture was stirred at −78° C. for 45 minutes. 1,3-dibromo-5,5-dimethylimidazolidine-2,4-dione (244 mg, 0.854 mmol) was then added. The cooling bath was removed, and the solution warmed to room temperature and stirred for 60 minutes. The mixture was then diluted with ethyl acetate and washed with sodium thiosulfate (2×) and brine (1×). The organic layer was dried over magnesium sulfate, filtered, and concentrated. The resulting residue was purified via silica gel chromatography (0-100% ethyl acetate/hexanes) to afford 7-bromo-4-(5-chloropyridin-3-yl)-3-[(trans-4-methylcyclohexyl)methyl]-2-[(3R)-3-phenylmorpholin-4-yl]-3H-imidazo[4,5-c]pyridine-6-carbonitrile as a white solid that was contaminated with unreacted starting material. MS ESI calc'd. for $C_{30}H_{30}BrClN_6O$ $[M+1]^+$, $[M+3]^+$ 605, 607. found 605, 607.

Step 2: 7-Bromo-4-(5-chloropyridin-3-yl)-N'-hydroxy-3-[(trans-4-methylcyclohexyl)methyl]-2-[(3R)-3-phenylmorpholin-4-yl]-3H-imidazo[4,5-c]pyridine-6-carboximidamide was prepared in analogy to Example 2.1, Step 5 using 7-bromo-4-(5-chloropyridin-3-yl)-3-[(trans-4-methylcyclohexyl)methyl]-2-[(3R)-3-phenylmorpholin-4-yl]-3H-imidazo[4,5-c]pyridine-6-carbonitrile (140 mg, 0.231 mmol) as starting material. MS ESI calc'd. for $C_{30}H_{33}BrClN_7O_2$ $[M+1]^+$, $[M+3]^+$ 638, 640. found 638, 640.

Step 3: 3-{7-Bromo-4-(5-chloropyridin-3-yl)-3-[(trans-4-methylcyclohexyl)methyl]-2-[(3R)-3-phenylmorpholin-4-yl]-3H-imidazo[4,5-d]pyridin-6-yl}-1,2,4-oxadiazol-5(4H)-one was prepared in analogy to Example 2.1, Step 6 using 7-bromo-4-(5-chloropyridin-3-yl)-N'-hydroxy-3-[(trans-4-methylcyclohexyl)methyl]-2-[(3R)-3-phenylmorpholin-4-yl]-3H-imidazo[4,5-c]pyridine-6-carboximidamide (148 mg, 0.231 mmol) as starting material and mass guided reverse phase HPLC (acetonitrile/water+0.1% TFA modifier) for purification. Desired fractions were then diluted with ethyl acetate, washed with saturated aqueous sodium bicarbonate, dried over magnesium sulfate, filtered, and concentrated under reduced pressure. MS ESI calc'd. for $C_{31}H_{31}BrClN_7O_3$ $[M+1]^+$, $[M+3]^+$ 664, 666. found 664, 666. $^1$H NMR (500 MHz, DMSO-$d_6$) δ 12.72 (s, 1H), 8.89 (s, 1H), 8.80 (d, J=2.5 Hz, 1H), 8.44 (s, 1H), 7.47 (d, J=7.5; H, 2H), 7.29-7.26 (m, 2H), 7.23-7.20 (m, 1H), 4.92-4.90 (m, 1H), 4.04-3.99 (m, 1H), 3.96-3.86 (m, 3H), 3.82-3.77 (m, 1H), 3.63-3.55 (m, 2H). 3.38-3.31 (m, 1H), 1.39-1.34 (m, 2H), 1.10-1.01 (m, 1H), 0.84-0.54 (m, 2H), 0.68 (d, J=6.5 Hz, 3H), 0.66-0.56 (m, 2H), 0.44-0.27 (m, 3H).

Example 11.2

3-{7-chloro-4-(5-chloropyridin-3-yl)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one

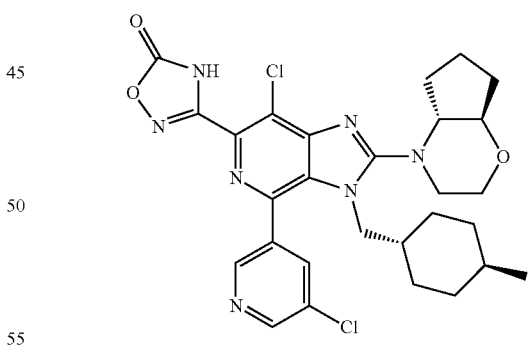

Step 1: To a −78° C. solution of 4-(5-chloropyridin-3-yl)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridine-6-carbonitrile (Example 3.2, Step 3; 250 mg, 0.509 mmol) in THF (7 mL) was added 2,2,6,6-tetramethylpiperidinylmagnesium chloride lithium chloride complex (Aldrich, 1M in THF/toluene) (1.02 mL, 1.02 mmol). The resulting solution was stirred at −78° C. for 45 minutes, and then hexachloroethane (301 mg, 1.273 mmol) was added as a solid in one portion. The reaction was allowed to warm slowly to 10° C. over 2 hours and then quenched with saturated NH$_4$Cl (10 mL). EtOAc (75 ml) was added, and the organic layer was washed with water and brine (25 mL each). The organic layer was dried over Na$_2$SO$_4$, filtered, and concentrated. Purification of the residue on a silica gel column eluting with 0 to 50% EtOAc/DCM afforded 7-chloro-4-(5-chloropyridin-3-yl)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridine-6-carbonitrile. MS ESI calc'd for C$_{27}$H$_{30}$Cl$_2$N$_6$O [M+H]$^+$=525. found=525.

Step 2: Hydroxylamine hydrochloride (8.2 mg, 0.118 mmol) was dissolved in water (600 μL), and sodium bicarbonate (14.9 mg, 0.177 mmol) was added. The solution was stirred for 30 minutes, and gas evolved. The solution was then added to 7-chloro-4-(5-chloropyridin-3-yl)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridine-6-carbonitrile (31 mg, 0.059 mmol) suspended in EtOH (1.2 mL). The reaction vial was sealed and heated to 90° C. for 30 minutes. The reaction was then cooled to room temperature, diluted with EtOAc (40 mL) and washed with water (10 mL) and brine (10 mL). The organic layer was dried over Na$_2$SO$_4$, filtered and concentrated. The crude product, 7-chloro-4-(5-chloropyridin-3-yl)-2-[(4aR,7aR)-hexahydrocyclopenta[b][1,4]oxazin-4(4aH)-yl]-N'-hydroxy-3-[(trans-4-methylcyclohexyl)methyl]-3H-imidazo[4,5-c]pyridine-6-carboximidamide, was used in Step 3. MS ESI calc'd for C$_{27}$H$_{33}$Cl$_2$N$_7$O$_2$ [M+H]$^+$=558. found=558.

Step 3: To 7-chloro-4-(5-chloropyridin-3-yl)-2-[(4aR,7aR)-hexahydrocyclopenta[b][1,4]oxazin-4(4aH)-yl]-N'-hydroxy-3-[(trans-4-methylcyclohexyl)methyl]-3H-imidazo[4,5-c]pyridine-6-carboximidamide (33.3 mg, 0.06 mmol) in acetonitrile (2 mL) were added 1,1'-carbonyldiimidazole (19.3 mg, 0.119 mmol) and 1,8-diazabicyclo[5.4.0]undec-7-ene (0.036 mL, 0.238 mmol). The reaction was stirred at room temperature for 1 hour and then concentrated. The residue was purified by mass triggered reverse phase HPLC (C-18) eluting with acetonitrile/water+0.1% TFA to afford 3-{7-chloro-4-(5-chloropyridin-3-yl)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one (TFA salt). MS ESI calc'd for C$_{28}$H$_{31}$Cl$_2$N$_7$O$_3$ [M+H]$^+$=584. found=584. $^1$H NMR (600 MHz, DMSO-d$_6$) δ 12.74 (s, 1H), 8.92 (d, J=1.2 Hz, 1H), 8.80 (d, J=2.4 Hz, 1H), 8.46 (m, 1H), 3.94 (d, J=9.6 Hz, 1H), 3.77-3.86 (m, 2H), 3.56-3.62 (m, 2H), 3.39 (m, 1H), 3.05 (m, 1H), 2.87 (m, 1H), 2.31 (m, 1H), 1.86 (m, 1H), 1.71 (m, 1H), 1.51-1.64 (m, 2H), 1.32-1.41 (m, 2H), 1.12 (m, 1H), 1.04 (m, 1H), 0.81 (m, 1H), 0.65-0.74 (m, 6H), 0.46 (m, 1H), 0.30-0.42 (m, 2H).

Example 11.3

3-{4-(5-chloropyridin-3-yl)-7-fluoro-2-[(4aR,7aR)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one

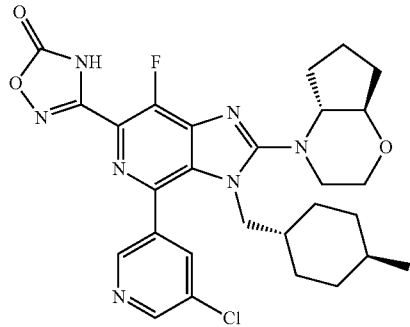 [SMILES: C[C@H]1CC[C@H](Cn2c(N3CCO[C@@H]4CCC[C@H]43)nc3c(F)c(-c4noc(=O)[nH]4)nc(-c4cncc(Cl)c4)c32)CC1]

Step 1: A dry vial, under an atmosphere of nitrogen was charged with 7-chloro-4-(5-chloropyridin-3-yl)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridine-6-carbonitrile (Example 11.2, step 125 mg, 0.048 mmol), CsF (50.6 mg, 0.333 mmol), and DMSO (300 μL). The vial was sealed and heated to 100° C. for 3 hours. The reaction was cooled to room temperature, diluted with EtOAc (25 mL) and washed with water (5 mL) and brine (5 mL). The organic layer was dried over Na$_2$SO$_4$, filtered, and concentrated. The residue was purified on a silica gel column with 0 to 100% EtOAc/hexanes to afford a 3:1 mixture of 4-(5-chloropyridin-3-yl)-7-fluoro-2-[(4aR,7aR)-hexahydrocyclopenta[b][1,4]oxazin-4(4aH)-yl]-3-[(trans-4-methylcyclohexyl)methyl]-3H-imidazo[4,5-c]pyridine-6-carbonitrile and 7-chloro-4-(5-chloropyridin-3-yl)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridine-6-carbonitrile. MS ESI calc'd for C$_{27}$H$_{30}$ClFN$_6$O [M+H]$^+$=509. found=509. MS ESI calc'd for C$_{27}$H$_{30}$Cl$_2$N$_6$O [M+H]$^+$=525. found=525.

Step 2: Hydroxylamine hydrochloride (7.5 mg, 0.11 mmol) was dissolved in water (500 μL), and sodium bicarbonate (13.5 mg, 0.16 mmol) was added. The solution was stirred for 30 minutes and gas evolved. The solution was then added to a 3:1 mixture of 4-(5-chloropyridin-3-yl)-7-fluoro-2-[(4aR,7aR)-hexahydrocyclopenta[b][1,4]oxazin-4(4aH)-yl]-3-[(trans-4-methylcyclohexyl)methyl]-3H-imidazo[4,5-c]pyridine-6-carbonitrile and 7-chloro-4-(5-chloropyridin-3-yl)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridine-6-carbonitrile (27.5 mg, 0.05 mmol) suspended in EtOH (1 mL). The reaction vial was sealed and heated to 55° C. for 30 minutes. The reaction was then cooled to room temperature, diluted with EtOAc (40 mL) and washed with water (10 mL) and brine (10 mL). The organic layer was dried over Na$_2$SO$_4$, filtered and concentrated. The crude 3:1 mixture of products, 4-(5-chloropyridin-3-yl)-7-fluoro-2-[(4aR,7aR)-hexahydrocyclopenta [b][1,4]oxazin-4(4aH)-yl]-N'-hydroxy-3-[(trans-4-methylcyclohexyl)methyl]-3H-imidazo[4,5-c]pyridine-6-carboximidamide and 7-chloro-4-(5-chloropyridin-3-yl)-2-[(4aR,7aR)-hexahydrocyclopenta[b][1,4]oxazin-4(4aH)-yl]-N'-hydroxy-3-[(trans-4-methylcyclohexyl)methyl]-3H-imidazo[4,5-c]pyridine-6-carboximidamide, was used in Step 3. MS ESI calc'd for C$_{27}$H$_{33}$ClFN$_7$O$_2$ [M+H]$^+$=542. found=542. MS ESI calc'd for C$_{27}$H$_{33}$Cl$_2$N$_7$O$_2$ [M+H]$^+$=558. found=558.

Step 3: To 3:1 mixture of 4-(5-chloropyridin-3-yl)-7-fluoro-2-[(4aR,7aR)-hexahydrocyclopenta[b][1,4]oxazin-4(4aH)-yl]-N'-hydroxy-3-[(trans-4-methylcyclohexyl)methyl]-3H-imidazo[4,5-c]pyridine-6-carboximidamide and 7-chloro-4-(5-chloropyridin-3-yl)-2-[(4aR,7aR)-hexahydrocyclopenta[b][1,4]oxazin-4(4aH)-yl]-N'-hydroxy-3-[(trans-4-methylcyclohexyl)methyl]-3H-imidazo[4,5-c]pyridine-6-carboximidamide (33 mg, 0.06 mmol) in acetonitrile (2 mL) was added 1,1'-carbonyldiimidazole (19.7 mg, 0.122 mmol) and 1,8-diazabicyclo[5.4.0]undec-7-ene (0.037 mL, 0.244 mmol). The reaction was stirred at room temperature for 1 hour and then concentrated. The residue was purified by mass triggered reverse phase HPLC(C-18) eluting with acetonitrile/water+0.1% TFA to afford pure 3-{4-(5-chloropyridin-3-yl)-7-fluoro-2-[(4aR,7aR)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one (TFA salt). MS ESI calc'd for C$_{28}$H$_{31}$ClFN$_7$O$_3$ [M+H]$^+$=568. found=568. $^1$H NMR (600 MHz, DMSO-d$_6$) δ 12.83 (s, 1H), 8.91 (d, J=1.8 Hz, 1H), 8.79 (d, J=2.4 Hz, 1H), 8.43 (m, 1H), 3.94 (d, J=9.6 Hz, 1H), 3.78-3.87 (m, 2H), 3.63 (dd, J=14.4, 3.6 Hz, 1H), 3.56 (d, J=12.6 Hz, 1H), 3.39 (m, 1H), 3.04 (m, 1H), 2.84 (m, 1H), 2.27 (m, 1H), 1.86 (m, 1H), 1.69 (m, 1H), 1.51-1.64 (m, 2H), 1.32-1.41 (m, 2H), 1.12 (m, 1H), 1.04 (m, 1H), 0.80 (m, 1H), 0.63-0.74 (m, 6H), 0.47 (m, 1H), 0.29-0.42 (m, 2H).

Example 11.4

3-{4-(5-chloropyridin-3-yl)-2-[(4aR,7aR)-hexahydrocyclopenta[b][1,4]oxazin-4(4aH)-yl]-7-methoxy-3-[(trans-4-methylcyclohexyl)methyl]-3H-imidazo[4,5-c]pyridin-6-yl}-1,2,4-oxadiazol-5(4H)-one

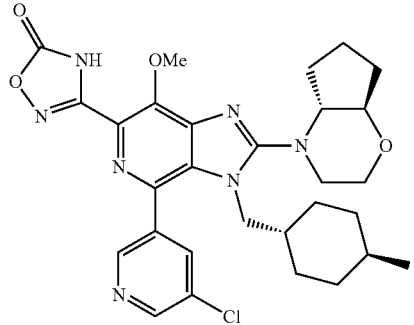 [SMILES: COc1c(-c2noc(=O)[nH]2)nc(-c2cncc(Cl)c2)c2c1nc(N1CCO[C@@H]3CCC[C@H]31)n2C[C@H]1CC[C@H](C)CC1]

Step 1: A vial was charged with 7-chloro-4-(5-chloropyridin-3-yl)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridine-6-carbonitrile (Example 11.2, step 1; 25 mg, 0.048 mmol), CsF (50.6 mg, 0.333 mmol), and DMSO (500 μL). The vial was sealed and heated to 100° C. for 6 hours and then water (20 μL) was added and heating at 100° C. was continued for an additional 20 hours. The reaction was cooled to room temperature, diluted with EtOAc (40 mL), and washed with water (2×10 mL) and brine (2×10 mL). The organic layer was dried over Na$_2$SO$_4$, filtered, and concentrated. The residue, crude 4-(5-chloropyridin-3-yl)-2-[(4aR,7aR)-hexahydrocyclopenta[b][1,4]oxazin-4(4aH)-yl]-7-hydroxy-3-[(trans-4-methylcyclohexyl)methyl]-3H-imidazo[4,5-c]pyridine-6-carbonitrile, was used directly in Step 2. MS ESI calc'd for C$_{27}$H$_{31}$ClN$_6$O$_2$ [M+H]$^+$=507. found=507.

Step 2: To a solution of 4-(5-chloropyridin-3-yl)-2-[(4aR,7aR)-hexahydrocyclopenta[b][1,4]oxazin-4(4aH)-yl]-7-hydroxy-3-[(trans-4-methylcyclohexyl)methyl]-3H-imidazo[4,5-c]pyridine-6-carbonitrile (24.5 mg, 0.048 mmol) in DMF (2 mL) were added Cs$_2$CO$_3$ (31.5 mg, 0.097 mmol) and MeI (6 μL, 0.097 mmol). The reaction was stirred at room temperature for 15 minutes and then diluted with EtOAc (40 mL) and washed with water (10 mL) and brine (10 mL). The organic layer was dried over Na$_2$SO$_4$, filtered, and concentrated. The residue was purified on a silica gel column with 0 to 100% EtOAc/hexanes to afford 4-(5-chloropyridin-3-yl)-2-[(4aR,7aR)-hexahydrocyclopenta[b][1,4]oxazin-4(4aH)-yl]-7-methoxy-3-[(trans-4-methylcyclohexyl)methyl]-3H-imidazo[4,5-c]pyridine-6-carbonitrile. MS ESI calc'd for C$_{28}$H$_{33}$ClN$_6$O$_2$ [M+H]$^+$=521. found=521.

Steps 3 and 4: Using a procedure analagous to that described in Example 11.2 (Steps 2 and 3) and starting with 4-(5-chloropyridin-3-yl)-2-[(4aR,7aR)-hexahydrocyclopenta[b][1,4]oxazin-4(4aH)-yl]-7-methoxy-3-[(trans-4-methylcyclohexyl)methyl]-3H-imidazo[4,5-c]pyridine-6-carbonitrile, 3-{4-(5-chloropyridin-3-yl)-2-[(4aR,7aR)-hexahydrocyclopenta[b][1,4]oxazin-4(4aH)-yl]-7-methoxy-3-[(trans-4-methylcyclohexyl)methyl]-3H-imidazo[4,5-c]pyridin-6-yl}-1,2,4-oxadiazol-5(4H)-one (TFA salt) was prepared. MS ESI calc'd for C$_{29}$H$_{34}$ClN$_7$O$_4$ [M+H]$^+$=580. found=580. $^1$H NMR (600 MHz, DMSO-d$_6$) δ 12.41 (s, 1H), 8.84 (d, J=1.8 Hz, 1H), 8.75 (d, J=2.4 Hz, 1H), 8.37 (m, 1H), 4.38 (s, 3H) 3.93 (d, J=9.6 Hz, 1H), 3.77-3.84 (m, 2H), 3.59 (dd, J=14.4, 2.4 Hz, 1H), 3.52 (d, J=12.0 Hz, 1H), 3.38 (m, 1H), 3.01 (m, 1H), 2.82 (m, 1H), 2.27 (m, 1H), 1.85 (m, 1H), 1.68 (m, 1H), 1.51-1.64 (m, 2H), 1.32-1.41 (m, 2H), 1.13 (m, 1H), 1.04 (m, 1H), 0.80 (m, 1H), 0.63-0.76 (m, 6H), 0.45 (m, 1H), 0.31-0.42 (m, 2H).

Example 11.5

3-{4-(5-chloropyridin-3-yl)-2-[(4aR,7aR)-hexahydrocyclopenta[b][1,4]oxazin-4(4aH)-yl]-7-methyl-3-[(trans-4-methylcyclohexyl)methyl]-3H-imidazo[4,5-c]pyridin-6-yl}-1,2,4-oxadiazol-5(4H)-one

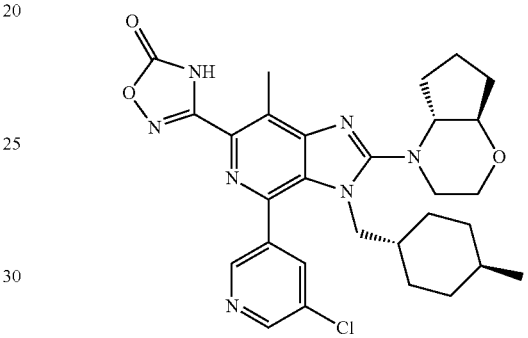

Step 1: To a −78° C. solution of 4-(5-chloropyridin-3-yl)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridine-6-carbonitrile (Example 3.2, Step 3; 300 mg, 0.611 mmol) in THF (8 mL) was added 2,2,6,6-tetramethylpiperidinylmagnesium chloride lithium chloride complex (Aldrich, 1M in THF/toluene) (1.22 mL, 1.22 mmol). The resulting yellow solution was stirred at −78° C. for 45 minutes, and then 1,3-dibromo-5,5-dimethylhydantoin (437 mg, 1.527 mmol) was added as a solid in one portion. The reaction was allowed to warm slowly to 0° C. over 90 minutes and then quenched with saturated NH$_4$Cl (10 mL). EtOAc (75 ml) was added, and the organic layer was washed with water and brine (25 mL each). The organic layer was dried over Na$_2$SO$_4$, filtered, and concentrated. Purification of the residue on a silica gel column eluting with 0 to 50% EtOAc/DCM afforded 7-bromo-4-(5-chloropyridin-3-yl)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridine-6-carbonitrile. MS ESI calc'd for C$_{27}$H$_{30}$BrClN$_6$O [M+H]$^+$=571. found=571.

Step 2: A vial was charged with 7-bromo-4-(5-chloropyridin-3-yl)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridine-6-carbonitrile (40 mg, 0.07 mmol), trimethylboroxine (10 μL, 0.07 mmol), [1,1'-bis(diphenylphosphino)ferrocene]dichloropalladium(II) (5 mg, 0.007 mmol), K$_3$PO$_4$ (37.2 mg, 0.175 mmol), dioxane (0.8 mL), and water (0.2 mL). The mixture was sparged with N$_2$, the vial was sealed, and the reaction was heated at 100° C. for 90 minutes. The reaction was then cooled to room temperature, diluted with EtOAc (40 mL), and washed with water (10 mL) and brine (10 mL). The organic layer was dried over Na$_2$SO$_4$, filtered, and concentrated. The residue was purified on a silica gel column with 0 to 100% EtOAc/hexanes to afford 4-(5-chloropyridin-3-yl)-2-[(4aR,7aR)-hexahydrocyclopenta[b][1,4]oxazin-4(4aH)-yl]-7-methyl-3-[(trans-4-methylcyclohexyl)methyl]-3H-imidazo[4,5-c]pyridine-6-carbonitrile. MS ESI calc'd for $C_{28}H_{33}ClN_6O$ $[M+H]^+$=505. found=505.

Steps 3 and 4: Using a procedure analogous to that described in Example 11.2 (Steps 2 and 3) and starting with 4-(5-chloropyridin-3-yl)-2-[(4aR,7aR)-hexahydrocyclopenta[b][1,4]oxazin-4(4aH)-yl]-7-methyl-3-[(trans-4-methylcyclohexyl)methyl]-3H-imidazo[4,5-c]pyridine-6-carbonitrile, 3-{4-(5-chloropyridin-3-yl)-2-[(4aR,7aR)-hexahydrocyclopenta[b][1,4]oxazin-4(4aH)-yl]-7-methyl-3-[(trans-4-methylcyclohexyl)methyl]-3H-imidazo[4,5-c]pyridin-6-yl}-1,2,4-oxadiazol-5(4H)-one (TFA salt) was prepared. MS ESI calc'd for $C_{29}H_{34}ClN_7O_3$ $[M+H]^+$=564. found=564. $^1$H NMR (600 MHz, DMSO-$d_6$) δ 12.56 (s, 1H), 8.90 (s, 1H), 8.77 (d, J=2.4 Hz, 1H), 8.44 (5, 1H), 3.93 (d, J=9.6 Hz, 1H), 3.77-3.86 (m, 2H), 3.63 (dd, J=14.4, 3.0 Hz, 1H), 3.52 (d, J=12.0 Hz, 1H), 3.38 (m, 1H), 3.02 (m, 1H), 2.83 (m, 1H), 2.74 (s, 3H), 2.30 (m, 1H), 1.85 (m, 1H), 1.69 (m, 1H), 1.51-1.63 (m, 2H), 1.30-1.41 (m, 2H), 1.12 (m, 1H), 1.04 (m, 1H), 0.78 (m, 1H), 0.59-0.72 (m, 6H), 0.49 (d, J=12 Hz, 1H), 0.28-0.38 (m, 2H).

Example 11.6

4-(5-chloropyridin-3-yl)-7-(dimethylamino)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridine-6-carboxylic acid

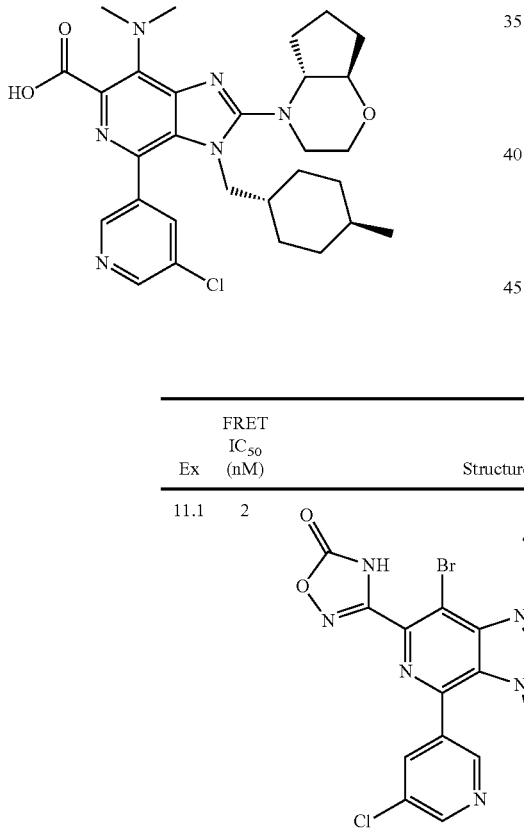

Step 1: A dry vial, under an atmosphere of nitrogen, was charged with 7-chloro-4-(5-chloropyridin-3-yl)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridine-6-carbonitrile (Example 11.2, step 1; 50 mg, 0.095 mmol), CsF (101 mg, 0.666 mmol), dimethylamine (0.476 mL of a 2M solution in THF, 0.952 mmol) and DMSO (1 mL). The vial was sealed and heated to 100° C. for 8 hours. The reaction was cooled to room temperature, diluted with EtOAc (25 mL) and washed with water (5 mL) and brine (5 mL). The organic layer was dried over $Na_2SO_4$, filtered, and concentrated. The residue was purified on a silica gel column with 0 to 100% EtOAc/hexanes to afford 4-(5-chloropyridin-3-yl)-7-(dimethylamino)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridine-6-carbonitrile. MS ESI calc'd for $C_{29}H_{36}ClN_7O$ $[M+H]^+$=534. found=534.

Step 2: To a suspension of 4-(5-chloropyridin-3-yl)-7-(dimethylamino)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridine-6-carbonitrile (31.8 mg, 0.06 mmol) in EtOH (1 mL) was added NaOH (0.2 mL of a 5M aq. solution, 1 mmol). The reaction was heated at 70° C. for 60 hours and then cooled to room temperature. HOAc (60 μL, 1 mmol) was added followed by DMSO (1.5 mL). After sonication and filtration to remove solids, the filtrate was purified by mass triggered reverse phase HPLC(C-18) eluting with acetonitrile/water+0.1% TFA to afford 4-(5-chloropyridin-3-yl)-7-(dimethylamino)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridine-6-carboxylic acid (TFA salt). MS ESI calc'd for $C_{29}H_{37}ClN_6O_3$ $[M+H]^+$=553. found=553. $^1$H NMR (600 MHz, DMSO-$d_6$) δ 8.75-8.77 (m, 2H), 8.27 (m, 1H), 3.93 (dd, J=12.0, 1.8 Hz, 1H), 3.75-3.81 (m, 2H), 3.47-3.52 (m, 2H), 3.38 (m, 1H), 3.15 (s, 6H), 3.03 (m, 1H), 2.81 (m, 1H), 2.26 (m, 1H), 1.85 (m, 1H), 1.69 (m, 1H), 1.51-1.63 (m, 2H), 1.31-1.41 (m, 2H), 1.13 (m, 1H), 1.05 (m, 1H), 0.83 (m, 1H), 0.64-0.73 (m, 6H), 0.34-0.46 (m, 3H).

The examples in Table 11 were prepared as described above.

TABLE 11

| Ex | FRET IC$_{50}$ (nM) | Structure | Chemical Name | Salt | [M+H]+ Calc'd | [M+H]+ Obsv'd |
|---|---|---|---|---|---|---|
| 11.1 | 2 | 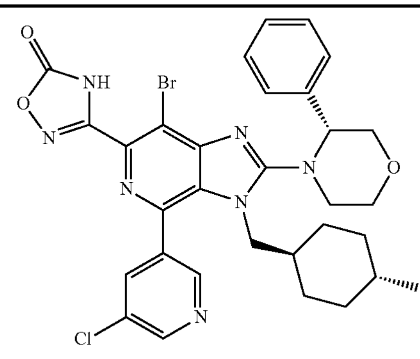 | 3-{7-bromo-4-(5-chloropyridin-3-yl)-3-[(trans-4-methylcyclohexyl)methyl]-2-[(3R)-3-phenylmorpholin-4-yl]-3H-imidazo[4,5-c]pyridin-6-yl}-1,2,4-oxadiazol-5(4H)-one | | 664 | 664 |

TABLE 11-continued

| Ex | FRET IC$_{50}$ (nM) | Structure | Chemical Name | Salt | [M+H]+ Calc'd | [M+H]+ Obsv'd |
|---|---|---|---|---|---|---|
| 11.2 | 1 | 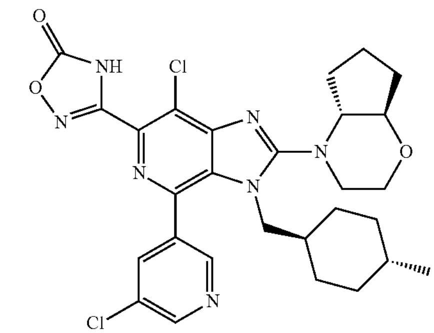 [SMILES: C[C@H]1CC[C@H](Cn2c(N3CCO[C@@H]4CCC[C@H]43)nc3c(Cl)c(-c4noc(=O)[nH]4)nc(-c4cncc(Cl)c4)c32)CC1] | 3-{7-chloro-4-(5-chloropyridin-3-yl)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridin-6-yl]-1,2,4-oxadiazol-5(4H)-one | TFA | 584 | 584 |
| 11.3 | 1 | 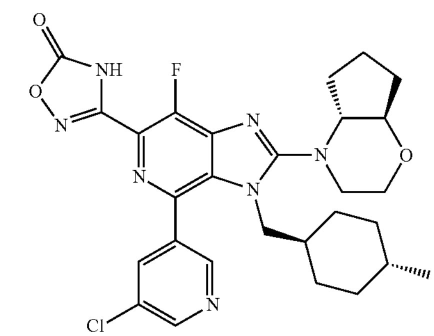 [SMILES: C[C@H]1CC[C@H](Cn2c(N3CCO[C@@H]4CCC[C@H]43)nc3c(F)c(-c4noc(=O)[nH]4)nc(-c4cncc(Cl)c4)c32)CC1] | 3-{4-(5-chloropyridin-3-yl)-7-fluoro-2-[(4aR,7aR)-hexahydrocyclopenta[b][1,4]oxazin-4(4aH)-yl]-3-[(trans-4-methylcyclohexyl)methyl]-3H-imidazo[4,5-c]pyridin-6-yl]-1,2,4-oxadiazol-5(4H)-one | TFA | 568 | 568 |
| 11.4 | 1 | 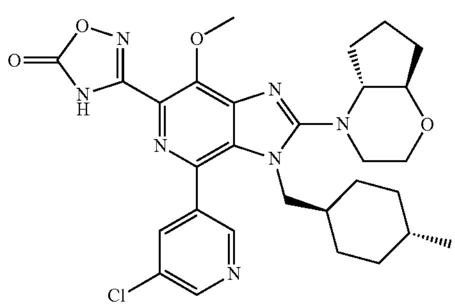 [SMILES: COc1c(-c2noc(=O)[nH]2)nc(-c2cncc(Cl)c2)c2c1nc(N1CCO[C@@H]3CCC[C@H]31)n2C[C@H]1CC[C@H](C)CC1] | 3-{4-(5-chloropyridin-3-yl)-2-[(4aR,7aR)-hexahydrocyclopenta[b][1,4]oxazin-4(4aH)-yl]-7-methoxy-3-[(trans-4-methylcyclohexyl)methyl]-3H-imidazo[4,5-c]pyridin-6-yl}-1,2,4-oxadiazol-5(4H)-one | TFA | 580 | 580 |
| 11.5 | 2 | 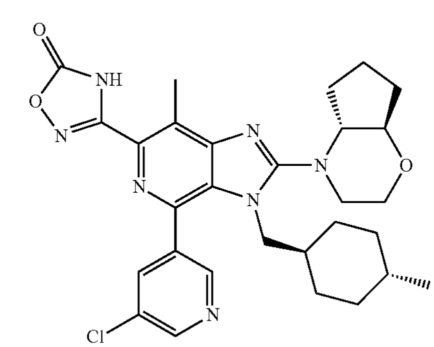 [SMILES: Cc1c(-c2noc(=O)[nH]2)nc(-c2cncc(Cl)c2)c2c1nc(N1CCO[C@@H]3CCC[C@H]31)n2C[C@H]1CC[C@H](C)CC1] | 3-{4-(5-chloropyridin-3-yl)-2-[(4aR,7aR)-hexahydrocyclopenta[b][1,4]oxazin-4(4aH)-yl]-7-methyl-3-[(trans-4-methylcyclohexyl)methyl]-3H-imidazo[4,5-c]pyridin-6-yl}-1,2,4-oxadiazol-5(4H)-one | TFA | 564 | 564 |

TABLE 11-continued
| Ex | FRET IC$_{50}$ (nM) | Structure | Chemical Name | Salt | [M+H]+ Calc'd | [M+H]+ Obsv'd |
|---|---|---|---|---|---|---|
| 11.6 | 24 | 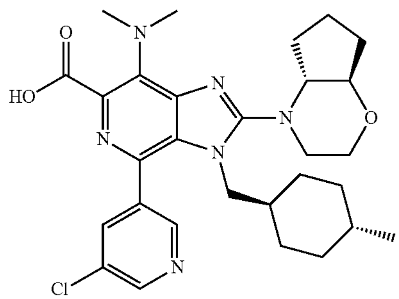 [SMILES: CN(C)c1c(C(=O)O)nc(-c2cncc(Cl)c2)c2c1nc(N1CCO[C@@H]3CCC[C@H]31)n2C[C@H]1CC[C@H](C)CC1] | 4-(5-chloropyridin-3-yl)-7-(dimethylamino)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridine-6-carboxylic acid | TFA | 553 | 553 |
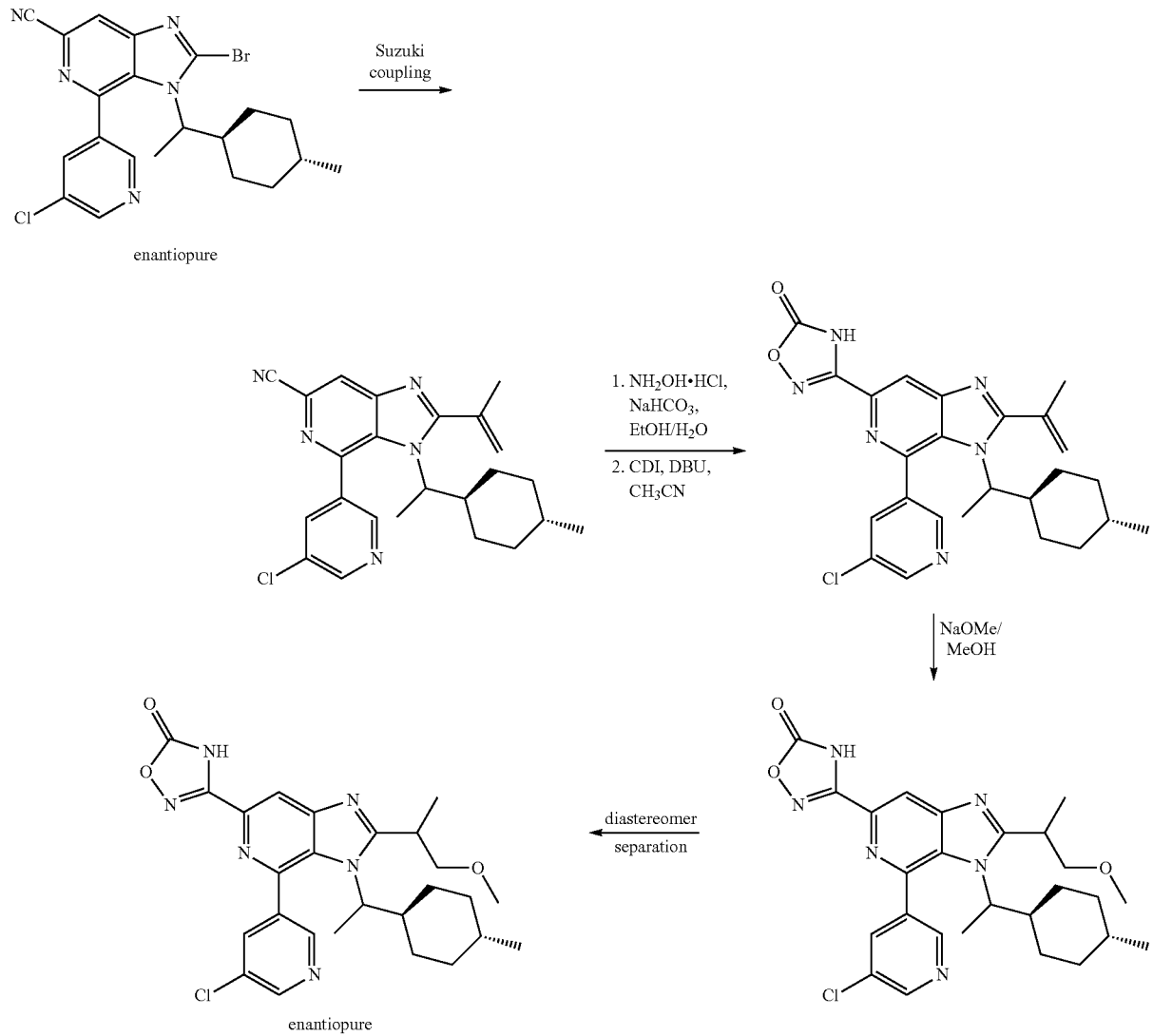
Scheme 16

Examples 12.1 and 12.2

3-{4-(5-chloropyridin-3-yl)-2-[(2R or S)-1-methoxypropan-2-yl]-3-[(1R or S)-1-(trans-4-methylcyclohexyl)ethyl]-3H-imidazo[4,5-c]pyridin-6-yl}-1,2,4-oxadiazol-5(4H)-one and 3-{4-(5-chloropyridin-3-yl)-2-[(2S or R)-1-methoxypropan-2-yl]-3-[(1R or S)-1-(trans-4-methylcyclohexyl)ethyl]-3H-imidazo[4,5-c]pyridin-6-yl}-1,2,4-oxadiazol-5(4H)-one

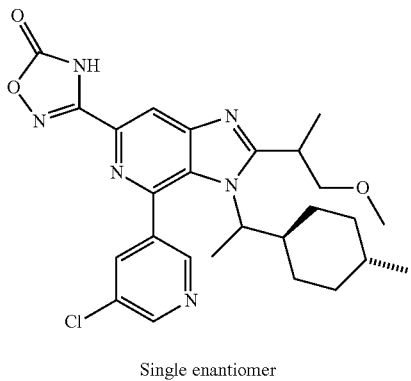 [SMILES: COCC(C)c1nc2cc(-c3noc(=O)[nH]3)nc(-c3cncc(Cl)c3)c2n1C(C)[C@H]1CC[C@H](C)CC1]

Single enantiomer and

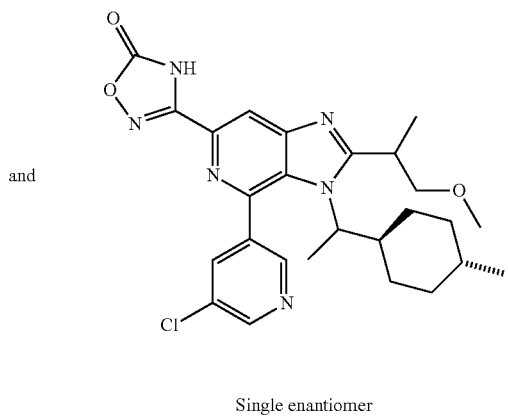 [SMILES: "and" ; COCC(C)c1nc2cc(-c3noc(=O)[nH]3)nc(-c3cncc(Cl)c3)c2n1C(C)[C@H]1CC[C@H](C)CC1]

Single enantiomer

Step 1: A vial was charged with the faster eluting enantiomer (enantiomer 1) of 2-bromo-4-(5-chloropyridin-3-yl)-3-[(1R or S)-1-(trans-4-methylcyclohexyl)ethyl]-3H-imidazo[4,5-c]pyridine-6-carbonitrile (Example 4.1, Step 3; 150 mg, 0.33 mmol), potassium phosphate (208 mg, 0.98 mmol), and [1,1'-bis(diphenylphosphino)ferrocene]dichloropalladium (II) (23.9 mg, 0.033 mmol). The tube was evacuated and backfilled with argon (3×). Fully degassed dioxane (1.5 mL) and water (0.15 mL) were added, followed by 4,4,5,5-tetramethyl-2-(prop-1-en-2-yl)-1,3,2-dioxaborolane (0.078 mL, 0.392 mmol). The vial was sealed and heated to 50° C. for 16 hours. The reaction mixture was cooled to room temperature and partitioned between water and ethyl acetate. The organic layer was dried over sodium sulfate, filtered, and concentrated under reduced pressure. The residue was purified by silica gel chromatography (0-100% ethyl acetate/hexanes, linear gradient) to afford 4-(5-chloropyridin-3-yl)-3-[(1R or S)-1-(trans-4-methylcyclohexyl)ethyl]-2-(prop-1-en-2-yl)-3H-imidazo[4,5-c]pyridine-6-carbonitrile. MS ESI calc'd. for $C_{24}H_{26}ClN_5$ [M+H]$^+$ 420. found 420.

Step 2: Hydroxylamine hydrochloride (37.7 mg, 0.54 mmol), sodium bicarbonate (68.4 mg, 0.81 mmol), and water (0.54 mL) were combined in a vial and stirred for 15 minutes. This solution was added to a vial containing 4-(5-chloropyridin-3-yl)-3-[(1R or S)-1-(trans-4-methylcyclohexyl)ethyl]-2-(prop-1-en-2-yl)-3H-imidazo[4,5-c]pyridine-6-carbonitrile (114 mg, 0.27 mmol) dissolved in ethanol (1.3 mL). The mixture was sealed and heated at 100° C. for 1 hour. The reaction was cooled to room temperature, quenched with water, and extracted with ethyl acetate (2×). The combined organic layers were dried over sodium sulfate, filtered, and concentrated to afford 4-(5-chloropyridin-3-yl)-N-hydroxy-3-[(1R or S)-1-(trans-4-methylcyclohexyl)ethyl]-2-(prop-1-en-2-yl)-3H-imidazo[4,5-c]pyridine-6-carboximidamide. MS ESI calc'd. for $C_{24}H_{29}ClN_6O$ [M+H]$^+$ 453. found 453.

Step 3: To a solution of 4-(5-chloropyridin-3-yl)-N-hydroxy-3-[(1R or S)-1-(trans-4-methylcyclohexypethyl]-2-(prop-1-en-2-yl)-3H-imidazo[4,5-c]pyridine-6-carboximidamide (109 mg, 0.24 mmol) and 1,1'-carbonyldiimidazole (42.9 mg, 0.26 mmol) dissolved in acetonitrile (1.6 mL) was added 1,8-diazabicyclo[5.4.0]undec-7-ene (0.144 mL, 0.96 mmol). The reaction mixture was stirred at room temperature for 1 hour. The reaction was diluted with water and extracted with dichloromethane. The organic layer was dried over sodium sulfate, filtered, and concentrated under reduced pressure. The residue was purified by silica gel chromatography (0-15% methanol/dichloromethane, linear gradient) to afford 3-[4-(5-chloropyridin-3-yl)-3-[(1R or S)-1-(trans-4-methylcyclohexyl)ethyl]-2-(prop-1-en-2-yl)-3H-imidazo[4,5-c]pyridin-6-yl]-1,2,4-oxadiazol-5(4H)-one. MS ESI calc'd. for $C_{25}H_{27}ClN_6O_2$ [M+H]$^+$ 479. found 479.

Step 4: 3-[4-(5-chloropyridin-3-yl)-3-[(1R or S)-1-(trans-4-methylcyclohexyl)ethyl]-2-(prop-1-en-2-yl)-3H-imidazo[4,5-c]pyridin-6-yl]-1,2,4-oxadiazol-5(4H)-one (107 mg, 0.22 mmol) was taken up in methanol (1.1 mL) at room temperature, and sodium methoxide (25 wt % in methanol, 1.3 mL, 5.58 mmol) was added. The reaction was capped and heated to 75° C. for three days. The mixture was cooled to room temperature and quenched with saturated aqueous ammonium chloride. The mixture was extracted with ethyl acetate, and the organic layer was dried over sodium sulfate, filtered, and concentrated under reduced pressure. The residue was purified by mass triggered, reverse phase (C-18) preparative HPLC (acetonitrile:water: 0.1% v/v trifluoroacetic acid modifier) to afford 3-{4-(5-chloropyridin-3-yl)-2-[(2RS)-1-methoxypropan-2-yl]-3-[(1R or S)-1-(trans-4-methylcyclohexyl)ethyl]-3H-imidazo[4,5-c]pyridin-6-yl}-1,2,4-oxadiazol-5(4H)-one as a TFA salt. MS ESI calc'd. for $C_{26}H_{31}ClN_6O_3$ [M+H]$^+$ 511. found 511. The diastereomers of 3-{4-(5-chloropyridin-3-yl)-2-[(2RS)-1-methoxypropan-2-yl]-3-[(1R or S)-1-(trans-4-methylcyclohexyl)ethyl]-3H-imidazo[4,5-c]pyridin-6-yl}-1,2,4-oxadiazol-5(4H)-one were separated by chiral supercritical fluid chromatography (Chiralpak AD-H, 21×250 mm, 20% ethanol in $CO_2$) to afford 3-{4-(5-chloropyridin-3-yl)-2-[(2R or S)-1-methoxypropan-2-yl]-3-[(1R or S)-1-(trans-4-methylcyclohexyl)ethyl]-3H-imidazo[4,5-c]pyridin-6-yl}-1,2,4-oxadiazol-5(4H)-one and 3-{4-(5-chloropyridin-3-yl)-2-[(2S or R)-1-methoxypropan-2-yl]-3-[(1R or S)-1-(trans-4-methylcyclohexyl)ethyl]-3H-imidazo[4,5-d]pyridin-6-yl}-1,2,4-oxadiazol-5(4H)-one.

Faster eluting diastereomer: MS ESI calc'd. for $C_{26}H_{31}ClN_6O_3$ [M+H]$^+$ 511. found 511. $^1$H NMR (500 MHz, DMSO-$d_6$) δ 12.89 (s, 1H), 8.84 (d, J=2.4, 1H), 8.81 (s, 1H), 8.35 (s, 1H), 8.20 (s, 1H), 3.84 (t, J=8.9, 1H), 3.78 (dd, J=7.3, 10.8, 1H), 3.64 (dd, J=5.2, 8.7, 1H), 3.61-3.51 (m, 1H), 3.17 (s, 3H), 1.90-1.80 (m, 1H), 1.76-1.69 (m, 1H), 1.56 (s, 1H), 1.53 (d, J=7.1, 3H), 1.34 (d, J=12.0, 1H), 1.25 (d, J=6.7, 3H), 0.98 (s, 1H), 0.81-0.74 (m, 1H), 0.73 (d, J=6.4, 3H), 0.63-0.49 (m, 2H), 0.25-0.10 (m, 2H).
Slower eluting diastereomer: MS ESI calc'd. for $C_{26}H_{31}ClN_6O_3$ [M+H]⁺ 511. found 511. ¹H NMR (500 MHz, DMSO-$d_6$) δ 12.90 (s, 1H), 8.85 (d, J=2.4, 1H), 8.80 (d, J=1.6, 1H), 8.36 (d, J=2.0, 1H), 8.21 (s, 1H), 3.79-3.69 (m, 2H), 3.64-3.50 (m, 2H), 3.21 (s, 3H), 1.79-1.68 (m, 2H), 1.59-1.53 (m, 1H), 1.51 (d, J=7.1, 3H), 1.39 (d, J=11.9, 1H), 1.26 (d, J=6.5, 3H), 1.01 (s, 1H), 0.90-0.78 (m, 1H), 0.74 (d, J=6.5, 3H), 0.66-0.56 (m, 1H), 0.52-0.45 (m, 1H), 0.38-0.29 (m, 1H), 0.24-0.15 (m, 1H).

Examples 12.3 and 12.4 were prepared in the same manner as Examples 12.1 and 12.2, starting from the slower eluting enantiomer (enantiomer 2) of 2-bromo-4-(5-chloropyridin-3-yl)-3-[(1S or R)-1-(trans-4-methylcyclohexyl)ethyl]-3H-imidazo[4,5-c]pyridine-6-carbonitrile (Example 4.1, Step 3).

TABLE 12

| Ex. | FRET IC₅₀ (nM) | Structure | Chemical Name | Salt | [M + H]+ Calc'd | [M + H]+ Obsv'd |
|---|---|---|---|---|---|---|
| 12.1 | 1 | 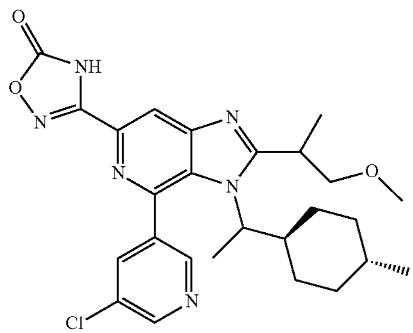 [SMILES: COCC(C)c1nc2cc(-c3noc(=O)[nH]3)nc(-c3cncc(Cl)c3)c2n1C(C)[C@H]1CC[C@H](C)CC1] | 3-{4-(5-chloropyridin-3-yl)-2-[(2R or S)-1-methoxypropan-2-yl]-3-[(1R or S)-1-(trans-4-methylcyclohexyl)ethyl]-3H-imidazo[4,5-c]pyridin-6-yl}-1,2,4-oxadiazol-5(4H)-one (stereoisomer 1) | | 511 | 511 |
| 12.2 | 1 | 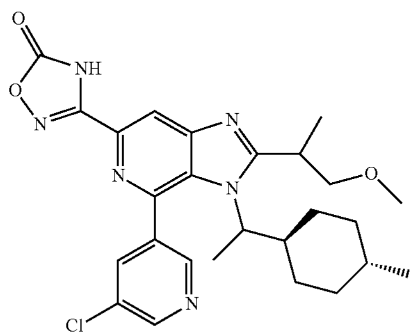 [SMILES: COCC(C)c1nc2cc(-c3noc(=O)[nH]3)nc(-c3cncc(Cl)c3)c2n1C(C)[C@H]1CC[C@H](C)CC1] | 3-{4-(5-chloropyridin-3-yl)-2-[(2S or R)-1-methoxypropan-2-yl]-3-[(1R or S)-1-(trans-4-methylcyclohexyl)ethyl]-3H-imidazo[4,5-c]pyridin-6-yl}-1,2,4-oxadiazol-5(4H)-one (stereoisomer 2) | | 511 | 511 |
| 12.3 | 44 | 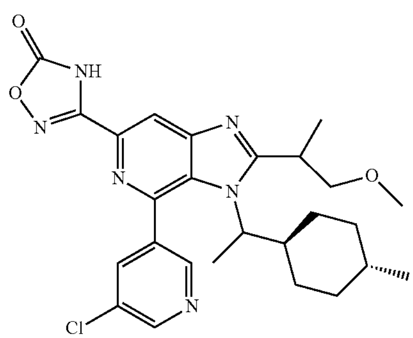 [SMILES: COCC(C)c1nc2cc(-c3noc(=O)[nH]3)nc(-c3cncc(Cl)c3)c2n1C(C)[C@H]1CC[C@H](C)CC1] | 3-{4-(5-chloropyridin-3-yl)-2-[(2R or S)-1-methoxypropan-2-yl]-3-[(1S or R)-1-(trans-4-methylcyclohexyl)ethyl]-3H-imidazo[4,5-c]pyridin-6-yl}-1,2,4-oxadiazol-5(4H)-one (stereoisomer 3) | | 511 | 511 |
| 12.4 | 161 | 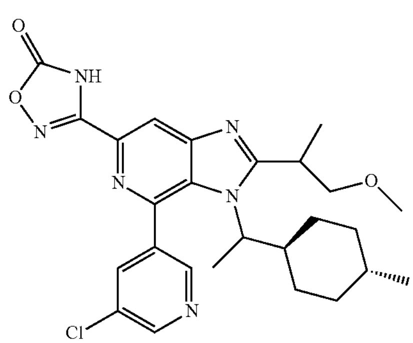 [SMILES: COCC(C)c1nc2cc(-c3noc(=O)[nH]3)nc(-c3cncc(Cl)c3)c2n1C(C)[C@H]1CC[C@H](C)CC1] | 3-{4-(5-chloropyridin-3-yl)-2-[(2S or R)-1-methoxypropan-2-yl]-3-[(1S or R)-1-(trans-4-methylcyclohexyl)ethyl]-3H-imidazo[4,5-c]pyridin-6-yl}-1,2,4-oxadiazol-5(4H)-one (stereoisomer 4) | | 511 | 511 |

Scheme 17

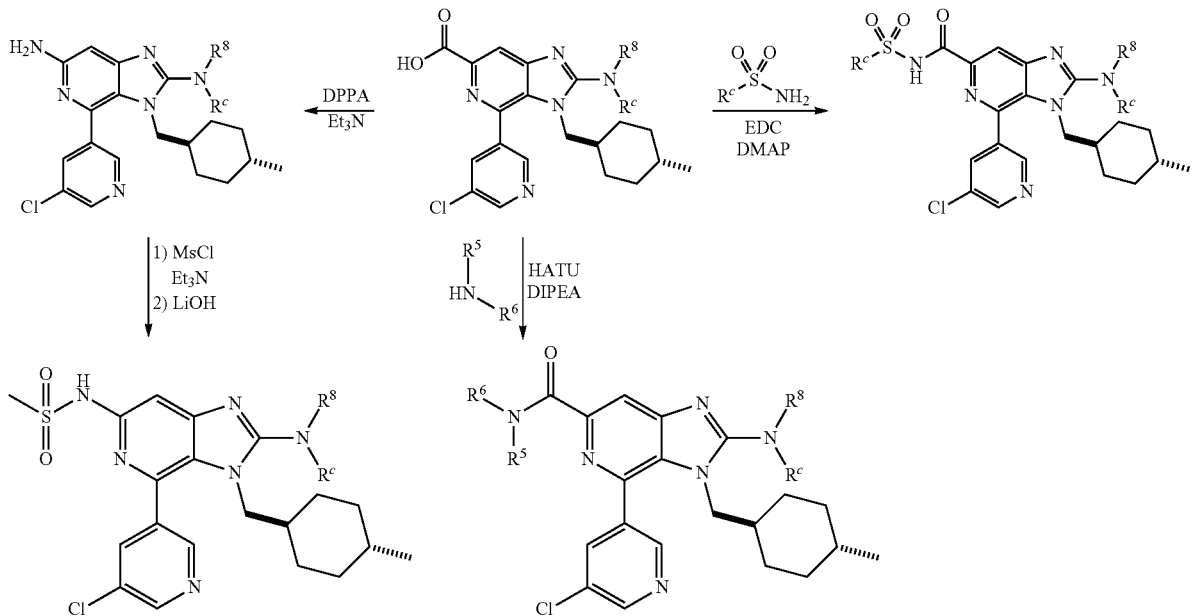

Example 13.1

4-(5-chloropyridin-3-yl)-2-((4aR,7aR)-hexahydrocyclopenta[b][1,4]oxazin-4(4aH)-yl)-3-((trans-4-methylcyclohexyl)methyl)-N-(methylsulfonyl)-3H-imidazo[4,5-c]pyridine-6-carboxamide

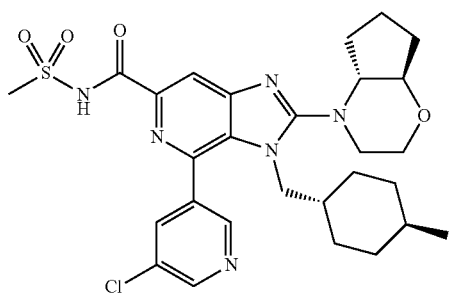

To a stirred mixture of 4-(5-chloropyridin-3-yl)-2-((4aR,7aR)-hexahydrocyclopenta[b][1,4]oxazin-4(4aH)-yl)-3-((trans-4-methylcyclohexyl)methyl)-3H-imidazo[4,5-c]pyridine-6-carboxylic acid (Example 3.55, prepared from Example 3.2, Step 3 using a procedure analogous to that described in Example 1.1, Step 5; 93 mg, 0.183 mmol) and methanesulfonamide (34.8 mg, 0.366 mmol) in DCM (2 ml) were added DMAP (44.7 mg, 0.366 mmol) and EDC (70.2 mg, 0.366 mmol). The reaction mixture was allowed to stir at room temperature under nitrogen overnight. The reaction mixture was diluted with DCM and washed with water and aq. 2N HCl before being dried over sodium sulfate, filtered, and concentrated. The residue was purified by mass triggered, reverse phase (C-18) preparative HPLC (acetonitrile:water: 0.1% v/v trifluoroacetic acid modifier) to afford 4-(5-chloropyridin-3-yl)-2-((4aR,7aR)-hexahydrocyclopenta[b][1,4]oxazin-4(4aH)-yl)-3-((trans-4-methylcyclohexyl)methyl)-N-(methylsulfonyl)-3H-imidazo[4,5-c]pyridine-6-carboxamide as a TFA salt. MS ESI calc'd. for $C_{28}H_{36}ClN_6O_4S$ $[M+H]^+$ 587. found 587. $^1$H NMR (500 MHz, DMSO-$d_6$) δ 8.99 (s, 1H); 8.82 (s, 1H); 8.57 (s, 1H); 8.20 (s, 1H); 3.96 (d, J=14.9 Hz, 1H); 3.79-3.88 (m, 2H); 3.53-3.61 (m, 2H); 3.39-3.41 (m, 1H); 3.38 (s, 3H); 3.03 (m, 1H); 2.81-2.87 (m, 1H); 2.24-2.30 (m, 1H); 1.84-1.89 (m, 1H); 1.52-1.71 (m, 3H); 1.34-1.43 (m, 2H); 1.01-1.15 (m, 2H); 0.76-0.84 (m, 1H); 0.66-0.72 (m, 5H); 0.59-0.61 (m, 1H); 0.46-0.48 (m, 1H); 0.35 (q, J=12.4 Hz, 2H).

Example 13.3

4-(5-chloropyridin-3-yl)-N-methyl-3-[(trans-4-methylcyclohexyl)methyl]-2-[(3R)-3-phenylmorpholin-4-yl]-3H-imidazo[4,5-c]pyridine-6-carboxamide

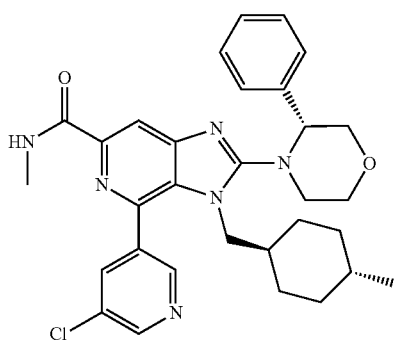 [SMILES: CNC(=O)c1cc2nc(N3CCOC[C@H]3c3ccccc3)n(C[C@H]3CC[C@H](C)CC3)c2c(-c2cncc(Cl)c2)n1]

To a solution of 4-(5-chloropyridin-3-yl)-3-[(trans-4-methylcyclohexyl)methyl]-2-[(3R)-3-phenylmorpholin-4-yl]-3H-imidazo[4,5-c]pyridine-6-carboxylic acid (Example 3.22, prepared from Example 2.1, Step 4 using a procedure similar to that described for Example 1.1, Step 5; 50 mg, 0.09 mmol) in DMF (2.0 mL) were added HATU (15 mg, 0.11 mmol), DIPEA (0.03 mL, 0.18 mmol), and 2.0 M methylamine in MeOH (0.09 mL, 0.18 mmol) at room temperature. After being stirred for 2 hours, the reaction mixture was diluted with H$_2$O (10 mL), the aqueous layer was extracted with EtOAc and then the organic layer was washed with water and brine, dried over anhydrous Na$_2$SO$_4$, filtered, and concentrated in vacuo. Purification of the residue on a silica gel column (0 to 10% MeOH/CH$_2$Cl$_2$) afforded 4-(5-chloropyridin-3-yl)-N-methyl-3-[(trans-4-methylcyclohexyl)methyl]-2-[(3R)-3-phenylmorpholin-4-yl]-3H-imidazo[4,5-c]pyridine-6-carboxamide. $^1$H NMR (300 MHz, CD$_3$OD) δ 8.71 (d, J=2.1 Hz, 1H), 8.66 (s, 1H), 8.17-8.19 (m, 2H) 7.40-7.42 (m, 2H), 7.24-7.26 (m, 3H), 4.66-4.69 (m, 1H), 3.98-4.06 (m, 4H), 3.66-3.75 (m, 2H), 3.41-3.50 (m, 2H), 3.48 (s, 3H), 1.28-1.43 (m, 2H), 1.10-1.19 (m, 1H), 0.82-0.99 (m, 2H), 0.74 (d, J=6.3 Hz, 3H) 0.61-0.65 (m, 3H), 0.41-0.45 (m, 2H). MS APCl calc'd. for C$_{31}$H$_{35}$ClN$_6$O$_2$ [M+H]$^+$ 559. found 559.

Example 13.5

N-{4-(5-chloropyridin-3-yl)-3-[(trans-4-methylcyclohexyl)methyl]-2-[(3R)-3-phenylmorpholin-4-yl]-3H-imidazo[4,5-c]pyridin-6-yl}methanesulfonamide

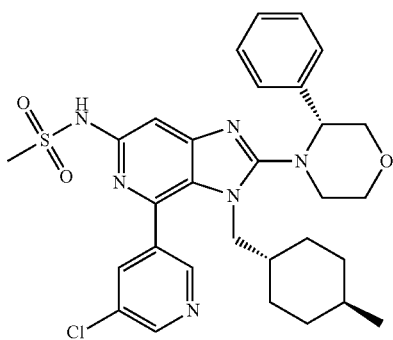

Step 1: To a solution of 4-(5-chloropyridin-3-yl)-3-[(trans-4-methylcyclohexyl)methyl]-2-[(3R)-3-phenylmorpholin-4-yl]-3H-imidazo[4,5-c]pyridine-6-carboxylic acid (Example 3.22, prepared from Example 2.1, Step 4 using a procedure similar to that described for Example 1.1, Step 5; 500 mg, 0.91 mmol) in DMF (6 mL) was added TEA (0.2 mL, 1.83 mmol), and the reaction was deoxygenated by purging with nitrogen for 5 minutes. To this reaction mixture was added diphenyl phosphoryl azide (0.4 mL, 1.83 mmol) and the reaction flask was sealed. The mixture was stirred at rt for 1 h and then H$_2$O (2 mL) was added. Again, the reaction flask was sealed and the reaction was heated at 90° C. for 1.5 h. The reaction was then diluted with water and EtOAc. The organic layer was separated and washed with water and brine. The organic layer was dried over anhydrous Na$_2$SO$_4$, filtered, and concentrated. The residue was purified by silica gel chromatography (2% MeOH/CH$_2$Cl$_2$) to yield 4-(5-chloropyridin-3-yl)-3-[(trans-4-methylcyclohexyl)methyl]-2-[(3R)-3-phenylmorpholin-4-yl]-3H-imidazo[4,5-c]pyridin-6-amine. MS ES/APCl calc'd. for C$_{29}$H$_{33}$ClN$_6$O [M+H]$^+$ 517. found 517.

Step 2: To a solution of 4-(5-chloropyridin-3-yl)-3-[(trans-4-methylcyclohexyl)methyl]-2-[(3R)-3-phenylmorpholin-4-yl]-3H-imidazo[4,5-c]pyridin-6-amine (70 mg, 0.13 mmol) in dichloromethane (2.0 mL) was added TEA (27 mg, 0.27 mmol) at 0° C. followed by slow addition of methane sulfonyl chloride (15 mg, 0.13 mmol). The reaction was warmed slowly to room temperature and stirred for 2 h. The reaction was then diluted with CH$_2$Cl$_2$ (70 mL) and water (10 mL). The organic layer was separated, washed with saturated brine solution (2×20 mL), dried over anhydrous Na$_2$SO$_4$, filtered, and concentrated. The residue was dissolved in THF (1 mL), MeOH (1 mL), and H$_2$O (0.5 mL), and then LiOH (20 mg, 0.48 mmol) was added. The reaction was stirred at room temperature for 1 h. The reaction was then concentrated under reduced pressure. The residue was purified by silica gel chromatography (90% EtOAc/petroleum ether). The isolated product was further purified by preparative HPLC (acetonitrile:water: 0.1% v/v trifluoroacetic acid modifier) to afford N-{4-(5-chloropyridin-3-yl)-3-[(trans-4-methylcyclohexyl)methyl]-2-[(3R)-3-phenylmorpholin-4-yl]-3H-imidazo[4,5-c]pyridin-6-yl}methanesulfonamide (TFA salt). MS ES/APCl calc'd. for C$_{30}$H$_{36}$ClN$_6$O$_3$S[M+H]$^+$ 595. found 595. $^1$H NMR (400 MHz, DMSO-d$_6$): δ 10.26 (bs, 1H), 8.77 (d, J=2.0 Hz, 2H), 8.23 (t, J=2.0 Hz, 1H), 7.43 (d, J=7.2 Hz, 2H), 7.29-7.21 (m, 3H), 6.99 (s, 1H), 4.75 (t, J=5.2 Hz, 1H), 3.92-3.88 (m, 4H), 3.75-3.70 (m, 1H), 3.54-3.49 (m, 2H), 3.26 (s, 3H), 3.25-3.20 (m, 1H), 1.41-1.35 (m, 2H), 1.08-1.07 (m, 1H), 0.76-0.74 (m, 3H), 0.70 (d, J=6.8 Hz, 3H), 0.58-0.55 (m, 1H), 0.50-0.47 (m, 1H), 0.40-0.27 (m, 2H).

Examples in Table 13 (other than Examples 13.1, 13.3, and 13.5) were prepared using procedures that were analogous to those described above.

TABLE 13

| Ex. | FRET IC$_{50}$ (nM) | Structure | Chemical Name | Salt | [M + H]+ Calc'd | [M + H]+ Obsv'd |
|---|---|---|---|---|---|---|
| 13.1 | 1 | 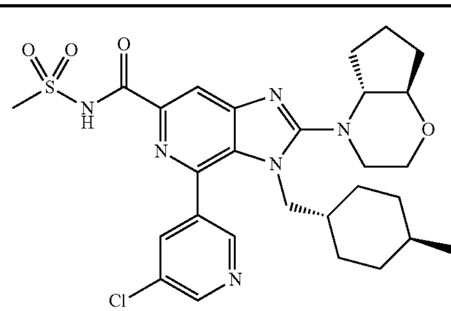 | 4-(5-chloropyridin-3-yl)-2-[(4aR,7aR)-hexahydrocyclopenta[b][1,4]oxazin-4(4aH)-yl]-3-[(trans-4-methylcyclohexyl)methyl]-N-(methylsulfonyl)-3H-imidazo[4,5-c]pyridine-6-carboxamide | TFA | 587 | 587 |

TABLE 13-continued

| Ex. | FRET IC$_{50}$ (nM) | Structure | Chemical Name | Salt | [M + H]+ Calc'd | [M + H]+ Obsv'd |
|---|---|---|---|---|---|---|
| 13.2 | 2 | 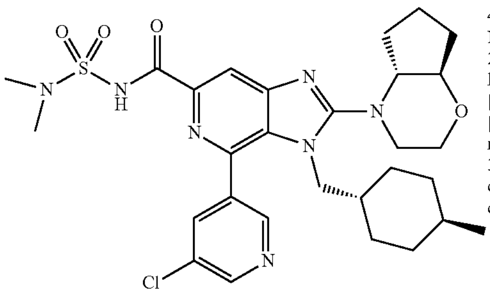 | 4-(5-chloropyridin-3-yl)-N-(dimethylsulfamoyl)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridine-6-carboxamide | TFA | 616 | 616 |
| 13.3 | 160 | 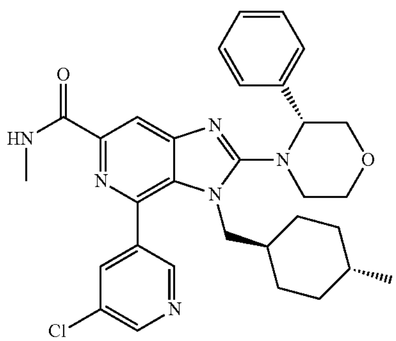 [SMILES: CNC(=O)c1cc2nc(N3CCOC[C@H]3c3ccccc3)n(C[C@H]3CC[C@H](C)CC3)c2c(-c2cncc(Cl)c2)n1] | 4-(5-chloropyridin-3-yl)-N-methyl-3-[(trans-4-methylcyclohexyl)methyl]-2-[(3R)-3-phenylmorpholin-4-yl]-3H-imidazo[4,5-c]pyridine-6-carboxamide | | 559 | 559 |
| 13.4 | 175 | 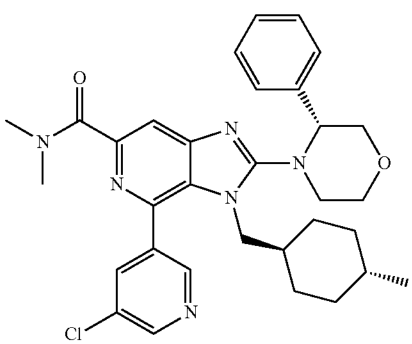 | 4-(5-chloropyridin-3-yl)-N,N-dimethyl-3-[(trans-4-methylcyclohexyl)methyl]-2-[(3R)-3-phenylmorpholin-4-yl]-3H-imidazo[4,5-c]pyridine-6-carboxamide | | 573 | 573 |
| 13.5 | 122 | 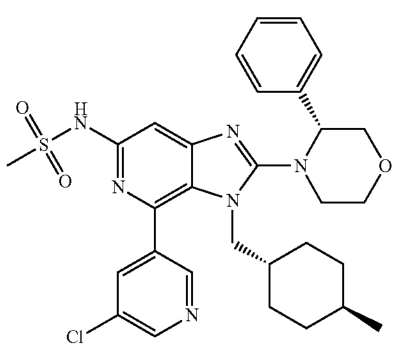 [SMILES: CS(=O)(=O)Nc1cc2nc(N3CCOC[C@H]3c3ccccc3)n(C[C@H]3CC[C@H](C)CC3)c2c(-c2cncc(Cl)c2)n1] | N-{4-(5-chloropyridin-3-yl)-3-[(trans-4-methylcyclohexyl)methyl]-2-[(3R)-3-phenylmorpholin-4-yl]-3H-imidazo[4,5-c]pyridin-6-yl}methanesulfonamide | TFA | 595 | 595 |

Scheme 18

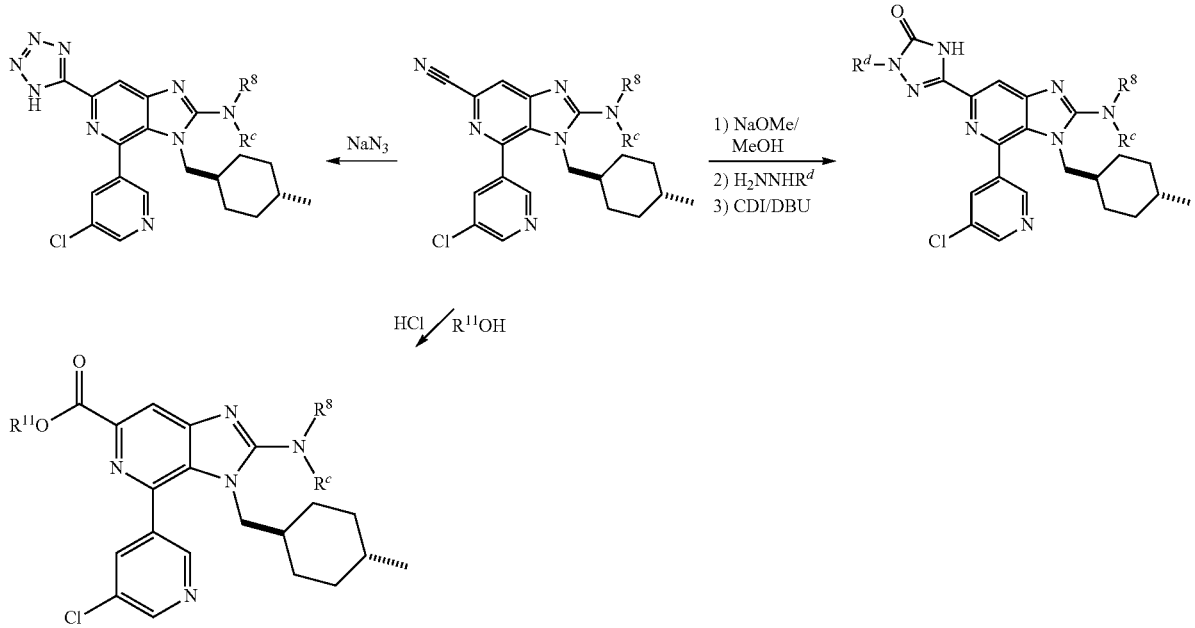

Example 14.1

4-(5-chloropyridin-3-yl)-3-[(trans-4-methylcyclohexyl)methyl]-6-(1H-tetrazol-5-yl)-2-[(2S)-2-(trifluoromethyl)pyrrolidin-1-yl]-3H-imidazo[4,5-c]pyridine

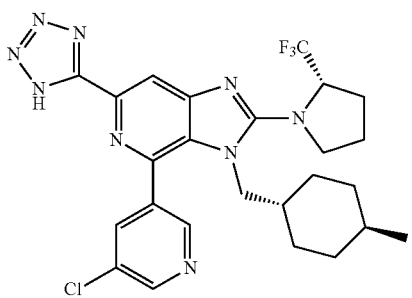 [SMILES: C[C@H]1CC[C@H](Cn2c(N3CCC[C@H]3C(F)(F)F)nc3cc(-c4nnn[nH]4)nc(-c4cncc(Cl)c4)c32)CC1]

A vial equipped with a stir bar was charged with 4-(5-chloropyridin-3-yl)-3-[(trans-4-methylcyclohexyl)methyl]-2-[(2S)-2-(trifluoromethyl)pyrrolidin-1-yl]-3H-imidazo[4,5-c]pyridine-6-carbonitrile (Example 3.3, Step 1) (67 mg, 0.133 mmol), sodium azide (87 mg, 1.332 mmol), and ammonium chloride (72.0 mg, 1.345 mmol). DMF (1.3 mL) was added, and the mixture was degassed with $N_2$. The vial was then sealed and heated at 120° C. for 16 hours. The reaction was then cooled to room temperature, diluted with EtOAc, and washed with water and brine. The organic layer was dried over $Na_2SO_4$, filtered, and concentrated. Purification of the residue by mass triggered reverse phase HPLC(C-18), eluting with acetonitrile/water containing 0.1% TFA afforded 4-(5-chloropyridin-3-yl)-3-[(trans-4-methylcyclohexyl)methyl]-6-(1H-tetrazol-5-yl)-2-[(2S)-2-(trifluoromethyl)pyrrolidin-1-yl]-3H-imidazo[4,5-c]pyridine (TFA salt). MS ESI calc'd. for $C_{25}H_{27}ClF_3N_9$ $[M+H]^+$ 546. found 546. $^1$H NMR (600 MHz, $CD_3OD$) δ 8.86 (d, J=1.5, 1H), 8.74 (d, J=2.2 Hz, 1H), 8.38 (t, J=2.1 Hz, 1H), 8.26 (s, 1H), 5.36-5.27 (m, 1H), 3.92 (dd, J=9.0, 14.7 Hz, 1H), 3.87-3.79 (m, 1H), 3.73-3.66 (m, 1H), 3.61 (dd, J=5.5, 14.7 Hz, 1H), 2.48-2.36 (m, 1H), 2.21-2.10 (m, 2H), 2.08-1.98 (m, 1H), 1.45 (dd, J=1.4, 11.7 Hz, 2H), 1.23-1.13 (m, 1H), 1.13-1.04 (m, 1H), 1.02-0.94 (m, 1H), 0.72 (d, J=6.6 Hz, 3H), 0.71-0.56 (m, 3H), 0.57-0.46 (m, 2H).

Example 14.2

5-{4-(5-chloropyridin-3-yl)-2-[(2S)-2-(fluoromethyl)pyrrolidin-1-yl]-3-[(trans-4-methylcyclohexyl)methyl]-3H-imidazo[4,5-c]pyridin-6-yl}-2-methyl-1,2-dihydro-3H-1,2,4-triazol-3-one

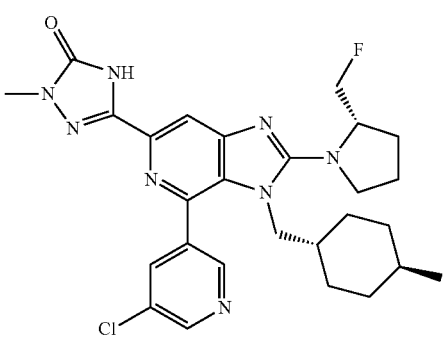

Step 1: Sodium methoxide (5.20 mg, 0.096 mmol) was added to a solution of 4-(5-chloropyridin-3-yl)-2-[(2S)-2-(fluoromethyl)pyrrolidin-1-yl]-3-[(trans-4-methylcyclohexyl)methyl]-3H-imidazo[4,5-c]pyridine-6-carbonitrile (Example 3.1, Step 1; 150 mg, 0.321 mmol) in methanol (321 μL), and the vial was sealed and allowed to stir at ambient temperature overnight. The reaction was concentrated to afford crude methyl-4-(5-chloropyridin-3-yl)-2-[(2S)-2-(fluoromethyl)pyrrolidin-1-yl]-3-[(trans-4-methylcyclohexyl)methyl]-3H-imidazo[4,5-c]pyridin-6-carbimidate. MS ESI calc'd. for $C_{26}H_{32}ClFN_6O$ [M+H]$^+$ 499. found 499. This material was taken on to Step 2 without further purification.

Step 2: Methylhydrazine (79.2 μL, 1.502 mmol) was added to a solution of crude methyl-4-(5-chloropyridin-3-yl)-2-[(2S)-2-(fluoromethyl)pyrrolidin-1-yl]-3-[(trans-4-methylcyclohexyl)methyl]-3H-imidazo[4,5-c]pyridin-6-carbimidate (75 mg, 0.150 mmol) in methanol (1503 μL) in a vial, and the reaction was sealed and stirred at 50° C. for 16 hr. The reaction was cooled to room temperature, diluted with EtOAc, and washed with water and brine. The organic layer was dried over Na$_2$SO$_4$, filtered, and concentrated to afford crude 4-(5-chloropyridin-3-yl)-2-[(2S)-2-(fluoromethyl)pyrrolidin-1-yl]-N'-methyl-3-[(trans-4-methylcyclohexyl)methyl]-3H-imidazo[4,5-c]pyridin-6-carboximidohydrazide. MS ESI calc'd. for $C_{26}H_{34}ClFN_8$ [M+H]$^+$ 513. found 513. This material was taken on to Step 3 without further purification.

Step 3: CDI (26.5 mg, 0.164 mmol) and DBU (99 μL, 0.655 mmol) were added to a solution of crude 4-(5-chloropyridin-3-yl)-2-[(2S)-2-(fluoromethyl)pyrrolidin-1-yl]-N'-methyl-3-[(trans-4-methylcyclohexyl)methyl]-3H-imidazo[4,5-c]pyridin-6-carboximidohydrazide (56.0 mg, 0.109 mmol) in acetonitrile (1213 μL), and the reaction was stirred at ambient temperature for 1 hr. Purification by mass triggered reverse phase HPLC (C-18), eluting with acetonitrile/water containing 0.1% TFA afforded impure 5-{4-(5-chloropyridin-3-yl)-2-[(2S)-2-(fluoromethyl)pyrrolidin-1-yl]-3-[(trans-4-methylcyclohexyl)methyl]-3H-imidazo[4,5-c]pyridin-6-yl}-2-methyl-1,2-dihydro-3H-1,2,4-triazol-3-one (TFA salt). Further purification by PTLC with 5% MeOH/DCM afforded pure 5-{4-(5-chloropyridin-3-yl)-2-[(2S)-2-(fluoromethyl)pyrrolidin-1-yl]-3-[(trans-4-methylcyclohexyl)methyl]-3H-imidazo[4,5-c]pyridin-6-yl}-2-methyl-1,2-dihydro-3H-1,2,4-triazol-3-one. $^1$H NMR (600 MHz, CD$_3$OD) δ 8.82 (d, J=1.8 Hz, 1H), 8.69 (d, J=2.3 Hz, 1H), 8.36 (t, J=2.1 Hz, 1H), 7.92 (s, 1H), 4.66 (dd, J=3.7, 9.8 Hz, 0.5H), 4.63-4.49 (m, 2H), 4.44 (dd, J=3.1, 9.5 Hz, 0.5H), 3.86 (dd, J=8.5, 14.8 Hz, 1H), 3.73-3.85 (m, 2H), 3.53 (d, J=6.1 Hz, 1H), 3.49 (s, 3H), 2.28-2.18 (m, 1H), 2.18-2.08 (m, 1H), 2.07-1.90 (m, 2H), 1.49-1.39 (m, 2H), 1.25-1.16 (m, 1H), 1.15-1.01 (m, 1H), 0.99-0.93 (m, 1H), 0.70 (dd, J=9.1, 19.3 Hz, 3H), 0.70-0.61 (m, 1H), 0.61-0.46 (m, 4H). MS ESI calc'd. for $C_{27}H_{32}ClFN_8O$ [M+H]$^+$ 539. found 539.

Example 14.3

5-{4-(5-chloropyridin-3-yl)-2-[(2S)-2-(fluoromethyl)pyrrolidin-1-yl]-3-[(trans-4-methylcyclohexyl)methyl]-3H-imidazo[4,5-c]pyridin-6-yl}-2,4-dihydro-3H-1,2,4-triazol-3-one

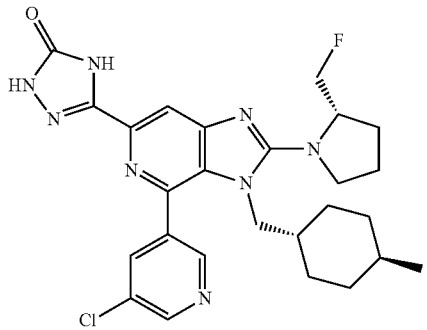 [SMILES: C[C@H]1CC[C@H](Cn2c(N3CCC[C@H]3CF)nc3cc(-c4n[nH]c(=O)[nH]4)nc(-c4cncc(Cl)c4)c32)CC1]

Step 1: Tert-butyl carbazate (106 mg, 0.802 mmol) and triethylamine (418 μL, 3.006 mmol) were added to a solution of crude methyl-4-(5-chloropyridin-3-yl)-2-[(2S)-2-(fluoromethyl)pyrrolidin-1-yl]-3-[(trans-4-methylcyclohexyl)methyl]-3H-imidazo[4,5-c]pyridin-6-carbimidate (Example 14.2, Step 1; 50 mg, 0.100 mmol) in ethanol (100 μL) in a vial, and the reaction was capped and stirred at ambient temperature for 72 hr. The reaction was diluted with EtOAc and washed with water and brine. The organic layer was dried over Na$_2$SO$_4$, filtered, and concentrated to afford crude tert-butyl 2-((4-(5-chloropyridin-3-yl)-2-((S)-2-(fluoromethyl)pyrrolidin-1-yl)-3-((trans-4-methylcyclohexyl)methyl)-3H-imidazo[4,5-c]pyridin-6-yl)(imino)methyl)hydrazinecarboxylate. MS ESI calc'd. for $C_{30}H_{40}ClFN_8O_2$ [M+H]$^+$ 599. found 599. This material was taken on to Step 2 without further purification.

Step 2: A solution of crude tert-butyl 2-((4-(5-chloropyridin-3-yl)-2-(S)-2-(fluoromethyl)pyrrolidin-1-yl)-3-((trans-4-methylcyclohexyl)methyl)-3H-imidazo[4,5-c]pyridin-6-yl)(imino)methyl)hydrazinecarboxylate (19.0 mg, 0.032 mmol) in acetonitrile (793 μL) was stirred at 80° C. for 72 hr. Purification of the reaction by mass triggered reverse phase HPLC (C-18), eluting with acetonitrile/water containing 0.1% TFA afforded 5-{4-(5-chloropyridin-3-yl)-2-[(2S)-2-(fluoromethyl)pyrrolidin-1-yl]-3-[(trans-4-methylcyclohexyl)methyl]-3H-imidazo[4,5-c]pyridin-6-yl}-2,4-dihydro-3H-1,2,4-triazol-3-one (TFA salt). $^1$H NMR (600 MHz, CD$_3$OD) δ 8.83 (d, J=1.8 Hz, 1H), 8.72 (d, J=2.3 Hz, 1H), 8.38 (t, J=2.1 Hz, 1H), 7.96 (s, 1H), 4.70 (dd, J=3.3, 9.9 Hz, 0.5H), 4.65-4.51 (m, 2H), 4.45 (dd, J=4.1, 9.9 Hz, 0.5H), 3.90 (dd, J=8.4, 14.9 Hz, 1H), 3.85-3.74 (m, 2H), 3.55 (dd, J=6.0, 14.9 Hz, 1H), 2.32-2.24 (m, 1H), 2.19-2.11 (m, 1H), 2.05-1.93 (m, 2H), 1.50-1.42 (m, 2H), 1.27-1.19 (m, 1H), 1.15-1.04 (m, 1H), 1.04-0.97 (m, 1H), 0.73 (d, J=6.6 Hz, 3H), 0.72-0.63 (m, 1H), 0.63-0.50 (m, 4H). MS ESI calc'd. for $C_{26}H_{30}ClFN_8O$ [M+H]$^+$ 525. found 525.

Example 14.5

Methyl 4-(5-chloropyridin-3-yl)-3-[(trans-4-methylcyclohexyl)methyl]-2-[(3R)-3-phenylmorpholin-4-yl]-3H-imidazo[4,5-c]pyridine-6-carboxylate

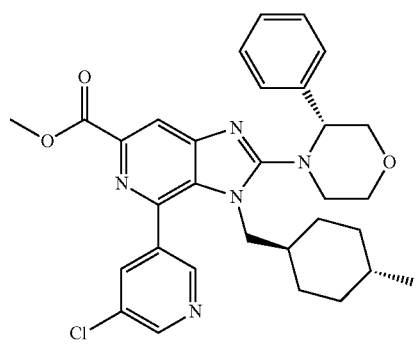

4-(5-chloropyridin-3-yl)-3-[(trans-4-methylcyclohexyl)methyl]-2-[(3R)-3-phenylmorpholin-4-yl]-3H-imidazo[4,5-c]pyridine-6-carbonitrile (Example 2.1, Step 4; 50 mg, 0.14 mmol) was dissolved in HCl (3 M in MeOH; 10 mL) and stirred at reflux for 4 hours. The reaction was cooled to room temperature, and the solvent was removed under vacuum. The residue was partitioned between water and EtOAc. The organic layer was dried over anhydrous Na$_2$SO$_4$, filtered, and concentrated. Purification of the residue on a silica gel column (0 to 100% EtOAc/hexanes) afforded methyl 4-(5-chloropyridin-3-yl)-3-[(trans-4-methylcyclohexyl)methyl]-2-[(3R)-3-phenylmorpholin-4-yl]-3H-imidazo[4,5-c]pyridine-6-carboxylate. $^1$H NMR (300 MHz, CD$_3$OD) δ 8.72 (d, J=2.4 Hz, 1H), 8.63 (d, J=1.6 Hz, 1H), 8.23 (s, 1H), 8.14 (br s, 1H) 7.41-7.43 (m, 2H), 7.24-7.27 (m, 3H), 4.67-4.69 (m, 1H), 3.98-4.06 (m, 4H), 3.97 (s, 3H), 3.69-3.70 (m, 2H), 3.31-3.56 (m, 2H), 1.28-1.43 (m, 2H), 1.10-1.19 (m, 1H), 0.82-0.99 (m, 2H), 0.74 (d, J=6.3 Hz, 3H) 0.61-0.65 (m, 3H), 0.41-0.45 (m, 2H). MS APCl calc'd. for C$_{31}$H$_{34}$ClN$_5$O$_3$ [M+H]$^+$ 560. found 560.

Examples in Table 14 (other than Examples 14.1-14.3 and 14.5) were prepared using procedures that were analogous to those described above.

TABLE 14

| Ex. | FRET IC$_{50}$ (nM) | Structure | Chemical Name | Salt | [M + H]+ Calc'd | [M + H]+ Obsv'd |
|---|---|---|---|---|---|---|
| 14.1 | <1 | 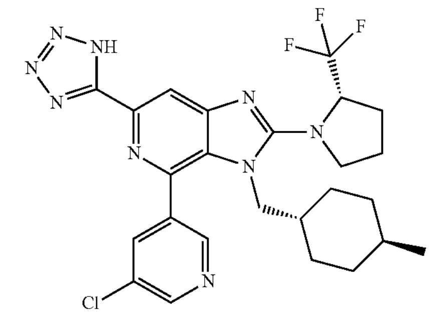 [SMILES: C[C@H]1CC[C@H](Cn2c(N3CCC[C@H]3C(F)(F)F)nc3cc(-c4nnn[nH]4)nc(-c4cncc(Cl)c4)c32)CC1] | 4-(5-chloropyridin-3-yl)-3-[(trans-4-methylcyclohexyl)methyl]-6-(1H-tetrazol-5-yl)-2-[(2S)-2-(trifluoromethyl)pyrrolidin-1-yl]-3H-imidazo[4,5-c]pyridine | TFA | 546 | 546 |
| 14.2 | 20 | 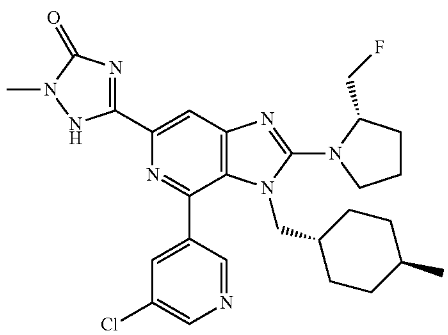 | 5-{4-(5-chloropyridin-3-yl)-2-[(2S)-2-(fluoromethyl)pyrrolidin-1-yl]-3-[(trans-4-methylcyclohexyl)methyl]-3H-imidazo[4,5-c]pyridin-6-yl}-2-methyl-1,2-dihydro-3H-1,2,4-triazol-3-one | | 539 | 539 |
| 14.3 | 10 | 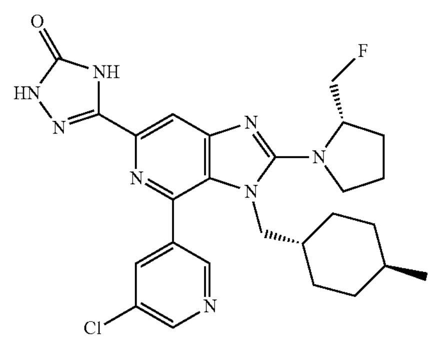 [SMILES: C[C@H]1CC[C@H](Cn2c(N3CCC[C@H]3CF)nc3cc(-c4n[nH]c(=O)[nH]4)nc(-c4cncc(Cl)c4)c32)CC1] | 5-{4-(5-chloropyridin-3-yl)-2-[(2S)-2-(fluoromethyl)pyrrolidin-1-yl]-3-[(trans-4-methylcyclohexyl)methyl]-3H-imidazo[4,5-c]pyridin-6-yl}-2,4-dihydro-3H-1,2,4-triazol-3-one | TFA | 525 | 525 |
| 14.4 | <1 | 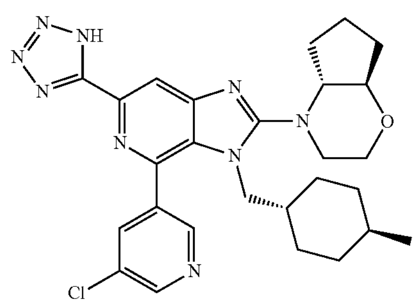 [SMILES: C[C@H]1CC[C@H](Cn2c(N3CCO[C@@H]4CCC[C@H]43)nc3cc(-c4nnn[nH]4)nc(-c4cncc(Cl)c4)c32)CC1] | 4-(5-chloropyridin-3-yl)-2-[(4aR,7aR)-hexahydrocyclopenta[b][1,4]oxazin-4(4aH)-yl]-3-[(trans-4-methylcyclohexyl)methyl]-6-(1H-tetrazol-5-yl)-3H-imidazo[4,5-c]pyridine | TFA | 534 | 534 |

TABLE 14-continued
| Ex. | FRET IC$_{50}$ (nM) | Structure | Chemical Name | Salt | [M + H]+ Calc'd | [M + H]+ Obsv'd |
|---|---|---|---|---|---|---|
| 14.5 | 28 | 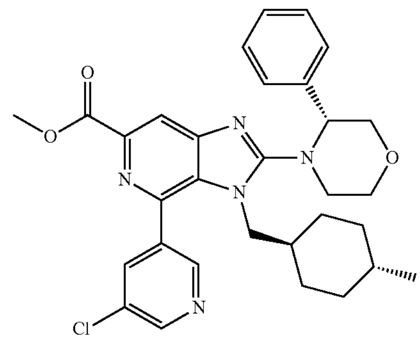 | methyl 4-(5-chloropyridin-3-yl)-3-[(trans-4-methylcyclohexyl)methyl]-2-[(3R)-3-phenylmorpholin-4-yl]-3H-imidazo[4,5-c]pyridine-6-carboxylate | | 560 | 560 |
| 14.6 | 53 | 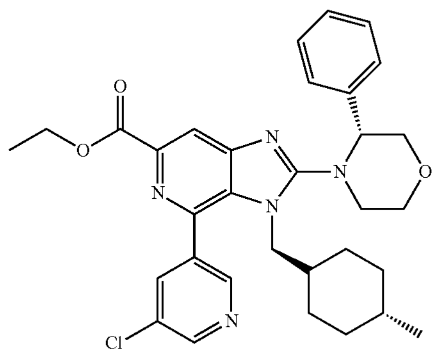 | ethyl 4-(5-chloropyridin-3-yl)-3-[(trans-4-methylcyclohexyl)methyl]-2-[(3R)-3-phenylmorpholin-4-yl]-3H-imidazo[4,5-c]pyridine-6-carboxylate | | 574 | 574 |
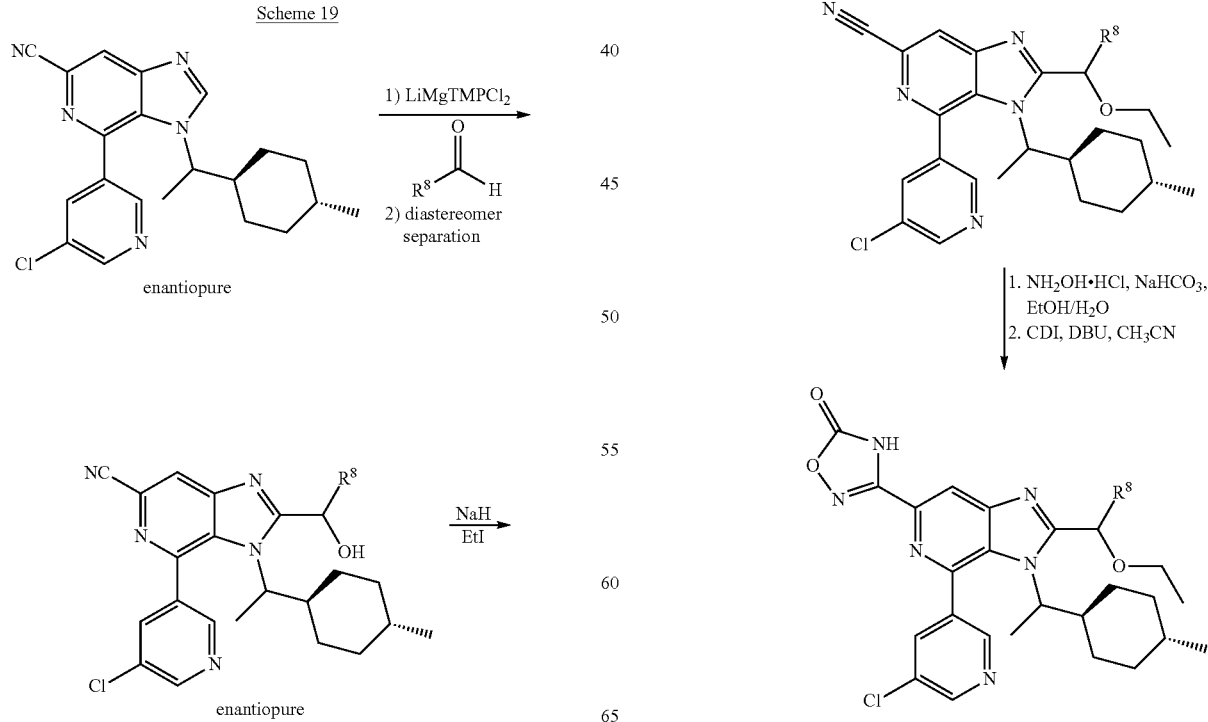
Scheme 19

Preparative Example 15.1

4-(5-chloropyridin-3-yl)-3-[(1S)-1-(trans-4-methyl-cyclohexyl)ethyl]-3H-imidazo[4,5-c]pyridine-6-carbonitrile and 4-(5-chloropyridin-3-yl)-3-[(1R)-1-(trans-4-methylcyclohexyl)ethyl]-3H-imidazo[4,5-d]pyridine-6-carbonitrile

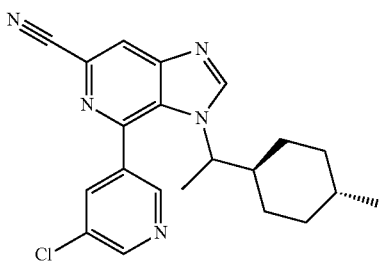 [SMILES: CC([C@H]1CC[C@H](C)CC1)n1cnc2cc(C#N)nc(-c3cncc(Cl)c3)c21]

Racemic 4-(5-chloropyridin-3-yl)-3-[(1RS)-1-(trans-4-methylcyclohexyl)ethyl]-3H-imidazo[4,5-c]pyridine-6-carbonitrile (Example 4.1/4.2, Step 2) was separated into its enantiomers using chiral supercritical fluid chromatography (Phenomenex, 21×250 mm, 25% methanol in $CO_2$) to afford 4-(5-chloropyridin-3-yl)-3-[(1S)-1-(trans-4-methylcyclohexyl)ethyl]-3H-imidazo[4,5-c]pyridine-6-carbonitrile and 4-(5-chloropyridin-3-yl)-3-[(1R)-1-(trans-4-methylcyclohexyl)ethyl]-3H-imidazo[4,5-c]pyridine-6-carbonitrile. Faster eluting enantiomer: MS ESI calc'd. for $O_{21}H_{22}ClN_5$ [M+H]$^+$ 380. found 380. $^1$H NMR (600 MHz, DMSO-$d_6$) δ 8.93 (s, 1H), 8.84 (d, J=2.2, 1H), 8.77 (d, J=1.5, 1H), 8.56 (s, 1H), 8.33 (t, J=1.7, 1H), 3.69 (m, 1H), 1.57-1.28 (m, 7H), 1.11-0.97 (m, 1H), 0.72 (d, J=6.5, 3H), 0.70-0.46 (m, 5H). Slower eluting enantiomer: MS ESI calc'd. for $O_{21}H_{22}ClN_5$ [M+H]$^+$ 380. found 380.

$^1$H NMR (600 MHz, DMSO-$d_6$) δ 8.93 (s, 1H), 8.84 (d, J=2.2, 1H), 8.77 (d, J=1.5, 1H), 8.56 (s, 1H), 8.33 (t, J=1.7, 1H), 3.69 (m, 1H), 1.58-1.28 (m, 7H), 1.11-0.96 (m, 1H), 0.72 (d, J=6.5, 3H), 0.70-0.46 (m, 5H).

Preparative Example 15.2

4-(5-chloropyridin-3-yl)-2-[(1R or S)-1-hydroxyethyl]-3-[(1R or S)-1-(trans-4-methylcyclohexyl)ethyl]-3H-imidazo[4,5-c]pyridine-6-carbonitrile and 4-(5-chloropyridin-3-yl)-2-[(1S or R)-1-hydroxyethyl]-3-[(1R or S)-1-(trans-4-methylcyclohexyl)ethyl]-3H-imidazo[4,5-c]pyridine-6-carbonitrile

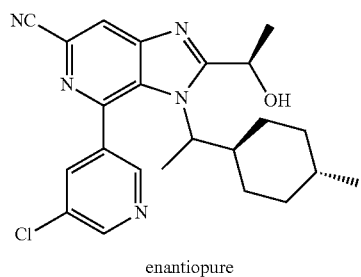 [SMILES: CC([C@H]1CC[C@H](C)CC1)n1c([C@@H](C)O)nc2cc(C#N)nc(-c3cncc(Cl)c3)c21]

enantiopure

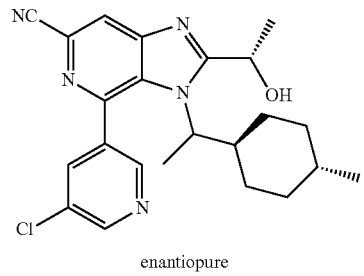 [SMILES: CC([C@H]1CC[C@H](C)CC1)n1c([C@H](C)O)nc2cc(C#N)nc(-c3cncc(Cl)c3)c21]

enantiopure 4-(5-chloropyridin-3-yl)-3-[(1R or S)-1-(trans-4-methylcyclohexyl)ethyl]-3H-imidazo[4,5-c]pyridine-6-carbonitrile (Preparative Example 15.1, slower eluting enantiomer; 400 mg, 1.053 mmol) was dissolved in THF (10.4 mL) and cooled to −78° C. under nitrogen before adding 2,2,6,6-tetramethylpiperidinylmagnesium chloride lithium chloride complex (Aldrich, 1M in THF/toluene, 2.32 mL, 2.32 mmol). After stirring at −78° C. for 1 hr, acetaldehyde (190 µL, 3.37 mmol) was added, and the reaction was allowed to stir at −78° C. for 1.5 hr. The reaction was then quenched with saturated aqueous ammonium chloride and extracted with EtOAc. The organic layer was dried over sodium sulfate, filtered, and concentrated. The residue was purified by silica gel chromatography (5-75% EtOAc/DCM) to afford 4-(5-chloropyridin-3-yl)-2-[(1R or S)-1-hydroxyethyl]-3-[(1R or S)-1-(trans-4-methylcyclohexyl)ethyl]-3H-imidazo[4,5-c]pyridine-6-carbonitrile and 4-(5-chloropyridin-3-yl)-2-[(1S or R)-1-hydroxyethyl]-3-[(1R or S)-1-(trans-4-methylcyclohexyl)ethyl]-3H-imidazo[4,5-c]pyridine-6-carbonitrile. Faster eluting diastereomer: MS ESI calc'd. for $C_{23}H_{26}ClN_5O$ [M+H]$^+$ 424. found 424. Slower eluting diastereomer: MS ESI calc'd. for $C_{23}H_{26}ClN_5O$ [M+H]$^+$ 424. found 424.

Example 15.1

3-{4-(5-chloropyridin-3-yl)-2-[(S or R)-cyclopropyl(ethoxy)methyl]-3-[(1R or S)-1-(trans-4-methylcyclohexyl)ethyl]-3H-imidazo[4,5-c]pyridin-6-yl}-1,2,4-oxadiazol-5(4H)-one (stereoisomer 1)

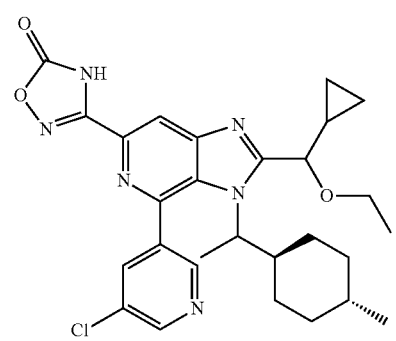

single enantiopure diastereomer

Step 1: 4-(5-chloropyridin-3-yl)-3-[(1R or S)-1-(trans-4-methylcyclohexyl)ethyl]-3H-imidazo[4,5-c]pyridine-6-carbonitrile (Preparative Example 15.1, slower eluting enantiomer; 580 mg, 1.53 mmol) was dissolved in THF (15 mL) and cooled to −78° C. under nitrogen. Cyclopropanecarboxaldehyde (0.396 mL, 5.34 mmol) was added, followed by 2,2,6,6-tetramethylpiperidinylmagnesium chloride lithium chloride complex (Aldrich, 1M in THF/toluene, 3.05 mL, 3.05 mmol) and the reaction was stirred at −78° C. After 30 minutes, additional 2,2,6,6-tetramethylpiperidinylmagnesium chloride lithium chloride complex (Aldrich, 1M in THF/toluene, 1.5 mL, 1.5 mmol) was added, and the reaction was stirred for a further 30 minutes at −78° C. The reaction was quenched by pouring it into 30 mL of saturated $NH_4Cl$. The mixture was extracted with EtOAc (100 mL), and the organic layer was washed with brine (25 mL). The organic layer was dried over $Na_2SO_4$, filtered, and concentrated. Purification of the residue on a silica gel column with 0 to 100% EtOAc/DCM afforded a first and second eluting diastereomer. 4-(5-chloropyridin-3-yl)-2-[(R or Sy cyclopropyl(hydroxy)methyl]-3-[(1R or S)-1-(trans-4-methylcyclohexyl)ethyl]-3H-imidazo[4,5-c]pyridine-6-carbonitrile; Diastereomer 1 (faster eluting): MS ESI calc'd. for $C_{25}H_{28}ClN_5O$ [M+H]$^+$ 450. found 450. 4-(5-chloropyridin-3-yl)-2-[(S or R)-cyclopropyl(hydroxy)methyl]-3-[(1R or S)-1-(trans-4-methylcyclohexyl)ethyl]-3H-imidazo[4,5-c]pyridine-6-carbonitrile; Diastereomer 2 (slower eluting): MS ESI calc'd. for $C_{25}H_{28}ClN_5O$ [M+H]$^+$ 450. found 450.

Step 2: 4-(5-chloropyridin-3-yl)-2-[(S or R)-cyclopropyl(hydroxy)methyl]-3-[(1R or S)-1-(trans-4-methylcyclohexyl)ethyl]-3H-imidazo[4,5-c]pyridine-6-carbonitrile (Diastereomer 2 (slower eluting); 165 mg, 0.367 mmol) was dissolved in THF (4 mL) and cooled to 0° C. NaH (60%, 29.3 mg, 0.733 mmol) was added followed after 5 minutes by iodoethane. The reaction was allowed to warm to room temperature and stirred for 18 hours. The reaction was then quenched with saturated $NH_4Cl$ (5 mL) and diluted with EtOAc (50 mL). The organic layer was washed with water and brine (15 mL each), dried over $Na_2SO_4$, filtered, and concentrated. Purification of the residue on a silica gel column with 0 to 60% EtOAc/hexanes afforded 4-(5-chloropyridin-3-yl)-2-[(S or R)-cyclopropyl(ethoxy)methyl]-3-[(1R or S)-1-(trans-4-methylcyclohexyl)ethyl]-3H-imidazo[4,5-c]pyridine-6-carbonitrile. MS ESI calc'd. for $C_{27}H_{32}ClN_5O$ [M+H]$^+$ 478. found 478.

Step 3: Hydroxylamine hydrochloride (38.7 mg, 0.556 mmol) was dissolved in water (1.5 mL), and sodium bicarbonate (70.1 mg, 0.835 mmol) was added. The solution was stirred for 30 minutes, and gas evolved. The solution was then added to 4-(5-chloropyridin-3-yl)-2-[(S or R)cyclopropyl(ethoxy)methyl]-3-[(1R or S)-1-(trans-4-methylcyclohexyl)ethyl]-3H-imidazo[4,5-c]pyridine-6-carbonitrile (133 mg, 0.278 mmol) suspended in EtOH (3 mL). The reaction vial was sealed and heated to 60° C. for 1 hour. The reaction was then cooled to room temperature, diluted with EtOAc (100 mL) and washed with water (2×10 mL) and brine (10 mL). The organic layer was dried over $Na_2SO_4$, filtered, and concentrated. The crude product, 4-(5-chloropyridin-3-yl)-2-[(S or R)-cyclopropyl(ethoxy)methyl]-N-hydroxy-3-[(1R or S)-1-(trans-4-methylcyclohexyl)ethyl]-3H-imidazo[4,5-c]pyridine-6-carboximidamide, was used in Step 4. MS ESI calc'd for $C_{27}H_{35}ClN_6O_2$ [M+H]$^+$=511. found=511.

Step 4: To 4-(5-chloropyridin-3-yl)-2-[(S or R)-cyclopropyl(ethoxy)methyl]-N-hydroxy-3-[(1R or S)-1-(trans-4-methylcyclohexyl)ethyl]-3H-imidazo[4,5-c]pyridine-6-carboximidamide (143.2 mg, 0.28 mmol) in acetonitrile (10 mL) were added 1,1'-carbonyldiimidazole (91 mg, 0.560 mmol) and 1,8-diazabicyclo[5.4.0]undec-7-ene (0.169 mL, 1.12 mmol). The reaction was stirred at room temperature for 1 hour and then diluted with EtOAc (100 mL) and washed with 0.25 M HCl (10 mL) and brine (10 mL). The organic layer was dried over $Na_2SO_4$, filtered, and concentrated. The residue was purified by silica gel chromatography with 3:1 hexanes:DCM containing 2% MeOH followed by further purification on silica gel with 50 to 100% EtOAc/hexanes to afford 3-{4-(5-chloropyridin-3-yl)-2-[(S or R)-cyclopropyl(ethoxy)methyl]-3-[(1R or S)-1-(trans-4-methylcyclohexyl)ethyl]-3H-imidazo[4,5-c]pyridin-6-yl}-1,2,4-oxadiazol-5 (4H)-one. MS ESI calc'd for $C_{28}H_{33}ClN_6O_3$ [M+H]$^+$=537. found=537. $^1$H NMR (600 MHz, DMSO-$d_6$) δ 12.89 (s, 1H), 8.82 (d, J=11.4 Hz, 2H), 8.36 (s, 1H), 8.27 (s, 1H), 8.15 (d, J=9.0 Hz, 1H), 3.78 (m, 2H), 3.52 (m, 1H), 0.60-1.74 (m, 18H), 0.44-0.56 (m, 2H), 0.24-0.39 (m, 2H), −0.03-0.16 (m, 2H).

Examples in Table 15 (other than Example 15.1) were prepared using procedures that were analogous to those described above. Example 15.2 was prepared from the faster eluting diastereomer (diastereomer 1) of Ex. 15.1, Step 1. Examples 15.3 and 15.4 were prepared starting from the faster eluting enantiomer of Preparative Example 15.1. Examples 15.5-15.8 were prepared starting from the slower eluting enantiomer of Preparative Example 15.1.

TABLE 15

| Ex. | FRET IC$_{50}$ (nM) | Structure | Chemical Name | Salt | [M + H]+ Calc'd | [M + H]+ Obsv'd |
|---|---|---|---|---|---|---|
| 15.1 | <1 | 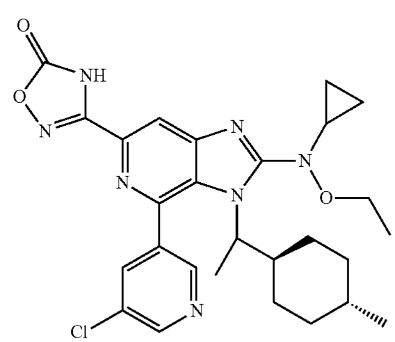 [SMILES: CCON(c1nc2cc(-c3noc(=O)[nH]3)nc(-c3cncc(Cl)c3)c2n1C(C)[C@H]1CC[C@H](C)CC1)C1CC1] | 3-{4-(5-chloropyridin-3-yl)-2-[(S or R)-cyclopropyl(ethoxy)methyl]-3-[(1R or S)-1-(trans-4-methylcyclohexyl)ethyl]-3H-imidazo[4,5-c]pyridin-6-yl}-1,2,4-oxadiazol-5(4H)-one (stereoisomer 1) | | 537 | 537 |

TABLE 15-continued

| Ex. | FRET IC$_{50}$ (nM) | Structure | Chemical Name | Salt | [M + H]+ Calc'd | [M + H]+ Obsv'd |
|---|---|---|---|---|---|---|
| 15.2 | 2 | 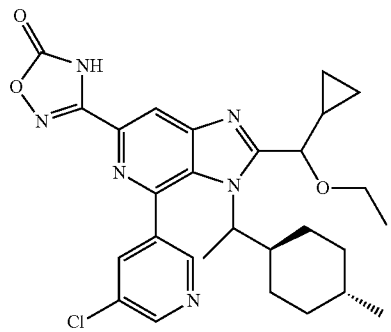 [SMILES: CCOC(c1nc2cc(-c3noc(=O)[nH]3)nc(-c3cncc(Cl)c3)c2n1C(C)[C@H]1CC[C@H](C)CC1)C1CC1] | 3-{4-(5-chloropyridin-3-yl)-2-[(R or S)-cyclopropyl(ethoxy)methyl]-3-[(1R or S)-1-(trans-4-methylcyclohexyl)ethyl]-3H-imidazo[4,5-c]pyridin-6-yl}-1,2,4-oxadiazol-5(4H)-one (stereoisomer 2) | TFA | 537 | 537 |
| 15.3 | 13 | 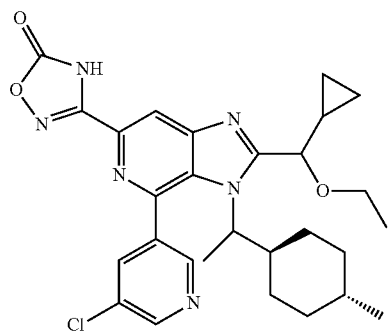 [SMILES: CCOC(c1nc2cc(-c3noc(=O)[nH]3)nc(-c3cncc(Cl)c3)c2n1C(C)[C@H]1CC[C@H](C)CC1)C1CC1] | 3-{4-(5-chloropyridin-3-yl)-2-[(R or S)-cyclopropyl(ethoxy)methyl]-3-[(1S or R)-1-(trans-4-methylcyclohexyl)ethyl]-3H-imidazo[4,5-c]pyridin-6-yl}-1,2,4-oxadiazol-5(4H)-one (stereoisomer 3) | TFA | 537 | 537 |
| 15.4 | 4 | 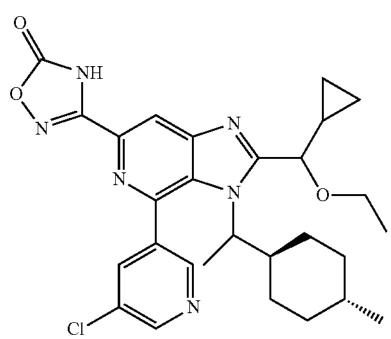 [SMILES: CCOC(c1nc2cc(-c3noc(=O)[nH]3)nc(-c3cncc(Cl)c3)c2n1C(C)[C@H]1CC[C@H](C)CC1)C1CC1] | 3-{4-(5-chloropyridin-3-yl)-2-[(S or R)-cyclopropyl(ethoxy)methyl]-3-[(1S or R)-1-(trans-4-methylcyclohexyl)ethyl]-3H-imidazo[4,5-c]pyridin-6-yl}-1,2,4-oxadiazol-5(4H)-one (stereoisomer 4) | TFA | 537 | 537 |
| 15.5 | 4 | 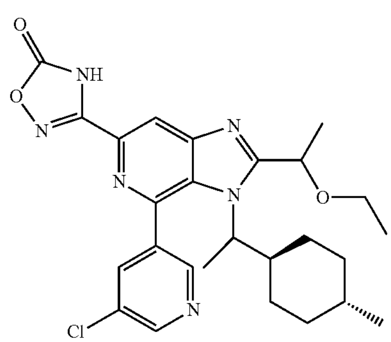 [SMILES: CCOC(C)c1nc2cc(-c3noc(=O)[nH]3)nc(-c3cncc(Cl)c3)c2n1C(C)[C@H]1CC[C@H](C)CC1] | 3-{4-(5-chloropyridin-3-yl)-2-[(1S or R)-1-ethoxyethyl]-3-[(1R or S)-1-(trans-4-methylcyclohexyl)ethyl]-3H-imidazo[4,5-c]pyridin-6-yl}-1,2,4-oxadiazol-5(4H)-one (stereoisomer 1) | TFA | 511 | 511 |

TABLE 15-continued

| Ex. | FRET IC$_{50}$ (nM) | Structure | Chemical Name | Salt | [M + H]+ Calc'd | [M + H]+ Obsv'd |
|---|---|---|---|---|---|---|
| 15.6 | 5 | 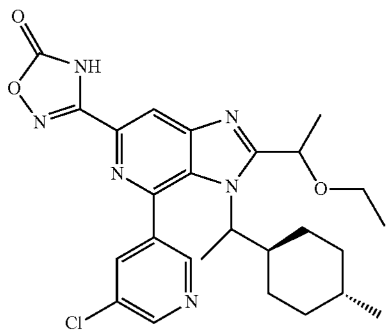 [SMILES: CCOC(C)c1nc2cc(-c3noc(=O)[nH]3)nc(-c3cncc(Cl)c3)c2n1C(C)[C@H]1CC[C@H](C)CC1] | 3-{4-(5-chloropyridin-3-yl)-2-[(1R or S)-1-ethoxyethyl]-3-[(1R or S)-1-(trans-4-methylcyclohexyl)ethyl]-3H-imidazo[4,5-c]pyridin-6-yl}-1,2,4-oxadiazol-5(4H)-one (stereoisomer 2) | TFA | 511 | 511 |
| 15.7 | 5 | 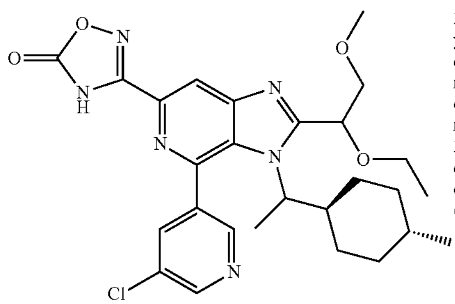 [SMILES: CCOC(COC)c1nc2cc(-c3noc(=O)[nH]3)nc(-c3cncc(Cl)c3)c2n1C(C)[C@H]1CC[C@H](C)CC1] | 3-{4-(5-chloropyridin-3-yl)-2-[(1R or S)-1-ethoxy-2-methoxyethyl]-3-[(1R or S)-1-(trans-4-methylcyclohexyl)ethyl]-3H-imidazo[4,5-c]pyridin-6-yl}-1,2,4-oxadiazol-5(4H)-one (stereoisomer 1) | TFA | 541 | 541 |
| 15.8 | 3 | 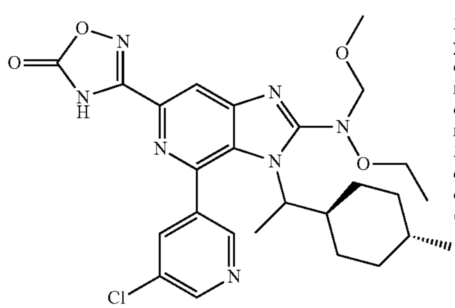 [SMILES: CCON(COC)c1nc2cc(-c3noc(=O)[nH]3)nc(-c3cncc(Cl)c3)c2n1C(C)[C@H]1CC[C@H](C)CC1] | 3-{4-(5-chloropyridin-3-yl)-2-[(1S or R)-1-ethoxy-2-methoxyethyl]-3-[(1R or S)-1-(trans-4-methylcyclohexyl)ethyl]-3H-imidazo[4,5-c]pyridin-6-yl}-1,2,4-oxadiazol-5(4H)-one (stereoisomer 2) | TFA | 541 | 541 |

Scheme 20

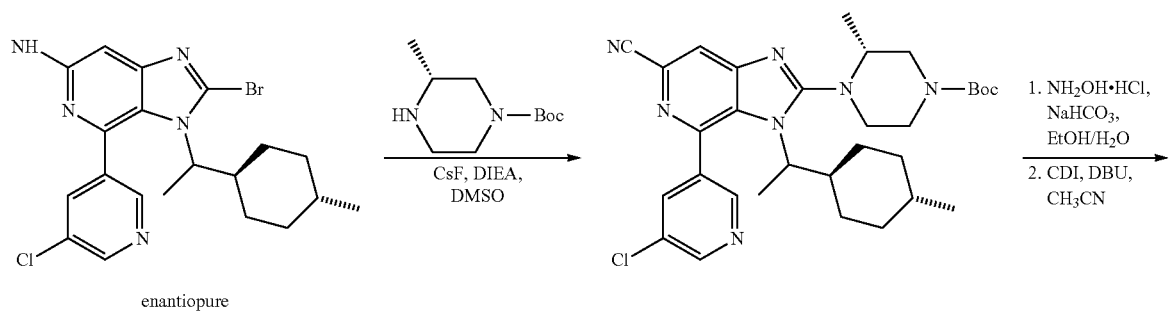

-continued

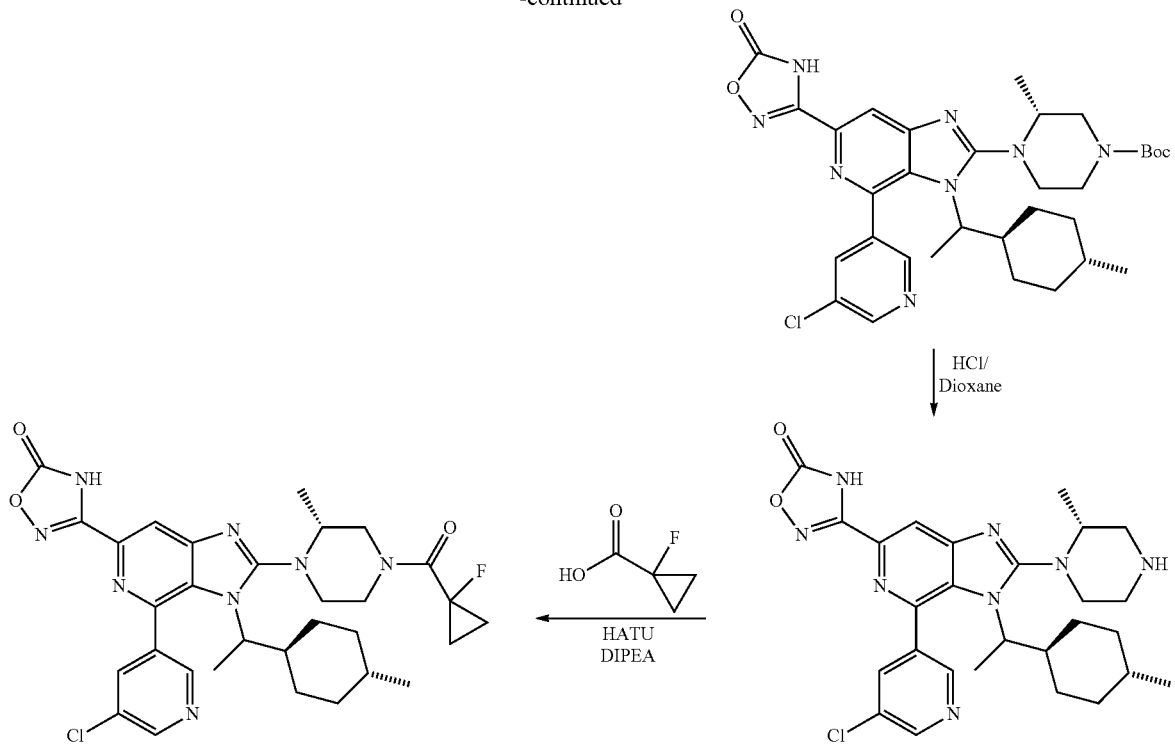

↓ HCl/Dioxane

Example 16.1

3-{4-(5-chloropyridin-3-yl)-2-{(2R)-4-[(1-fluorocyclopropyl)carbonyl]-2-methylpiperazin-1-yl}-3-[(1R or S)-1-(trans-4-methylcyclohexyl)ethyl]-3H-imidazo[4,5-c]pyridin-6-yl}-1,2,4-oxadiazol-5(4H)-one

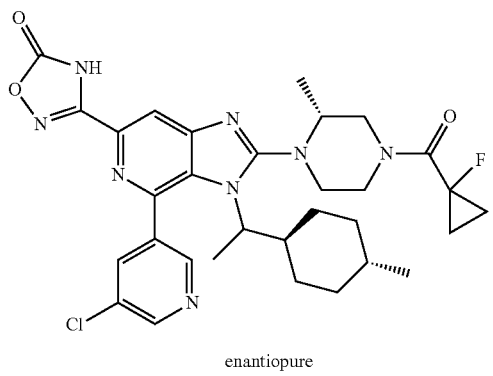 [SMILES: CC([C@H]1CC[C@H](C)CC1)n1c(N2CCN(C(=O)C3(F)CC3)C[C@H]2C)nc2cc(-c3noc(=O)[nH]3)nc(-c3cncc(Cl)c3)c21]

enantiopure

Step 1: To a microwave vial were added (R)-tert-butyl 3-methylpiperazine-1-carboxylate (purchased from Astatech) (155 mg, 0.776 mmol), 2-bromo-4-(5-chloropyridin-3-yl)-3-[(1R or S)-1-(trans-4-methylcyclohexyl)ethyl]-3H-imidazo[4,5-c]pyridine-6-carbonitrile (faster eluting enantiomer 1 from Example 4.1/4.2, Step 3; 178 mg, 0.388 mmol), cesium fluoride (177 mg, 1.164 mmol), DMSO (1 ml) and DIEA (0.203 ml, 1.164 mmol). The reaction vial was capped and heated to 100° C. overnight. The reaction was then cooled to room temperature, diluted with EtOAc, washed with water and brine, dried over sodium sulfate, filtered, and concentrated. The residue was purified by column chromatography on silica gel, eluting with EtOAc/hexanes to give tert-butyl (3R)-4-{4-(5-chloropyridin-3-yl)-6-cyano-3-[(1R or S)-1-(trans-4-methylcyclohexyl)ethyl]-3H-imidazo[4,5-c]pyridin-2-yl}-3-methylpiperazine-1-carboxylate. MS ESI calc'd. for $C_{31}H_{40}ClN_7O_2$ [M+H]$^+$ 578. found 578.

Step 2: Using a procedure analogous to that described in Example 2.1 (Step 5), and starting with tert-butyl (3R)-4-{4-(5-chloropyridin-3-yl)-6-cyano-3-[(1R or S)-1-(trans-4-methylcyclohexyl)ethyl]-3H-imidazo[4,5-c]pyridin-2-yl}-3-methylpiperazine-1-carboxylate, tert-butyl (3R)-4-{4-(5-chloropyridin-3-yl)-6-(N-hydroxycarbamimidoyl)-3-[(1R or S)-1-(trans-4-methylcyclohexyl)ethyl]-3H-imidazo[4,5-c]pyridin-2-yl}-3-methylpiperazine-1-carboxylate was prepared. MS ESI calc'd. for $C_{31}H_{43}ClN_8O_3$ [M+H]$^+$ 611. found 611.

Step 3: Using a procedure analogous to that described in Example 2.1 (Step 6), and starting with tert-butyl (3R)-4-{4-(5-chloropyridin-3-yl)-6-(N-hydroxycarbamimidoyl)-3-[(1R or S)-1-(trans-4-methylcyclohexyl)ethyl]-3H-imidazo[4,5-c]pyridin-2-yl}-3-methylpiperazine-1-carboxylate, tert-butyl (3R)-4-[4-(5-chloropyridin-3-yl)-3-[(1R or S)-1-(trans-4-methylcyclohexyl)ethyl]-6-(5-oxo-4,5-dihydro-1,2,4-oxadiazol-3-yl)-3H-imidazo[4,5-c]pyridin-2-yl]-3-methylpiperazine-1-carboxylate was prepared. MS ESI calc'd. for $C_{32}H_{41}ClN_8O_4$ [M+H]$^+$ 637. found 637.

Step 4: A solution of HCl in 1,4-Dioxane (4.0 M, 0.718 ml, 2.9 mmol) was added to a stirred solution of tert-butyl (3R)-4-[4-(5-chloropyridin-3-yl)-3-[(1R or S)-1-(trans-4-methylcyclohexyl)ethyl]-6-(5-oxo-4,5-dihydro-1,2,4-oxadiazol-3-yl)-3H-imidazo[4,5-c]pyridin-2-yl]-3-methylpiperazine-1-carboxylate (61 mg, 0.096 mmol) in 1,4-dioxane (0.736 ml) at room temperature, and the mixture was stirred at room temperature for 1.75 hr. The solvent was evaporated under reduced pressure to give 3-{4-(5-chloropyridin-3-yl)-3-[(1R or S)-1-(trans-4-methylcyclohexyl)ethyl]-2-[(2R)-2-methylpiperazin-1-yl]-3H-imidazo[4,5-c]pyridin-6-yl}-1,2,4-oxadiazol-5(4H)-one (HCl salt). MS ESI calc'd. for $C_{27}H_{33}ClN_8O_2$ [M+H]$^+$ 537. found 537.

Step 5: 1-fluorocyclopropanecarboxylic acid (purchased from Wuxi AppTec) (25.4 mg, 0.244 mmol), N,N-diisopropylethylamine (63.1 mg, 0.488 mmol) and HATU (93.0 mg, 0.244 mmol) were added to a 0° C. solution of 3-{4-(5-chloropyridin-3-yl)-3-[(1R or S)-1-(trans-4-methylcyclohexyl)ethyl]-2-[(2R)-2-methylpiperazin-1-yl]-3H-imidazo[4,5-c]pyridin-6-yl}-1,2,4-oxadiazol-5(4H)-one (HCl salt) (70.0 mg, 0.122 mmol) in DMF (1 ml), and the reaction was warmed to room temperature and stirred for two hours. The reaction was then diluted with EtOAc, washed with water and brine, dried over sodium sulfate, filtered, and concentrated. The residue was purified by preparative HPLC (reverse phase, C-18), eluting with acetonitrile/water+0.1% TFA, to give 3-{4-(5-chloropyridin-3-yl)-2-{(2R)-4-[(1-fluorocyclopropyl)carbonyl]-2-methylpiperazin-1-yl}-3-[(1R or S)-1-(trans-4-methylcyclohexyl)ethyl]-3H-imidazo[4,5-c]pyridin-6-yl}-1,2,4-oxadiazol-5(4H)-one (TFA salt). MS ESI calc'd. for $C_{31}H_{36}ClFN_8O_3$ [M+H]$^+$ 623. found 623. $^1$H NMR (600 MHz, DMSO-d$_6$) δ 12.86 (s, 1H), 8.88 (s, 1H), 8.80 (d, J=2.2, 1H), 8.40 (s, 1H), 8.10 (s, 1H), 4.06-3.39 (m, 5H), 3.00-2.83 (m, 1H), 2.08-1.82 (m, 1H), 1.66-0.65 (m, 20H), 0.54-0.09 (m, 4H).

Example 16.1 was prepared as described above.

TABLE 16

| Ex. | FRET IC$_{50}$ (nM) | Structure | Chemical Name | Salt | [M + H]+ Calc'd | [M + H]+ Obsv'd |
|---|---|---|---|---|---|---|
| 16.1 | 1 | 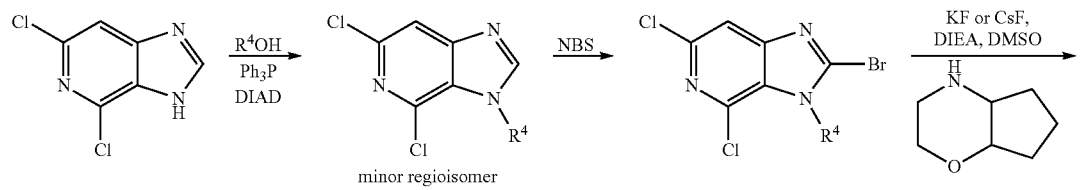 | 3-{4-(5-chloropyridin-3-yl)-2-{(2R)-4-[(1-fluorocyclopropyl)carbonyl]-2-methylpiperazin-1-yl}-3-[(1R or S)-1-(trans-4-methylcyclohexyl)ethyl]-3H-imidazo[4,5-c]pyridin-6-yl}-1,2,4-oxadiazol-5(4H)-one (single enatiomer) | | 623 | 623 |

Scheme 21

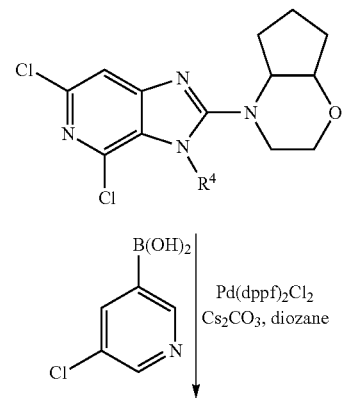

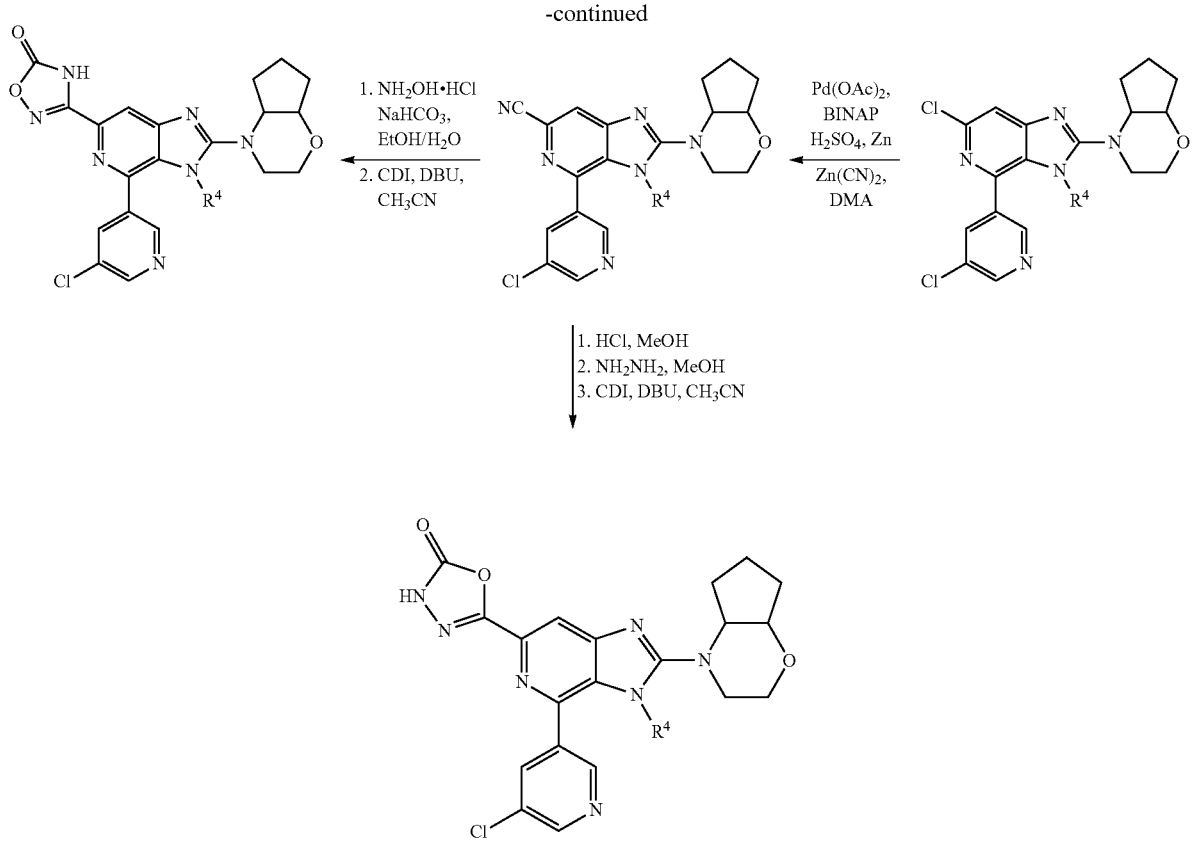

Preparative Example 17.1

(Trans-4-ethylcyclohexyl)methanol

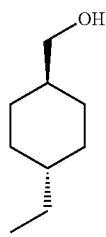

Borane in THF (1 M, 64.1 mL, 64.1 mmol) was added dropwise to trans-4-ethylcyclohexanecarboxylic acid (10.0 g, 64.1 mmol) in dry THF (100 mL) at −60° C. under a nitrogen atmosphere. The reaction was allowed to warm to room temperature and stirred for 12 h. The reaction was quenched with saturated ammonium chloride solution at 0° C., diluted with water (200 mL) and extracted with ethyl acetate (3×100 mL). The organic layer was washed with water (2×200 mL) and brine (100 mL), dried over anhydrous $Na_2SO_4$, filtered, and concentrated in vacuo to obtain (trans-4-ethylcyclohexyl) methanol. $^1H$ NMR (300 MHz, $CDCl_3$): δ 3.44 (d, J=6.0 Hz, 2H); 1.85-1.70 (dd, J=1.19, 10.5 Hz, 4H); 1.50-1.35 (m, 1H); 1.30-1.10 (m, 4H); 0.95-0.85 (m, 6H).

Preparative Example 17.2

[Trans-4-(trifluoromethyl)cyclohexyl]methanol

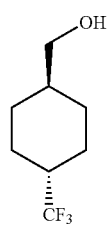

$BH_3$ (100 mL, 0.1 mol, 1.0 M solution in THF) was added dropwise to 0° C. solution of trans-4-(trifluoromethyl)cyclohexanecarboxylic acid (19.6 g, 0.1 mol) in dry THF (100 mL). The reaction was stirred at room temperature for 5 h, quenched with water, extracted with EtOAc, washed with brine, dried over $Na_2SO_4$, filtered, and concentrated to give [trans-4-(trifluoromethyl)cyclohexyl]methanol. $^1H$ NMR (300 MHz, CDCl₃): δ 3.48-3.47 (d, 2H), 2.00-1.89 (m, 5H), 1.51-1.43 (m, 1H), 1.35-1.26 (m, 2H), 1.05-0.96 (m, 2H).

Preparative Example 17.3

(3-ethylcyclopentyl)methanol (mixture of cis and trans stereoisomers)

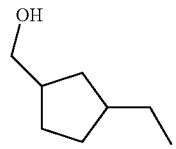

Step 1: To a stirred solution of 3-ethylcyclopentanone (4.00 g, 35.7 mmol) in THF (70 mL) was added LDA (2 M in THF, 22.8 mL, 46.4 mmol) at −78° C., and the reaction was stirred at that temperature for 30 minutes. 1,1,1-trifluoro-N-phenyl-N—[(trifluoromethyl)sulfonyl]methanesulfonamide (14.0 g, 39.2 mmol) in THF (70 mL) was added at −78° C. The mixture was allowed to warm to room temperature and stirred for 17 hours under a nitrogen atmosphere. The reaction mixture was cooled to 0° C., slowly quenched with aqueous ammonium chloride, and extracted with MTBE (3×30 mL). The combined organic layers were washed with brine (2×30 mL), dried over anhydrous Na₂SO₄, filtered, and concentrated. Purification of the residue on a silica gel column (10 to 100% EtOAc/hexanes) afforded 3-ethylcyclopent-1-en-1-yl trifluoromethanesulfonate.

Step 2: To a stirred solution of 3-ethylcyclopent-1-en-1-yl trifluoromethanesulfonate (1.0 g, 4.08 mmol) in methanol (15 mL) and DMF (10 mL) were added Pd(OAc)₂ (45 mg, 0.20 mmol), DPPF (226 mg, 0.40 mmol), and Et₃N (2.3 mL, 16.3 mmol), and the mixture was degassed with CO for 15 minutes. Then the reaction mixture was stirred at room temperature under a CO atmosphere (balloon) for 16 hours. Water was added to the reaction mixture, and it was extracted with MTBE (3×30 mL). The combined organic layers were washed with brine, dried over Na₂SO₄, and concentrated. Purification of the residue on a silica gel column (0 to 100% EtOAc/hexanes) afforded methyl 3-ethylcyclopent-1-enecarboxylate.

Step 3: To a stirred solution of methyl 3-ethylcyclopent-1-enecarboxylate (1.60 g, 10.3 mmol) in methanol (15 mL) was added 10% Pd/C (100 mg), and the mixture was purged with hydrogen for 10 minutes. Then reaction mixture was then stirred at room temperature for 16 hours under a hydrogen atmosphere (balloon). The reaction mixture was then filtered through a pad of celite, and the filtrate was concentrated to dryness to afford methyl 3-ethylcyclopentanecarboxylate as a mixture of cis and trans isomers.

Step 4: To a stirred solution of methyl 3-ethylcyclopentanecarboxylate (1.50 g, 9.61 mmol) in THF (10 mL) was added LAH (1 M in THF; 9.6 mL, 9.6 mmol) at 0° C., and the reaction mixture was stirred at 0° C. for 1 hour. The reaction mixture was quenched with saturated Na₂SO₄, filtered through a pad of celite, washing with ethyl acetate, and the filtrate was concentrated to dryness to afford (3-ethylcyclopentyl)methanol (mixture of cis and trans isomers).

Example 17.1

3-{4-(5-chloropyridin-3-yl)-2-[(trans)-hexahydrocyclopenta[b][1,4]oxazin-4(4aH)-yl]-3-[4-(trifluoromethyl)benzyl]-3H-imidazo[4,5-c]pyridin-6-yl}-1,2,4-oxadiazol-5(4H)-one (racemic)

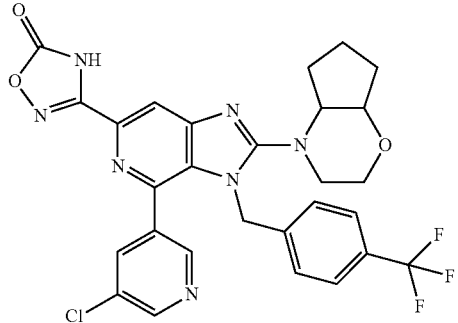 [SMILES: O=c1[nH]c(-c2cc3nc(N4CCOC5CCCC54)n(Cc4ccc(C(F)(F)F)cc4)c3c(-c3cncc(Cl)c3)n2)no1]

Step 1: 4,6-dichloro-3H-imidazo[4,5-c]pyridine (500 mg, 2.6 mmol), PPh₃ (762 mg, 2.91 mmol) and THF (20 mL) were combined and stirred under a nitrogen atmosphere. A solution of 4-trifluoromethyl benzyl alcohol (513 mg, 2.91 mmol) in THF (5 mL) was added at rt. The reaction mixture was cooled to 0° C., and diisopropyl azodicarboxylate (587 mg, 2.91 mmol) was added dropwise. The reaction was warmed to rt and stirred overnight under N₂. The reaction was then diluted with EtOAc, washed with brine, dried over Na₂SO₄, filtered, and concentrated. The crude residue was dissolved in EtOAc (20 ml), p-toluenesulfonic acid (500 mg, 2.91 mmol) was added at rt, and the mixture was stirred for 3 h. The precipitate which formed was collected by filtration and rinsed with EtOAc. The collected precipitate was slurried in EtOAc (50 mL) and was stirred vigorously with aqueous sat'd NaHCO₃ (5 mL) for 30 min. The organic layer was separated, and the aqueous layer was extracted several times with EtOAc. The combined organic layers were dried over Na₂SO₄, filtered, and concentrated. The crude product was purified by silica gel chromatography with 20% to 100% EtOAc/hexanes to obtain the desired isomer, 4,6-dichloro-3-(4-(trifluoromethyl)benzyl)-3H-imidazo[4,5-c]pyridine. ¹H NMR (400 MHz, CDCl₃): δ8.85 (s, 1H); 7.96 (s, 1H); 7.71 (d, J=8.0 Hz, 2H), 7.33 (d, J=8.0 Hz, 2H), 5.89 (s, 2H). MS APCl calc'd. for C₁₄H₈Cl₂F₃N₃ [M+H]⁺ 346, found 346.

Step 2: N-bromosuccinimide (352 mg, 1.98 mmol) was added to a solution of 4,6-dichloro-3-(4-(trifluoromethyl)benzyl)-3H-imidazo[4,5-c]pyridine (200 mg, 0.99 mmol) stirring in degassed chloroform (20 mL) at room temperature. The reaction was heated to reflux for 1 hour. The mixture was cooled to room temperature, diluted with dichloromethane, and washed with saturated aqueous sodium thiosulfate and brine. The organic layer was dried over sodium sulfate, filtered, and concentrated under reduced pressure. The residue was purified by silica gel chromatography (0-100% ethyl acetate/hexanes, linear gradient) to afford 2-bromo-4,6-dichloro-3-(4-(trifluoromethyl)benzyl)-3H-imidazo[4,5-c] pyridine. MS APCl calc'd. for C₁₄H₇BrCl₂F₃N₃ [M+H]⁺ 426. found 426.

Step 3: To a vial were added 2-bromo-4,6-dichloro-3-(4-(trifluoromethyl)benzyl)-3H-imidazo[4,5-c]pyridine (200 mg, 0.47 mmol), octahydrocyclopenta[b][1,4]oxazine hydrochloride (purchased from Enamine); 147 mg, 0.9 mmol), potassium fluoride (81 mg, 1.41 mmol), DIEA (246 µL, 1.41 mmol), and DMSO (2 mL). The vial was sealed and heated to 90° C. for 1 hour. The reaction mixture was cooled to room temperature, diluted with ethyl acetate, and washed with water and brine. The organic layer was dried over sodium sulfate, filtered, and concentrated under reduced pressure. The residue was purified by silica gel chromatography (0-60% ethyl acetate/hexanes, linear gradient) to afford 4,6-dichloro-2-[(trans)-hexahydrocyclopenta[b][1,4]oxazin-4(4aH)-yl]-3-[4-(trifluoromethyl)benzyl]-3H-imidazo[4,5-c]pyridine (racemate). MS APCl calc'd. for $C_{21}H_{19}Cl_2F_3N_4O$ [M+H]$^+$ 471. found 471.

Step 4: 4,6-dichloro-2-[(trans)-hexahydrocyclopenta[b][1,4]oxazin-4(4aH)-yl]-3-[4-(trifluoromethyl)benzyl]-3H-imidazo[4,5-c]pyridine (racemate, 180 mg, 0.38 mmol), 5-chloropyridine-3-boronic acid (65.7 mg, 0.42 mmol), cesium carbonate (617 mg, 1.9 mmol), and 1,1'-Bis(diphenylphosphino) ferrocene-palladium(II)dichloride (46.3 mg, 0.076 mmol) were combined in a vial that had been oven-dried and flushed with nitrogen. Dioxane (75 mL) was added, and the vial was sealed and heated to 90° C. for 4 hours. The reaction mixture was cooled to room temperature, filtered through celite, and the filtrate was concentrated under reduced pressure. The residue was purified by silica gel chromatography (0-100% ethyl acetate/hexanes, linear gradient) to afford 6-chloro-4-(5-chloropyridin-3-yl)-2-[(trans)-hexahydrocyclopenta[b][1,4]oxazin-4(4aH)-yl]-3-[4-(trifluoromethyl)benzyl]-3H-imidazo[4,5-c]pyridine (racemic). MS APCl calc'd. for $C_{26}H_{22}Cl_2F_3N_5O$ [M+H]$^+$ 548. found 548.

Step 5: Palladium(II) acetate (70 mg, 0.312 mmol) and (R)-(+)-2,2'-bis(diphenylphosphino)-1,1'-binaphthyl (195 mg, 0.313 mmol) were placed in a dry flask. N,N-dimethylacetamide (18.7 mL) was added and the mixture was degassed for three minutes with nitrogen. Sulfuric acid (0.015 mL) was added, and the mixture was degassed for an additional three minutes with nitrogen. The flask was sealed and heated to 80° C. for 30 minutes. The mixture was cooled to room temperature and added to a separate nitrogen purged flask containing 6-chloro-4-(5-chloropyridin-3-yl)-2-[(trans)-hexahydrocyclopenta[b][1,4]oxazin-4(4aH)-yl]-3-[4-(trifluoromethyl)benzyl]-3H-imidazo[4,5-c]pyridine (racemic; 0.5 g, 0.9 mmol), zinc cyanide (46 mg, 0.45 mmol), and zinc (6 mg, 0.09 mmol). The flask was purged with nitrogen for five minutes, sealed, and heated to 100° C. for 2 hrs. The reaction mixture was cooled to room temperature, filtered, diluted with ethyl acetate, and washed with water and brine. The organic layer was dried over sodium sulfate, filtered, and concentrated under reduced pressure. The residue was purified by silica gel chromatography (0-100% ethyl acetate/hexanes, linear gradient) to afford 4-(5-chloropyridin-3-yl)-2-[(trans)-hexahydrocyclopenta[b][1,4]oxazin-4(4aH)-yl]-3-[4-(trifluoromethyl)benzyl]-3H-imidazo[4,5-c]pyridine-6-carbonitrile (racemic). MS APCl calc'd. for $C_{27}H_{22}ClF_3N_6O$ [M+H]$^+$ 539. found 539.

Steps 6 and 7: Using a procedure analagous to that described in Example 2.1 (Steps 5 and 6) and starting with 4-(5-chloropyridin-3-yl)-2-[(trans)-hexahydrocyclopenta[b][1,4]oxazin-4(4aH)-yl]-3-[4-(trifluoromethyl)benzyl]-3H-imidazo[4,5-c]pyridine-6-carbonitrile (racemic), 3-{4-(5-chloropyridin-3-yl)-2-[(trans)-hexahydrocyclopenta[b][1,4]oxazin-4(4aH)-yl]-3-[4-(trifluoromethyl)benzyl]-3H-imidazo[4,5-c]pyridin-6-yl}-1,2,4-oxadiazol-5(4H)-one (racemic) was prepared. $^1$H NMR (500 MHz, CD$_3$OD) δ 8.59 (s, 1H), 8.51 (s, 1H), 8.23 (s, 1H), 7.65 (d, J=6.0 Hz, 1H), 7.35 (d, J=8.4, 2H), 6.43 (d, J=8.0 Hz, 2H), 5.55 (d, J=17.2 Hz, 1H), 4.82 (d, J=17.2 Hz, 1H), 3.92-4.00 (m, 2H), 3.46-3.51 (m, 2H), 3.10-3.25 (m, 1H), 3.05-3.10 (m, 1H), 1.24-1.32 (m, 4H), 0.86-0.91 (m, 2H). MS APCl calc'd. for $C_{28}H_{23}ClF_3N_7O_3$ [M+H]$^+$ 598. found 598.

The examples in Table 17 (other than Example 17.1) were prepared using procedures similar to those described above.

TABLE 17

| Ex. | FRET IC$_{50}$ (nM) | Structure | Chemical Name | Salt | [M + H]+ Calc'd | [M + H]+ Obsv'd |
|---|---|---|---|---|---|---|
| 17.1 | 39 | 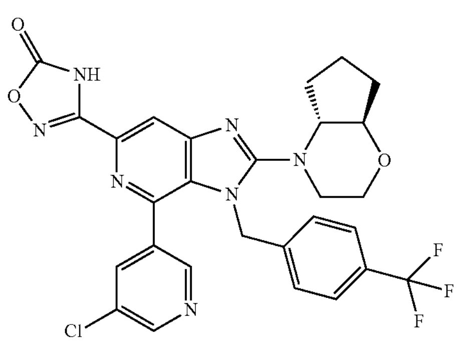 [SMILES: O=c1[nH]c(-c2cc3nc(N4CCO[C@@H]5CCC[C@H]54)n(Cc4ccc(C(F)(F)F)cc4)c3c(-c3cncc(Cl)c3)n2)no1] | 3-{4-(5-chloropyridin-3-yl)-2-[(trans)-hexahydrocyclopenta[b][1,4]oxazin-4(4aH)-yl]-3-[4-(trifluoromethyl)benzyl]-3H-imidazo[4,5-c] pyridin-6-yl}-1,2,4-oxadiazol-5(4H)-one (racemic) | | 598 | 598 |

TABLE 17-continued

| Ex. | FRET IC$_{50}$ (nM) | Structure | Chemical Name | Salt | [M + H]+ Calc'd | [M + H]+ Obsv'd |
|---|---|---|---|---|---|---|
| 17.2 | 5 | 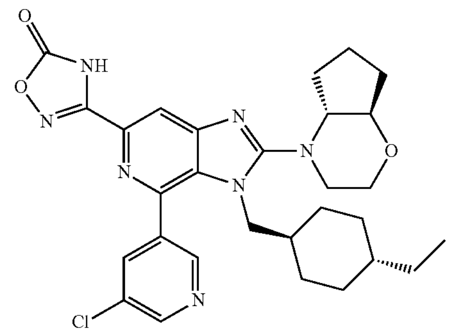 [SMILES: CC[C@H]1CC[C@H](Cn2c(N3CCO[C@@H]4CCC[C@H]43)nc3cc(-c4noc(=O)[nH]4)nc(-c4cncc(Cl)c4)c32)CC1] | 3-{4-(5-chloropyridin-3-yl)-3-[(trans-4-ethylcyclohexyl)methyl]-2-[(trans)-hexahydrocyclopenta[b][1,4]oxazin-4(4aH)-yl]-3H-imidazo[4,5-c]pyridin-6-yl}-1,2,4-oxadiazol-5(4H)-one (racemic) | | 564 | 564 |
| 17.3 | 25 | 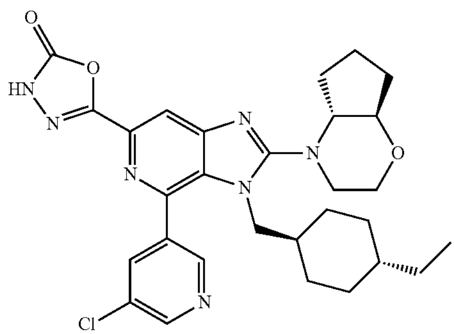 [SMILES: CC[C@H]1CC[C@H](Cn2c(N3CCO[C@@H]4CCC[C@H]43)nc3cc(-c4n[nH]c(=O)o4)nc(-c4cncc(Cl)c4)c32)CC1] | 5-{4-(5-chloropyridin-3-yl)-3-[(trans-4-ethylcyclohexyl)methyl]-2-[{trans)-hexahydrocyclopenta[b][1,4]oxazin-4(4aH)-yl]-3H-imidazo[4,5-c]pyridin-6-yl}-1,3,4-oxadiazol-2(3H)-one (racemic) | | 564 | 564 |
| 17.4 | 244 | 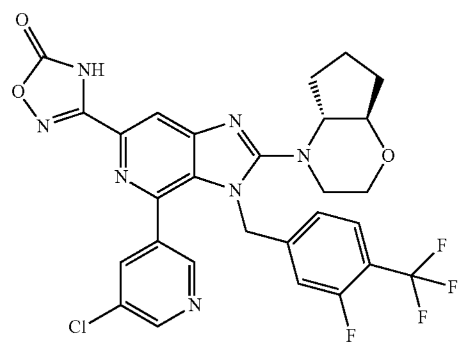 [SMILES: O=c1[nH]c(-c2cc3nc(N4CCO[C@@H]5CCC[C@H]54)n(Cc4ccc(C(F)(F)F)c(F)c4)c3c(-c3cncc(Cl)c3)n2)no1] | 3-{4-(5-chloropyridin-3-yl)-3-[3-fluoro-4-(trifluoromethyl)benzyl]-2-[(trans)-hexahydrocyclopenta[b][1,4]oxazin-4(4aH)-yl]-3H-imidazo[4,5-c]pyridin-6-yl}-1,2,4-oxadiazol-5(4H)-one (enantiomer 1) | | 616 | 616 |
| 17.5 | 28 | 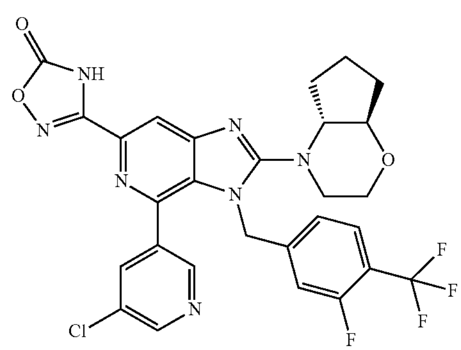 [SMILES: O=c1[nH]c(-c2cc3nc(N4CCO[C@@H]5CCC[C@H]54)n(Cc4ccc(C(F)(F)F)c(F)c4)c3c(-c3cncc(Cl)c3)n2)no1] | 3-{4-(5-chloropyridin-3-yl)-3-[3-fluoro-4-(trifluoromethyl)benzyl]-2-[{trans)-hexahydrocyclopenta[b][1,4]oxazin-4(4aH)-yl]-3H-imidazo[4,5-c]pyridin-6-yl}-1,2,4-oxadiazol-5(4H)-one (enantiomer 2) | | 616 | 616 |

TABLE 17-continued

| Ex. | FRET IC$_{50}$ (nM) | Structure | Chemical Name | Salt | [M + H]+ Calc'd | [M + H]+ Obsv'd |
|---|---|---|---|---|---|---|
| 17.6 | 38 | 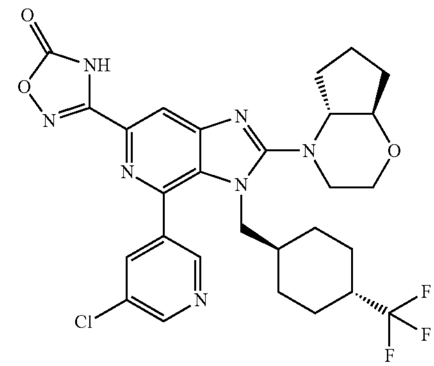 [SMILES: O=c1[nH]c(-c2cc3nc(N4CCO[C@@H]5CCC[C@H]54)n(C[C@H]4CC[C@H](C(F)(F)F)CC4)c3c(-c3cncc(Cl)c3)n2)no1] | 3-[4-(5-chloropyridin-3-yl)-2-[(trans)-hexahydrocyclopenta[b][1,4]oxazin-4(4aH)-yl]-3-{[trans-4-(trifluoromethyl)cyclohexyl]methyl}-3H-imidazo[4,5-c]pyridin-6-yl]-1,2,4-oxadiazol-5(4H)-one (racemic) | | 604 | 604 |
| 17.7 | 16 | 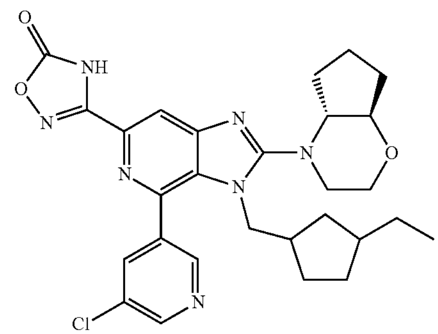 [SMILES: CCC1CCC(Cn2c(N3CCO[C@@H]4CCC[C@H]43)nc3cc(-c4noc(=O)[nH]4)nc(-c4cncc(Cl)c4)c32)C1] | 3-{4-(5-chloropyridin-3-yl)-3-[(3-ethylcyclopentyl)methyl]-2-[(4aR,7aR)-hexahydrocyclopenta[b] [1,4]oxazin-4(4aH)-yl]-3H-imidazo[4,5-c] pyridin-6-yl]-1,2,4-oxadiazol-5(4H)-one (mixture of diastereomers) | | 550 | 550 |

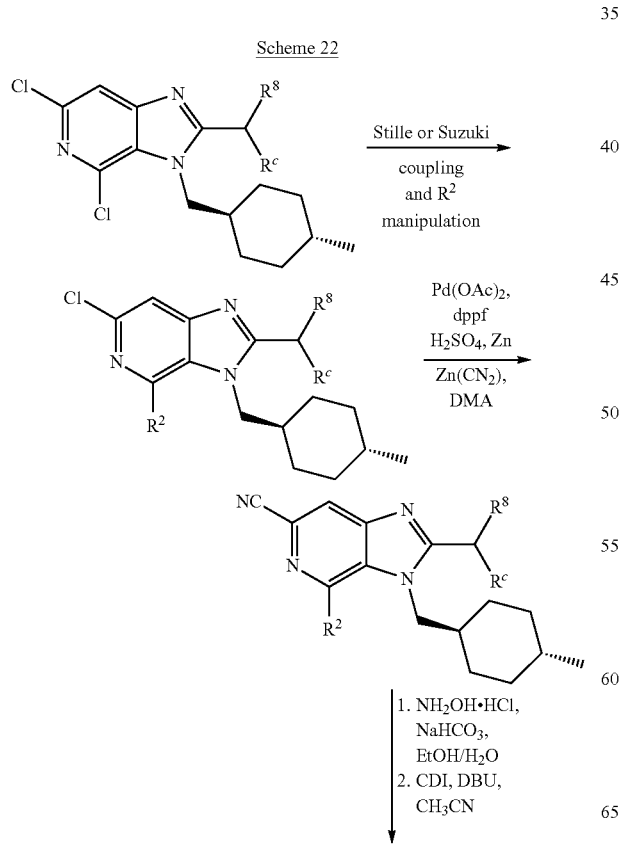

Scheme 22

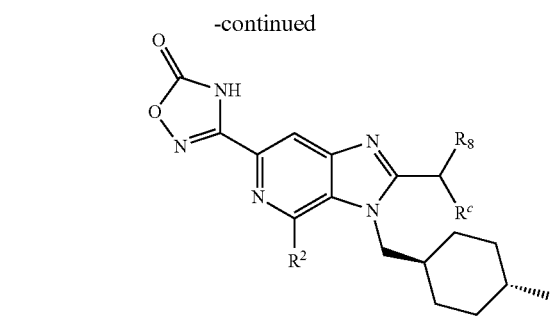

Preparative Example 18.1

4,6-dichloro-2-[(trans)-hexahydrocyclopenta [b][1,4]oxazin-4(4aH)-yl]-3-[(trans-4-methylcyclohexyl)methyl]-3H-imidazo[4,5-c]pyridine (racemic)

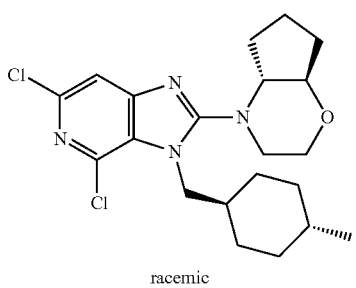 [SMILES: C[C@H]1CC[C@H](Cn2c(N3CCO[C@@H]4CCC[C@H]43)nc3cc(Cl)nc(Cl)c32)CC1]

racemic

Using a procedure analogous to that described in Example 2.1 (Steps 1 and 2) and starting with 4,6-dichloro-3-((trans- 4-methylcyclohexyl)methyl)-3H-imidazo[4,5-c]pyridine (Preparative Example 2.3) and (trans)-octahydrocyclopenta[b][1,4]oxazine.HCl (purchased from Enamine), 4,6-dichloro-2-[(trans)-hexahydrocyclopenta[b][1,4]oxazin-4(4aH)-yl]-3-[(trans-4-methylcyclohexyl)methyl]-3H-imidazo[4,5-c]pyridine (racemic) was prepared.

Preparative Example 18.2

3-(tributylstannanyl)pyridazine

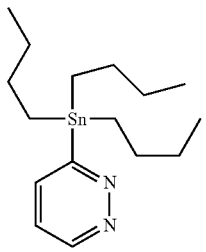 [SMILES: CCC[CH2][Sn]([CH2]CCC)([CH2]CCC)[c]1cccnn1]

In a sealable tube were placed 3-bromopyridazine (1.0 g, 6.28 mmol) and hexabutyldistannane (3.6 mL, 6.28 mmol). 1,4-dioxane (4 mL) was added, and the reaction mixture was purged with nitrogen for five minutes. Pd(dppf)Cl$_2$.CH$_2$Cl$_2$ (153 mg, 0.018 mmol) was added, and the mixture was degassed with nitrogen again for 5 minutes. The tube was sealed and heated to 100° C. for 16 hours. The reaction mixture was cooled to room temperature, filtered through celite, washing with ethyl acetate, and the filtrate was concentrated under reduced pressure. The residue was purified by column chromatography with 10% EtOAc/petroleum ether containing 0.1% Et$_3$N to afford 3-(tributylstannyl)pyridazine. MS ES/APCI calc'd. for C$_{16}$H$_{30}$N$_2$Sn [M+H]$^+$ 371. found 371. $^1$H NMR (400 MHz, CDCl$_3$): δ 8.72 (dd, J=1.5, 2.4 Hz, 1H), 8.56 (d, J=1.7 Hz, 1H), 8.37 (d, J=2.6 Hz, 1H), 1.62-1.53 (m, 8H), 1.39-1.33 (m, 6H), 1.31-1.19 (m, 5H), 0.95-0.90 (m, 8H).

Example 18.1

3-{4-[5-chloro-2-(dimethylamino)pyridin-3-yl]-2-[(trans)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one (racemic)

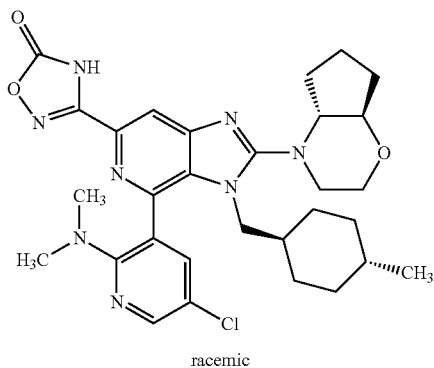 [SMILES: CN(C)c1ncc(Cl)cc1-c1nc(-c2noc(=O)[nH]2)cc2nc(N3CCO[C@@H]4CCC[C@H]43)n(C[C@H]3CC[C@H](C)CC3)c12]

racemic

Step 1: 4,6-dichloro-2-[(trans)-hexahydrocyclopenta[b][1,4]oxazin-4(4aH)-yl]-3-[(trans-4-methylcyclohexyl)methyl]-3H-imidazo[4,5-c]pyridine (racemic, 422 mg, 1 mmol), 5-chloro-2-fluoro-3-(4,4,5,5-tetramethyl-1,3,2-dioxaborolan-2-yl)pyridine (340 mg, 2 mmol) and Cs$_2$CO$_3$ (980 mg, 3 mmol) were added to degassed dioxane:water (10 mL: 2 mL), followed by the addition of [1,1'-bis(di-tert-butylphosphino)ferrocene]PdCl$_2$ (130 mg, 0.2 mmol). The reaction was heated at 90° C. for 24 hours. Water and EtOAc were added. The aqueous layer was extracted with EtOAc several times. The combined organic layers were dried over anhydrous Na$_2$SO$_4$, filtered, and concentrated in vacuo. The residue was purified on a silica gel column (0 to 60% EtOAc/hexanes) to afford 6-chloro-4-(5-chloro-2-fluoropyridin-3-yl)-2-[(trans)-hexahydrocyclopenta[b][1,4]oxazin-4(4aH)-yl]-3-[(trans-4-methylcyclohexyl)methyl]-3H-imidazo[4,5-c]pyridine (racemic). MS ES calc'd. for C$_{26}$H$_{30}$Cl$_2$FN$_5$O [M+H]$^+$ 518. found 518.

Step 2: To a solution of dimethylamine hydrochloride (580 mg, 7.25 mmol) and sodium bicarbonate (812 mg, 9.67 mmol) in EtOH:water (4 mL:2 mL) was added 6-chloro-4-(5-chloro-2-fluoropyridin-3-yl)-2-[(trans)-hexahydrocyclopenta[b][1,4]oxazin-4(4aH)-yl]-3-[(trans-4-methylcyclohexyl)methyl]-3H-imidazo[4,5-c]pyridine (racemic) (125 mg, 0.24 mmol). The reaction was heated to 90° C. for 5 hours. The reaction was then concentrated and diluted with EtOAc. The organic layer was washed with water and brine, dried over sodium sulfate, filtered, and concentrated. Purification of the residue on a silica gel column (0 to 45% EtOAc/hexanes) afforded 5-chloro-3-{6-chloro-2-[(trans)-hexahydrocyclopenta[b][1,4]oxazin-4(4aH)-yl]-3-[(trans-4-methylcyclohexyl)methyl]-3H-imidazo[4,5-c]pyridin-4-yl}-N,N-dimethylpyridin-2-amine (racemic). MS ES calc'd. for C$_{28}$H$_{36}$Cl$_2$N$_6$O [M+H]$^+$ 543. found 543.

Step 3: A vial was charged with H$_2$SO$_4$ (6 mg, 0.005 mmol) and DMA (3 mL) and was degassed with N$_2$ for 3 minutes. Pd(OAc)$_2$ (13.5 mg, 0.005 mmol) and dppf (33.4 mg, 0.005 mmol) were added. The vial was sealed and heated at 80° C. for 30 minutes and then was cooled to room temperature. 1 mL of this solution was added to a second vial containing 5-chloro-3-{6-chloro-2-[(trans)-hexahydrocyclopenta[b][1,4]oxazin-4(4aH)-yl]-3-[(trans-4-methylcyclohexyl)methyl]-3H-imidazo[4,5-c]pyridin-4-yl}-N,N-dimethylpyridin-2-amine (racemic, 81 mg, 0.14 mmol), Zn(CN)$_2$ (7.8 mg, 0.06 mmol) and Zn (1.0 mg, 0.014 mmol) under an atmosphere of N$_2$. The reaction was sealed and heated at 95° C. for 18 hours. Water (5 mL) was added, and the aqueous layer was extracted with EtOAc (2×5 mL). The combined organic layers were dried over anhydrous Na$_2$SO$_4$, filtered and concentrated in vacuo. The residue was purified on a silica gel column (0 to 50% EtOAc/hexanes) to afford 4-[5-chloro-2-(dimethylamino)pyridin-3-yl]-2-[(trans)-hexahydrocyclopenta[b][1,4]oxazin-4(4aH)-yl]-3-[(trans-4-methylcyclohexyl)methyl]-3H-imidazo[4,5-c]pyridine-6-carbonitrile (racemic). MS ES calc'd. for C$_{29}$H$_{38}$ClN$_7$O [M+H]$^+$ 534. found 534.

Step 4: Hydroxylamine hydrochloride (4.3 mg, 0.07 mmol) and sodium bicarbonate (7 mg, 0.08 mmol) were dissolved in water (0.4 mL) and stirred at room temperature for 10 minutes, allowing gas to evolve. This solution was then added to a solution of 4-[5-chloro-2-(dimethylamino)pyridin-3-yl]-2-[(trans)-hexahydrocyclopenta[b][1,4]oxazin-4(4aH)-yl]-3-[(trans-4-methylcyclohexyl)methyl]-3H-imidazo[4,5-c]pyridine-6-carbonitrile (racemic, 26 mg, 0.05 mmol) in ethanol (0.2 mL). This reaction mixture was stirred at 90° C. for 1 hour. The reaction mixture was concentrated and diluted with water (2 mL). The solid was filtered off to afford (crude) 4-[5-chloro-2-(dimethylamino)pyridin-3-yl]-

2-[(trans)-hexahydrocyclopenta[b][1,4]oxazin-4(4aH)-yl]-N-hydroxy-3-[(trans-4-methylcyclohexyl)methyl]-3H-imidazo[4,5-c]pyridine-6-carboximidamide (racemic). MS ES calc'd. for $C_{29}H_{39}ClN_8O_2$ [M+H]$^+$ 567. found 567.

Step 5: To a solution of 4-[5-chloro-2-(dimethylamino)pyridin-3-yl]-2-[(trans)-hexahydrocyclopenta[b][1,4]oxazin-4(4aH)-yl]-N-hydroxy-3-[(trans-4-methylcyclohexyl)methyl]-3H-imidazo[4,5-c]pyridine-6-carboximidamide (racemic, 22 mg, 0.075 mmol) and 1,1'-carbonyldiimidazole (12 mg, 0.07 mmol) in acetonitrile (1 mL) was added 1,8-diazabicycloundec-7-ene (23 mg, 0.15 mmol). The reaction was stirred at room temperature for 18 hours. The reaction was then diluted with $CH_2Cl_2$ and washed with water. The organic layer was dried over anhydrous $Na_2SO_4$ and concentrated. The residue was purified on a silica gel column (0 to 10% MeOH/$CH_2Cl_2$) to afford 3-{4-[5-chloro-2-(dimethylamino)pyridin-3-yl]-2-[(trans)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one (racemic). NMR shows 8:2 mixture of rotamers, $^1$H NMR (400 MHz, CD$_3$OD) (for major rotamer) δ 8.27 (d, J=2.8 Hz, 1H), 8.12 (s, 1H), 7.98 (d, J=2.8 Hz, 1H), 3.76-4.04 (m, 3H), 3.35-3.51 (m, 3H), 3.13 (m, 1H), 2.98 (m, 1H), 2.53 (s, 6H), 2.34 (m, 1H), 1.64-1.77 (m, 3H), 1.44-1.56 (m, 3H), 1.12-1.24 (m, 3H), 0.71-0.84 (m, 7H), 0.50-0.62 (m, 2H). MS ES calc'd. for $C_{30}H_{37}ClN_8O_3$ [M+H]$^+$ 593. found 593

Example 18.4

3-{4-[5-chloro-2-(2-hydroxyethoxy)pyridin-3-yl]-2-[(trans)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one (racemic)

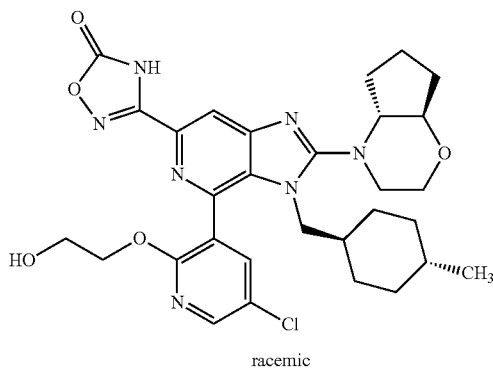 [SMILES: C[C@H]1CC[C@H](Cn2c(N3CCO[C@@H]4CCC[C@H]43)nc3cc(-c4noc(=O)[nH]4)nc(-c4cc(Cl)cnc4OCCO)c32)CC1]

racemic

Step 1: NaH (24 mg, 0.6 mmol) was added to solution of 2-((tert-butyldimethylsilyl)oxy)ethanol (70 mg, 0.4 mmol) in DMF (1.0 mL) at 0° C., and the reaction was stirred at 0° C. for 30 minutes. A solution of 6-chloro-4-(5-chloro-2-fluoropyridin-3-yl)-2-[(trans)-hexahydrocyclopenta[b][1,4]oxazin-4(4aH)-yl]-3-[(trans-4-methylcyclohexyl)methyl]-3H-imidazo[4,5-c]pyridine (racemic, Example 18.1, Step 1; 100 mg, 0.2 mmol) was added, and the reaction was stirred at 0° C. for 30 minutes. The reaction was quenched by adding saturated aqueous NH$_4$Cl solution and extracted using EtOAc. The organic layer was washed with brine, dried over Na$_2$SO$_4$, filtered and concentrated. Purification of the residue on a silica gel column with 0 to 50% EtOAc/hexane afforded 4-[2-(2-{[tert-butyl(dimethyl)silyl]oxy}ethoxy)-5-chloropyridin-3-yl]-6-chloro-2-[(trans)-hexahydrocyclopenta[b][1,4]oxazin-4(4aH)-yl]-3-[(trans-4-methylcyclohexyl)methyl]-3H-imidazo[4,5-c]pyridine (racemic). MS APCl calc'd. for $C_{34}H_{49}Cl_2N_5O_3Si$ [M+H]$^+$ 674. found 674.

Steps 2-4: Following procedures similar to those descrbed in Example 18.1 (Steps 3-5), and starting with 4-[2-(2-{[tert-butyl(dimethyl)silyl]oxy}ethoxy)-5-chloropyridin-3-yl]-6-chloro-2-[(trans)-hexahydrocyclopenta[b][1,4]oxazin-4(4aH)-yl]-3-[(trans-4-methylcyclohexyl)methyl]-3H-imidazo[4,5-c]pyridine (racemic), 3-{4-[2-(2-{[tert-butyl(dimethyl)silyl]oxy}ethoxy)-5-chloropyridin-3-yl]-2-[(trans)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one (racemic) was prepared.

Step 5: TBAF (0.1 mL, 1 M in THF, 0.1 mmol) was added to solution of 3-{4-[2-(2-{[tert-butyl(dimethyl)silyl]oxy]ethoxy)-5-chloropyridin-3-yl}-2-[(trans)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one (racemic, 20 mg, 0.027 mmol) in THF (1.0 mL) at room temperature and stirred for 16 hours. The reaction was concentrated, and the residue was dissolved in $CH_2Cl_2$/IPA (4:1, 15 mL) and washed twice using water (10 mL). The layers were separated, and the organic layer was concentrated under reduced pressure. Purification of the residue on a silica gel column with 0 to 10% MeOH/$CH_2Cl_2$ afforded 3-{4-[5-chloro-2-(2-hydroxyethoxy)pyridin-3-yl]-2-[(trans)-hexahydrocyclopenta[b][1,4]oxazin-4(4aH)-yl]-3-[(trans-4-methylcyclohexyl)methyl]-3H-imidazo[4,5-d]pyridin-6-yl}-1,2,4-oxadiazol-5(4H)-one (racemic). $^1$H NMR (400 MHz, CDCl$_3$) δ 8.28 (br s, 2H), 7.26 (s, 1H), 4.70 (d, J=10.2 Hz, 1H), 3.90 (t, J=12.2 Hz, 2H), 3.70-3.80 (m, 3H), 3.45-3.74 (m, 2H), 3.17-3.32 (m, 2H), 3.10 (t, J=12.4 Hz, 2H), 2.39 (m, 1H), 1.99 (m, 1H), 1.88 (m, 1H), 1.66-1.76 (m, 2H), 1.45-1.62 (m, 6H), 1.02-1.32 (m, 2H), 0.88 (m, 1H), 0.77 (d, J=7.4 Hz, 3H), 0.42-0.60 (m, 2H). MS ES calc'd. for $C_{30}H_{36}ClN_7O_5$ [M−1]$^-$ 608. found 608.

Example 18.9

5-chloro-3-{2-[(4aR,7aR)-hexahydrocyclopenta[b][1,4]oxazin-4(4aH)-yl]-3-[(trans-4-methylcyclohexyl)methyl]-6-(5-oxo-4,5-dihydro-1,2,4-oxadiazol-3-yl)-3H-imidazo[4,5-c]pyridin-4-yl}pyridin-2(1H)-one

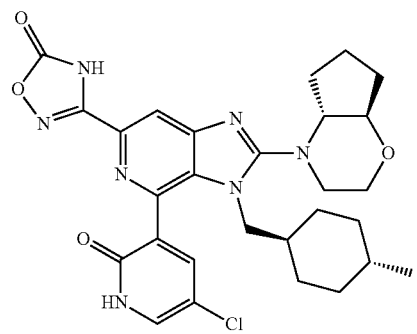 [SMILES: C[C@H]1CC[C@H](Cn2c(N3CCO[C@@H]4CCC[C@H]43)nc3cc(-c4noc(=O)[nH]4)nc(-c4cc(Cl)c[nH]c4=O)c32)CC1]

Step 1: 4,6-dichloro-2-[(trans)-hexahydrocyclopenta[b][1,4]oxazin-4(4aH)-yl]-3-[(trans-4-methylcyclohexyl)methyl]-3H-imidazo[4,5-c]pyridine (racemic, 460 mg, 1.08 mmol), (2-(benzyloxy)-5-chloropyridin-3-yl)boronic acid (purchased from Combi-Blocks Inc.; 372 mg, 1.41 mmol) and 2M aqueous Na$_2$CO$_3$ (5 mL, 10 mmol) were added to degassed 1,2-dimethoxyethane (15 mL), followed by the addition of [1,1'-bis(diphenylphosphino)ferrocene]dichloropalladium (II) (159 mg, 0.2 mmol). The reaction was heated at 90° C. for 6 hours. Water and EtOAc were added. The aqueous layer was extracted several times with EtOAc. The combined organic layers were dried over anhydrous Na$_2$SO$_4$, filtered, and concentrated in vacuo. The residue was purified on a silica gel column (0 to 30% EtOAc/hexanes) to afford 4-[2-(benzyloxy)-5-chloropyridin-3-yl]-6-chloro-2-[(trans)-hexahydrocyclopenta[b][1,4]oxazin-4(4aH)-yl]-3-[(trans-4-methylcyclohexyl)methyl]-3H-imidazo[4,5-c]pyridine (racemic). MS ES calc'd. for C$_{33}$H$_{37}$Cl$_2$N$_5$O$_2$ [M+H]$^+$ 606. found 606.

Step 2: 4-[2-(benzyloxy)-5-chloropyridin-3-yl]-6-chloro-2-[(trans)-hexahydrocyclopenta[b][1,4]oxazin-4(4aH)-yl]-3-[(trans-4-methylcyclohexyl)methyl]-3H-imidazo[4,5-c]pyridine (racemic, 450 mg, 0.74 mmol), zinc cyanide (43 mg, 0.37 mmol) and Pd(PPh$_3$)$_4$ (128 mg, 0.11 mmol) were placed in a dry vial. Degassed DMA (4 mL) was added to the reaction, and the reaction was placed under an atmosphere of Ar, sealed, and heated at 90° C. for 12 hours. The reaction was then cooled to room temperature, and cold water was added slowly. The aqueous layer was extracted with EtOAc. The combined organic layers were dried over Na$_2$SO$_4$, filtered, and concentrated under reduced pressure. Purification of the residue on a silica gel column (0 to 50% EtOAc/hexanes) afforded 4-[2-(benzyloxy)-5-chloropyridin-3-yl]-2-[(trans)-hexahydrocyclopenta[b][1,4]oxazin-4(4aH)-yl]-3-[(trans-4-methylcyclohexyl)methyl]-3H-imidazo[4,5-c]pyridine-6-carbonitrile as a racemic mixture. The enantiomers were separated on a chiral OD column using 2% IPA/98% heptanes. MS ES calc'd. for C$_{34}$H$_{37}$ClN$_6$O$_2$ [M+H]$^+$ 597. found 597.

Steps 3 and 4: Starting with the faster eluting enantiomer of 4-[2-(benzyloxy)-5-chloropyridin-3-yl]-2-[(trans)-hexahydrocyclopenta[b][1,4]oxazin-4(4aH)-yl]-3-[(trans-4-methylcyclohexyl)methyl]-3H-imidazo[4,5-c]pyridine-6-carbonitrile, 3-{4-[2-(benzyloxy)-5-chloropyridin-3-yl]-2-[(4aR,7aR)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one was prepared using procedures similar to those described in Example 18.1 (Steps 4 and 5)

Step 5: To a solution of 3-{4-[2-(benzyloxy)-5-chloropyridin-3-yl]-2-[(4aR,7aR)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one (23 mg, 0.03 mmol) in anhydrous CH$_2$Cl$_2$ at 0° C., Et$_3$SiH (0.029 mL, 0.18 mmol) and PdCl$_2$ (2 mg, 0.01 mmol) were added. The reaction was stirred at 0° C. for 0.5 hour and then concentrated. The residue was purified on a C-18 column eluting with 40% water/60% acetonitrile to afford 5-chloro-3-{2-[(4aR,7aR)-hexahydrocyclopenta[b][1,4]oxazin-4(4aH)-yl]-3-[(trans-4-methylcyclohexyl)methyl]-6-(5-oxo-4,5-dihydro-1,2,4-oxadiazol-3-yl)-3H-imidazo[4,5-c]pyridin-4-yl}pyridin-2(1H)-one. $^1$H NMR (400 MHz, CD$_3$OD) δ 8.09 (s, 1H), 8.04 (br s, 1H), 7.76 (d, J=2.8 Hz, 1H), 4.01 (m, 1H), 3.83-3.93 (m, 3H), 3.62 (m, 1H), 3.54 (m, 1H), 3.38 (m, 1H), 3.12 (m, 1H), 2.96 (m, 1H), 2.28 (m, 1H), 1.97 (m, 1H), 1.49-1.82 (m, 6H), 1.19-1.25 (m, 2H), 0.91-1.00 (m, 2H), 0.78 (d, J=6.4 Hz, 3H), 0.57-0.74 (m, 3H). MS ES calc'd. for C$_{28}$H$_{32}$ClN$_7$O$_4$ [M+H]$^+$ 566. found 566.

Example 18.15

3-{3-[(trans-4-methylcyclohexyl)methyl]-2-[(3R)-3-phenylmorpholin-4-yl]-4-(pyrazin-2-yl)-3H-imidazo[4,5-c]pyridin-6-yl}-1,2,4-oxadiazol-5(4H)-one

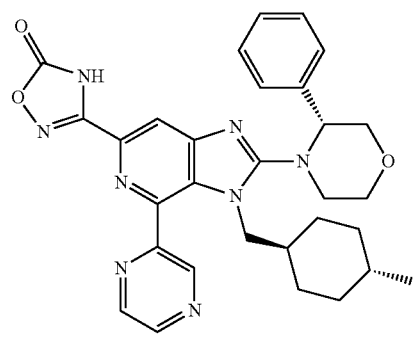

Step 1: In a sealable tube were placed 4,6-dichloro-3-[(trans-4-methylcyclohexyl)methyl]-2-[(3R)-3-phenylmorpholin-4-yl]-3H-imidazo[4,5-c]pyridine (Example 2.1, Step 2; 700 mg, 1.52 mmol), 4-(tributylstannyl)pyridazine (619 mg, 1.67 mmol), and Pd(dppf)Cl$_2$, dichlormethane complex (68 mg, 0.084 mmol). Dioxane (8 mL) that had been purged with nitrogen was added. The tube was sealed and heated to 100° C. for 16 hours. The reaction mixture was cooled to room temperature, filtered through celite, and the filtrate was concentrated under reduced pressure. The residue was purified on a silica gel column using 25-40% ethyl acetate/petroleum ether as eluent to afford 6-chloro-3-[(trans-4-methylcyclohexyl)methyl]-2-[(3R)-3-phenylmorpholin-4-yl]-4-(pyrazin-2-yl)-3H-imidazo[4,5-c]pyridine. MS ES/APCl calc'd. for C$_{28}$H$_{31}$ClN$_6$O [M+H]$^+$ 503. found 503.

Step 2: To a sealable tube were added 6-chloro-3-[(trans-4-methylcyclohexyl)methyl]-2-[(3R)-3-phenylmorpholin-4-yl]-4-(pyrazin-2-yl)-3H-imidazo[4,5-c]pyridine (250 mg, 0.497 mmol) and Zn(CN)$_2$ (46 mg, 0.397 mmol). DMF (4 mL) was added, and the mixture was purged with nitrogen for 5 minutes. Pd(dppf)Cl$_2$ dichloromethane complex (20.2 mg, 0.024 mmol) was added, and the mixture was degassed with nitrogen again for 5 minutes. The tube was sealed and heated to 140° C. for 2.5 hours. The reaction mixture was cooled to room temperature, filtered, diluted with ethyl acetate, and washed with water and brine. The organic layer was dried over anhydrous sodium sulfate, filtered, and concentrated under reduced pressure. The residue was purified on a silica gel column using 30-45% ethyl acetate/petroleum ether as eluent to afford 3-[(trans-4-methylcyclohexyl)methyl]-2-[(3R)-3-phenylmorpholin-4-yl]-4-(pyrazin-2-yl)-3H-imidazo[4,5-c]pyridine-6-carbonitrile. MS ES/APCl calc'd. for C$_{29}$H$_{31}$N$_7$O [M+H]$^+$ 494. found 494.

Steps 3 and 4: Using procedures analogous to those described in Example 2.1 (Steps 5 and 6), 3-[(trans-4-methylcyclohexyl)methyl]-2-[(3R)-3-phenylmorpholin-4-yl]-4-(pyrazin-2-yl)-3H-imidazo[4,5-c]pyridine-6-carbonitrile was converted to 3-{3-[(trans-4-methylcyclohexyl)methyl]-2-[(3R)-3-phenylmorpholin-4-yl]-4-(pyrazin-2-yl)-3H-imidazo[4,5-c]pyridin-6-yl}-1,2,4-oxadiazol-5(4H)-one. MS ES/APCl calc'd. for C$_{30}$H$_{32}$N$_8$O$_3$ [M+H]$^+$ 553. found 553. $^1$H NMR (400 MHz, DMSO-d$_6$): δ 12.91 (s, 1H), 9.73 (s, 1H), 9.46 (d, J=5.2 Hz, 1H), 8.10 (dd, J=2.0, 5.4 Hz, 1H), 7.97 (s, 1H), 7.48 (d, J=7.2 Hz, 2H), 7.31-7.21 (m, 3H), 4.95-4.90 (m, 1H), 4.07-3.82 (m, 5H), 3.67-3.56 (m, 2H), 3.40-3.30 (m, 1H), 1.40-1.30 (m, 2H), 1.10-1.00 (m, 1H), 0.77-0.42 (m, 8H), 0.37-0.34 (m, 2H).

The examples in Table 18 (other than Examples 18.1, 18.4, 18.9, and 18.15) were prepared using procedures similar to those described above. In some cases, enantiomers were separated using chiral columns and standard separation techniques.

TABLE 18

| Ex. | FRET IC$_{50}$ (nM) | Structure | Chemical Name | Salt | [M + H]+ Calc'd | [M + H]+ Obsv'd |
|---|---|---|---|---|---|---|
| 18.1 | 2 | 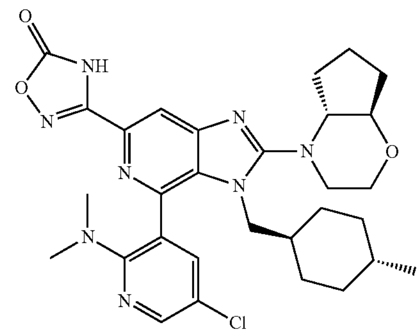 [SMILES: CN(C)c1ncc(Cl)cc1-c1nc(-c2noc(=O)[nH]2)cc2nc(N3CCO[C@@H]4CCC[C@H]43)n(C[C@H]3CC[C@H](C)CC3)c12] | 3-{4-[5-chloro-2-(dimethylamino)pyridin-3-yl]-2-[(trans)-(hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one (racemic) | | 593 | 593 |
| 18.2 | 33 | 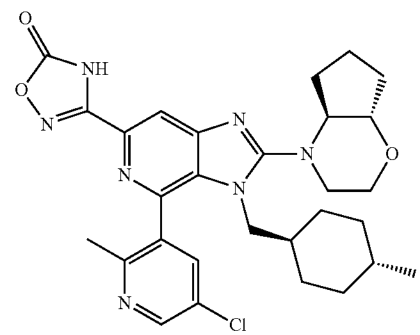 [SMILES: Cc1ncc(Cl)cc1-c1nc(-c2noc(=O)[nH]2)cc2nc(N3CCO[C@H]4CCC[C@@H]43)n(C[C@H]3CC[C@H](C)CC3)c12] | 3-{4-(5-chloro-2-methylpyridin-3-yl)-2-[(4aS,7aS)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one | | 564 | 564 |
| 18.3 | 1 | 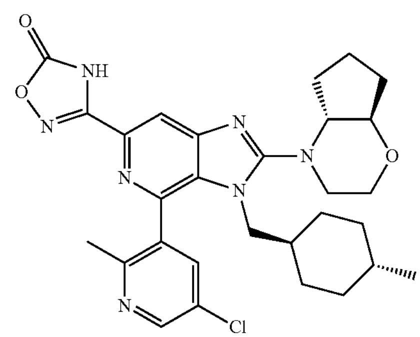 [SMILES: Cc1ncc(Cl)cc1-c1nc(-c2noc(=O)[nH]2)cc2nc(N3CCO[C@@H]4CCC[C@H]43)n(C[C@H]3CC[C@H](C)CC3)c12] | 3-{4-(5-chloro-2-methylpyridin-3-yl)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one | | 564 | 564 |
| 18.4 | 1 | 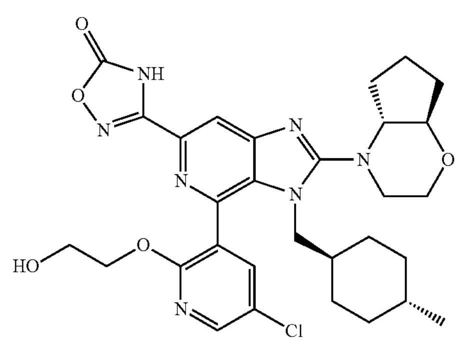 [SMILES: C[C@H]1CC[C@H](Cn2c(N3CCO[C@@H]4CCC[C@H]43)nc3cc(-c4noc(=O)[nH]4)nc(-c4cc(Cl)cnc4OCCO)c32)CC1] | 3-{4-[5-chloro-2-(2-hydroxyethoxy)pyridin-3-yl]-2-[(trans)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one (racemic) | | 608 (M − 1) | 608 (M − 1) |

TABLE 18-continued

| Ex. | FRET IC$_{50}$ (nM) | Structure | Chemical Name | Salt | [M + H]+ Calc'd | [M + H]+ Obsv'd |
|---|---|---|---|---|---|---|
| 18.5 | 24 | 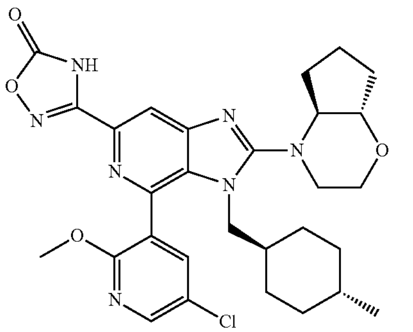 [SMILES: COc1ncc(Cl)cc1-c1nc(-c2noc(=O)[nH]2)cc2nc(N3CCO[C@H]4CCC[C@@H]43)n(C[C@H]3CC[C@H](C)CC3)c12] | 3-{4-(5-chloro-2-methoxypyridin-3-yl)-2-[(4aS,7aS)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one | | 580 | 580 |
| 18.6 | 1 | 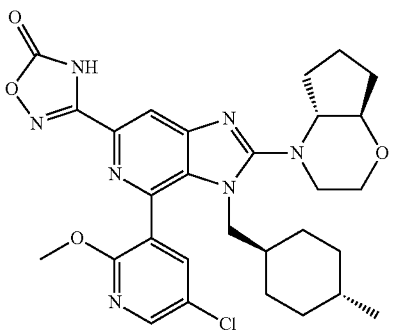 [SMILES: COc1ncc(Cl)cc1-c1nc(-c2noc(=O)[nH]2)cc2nc(N3CCO[C@@H]4CCC[C@H]43)n(C[C@H]3CC[C@H](C)CC3)c12] | 3-{4-(5-chloro-2-methoxypyridin-3-yl)-2-[(4aR,7aR)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one | | 580 | 580 |
| 18.7 | 1 | 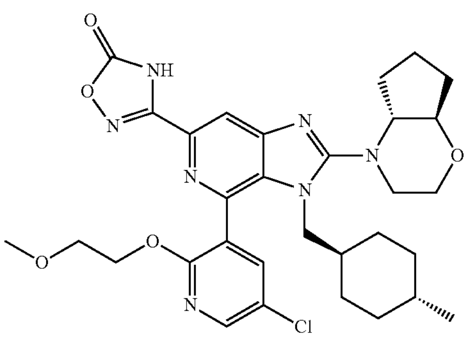 [SMILES: COCCOc1ncc(Cl)cc1-c1nc(-c2noc(=O)[nH]2)cc2nc(N3CCO[C@@H]4CCC[C@H]43)n(C[C@H]3CC[C@H](C)CC3)c12] | 3-{4-[5-chloro-2-(2-methoxyethoxy)pyridin-3-yl]-2-[(4aR,7aR)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one | | 624 | 624 |
| 18.8 | 21 | 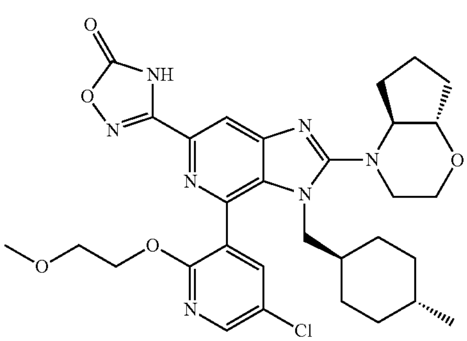 [SMILES: COCCOc1ncc(Cl)cc1-c1nc(-c2noc(=O)[nH]2)cc2nc(N3CCO[C@H]4CCC[C@@H]43)n(C[C@H]3CC[C@H](C)CC3)c12] | 3-{4-[5-chloro-2-(2-methoxyethoxy)pyridin-3-yl]-2-[(4aS,7aS)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one | | 624 | 624 |

TABLE 18-continued

| Ex. | FRET IC$_{50}$ (nM) | Structure | Chemical Name | Salt | [M + H]+ Calc'd | [M + H]+ Obsv'd |
|---|---|---|---|---|---|---|
| 18.9 | 2 | 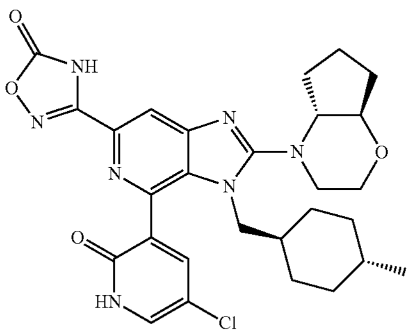 [SMILES: C[C@H]1CC[C@H](Cn2c(N3CCO[C@@H]4CCC[C@H]43)nc3cc(-c4noc(=O)[nH]4)nc(-c4cc(Cl)c[nH]c4=O)c32)CC1] | 5-chloro-3-{2-[(4aR,7aR)-hexahydrocyclopenta[b][1,4]oxazin-4(4aH)-yl]-3-[(trans-4-methylcyclohexyl)methyl]-6-(5-oxo-4,5-dihydro-1,2,4-oxadiazol-3-yl)-3H-imidazo[4,5-c]pyridin-4-yl}pyridin-2(1H)-one | | 566 | 566 |
| 18.10 | 2 | 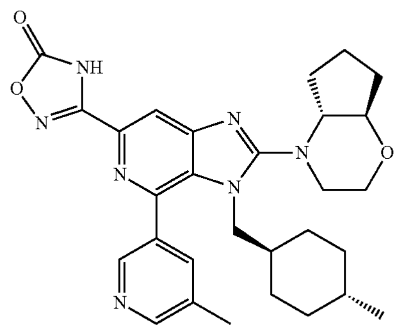 [SMILES: Cc1cncc(-c2nc(-c3noc(=O)[nH]3)cc3nc(N4CCO[C@@H]5CCC[C@H]54)n(C[C@H]4CC[C@H](C)CC4)c23)c1] | 3-{2-[(4aR,7aR)-hexahydrocyclopenta[b][1,4]oxazin-4(4aH)-yl]-3-[(trans-4-methylcyclohexyl)methyl]-4-(5-methylpyridin-3-yl)-3H-imidazo[4,5-c]pyridin-6-yl}-1,2,4-oxadiazol-5(4H)-one | | 528 (M − 1) | 528 (M − 1) |
| 18.11 | 210 | 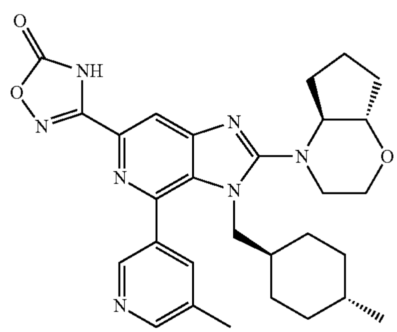 [SMILES: Cc1cncc(-c2nc(-c3noc(=O)[nH]3)cc3nc(N4CCO[C@H]5CCC[C@@H]54)n(C[C@H]4CC[C@H](C)CC4)c23)c1] | 3-{2-[(4aS,7aS)-hexahydrocyclopenta[b][1,4]oxazin-4(4aH)-yl]-3-[(trans-4-methylcyclohexyl)methyl]-4-(5-methylpyridin-3-yl)-3H-imidazo[4,5-c]pyridin-6-yl}-1,2(4-oxadiazol-5(4H)-one | | 528 (M − 1) | 528 (M − 1) |
| 18.12 | 2 | 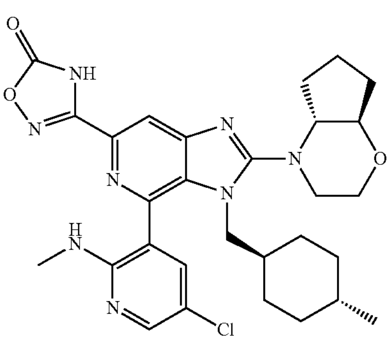 [SMILES: CNc1ncc(Cl)cc1-c1nc(-c2noc(=O)[nH]2)cc2nc(N3CCO[C@@H]4CCC[C@H]43)n(C[C@H]3CC[C@H](C)CC3)c12] | 3-{4-[5-chloro-2-(methylamino)pyridin-3-yl]-2-[(trans)-hexahydrocyclopenta[b][1,4]oxazin-4(4aH)-yl]-3-[(trans-4-methylcyclohexyl)methyl]-3H-imidazo[4,5-c]pyridin-6-yl}-1,2,4-oxadiazol-5(4H)-one (racemic) | | 579 | 579 |

TABLE 18-continued

| Ex. | FRET IC$_{50}$ (nM) | Structure | Chemical Name | Salt | [M + H]+ Calc'd | [M + H]+ Obsv'd |
|---|---|---|---|---|---|---|
| 18.13 | 1 | 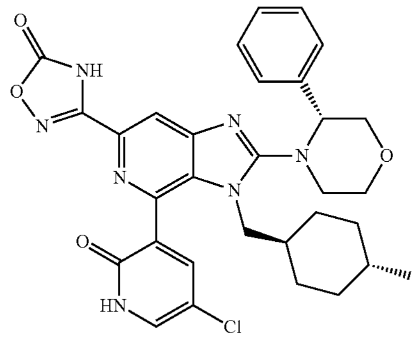 [SMILES: C[C@H]1CC[C@H](Cn2c(N3CCOC[C@H]3c3ccccc3)nc3cc(-c4noc(=O)[nH]4)nc(-c4cc(Cl)c[nH]c4=O)c32)CC1] | 5-chloro-3-{3-[(trans-4-methylcyclohexyl)methyl]-6-(5-oxo-4,5-dihydro-1,2,4-oxadiazol-3-yl)-2-[(3R)-3-phenylmorpholin-4-yl]-3H-imidazo[4,5-c]pyridin-4-yl}pyridin-2(1H)-one | | 602 | 602 |
| 18.14 | 65 | 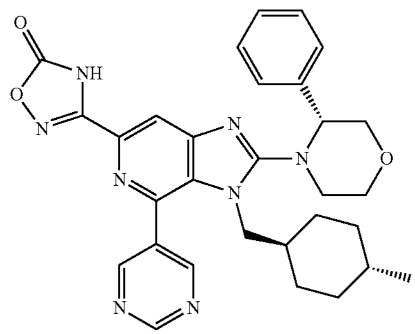 | 3-{3-[(trans-4-methylcyclohexyl)methyl]-2-[(3R)-3-phenylmorpholin-4-yl]-4-pyrimidin-5-yl-3H-imidazo[4,5-c]pyridin-6-yl}-1,2,4-oxadiazol-5(4H)-one | | 553 | 553 |
| 18.15 | 119 | 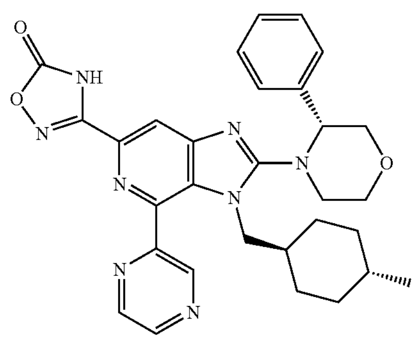 [SMILES: C[C@H]1CC[C@H](Cn2c(N3CCOC[C@H]3c3ccccc3)nc3cc(-c4noc(=O)[nH]4)nc(-c4cnccn4)c32)CC1] | 3-{3-[{trans-4-methylcyclohexyl)methyl]-2-[(3R)-3-phenylmorpholin-4-yl]-4-(pyrazin-2-yl)-3H-imidazo[4,5-c]pyridin-6-yl}-1,2,4-oxadiazol-5(4H)-one | TFA | 553 | 553 |
| 18.16 | 72 | 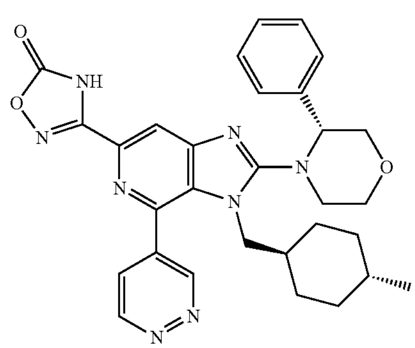 [SMILES: C[C@H]1CC[C@H](Cn2c(N3CCOC[C@H]3c3ccccc3)nc3cc(-c4noc(=O)[nH]4)nc(-c4ccnnc4)c32)CC1] | 3-{3-[{trans-4-methylcyclohexyl)methyl]-2-[(3R)-3-phenylmorpholin-4-yl]-4-(pyridazin-4-yl)-3H-imidazo[4,5-c]pyridin-6-yl}-1,2,4-oxadiazol-5(4H)-one | TFA | 553 | 553 |

TABLE 18-continued

| Ex. | FRET IC$_{50}$ (nM) | Structure | Chemical Name | Salt | [M + H]+ Calc'd | [M + H]+ Obsv'd |
|---|---|---|---|---|---|---|
| 18.17 | 112 | 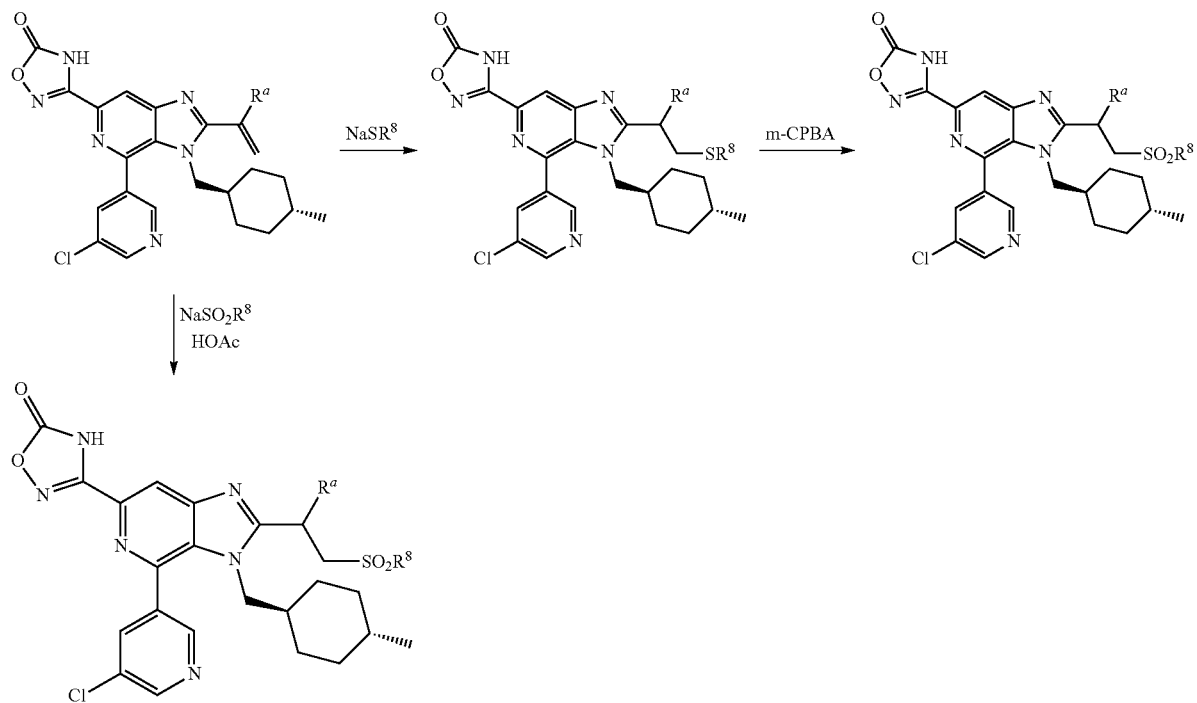 | 3-{3-[((rans-4-methylcyclohexyl)methyl]-2-[(3R)-3-phenylmorpholin-4-yl]-4-(pyridazin-3-yl)-3H-imidazo[4,5-c]pyridin-6-yl}-1,2,4-oxadiazol-5(4H)-one | TFA | 553 | 553 |

Scheme 23

Example 19.1

3-{4-(5-chloropyridin-3-yl)-3-[(trans-4-methylcyclohexyl)methyl]-2-[1-methyl-2-(methylsulfanyl)ethyl]-3H-imidazo[4,5-c]pyridin-6-yl}-1,2,4-oxadiazol-5(4H)-one (racemate)

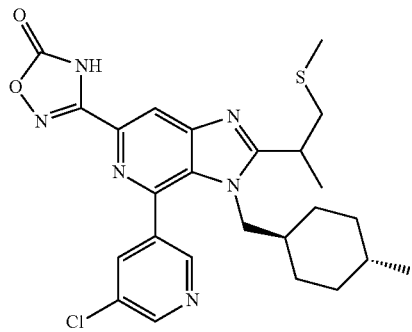 [SMILES: CSCC(C)c1nc2cc(-c3noc(=O)[nH]3)nc(-c3cncc(Cl)c3)c2n1C[C@H]1CC[C@H](C)CC1]

3-[4-(5-chloropyridin-3-yl)-3-[(trans-4-methylcyclohexyl)methyl]-2-(1-methylethenyl)-3H-imidazo[4,5-c]pyridin-6-yl]-1,2,4-oxadiazol-5(4H)-one (synthesized in a manner similar to Example 9.1; 100 mg, 0.22 mmol) was taken up in MeOH (1.5 mL) at room temperature, and sodium thiomethoxide (376 mg, 5.4 mmol) was added. The reaction was sealed and heated at 65° C. for 2 hours. The reaction was then quenched with saturated ammonium chloride and extracted with ethyl acetate. The organic layer was washed with brine, dried over anhydrous MgSO$_4$, filtered, and concentrated under reduced pressure. The residue was purified by silica gel column chromatography (0 to 100% EtOAc/hexanes) to afford 3-{4-(5-chloropyridin-3-yl)-3-[(trans-4-methylcyclohexyl)methyl]-2-[1-methyl-2-(methylsulfanyl)ethyl]-3H-imidazo[4,5-c]pyridin-6-yl}-1,2,4-oxadiazol-5(4H)-one (racemate). $^1$H NMR (300 MHz, CDCl$_3$) δ 8.69-8.74 (m, 1H), 8.57-8.62 (m, 1H), 8.43 (s, 1H), 7.89-7.94 (m, 1H), 3.71-3.93 (m, 2H), 3.22-3.38 (m, 1H), 3.06-3.19 (m, 1H), 2.88-2.99 (m, 1H), 2.07 (s, 3H), 1.48-1.59 (m, 1H), 1.53 (d, J=6.7 Hz, 3H), 1.22-1.38 (m, 2H), 1.08-1.21 (m, 1H), 0.85-1.07 (m, 3H), 0.78 (d, J=6.4 Hz, 3H), 0.66-0.75 (m, 1H), 0.47-0.66 (m, 2H); MS ES calc'd. for $C_{25}H_{29}ClN_6O_2S$ [M+H]$^+$ 513. found 513.

Example 19.2

3-{4-(5-chloropyridin-3-yl)-3-[(trans-4-methylcyclohexyl)methyl]-2-[1-methyl-2-(methylsulfonyl)ethyl]-3H-imidazo[4,5-c]pyridin-6-yl}-1,2,4-oxadiazol-5(4H)-one (racemate)

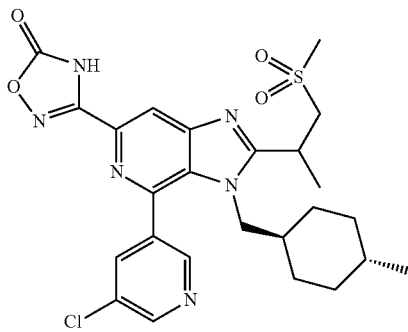 [SMILES: CC(CS(C)(=O)=O)c1nc2cc(-c3noc(=O)[nH]3)nc(-c3cncc(Cl)c3)c2n1C[C@H]1CC[C@H](C)CC1]

To 3-{4-(5-chloropyridin-3-yl)-3-[(trans-4-methylcyclohexyl)methyl]-2-[1-methyl-2-(methylsulfanyl)ethyl]-3H-imidazo[4,5-c]pyridin-6-yl}-1,2,4-oxadiazol-5(4H)-one (Example 19.1, 10 mg, 0.02 mmol) in dichloromethane (1.0 mL) was added m-CPBA (10 mg, 0.06 mmol) at 0° C., and the reaction mixture was stirred for 1 hour at 0° C. and then for 14 hours at room temperature under a nitrogen atmosphere. The reaction was quenched with aqueous saturated NaHCO$_3$ solution (2 mL) and extracted with ethyl acetate (3×10 mL). The combined organic extracts were washed with brine (5 mL), dried over anhydrous Na$_2$SO$_4$, filtered, and concentrated. Purification of the residue by C-18 reverse phase chromatography (0 to 100% CH$_3$CN/H$_2$O) afforded 3-{4-(5-chloropyridin-3-yl)-3-[(trans-4-methylcyclohexyl)methyl]-241-methyl-2-(methylsulfonyl)ethyl]-3H-imidazo[4,5-c]pyridin-6-yl}-1,2,4-oxadiazol-5(4H)-one (racemate). $^1$H NMR (300 MHz, CD$_3$OD) δ 8.72-8.85 (m, 2H), 8.24-8.35 (m, 2H), 3.81-4.17 (m, 4H), 3.48-3.79 (m, 1H), 2.98 (s, 3H), 1.99-2.14 (m, 1H), 1.46-1.65 (m, 1H), 1.59 (d, J=6.7 Hz, 3H), 1.02-1.37 (m, 3H), 0.82-1.02 (m, 3H), 0.78 (d, J=6.7 Hz, 3H), 0.44-0.68 (m, 2H); MS ES calc'd. for $C_{25}H_{29}ClN_6O_4S$ [M+H]$^+$ 545. found 545.

Example 19.5

3-[4-(5-chloropyridin-3-yl)-3-[(trans-4-methylcyclohexyl)methyl]-2-{2-methyl-1-[(methylsulfonyl)methyl]propyl}-3H-imidazo[4,5-c]pyridin-6-yl]-1,2,4-oxadiazol-5(4H)-one (racemic)

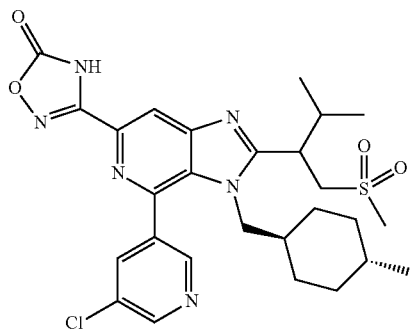 [SMILES: CC(C)C(CS(C)(=O)=O)c1nc2cc(-c3noc(=O)[nH]3)nc(-c3cncc(Cl)c3)c2n1C[C@H]1CC[C@H](C)CC1]

To a stirred solution of 3-{4-(5-chloropyridin-3-yl)-2-(3-methylbut-1-en-2-yl)-3-[(trans-4-methylcyclohexyl)methyl]-3H-imidazo[4,5-c]pyridin-6-yl}-1,2,4-oxadiazol-5(4H)-one (synthesized in a manner similar to Example 9.1; 20 mg, 0.046 mmol) in dry ethanol (0.7 mL) was added sodium methanesulfinate (47 mg, 0.46 mmol) followed by acetic acid (27 μL, 0.046 mmol). The reaction mixture was heated to 60° C. for 12 h. The reaction mixture was then cooled to room temperature and concentrated under reduced pressure. The residue was dissolved in ethyl acetate and washed with water and brine. The organic layer was dried over anhydrous Na$_2$SO$_4$, filtered, and concentrated under reduced pressure. The residue obtained was purified by reverse phase prep-HPLC (Kromasil C18, water/MeOH+0.1% TFA) to give 3-[4-(5-chloropyridin-3-yl)-3-[(trans-4-methylcyclohexyl)methyl]-2-{2-methyl-1-[(methylsulfonyl)methyl]propyl}-3H-imidazo[4,5-c]pyridin-6-yl]-1,2,4-oxadiazol-5(4H)-one (TFA salt, racemate). $^1$H NMR (400 MHz, DMSO-d$_6$): δ 12.90 (br s, 1H), 8.86 (s, 1H), 8.85 (s, 1H), δ 8.43 (s, 1H), 8.24 (s, 1H), 4.07-3.96 (m, 2H), 3.84-3.79 (m, 1H), 3.67-3.64 (m, 2H), 3.02 (s, 3H), 2.21-2.16 (m, 1H), 1.39 (d, J=11.6 Hz, 2H), 1.22-1.15 (m, 2H), 1.04 (d, J=6.7 Hz, 3H), 0.83 (d, J=6.7 Hz, 3H), 0.70 (d, J=6.5 Hz, 3H), 0.78-0.41 (m, 6H). MS ES/APCl calc'd. for $C_{27}H_{33}ClN_6O_4S$ [M+H]$^+$ 573. found 573.

The examples in Table 19 (other than Examples 19.1, 19.2, and 19.5) were prepared using procedures similar to those described above.

TABLE 19

| Ex. | FRET IC$_{50}$ (nM) | Structure | Chemical Name | Salt | [M + H]+ Calc'd | [M + H]+ Obsv'd |
|---|---|---|---|---|---|---|
| 19.1 | 7 | 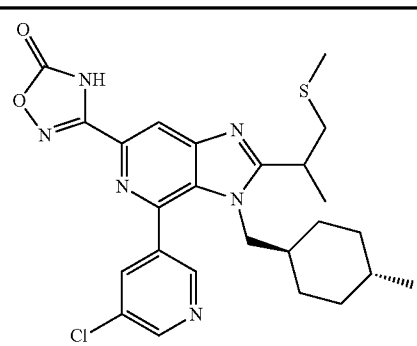 | 3-{4-(5-chloropyridin-3-yl)-3-[(trans-4-methylcyclohexyl)methyl]-2-[1-methyl-2-(methylsulfanyl)ethyl]-3H-imidazo[4,5-c]pyridin-6-yl}-1,2,4-oxadiazol-5(4H)-one (racemate) | | 513 | 513 |

TABLE 19-continued

| Ex. | FRET IC$_{50}$ (nM) | Structure | Chemical Name | Salt | [M + H]+ Calc'd | [M + H]+ Obsv'd |
|---|---|---|---|---|---|---|
| 19.2 | 37 | 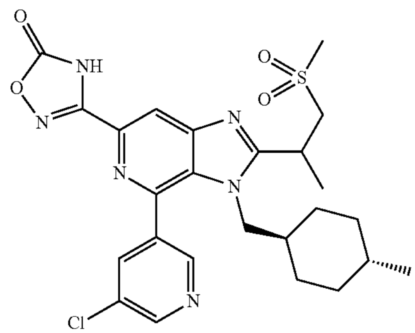 [SMILES: CC(CS(C)(=O)=O)c1nc2cc(-c3noc(=O)[nH]3)nc(-c3cncc(Cl)c3)c2n1C[C@H]1CC[C@H](C)CC1] | 3-{4-(5-chloropyridin-3-yl)-3-[(trans-4-methylcyclohexyl)methyl]-2-[1-methyl-2-(methylsulfonyl)ethyl]-3H-imidazo[4,5-c]pyridin-6-yl}-1,2,4-oxadiazol-5(4H)-one (racemate) | | 545 | 545 |
| 19.3 | 2 | 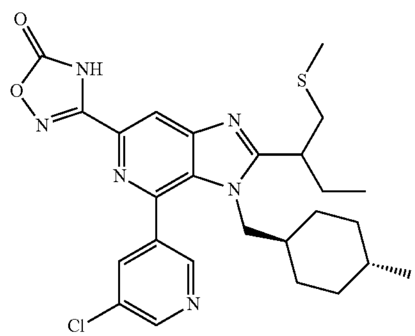 [SMILES: CCC(CSC)c1nc2cc(-c3noc(=O)[nH]3)nc(-c3cncc(Cl)c3)c2n1C[C@H]1CC[C@H](C)CC1] | 3-[4-(5-chloropyridin-3-yl)-3-[(trans-4-methylcyclohexyl)methyl]-2-{1-[(methylsulfanyl)methyl]propyl}-3H-imidazo[4,5-c]pyridin-6-yl]-1,2,4-oxadiazol-5(4H)-one (racemate) | | 527 | 527 |
| 19.4 | 7 | 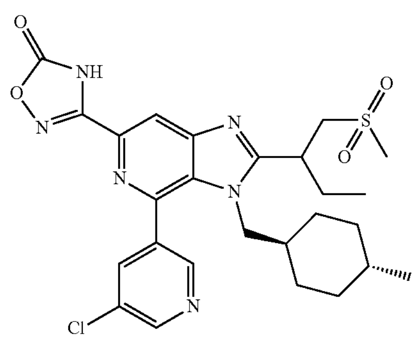 [SMILES: CCC(CS(C)(=O)=O)c1nc2cc(-c3noc(=O)[nH]3)nc(-c3cncc(Cl)c3)c2n1C[C@H]1CC[C@H](C)CC1] | 3-[4-(5-chloropyridin-3-yl)-3-[(trans-4-methylcyclohexyl)methyl]-2-{1-[(methylsulfonyl)methyl]propyl}-3H-imidazo[4,5-c]pyridin-6-yl]-1,2,4-oxadiazol-5(4H)-one (racemate) | | 559 | 559 |
| 19.5 | 5 | 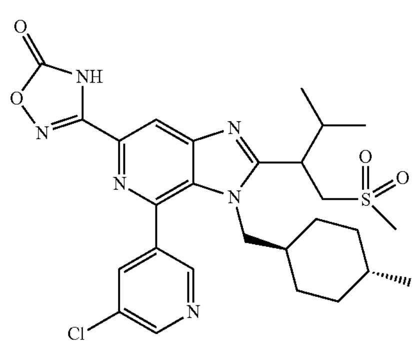 [SMILES: CC(C)C(CS(C)(=O)=O)c1nc2cc(-c3noc(=O)[nH]3)nc(-c3cncc(Cl)c3)c2n1C[C@H]1CC[C@H](C)CC1] | 3-[4-(5-chloropyridin-3-yl)-3-[(trans-4-methylcyclohexyl)methyl]-2-{2-methyl-1-[(methylsulfonyl)methyl]propyl}-3H-imidazo[4,5-c]pyridin-6-yl]-1,2,4-oxadiazol-5(4H)-one (racemic) | TFA | 573 | 573 |

Scheme 24

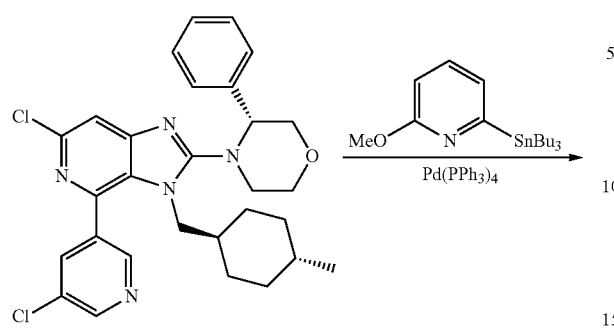

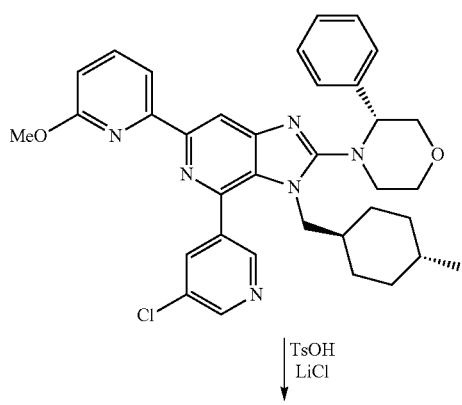

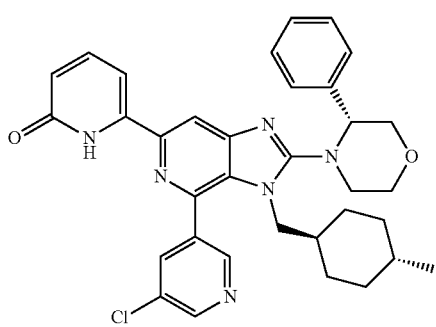

Example 20.1

6-{4-(5-chloropyridin-3-yl)-3-[(trans-4-methylcyclohexyl)methyl]-2-[(3R)-3-phenylmorpholin-4-yl]-3H-imidazo[4,5-c]pyridin-6-yl}pyridin-2(1H)-one

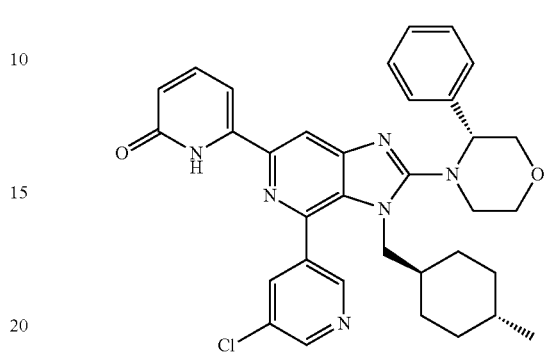

Step 1: A mixture of 6-chloro-4-(5-chloropyridin-3-yl)-3-[(trans-4-methylcyclohexyl)methyl]-2-[(3R)-3-phenylmorpholin-4-yl]-3H-imidazo[4,5-c]pyridine (Example 2.1, Step 3; 130 mg, 0.242 mmol), 2-methoxy-6-(tri-n-butylstannyl)pyridine (122 mg, 0.308 mmol), and Pd(PPh$_3$)$_4$ (28.0 mg, 0.0242 mmol) in DMF (2.9 mL) was degassed and heated at 100° C. for 16 hours under a nitrogen atmosphere. The reaction mixture was cooled to room temperature and diluted with water (10 mL). The reaction mixture was extracted with ethyl acetate (3×10 mL). The combined organic layers were washed with saturated aqueous KF solution (10 mL), water (2×10 mL) and brine (10 mL). The organic layer was dried over anhydrous Na$_2$SO$_4$, filtered, and concentrated. Purification of the residue on a silica gel column (0 to 50% EtOAc/hexanes) afforded 4-(5-chloropyridin-3-yl)-6-(6-methoxypyridin-2-yl)-3-[(trans-4-methylcyclohexyl)methyl]-2-[(3R)-3-phenylmorpholin-4-yl]-3H-imidazo[4,5-c]pyridine. MS ES calc'd. for C$_{35}$H$_{37}$ClN$_6$O$_2$ [M+H]$^+$ 609. found 609.

Step 2: A mixture of 4-(5-chloropyridin-3-yl)-6-(6-methoxypyridin-2-yl)-3-[(trans-4-methylcyclohexyl)methyl]-2-[(3R)-3-phenylmorpholin-4-yl]-3H-imidazo[4,5-c]pyridine (63.0 mg, 0.104 mmol), p-toluenesulfonic acid monohydrate (198 mg, 1.04 mmol), and lithium chloride (44.1 mg, 1.04 mmol) in DMA (1.0 mL) was heated at 100° C. for 24 hours under a nitrogen atmosphere. The reaction mixture was cooled to room temperature and diluted with water (10 mL). The reaction mixture was extracted with dichloromethane (3×10 mL). The combined organic layers were washed with water (2×10 mL), and brine (10 mL). The organic layer was dried over anhydrous Na$_2$SO$_4$, filtered, and concentrated. Purification of the residue on a silica gel column (0 to 10% CH$_2$Cl$_2$/MeOH) afforded 6-{4-(5-chloropyridin-3-yl)-3-[(trans-4-methylcyclohexyl)methyl]-2-[(3R)-3-phenylmorpholin-4-yl]-3H-imidazo[4,5-c]pyridin-6-yl}pyridin-2(1H)-one. $^1$H NMR (400 MHz, CDCl$_3$) δ 10.69 (br s, 1H), 8.71 (d, J=2.4 Hz, 1H), 8.50 (m, 1H), 8.02 (s, 1H), 7.86 (m, 1H), 7.50 (dd, J=9.0, 6.8 Hz, 1H), 7.32-7.41 (m, 2H), 7.23-7.31 (m, 3H), 6.79-6.86 (m, 1H), 6.58 (d, J=9.0 Hz, 1H), 4.66 (m, 1H), 4.08-4.14 (m, 2H), 3.92-4.07 (m, 2H), 3.62-3.74 (m, 1H), 3.36-3.54 (m, 3H), 1.39-1.51 (m, 2H), 1.02-1.18 (m, 1H), 0.80-0.94 (m, 1H), 0.75 (d, J=6.4 Hz, 3H), 0.55-0.71 (m, 4H), 0.36-0.52 (m, 2H). MS ES calc'd. for C$_{34}$H$_{35}$ClN$_6$O$_2$ [M+H]$^+$ 595. found 595.

Example 20.1 was prepared as described above.

TABLE 20
| Ex. | FRET IC$_{50}$ (nM) | Structure | Chemical Name | Salt | [M + H]+ Calc'd | [M + H]+ Obsv'd |
|---|---|---|---|---|---|---|
| 201.1 | 70 | 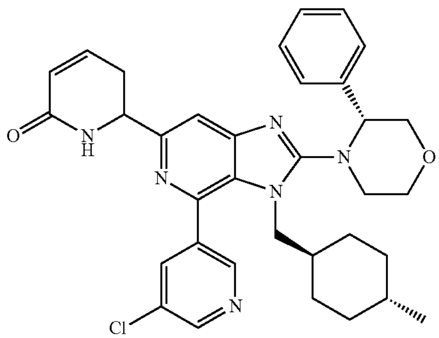 [SMILES: C[C@H]1CC[C@H](Cn2c(N3CCOC[C@H]3c3ccccc3)nc3cc(C4CC=CC(=O)N4)nc(-c4cncc(Cl)c4)c32)CC1] | 6-{4-(5-chloropyridin-3-yl)-3-[(trans-4-methylcyclohexyl)methyl]-2-[(3R)-3-phenylmorpholin-4-yl]-3H-imidazo[4,5-c]pyridin-6-yl}pyridin-2(1H)-one | | 595 | 595 |
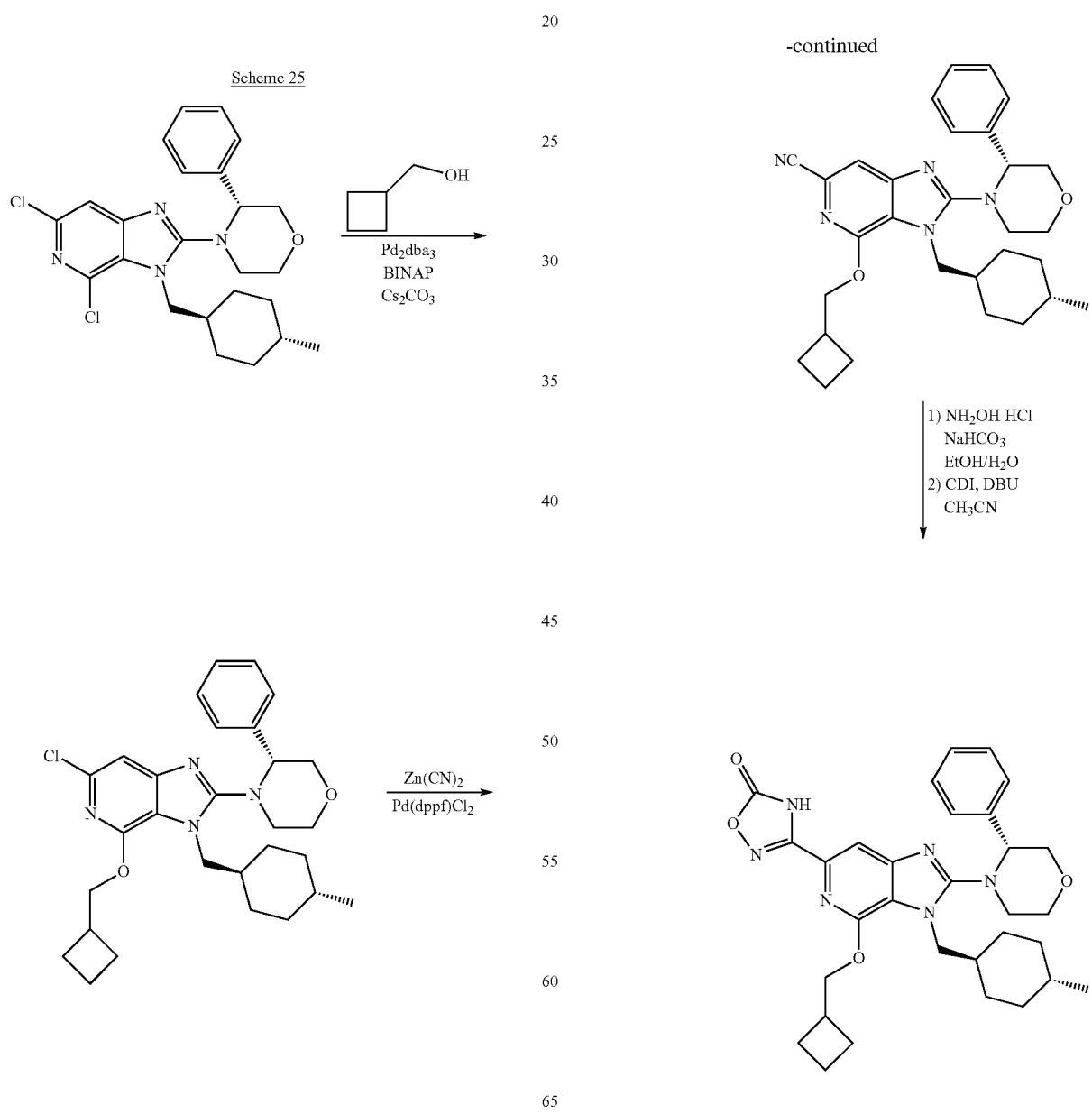
Scheme 25

Scheme 26

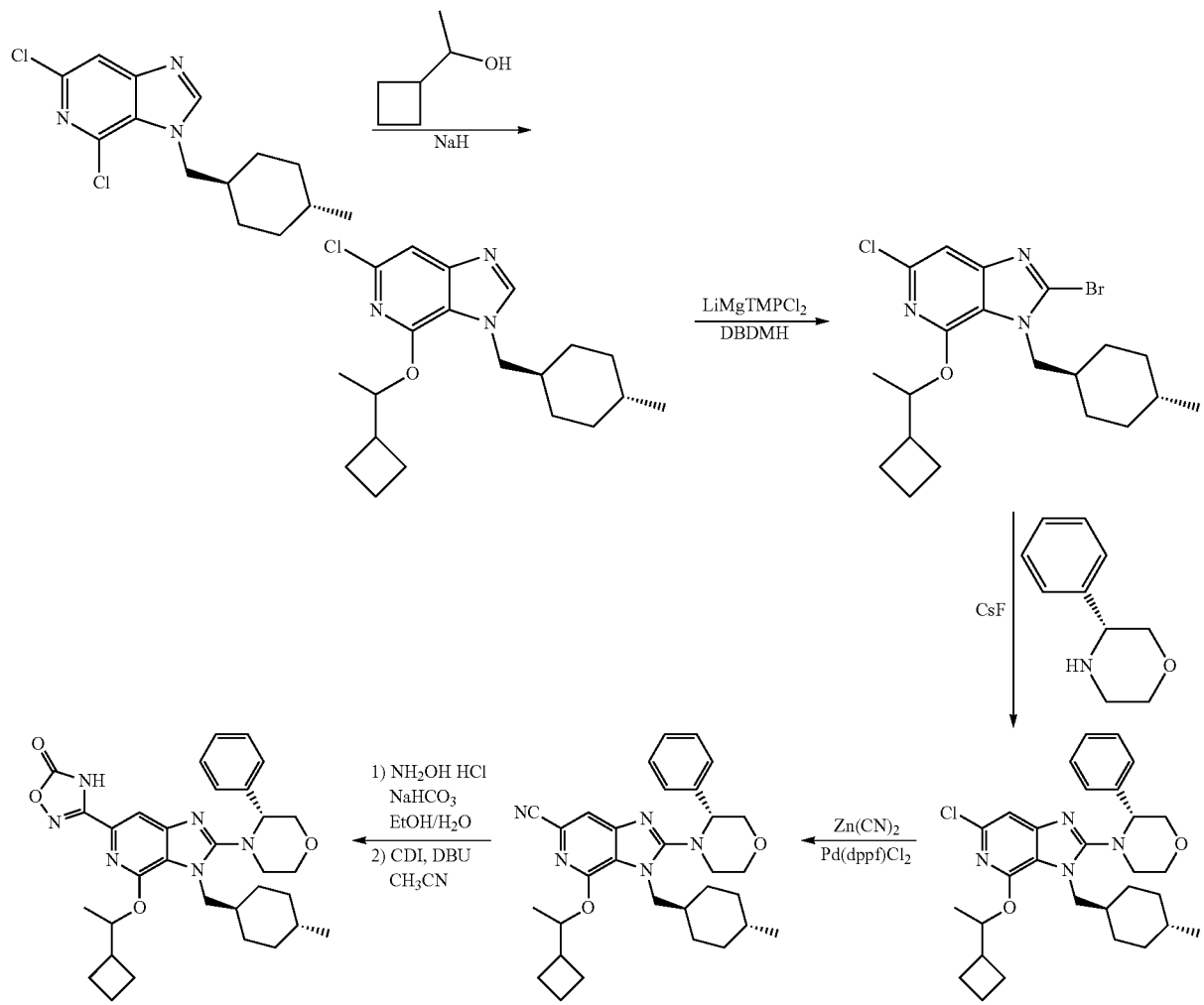

Example 21.1

3-{4-(cyclobutylmethoxy)-3-[(trans-4-methylcyclohexyl)methyl]-2-[(3R)-3-phenylmorpholin-4-yl]-3H-imidazo[4,5-c]pyridin-6-yl}-1,2,4-oxadiazol-5(4H)-one

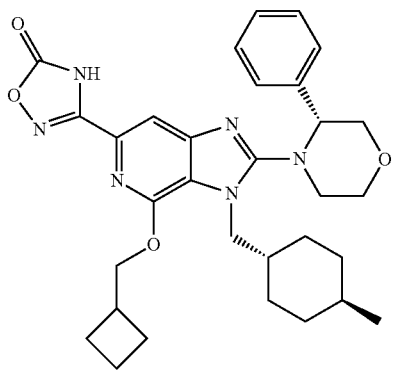 [SMILES: C[C@H]1CC[C@H](Cn2c(N3CCOC[C@H]3c3ccccc3)nc3cc(-c4noc(=O)[nH]4)nc(OCC4CCC4)c32)CC1]

Step 1: To a solution of 4,6-dichloro-3-[(trans-4-methylcyclohexyl)methyl]-2-[(3R)-3-phenylmorpholin-4-yl]-3H-imidazo[4,5-c]pyridine (Example 2.1, Step 2; 400 mg, 0.87 mmol) in DMSO (5 mL) was added cyclobutylmethanol (337 mg, 3.92 mmol), $Cs_2CO_3$ (848 mg, 2.61 mmol) and BINAP (108 mg, 0.17 mmol). The reaction mixture was deoxygenated by purging with nitrogen for 10 minutes and then $Pd_2dba_3$ (159 mg, 0.17 mmol) was added. The reaction was again deoxygenated for 5 minutes by purging with nitrogen. The reaction flask was sealed, and the mixture was heated at 100° C. for 16 h. The reaction mixture was then cooled, diluted with water (30 ml) and EtOAc (60 mL), and the organic layer was separated. The organic layer was washed with water (2×10 mL), followed by saturated brine (2×30 mL). The organic layer was dried over anhydrous $Na_2SO_4$, filtered, and concentrated. The residue was purified on a silica gel column (30% EtOAc/petroleum ether) to yield 6-chloro-4-(cyclobutylmethoxy)-3-[(trans-4-methylcyclohexyl)methyl]-2-[(3R)-3-phenylmorpholin-4-yl]-3H-imidazo[4,5-c]pyridine. MS ES/APCl calc'd. for $C_{29}H_{37}ClN_4O_2$ $[M+H]^+$ 509. found 509.

Step 2: To a solution of 6-chloro-4-(cyclobutylmethoxy)-3-[(trans-4-methylcyclohexyl)methyl]-2-[(3R)-3-phenylmorpholin-4-yl]-3H-imidazo[4,5-c]pyridine (120 mg, 0.23 mmol) in DMF (1.5 mL) was added $Zn(CN)_2$ (83 mg, 0.70 mmol), and the mixture was deoxygenated by purging with nitrogen for 10 minutes. $Pd(dppf)Cl_2$ dichloromethane adduct (57.7 mg, 0.07 mmol) was added and the reaction was again deoxygenated for 5 minutes. The reaction flask was sealed and the mixture was heated at 140° C. for 16 h. The reaction mixture was then cooled to room temperature, diluted with EtOAc (50 mL), and the organic layer was separated. The organic layer was washed with water (2×50 mL) followed by saturated brine solution (2×30 mL), dried over anhydrous $Na_2SO_4$, filtered, and concentrated. The residue was purified by silica gel chromatography (40% EtOAc/petroleum ether) to yield 4-(cyclobutylmethoxy)-3-[(trans-4-methylcyclohexyl)methyl]-2-[(3R)-3-phenylmorpholin-4-yl]-3H-imidazo[4,5-c]pyridine-6-carbonitrile. MS ES/APCl calc'd. for $C_{30}H_{37}N_6O_2$ [M+H]$^+$ 500. found 500.

Steps 3 & 4: Using procedures similar to those described for Example 2.1 (Steps 5 and 6), 4-(cyclobutylmethoxy)-3-[(trans-4-methylcyclohexyl)methyl]-2-[(3R)-3-phenylmorpholin-4-yl]-3H-imidazo[4,5-c]pyridine-6-carbonitrile was converted to 3-{4-(cyclobutylmethoxy)-3-[(trans-4-methylcyclohexyl)methyl]-2-[(3R)-3-phenylmorpholin-4-yl]-3H-imidazo[4,5-c]pyridin-6-yl}-1,2,4-oxadiazol-5(4H)-one. MS ES/APCl calc'd. for $C_{31}H_{38}N_6O_4$ [M+H]$^+$ 559. found 559. $^1$H NMR (400 MHz, DMSO-$d_6$): δ 12.66 (s, 1H), 7.58 (s, 1H), 7.39-7.37 (m, 2H), 7.24-7.15 (m, 3H), 4.60-4.54 (m, 2H), 4.43 (dd, J=6.7, 11.0 Hz, 1H), 4.25-4.15 (m, 1H), 4.05-3.95 (m, 1H), 3.92-3.82 (m, 4H), 3.45-3.35 (m, 1H), 3.12-3.05 (m, 1H), 2.80-2.73 (m, 1H), 2.12-2.09 (m, 2H), 1.96-1.85 (m, 4H), 1.68-1.60 (m, 2H), 1.32-1.29 (m, 3H), 1.20-1.16 (m, 1H), 1.01-0.99 (m, 2H), 0.84 (d, J=6.5 Hz, 3H), 0.80-0.77 (m, 2H).

Example 21.2

3-{4-(1-cyclobutylethoxy)-3-[(trans-4-methylcyclohexyl)methyl]-2-[(3R)-3-phenylmorpholin-4-yl]-3H-imidazo[4,5-c]pyridin-6-yl}-1,2,4-oxadiazol-5(4H)-one (mixture of diastereomers)

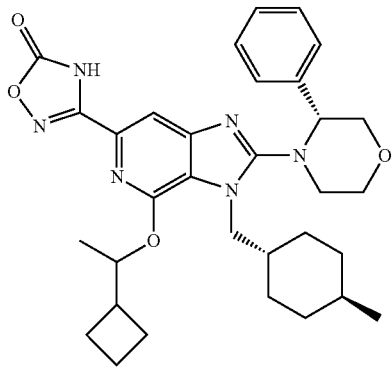 [SMILES: CC(Oc1nc(-c2noc(=O)[nH]2)cc2nc(N3CCOC[C@H]3c3ccccc3)n(C[C@H]3CC[C@H](C)CC3)c12)C1CCC1]

Step 1: To a stirred solution of 1-cyclobutylethan-1-ol (1.76 g, 17.60 mmol) in DMF (10 mL) was added 60% NaH (1.4 g, 35.19 mmol) in several portions at 0° C. After stirring for 20 minutes, 4,6-dichloro-3-((trans-4-methylcyclohexyl)methyl)-3H-imidazo[4,5-c]pyridine (Preparative Example 2.3, 3.5 g, 11.73 mmol) in DMF (30 mL) was added slowly over a time period of 10 minutes. The reaction was then warmed to room temperature and stirred for 16 h. After this time, the reaction was quenched with ice, diluted with water (80 mL), and extracted with ethyl acetate (3×30 mL). The combined organic extracts were washed with water (25 mL) and brine (25 mL), dried over anhydrous $Na_2SO_4$, filtered, and concentrated. The residue was purified by silica gel chromatography (eluting with (12-15% EtOAc/petroleum ether) to yield 6-chloro-4-(1-cyclobutylethoxy)-3-((trans-4-methylcyclohexyl)methyl)-3H-imidazo[4,5-c]pyridine. MS ES/APCl calc'd. for $C_{20}H_{28}ClN_3O$ [M+H]$^+$ 362. found 362.

Step 2: To a stirred solution of 6-chloro-4-(1-cyclobutylethoxy)-3-((trans-4-methylcyclohexyl)methyl)-3H-imidazo[4,5-c]pyridine (3.5 g, 11.73 mmol) in THF (20 mL) was added 2,2,6,6-tetramethylpiperidinyl magnesium chloride lithium chloride complex (1.0 M in THF/Toluene, 29.8 mL, 29.84 mmol) at −78° C. The resulting solution was stirred 2.5 hours and then 1,3 dibromo-5,5 dimethyl hydantoin (8.5 g, 29.84 mmol) in THF (20 mL) was added dropwise at −78° C. The reaction was stirred for 30 minutes then slowly warmed to room temperature over a period of 2 hours. The reaction was quenched with saturated NH$_4$Cl solution (50 mL) at 0° C. and extracted with EtOAc (2×20 mL). The combined organic extracts were washed with water (20 mL) and brine (20 mL), dried over anhydrous Na$_2$SO$_4$, filtered, and concentrated. The residue was purified by silica gel chromatography (eluting with 8-10% EtOAc/petroleum ether) to yield 2-bromo-6-chloro-4-(1-cyclobutylethoxy)-3-((trans-4-methylcyclohexyl)methyl)-3H-imidazo[4,5-c]pyridine. MS ES/APCl calc'd. for $C_{20}H_{27}BrClN_3O$ [M+H]$^+$ 440. found 440.

Step 3: To a solution of 2-bromo-6-chloro-4-(1-cyclobutylethoxy)-3-((trans-4-methylcyclohexyl)methyl)-3H-imidazo[4,5-c]pyridine (1.5 g, 3.40 mmol) in DMSO (15 mL), in a microwave tube was added (R)-3-phenylmorpholine (797 mg, 4.77 mmol) and cesium fluoride (3.6 g, 23.8 mmol). The reaction was heated at 125° C. in a microwave for 45 mins. The reaction was then diluted with water (50 mL) and extracted with ethyl acetate (2×30 mL). The combined organic extracts were washed with water (20 mL) and brine (20 mL), dried over anhydrous Na$_2$SO$_4$, filtered, and concentrated. The residue was purified by silica gel chromatography (eluting with 8-10% EtOAc/petroleum ether) to yield (3R)-4-(6-chloro-4-(1-cyclobutylethoxy)-3-((trans-4-methylcyclohexyl)methyl)-3H-imidazo[4,5-c]pyridin-2-yl)-3-phenylmorpholine. MS ES/APCl calc'd. for $C_{30}H_{39}ClN_4O_2$ [M+H]$^+$ 523. found 523.

Steps 4-6: Following procedures similar to those described for Example 21.1 (Step 2) and Example 2.1 (Steps 5 and 6), (3R)-4-(6-chloro-4-(1-cyclobutylethoxy)-3-((trans-4-methylcyclohexyl)methyl)-3H-imidazo[4,5-c]pyridin-2-yl)-3-phenylmorpholine was converted to 3-{4-(1-cyclobutylethoxy)-3-[(trans-4-methylcyclohexyl)methyl]-2-[(3R)-3-phenylmorpholin-4-yl]-3H-imidazo[4,5-c]pyridin-6-yl}-1,2,4-oxadiazol-5(4H)-one (mixture of diastereomers). $^1$H-NMR (400 MHz, DMSO-$d_6$): δ 12.70 (s, 1H), 7.56-7.55 (m, 1H), 7.40-7.37 (m, 2H), 7.24-7.15 (m, 3H), 5.72-5.65 (m, 1H), 4.59 (d, J=6.8 Hz, 1H), 4.00-3.95 (m, 1H), 3.91-3.79 (m, 5H), 3.12-3.10 (m, 1H), 2.60-2.55 (m, 1H), 2.01-1.94 (m, 7H), 1.83-1.80 (m, 2H), 1.28-1.24 (m, 4H), 1.16 (d, J=6.0 Hz, 3H), 1.04-1.01 (m, 2H), 0.84 (d, J=6.4 Hz, 3H), 0.81-0.75 (m, 2H). MS ES/APCl calc'd. for $C_{32}H_{40}N_6O_4$ [M−H]$^+$ 571. found 571.

Examples 21.1 and 21.2 were prepared as described above.

TABLE 21

| Ex. | FRET IC$_{50}$ (nM) | Structure | Chemical Name | Salt | [M + H]+ Calc'd | [M + H]+ Obsv'd |
|---|---|---|---|---|---|---|
| 21.1 | 37 | 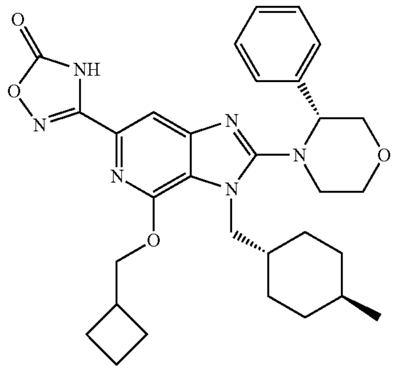 [SMILES: C[C@H]1CC[C@H](Cn2c(N3CCOC[C@H]3c3ccccc3)nc3cc(-c4noc(=O)[nH]4)nc(OCC4CCC4)c32)CC1] | 3-{4-(cyclobutylmethoxy)-3-[(trans-4-methylcyclohexyl (methyl]-2-[(3R)-3-phenylmorpholin-4-yl]-3H-imidazo[4,5-c]pyridin-6-yl}-1,2,4-oxadiazol-5(4H)-one | | 559 | 559 |
| 21.2 | 28 | 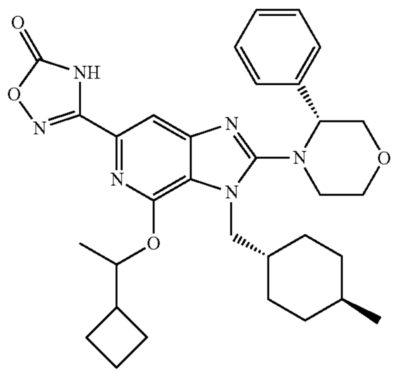 [SMILES: CC(Oc1nc(-c2noc(=O)[nH]2)cc2nc(N3CCOC[C@H]3c3ccccc3)n(C[C@H]3CC[C@H](C)CC3)c12)C1CCC1] | 3-{4-(1-cyclobutylethoxy)-3-[(trans-4-methylcyclohexyl)methyl]-2-[(3R)-3-phenylmorpholin-4-yl]-3H-imidazo[4,5-c]pyridin-6-yl}-1,2,4-oxadiazol-5(4H)-one (mixture of diastereomers) | | 571 [M − H] | 571 |

Example 2

FRET Assay

Methods: An HDM2 FRET assay was developed to assess the compounds' inhibitory activity towards binding of p53 protein. A truncated version of HDM2 with residues 17 to 125 (containing p53 binding surface, Science (1994) 265, 346-355), with N-terminal His and Thioredoxin tag was generated in pET32a expression vector and expressed in *E. coli* strain BL21(DE3)Rosetta. Protein was purified using Ni-affinity chromatography, followed by size exclusion chromatography using Superdex 75 26/60 column. To assess inhibition of p53 binding to HDM2, a FITC labeled 8-mer peptide (SEQ ID NO:1: Ac-Phe-Arg-Dpr-Ac6c-(6-Br)Trp-Glu-Glu-Leu-NH$_2$; Anal Biochem. 2004 Aug. 1; 331(1):138-46) with strong affinity towards the p53 binding pocket of HDM2 was used. The HDM2 assay buffer contained 1× Phosphate Buffered Saline (Invitrogen, Cat#14190), 0.01% BSA (Jackson ImmunoResearch, Cat#001-000-162), 0.01% Tween-20. In the 1× assay buffer recombinant HDM2 protein, peptide and Lumi-4-Tb Cryptate-conjugate mouse anti-6×His antibody (cisbio, Cat#Tb61 HISTLB) were added and transferred to ProxiPlate PLUS (PerkinElmer, Cat#6008269), containing compounds so that final DMSO concentration is 0.1%. Final concentrations of reagents in the assay wells are 0.5 nM HDM2, 0.25 nM anti HIS (Tb label) antibody and 3 nM peptide. After two hour incubation at room temperature in a humidified chamber plates were read on EnVision plate reader with the following settings: excitation: UV, 340 nM, two emission filters: 520 nm and 495 nm respectively. Ratio of em520/em495 was used to calculate % inhibition and to obtain IC$_{50}$ with 4-parameter logistic equation.

IC$_{50}$ DETERMINATIONS: Dose-response curves were plotted from the inhibition data, from 10 point serial dilutions of inhibitory compounds. Concentration of compound was plotted against em520/Cem495 ratio signal. To generate IC$_{50}$ values, the dose-response curves were fitted to a standard sigmoidal curve and IC$_{50}$ values were derived by nonlinear regression analysis. IC$_{50}$ values in the above table are rounded to the nearest integer.

Example 3

Cell Viability Assay

Additionally, compounds can be tested for activity at the HDM2 protein using the Cell Viability Assay (SJSA-1 or HCT-116 cell line), which measures the number of viable cells in culture after treatment with the inventive compound for a certain period of time e.g. 72 hours based on quantitation of the ATP present (Cell Viability. IC$_{50}$). [CellTiter-Glo® Luminescent Cell Viability Assay from Promega]. IC$_{50}$ of compounds of the examples which values were determined in the SJSA-1 cell line ranged from 32 to 7963 nM. IC$_{50}$ of compounds of the examples which values were determined in the HCT-116 cell line ranged from 31 to 9866 nM.

The invention claimed is:

1. A compound selected from the group consisting of:

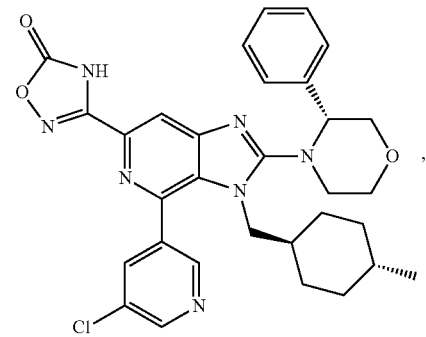

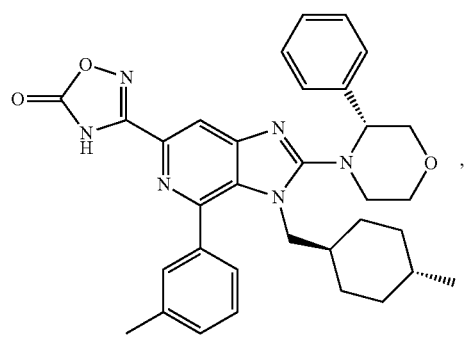

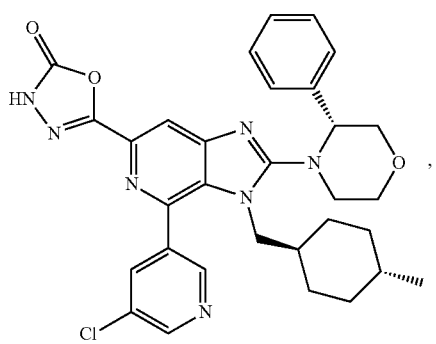

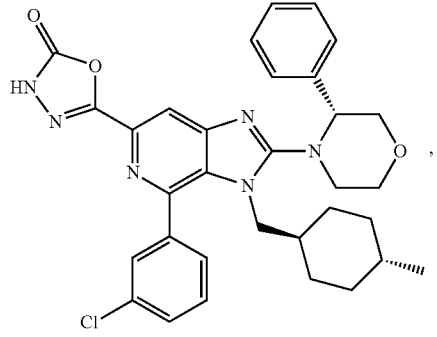

407
-continued
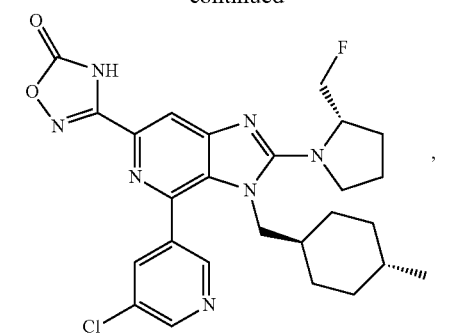,
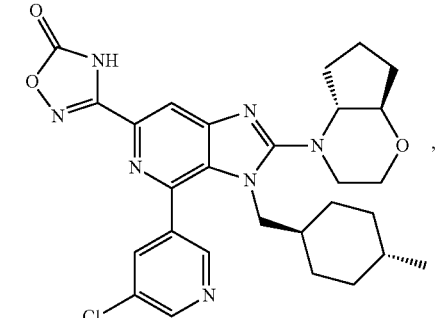,
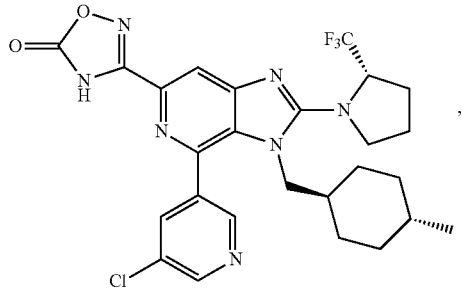,
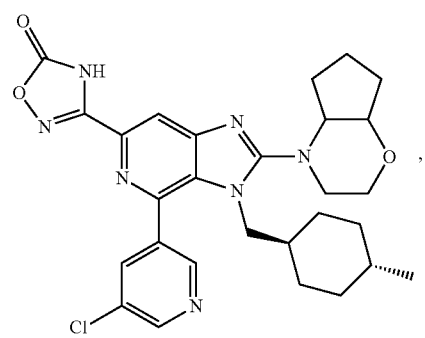,
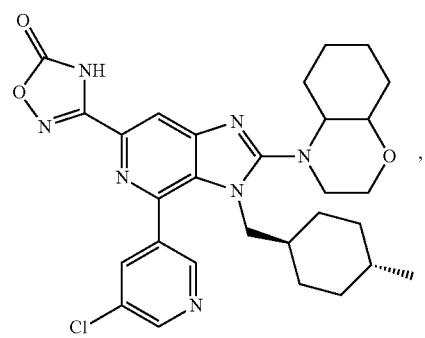,
408
-continued
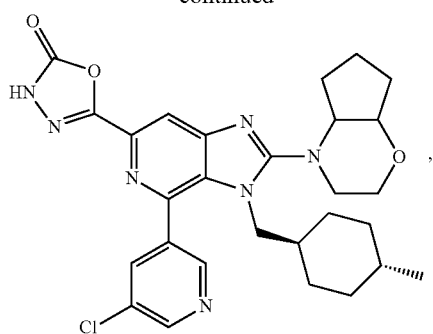,
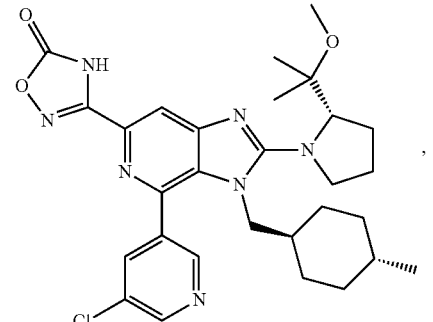,
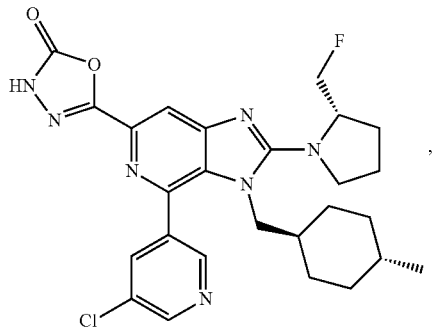,
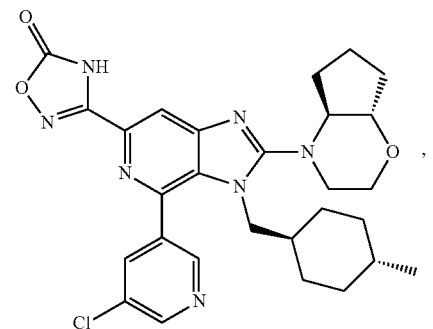,
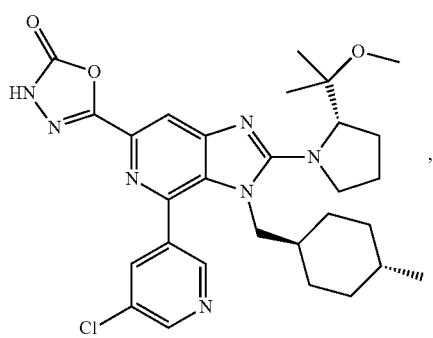, 409
-continued
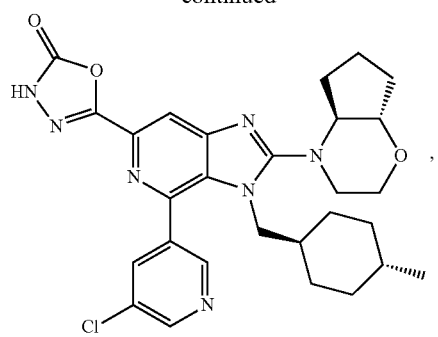
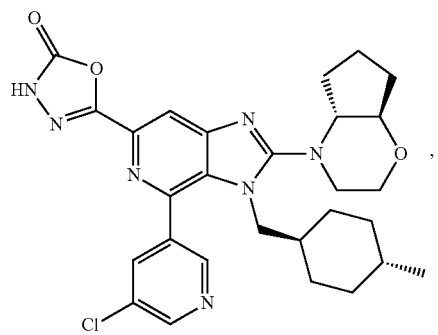
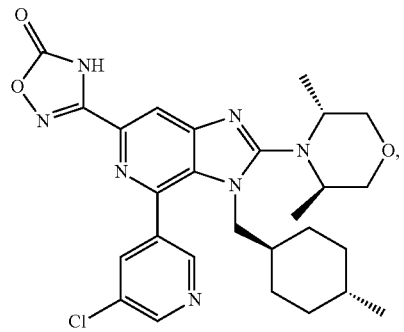
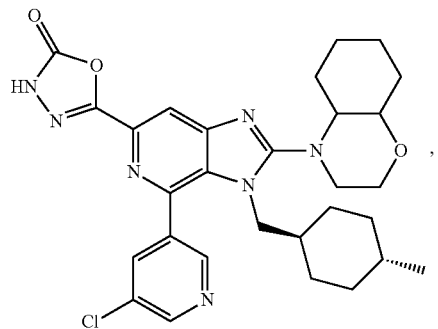
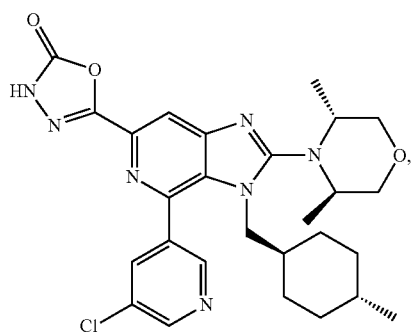
410
-continued
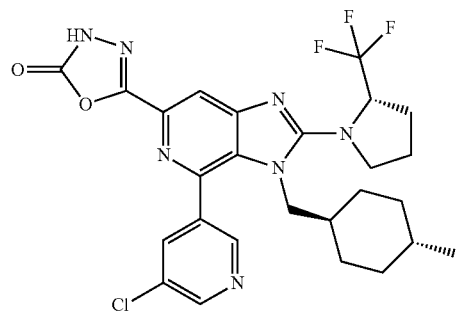
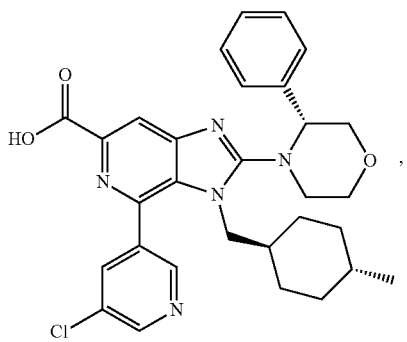
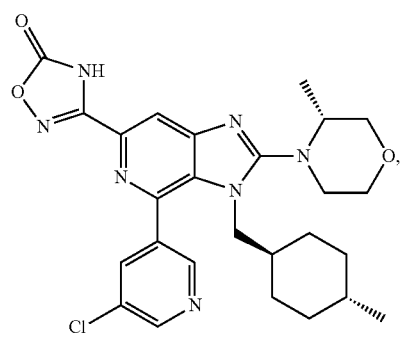
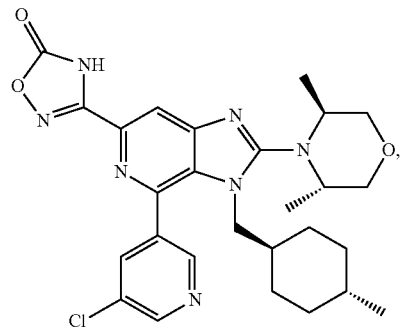
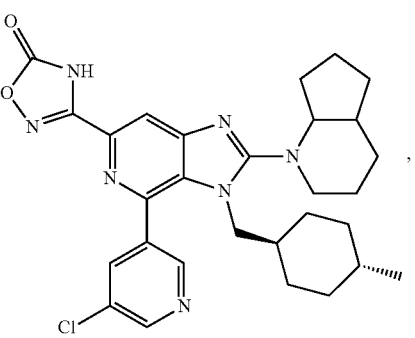

411
-continued
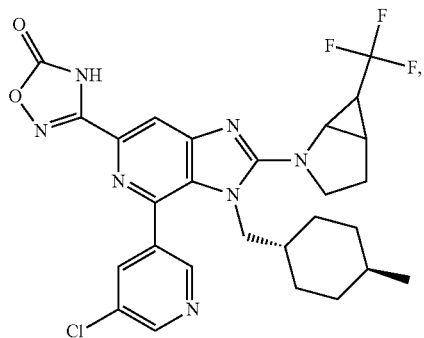
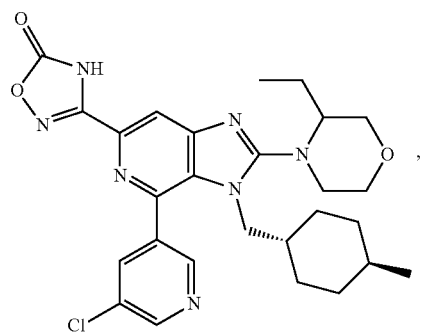
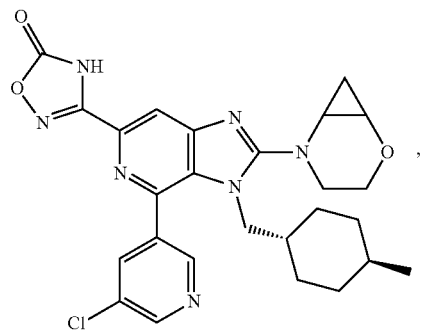
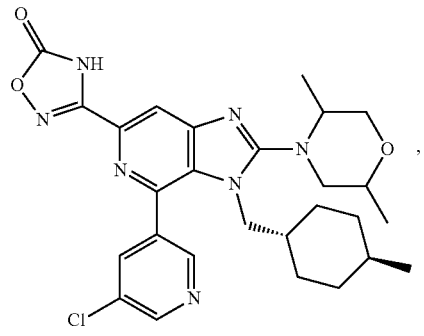
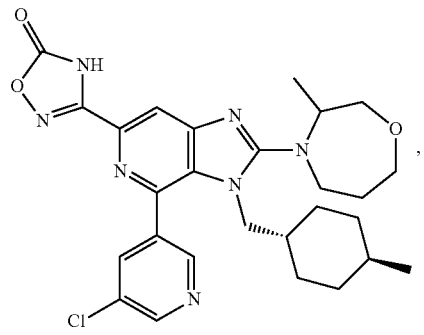
412
-continued
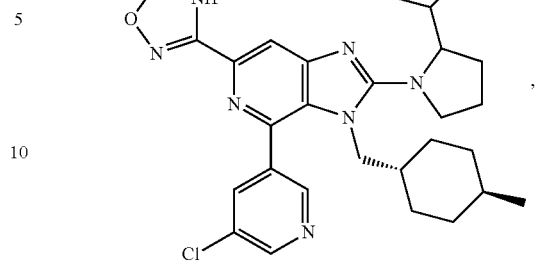
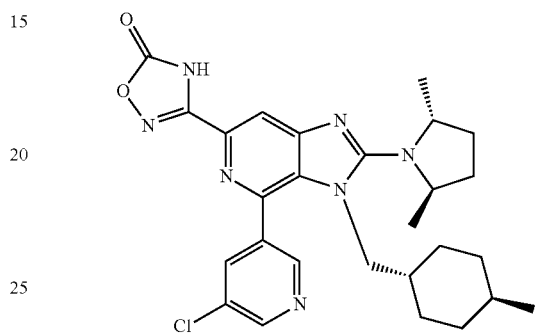
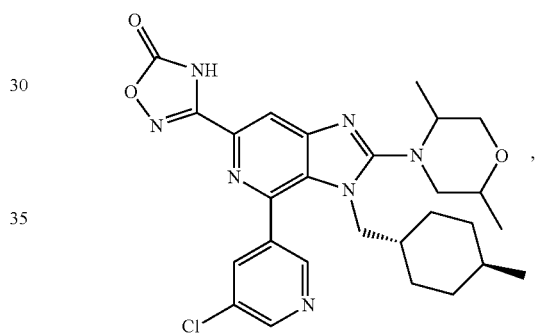
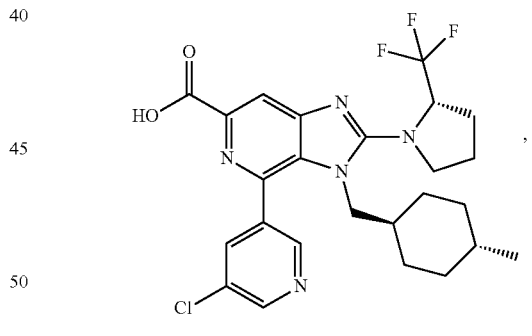
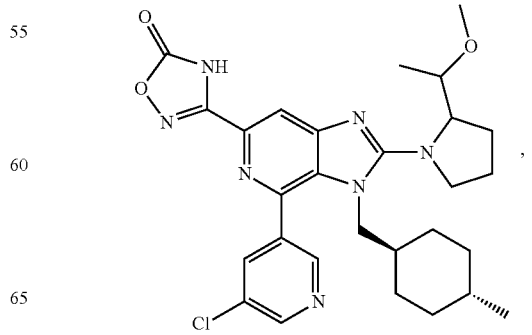

413
-continued
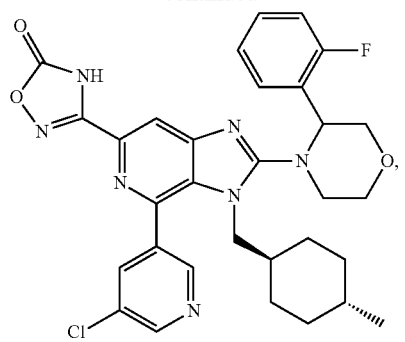
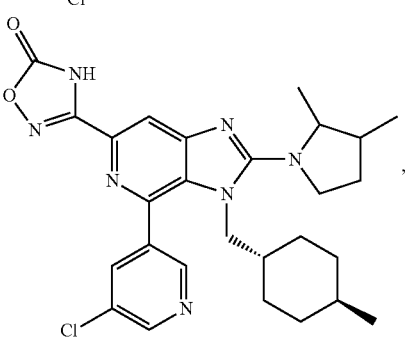
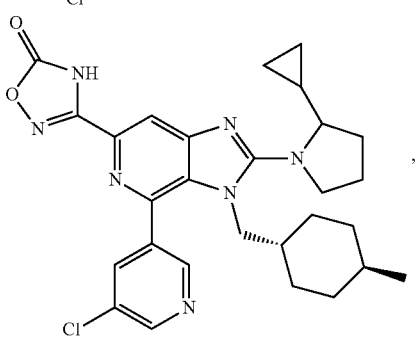
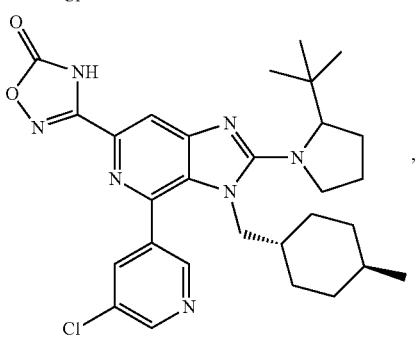
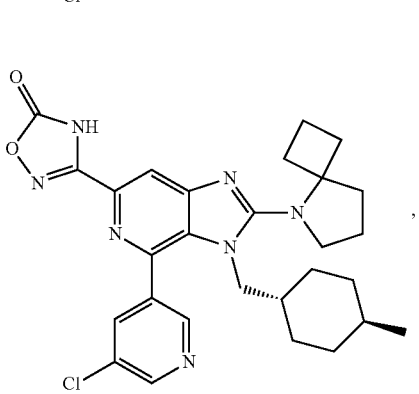
414
-continued
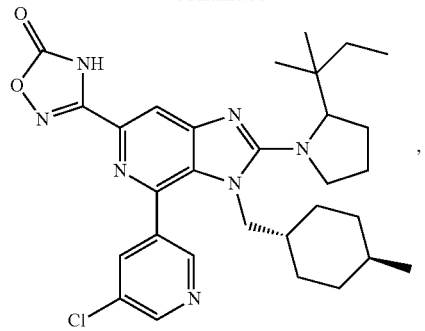
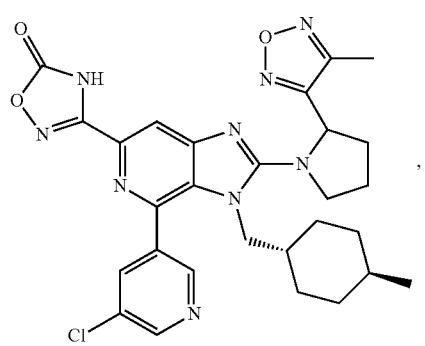
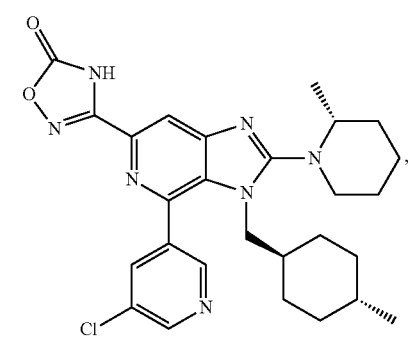
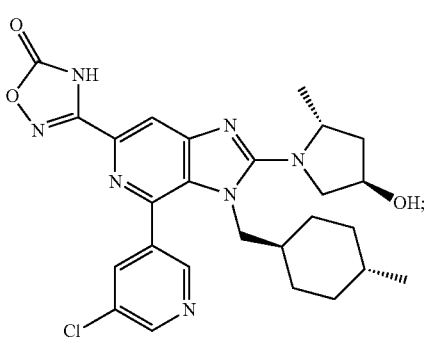
or a stereoisomer thereof;
or a pharmaceutically acceptable salt thereof;
or a pharmaceutically acceptable salt of the stereoisomer thereof.

2. A compound selected from the group consisting of:
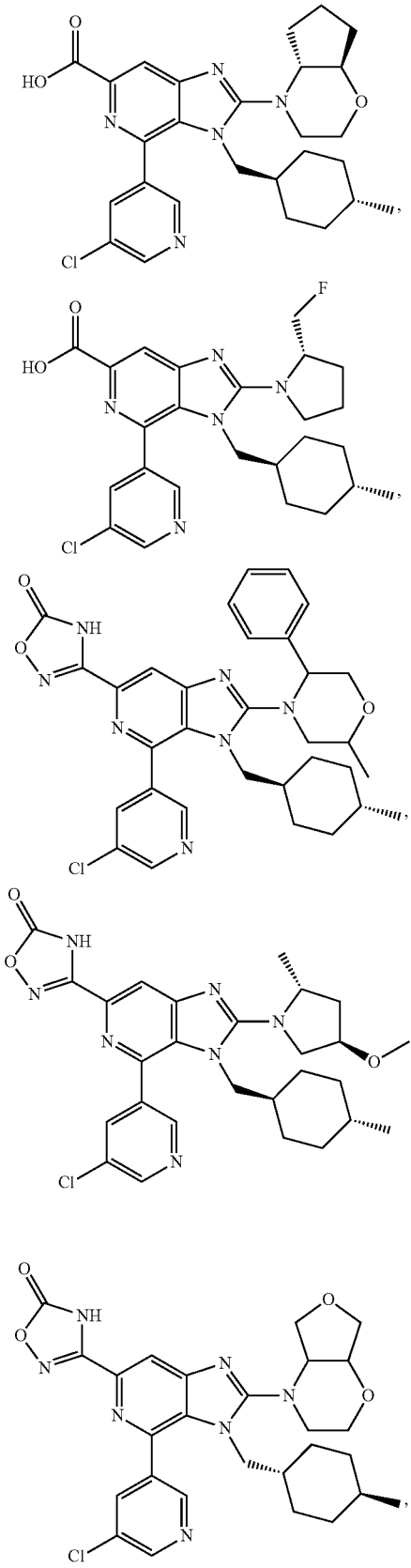
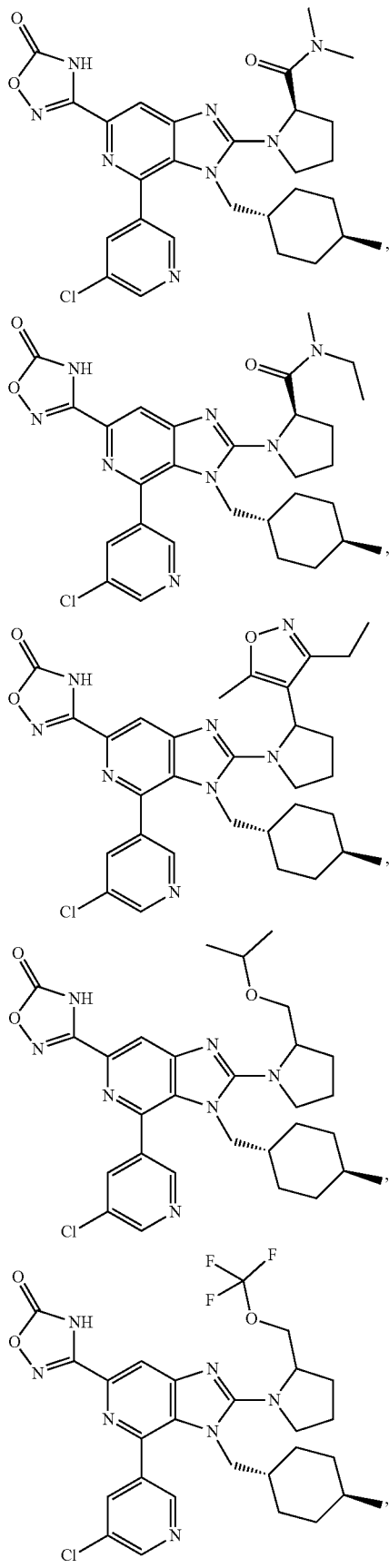 [SMILES: CN(C)C(=O)[C@H]1CCCN1c1nc2cc(-c3noc(=O)[nH]3)nc(-c3cncc(Cl)c3)c2n1C[C@H]1CC[C@H](C)CC1 ; CCN(C)C(=O)[C@H]1CCCN1c1nc2cc(-c3noc(=O)[nH]3)nc(-c3cncc(Cl)c3)c2n1C[C@H]1CC[C@H](C)CC1 ; CCc1noc(C)c1C1CCCN1c1nc2cc(-c3noc(=O)[nH]3)nc(-c3cncc(Cl)c3)c2n1C[C@H]1CC[C@H](C)CC1 ; CC(C)OCC1CCCN1c1nc2cc(-c3noc(=O)[nH]3)nc(-c3cncc(Cl)c3)c2n1C[C@H]1CC[C@H](C)CC1 ; C[C@H]1CC[C@H](Cn2c(N3CCCC3COC(F)(F)F)nc3cc(-c4noc(=O)[nH]4)nc(-c4cncc(Cl)c4)c32)CC1]

417
-continued
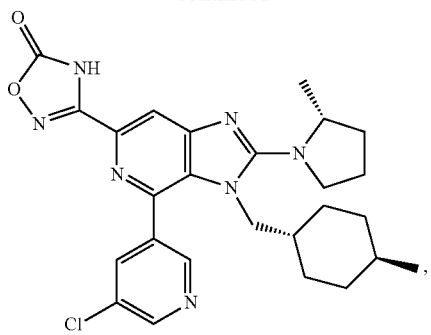
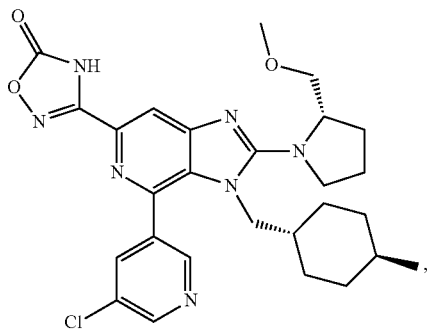
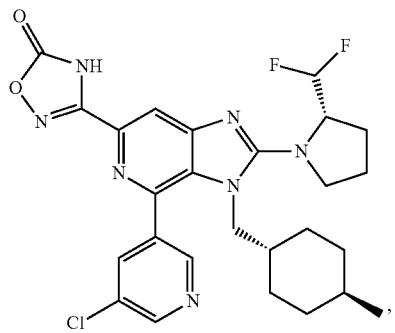
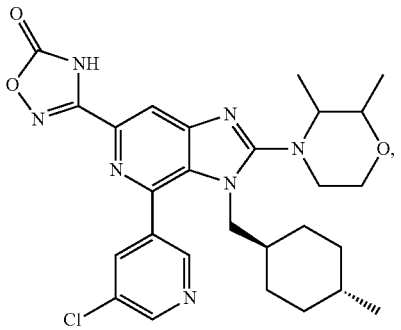
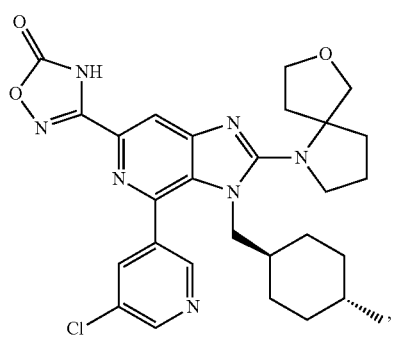
418
-continued
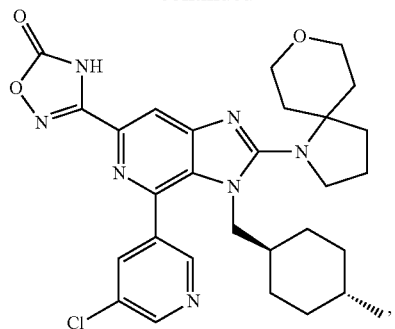
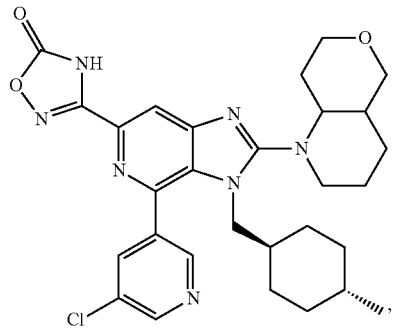
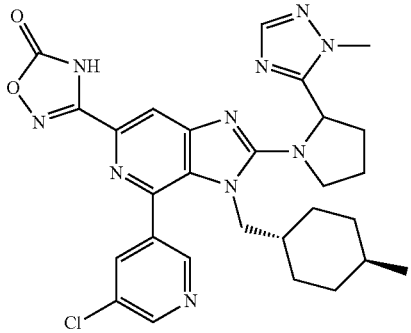
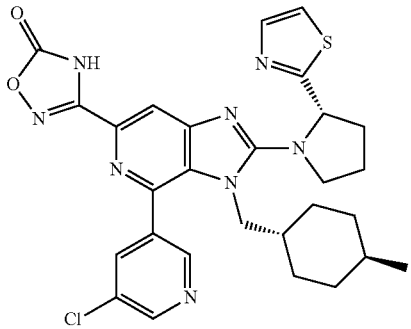
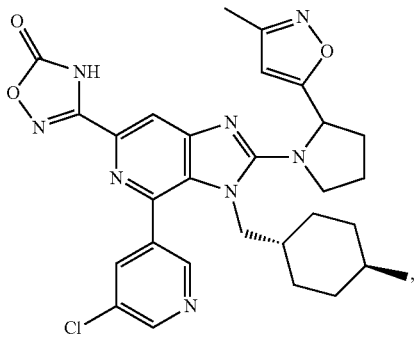

419
-continued
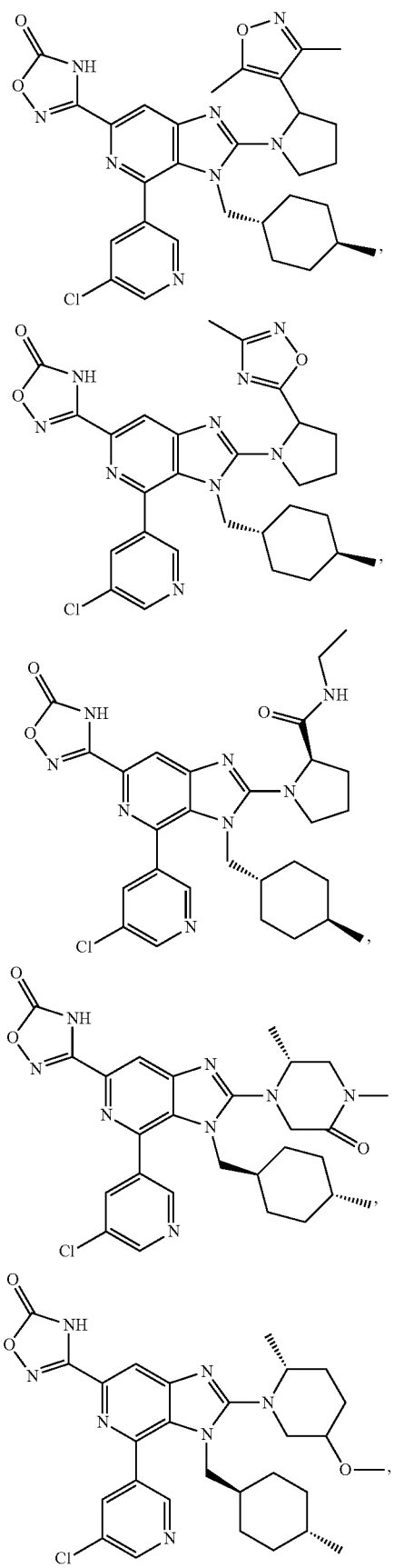
420
-continued
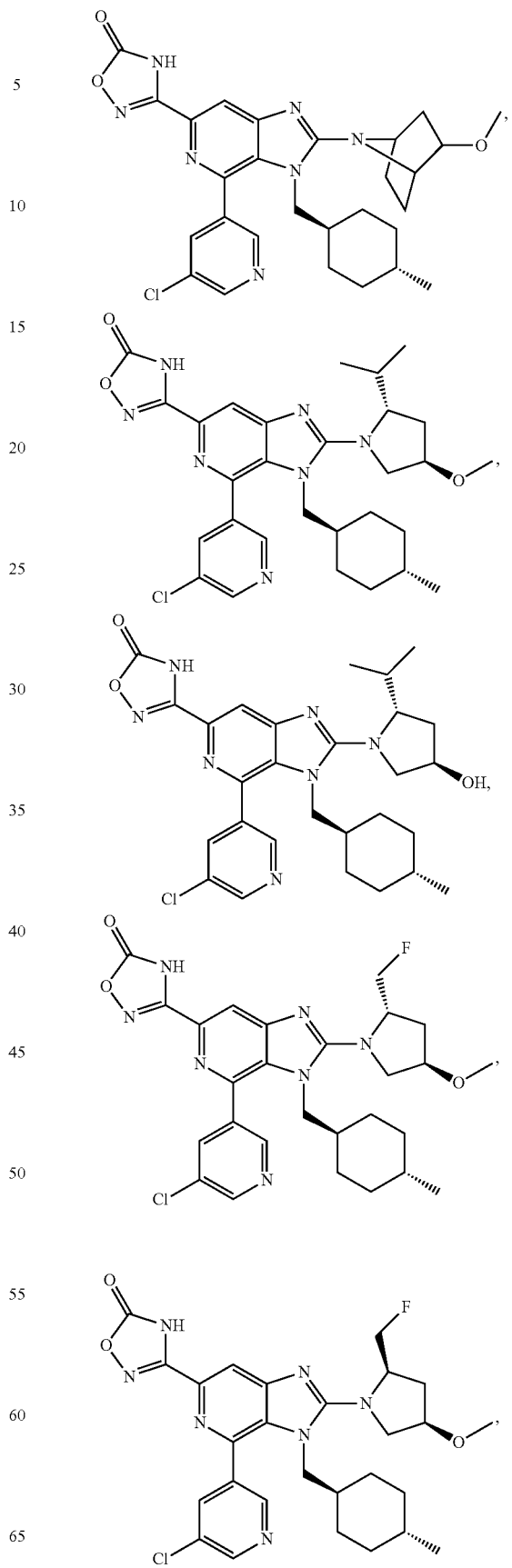

421
-continued
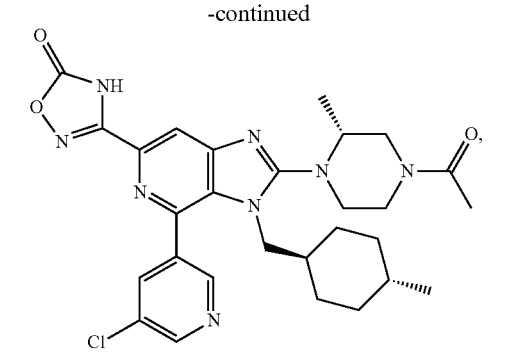
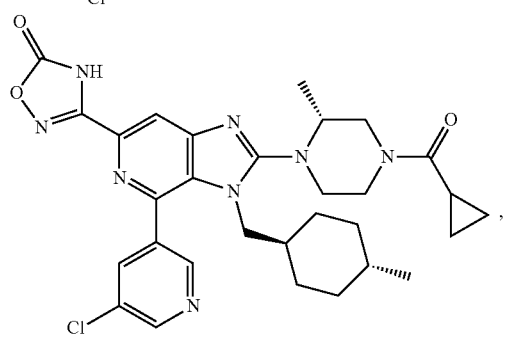
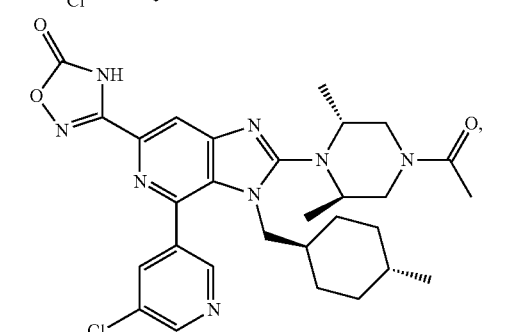
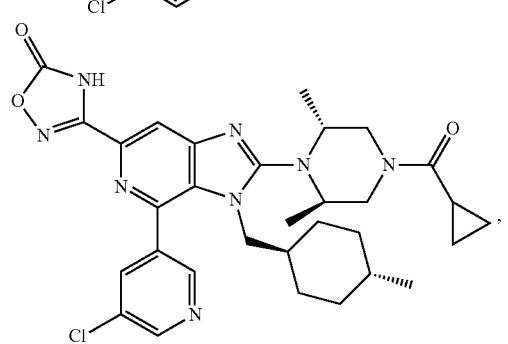
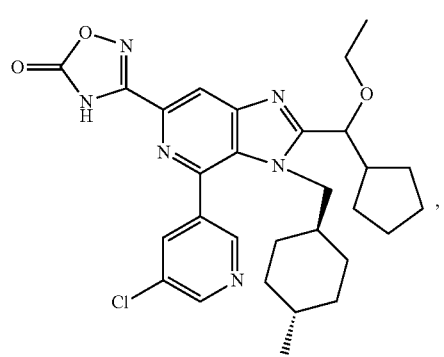
422
-continued
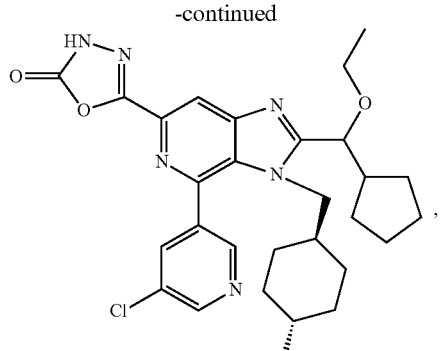
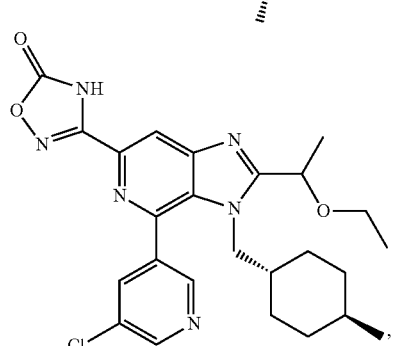
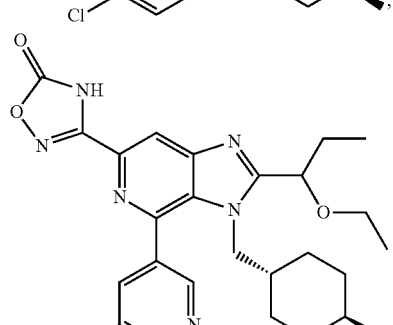
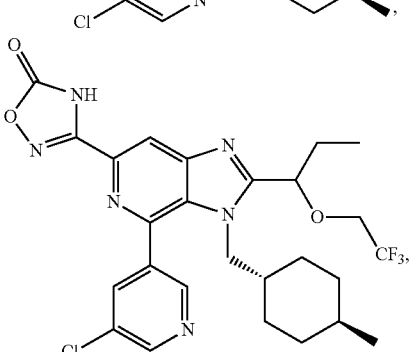
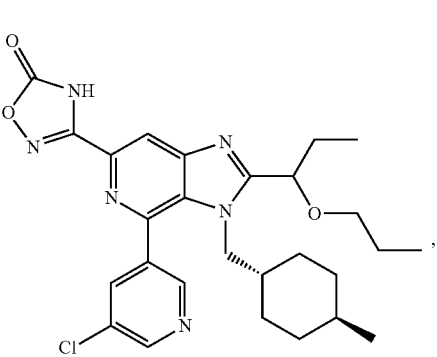

423
-continued
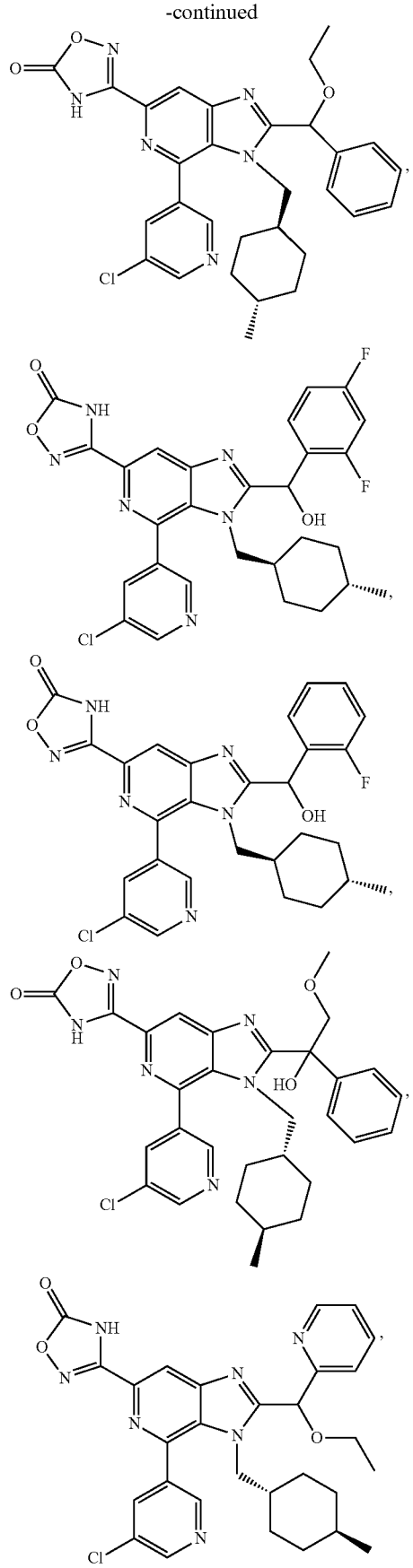
424
-continued
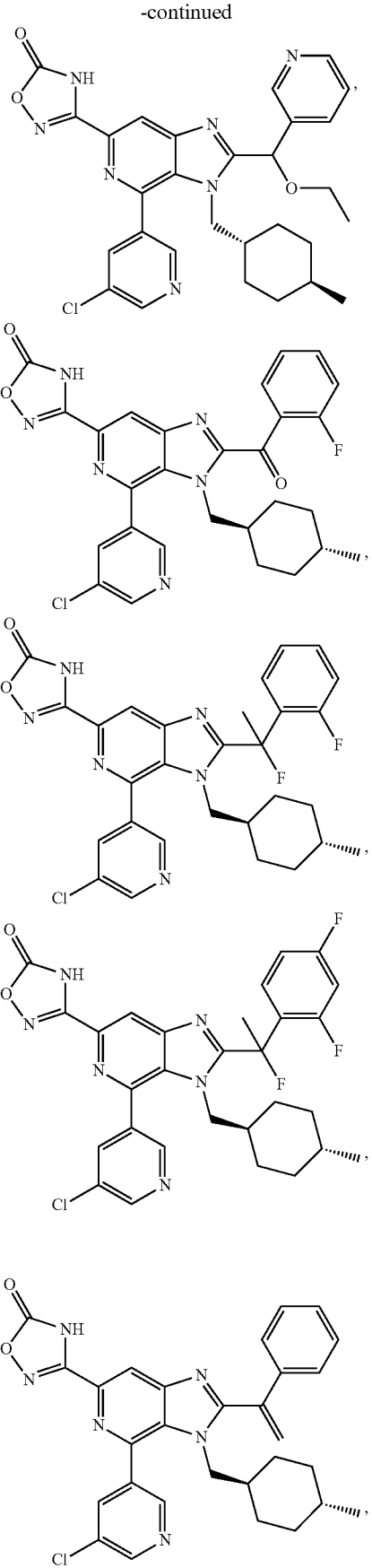

-continued

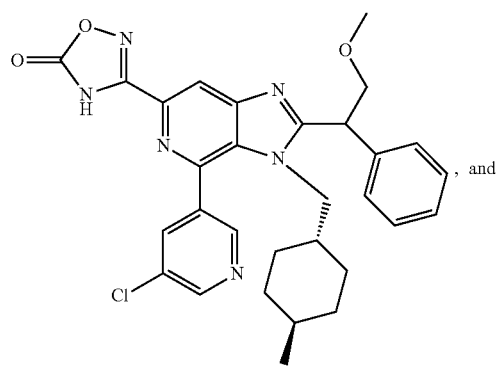, and

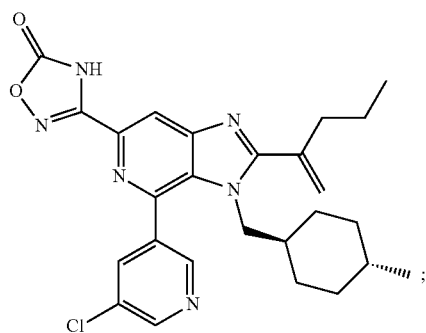;

or a stereoisomer thereof;
or a pharmaceutically acceptable salt thereof;
or a pharmaceutically acceptable salt of the stereoisomer thereof.

3. A pharmaceutical composition comprising a compound of claim 1, in combination with at least one pharmaceutically acceptable carrier.

4. A pharmaceutical composition comprising a compound of claim 2, in combination with at least one pharmaceutically acceptable carrier.

5. The compound of claim 1 that is

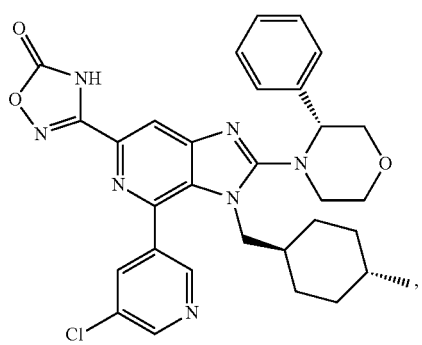 [SMILES: C[C@H]1CC[C@H](Cn2c(N3CCOC[C@H]3c3ccccc3)nc3cc(-c4noc(=O)[nH]4)nc(-c4cncc(Cl)c4)c32)CC1]

or a pharmaceutically acceptable salt thereof.

6. The compound of claim 1 that is

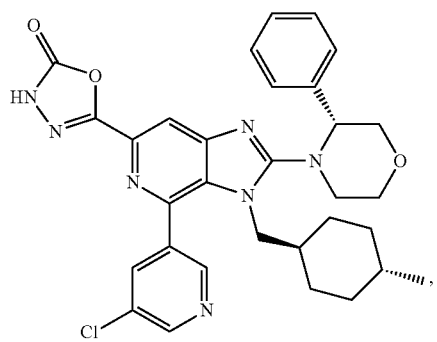 [SMILES: C[C@H]1CC[C@H](Cn2c(N3CCOC[C@H]3c3ccccc3)nc3cc(-c4n[nH]c(=O)o4)nc(-c4cncc(Cl)c4)c32)CC1]

or a pharmaceutically acceptable salt thereof.

7. The compound of claim 1 that is

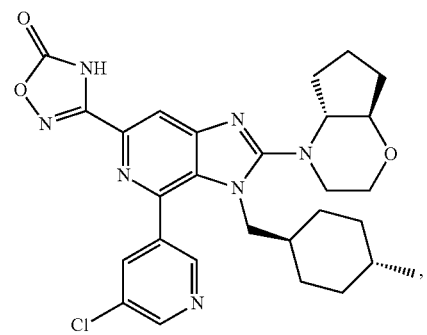

or a pharmaceutically acceptable salt thereof.

8. The compound of claim 1 that is

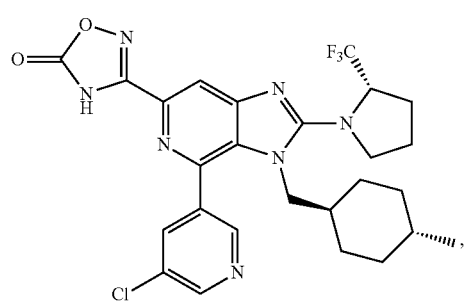 [SMILES: C[C@H]1CC[C@H](Cn2c(N3CCC[C@H]3C(F)(F)F)nc3cc(-c4noc(=O)[nH]4)nc(-c4cncc(Cl)c4)c32)CC1]

or a pharmaceutically acceptable salt thereof.

9. The compound of claim 1 that is

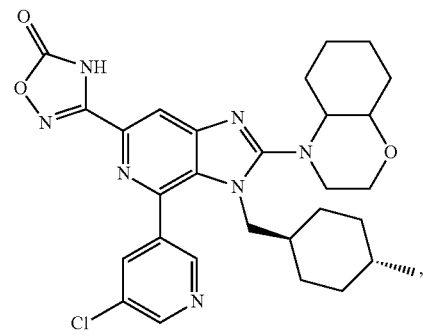 [SMILES: C[C@H]1CC[C@H](Cn2c(N3CCOC4CCCCC43)nc3cc(-c4noc(=O)[nH]4)nc(-c4cncc(Cl)c4)c32)CC1]

or a pharmaceutically acceptable salt thereof.

10. The compound of claim 1 that is

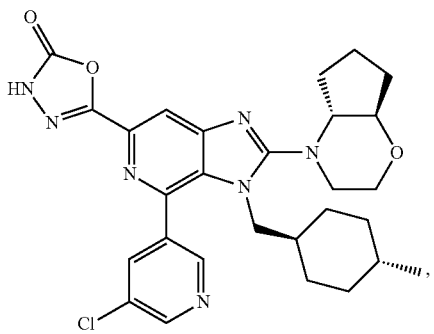 [SMILES: C[C@H]1CC[C@H](Cn2c(N3CCO[C@@H]4CCC[C@H]43)nc3cc(-c4n[nH]c(=O)o4)nc(-c4cncc(Cl)c4)c32)CC1]

or a pharmaceutically acceptable salt thereof.

11. The compound of claim 1 that is

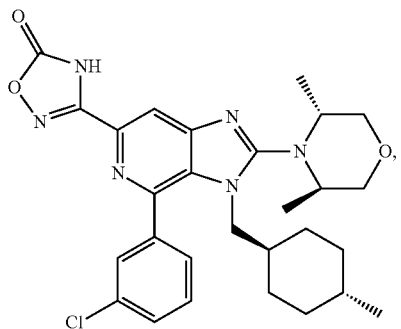 [SMILES: C[C@@H]1COC[C@@H](C)N1c1nc2cc(-c3noc(=O)[nH]3)nc(-c3cccc(Cl)c3)c2n1C[C@H]1CC[C@H](C)CC1]

or a pharmaceutically acceptable salt thereof.

12. The compound of claim 1 that is

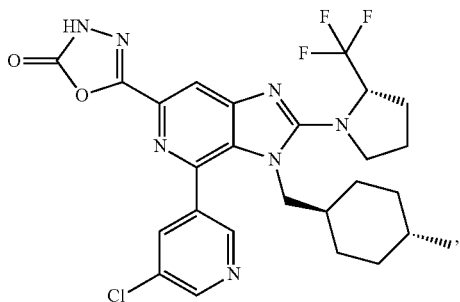 [SMILES: C[C@H]1CC[C@H](Cn2c(N3CCC[C@H]3C(F)(F)F)nc3cc(-c4n[nH]c(=O)o4)nc(-c4cncc(Cl)c4)c32)CC1]

or a pharmaceutically acceptable salt thereof.

13. The compound of claim 1 that is

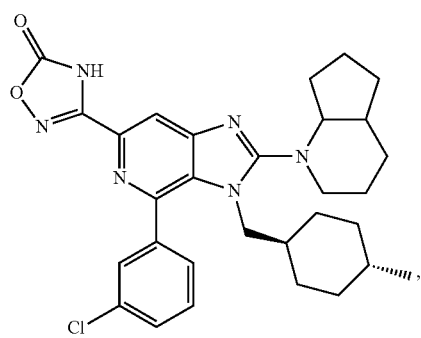 [SMILES: C[C@H]1CC[C@H](Cn2c(N3CCCC4CCCC43)nc3cc(-c4noc(=O)[nH]4)nc(-c4cccc(Cl)c4)c32)CC1]

or a pharmaceutically acceptable salt thereof.

14. The compound of claim 1 that is

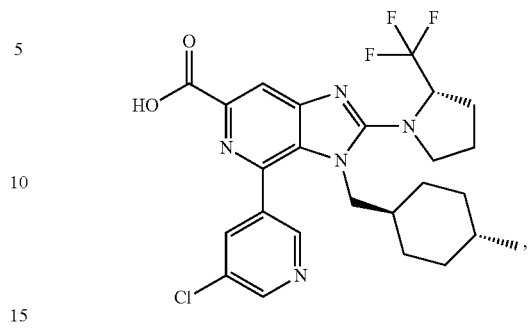

or a pharmaceutically acceptable salt thereof.

15. The compound of claim 2 that is

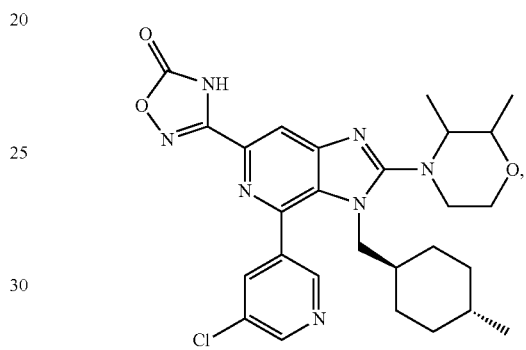

or a pharmaceutically acceptable salt thereof.

16. The compound of claim 2 that is

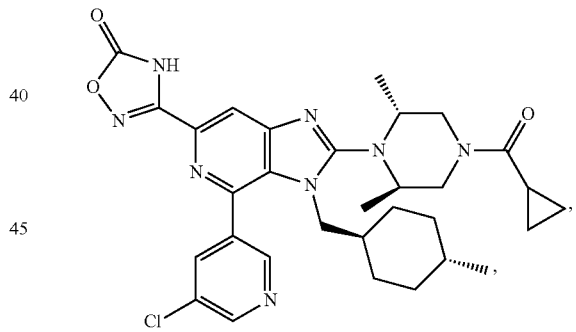

or a pharmaceutically acceptable salt thereof.

17. The compound of claim 2 that is

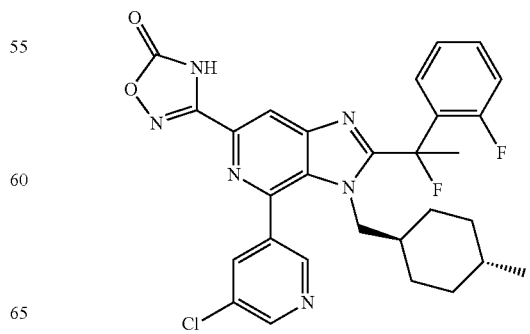

or a pharmaceutically acceptable salt thereof.

18. A pharmaceutical composition comprising a compound of claim 5, in combination with at least one pharmaceutically acceptable carrier.

19. A pharmaceutical composition comprising a compound of claim 6, in combination with at least one pharmaceutically acceptable carrier.

20. A pharmaceutical composition comprising a compound of claim 7, in combination with at least one pharmaceutically acceptable carrier.

21. A pharmaceutical composition comprising a compound of claim 8, in combination with at least one pharmaceutically acceptable carrier.

22. A pharmaceutical composition comprising a compound of claim 9, in combination with at least one pharmaceutically acceptable carrier.

23. A pharmaceutical composition comprising a compound of claim 10, in combination with at least one pharmaceutically acceptable carrier.

24. A pharmaceutical composition comprising a compound of claim 11, in combination with at least one pharmaceutically acceptable carrier.

25. A pharmaceutical composition comprising a compound of claim 12, in combination with at least one pharmaceutically acceptable carrier.

26. A pharmaceutical composition comprising a compound of claim 13, in combination with at least one pharmaceutically acceptable carrier.

27. A pharmaceutical composition comprising a compound of claim 14, in combination with at least one pharmaceutically acceptable carrier.

28. A pharmaceutical composition comprising a compound of claim 15, in combination with at least one pharmaceutically acceptable carrier.

29. A pharmaceutical composition comprising a compound of claim 16, in combination with at least one pharmaceutically acceptable carrier.

30. A pharmaceutical composition comprising a compound of claim 17, in combination with at least one pharmaceutically acceptable carrier.

* * * * *